(12) United States Patent
Cho et al.

(10) Patent No.: US 8,809,266 B2
(45) Date of Patent: Aug. 19, 2014

(54) ANTIVIRAL COMPOUNDS

(71) Applicant: Gilead Sciences, Inc., Foster City, CA (US)

(72) Inventors: Aesop Cho, Mountain View, CA (US); Michael O'Neil Hanrahan Clarke, Redwood City, CA (US); Choung U. Kim, San Carlos, CA (US); John O. Link, San Francisco, CA (US); Hyung-jung Pyun, Fremont, CA (US); Xiaoning C. Sheng, Guangzhou (CN); Qiaoyin Wu, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/794,389

(22) Filed: Mar. 11, 2013

(65) Prior Publication Data

US 2013/0274439 A1    Oct. 17, 2013

Related U.S. Application Data

(63) Continuation of application No. 13/598,430, filed on Aug. 29, 2012, now Pat. No. 8,420,597, which is a continuation of application No. 13/436,679, filed on Mar. 30, 2012, now Pat. No. 8,283,442, which is a continuation of application No. 12/215,605, filed on Jun. 26, 2008, now Pat. No. 8,178,491.

(60) Provisional application No. 60/937,752, filed on Jun. 29, 2007, provisional application No. 60/959,771, filed on Jul. 16, 2007, provisional application No. 61/037,988, filed on Mar. 19, 2008.

(51) Int. Cl.
*A61K 38/00* (2006.01)

(52) U.S. Cl.
USPC .......................................................... 514/4.3

(58) Field of Classification Search
None
See application file for complete search history.

(56) References Cited

U.S. PATENT DOCUMENTS

| | | | |
|---|---|---|---|
| 5,633,388 A | 5/1997 | Diana et al. | |
| 5,866,684 A | 2/1999 | Attwood et al. | |
| 5,869,253 A | 2/1999 | Draper | |
| 6,018,020 A | 1/2000 | Attwood et al. | |
| 6,225,284 B1 | 5/2001 | Albert et al. | |
| 6,265,380 B1 | 7/2001 | Tung et al. | |
| 6,268,207 B1 | 7/2001 | Bailey | |
| 6,323,180 B1 | 11/2001 | Llinas-Brunet et al. | |
| 6,329,379 B1 | 12/2001 | Llinas-Brunet et al. | |
| 6,410,531 B1 | 6/2002 | Llinas-Brunet et al. | |
| 6,420,380 B2 | 7/2002 | Llinas-Brunet et al. | |
| 6,534,523 B1 | 3/2003 | Llinas-Brunet et al. | |
| 6,608,027 B1 | 8/2003 | Tsantrizos et al. | |
| 6,642,204 B2 | 11/2003 | Llinas-Brunet et al. | |
| 6,867,185 B2 | 3/2005 | Campbell et al. | |
| 6,869,964 B2 | 3/2005 | Campbell et al. | |
| 6,872,805 B2 | 3/2005 | Campbell et al. | |
| 6,878,722 B2 | 4/2005 | Campbell et al. | |
| 6,908,901 B2 | 6/2005 | Bailey et al. | |
| 6,919,423 B2 | 7/2005 | Llinas-Brunet | |
| 6,995,174 B2 | 2/2006 | Wang et al. | |
| 7,041,698 B2 | 5/2006 | Ripka et al. | |
| 7,148,347 B2 | 12/2006 | Brandenburg et al. | |
| 7,749,961 B2 * | 7/2010 | Llinas-Brunet et al. | ....... 514/4.3 |
| 8,178,491 B2 | 5/2012 | Cho et al. | |
| 8,283,442 B2 | 10/2012 | Cho et al. | |
| 8,420,597 B2 | 4/2013 | Cho et al. | |
| 2003/0191067 A1 | 10/2003 | Llinas-Brunet et al. | |

FOREIGN PATENT DOCUMENTS

| | | |
|---|---|---|
| CA | 2429359 | 8/2002 |
| CA | 2486308 | 12/2004 |
| EP | 1162196 | 12/2001 |
| EP | 1437362 | 7/2004 |
| WO | WO-95/33764 | 12/1995 |
| WO | WO-97/06804 | 2/1997 |
| WO | WO-97/43310 | 11/1997 |
| WO | WO-98/17679 | 4/1998 |
| WO | WO-98/22496 | 5/1998 |
| WO | WO-98/46597 | 10/1998 |
| WO | WO-98/46630 | 10/1998 |
| WO | WO-99/07733 | 2/1999 |
| WO | WO-99/07734 | 2/1999 |
| WO | WO-99/38888 | 8/1999 |
| WO | WO-99/50230 | 10/1999 |
| WO | WO-99/64442 | 12/1999 |
| WO | WO-00/06529 | 2/2000 |
| WO | WO-00/09543 | 2/2000 |
| WO | WO-00/09558 | 2/2000 |
| WO | WO-00/10573 | 3/2000 |
| WO | WO-00/13708 | 3/2000 |
| WO | WO-00/18231 | 4/2000 |
| WO | WO 00/59929 | 10/2000 |
| WO | WO-01/32153 | 5/2001 |

(Continued)

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008 • 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4,461-485.*

(Continued)

*Primary Examiner* — Thomas Heard
(74) *Attorney, Agent, or Firm* — Sheppard, Mullin, Richter & Hampton LLP

(57) ABSTRACT

The invention is related to anti-viral compounds, compositions containing such compounds, and therapeutic methods that include the administration of such compounds, as well as to processes and intermediates useful for preparing such compounds.

14 Claims, No Drawings

(56) References Cited

FOREIGN PATENT DOCUMENTS

| WO | WO-01/85172 | 11/2001 |
|---|---|---|
| WO | WO-02/04425 | 1/2002 |
| WO | WO-02/06246 | 1/2002 |
| WO | WO-02/060926 | 8/2002 |
| WO | WO-2004/032827 | 5/2003 |
| WO | WO-03/053349 | 7/2003 |
| WO | WO-03/064416 | 8/2003 |
| WO | WO-03/064455 | 8/2003 |
| WO | WO-03/064456 | 8/2003 |
| WO | WO-03/066103 | 8/2003 |
| WO | WO-03/099274 | 12/2003 |
| WO | WO-03/099316 | 12/2003 |
| WO | WO-2004/094452 | 4/2004 |
| WO | WO-2004/043339 | 5/2004 |
| WO | WO-2004/072243 | 8/2004 |
| WO | WO-2004/093798 | 11/2004 |
| WO | WO-2004/101602 | 11/2004 |
| WO | WO-2004/103996 | 12/2004 |
| WO | WO-2004/113365 | 12/2004 |
| WO | WO-2005/010029 | 2/2005 |
| WO | WO-2005/037214 | 4/2005 |
| WO | WO-2005/046712 | 5/2005 |
| WO | WO-2005/070955 | 8/2005 |
| WO | WO-2005/095403 | 10/2005 |
| WO | WO-2006/007700 | 1/2006 |
| WO | WO-2006/007708 | 1/2006 |
| WO | WO-2006/020276 | 2/2006 |
| WO | WO-2006/086381 | 8/2006 |
| WO | WO-2006/122188 | 11/2006 |
| WO | WO-2007/001406 | 1/2007 |
| WO | WO-2007/008657 | 1/2007 |
| WO | WO-2007/009109 | 1/2007 |
| WO | WO-2007/011658 | 1/2007 |
| WO | WO-2007/015824 | 2/2007 |
| WO | WO-2007/044933 | 4/2007 |

OTHER PUBLICATIONS

Han, H.-K.. AAPS Pharmsci. (2000) 2(1 ), Article 6, pp. 1-11.*
Testa Prodrug research: futile or fertile? Biochemical Pharmacology (2004) 2097-2106.*
Beaulieu, P. et al. (2005) "Synthesis of (1R,2S)-1-amino-2-vinylcyclopropanecarboxylic acid vinyl-ACCA) Derivatives: Key Intermediates for the Preparation of Inhibitors in the Hepatitis C Virus NS3 Protease" Journal of Organic Chemistry, 70:5869-5879.
Beaumont, et al. (2003), "Design of ester prodrugs to enhance oral absorption of poorly permeable compounds: challenges to the discovery scientist." Curr Drug Metab. 4(6):461-85.
Belokon, Y. et al. (1990) "General Method for the Asymmetric Synthesis of anti-Diasteroisomers of—substituted L-2-aminobutanoic acids via chiral nickel-II Schiff's base complexes of dehydroaminobutanoic acid. X-Ray Crystal and Molecular Structure of the nickel(II) complex of the Schiff's base from [(benzylpropyl)amino]benzophenone and dehydroaminobutanoic acid" Journal of the Chemical Society Perkin Transactions I, 2301-2310.
Chu, M. et al. (1996) "Structure of Sch 68631: A New Hepatic C Virus Proteinase Inhibitor from *Streptmoyces* sp.", Tetrahedron Letters 37 (40):7229-7232.
Ettmayer, et al. (2004), "Lessons learned from marketed and investigational prodrugs." J Med Chem. 6;47(10):2393-2404.
Galgoci (1994) "A convenient synthesis of methyl (z)-1-carbamoyl-2-ethenylcyclopropanecarboxylate and (Z)-1-carbamoyl-2-ethenylcyclopropanecarboxylic acid" Synthetic Communications, 24:2477-2483.
Hach, V. (1997) "Terpenes and Terpenoids, 5. The four isomeric thujanols. Their preparative chemistry, conformation and reactivity, a comprehensive study." J. Org. Chem. vol. 42, No. 9, pp. 1616-1623.
Han, H. K. (2002) AAPS Pharmsci., 2(1), article 6, pp. 1-11.
Ingallinella, P. et al. (1998) "Potent Peptide Inhibitors of Human Hepatitis C Virus NS3 Protease Are Obtained by Optimizing the Cleavage Products," Biochemistry, 37:8906-8914.
International Search Report for PCT/US2008/007927, Jan. 20, 2009.
International Search Report for PCT/US2008/007928, Jan. 14, 2009.
Lauer (2001). New England Journal of Medicine 343: 41-52.
Lin, (2006), "HCV NS3-4A Serine Protease, in Hepatitis C Viruses: Genomes and Molecular Biology." Chapter 6, pp. 163-206, Tan SL, editor. Norfolk (UK): Horizon Bioscience.
Llinas-Brunet, M. et al. (1998) "Peptide-Based Inhibitors of the Hepatitis C Virus Serine Protease," Bioorganic & Medicinal Chemistry Letters, 8:1713-1718.
Llinas-Brunet, M. et al. (2004) "A Systematic Approach to the Optimization of Substrate-Based Inhibitors of the Hepatitis C Virus NS3 Protease: Discovery of Potent and Specific Tripeptide Inhibitors," Journal of Medicinal Chemistry, 47:6584-6594.
March, (1986)"Advanced Organic Chemistry," Third edition, p. 312.
Matsumoto, Y. et al. (1996) "3D Modeling of HCV Protease and Computer Screening of Its Inhibitors," Antiviral Research, Oreal Session III—Hepadnavirus, Papillomavirus, Other Infections. Abstract 19, p. A23.
Muller, et al.(2009), "Prodrug approaches for enhancing the bioavailability of drugs with low solubility." Chem Biodivers. 6(11):2071-83.
Nizi et al., (2002), "Capped dipeptide alpha-ketoacid inhibitors of the HCV NS3 protease." Bioorg. Med. Chem. Lett., 12(22):3325-8, (Abstract).
Office Actions and Responses in U.S. Appl. No. 12/215,605.
Office Communications in U.S. Appl. No. 13/436,679.
Office Communications in U.S. Appl. No. 13/598,430.
Pause, et al. (2003), "An NS3 Serine Protease Inhibitor Abrogates Replication of Subgenomic Hepatitis C Virus RNA." J. Biol. Chem., 278(22):20374-20380.
Poupart, M. et al. (2001) "Solid-Phase Synthesis of Peptidomimetic Inhibitors for the Hepatitis C Virus NS3 Protease," The Journal of Organic Chemistry, 66 (14):4743-4751.
Poynard, T. et al. (1998), "Randomised Trial of Interferon ☐2b Plus Ribarvirin for 48 Weeks or for 24 Weeks Versus Interferon ☐2b Plus Placebo for 48 Weeks for Treatment of Chronic Infection with Hepatitis C Virus," The Lancet, 352:1426-1432.
Singh, et al. (2008), "Recent trends in targeted anticancer prodrug and conjugate design." Curr Med Chem.,15(18):1802-26.
Spatola, A. (1983) "Peptide Backbone Modifications: A Structure-Activity Analysis of Peptides Containing Amide Bond Surrogates, Conformational Constraints and Rela," Chemistry and Biochemistry of Amino Acids, Peptides, and Proteins. A Survey of Recent Developments. 7:267-357. Marcell Dekker, Inc. New York, NY.
Steinkuhler, C. et al. (1998) "Product Inhibition of the Hepatitis C Virus NS3 Protease," Biochemistry 37:8899-8905.
Testa. (2004), "Prodrug research: futile or fertile?" Biochem Pharmacol. Dec. 1, 2004;68(11):2097-106.
Tsantrizos, Y. et al. (2003) "Macrocyclic Inhibitors of the NS3 Protease as Potential Therapeutic Agents of Hepatitis C Virus Infection," Angewandte Chemie Int. Ed., 42 (12):1356-1360.
Zeuzem, S. et al. (2000) "Peginterferon Alfa-2a in Patients with Chronic Hepatitis C," The New England Journal of Medicine. 343(23):1666-1672.

* cited by examiner

ANTIVIRAL COMPOUNDS

PRIORITY OF INVENTION

This application is a continuation of U.S. patent application Ser. No. 13/598,430, filed 29 Aug. 2012, now U.S. Pat. No. 8,420,597, which is a continuation of U.S. patent application Ser. No. 13/436,679, filed 30 Mar. 2012, now U.S. Pat. No. 8,283,442, which is a continuation of U.S. patent application Ser. No. 12/215,605, filed 26 Jun. 2008, now U.S. Pat. No. 8,178,491, which claims priority under 35 U.S.C. §119 (e) to U.S. Provisional Patent Application No. 60/937,752, filed 29 Jun. 2007; U.S. Provisional Patent Application No. 60/959,771, filed on 16 Jul. 2007; and to U.S. Provisional Patent Application No. 61/037,988, filed on 19 Mar. 2008. The entire content of each of these provisional patent applications is hereby incorporated herein by reference.

FIELD OF THE INVENTION

The invention relates generally to compounds with HCV inhibitory activity.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of HCV are useful to limit the establishment and progression of infection by HCV as well as in diagnostic assays for HCV.

There is a need for new HCV therapeutic agents.

SUMMARY OF THE INVENTION

In one embodiment the invention provides a compound of the invention which is a compound of formula I:

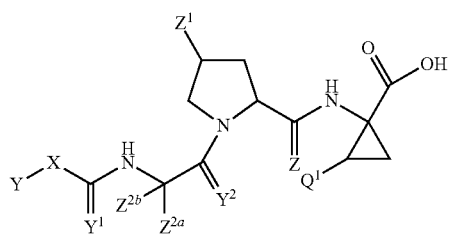

or a pharmaceutically acceptable salt, or prodrug thereof, wherein:

$Y^1$ is O, S, or $NR^3$;
$Y^2$ is O, S, or $NR^3$;
Z is O, S, or $NR^3$;

$Z^1$ is selected from the following structures:

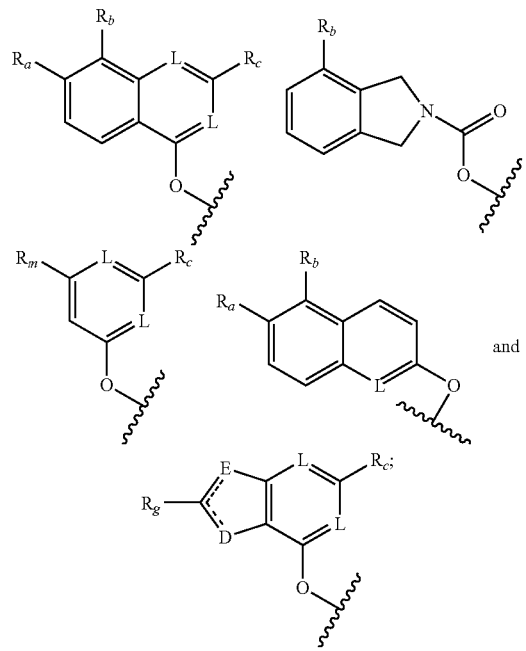

each $R_a$ is $R^1$, H, trifluoromethoxy, $NR_sR_t$, $C(=O)NR_sR_t$, $S(=O)_2NR_sR_t$ or (C1-10)alkyl, wherein one or more carbon atoms of said (C1-10)alkyl is optionally replaced by O, S, S(=O), $S(=O)_2$ or $NR_g$ and which (C1-10)alkyl is optionally substituted with one or more hydroxy, halo, cyano, $NR_nR_p$, $C(=O)NR_nR_p$, (C1-10)alkoxy, carboxy, (C1-10)alkoxycarbonyl, aryl, heteroaryl, or heterocyclyl and which heterocyclyl is optionally substituted with one or more $A^3$; or $R_a$ and $R_b$ taken together with the atoms to which they are attached form a 5 or 6 membered heterocyclic ring containing one or more O, S, or $NR_g$;

each $R_b$ is $R^1$, H, F, Cl, Br, I, $CF_3$, (C1-10)alkyl, or $XR^3$;
each $R_c$ is $R^1$, H, cyano, F, Cl, Br, I, $-C(=O)NR_dR_e$, $C(=O)NR_sR_t$, $NR_sR_t$, $S(=O)-_2NR_sR_t$, (C1-10)alkyl, (C2-10)alkenyl, (C2-10)alkynyl, (C1-10)alkoxy, cycloalkyl, $OR_r$, $SR_r$, $S(O)R_r$, $S(O)_2R_r$, aryl, or heteroaryl, which (C1-10)alkyl, (C1-10)alkoxy, cycloalkyl, aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

$R_d$ and $R_e$ are each independently H or (C1-10)alkyl;
each $R_f$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_g$ is H, $NR_sR_t$, $C(=O)NR_sR_t$, $S(=O)_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_h$ is H, $A^3$, $C(=O)NR_sR_t$, or $S(=O)_2NR_sR_t$;
each $R_m$, is H, cyano, F, Cl, Br, I, $-C(=O)NR_dR_e$, (C1-10)alkoxy, cycloalkyl, or phenyl that is optionally substituted with one or more F, Cl, Br, I, (C1-10)alkyl, or (C1-10)alkoxy;
each L is independently CH or N;
one of E or D is O, S, or $NR_f$ and the other E or D is $CR_h$ or N;

$Z^{2a}$ is H, (C1-10)alkyl, (C2-10)alkenyl, (C2-10)alkynyl, haloalkyl, (C1-10)alkyl, —S(=O)$_2$—(C1-10)alkyl, or cycloalkyl, wherein any carbon atom of $Z^{2a}$ may optionally be replaced with a heteroatom selected from O, S or NR$_g$ and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with $Q^1$;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^1$ or $R_c$; or $Q^1$ and $Z^{2a}$ taken together with the atoms to which they are attached form a heterocycle, which heterocycle may optionally be substituted with one or more oxo (=O), $R^1$, or $A^3$;

each X is independently a bond, O, S, or NR$^3$;

Y is a polycarbocycle or a polyheterocycle, which polycarbocycle or a polyheterocycle is optionally substituted with one or more $R^1$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$; SR$_r$, S(O)R$_r$, or S(O)$_2$R$_r$;

each $R^1$ is independently —P(Y$^3$)(OA$^2$)(OA$^2$), —P(Y$^3$)(OA$^2$)(N(A$^2$)$_2$), —P(Y$^3$)(A$^2$)(OA$^2$), —P(Y$^3$)(A$^2$)(N(A$^2$)$_2$), or P(Y$^3$)(N(A$^2$)$_2$)(N(A$^2$)$_2$);

each A$^2$ is independently H, (C1-10)alkyl, (C2-10)alkenyl, (C2-10)alkynyl, (C1-10)haloalkyl, (C3-10)cycloalkyl, aryl, or heteroaryl;

each Y$^3$ is independently O, S, or NR$^3$;

each R$_n$ and R$_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more R$^1$, halo, hydroxy, carboxy, cyano, or (C1-10)alkoxy; or R$_n$ and R$_p$ together with the nitrogen to which they are attached form a pyrrolidine, piperidine, piperazine, morpholino, or thiomorpholino ring; which ring is optionally substituted with one or more (C1-10)alkyl or (C1-10)alkoxy, and which (C1-10)alkyl or (C1-10)alkoxy is optionally substituted with one or more halo;

each R$_r$ is independently H, (C1-10)alkyl, cycloalkyl, (C2-10)alkenyl, (C2-10)alkynyl, (C1-10)alkanoyl, aryl, heteroaryl, or (C1-10)alkoxycarbonyl;

each R$_s$ and R$_t$ is independently H, (C1-10)alkyl, cycloalkyl, (C2-10)alkenyl, (C2-10)alkynyl, (C1-10)alkanoyl, S(=O)$_2$A$^2$, (C1-10)alkoxy, (C1-10)alkanoyloxy, or (C1-10)alkoxycarbonyl, which (C1-10)alkyl, cycloalkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more R$^1$, halo hydroxy, carboxy, cyano, or (C1-10)alkoxy; or R$_s$ and R$_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);

each A$^3$ is independently selected from halo, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$, SR$_r$, S(O)R$_r$, or S(O)$_2$R$_r$; and R$^3$ is H or (C1-10)alkyl.

The present invention also provides a pharmaceutical composition comprising a compound of formula I, or a pharmaceutically acceptable salt or prodrug thereof, and at least one pharmaceutically acceptable carrier.

The present invention also provides for a method of treating disorders associated with hepatitis C, said method comprising administering to an individual a pharmaceutical composition which comprises a therapeutically effective amount of a compound of formula I, or a pharmaceutically acceptable salt or prodrug thereof.

The present invention also provides a method of inhibiting HCV, comprising administering to a mammal afflicted with a condition associated with HCV activity, an amount of a compound of formula I, or a pharmaceutically acceptable salt or prodrug thereof, effective to inhibit HCV.

The present invention also provides a compound of formula I, or a pharmaceutically acceptable salt or prodrug thereof, for use in medical therapy (preferably for use in inhibiting HCV or treating a condition associated with HCV activity), as well as the use of a compound of formula I, or a pharmaceutically acceptable salt or prodrug thereof, for the manufacture of a medicament useful for inhibiting HCV or the treatment of a condition associated with HCV activity in a mammal.

The present invention also provides a compound of formula I, or a pharmaceutically acceptable salt, or prodrug thereof for use in the prophylactic or therapeutic treatment of a condition associated with HCV activity.

The present invention also provides synthetic processes and novel intermediates disclosed herein which are useful for preparing compounds of the invention. Some of the compounds of the invention are useful to prepare other compounds of the invention.

In another aspect the invention provides a method of inhibiting HCV activity in a sample comprising treating the sample with a compound of formula I, or a pharmaceutically acceptable salt or prodrug thereof.

In one embodiment the invention provides a compound having improved inhibitory or pharmacokinetic properties, including enhanced activity against development of viral resistance, improved oral bioavailability, greater potency or extended effective half-life in vivo. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "R$^1$", "L", or "A$^3$", then it will be understood that the groups may be the same or different, i.e., each group is independently selected.

"Alkyl" is a hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), cyclopropyl, 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$CH$_2$ CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, and cyclopropylmethyl

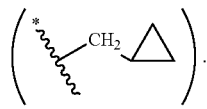

"Alkenyl" is a hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is a hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH).

"Alkylene" refers to a saturated, branched or straight chain or cyclic hydrocarbon radical having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Halo" includes F, Cl, Br, and I.

"Heteroaryl" as used herein includes 5-20 atom mono- or polycyclic ring systems wherein at least one ring is an aromatic ring comprising one or more heteroatoms (e.g. O, S, N, etc.). In one embodiment the term heteroaryl includes a radical of a monocyclic aromatic ring containing five or six ring atoms consisting of carbon and one to four heteroatoms each selected from the group consisting of non-peroxide oxygen, sulfur, and N(X) wherein X is absent or is H, O, (C$_1$-C$_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The term heterocycle also includes heteroaryl ring systems as defined herein. When Q$^1$ and Z$^{2a}$ taken together with the atoms to which they are attached form a heterocycle, the heterocycle formed by Q$^1$ and Z$^{2a}$ taken together with the atoms to which they are attached may typically comprise up to about 25 atoms.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

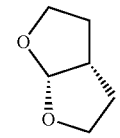

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl (spiro-fused rings) and naphthyl.

The term "polycarbocycle" refers to a saturated or unsaturated polycyclic ring system having from about 6 to about 25 carbon atoms and having two or more rings (e.g. 2, 3, 4, or 5 rings). The rings can be fused and/or bridged to foam the polycyclic ring system. For example, the term includes bicyclo [4,5], [5,5], [5,6] or [6,6] ring systems, as well as the following bridged ring systems:

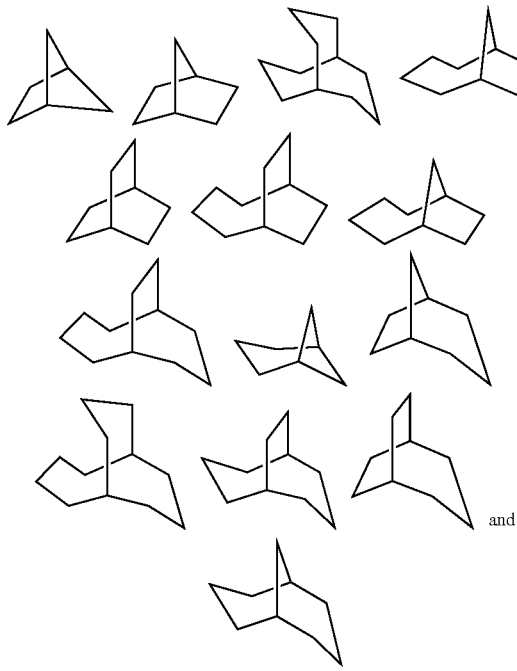

and (i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" refers to a polycarbocycle as defined herein, wherein one or more carbon atoms is replaced with a heteroatom (e.g. O, S, S(O), S(O)$_2$, N$^+$(O$^-$)R$_x$, or NR$_x$); wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR— S(=O)$_2$—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O$^-$), —C(=O)R, —C(=O)X, —C(S)R, —C(O)OR, —C(O)O$^-$, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "optionally substituted" in reference to a particular moiety of the compound of formula I, (e.g., an optionally substituted aryl group) refers to a moiety having 0, 1, 2, or more substituents.

The term " "-----" " means that a bond is a single or double bond. In a non-limiting example,

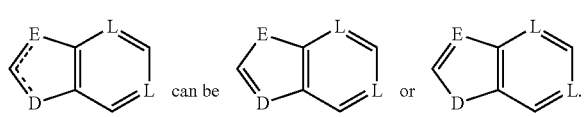

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Prodrugs

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, either systemically or inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphates. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^9$ and acyloxymethyl carbonates —$CH_2C(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.,* 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Cellular Accumulation

In one embodiment, the invention provides compounds capable of accumulating in human hepatic cells. Physiologically, hepatic cells are critical components of the mechanism against infection. Hepatic cells may be isolated from normal healthy donors washed (e.g. phosphate-buffered saline) and stored in freezing medium. Hepatic cells may be cultured in multi-well plates. At various times of culture, supernatant may be either removed for assessment, or cells may be harvested and analyzed (Smith R. et. al. (2003) *Blood* 102(7): 2532-2540). The compounds of this embodiment may further comprise a phosphonate or phosphonate prodrug. More typically, the phosphonate or phosphonate prodrug can have the structure $R^1$ as described herein.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels. Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semi-quantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV it should be kept in mind that the results of enzyme assays may not always correlate with cell culture assays. Thus, a cell based assay should typically be the primary screening tool.

Screens for HCV Inhibitors

Compounds of the invention are screened for inhibitory activity against HCV by any of the conventional techniques for evaluating enzyme activity. Within the context of the invention, typically compounds are first screened for inhibition of HCV in vitro and compounds showing inhibitory activity are then screened for activity in vivo. Compounds having in vitro Ki (inhibitory constants) of less then about $5 \times 10^{-6}$ M, typically less than about $1 \times 10^{-7}$ M and preferably less than about $5 \times 10^{-8}$ M are preferred for in vivo use. Useful in vitro screens have been described in detail.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention can also be used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Suitable active therapeutic agents or ingredients which can be combined with the compounds of formula I can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, levovirin VX-497, and viramidine (taribavirin); NS5a inhibitors, e.g., A-831 and A-689; NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereat and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+ actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) nonnucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV—inhibitory activity of their own.

Methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing). Other methods suitable for preparing compounds of the invention are described in International Patent Application Publication Number WO 2006/020276.

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113⊛3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Specific Embodiments of the Invention

Specific values and embodiments identified herein for radicals, substituents, and ranges, are for illustration only; they do not exclude other defined values or other values within defined ranges for the radicals and substituents.

In a specific embodiment of the invention $Z^1$ is selected from the following structures:

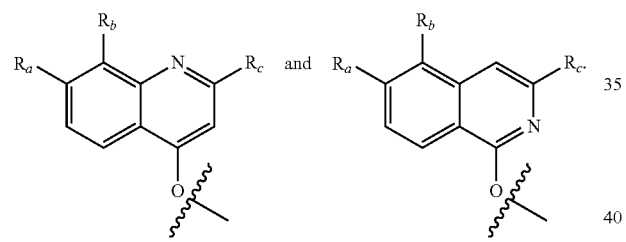

In a specific embodiment of the invention $R_c$ is a heteroaryl ring selected from:

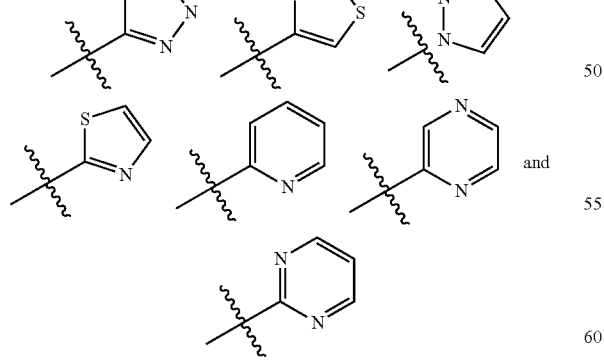

which heteroaryl ring is optionally substituted with one or more (C1-10)alkyl, halo, or $NR_nR_p$; wherein each $R_n$ and $R_p$ is independently H or (C1-10)alkyl.

In a specific embodiment of the invention $R_c$ is selected from:

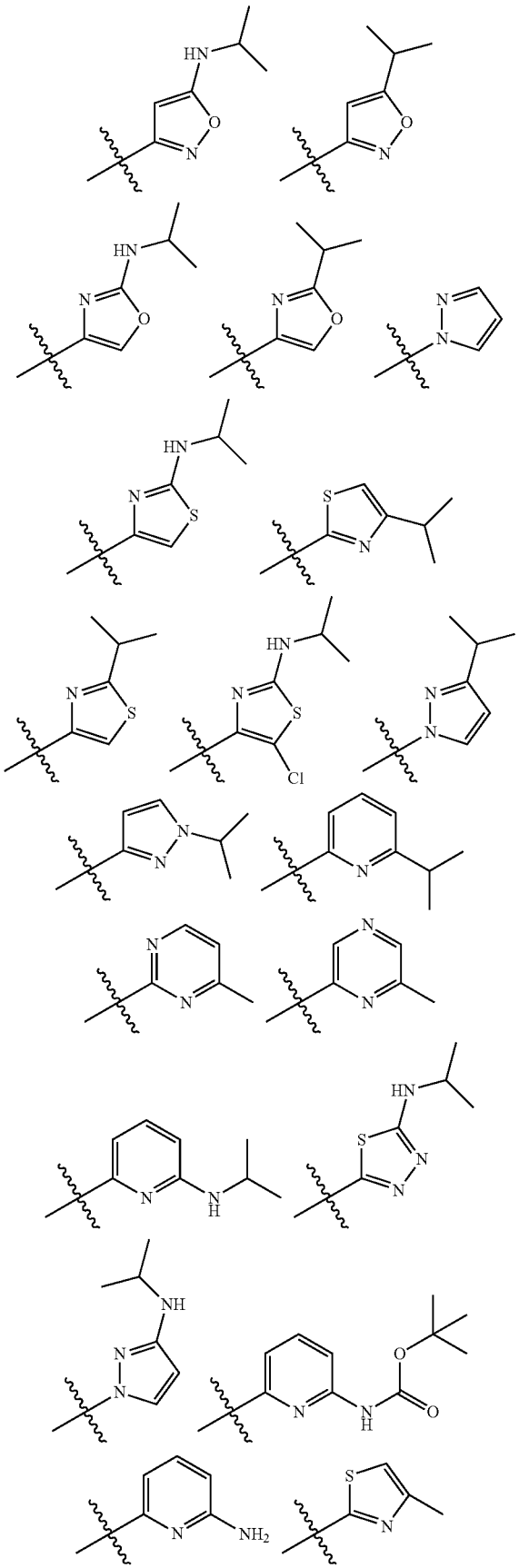

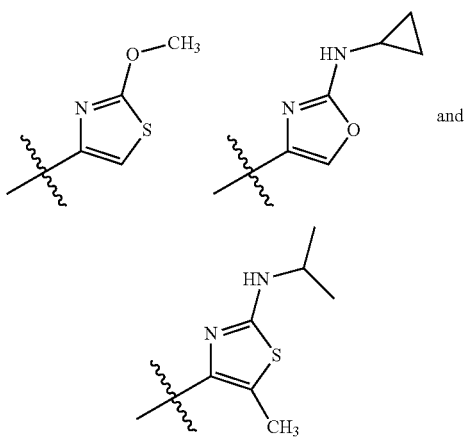

In a specific embodiment of the invention R$_c$ is selected from:

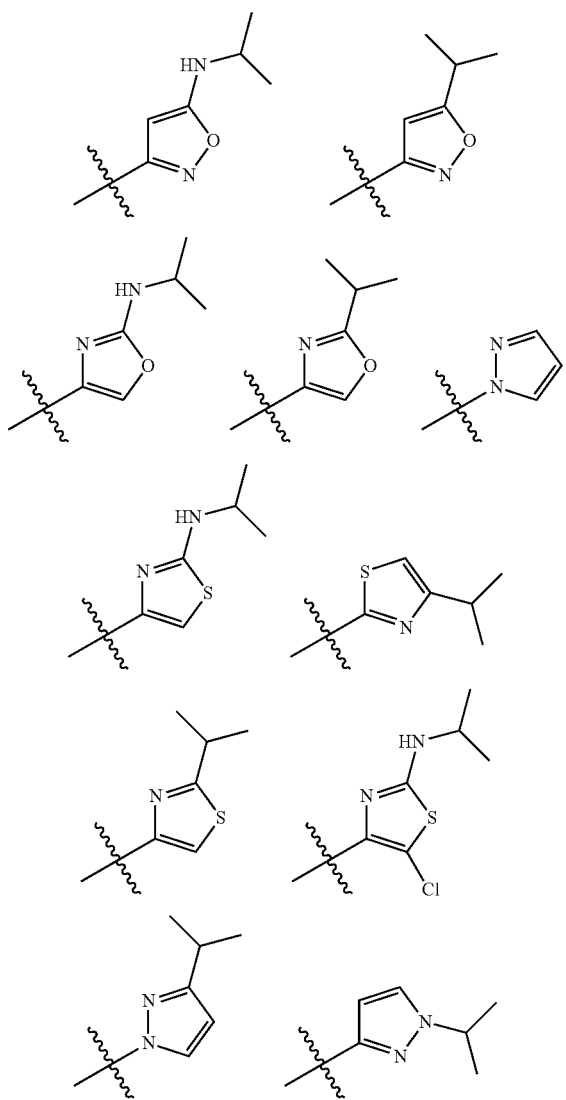

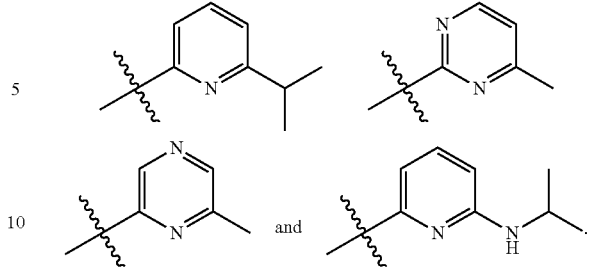

In a specific embodiment of the invention R$_c$ is selected from ethylthio, ethoxy, 2-methoxyethyl, cyclopropylamino, 2-methoxyethoxy, cyclopropyloxy, 1,3,4-triazol-2-ylthio, 1,3,4-thiadiazol-2-ylthio, 1,3,4-triazol-2-yloxy, 2-yloxy, or imidazol-2-yloxy.

In a specific embodiment of the invention R$_b$ is H or Cl.

In a specific embodiment of the invention R$_a$ is H, methoxy, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyanomethoxy, 2-piperazin-1-ylethoxy, 2-(N,N-dimentylamino)ethoxy, 2-(3,3-dimethylmorpholino)ethoxy, 2-(4-methylpiperazin-1-yl)ethoxy, or carboxymethoxy.

In a specific embodiment of the invention R$_a$ is H, methoxy, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, or 2-morpholinoethoxy.

In a specific embodiment of the invention Z$^1$ is selected from the following structures:

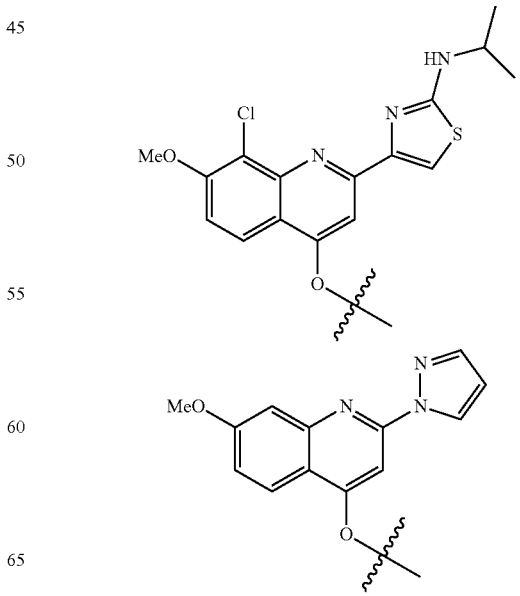

29
-continued
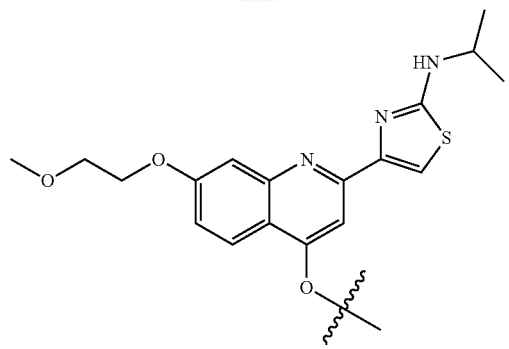
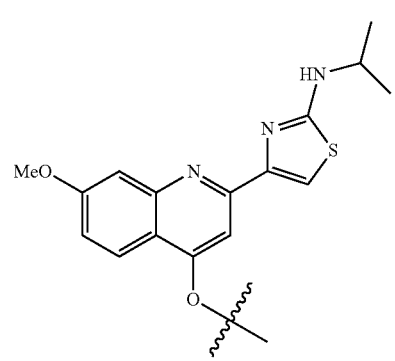
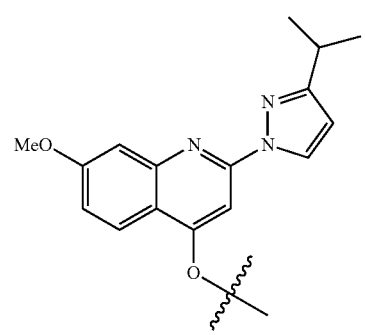
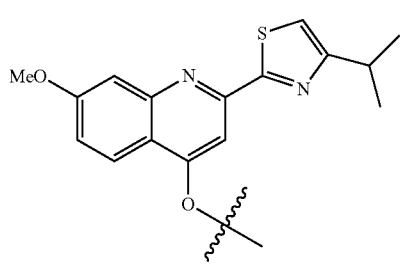
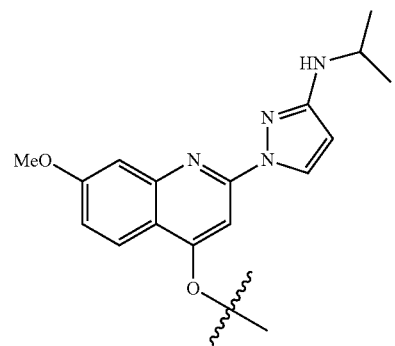
30
-continued
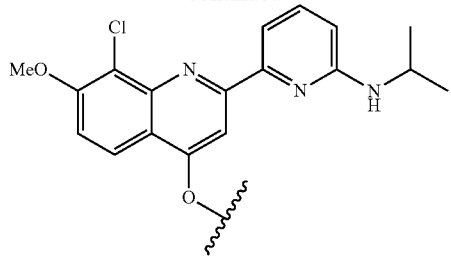
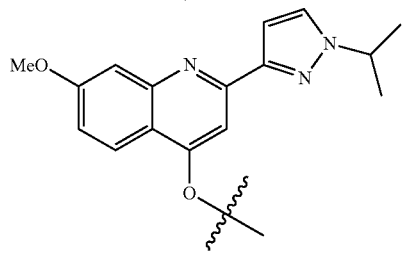
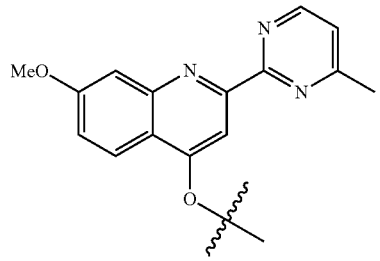
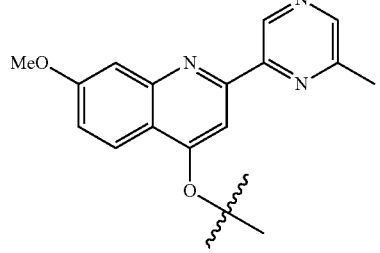
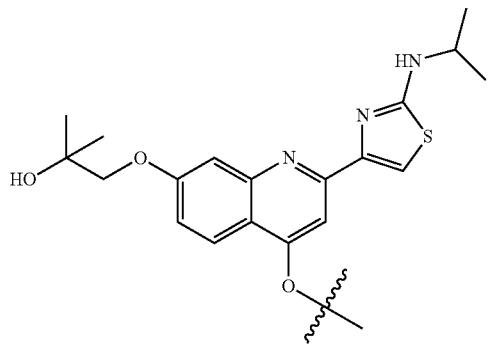
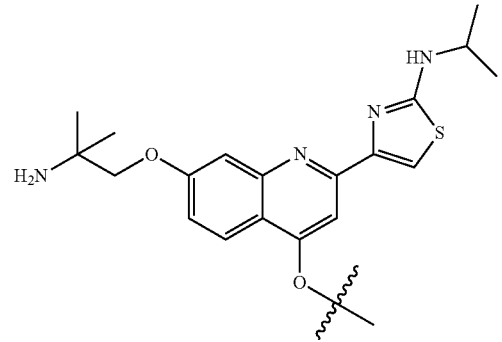

31
-continued
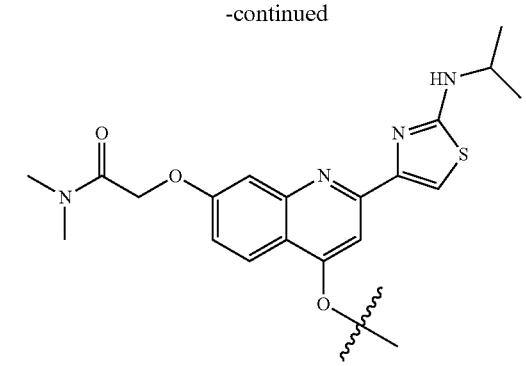
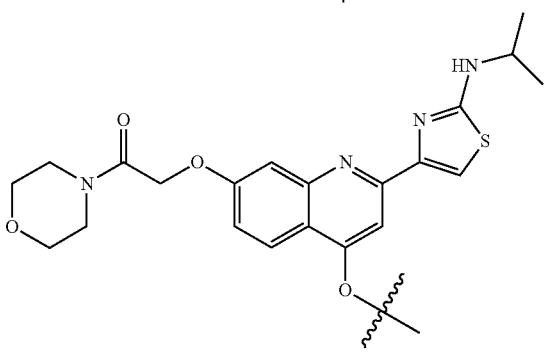
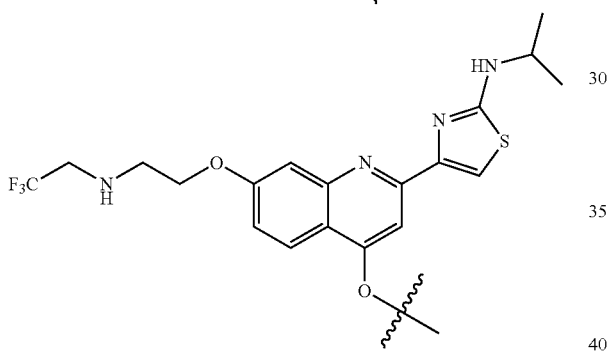
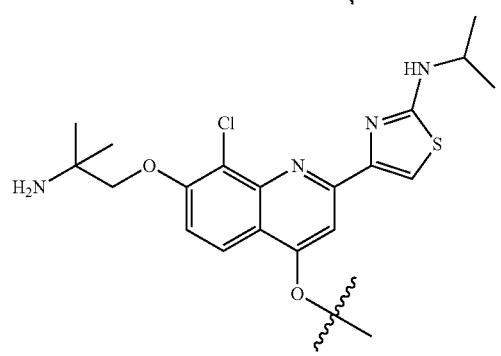
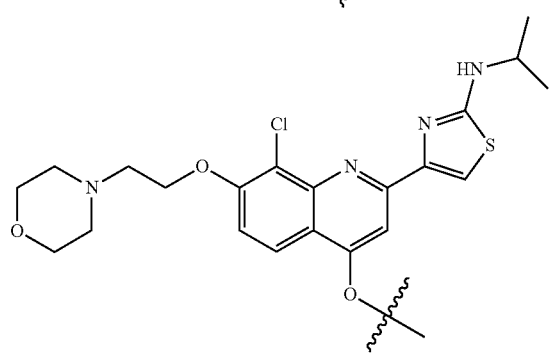
32
-continued
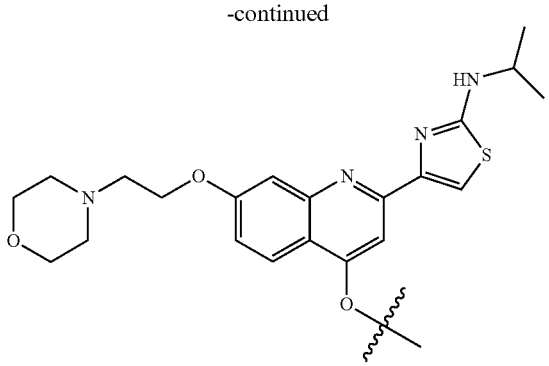
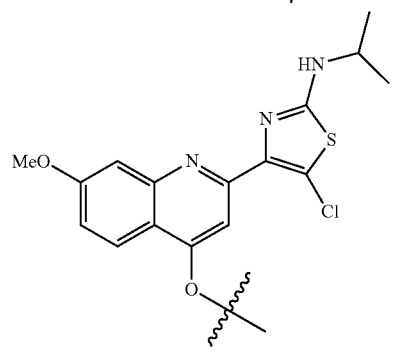
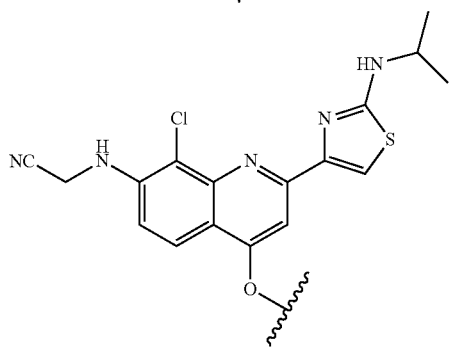
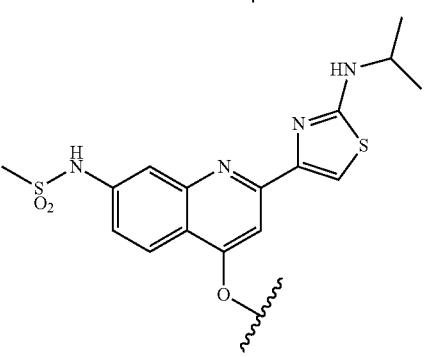
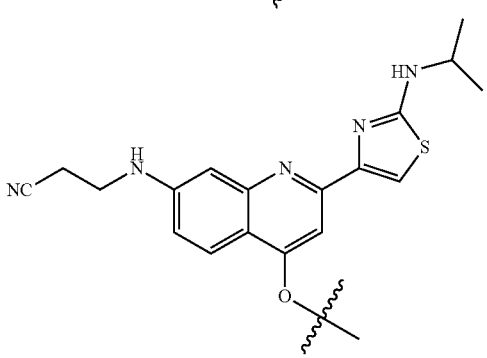

-continued

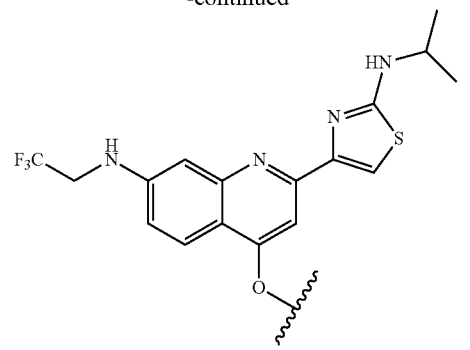

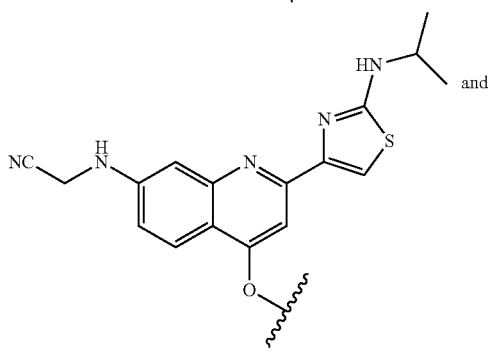

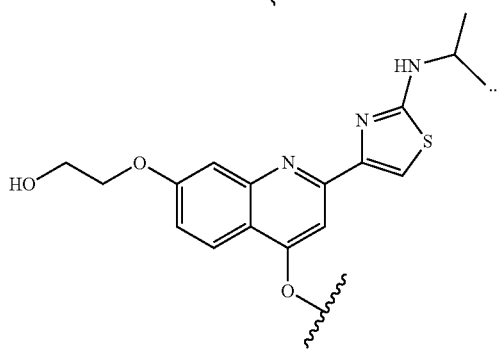

In a specific embodiment of the invention Z is O; $Y^1$ is O; and one of $Z^{2a}$ or $Z^{2b}$ is hydrogen.

In a specific embodiment of the invention $Q^1$ is vinyl or ethyl.

In a specific embodiment of the invention $Q^1$ and $Z^{2a}$ taken together with the atoms to which they are attached form a 12-18 membered heterocycle, which heterocycle may optionally be substituted with one or more oxo (=O) or $A^3$.

In a specific embodiment of the invention $Z^{2a}$ is tert-butyl.

In a specific embodiment of the invention X is a bond, O, S, or $NR^3$. In a preferred embodiment X is O, S, or $NR^3$. In another preferred embodiment X is O.

In a specific embodiment of the invention Y is a polycarbocycle.

In a specific embodiment of the invention Y is polyheterocycle.

In a specific embodiment of the invention Y is a fused carbocyclic ring system.

In a specific embodiment of the invention Y is a fused heterocyclic ring system.

In a specific embodiment of the invention Y is a fused carbocyclic ring system comprising one or more double bonds.

In a specific embodiment of the invention Y is a fused heterocyclic ring system comprising one or more double bonds.

In a specific embodiment of the invention Y is a bridged carbocyclic ring system.

In a specific embodiment of the invention Y is a bridged heterocyclic ring system.

In a specific embodiment of the invention Y is a bridged carbocyclic ring system comprising one or more double bonds.

In a specific embodiment of the invention Y is a bridged heterocyclic ring system comprising one or more double bonds.

In a specific embodiment of the invention Y comprises a bridged ring system selected from:

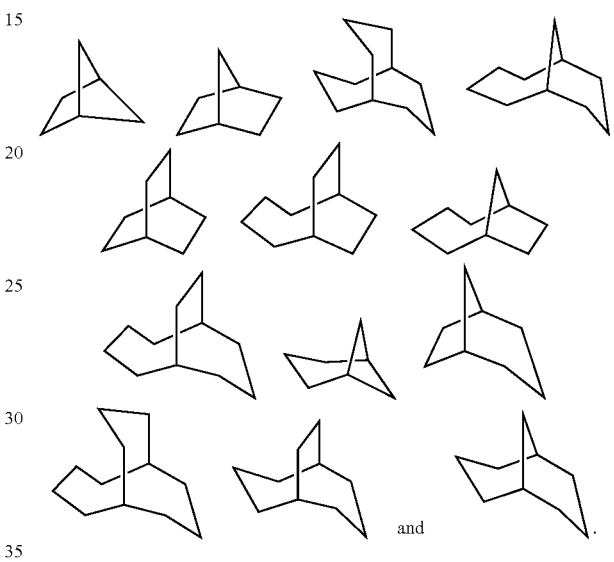

wherein one or more carbon atoms in the bridged ring system is optionally replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10) alkoxy is optionally substituted with one or more halo; R$_n$ and R$_p$ are as previously defined; and wherein the ring system optionally comprises one or more double bonds.

In a specific embodiment of the invention Y comprises a fused ring system selected from:

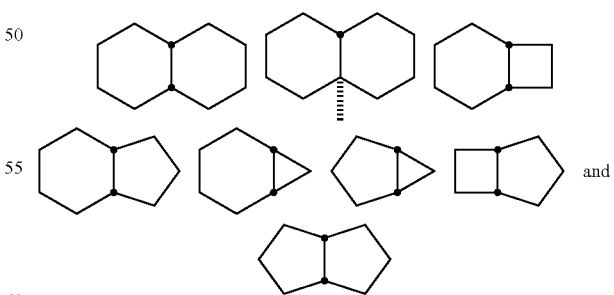

wherein one or more carbon atoms in the fused ring system is optionally replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)

alkoxy is optionally substituted with one or more halo; and wherein the ring system optionally comprises one or more double bonds.
In a specific embodiment of the invention Y is selected from:
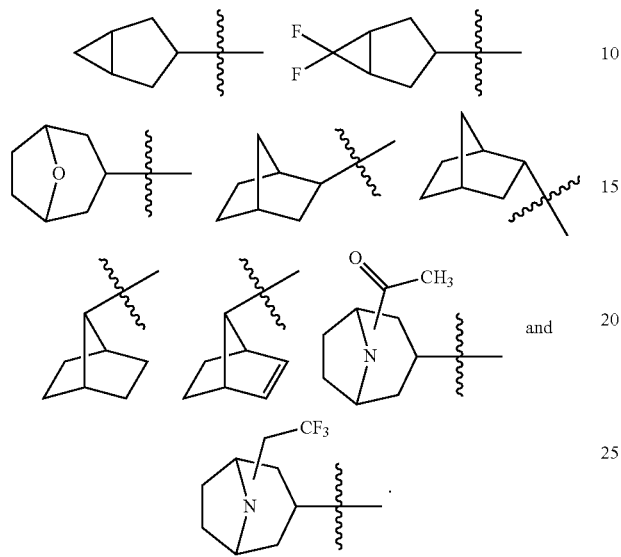
In a specific embodiment of the invention the compound of formula I is selected from:
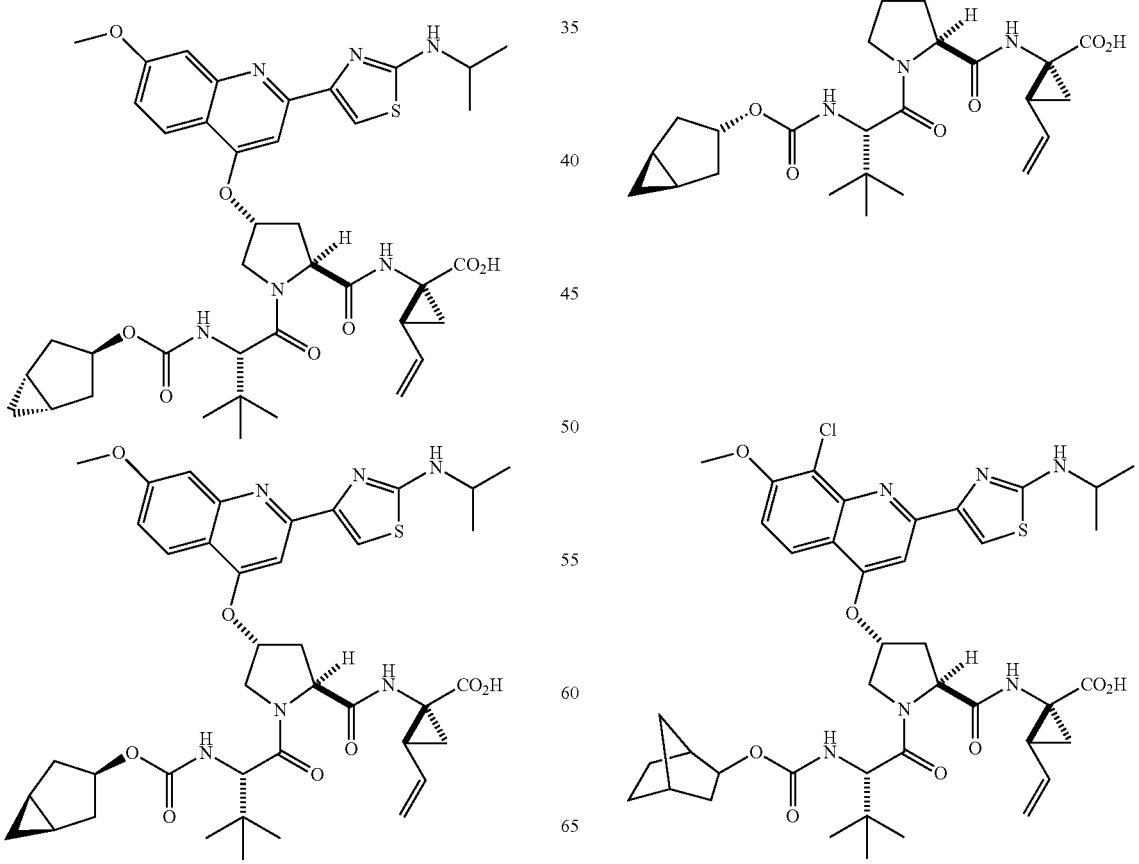

37
-continued
38
-continued
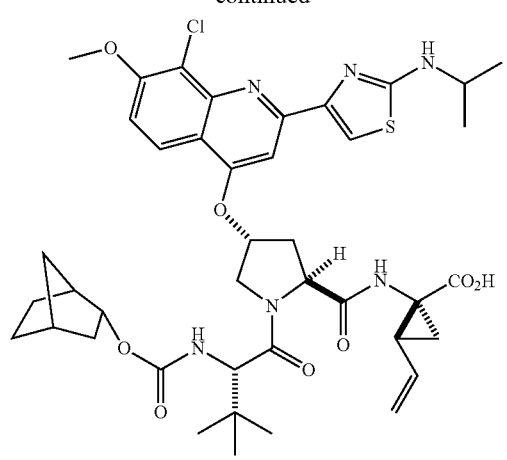
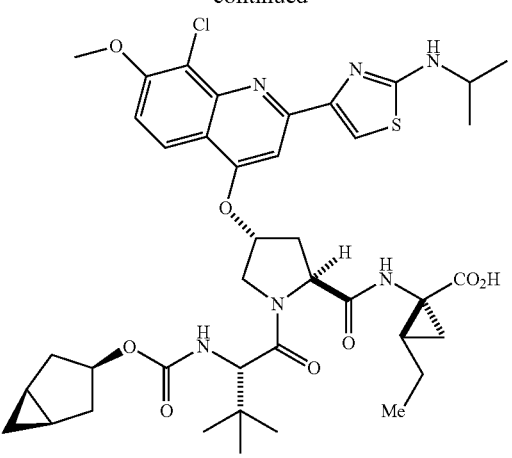
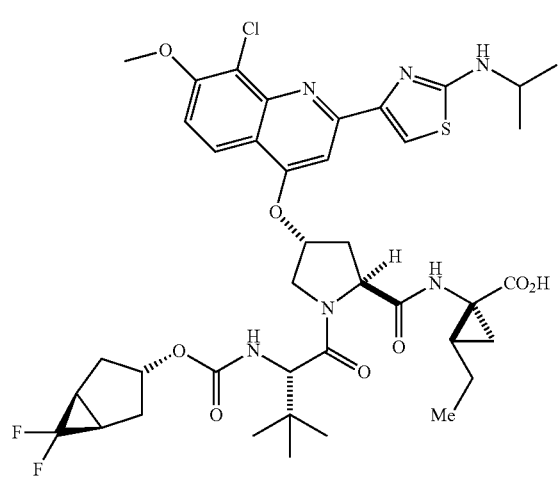
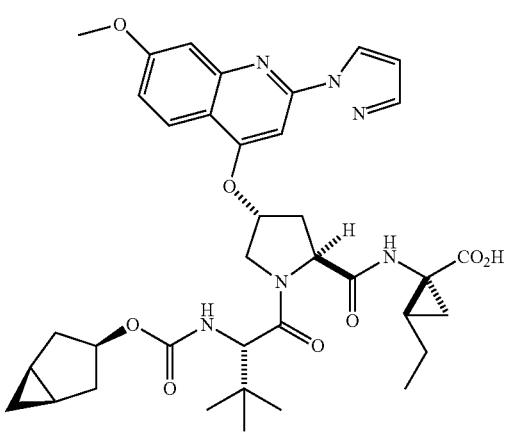
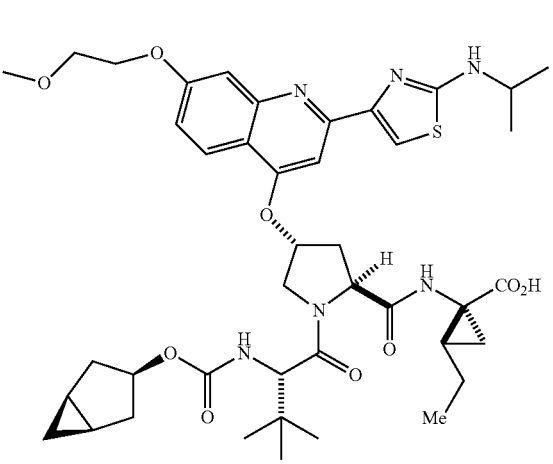

-continued
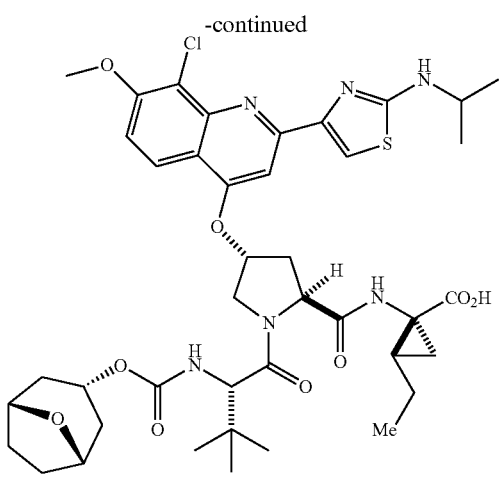
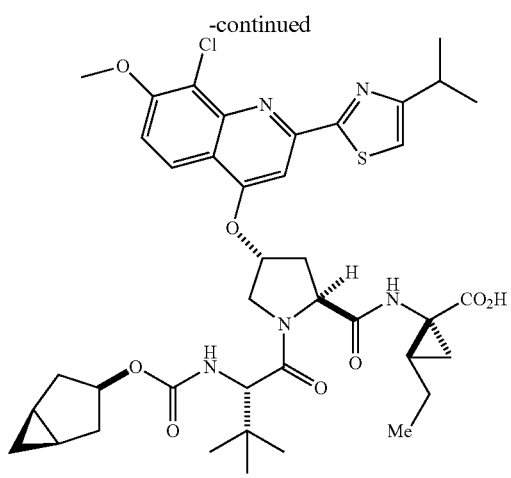
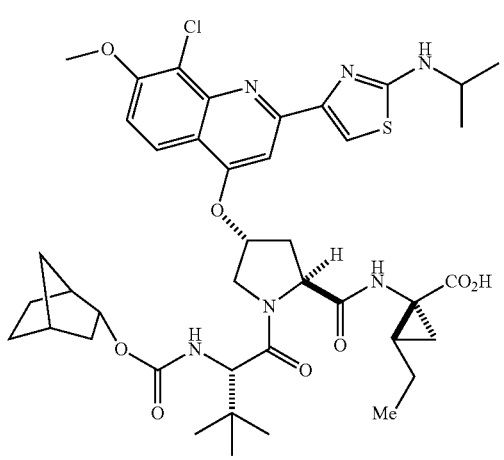
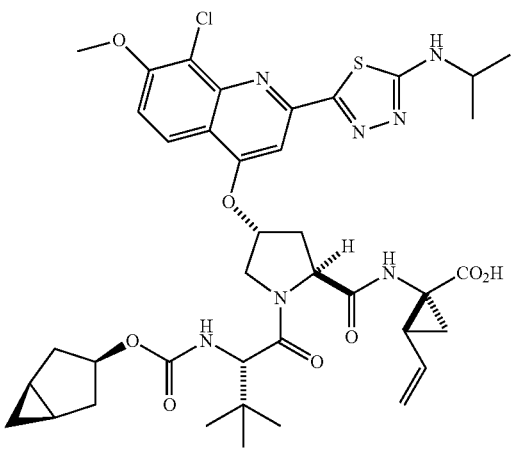
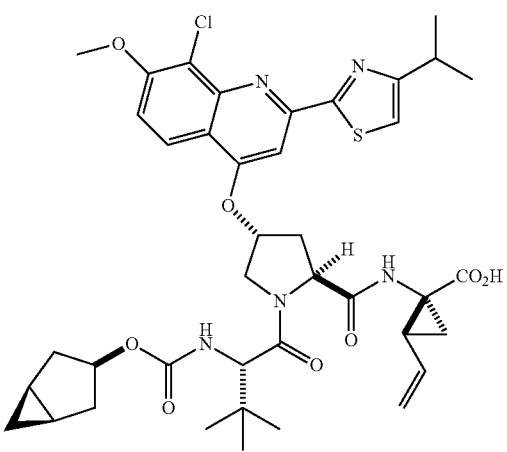
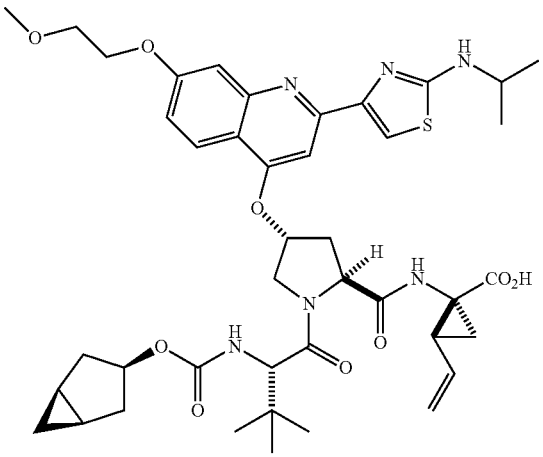

41
-continued
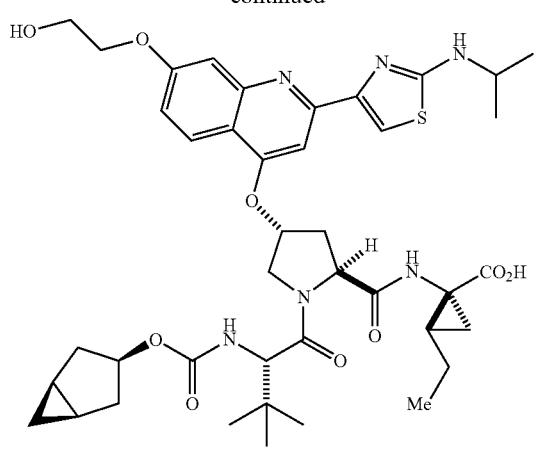
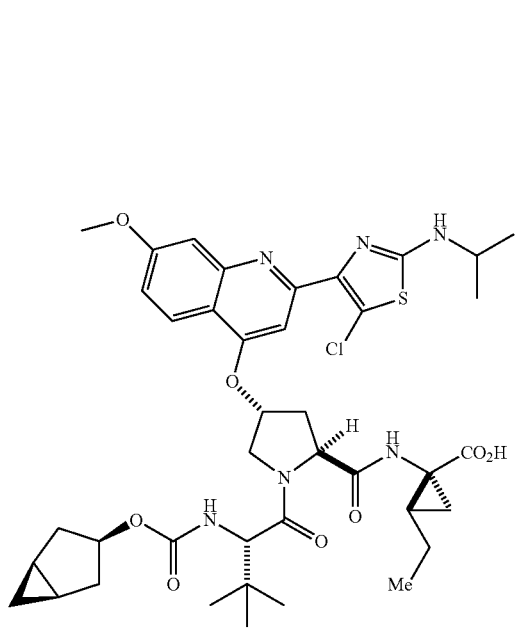
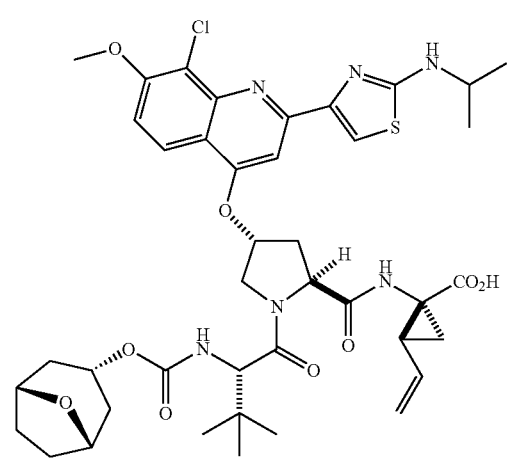
42
-continued
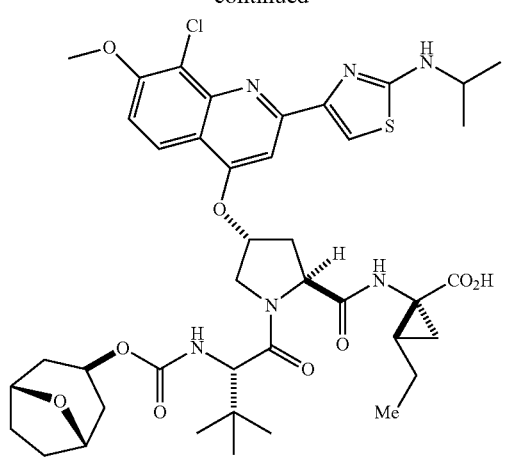
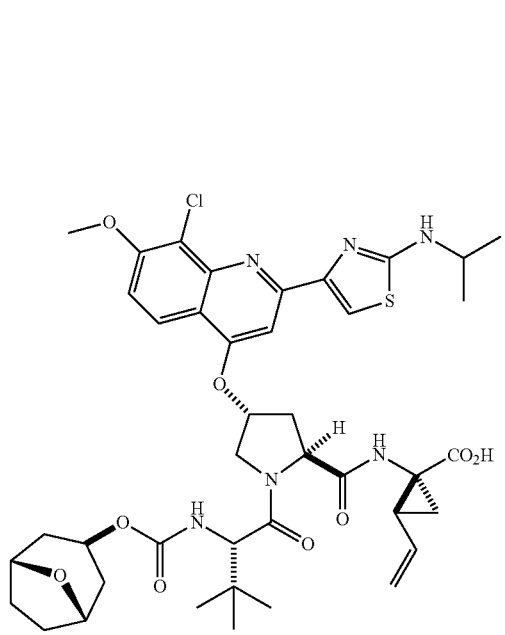
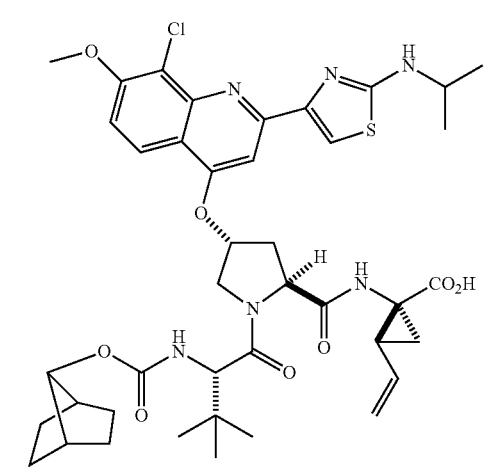

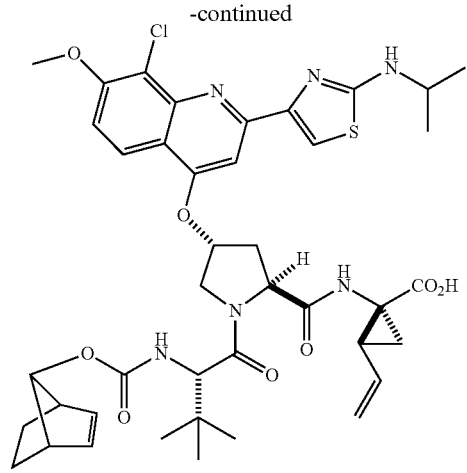
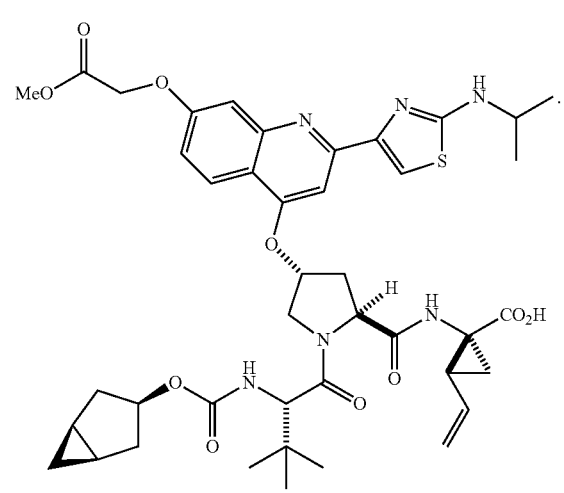
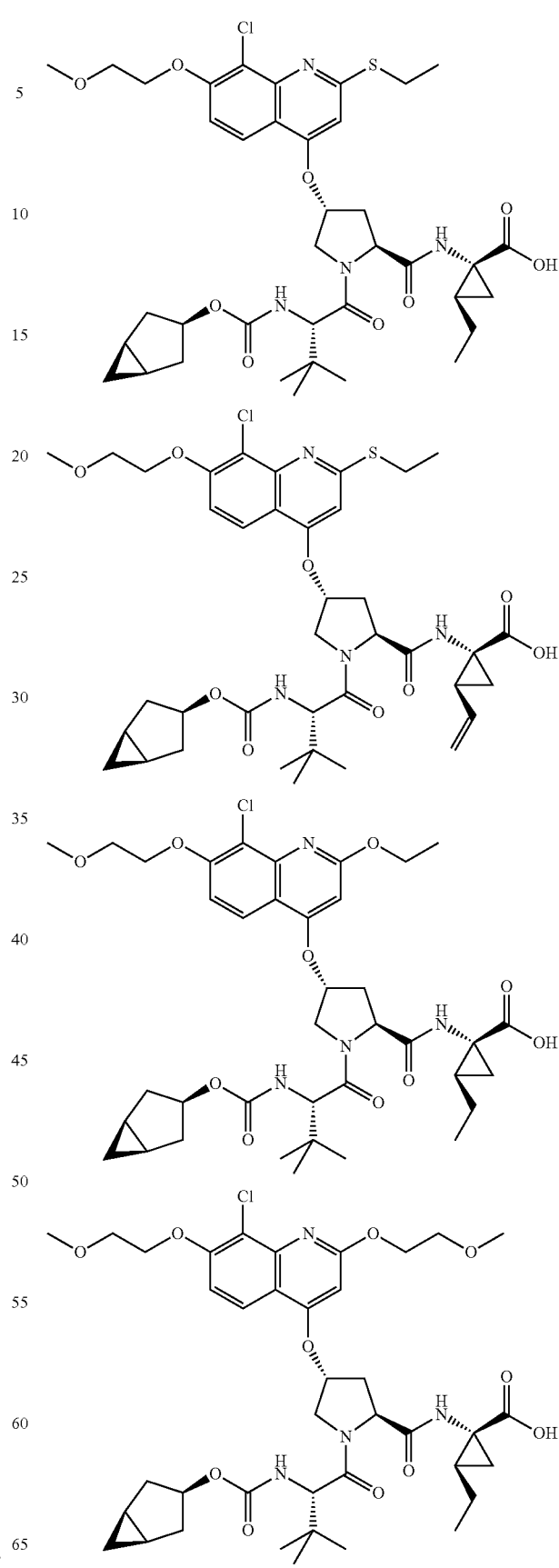
In a specific embodiment of the invention the compound of formula I is selected from:

45
-continued
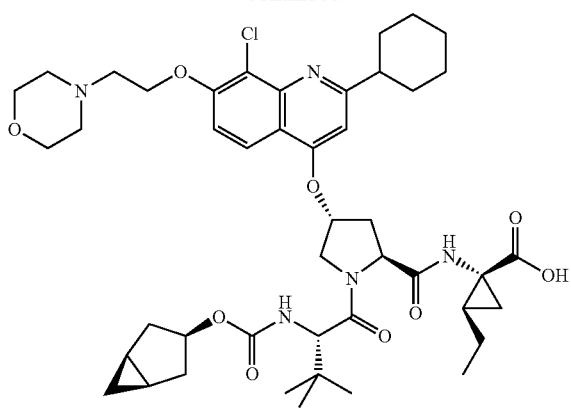
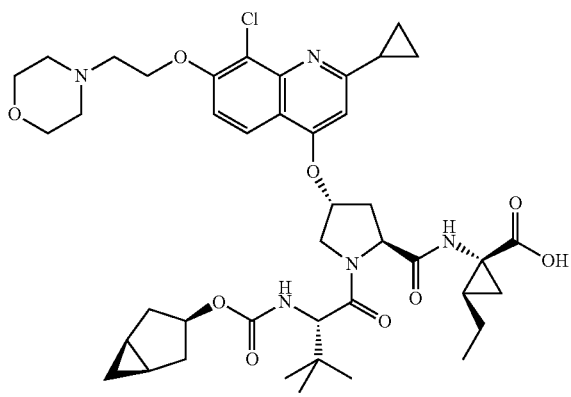
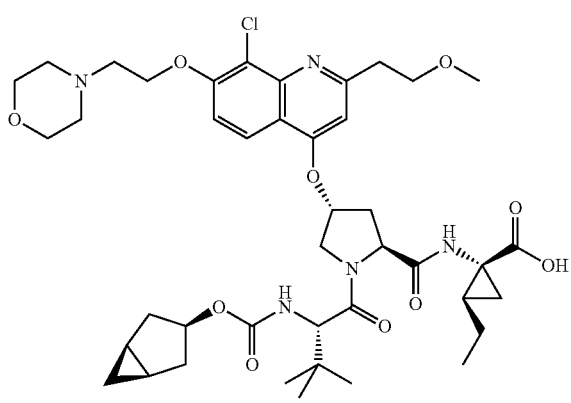
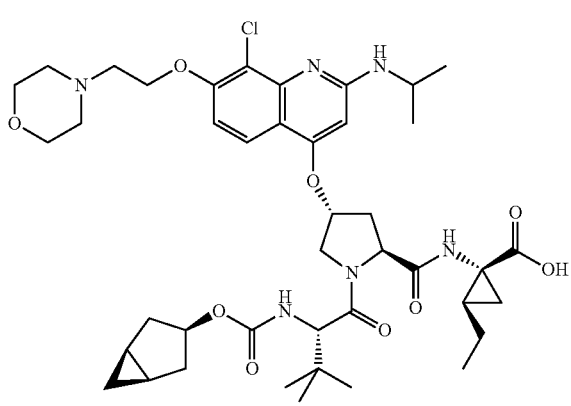
46
-continued
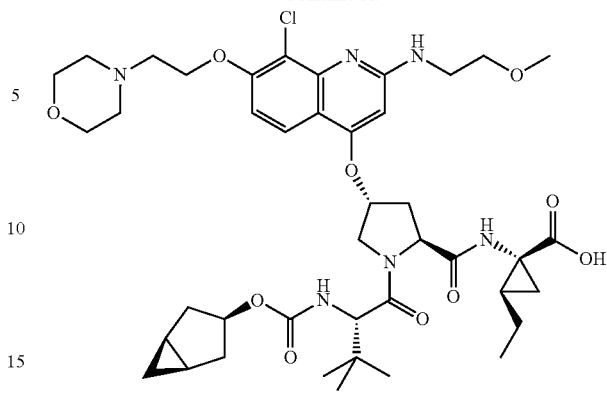
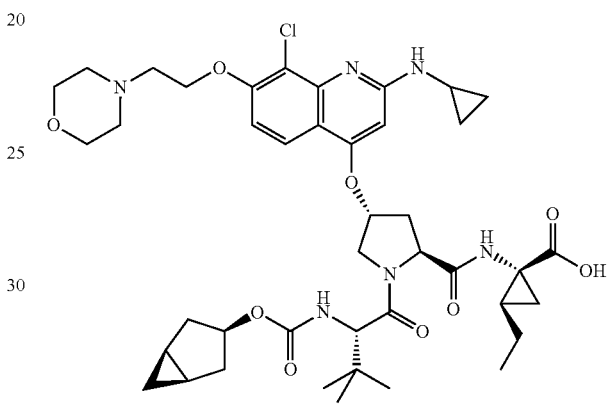
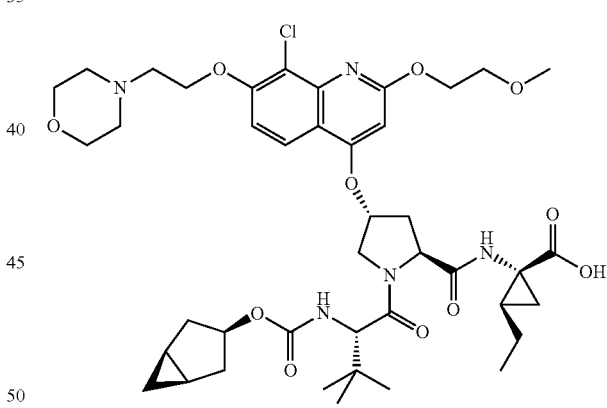
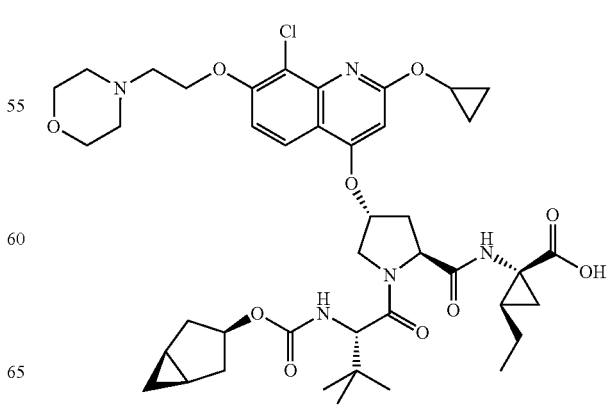

47
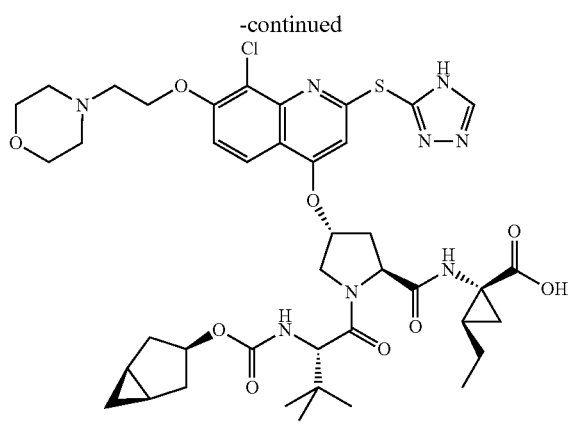
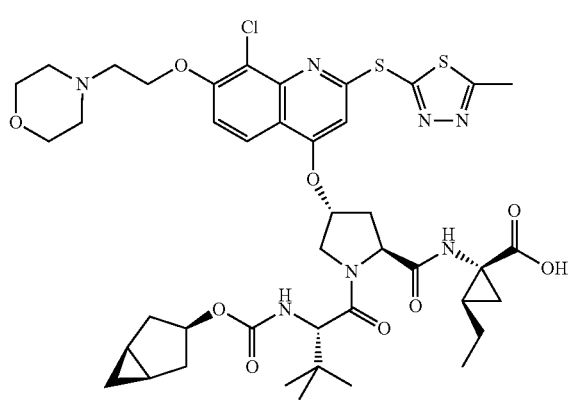
48
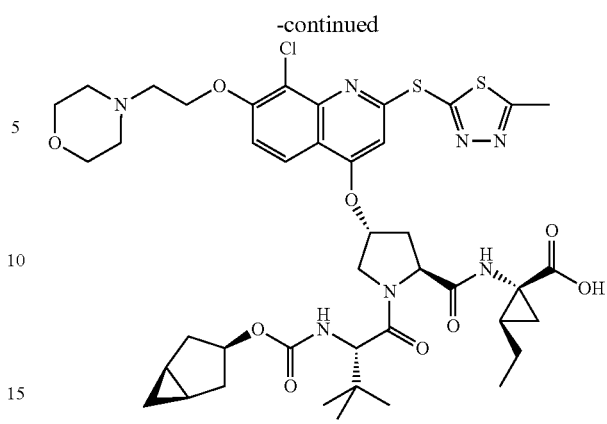
In a specific embodiment of the invention the compound of formula I is selected from:
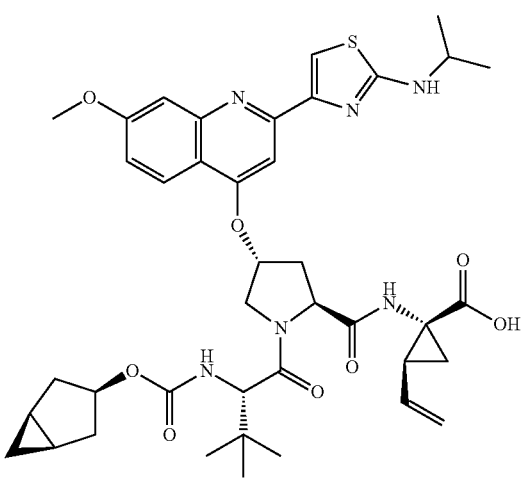

-continued
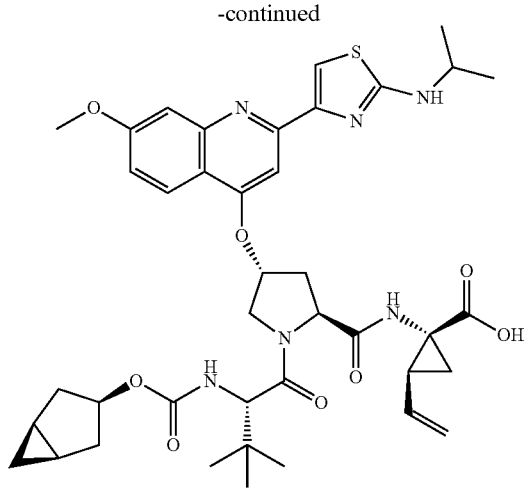
2
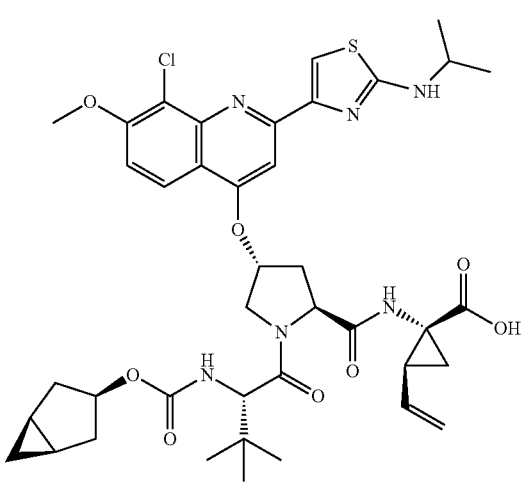
3
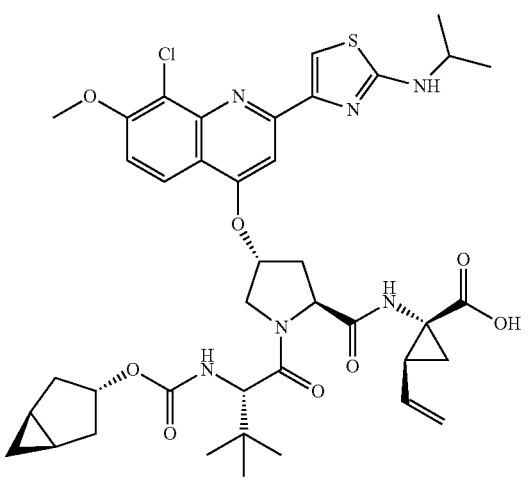
4
-continued
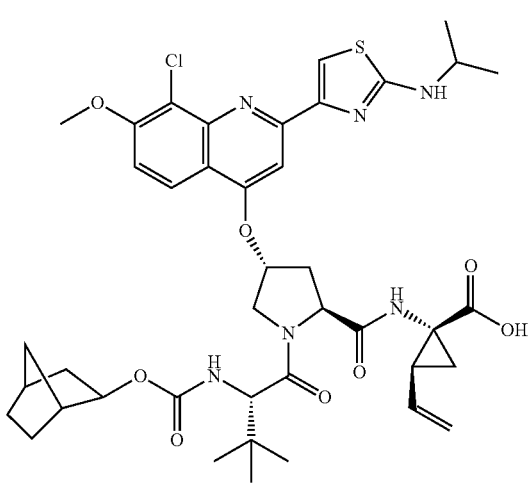
5
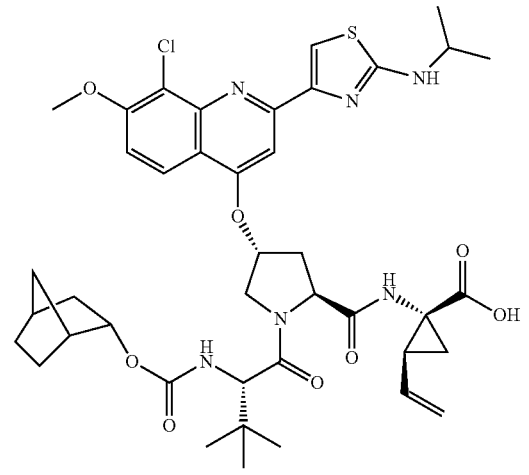
6
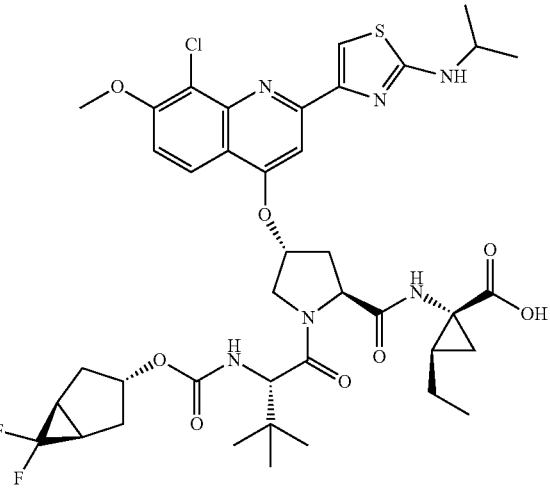
7

51
-continued
8
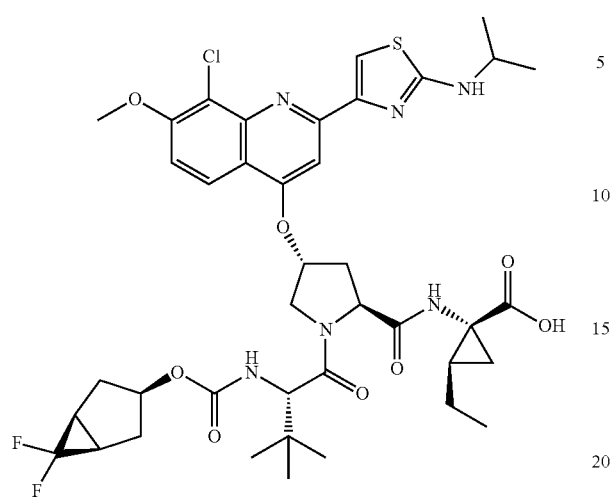
9
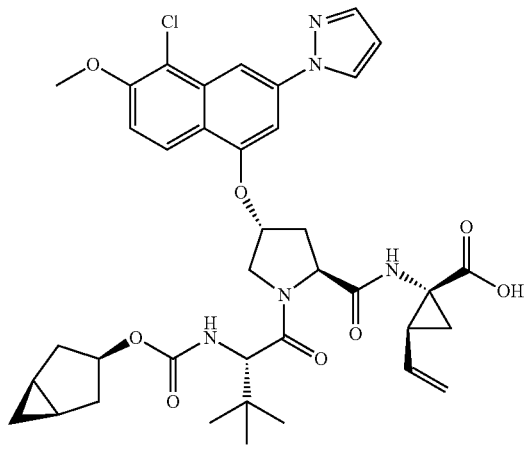
10
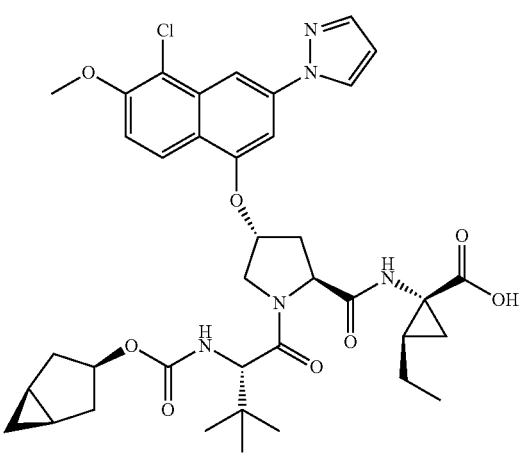
52
-continued
11
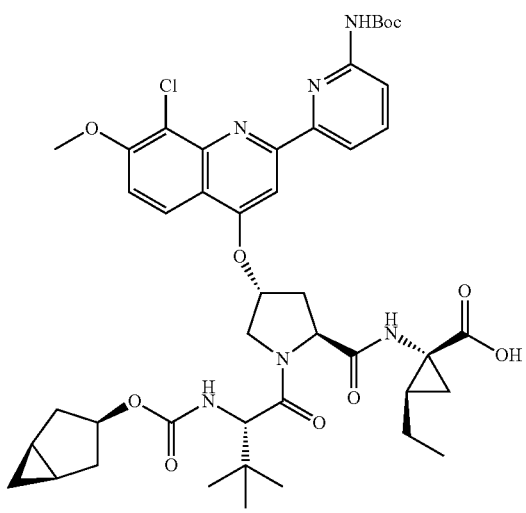
12
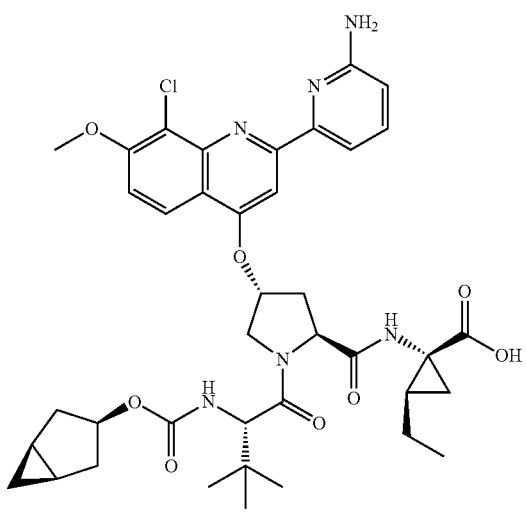
13
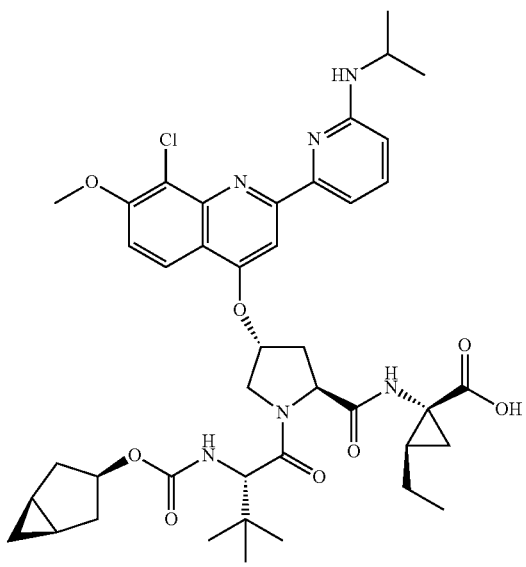

-continued
14
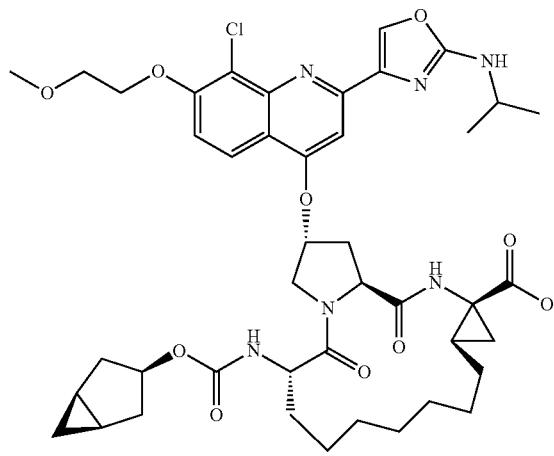
15
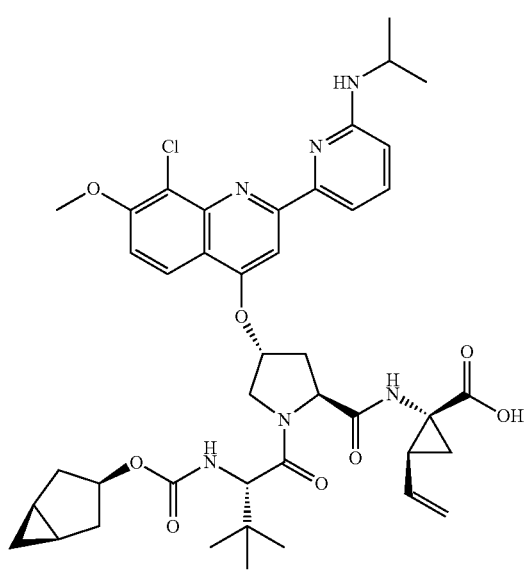
16
-continued
17
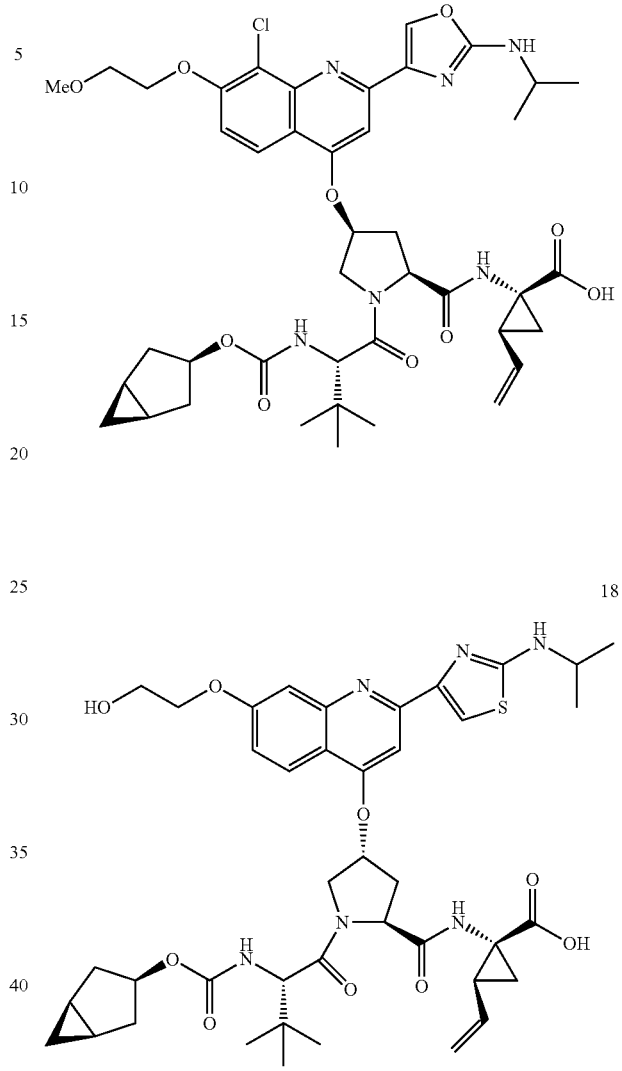
18
19
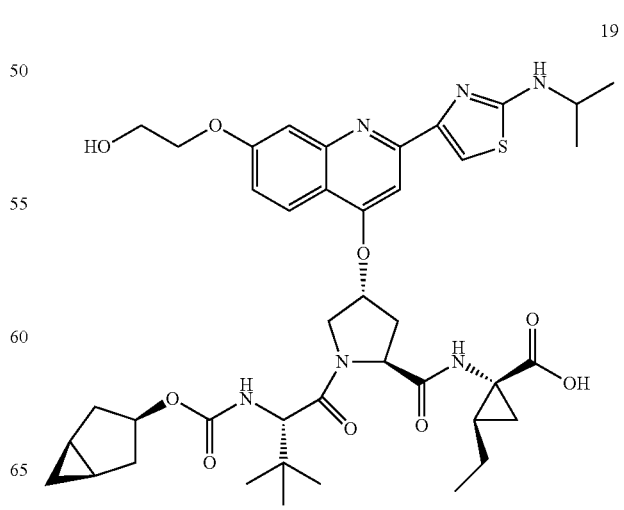

20
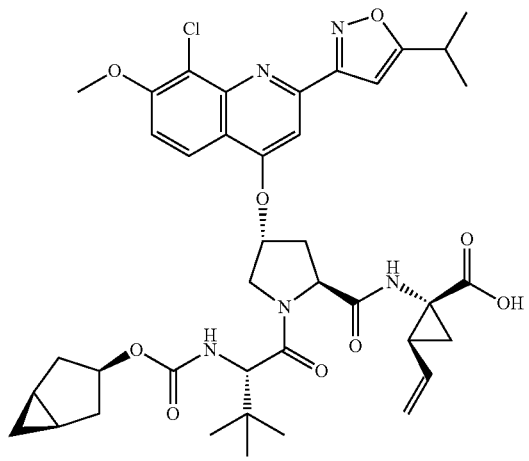
21
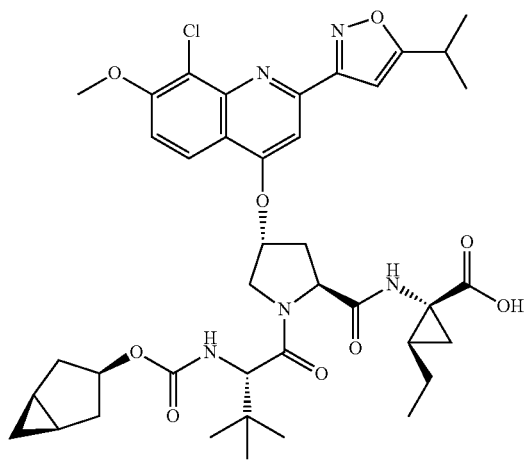
22
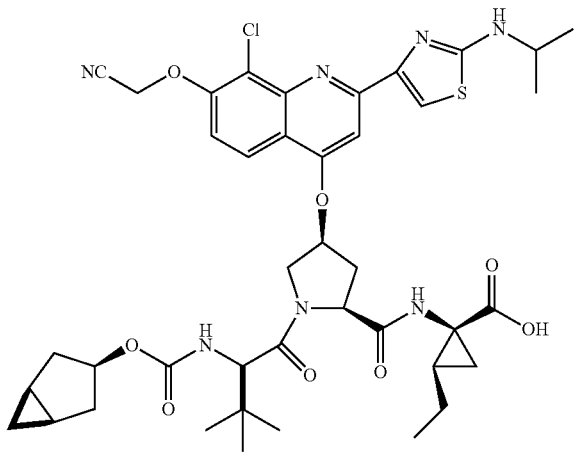
23
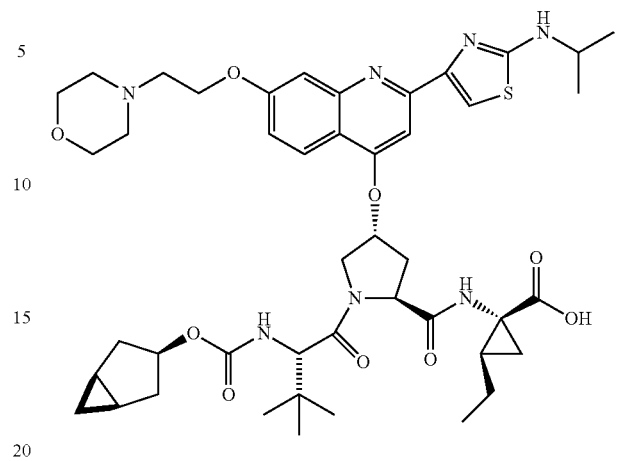
24
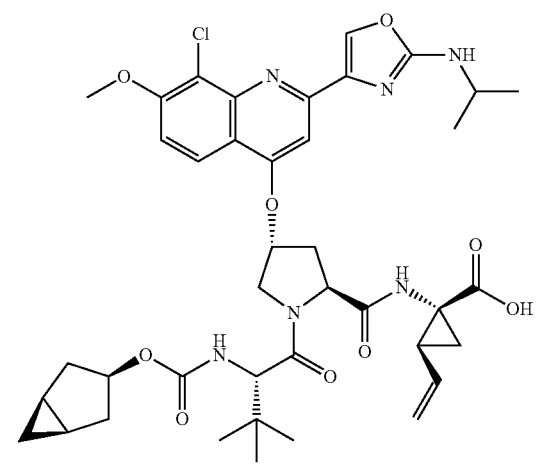
25
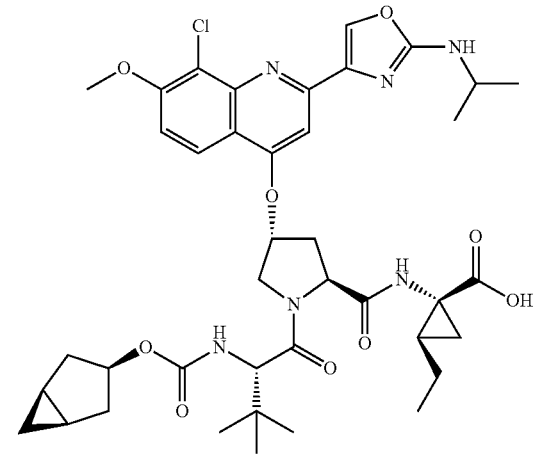

57
26
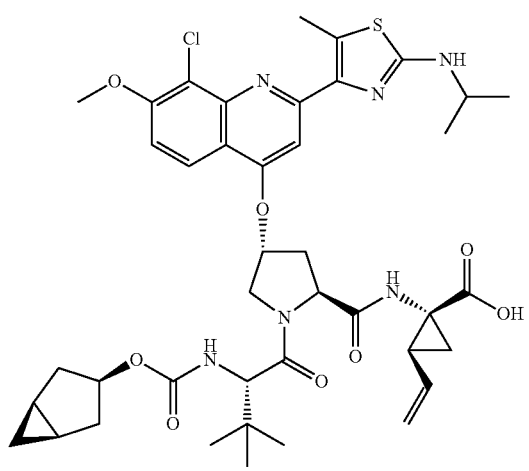
27
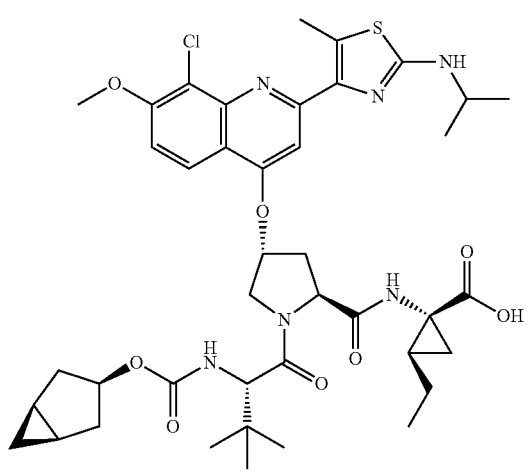
28
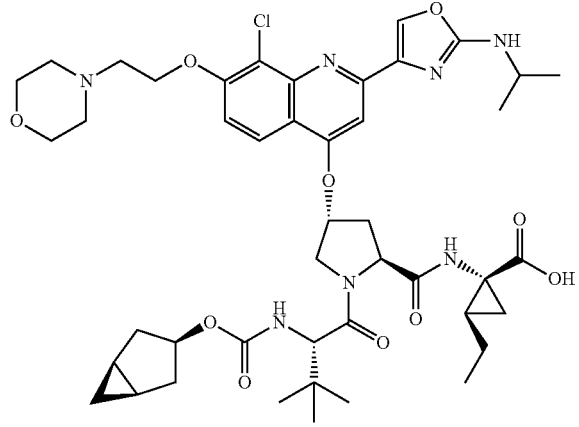
58
29
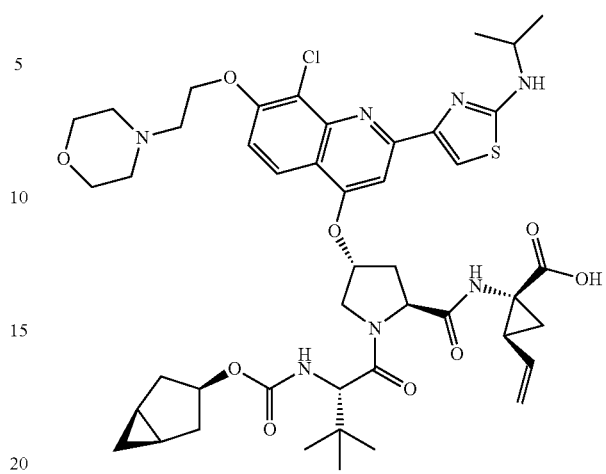
30
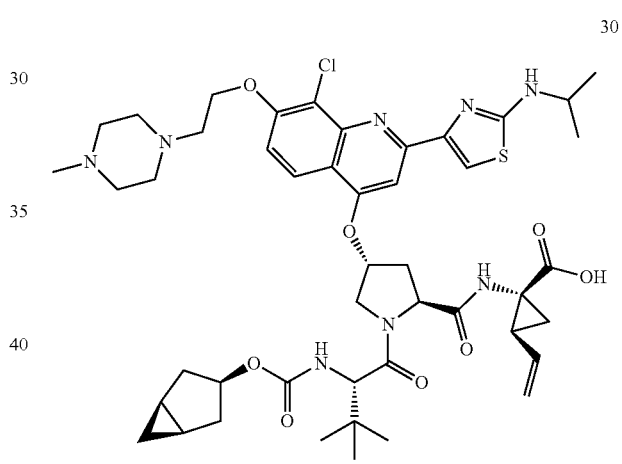
31
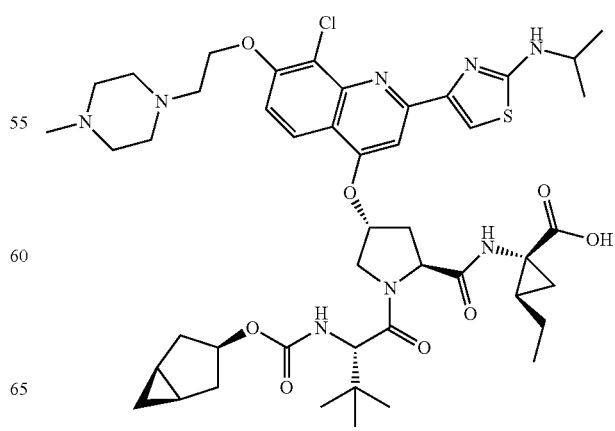

32
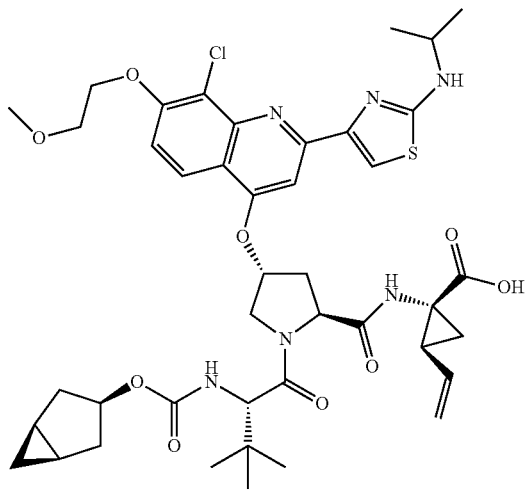
33
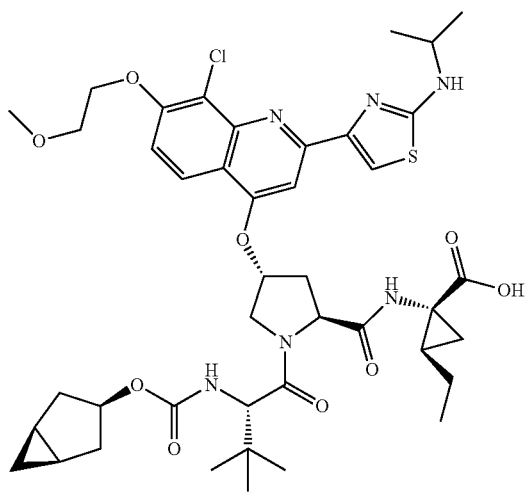
34
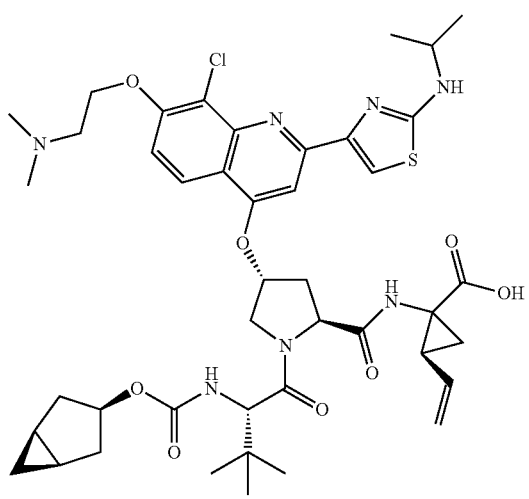
35
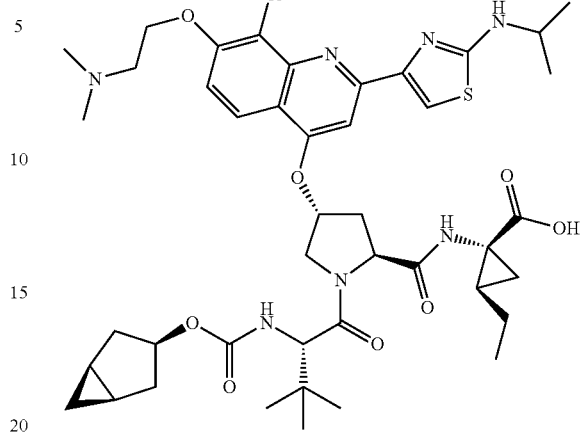
36
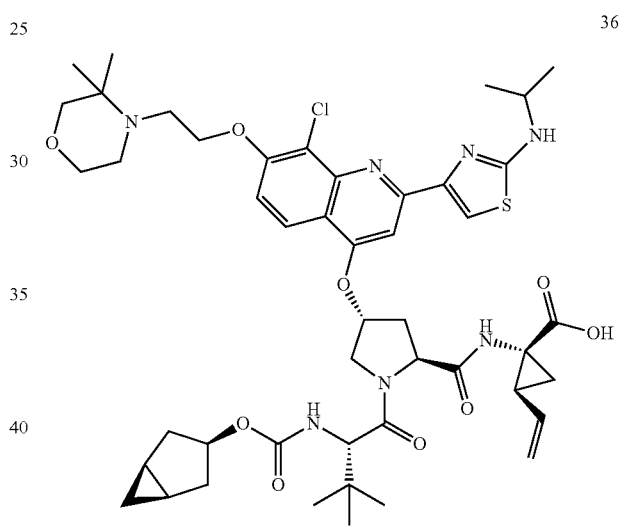
37
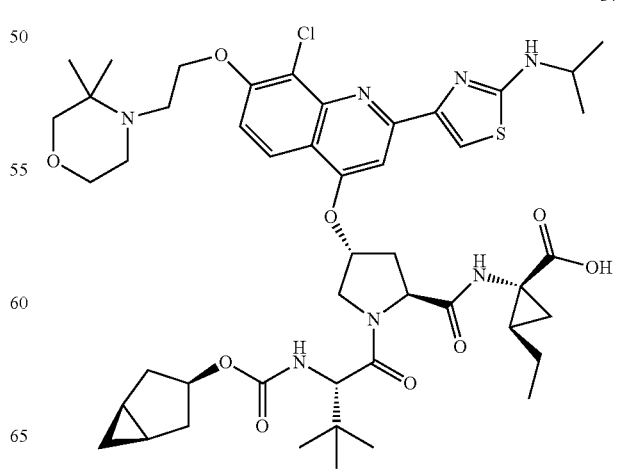

38
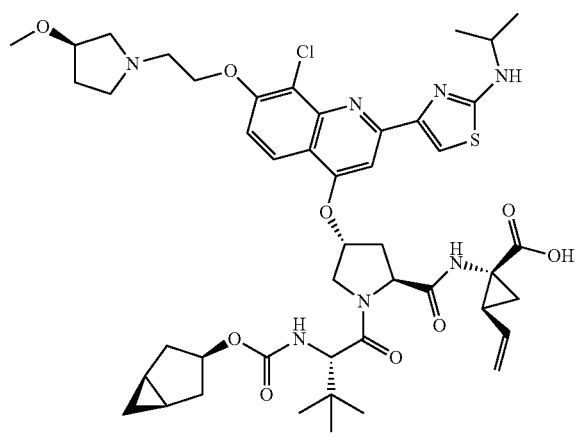
39
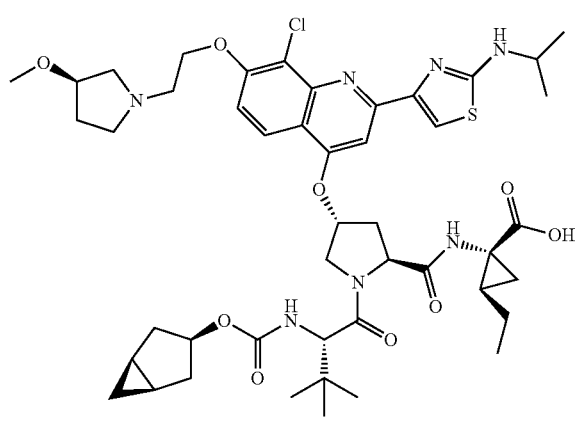
40
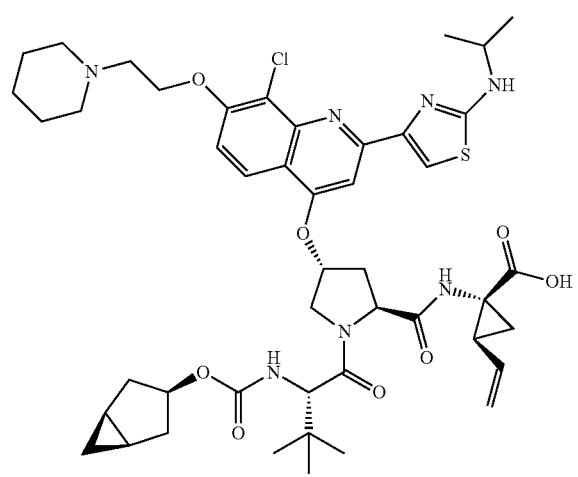
41
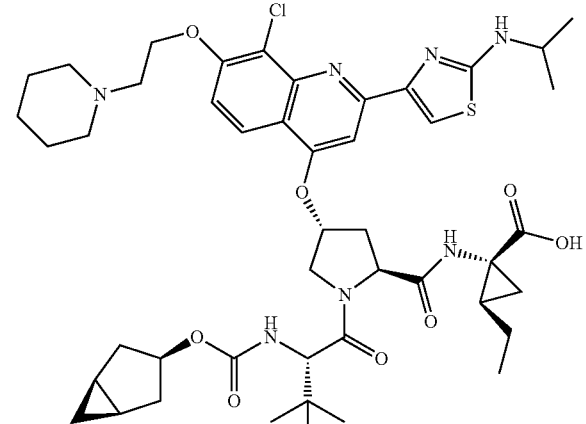
42
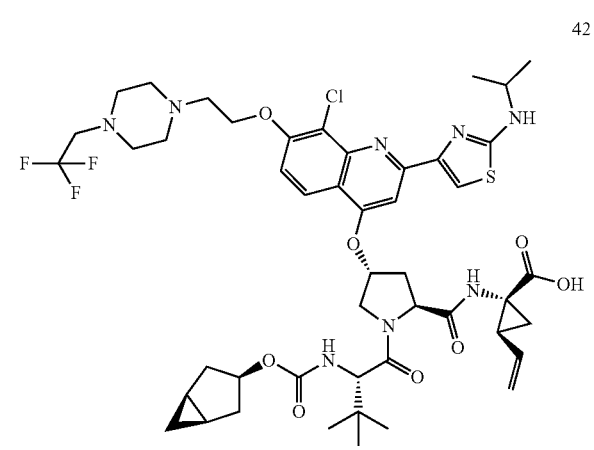
43
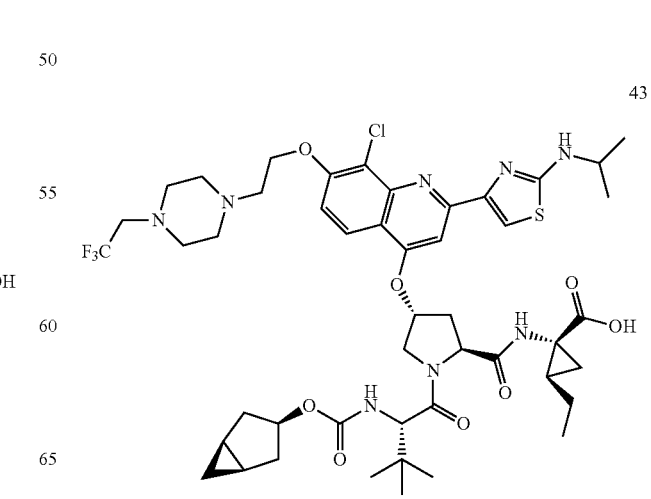

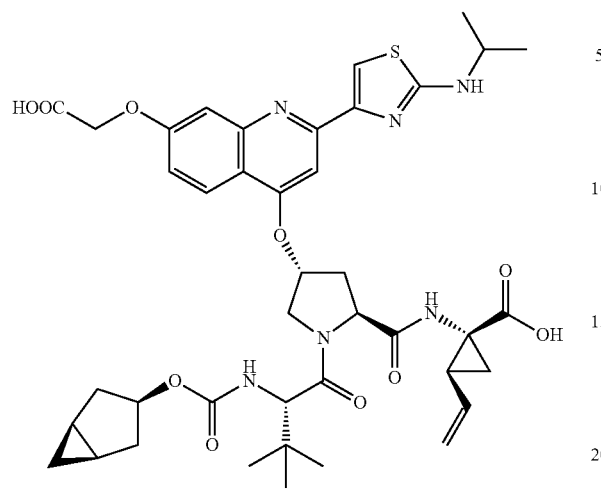
44
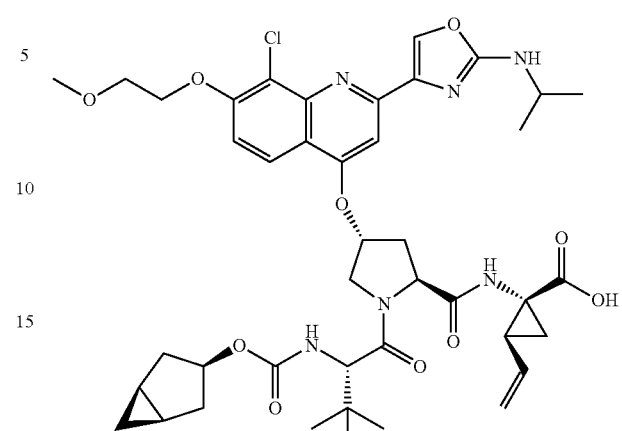
47
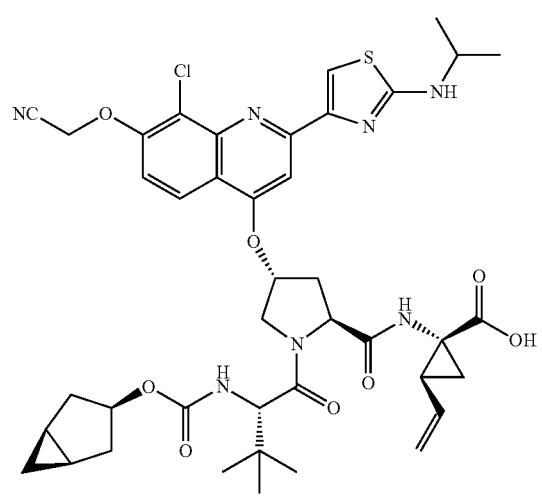
45
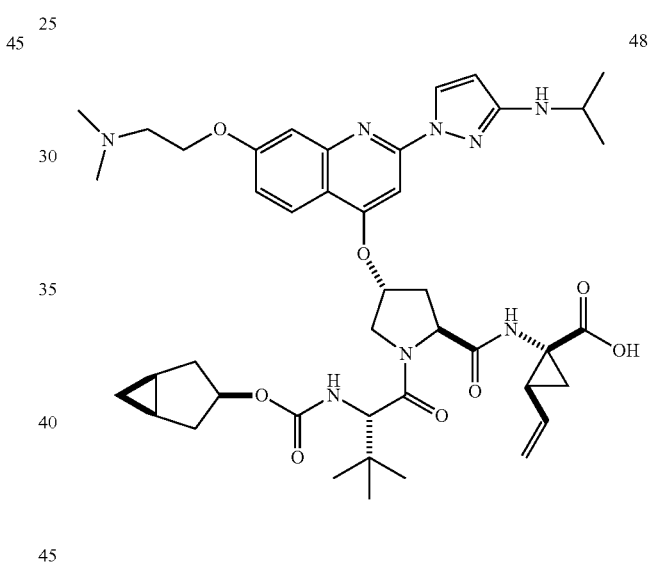
48
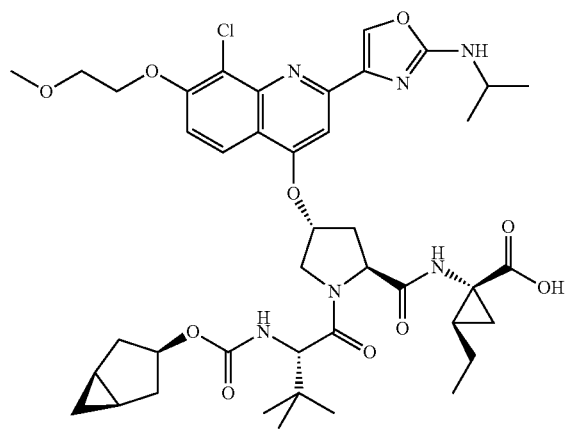
46
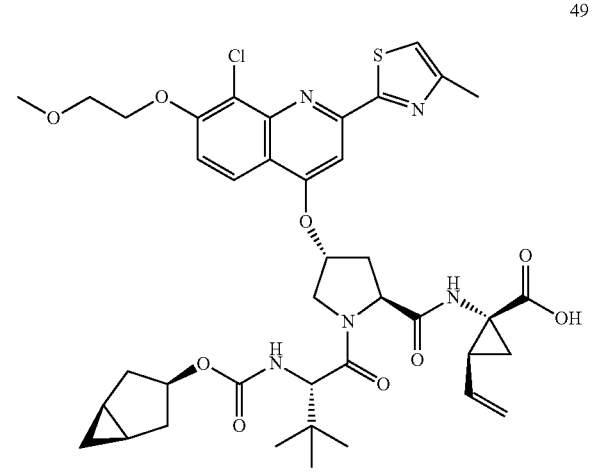
49

65
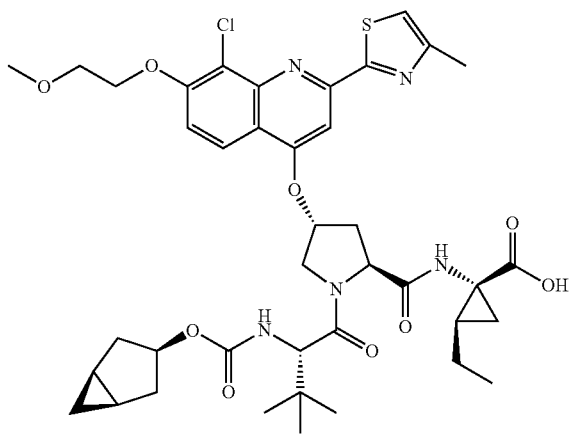
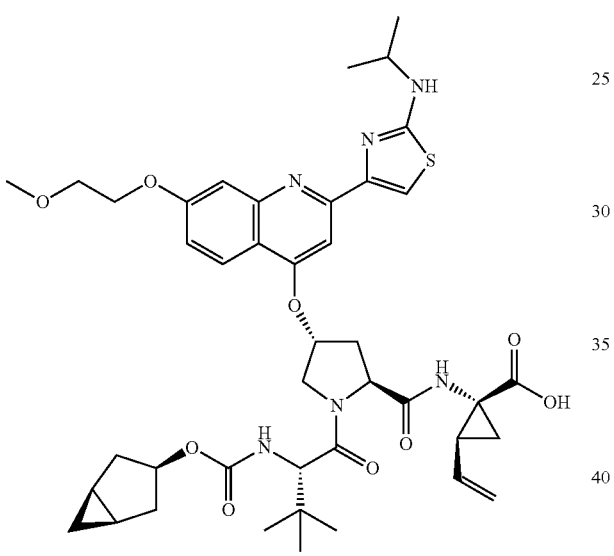
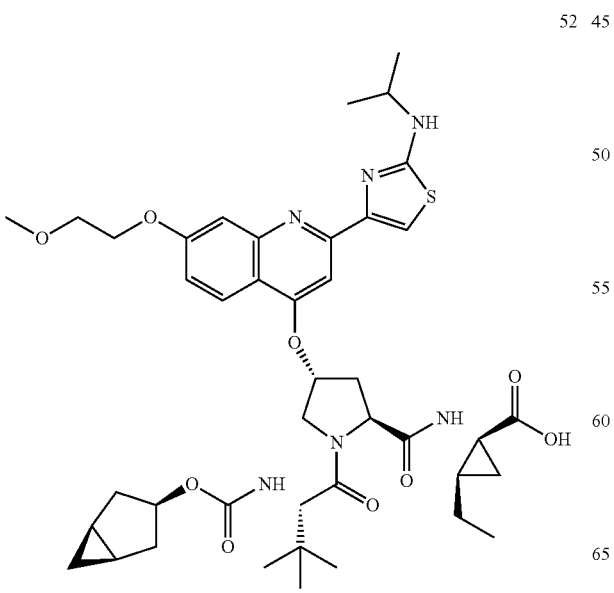
66
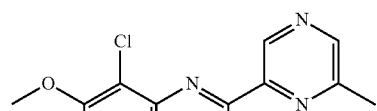
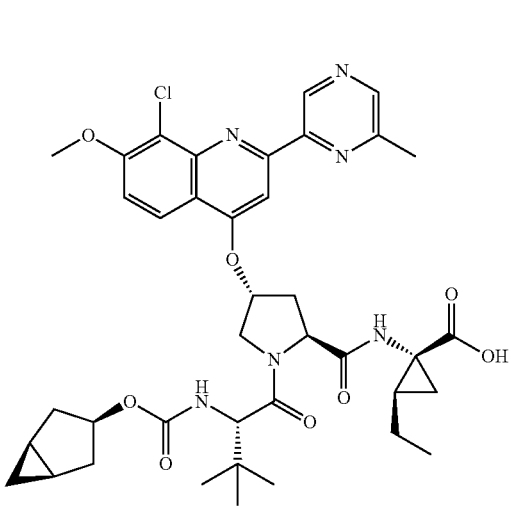
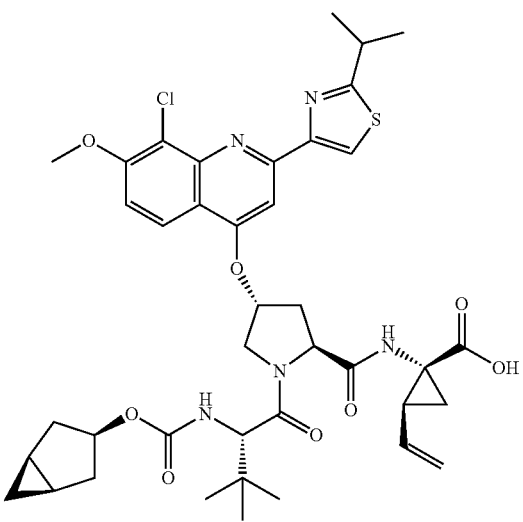

56
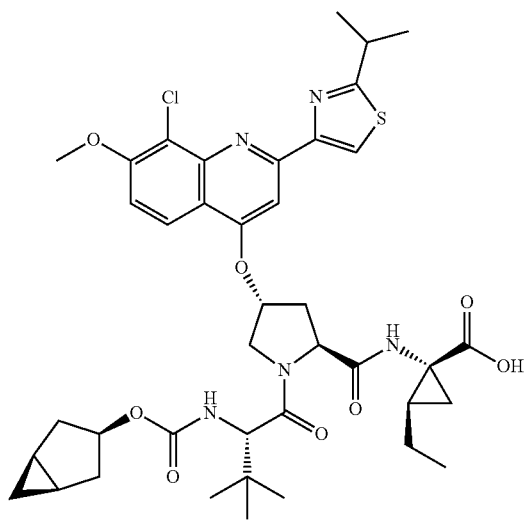
57
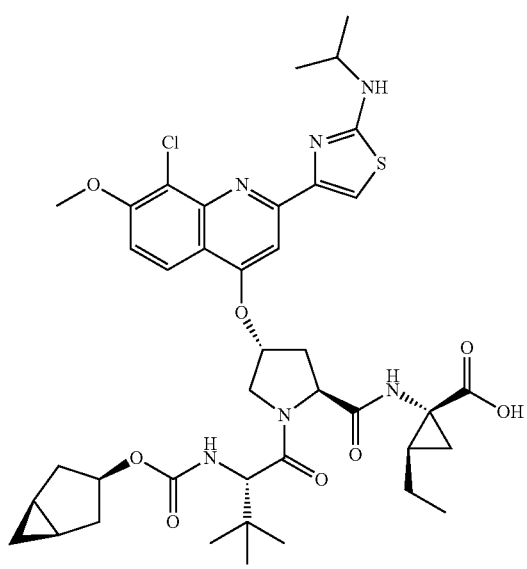
58
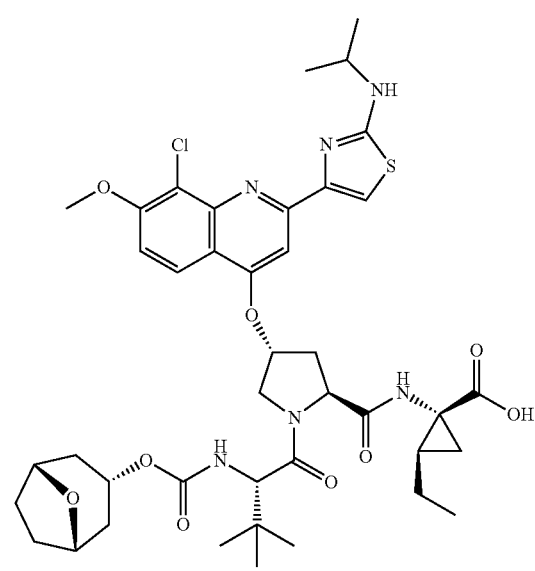
59
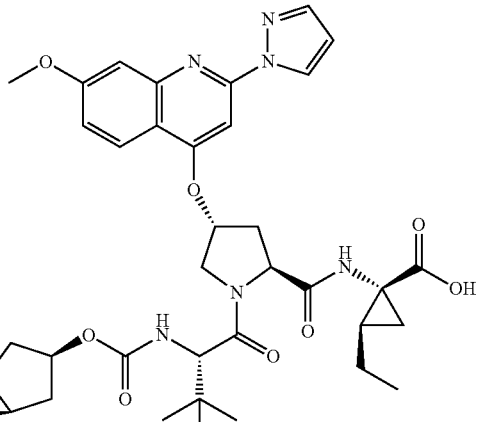
60
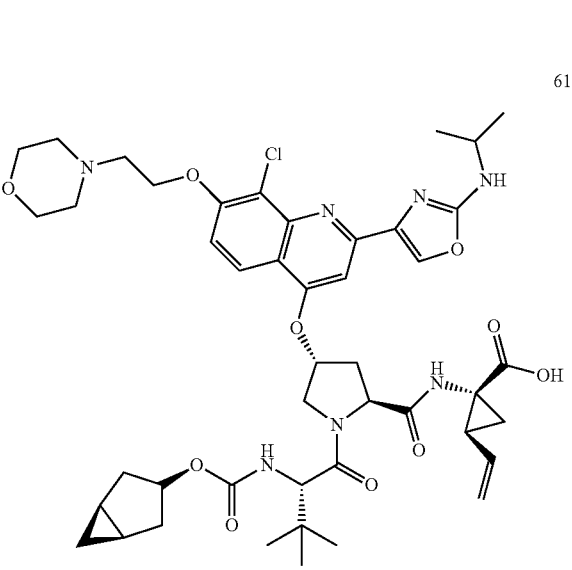
61

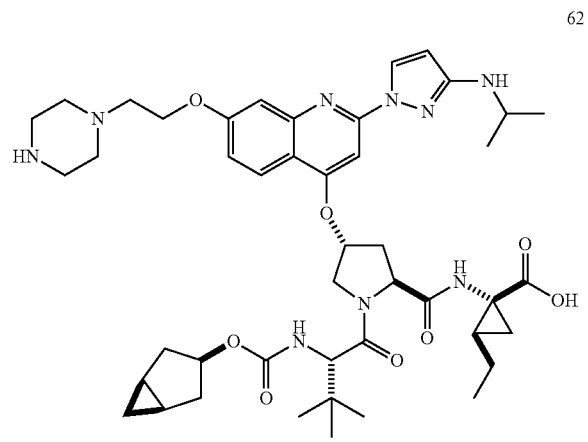
62
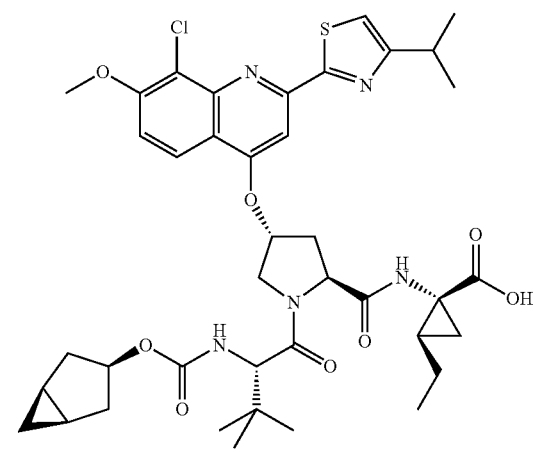
65
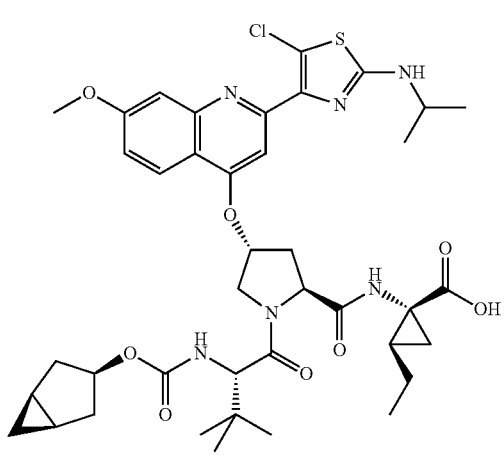
63
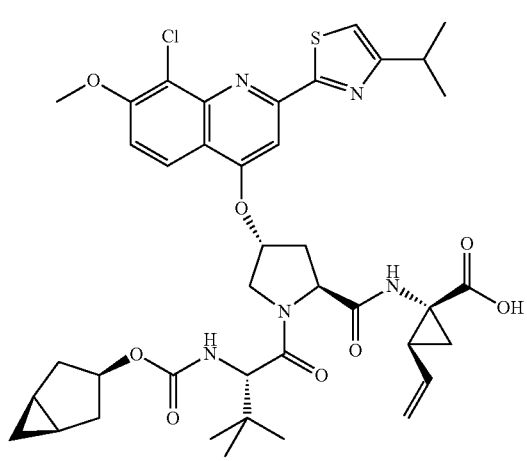
64
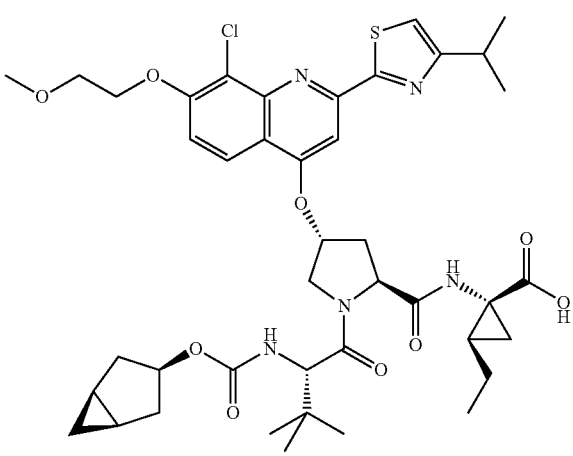
66
67

68
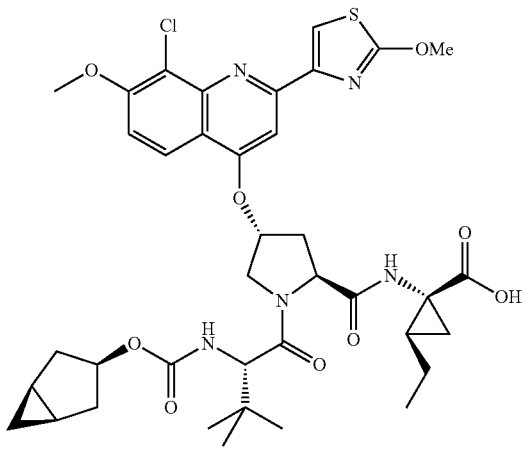
69
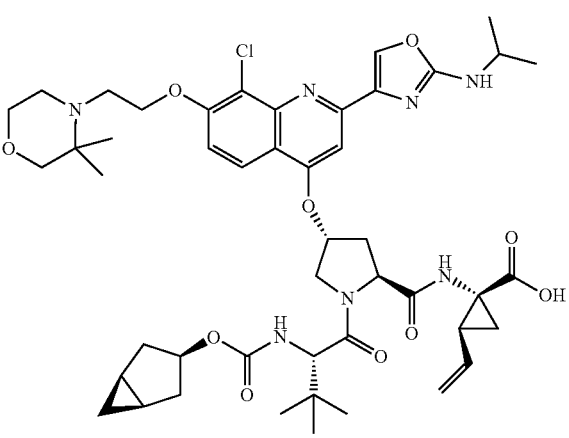
70
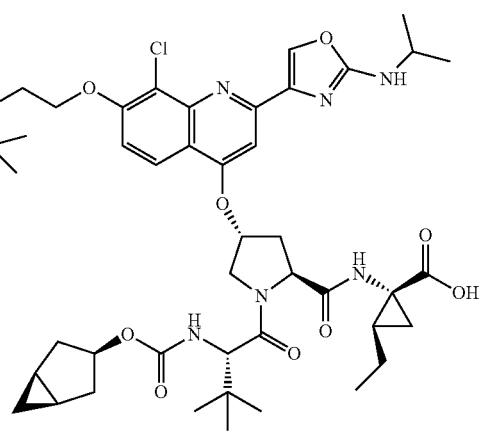
71
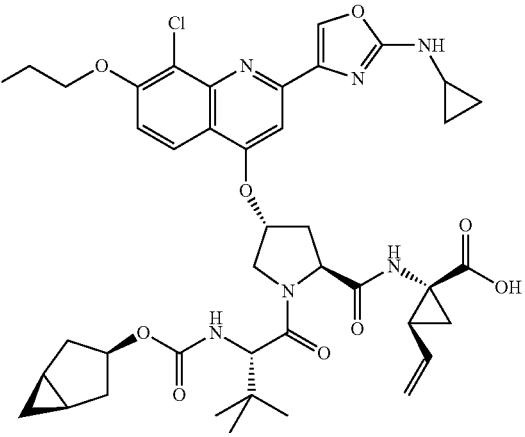
72
73

74
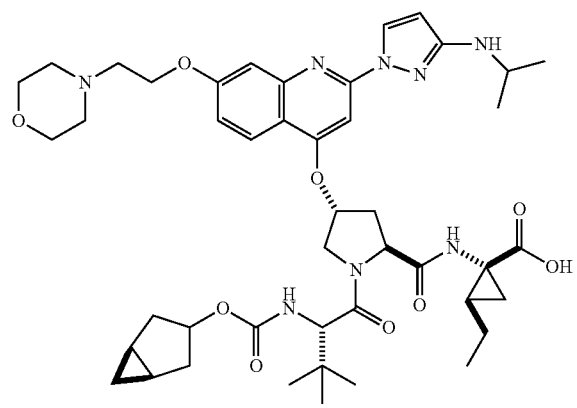
75
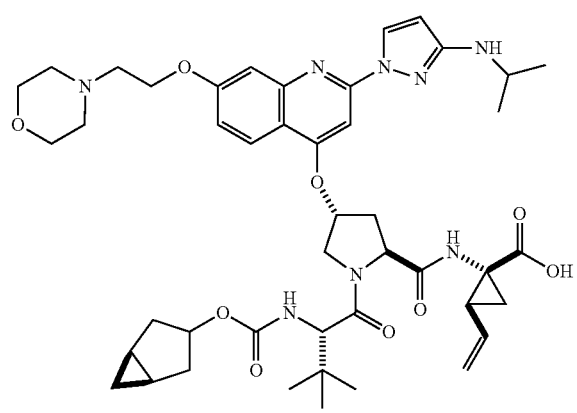
76
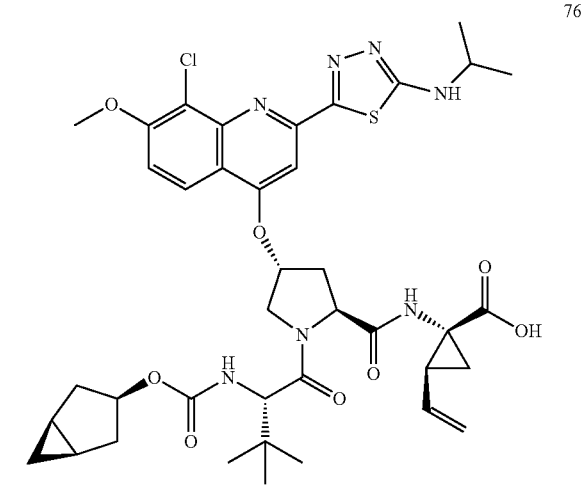
77
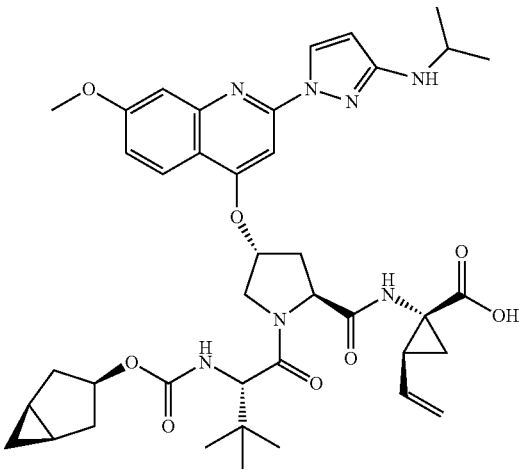
78
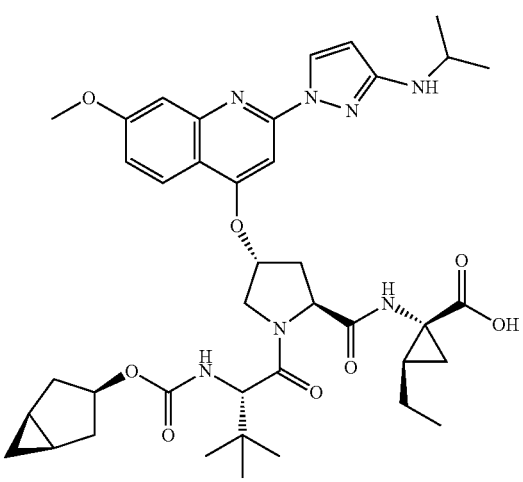
79
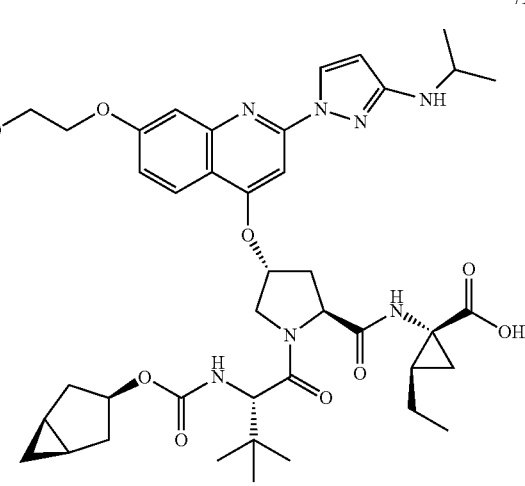

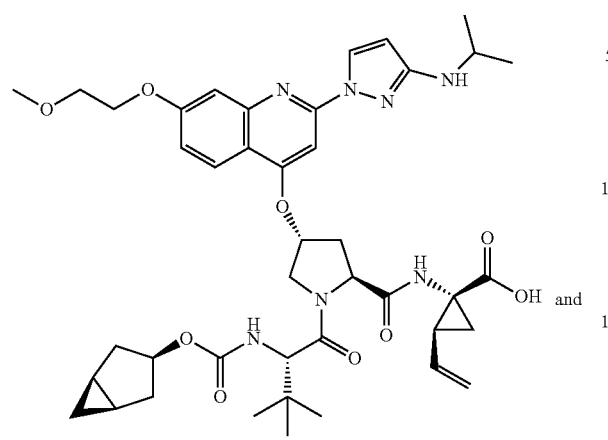
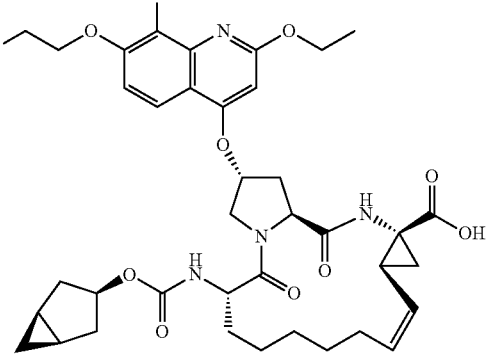
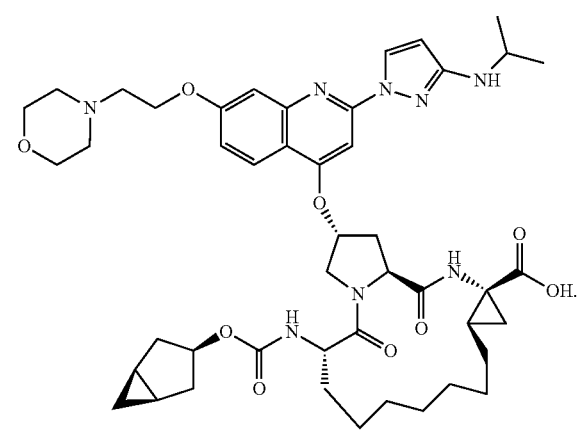
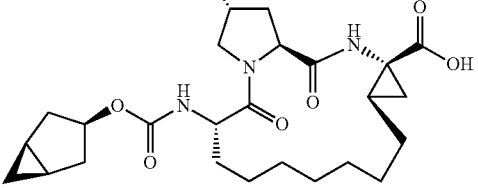
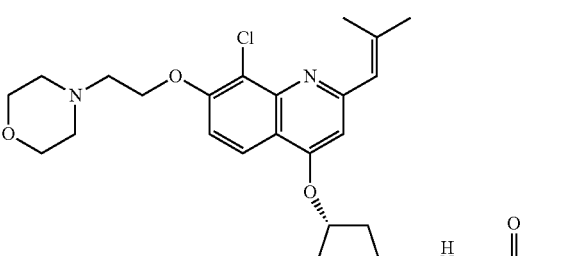
In a specific embodiment of the invention the compound of formula I is selected from:
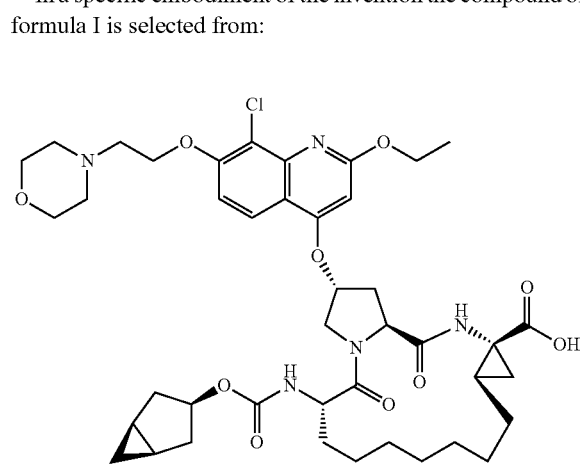
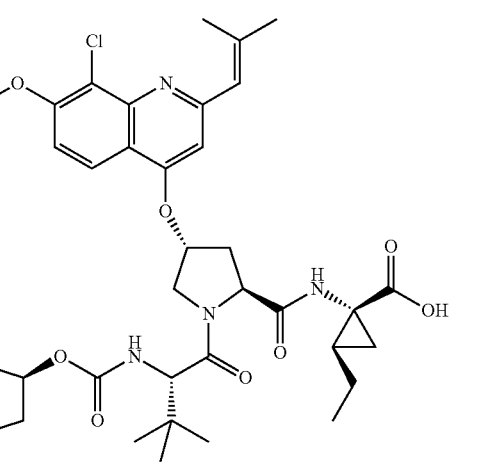

77
-continued
78
-continued
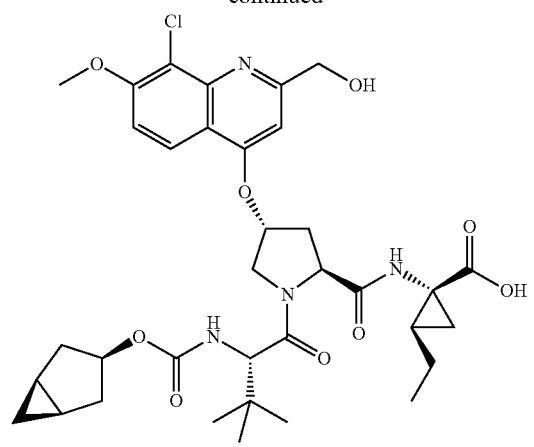
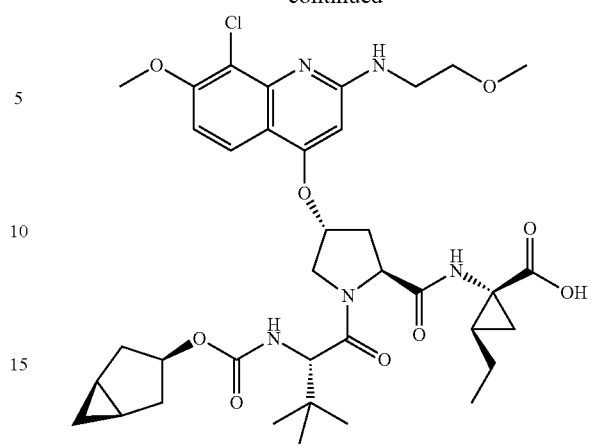

79
-continued
80
-continued
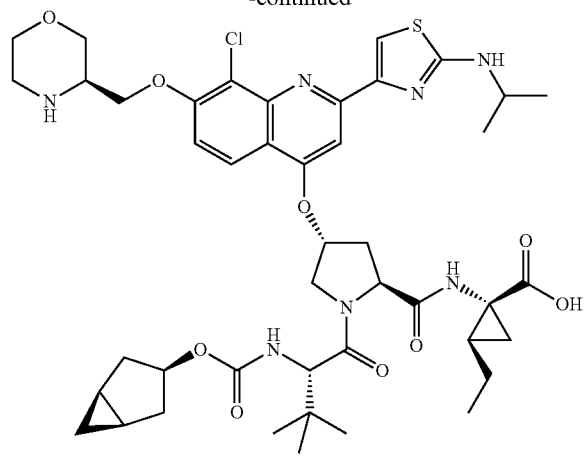
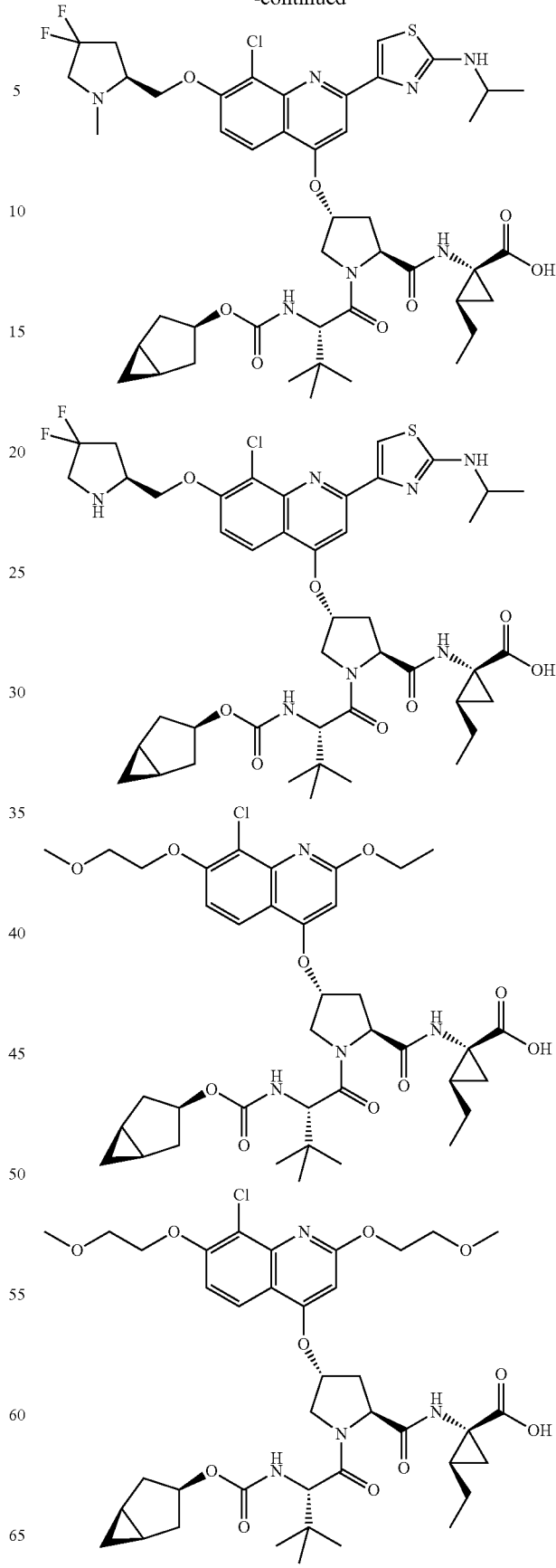

81
-continued
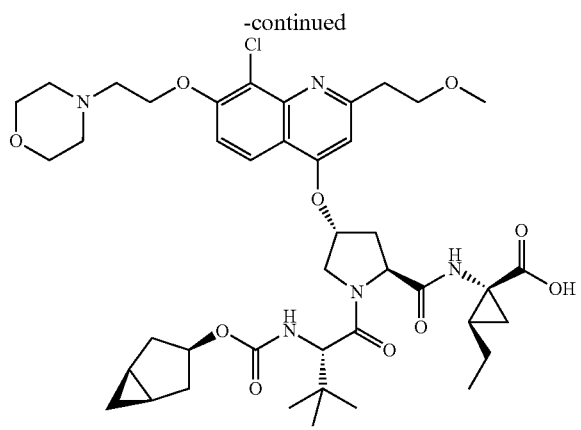
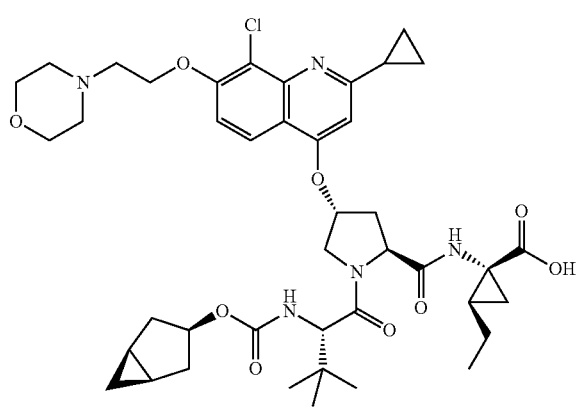
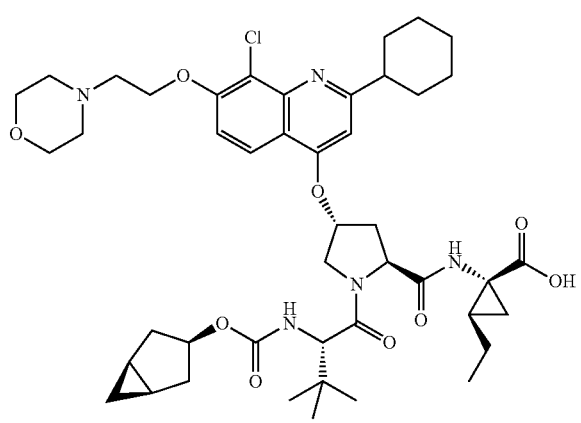 [SMILES: C=C[C@@H]1C[C@]1(NC(=O)[C@@H]1C[C@@H](Oc2cc(C=C(C)C)nc3c(Cl)c(OCCN4CCOCC4)ccc23)CN1C(=O)[C@@H](NC(=O)O[C@@H]1C[C@@H]2C[C@@H]2C1)C(C)(C)C)C(=O)O]
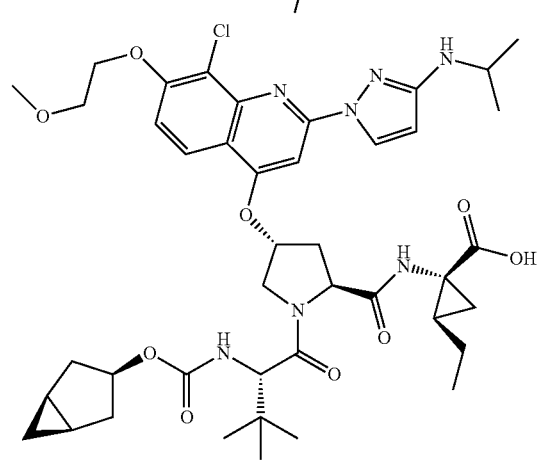
82
-continued
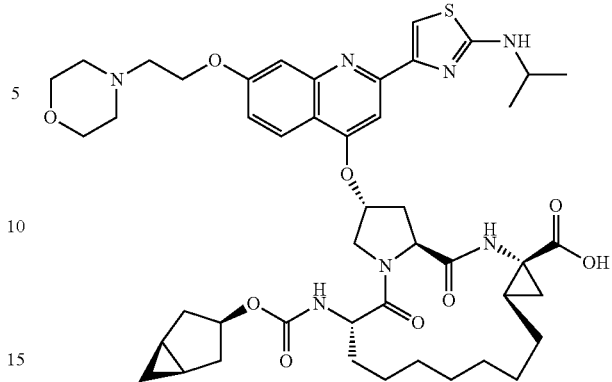
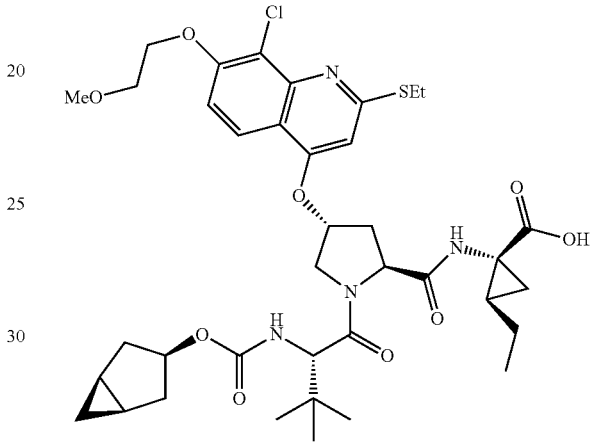
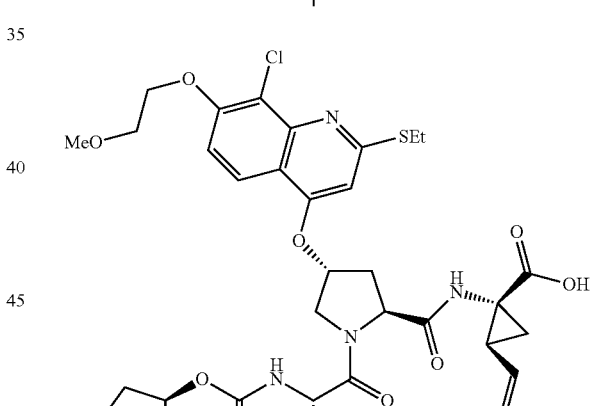
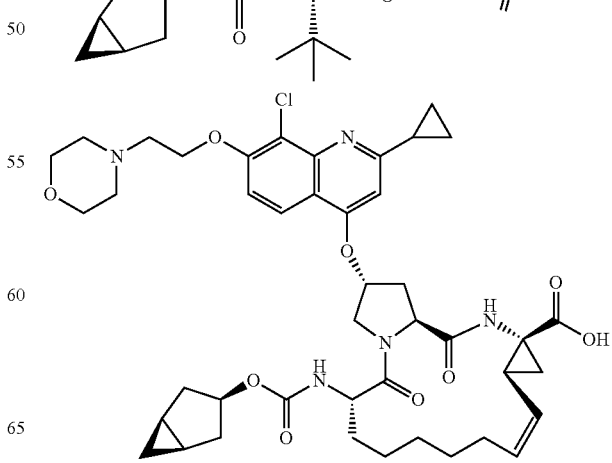

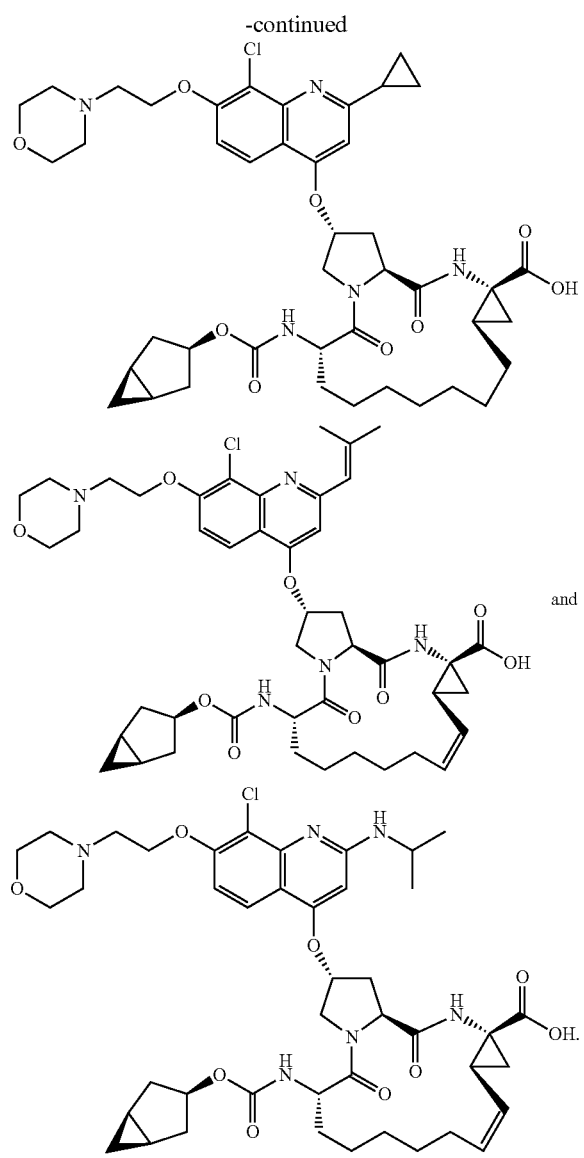
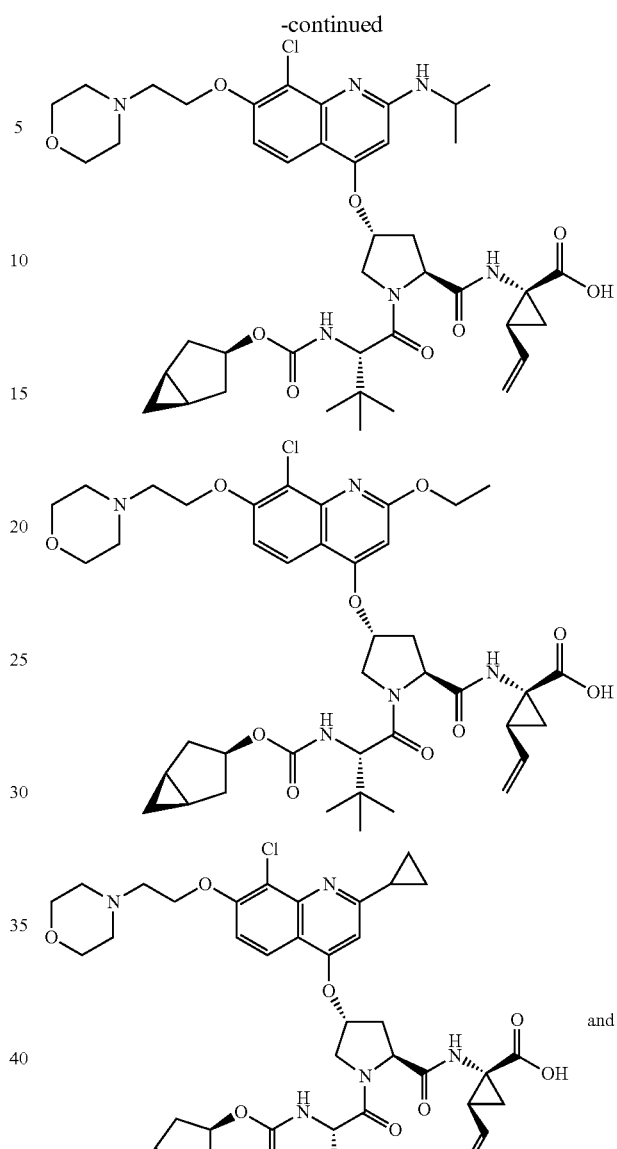
In a specific embodiment of the invention the compound of formula I is selected from:
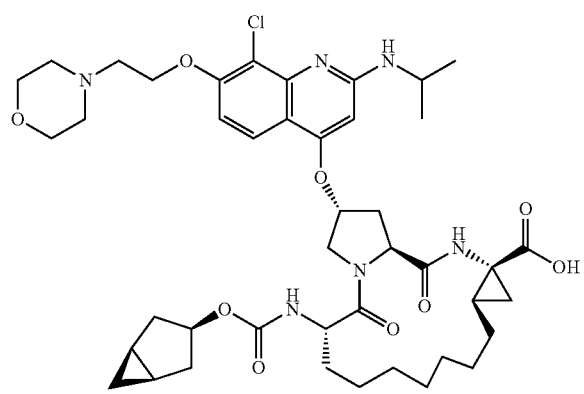
In a specific embodiment of the invention the compound of formula I is selected from:

85
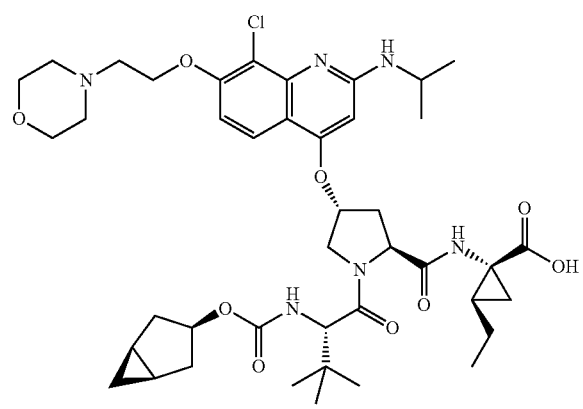
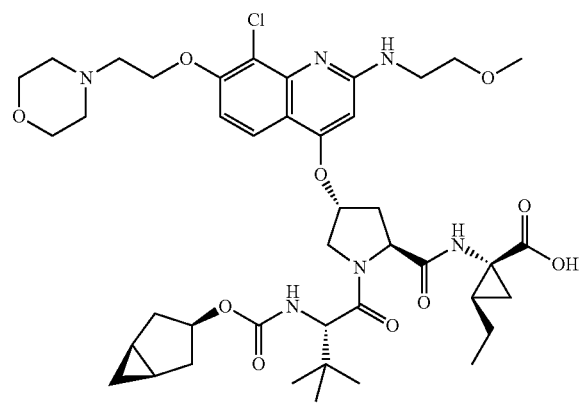
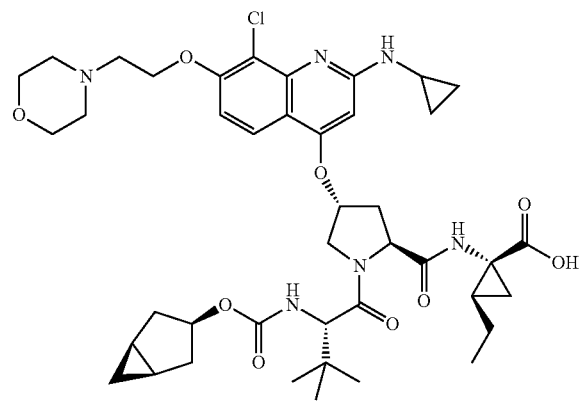
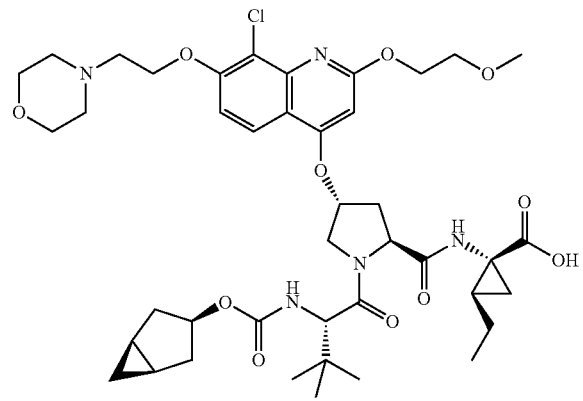
86
-continued
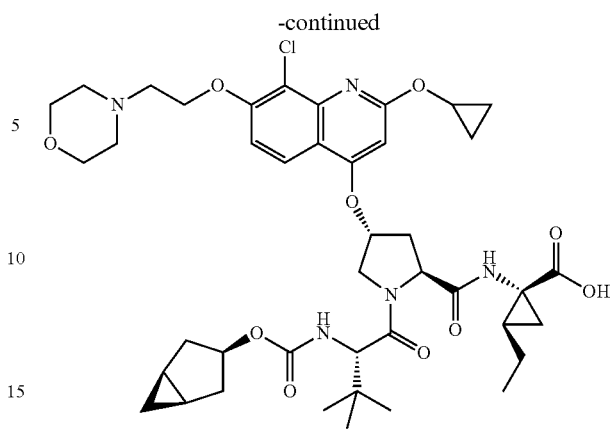
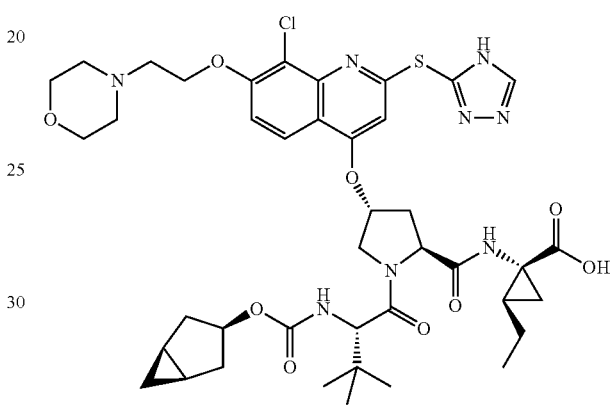
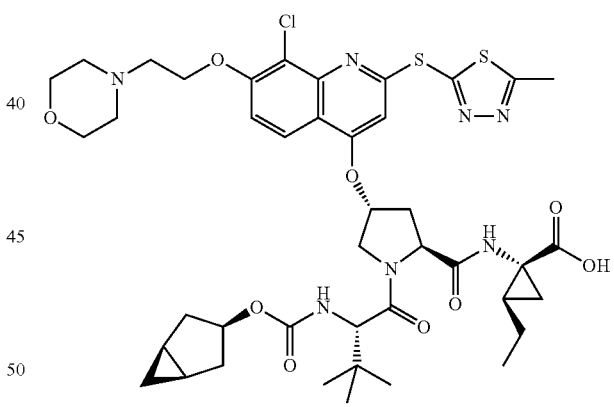
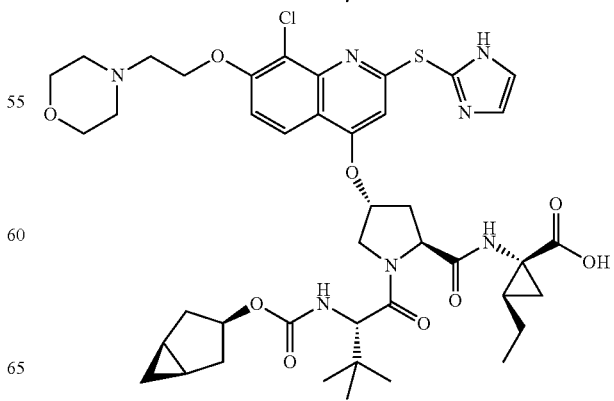

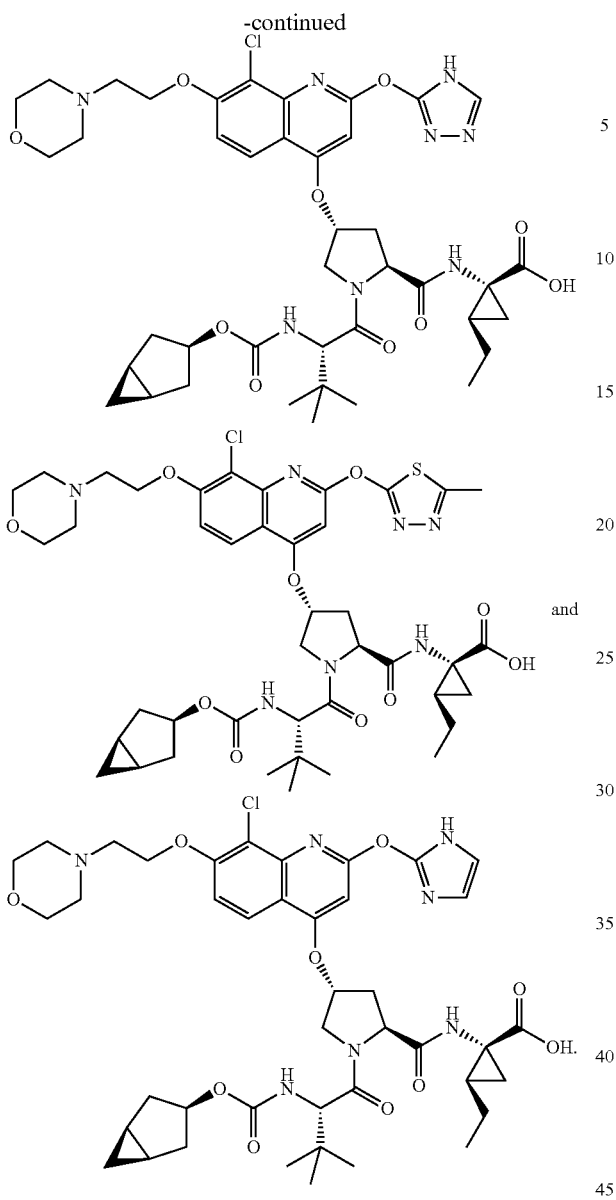

In a specific embodiment of the invention each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10) alkanoyloxy, or (C1-10)alkoxycarbonyl, is optionally substituted with one or more $R^1$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring. In a specific embodiment of the invention $R_a$ is H, methoxy, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyanomethoxy, 2-piperazin-1-ylethoxy, 2-(N,N-dimethyl)ethoxy, 2-(3,3-dimethylmorpholino)ethoxy, 2-(4-methylpiperazin-1-yl)ethoxy, carboxymethoxy, methoxycarbonylmethoxy.

In a specific embodiment of the invention $Z^1$ is selected from the following structures:

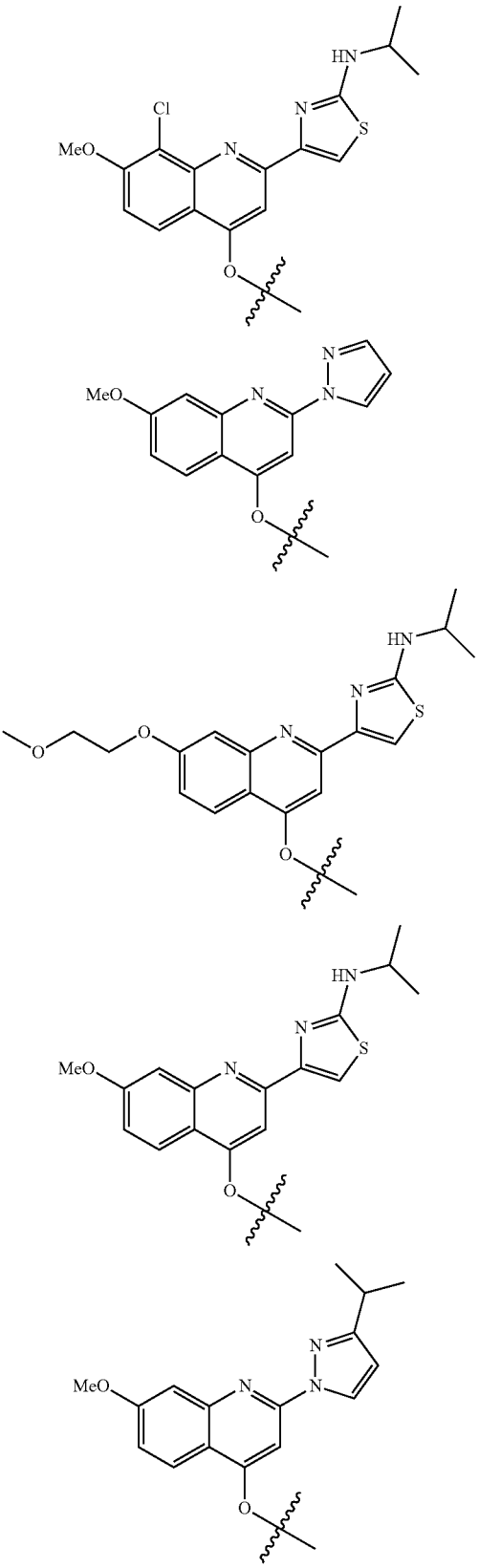

89
-continued
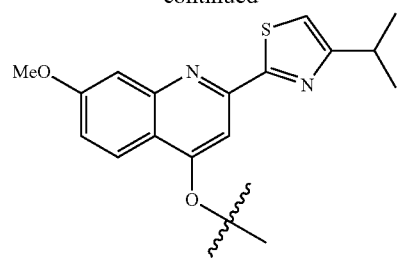
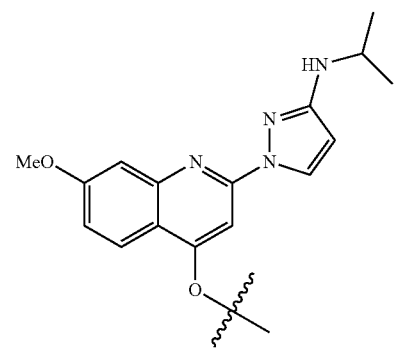
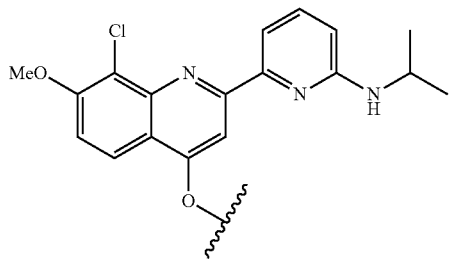
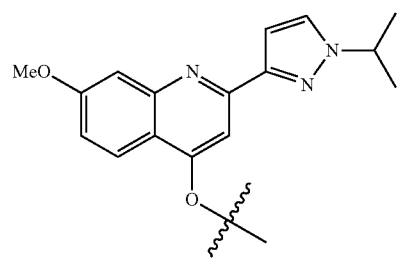
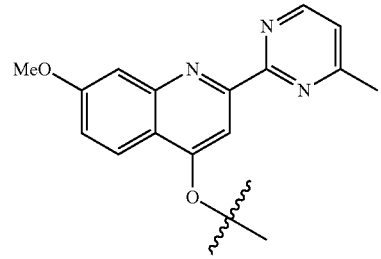
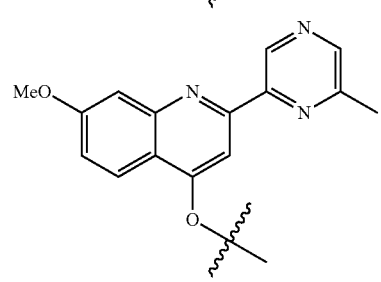
90
-continued
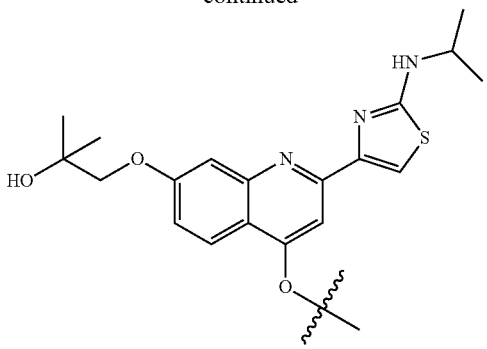
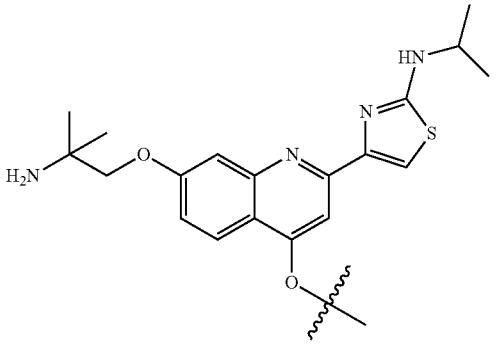
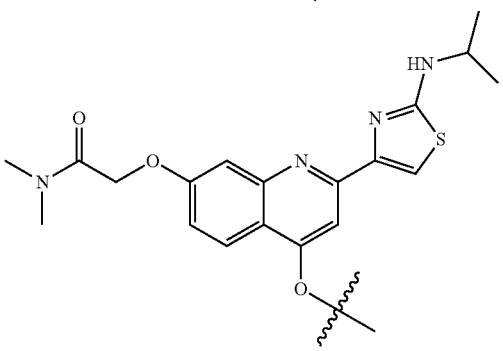
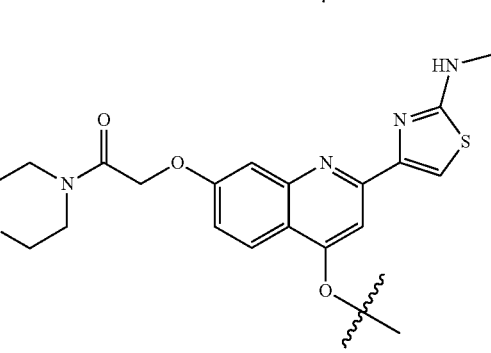
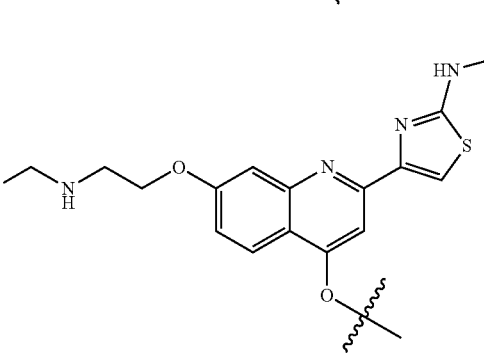

91
-continued
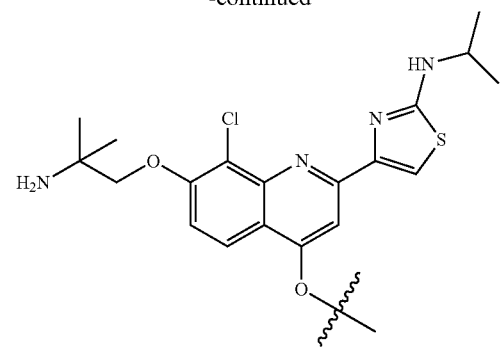
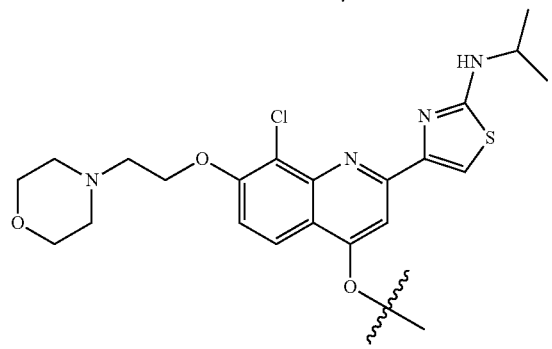
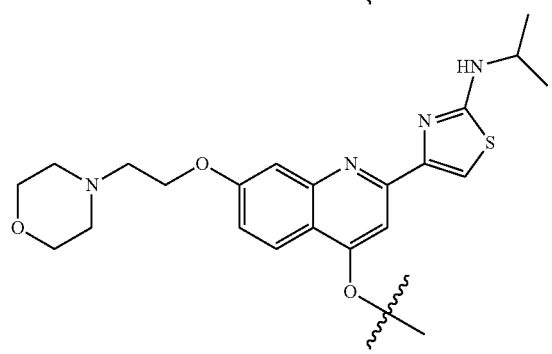
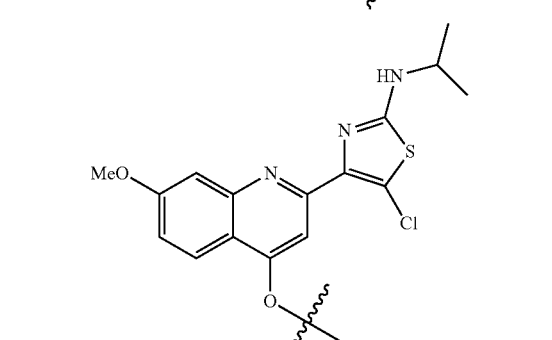
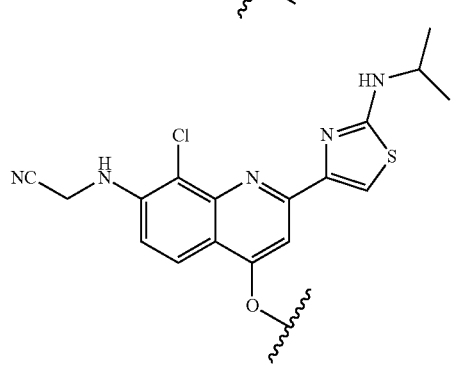
92
-continued
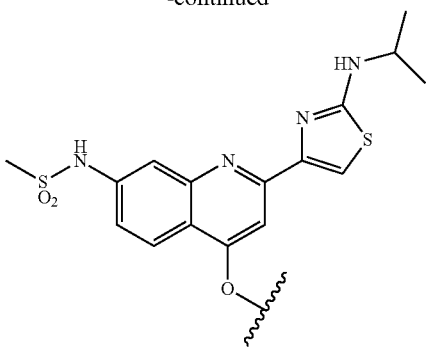
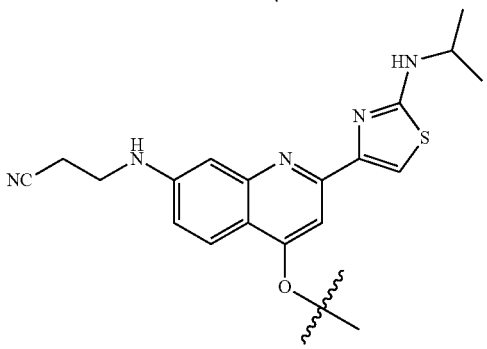
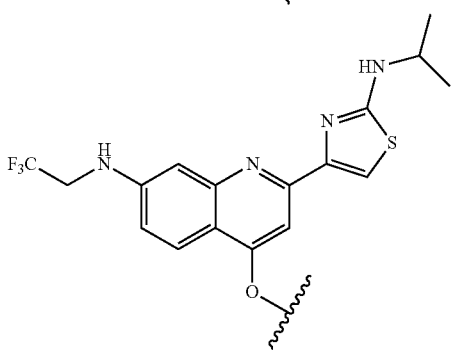
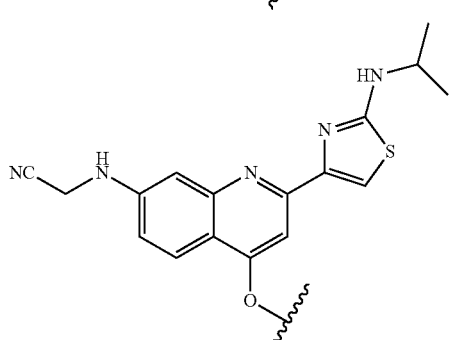
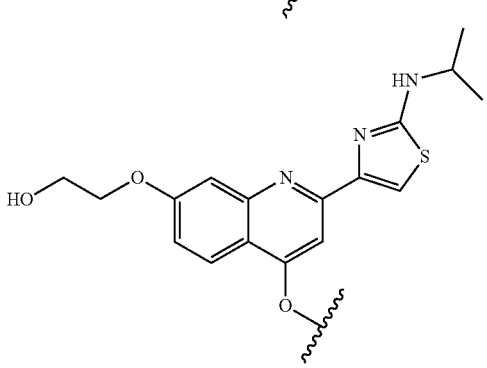

93
-continued
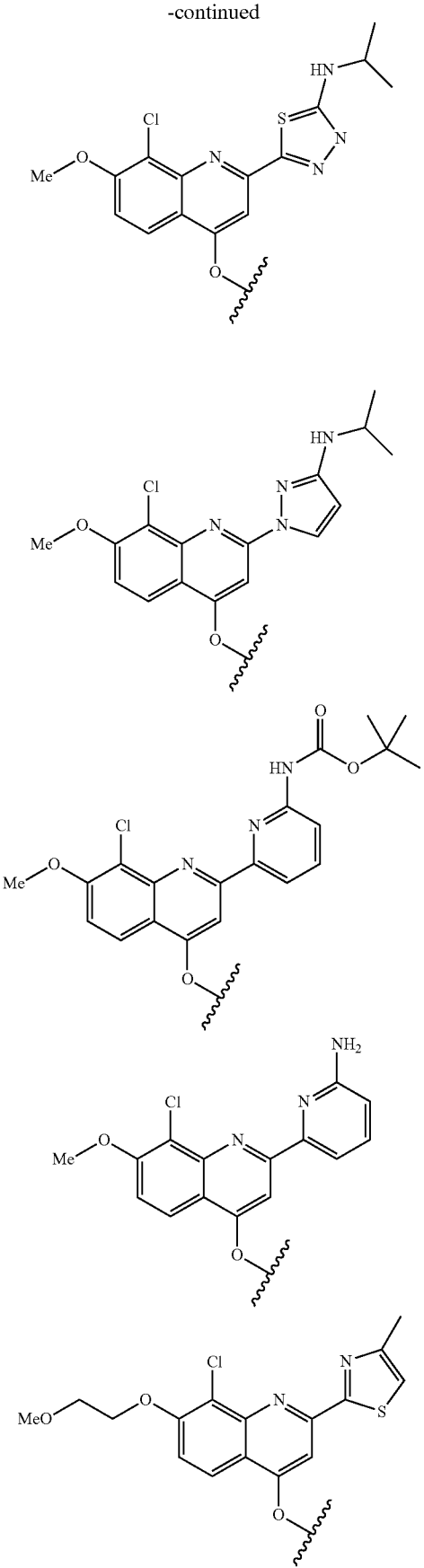
94
-continued
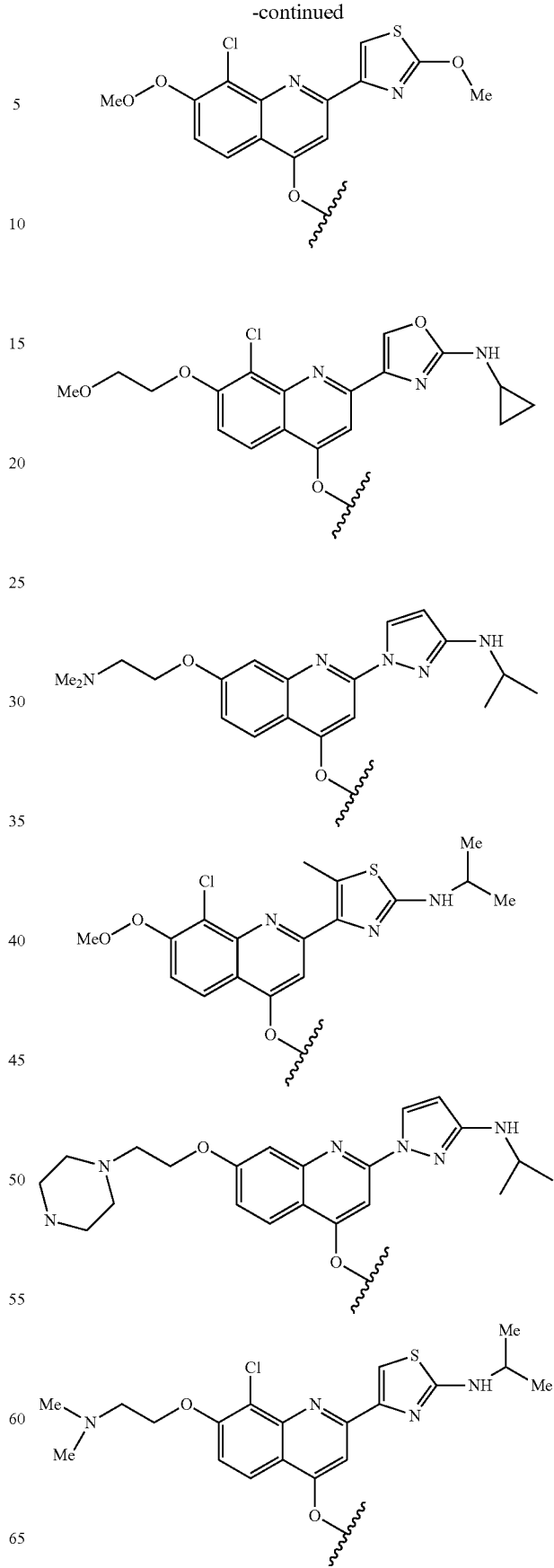

95
-continued
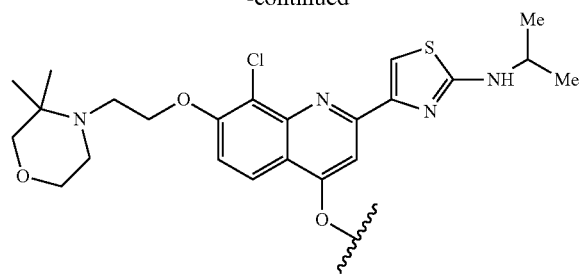
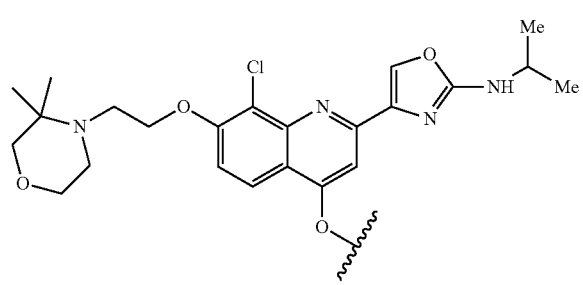
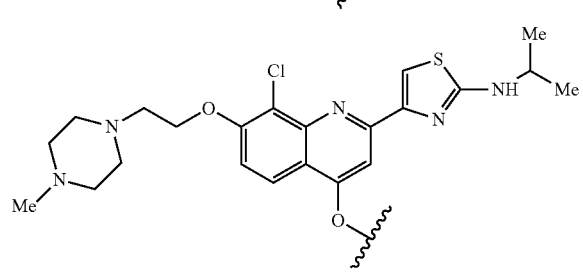
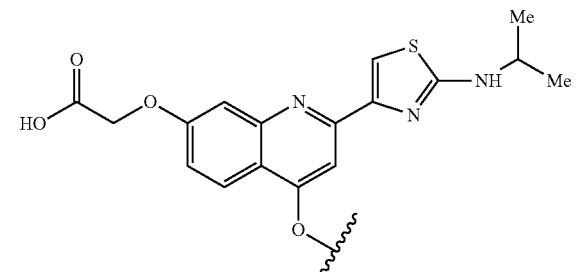
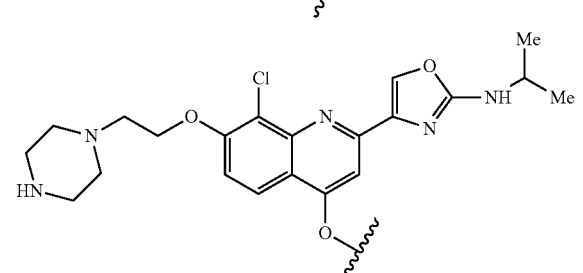
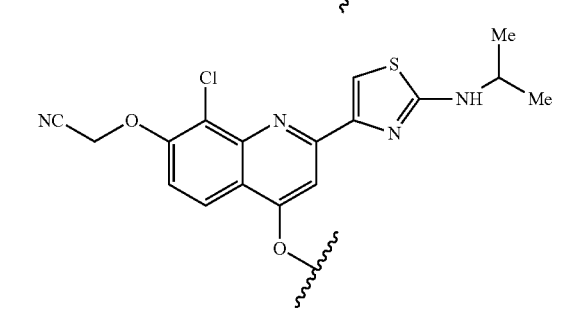
96
-continued
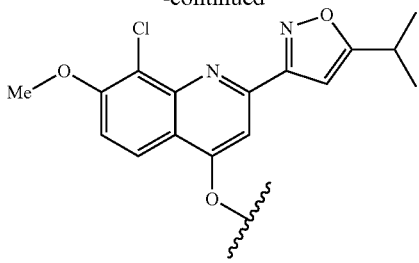
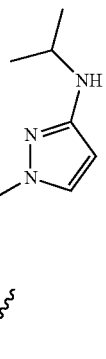
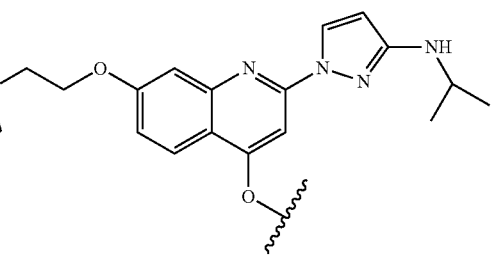
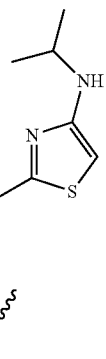
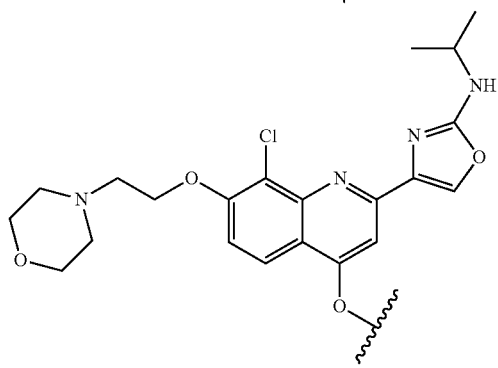

97
-continued
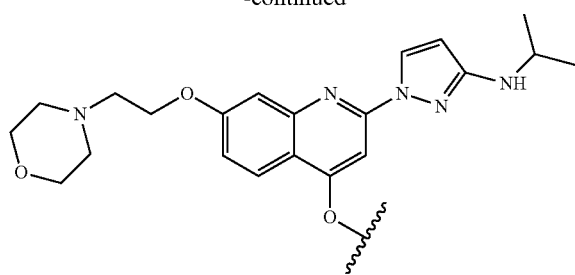
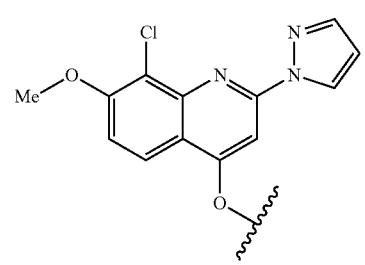
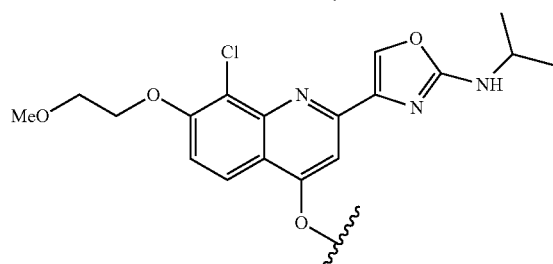
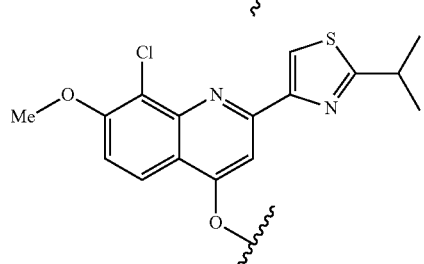
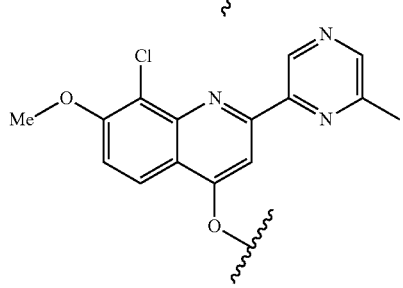
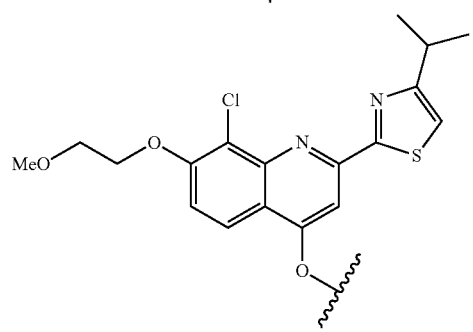
98
-continued
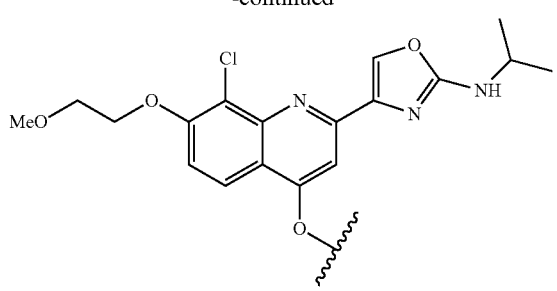
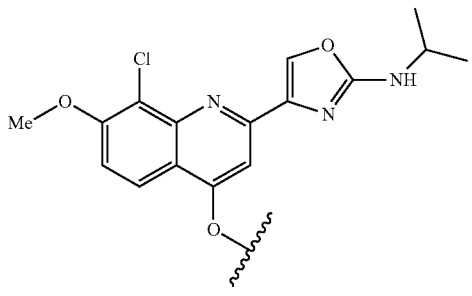
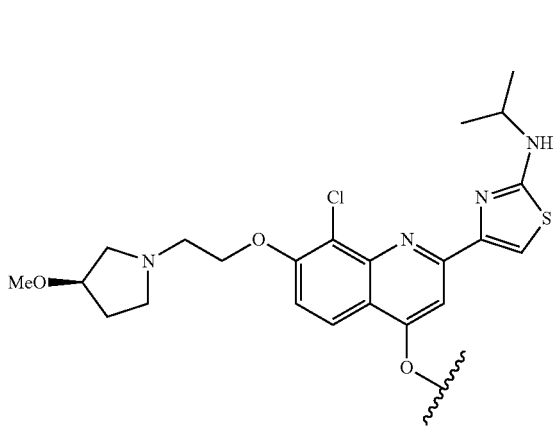
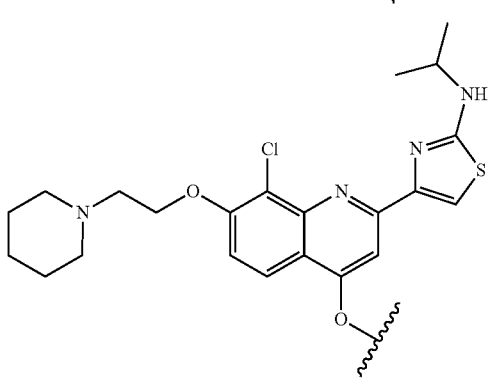
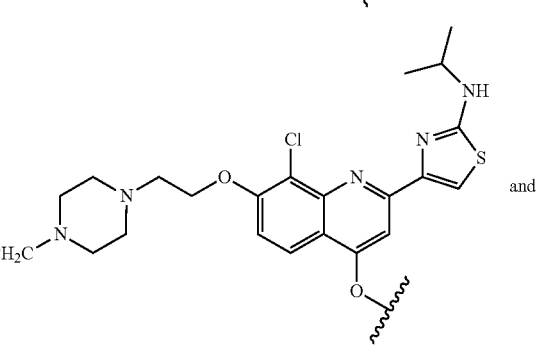 and

99
-continued
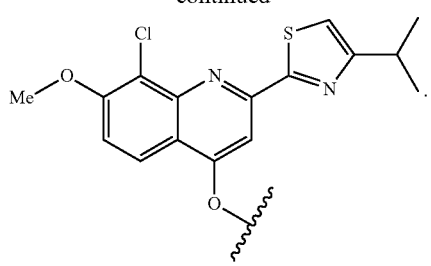
In a specific embodiment of the invention $Z^1$ is selected from the following structures:
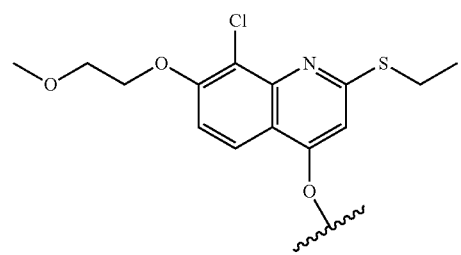
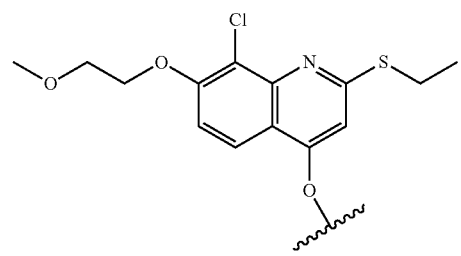
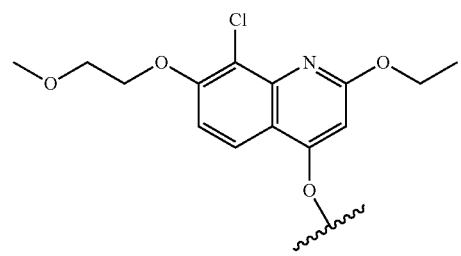
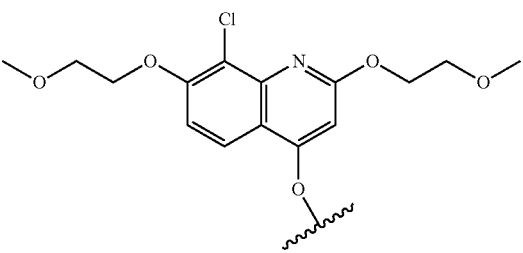
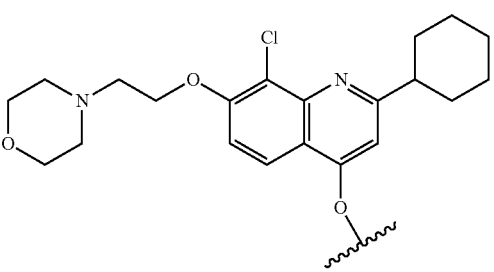
100
-continued
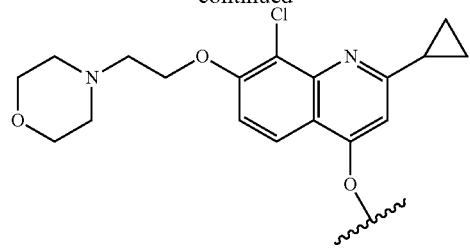
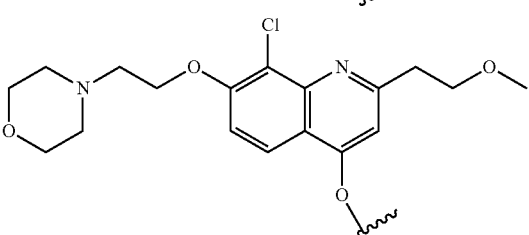
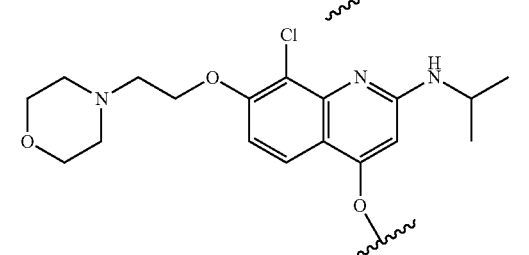
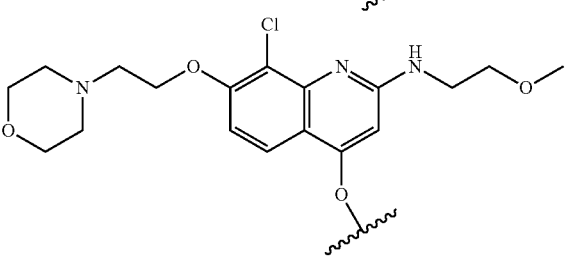
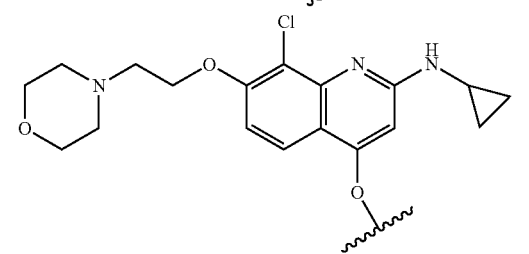
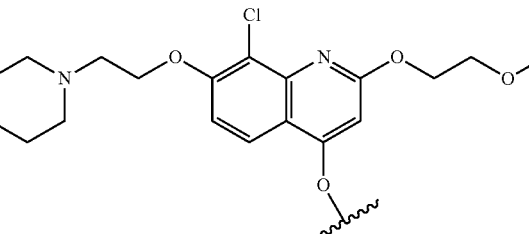
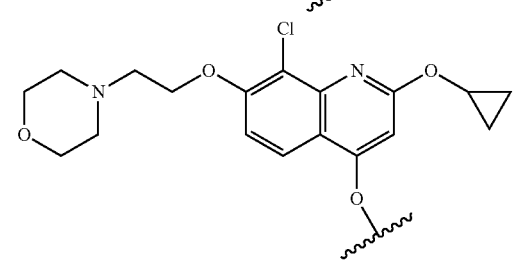

101
-continued
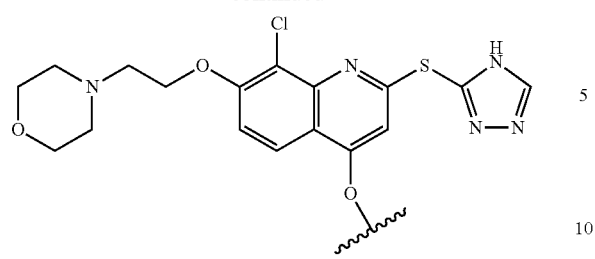
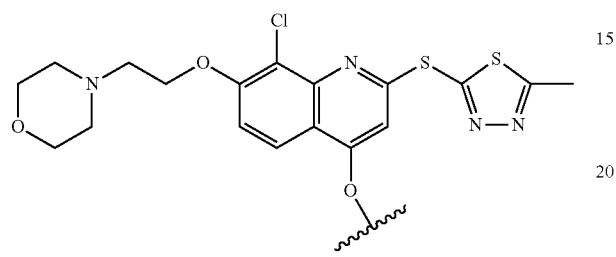
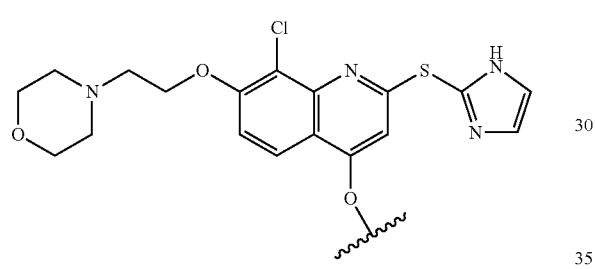
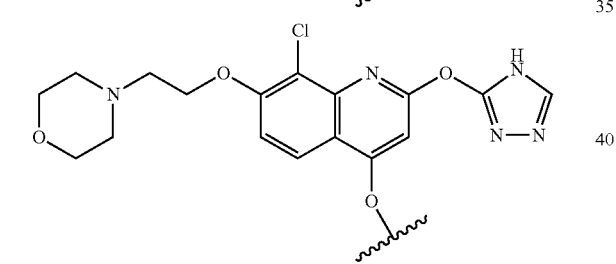
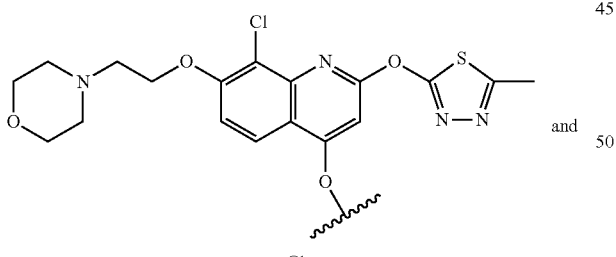
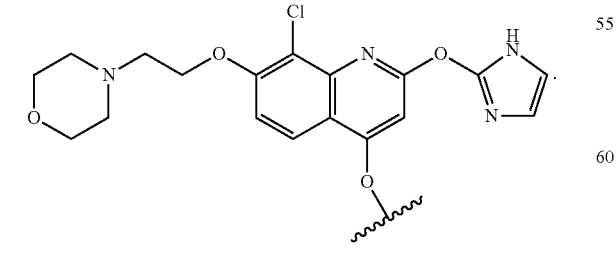
and
102
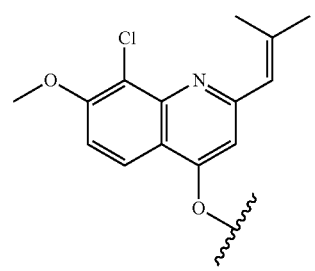
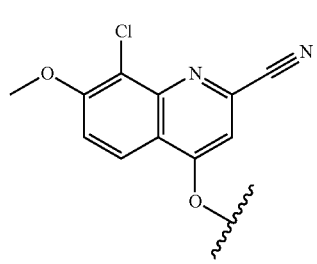
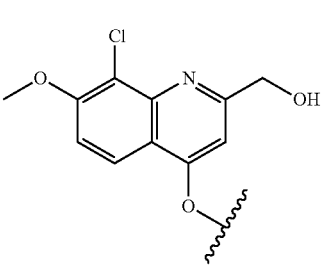
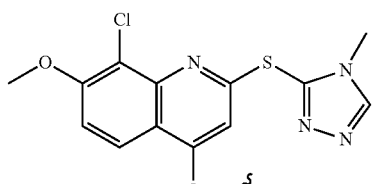
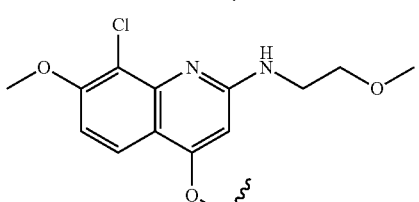
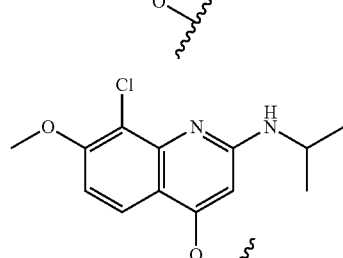
In a specific embodiment of the invention $Z^1$ is selected from the following structures:

103
-continued
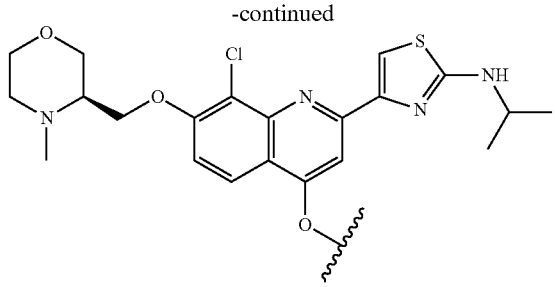
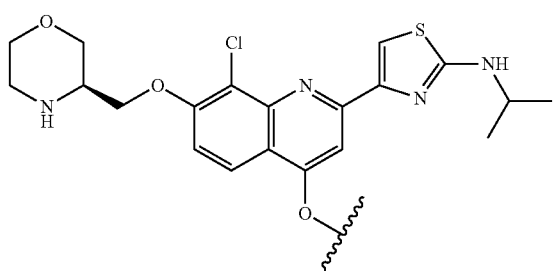
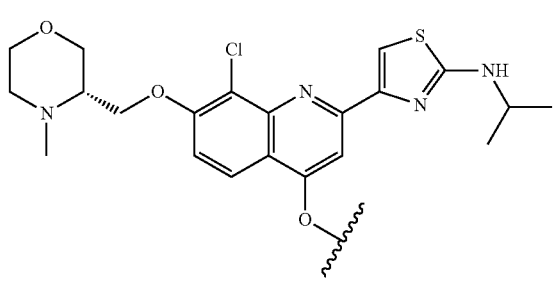
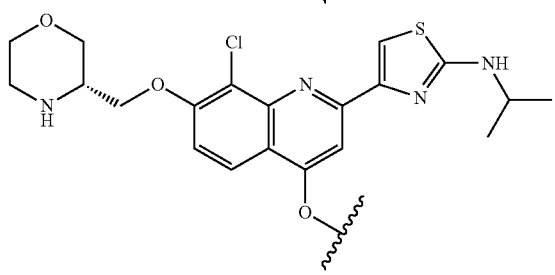
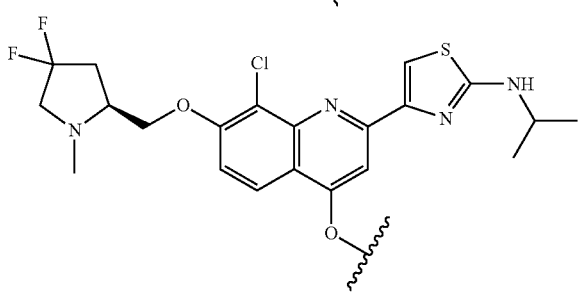
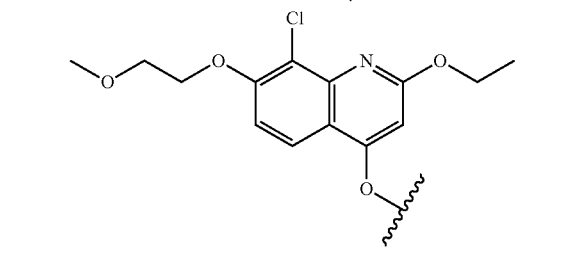
104
-continued
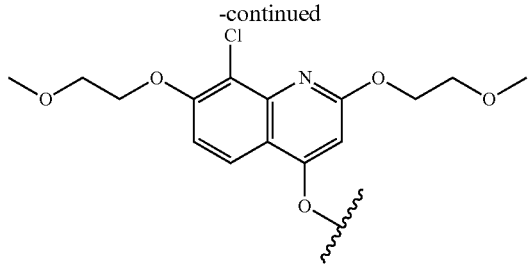
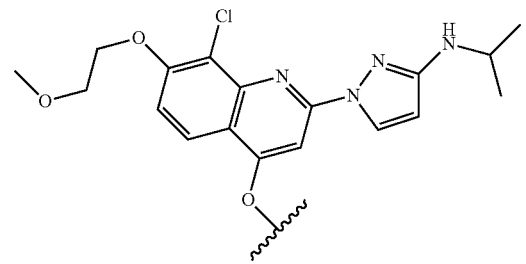
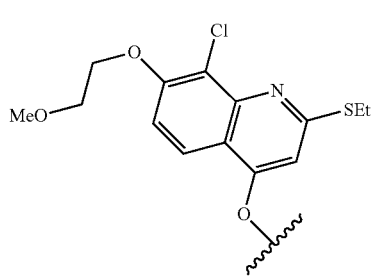
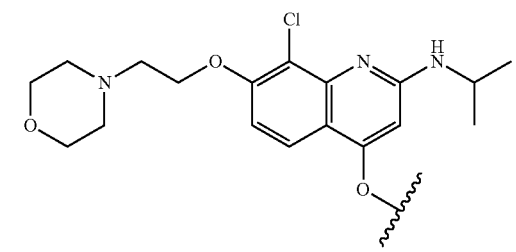
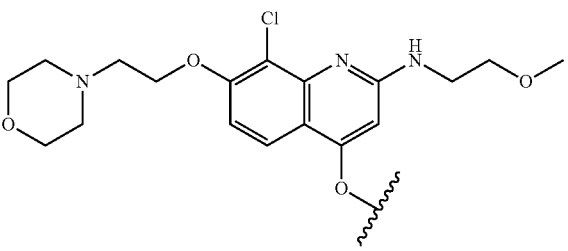
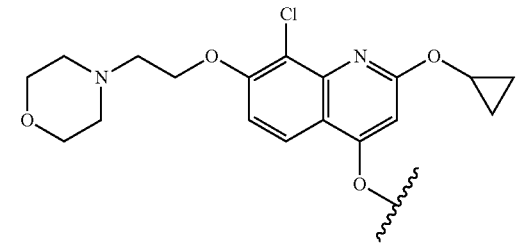

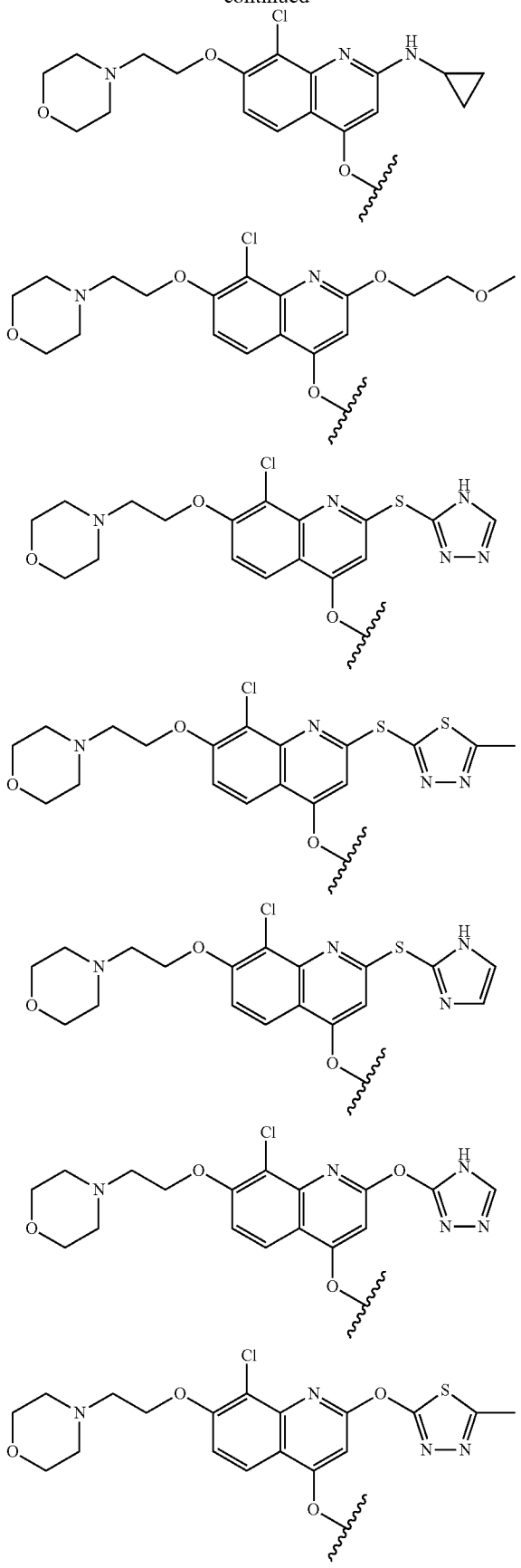
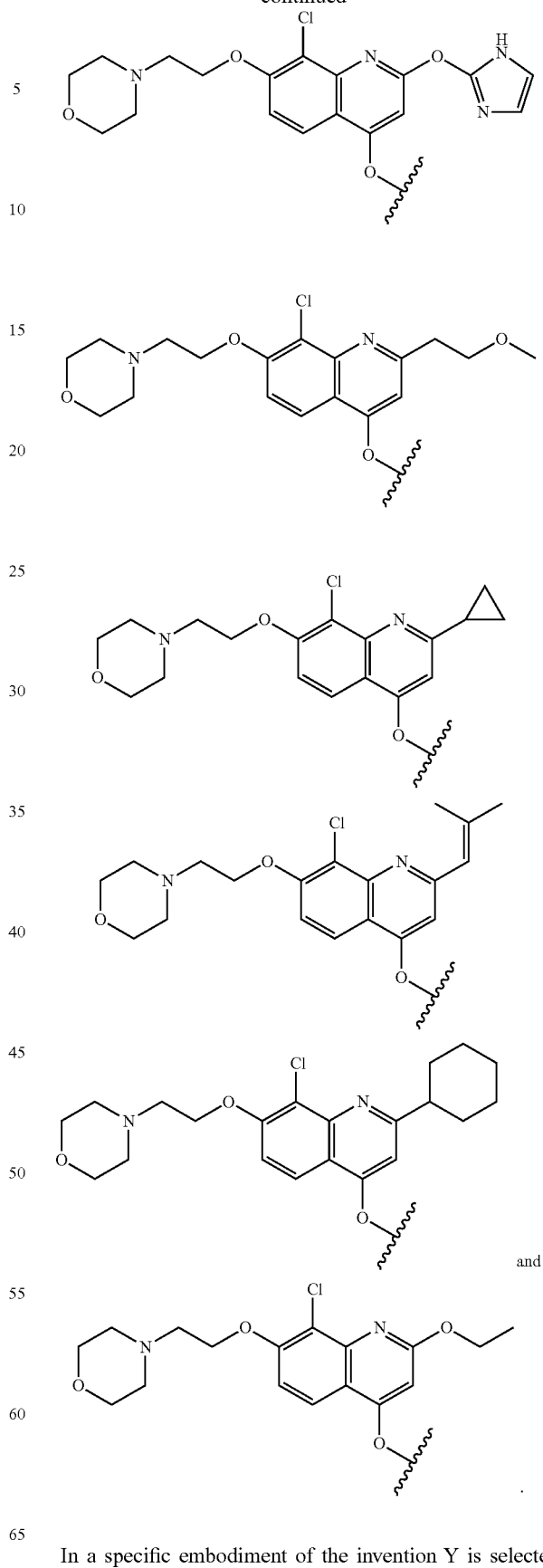
In a specific embodiment of the invention Y is selected from:

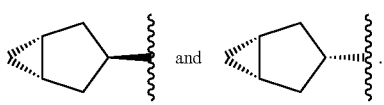 [SMILES: *[C@H]1C[C@@H]2C[C@@H]2C1 ; *[C@@H]1C[C@@H]2C[C@@H]2C1]

In a specific embodiment the invention provides a formula I:

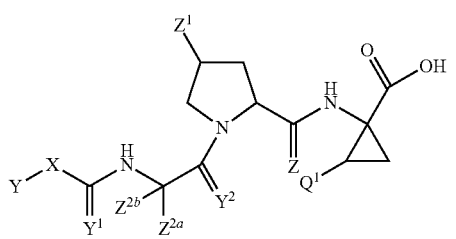

or a pharmaceutically acceptable salt, or prodrug thereof, wherein:

$Y^1$ is O, S, or $NR^3$;
$Y^2$ is O, S, or $NR^3$;
Z is O, S, or $NR^3$;
$Z^1$ is selected from the following structures:

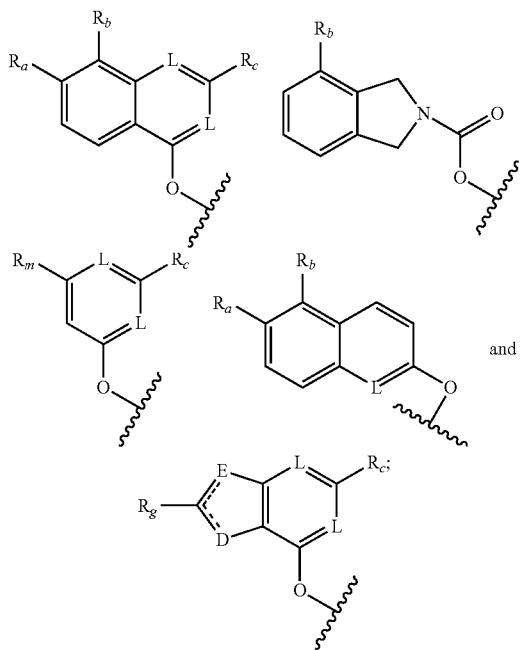

each $R_a$ is $R^1$, H, trifluoromethoxy, $NR_sR_t$, $C(=O)NR_sR_t$, $S(=O)_2NR_sR_t$ or (C1-10)alkyl, wherein one or more carbon atoms of said (C1-10)alkyl is optionally replaced by O, S, $S(=O)$, $S(=O)_2$ or $NR_g$ and which (C1-10)alkyl is optionally substituted with one or more hydroxy, halo, cyano, $NR_nR_p$, $C(=O)NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_g$;

each $R_b$ is $R^1$, H, F, Cl, Br, I, $CF_3$, (C1-10)alkyl, or $XR^3$;
each $R_c$ is $R^1$, H, cyano, F, Cl, Br, I, $-C(=O)NR_dR_e$, $C(=O)NR_dR_e$, $NR_sR_t$, $S(=O)_2NR_sR_t$, (C1-10)alkoxy, cycloalkyl, aryl, or heteroaryl, which aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

$R_d$ and $R_e$ are each independently H or (C1-10)alkyl;

each $R_f$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_g$ is H, $NR_sR_t$, $C(=O)NR_sR_t$, $S(=O)_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_sR_p$, $SR_r$, $S(O)R_r$, or $S(O)_2R_r$;

each $R_h$ is H, $A^3$, $C(=O)NR_sR_t$, or $S(=O)_2NR_sR_t$;

each $R_m$ is H, cyano, F, Cl, Br, I, $-C(=O)NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_f$ and the other E or D is $CR_h$ or N;

$Z^{2a}$ is H, (C1-10)alkyl, (C2-10)alkenyl, (C2-10)alkynyl, haloalkyl, (C1-10)alkyl, $-S(=O)_2-$(C1-10)alkyl, or cycloalkyl, wherein any carbon atom of $Z^{2a}$ may optionally be replaced with a heteroatom selected from O, S or $NR_g$ and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with $Q^1$;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^1$ or $R_c$; or $Q^1$ and $Z^{2a}$ taken together with the atoms to which they are attached form a heterocycle, which heterocycle may optionally be substituted with one or more oxo $(=O)$, $R^1$, or $A^3$;

each X is independently a bond, O, S, or $NR^3$;

Y is a polycarbocycle or a polyheterocycle, which polycarbocycle or a polyheterocycle is optionally substituted with one or more $R^1$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

each $R^1$ is independently $-P(Y^3)(OA^2)(OA^2)$, $-P(Y^3)(OA^2)(N(A^2)_2)$, $-P(Y^3)(A^2)(OA^2)$, $-P(Y^3)(A^2)(N(A^2)_2)$, or $P(Y^3)(N(A^2)_2)(N(A^2)_2)$;

each $A^2$ is independently H, (C1-10)alkyl, (C2-10)alkenyl, (C2-10)alkynyl, (C1-10)haloalkyl, (C3-10)cycloalkyl, aryl, or heteroaryl;

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring, which ring is optionally substituted with one or more (C1-10)alkyl or (C1-10)alkoxy, and which (C1-10)alkyl or (C1-10)alkoxy is optionally substituted with one or more halo;

each $R_r$ is independently H, (C1-10)alkyl, (C2-10)alkenyl, (C2-10)alkynyl, (C1-10)alkanoyl, or (C1-10)alkoxycarbonyl;

each $R_s$ and $R_t$ is independently H, (C1-10)alkyl, (C2-10)alkenyl, (C2-10)alkynyl, (C1-10)alkanoyl, $S(=O)_2A^2$, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by $S(=O)$, $S(=O)_2$, or $C(=O)$;

each $A^3$ is independently selected from halo, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$; and $R^3$ is H or (C1-10)alkyl.

In one embodiment the invention provides a compound of the invention which is a compound of formula I:

(I)

or a pharmaceutically acceptable salt, or prodrug thereof, wherein:

$Y^1$ is O, S, or $NR^3$;
$Y^2$ is O, S, or $NR^3$;
Z is O, S, or $NR^3$;
$Z^1$ is selected from the following structures:

and each $R_a$ is $R^1$, H, trifluoromethoxy, $NR_sR_t$, $C(=O)NR_sR_t$, $S(=O)_2NR_sR_t$ or (C1-10)alkyl, wherein one or more carbon atoms of said (C1-10)alkyl is optionally replaced by O, S, $S(=O)$, $S(=O)_2$ or $NR_g$ and which (C1-10)alkyl is optionally substituted with one or more hydroxy, halo, cyano, $NR_nR_p$, $C(=O)NR_nR_p$, (C1-10)alkoxy, carboxy, (C1-10)alkoxycarbonyl, aryl, heteroaryl, or heterocyclyl; or $R_a$ and $R_b$ taken together with the atoms to which they are attached form a 5 or 6 membered heterocyclic ring containing one or more O, S, or $NR_g$;

each $R_b$ is $R^1$, H, F, Cl, Br, I, $CF_3$, (C1-10)alkyl, or $XR^3$;

each $R_c$ is $R^1$, H, cyano, F, Cl, Br, I, $—C(=O)NR_dR_e$, $C(=O)NR_sR_t$, $NR_sR_t$, $S(=O)—_2NR_sR_t$, (C1-10)alkyl, (C1-10)alkoxy, cycloalkyl, $OR_r$, $SR_r$, $S(O)R_r$, $S(O)_2R_r$, aryl, or heteroaryl, which (C1-10)alkyl, (C1-10)alkoxy, cycloalkyl, aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

$R_d$ and $R_e$ are each independently H or (C1-10)alkyl;

each $R_f$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_g$ is H, $NR_sR_t$, $C(=O)NR_sR_t$, $S(=O)_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_h$ is H, $A^3$, $C(=O)NR_sR_t$, or $S(=O)_2NR_sR_t$;

each $R_m$ is H, cyano, F, Cl, Br, I, $—C(=O)NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_f$ and the other E or D is $CR_h$ or N;

$Z^{2a}$ is H, (C1-10)alkyl, (C2-10)alkenyl, (C2-10)alkynyl, haloalkyl, (C1-10)alkyl, $—S(=O)_2—$(C1-10)alkyl, or cycloalkyl, wherein any carbon atom of $Z^{2a}$ may optionally be replaced with a heteroatom selected from O, S or $NR_g$ and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with $Q^1$;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^1$ or $R_c$; or $Q^1$ and $Z^{2a}$ taken together with the atoms to which they are attached form a heterocycle, which heterocycle may optionally be substituted with one or more oxo (=O), $R^1$, or $A^3$;

each X is independently a bond, O, S, or $NR^3$;

Y is a polycarbocycle or a polyheterocycle, which polycarbocycle or a polyheterocycle is optionally substituted with one or more $R^1$, halo, carboxy, hydroxy, (C1-10)alkyl, (C2-10)alkenyl, (C2-10)alkynyl, (C1-10)alkanoyl, (C1-10)alkoxy, (C1-C10)alkanoyloxy, (C1-10)alkoxycarbonyl, $NR_nR_p$; $SR_r$, $S(O)R_r$, or $S(O)_2R_r$;

each $R^1$ is independently $—P(Y^3)(OA^2)(OA^2)$, $—P(Y^3)(OA^2)(N(A^2)_2)$, $—P(Y^3)(A^2)(OA^2)$, $—P(Y^3)(A^2)(N(A^2)_2)$, or $P(Y^3)(N(A^2)_2)(N(A^2)_2)$;

each $A^2$ is independently H, (C1-10)alkyl, (C2-10)alkenyl, (C2-10)alkynyl, (C1-10)haloalkyl, (C3-10)cycloalkyl, aryl, or heteroaryl;

each $Y^3$ is independently O, S, or $NR^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$ halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring; which ring is optionally substituted with one or more (C1-10)alkyl or (C1-10)alkoxy, and which (C1-10)alkyl or (C1-10)alkoxy is optionally substituted with one or more halo;

each $R_r$ is independently H, (C1-10)alkyl, cycloalkyl, (C2-10)alkenyl, (C2-10)alkynyl, (C1-10)alkanoyl, aryl, heteroaryl, or (C1-10)alkoxycarbonyl;

each $R_s$ and $R_t$ is independently H, (C1-10)alkyl, cycloalkyl, (C2-10)alkenyl, (C2-10)alkynyl, (C1-10)alkanoyl, $S(=O)_2A^2$, (C1-10)alkoxy, (C1-10)alkanoyloxy, or (C1-10)alkoxycarbonyl, which (C1-10)alkyl, cycloalkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by $S(=O)$, $S(=O)_2$, or $C(=O)$;

each $A^3$ is independently selected from halo, hydroxy, carboxy, cyano, (C1-10)alkyl, (C2-10)alkenyl, (C2-10)alkynyl, (C1-10)alkanoyl, (C1-10)alkoxy, (C1-C10)alkanoyloxy, (C1-10)alkoxycarbonyl, $NR_nR_p$, $SR_r$, $S(O)R_r$, or $S(O)_2R_r$; and $R^3$ is H or (C1-10)alkyl.

In a specific embodiment of the invention the compound is a prodrug or a pharmaceutically acceptable salt thereof.

Specific Embodiment 1

In one specific embodiment the invention provides a compound of formula I:

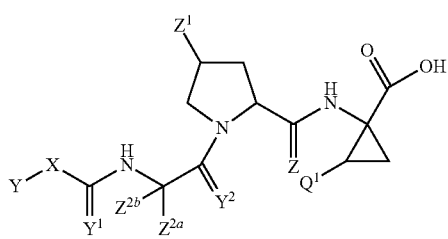

(I)

or a pharmaceutically acceptable salt, or prodrug thereof, wherein:

$Y^1$ is O, S, or $NR^3$;
$Y^2$ is O, S, or $NR^3$;
Z is O, S, or $NR^3$;

$Z^1$ is selected from the following structures:

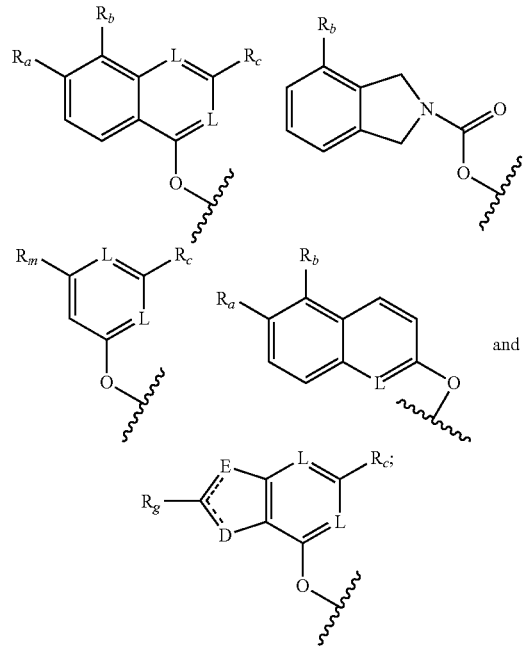

and each $R_a$ is $R^1$, H, trifluoromethoxy, $NR_sR_t$, $C(=O)NR_sR_t$, $S(=O)_2NR_sR_t$ or (C1-10)alkyl, wherein one or more carbon atoms of said (C1-10)alkyl is optionally replaced by O, S, $S(=O)$, $S(=O)_2$ or $NR_g$ and which (C1-10)alkyl is optionally substituted with one or more hydroxy, halo, cyano, $NR_nR_p$, $C(=O)NR_nR_p$, (C1-10)alkoxy, carboxy, (C1-10)alkoxycarbonyl, aryl, heteroaryl, or heterocyclyl and which heterocyclyl is optionally substituted with one or more $A^3$; or $R_a$ and $R_b$ taken together with the atoms to which they are attached form a 5 or 6 membered heterocyclic ring containing one or more O, S, or $NR_g$;

each $R_b$ is $R^1$, H, F, Cl, Br, I, $CF_3$, (C1-10)alkyl, or $XR^3$;

each $R_c$ is $R^1$, H, cyano, F, Cl, Br, I, —$C(=O)NR_dR_e$, $C(=O)NR_sR_t$, $NR_sR_t$, $S(=O)$—$_2NR_sR_t$, (C1-10)alkyl, (C2-10)alkenyl, (C2-10)alkynyl, (C1-10)alkoxy, cycloalkyl, $OR_r$, $SR_r$, $S(O)R_r$, $S(O)_2R_r$, aryl, or heteroaryl, which (C1-10)alkyl, (C1-10)alkoxy, cycloalkyl, aryl or heteroaryl is optionally substituted with one or more groups independently selected from halo, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$; $SR_r$, $S(O)R_r$, or $S(O)_2R_r$;

$R_d$ and $R_e$ are each independently H or (C1-10)alkyl;

each $R_f$ is H, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-C10)alkoxycarbonyl, $NR_nR_p$, $SR_r$, $S(O)R_r$, or $S(O)_2R_r$;

each $R_g$ is H, $NR_sR_t$, $C(=O)NR_sR_t$, $S(=O)_2NR_sR_t$, $A^2$, hydroxy, carboxy, cyano, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, $NR_nR_p$, $SR_r$, $S(O)R_r$, or $S(O)_2R_r$;

each $R_h$ is H, $A^3$, $C(=O)NR_sR_t$, or $S(=O)_2NR_sR_t$;

each $R_m$ is H, cyano, F, Cl, Br, I, —$C(=O)NR_dR_e$, (C1-10)alkoxy, cycloalkyl, or phenyl that is optionally substituted with one or more F, Cl, Br, I, (C1-10)alkyl, or (C1-10)alkoxy;

each L is independently CH or N;

one of E or D is O, S, or $NR_f$ and the other E or D is $CR_h$ or N;

$Z^{2a}$ is H, (C1-10)alkyl, (C2-10)alkenyl, (C2-10)alkynyl, haloalkyl, (C1-10)alkyl, —S(=O)$_2$—(C1-10)alkyl, or cycloalkyl, wherein any carbon atom of $Z^{2a}$ may optionally be replaced with a heteroatom selected from O, S or NR$_g$ and wherein any cycloalkyl is optionally substituted with one or more (C1-10)alkyl, (C2-10)alkenyl, (C2-10)alkynyl, F, Cl, Br, or I; or $Z^{2a}$ optionally forms a heterocycle with $Q^1$;

$Z^{2b}$ is H, (C1-10)alkyl, (C2-10)alkenyl, (C2-10)alkynyl;

$Q^1$ is (C1-10)alkyl, (C2-10)alkenyl, or (C2-10)alkynyl which $Q^1$ is optionally substituted with $R^1$ or $R_c$; or $Q^1$ and $Z^{2a}$ taken together with the atoms to which they are attached form a heterocycle, which heterocycle may optionally be substituted with one or more oxo (=O), $R^1$, or $A^3$;

each X is independently a bond, O, S, or NR$^3$;

Y is a polycarbocycle or a polyheterocycle, which polycarbocycle or a polyheterocycle is optionally substituted with one or more $R^1$, halo, carboxy, hydroxy, (C1-10)alkyl, (C2-10)alkenyl, (C2-10)alkynyl, (C1-10)alkanoyl, (C1-10)alkoxy, (C1-10)alkanoyloxy, (C1-10)alkoxycarbonyl, NR$_n$R$_p$; SR$_r$, S(O)R$_r$, or S(O)$_2$R$_r$;

each $R^1$ is independently —P(Y$^3$)(OA$^2$)(OA$^2$), —P(Y$^3$)(OA$^2$)(N(A$^2$)$_2$), —P(Y$^3$)(A$^2$)(OA$^2$), —P(Y$^3$)(A$^2$)(N(A$^2$)$_2$), or P(Y$^3$)(N(A$^2$)$_2$)(N(A$^2$)$_2$);

each $A^2$ is independently H, (C1-C10)alkyl, (C2-10)alkenyl, (C2-10)alkynyl, (C1-10)haloalkyl, (C3-10)cycloalkyl, aryl, or heteroaryl;

each $Y^3$ is independently O, S, or NR$^3$;

each $R_n$ and $R_p$ is independently H, (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, which (C1-10)alkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$, halo, hydroxy, carboxy, cyano, or (C1-10)alkoxy; or $R_n$ and $R_p$ together with the nitrogen to which they are attached form a pyrrolidine, piperidine, piperazine, morpholino, or thiomorpholino ring; which ring is optionally substituted with one or more (C1-10)alkyl or (C1-10)alkoxy, and which (C1-10)alkyl or (C1-10)alkoxy is optionally substituted with one or more halo;

each $R_r$ is independently H, (C1-10)alkyl, cycloalkyl, (C2-10)alkenyl, (C2-10)alkynyl, (C1-10)alkanoyl, aryl, heteroaryl, or (C1-10)alkoxycarbonyl;

each $R_s$ and $R_t$ is independently H, (C1-10)alkyl, cycloalkyl, (C2-10)alkenyl, (C2-10)alkynyl, (C1-10)alkanoyl, S(=O)$_2$A$^2$, (C1-10)alkoxy, (C1-10)alkanoyloxy, or (C1-10)alkoxycarbonyl, which (C1-10)alkyl, cycloalkyl, (C2-10)alkenyl, (C2-10)alkynyl, (C1-10)alkanoyl, (C1-10)alkoxy, (C1-10)alkanoyloxy, or (C1-10)alkoxycarbonyl, is optionally substituted with one or more $R^1$, halo hydroxy, carboxy, cyano, or (C1-10)alkoxy; or $R_s$ and $R_t$ together with the nitrogen to which they are attached form a pyrrolidine, piperidine, piperazine, morpholino, or thiomorpholino ring wherein one or more carbon atoms of said pyrrolidine, piperidine, piperazine, morpholino or thiomorpholino ring is optionally replaced by S(=O), S(=O)$_2$, or C(=O);

each $A^3$ is independently selected from halo, hydroxy, carboxy, cyano, (C1-10)alkyl, (C2-10)alkenyl, (C2-10)alkynyl, (C1-10)alkanoyl, (C1-10)alkoxy, (C1-C10)alkanoyloxy, (C1-10)alkoxycarbonyl, NR$_s$R$_p$, SR$_r$, S(O)R$_r$, or S(O)$_2$R$_r$; and $R^3$ is H or (C1-10)alkyl.

Specific Embodiment 2

In one specific embodiment the invention provides the compound of Specific Embodiment 1 wherein X is O, S, or NR$^3$.

Specific Embodiment 3

In one specific embodiment the invention provides the compound of Specific Embodiment 2 wherein $Z^1$ is selected from the following structures:

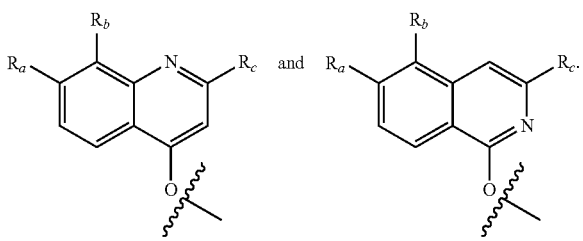

Specific Embodiment 4

In one specific embodiment the invention provides the compound of Specific Embodiment 3 wherein $R_c$ is a heteroaryl ring selected from:

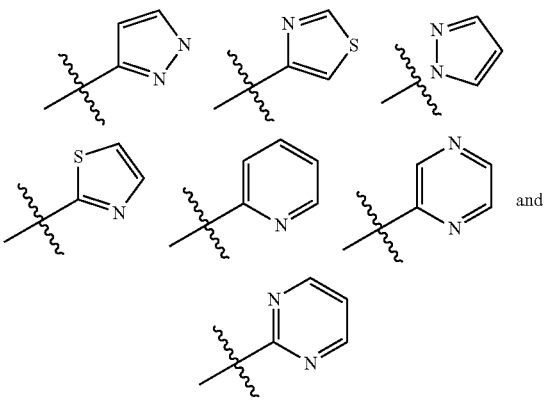

which heteroaryl ring is optionally substituted with one or more (C1-10)alkyl, halo, or NR$_n$R$_p$; wherein each $R_n$ and $R_p$ is independently H or (C1-10)alkyl.

Specific Embodiment 5

In one specific embodiment the invention provides the compound of Specific Embodiment 3 wherein each $R_c$ is selected from:

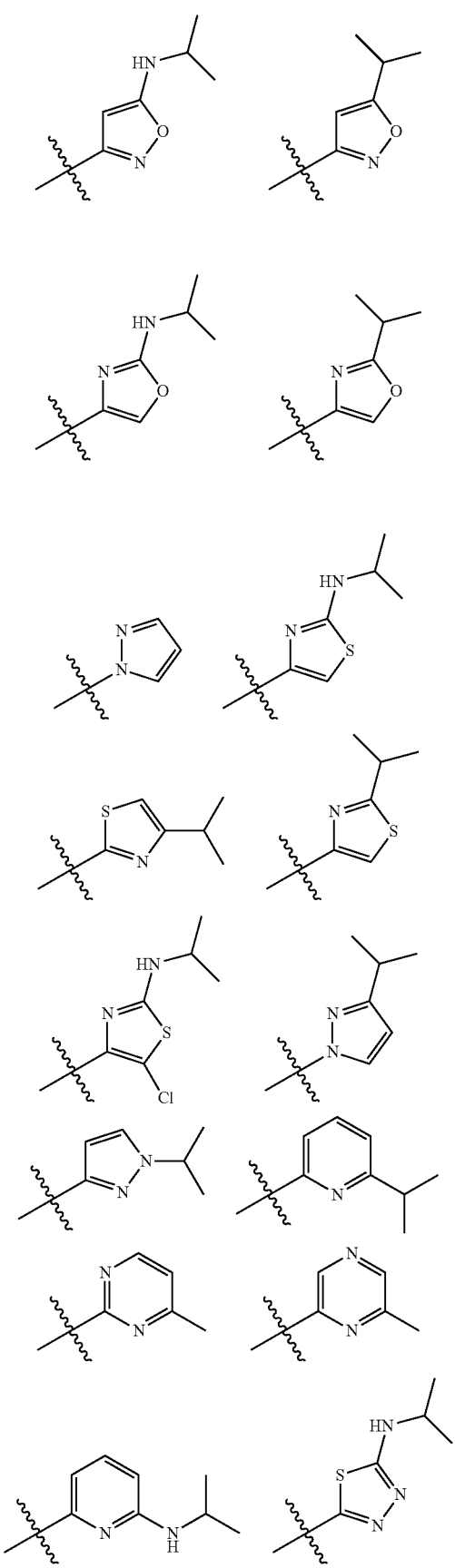
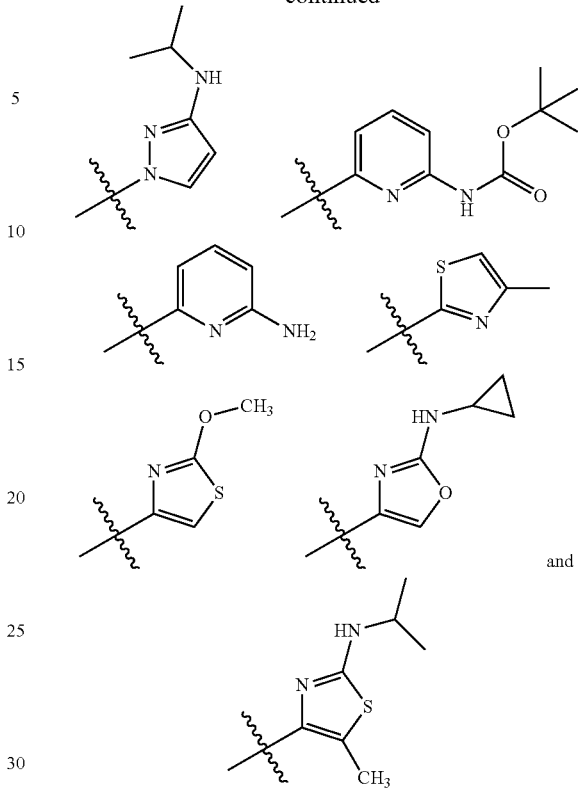

Specific Embodiment 6

In one specific embodiment the invention provides the compound of Specific Embodiment 3 wherein $R_b$ is H or Cl.

Specific Embodiment 7

In one specific embodiment the invention provides the compound of Specific Embodiment 3 wherein $R_a$ is H, methoxy, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, 2-morpholinoethoxy, cyanomethoxy, 2-piperazin-1-ylethoxy, 2-(N,N-dimentylamino)ethoxy, 2-(3,3-dimethylmorpholino)ethoxy, 2-(4-methylpiperazin-1-yl)ethoxy, or carboxymethoxy.

Specific Embodiment 8

In one specific embodiment the invention provides the compound of Specific Embodiment 3 wherein $R_a$ is H, methoxy, N-(2-cyanoethyl)amino, N-(3,3,3-trifluoroethyl)amino, 2-methoxyethoxy, 2-hydroxyethoxy, 2-hydroxy-2-methylpropoxy, 2-amino-2-methylpropoxy, N,N-dimethylaminocarbonylmethoxy, morpholinocarbonylmethoxy, 2-[N-(2,2,2-trifluoroethyl)amino]ethoxy, or 2-morpholinoethoxy.

Specific Embodiment 9

In one specific embodiment the invention provides the compound of Specific Embodiment 2 wherein $Z^1$ is selected from the following structures:

117
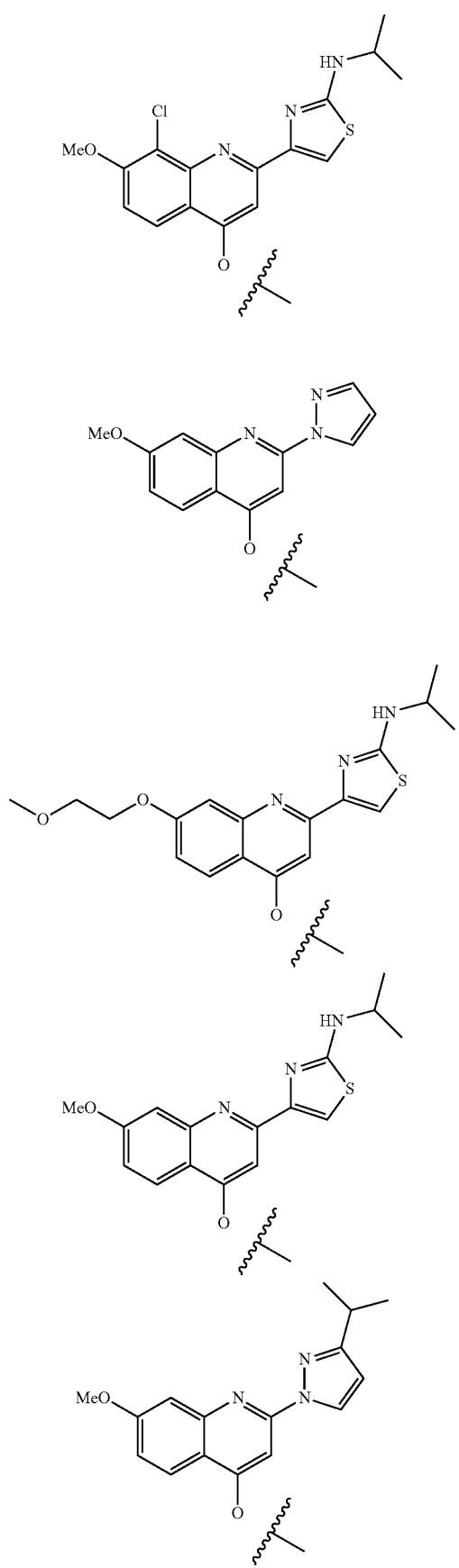
118
-continued
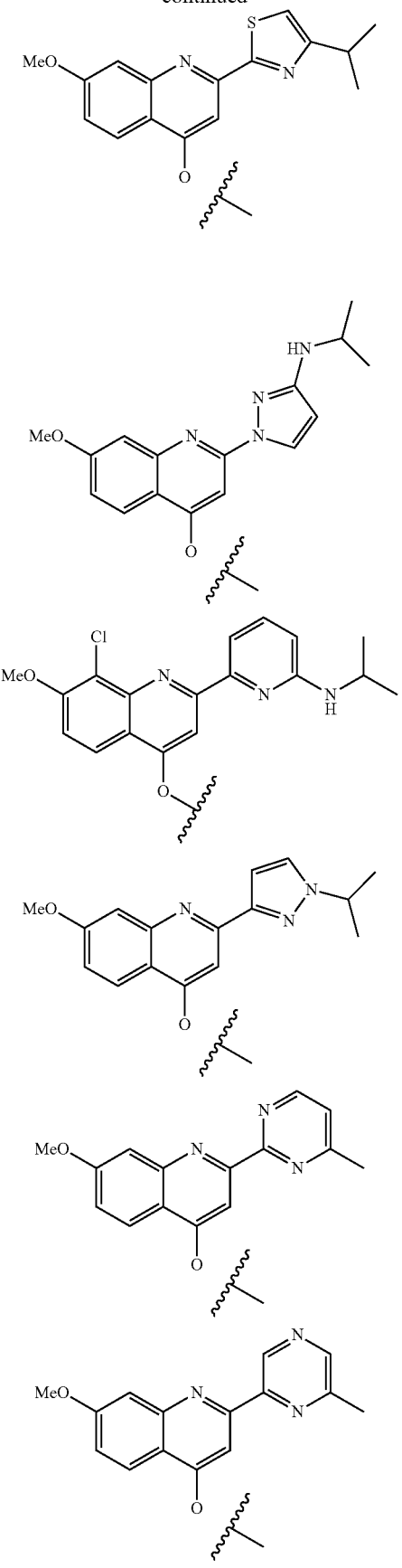

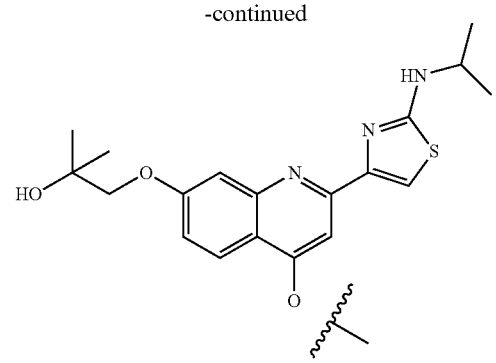
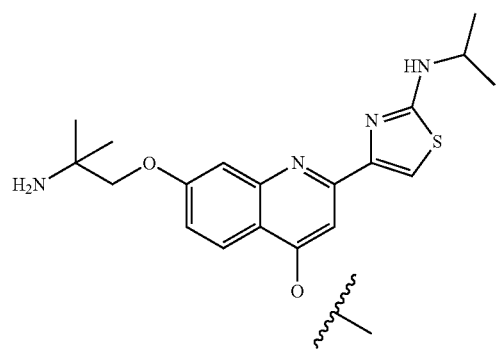
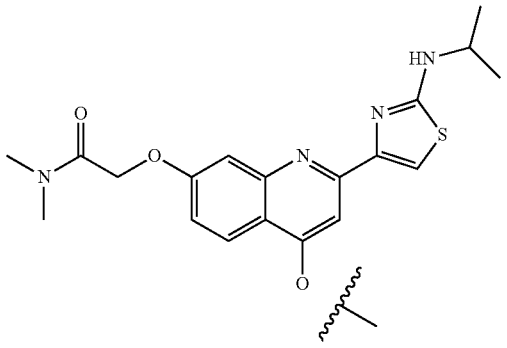
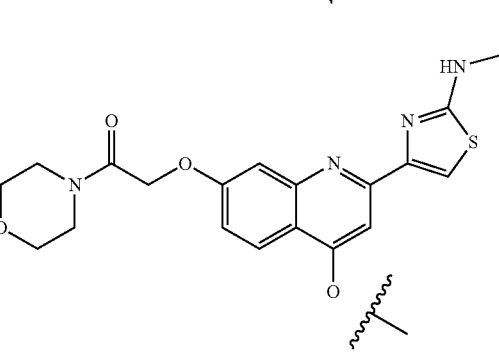
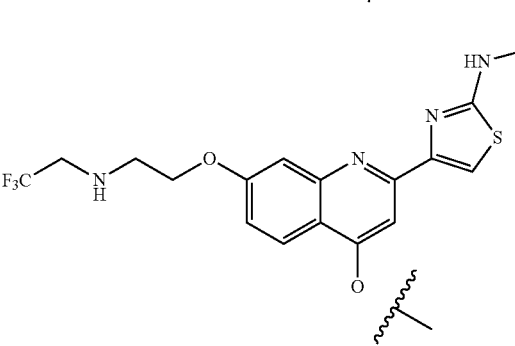
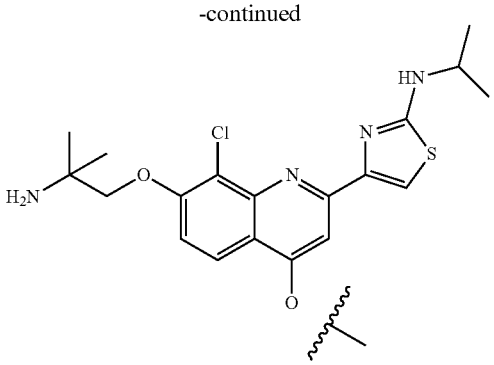
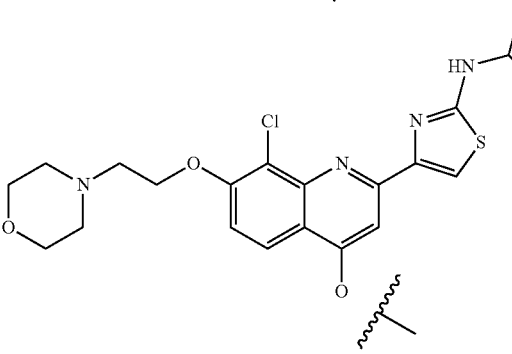
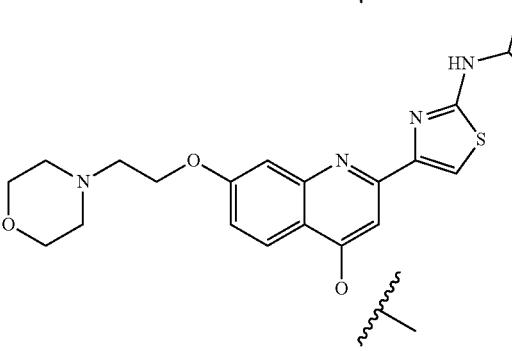
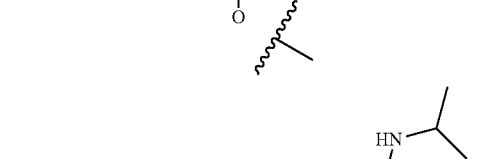
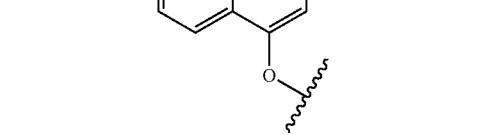

121
-continued
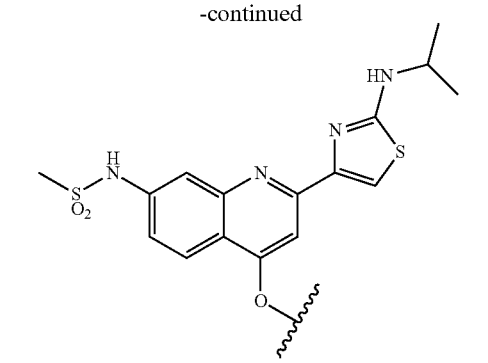
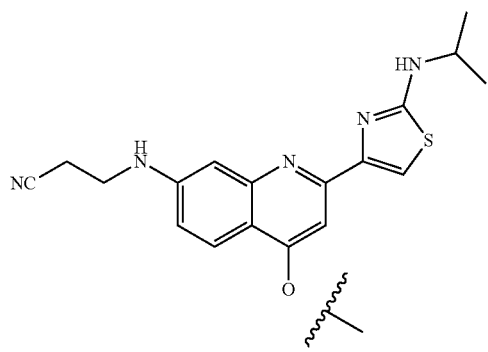
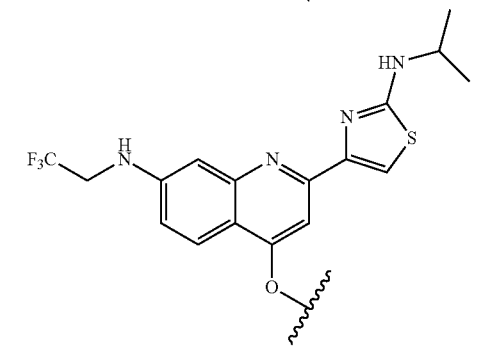
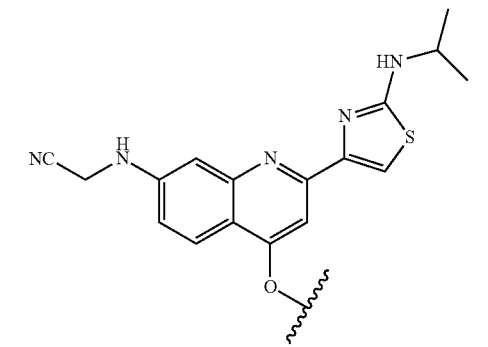
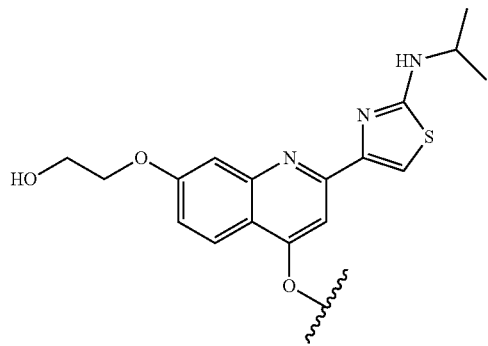
122
-continued
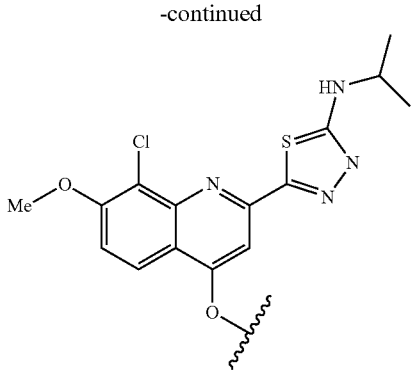
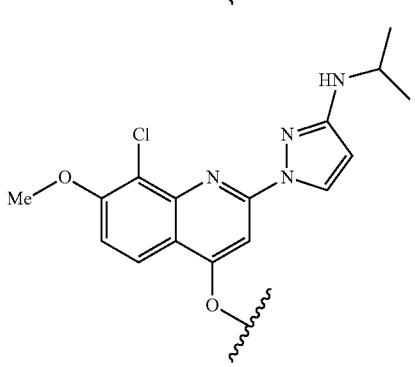
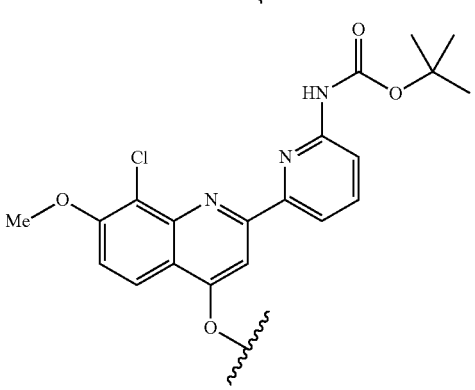
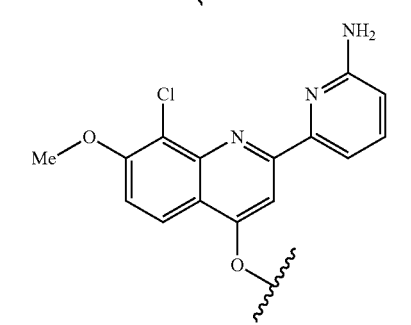
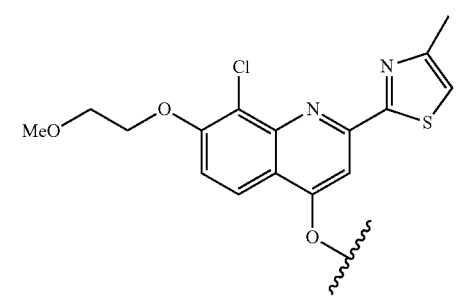

123
-continued
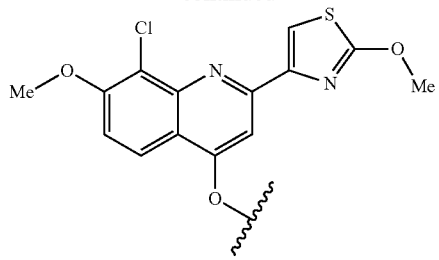
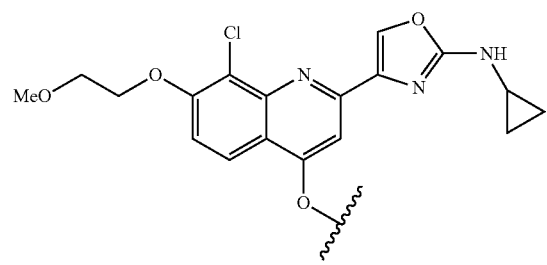
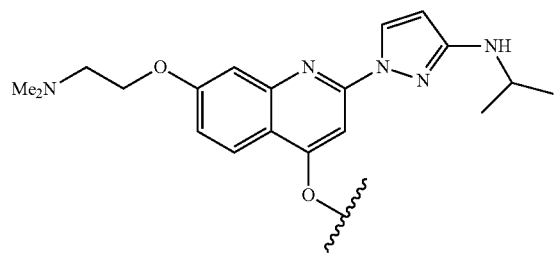
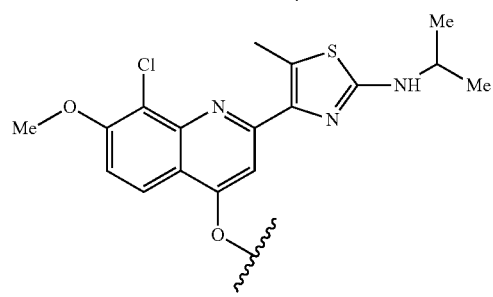
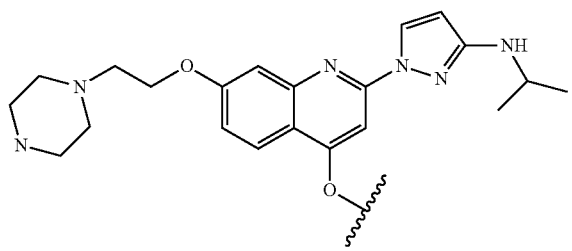
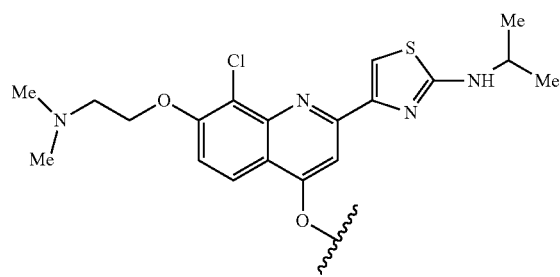
124
-continued
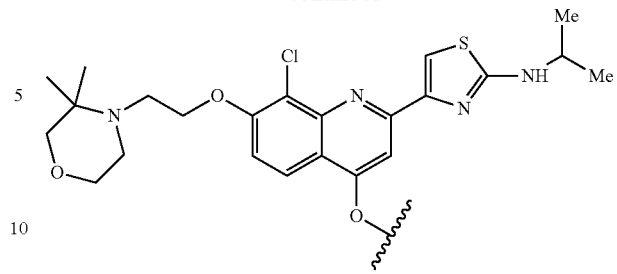
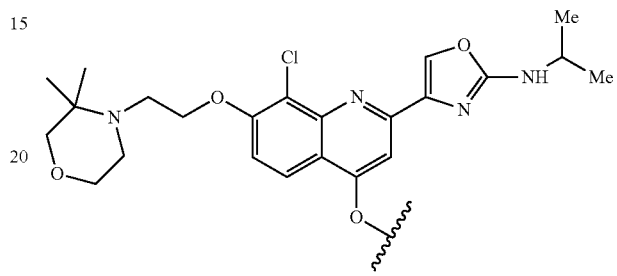
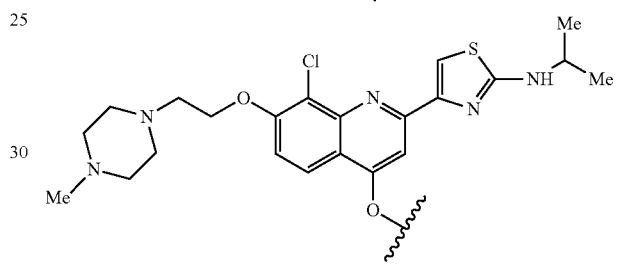
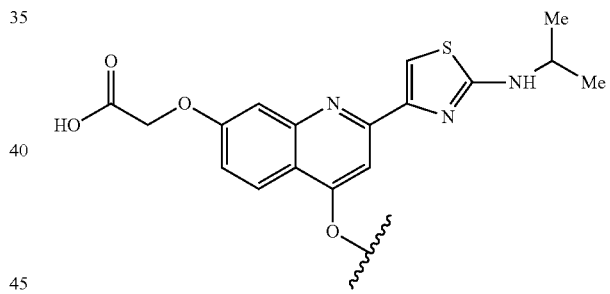
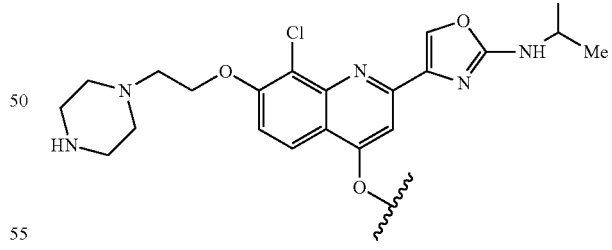
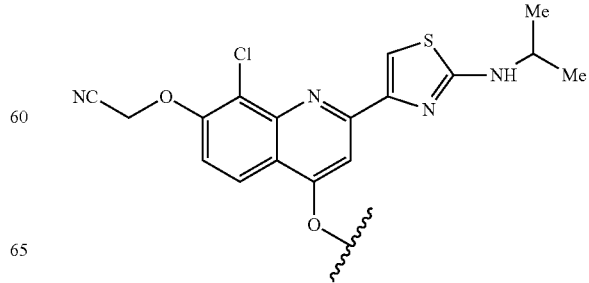

125
-continued
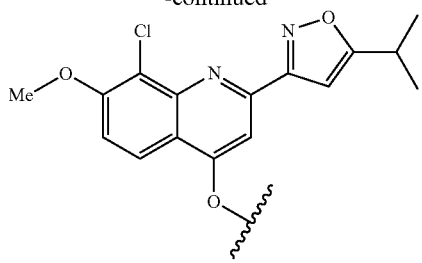
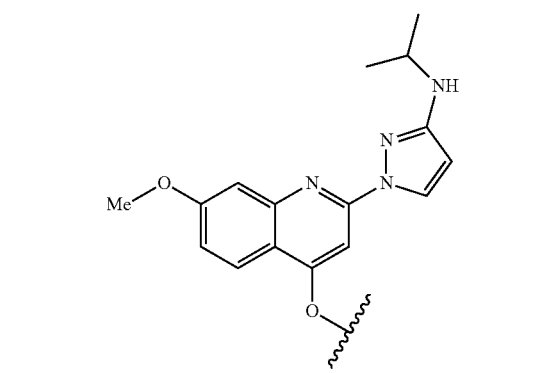
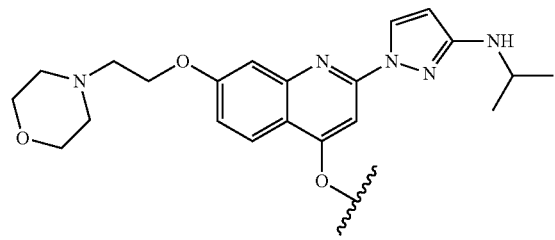
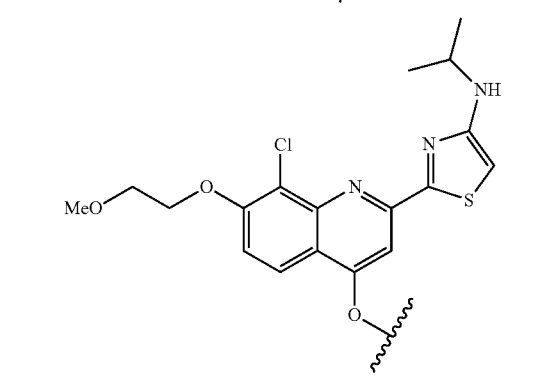
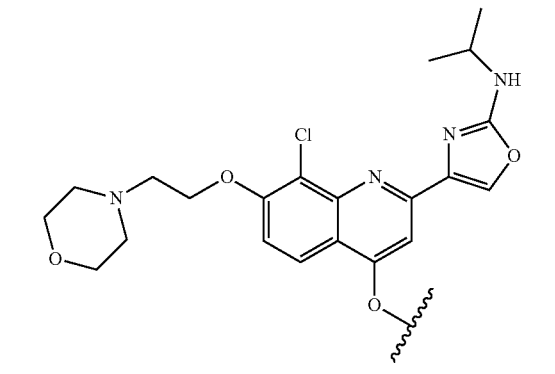
126
-continued
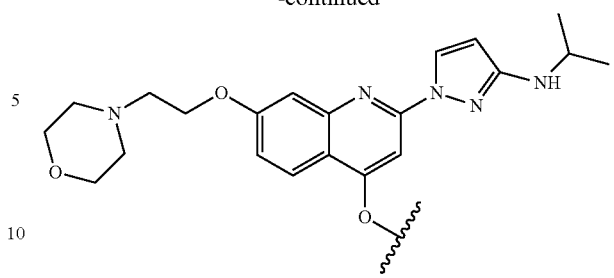
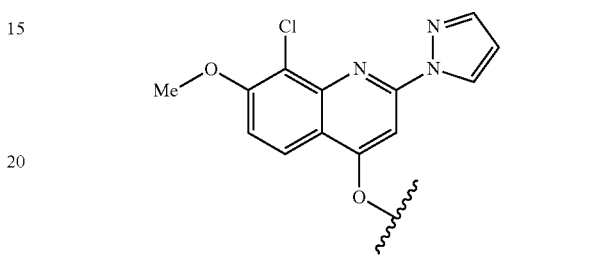
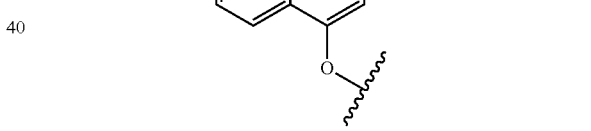
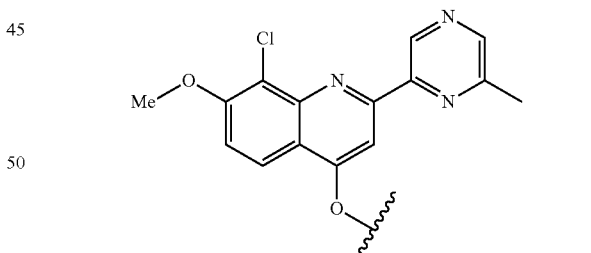
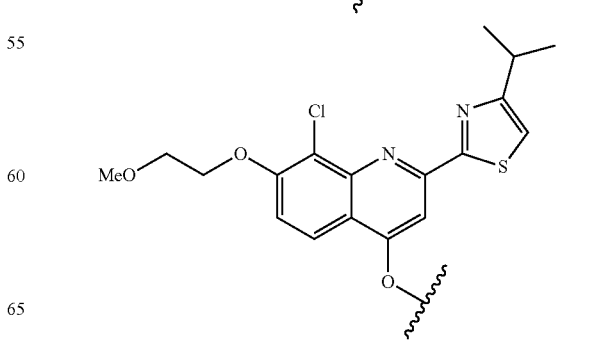

127
-continued
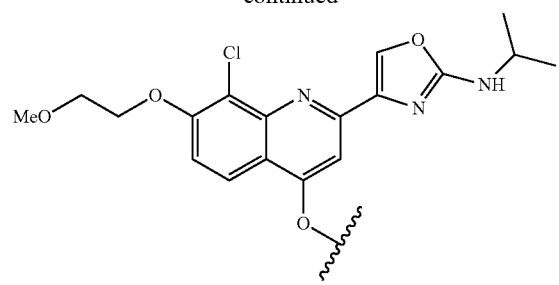
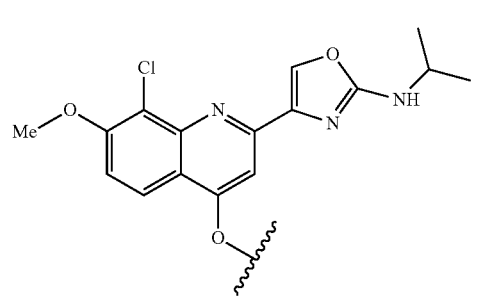
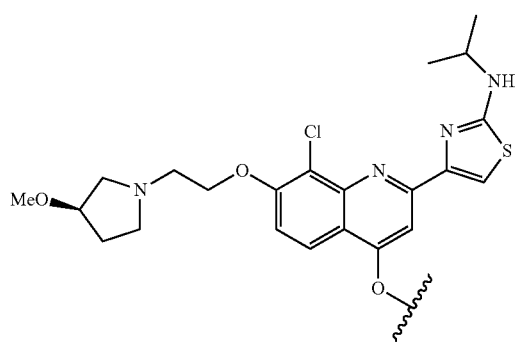
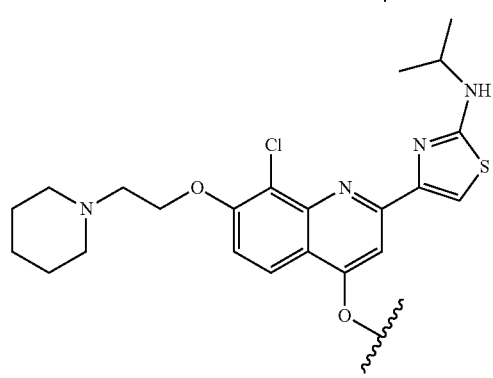
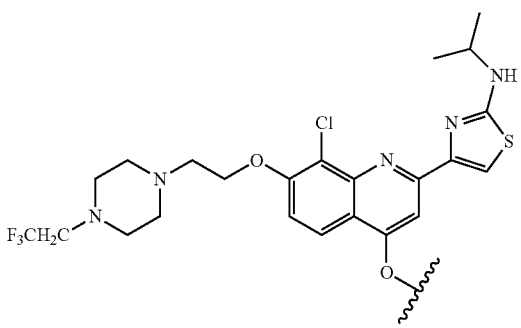
and
128
-continued
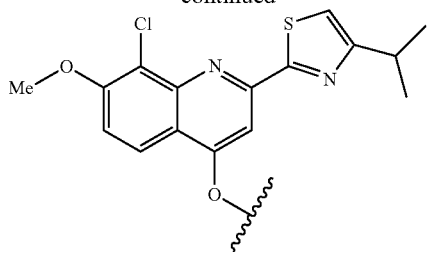
Specific Embodiment 10
In one specific embodiment the invention provides the compound of Specific Embodiment 2 wherein $Z^1$ is selected from the following structures:
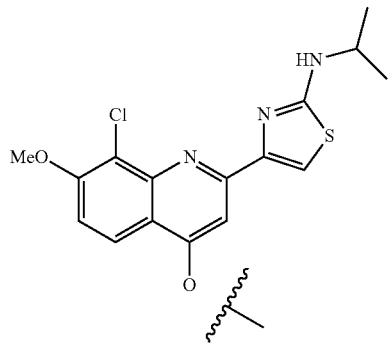
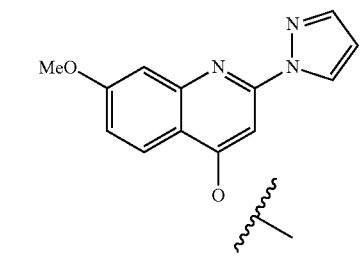
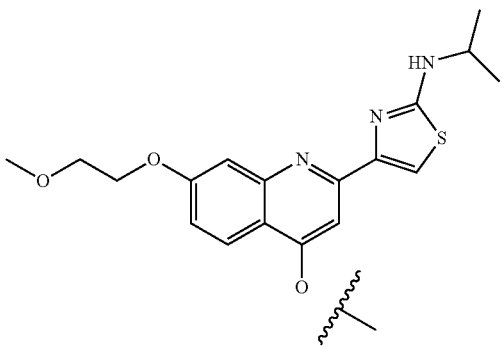

-continued
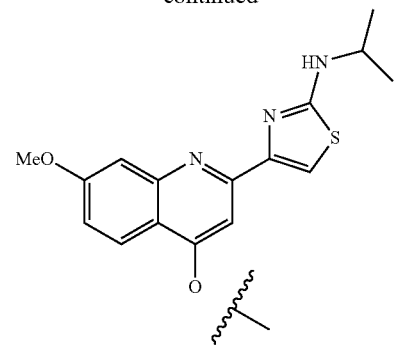
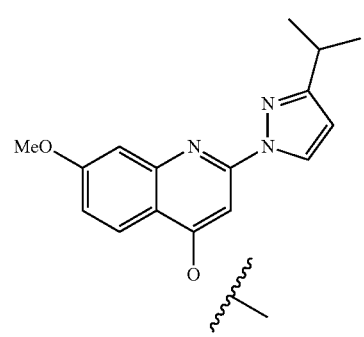
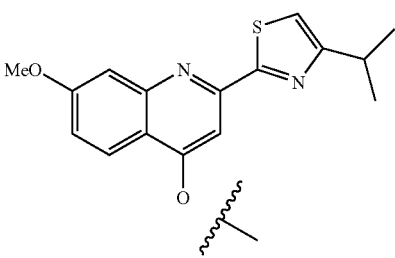
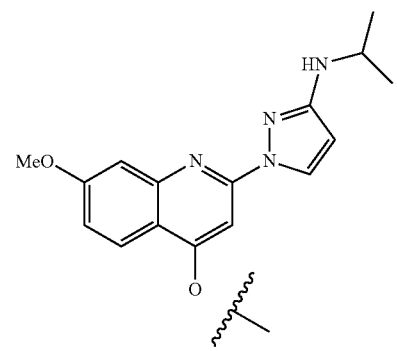
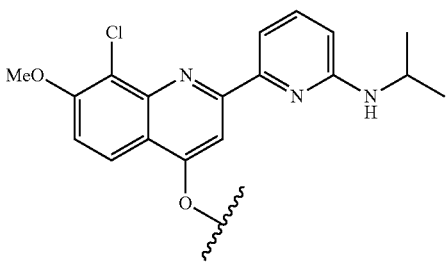
-continued
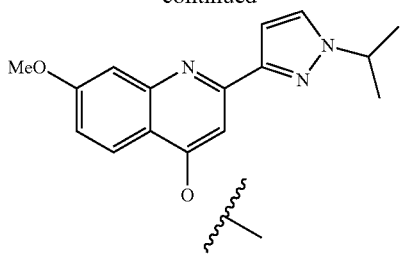
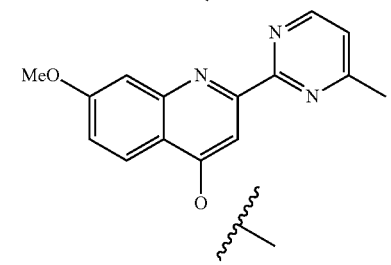
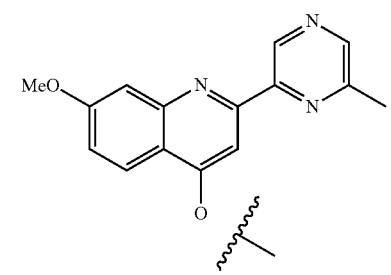
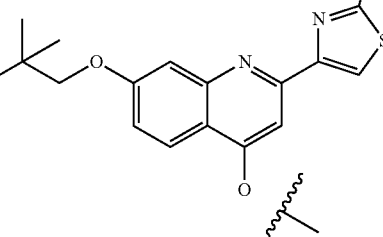
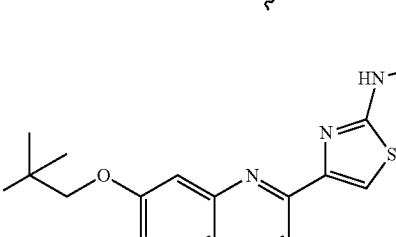
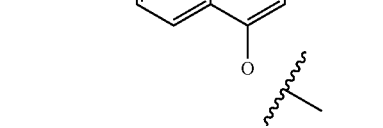

131
-continued
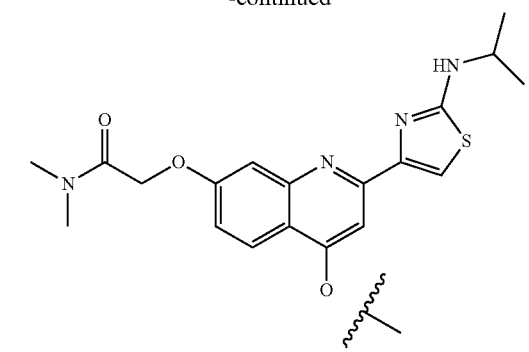
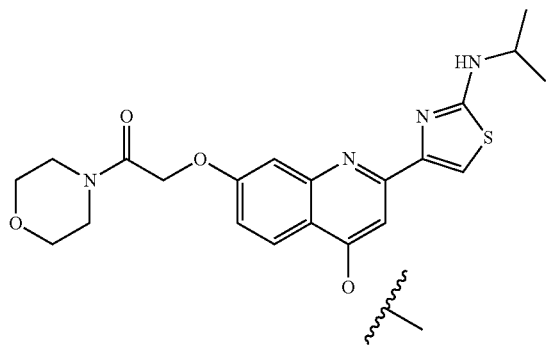
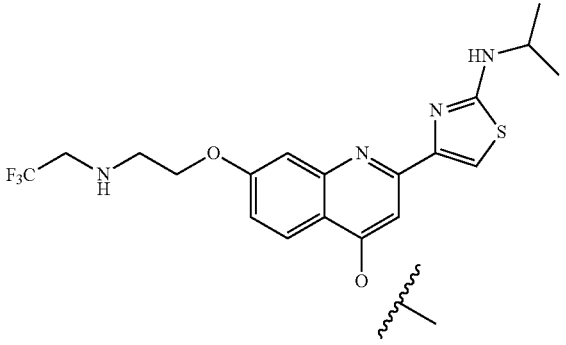
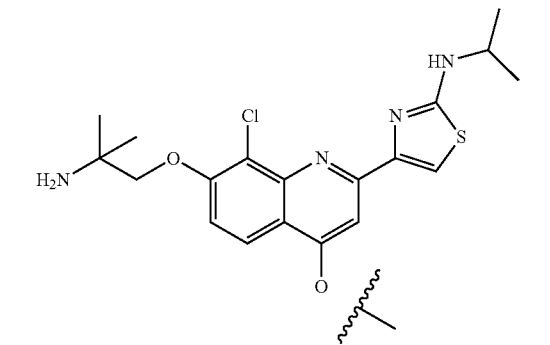
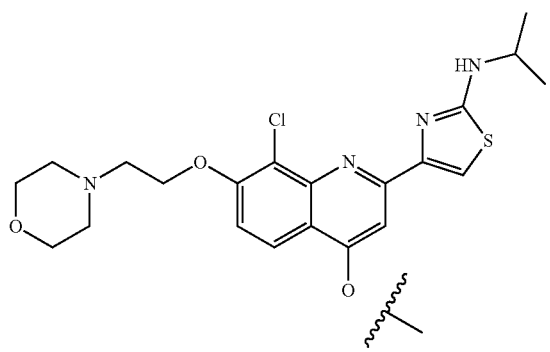
132
-continued
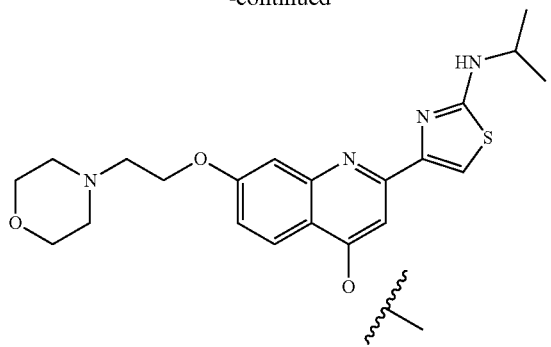
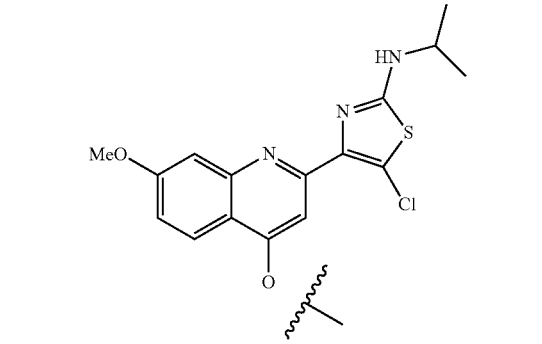
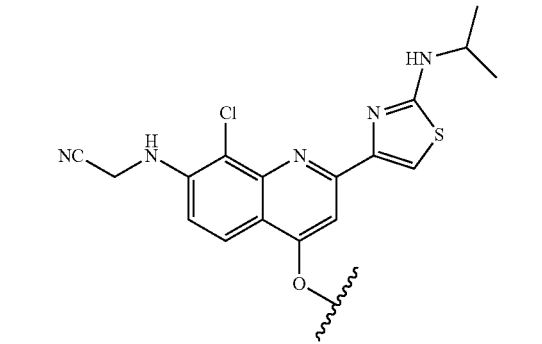
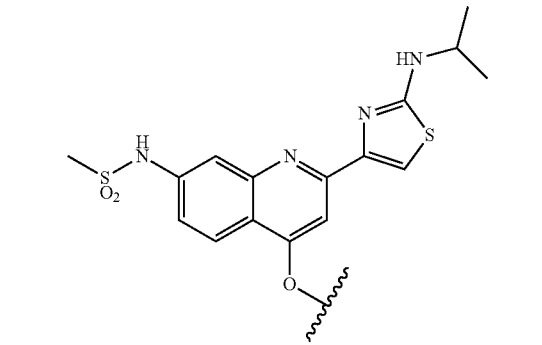
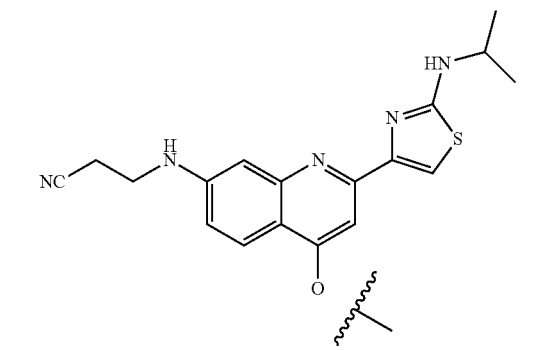

133
-continued
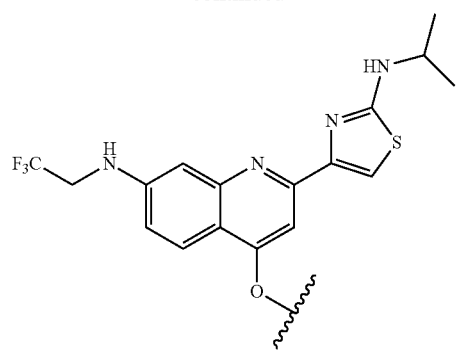
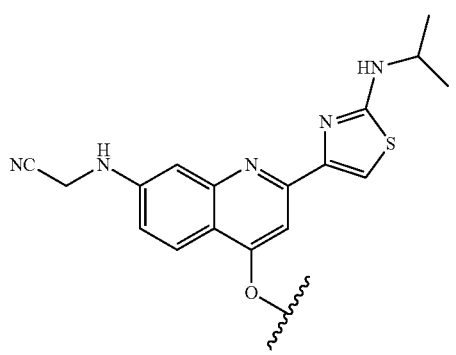
and
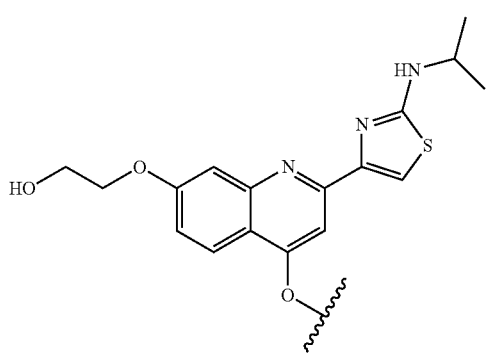
Specific Embodiment 11
In one specific embodiment the invention provides the compound of Specific Embodiment 2 wherein $Z^1$ is selected from the following structures:
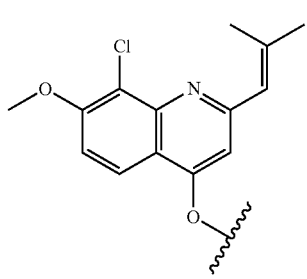
134
-continued
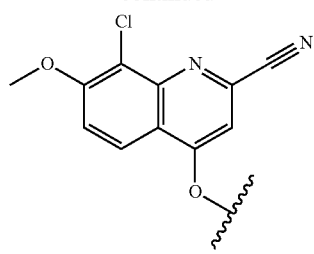
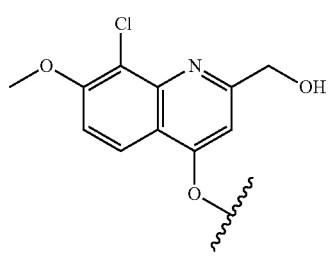
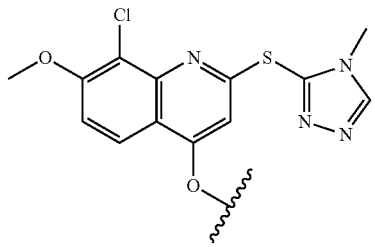
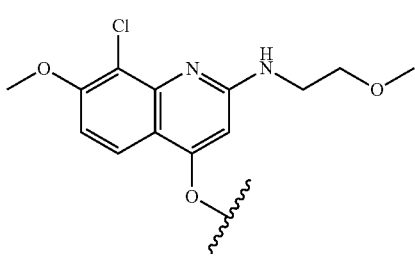
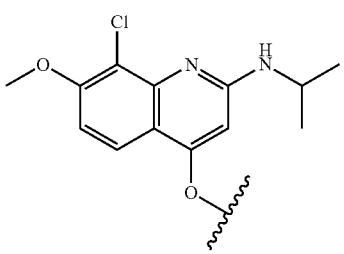
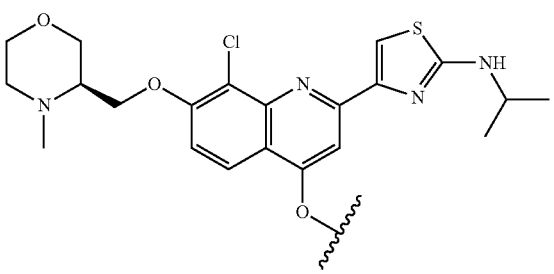

135
-continued
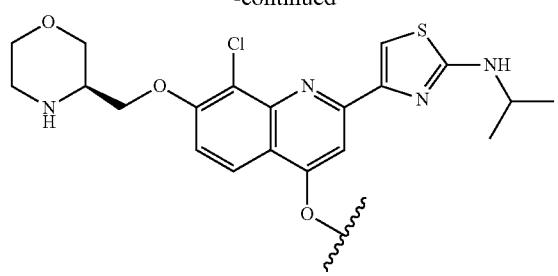
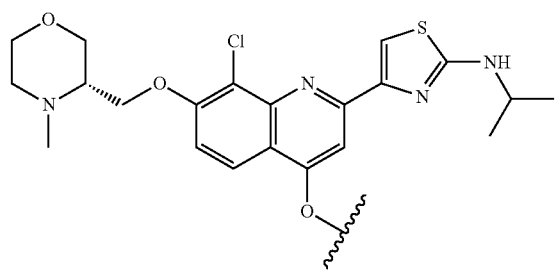
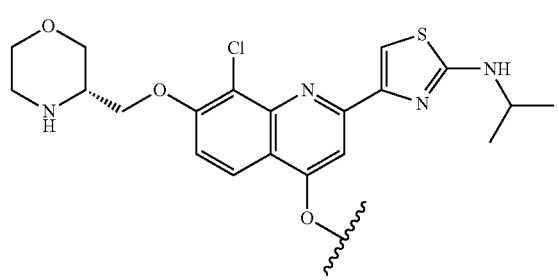
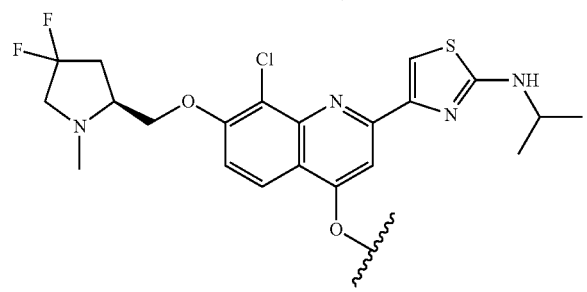
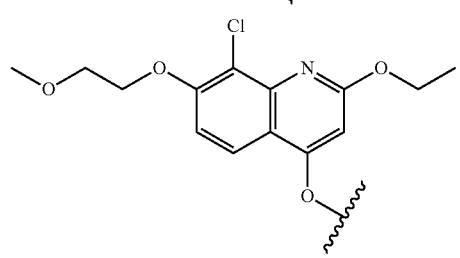
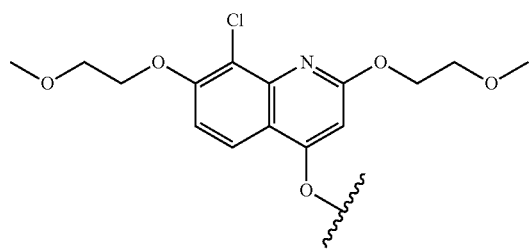
136
-continued
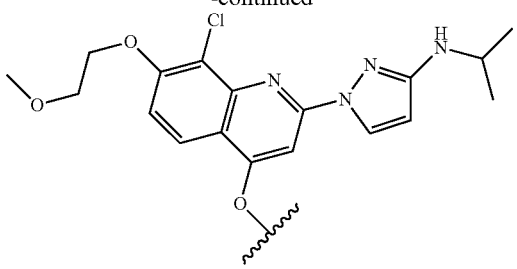
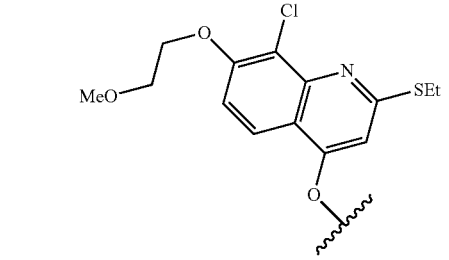
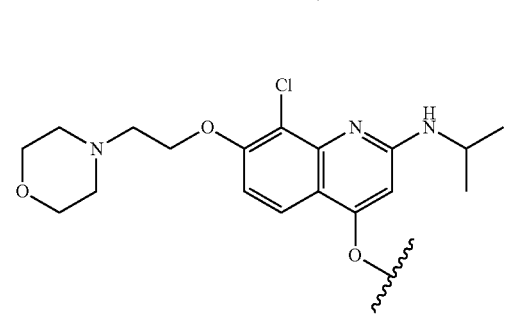
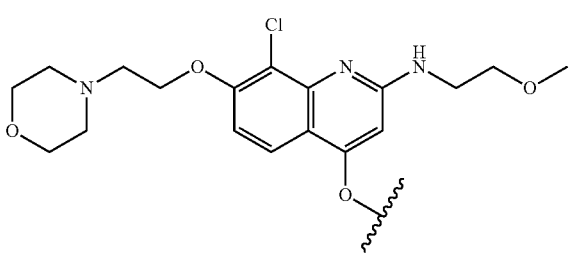
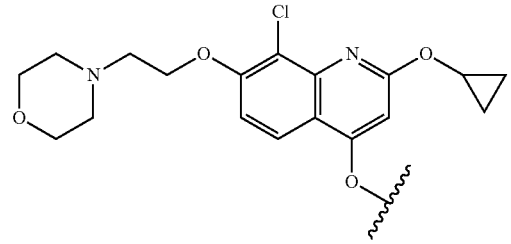
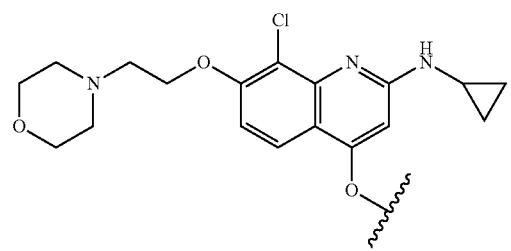

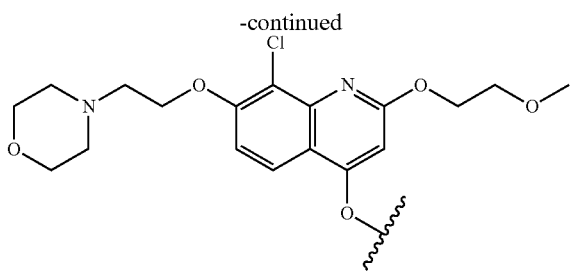

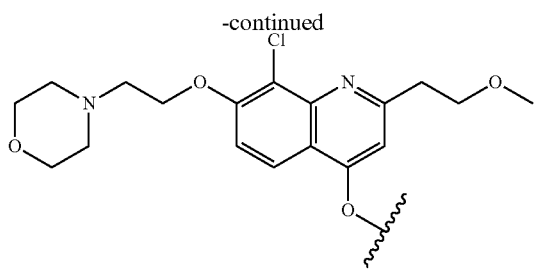

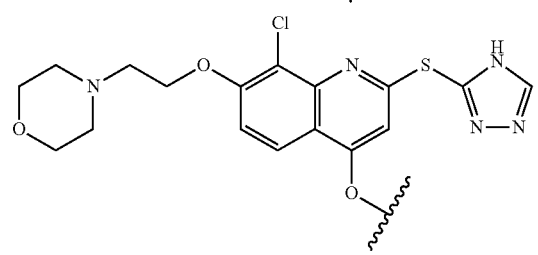

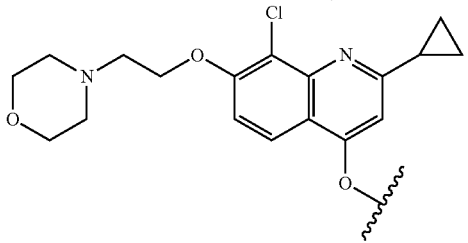

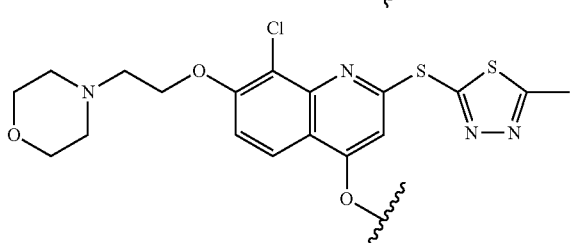

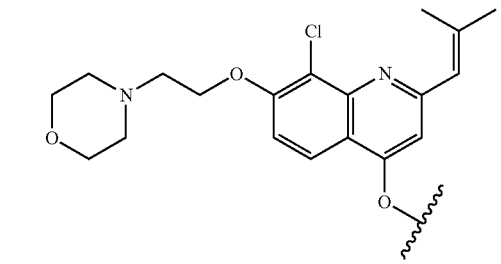

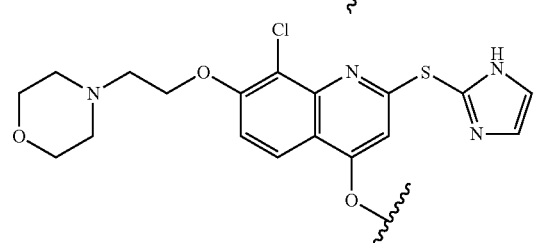

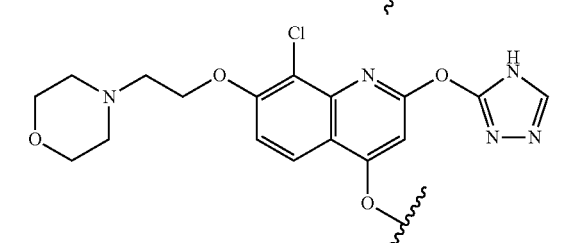

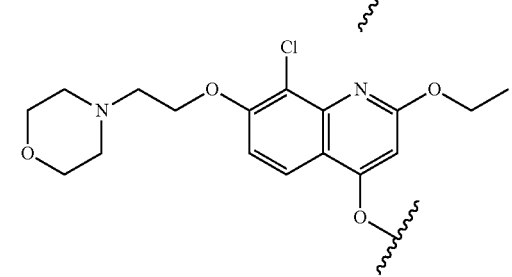

and

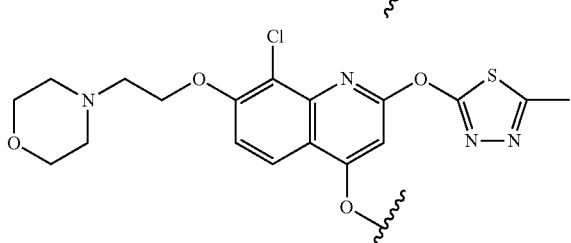

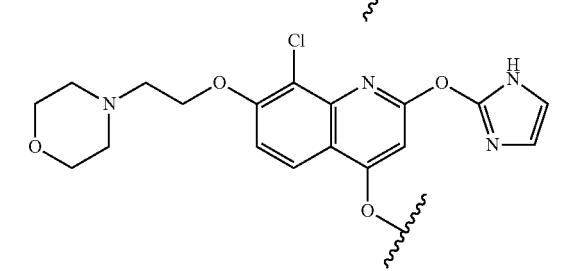

Specific Embodiment 12

In one specific embodiment the invention provides the compound of Specific Embodiment 7 wherein Z is O; $Y^1$ is O; and one of $Z^{2a}$ or $Z^{2b}$ is hydrogen.

Specific Embodiment 13

In one specific embodiment the invention provides the compound of any one of Specific Embodiments 1-12 wherein $Q^1$ is vinyl or ethyl.

Specific Embodiment 14

In one specific embodiment the invention provides the compound of any one of Specific Embodiments 1-12 wherein $Q^1$ and $Z^{2a}$ taken together with the atoms to which they are attached form a 12-18 membered heterocycle, which heterocycle may optionally be substituted with one or more oxo (=O) or A³.

Specific Embodiment 15

In one specific embodiment the invention provides the compound of Specific Embodiment 2 wherein $Z^{2a}$ is tert-butyl.

Specific Embodiment 16

In one specific embodiment the invention provides the compound of Specific Embodiment 2 wherein Y is a polycarbocycle.

Specific Embodiment 17

In one specific embodiment the invention provides the compound of Specific Embodiment 2 wherein Y is polyheterocycle.

Specific Embodiment 18

In one specific embodiment the invention provides the compound of Specific Embodiment 2 wherein Y is a fused carbocyclic ring system.

Specific Embodiment 19

In one specific embodiment the invention provides the compound of Specific Embodiment 2 wherein Y is a fused heterocyclic ring system.

Specific Embodiment 20

In one specific embodiment the invention provides the compound of Specific Embodiment 2 wherein Y is a fused carbocyclic ring system comprising one or more double bonds.

Specific Embodiment 21

In one specific embodiment the invention provides the compound of Specific Embodiment 2 wherein Y is a fused heterocyclic ring system comprising one or more double bonds.

Specific Embodiment 22

In one specific embodiment the invention provides the compound of Specific Embodiment 2 wherein Y is a bridged carbocyclic ring system.

Specific Embodiment 23

In one specific embodiment the invention provides the compound of Specific Embodiment 2 wherein Y is a bridged heterocyclic ring system.

Specific Embodiment 24

In one specific embodiment the invention provides the compound of Specific Embodiment 2 wherein Y is a bridged carbocyclic ring system comprising one or more double bonds.

Specific Embodiment 25

In one specific embodiment the invention provides the compound of Specific Embodiment 2 wherein Y is a bridged heterocyclic ring system comprising one or more double bonds.

Specific Embodiment 26

In one specific embodiment the invention provides the compound of Specific Embodiment 2 wherein Y comprises a bridged ring system selected from:

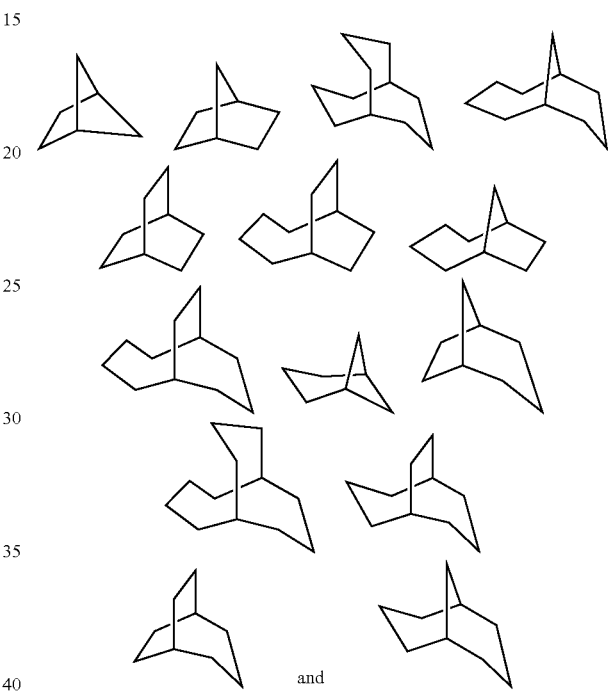

and wherein one or more carbon atoms in the bridged ring system is optionally replaced with O, S, S(O), S(O)₂, N⁺(O⁻)R$_x$, or NR$_x$; wherein each R$_x$ is independently H, (C1-10)alkyl, (C2-10)alkenyl, (C2-10)alkynyl, (C1-10)alkanoyl, S(O)₂NR$_n$R$_p$, S(O)₂R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo; and wherein the ring system optionally comprises one or more double bonds.

Specific Embodiment 27

In one specific embodiment the invention provides the compound of Specific Embodiment 26 wherein the bridged ring system comprises one or more double bonds.

Specific Embodiment 28

In one specific embodiment the invention provides the compound of Specific Embodiment 26 wherein one or more carbon atoms in the bridged ring system is replaced with O, S, S(O), S(O)₂, N⁺(O⁻)R$_x$, or NR$_x$; wherein each R$_x$ is independently H, (C1-10)alkyl, (C2-10)alkenyl, (C2-10)alkynyl, (C1-10)alkanoyl, S(O)₂NR$_n$R$_p$, S(O)₂R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

Specific Embodiment 29

In one specific embodiment the invention provides the compound of Specific Embodiment 2 wherein Y comprises a fused ring system selected from:

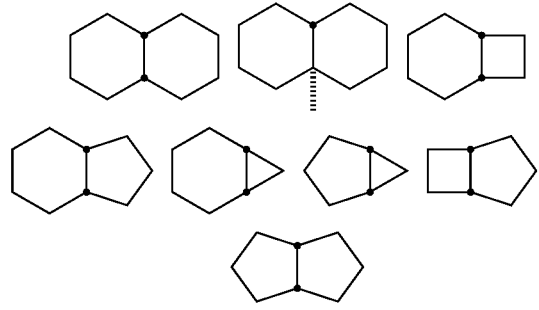

and wherein one or more carbon atoms in the fused ring system is optionally replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10) alkoxy is optionally substituted with one or more halo; and wherein the ring system optionally comprises one or more double bonds.

Specific Embodiment 30

In one specific embodiment the invention provides the compound of Specific Embodiment 29 wherein one or more carbon atoms in the bridged ring system is replaced with O, S, S(O), S(O)$_2$, N$^+$(O$^-$)R$_x$, or NR$_x$; wherein each R$_x$ is independently H, (C1-10)alkyl, (C2-10)alkenyl, (C2-10)alkynyl, (C1-10)alkanoyl, S(O)$_2$NR$_n$R$_p$, S(O)$_2$R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo.

Specific Embodiment 31

In one specific embodiment the invention provides the compound of Specific Embodiment 2 wherein Y is selected from:

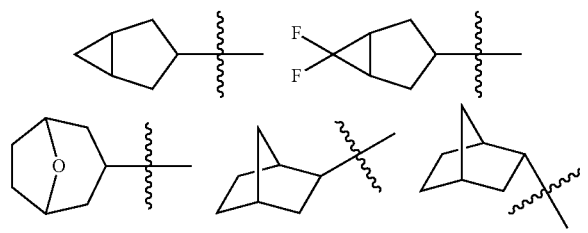

-continued

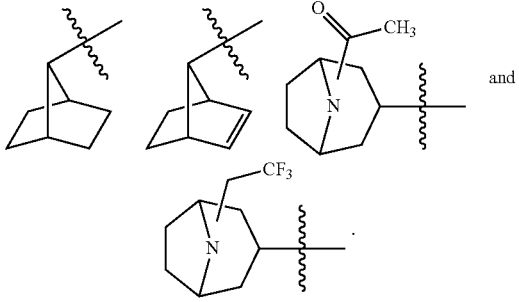

and

Specific Embodiment 32

In one specific embodiment the invention provides the compound of Specific Embodiment 2 wherein Y is selected from:

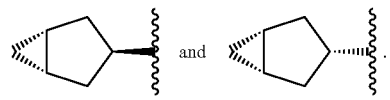 [SMILES: *[C@H]1C[C@@H]2C[C@@H]2C1 ; *[C@@H]1C[C@@H]2C[C@@H]2C1]

Specific Embodiment 33

In one specific embodiment the invention provides the compound of Specific Embodiment 1 which is selected from:

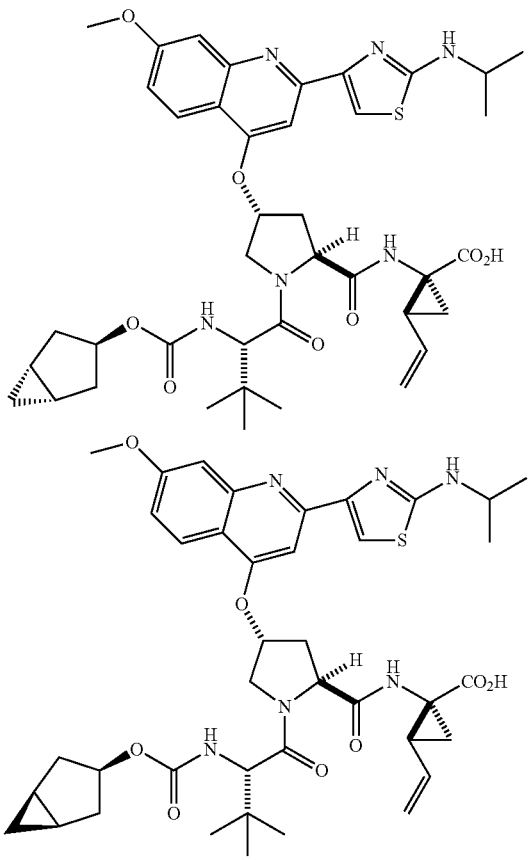

143
-continued
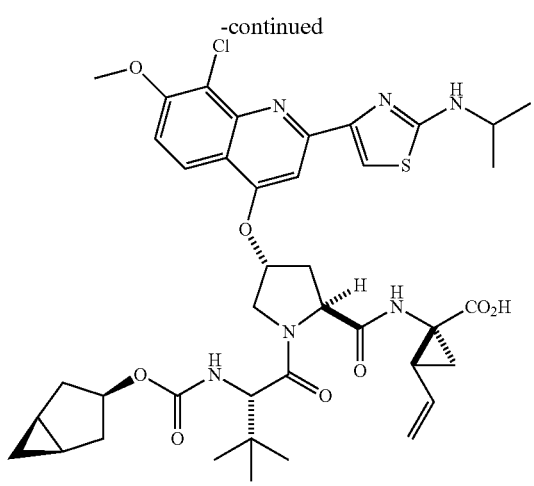
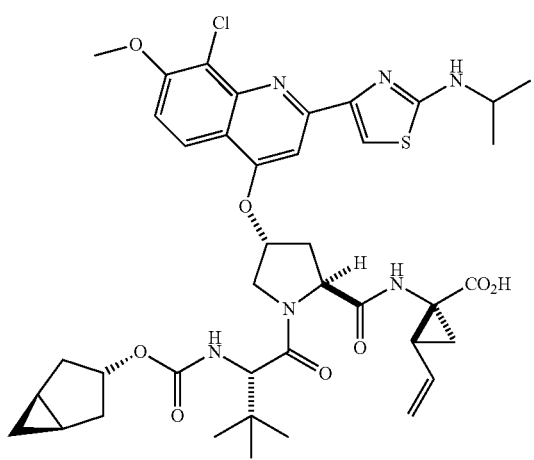
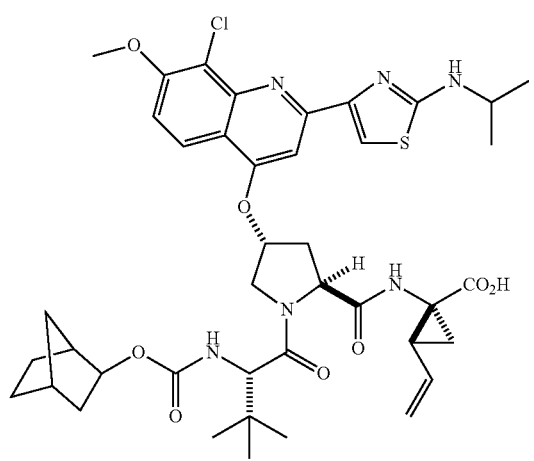
144
-continued
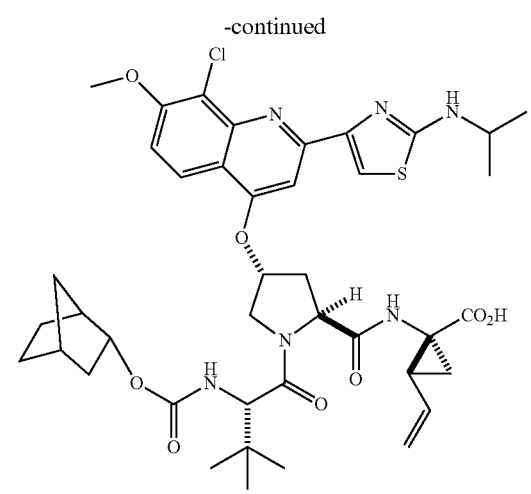
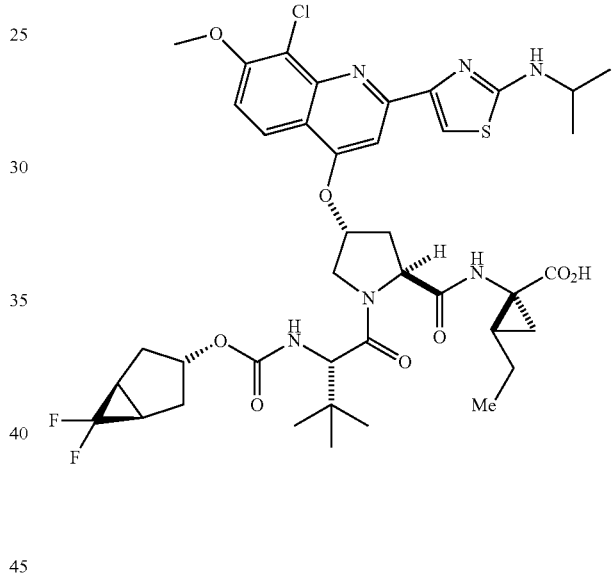
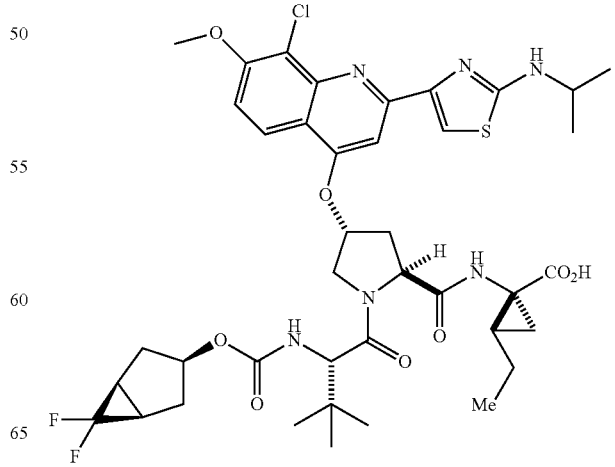

145
-continued
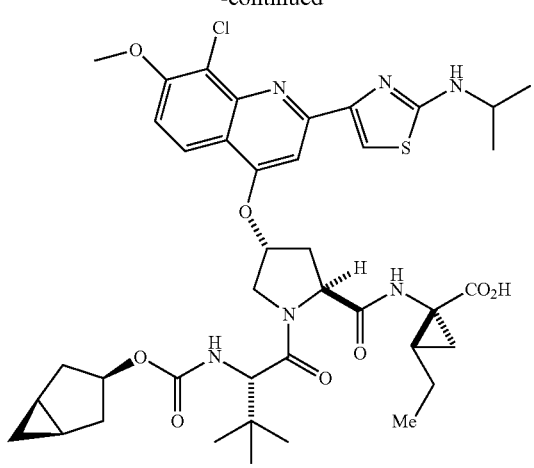
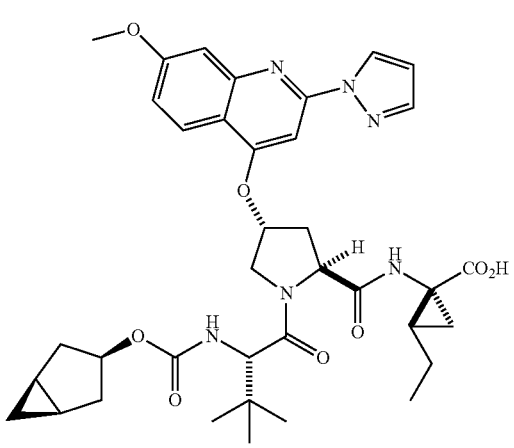
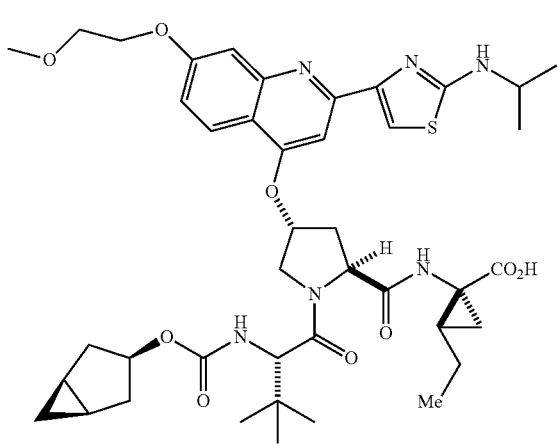
146
-continued
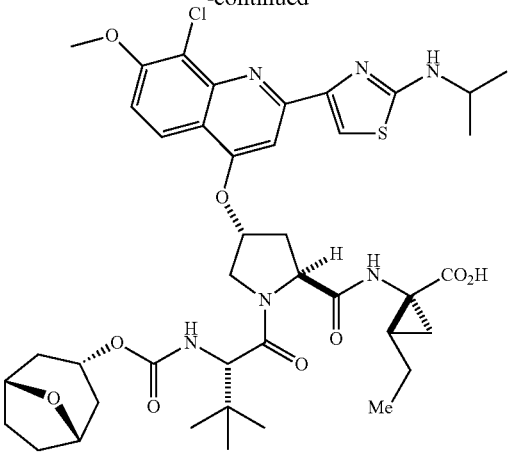
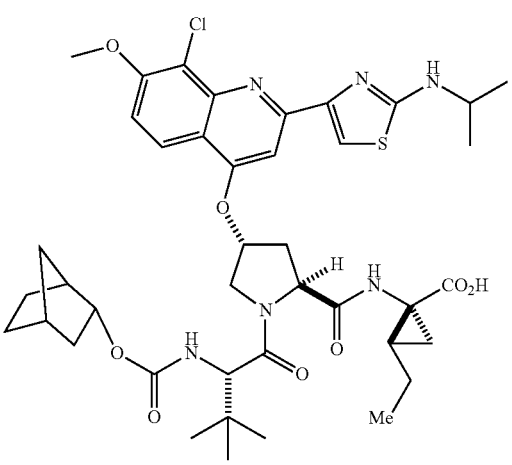
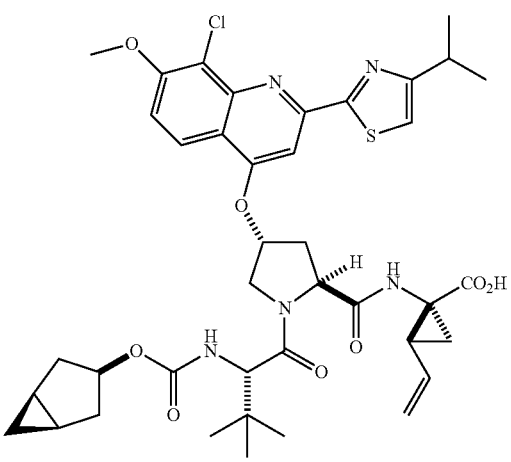

147
-continued
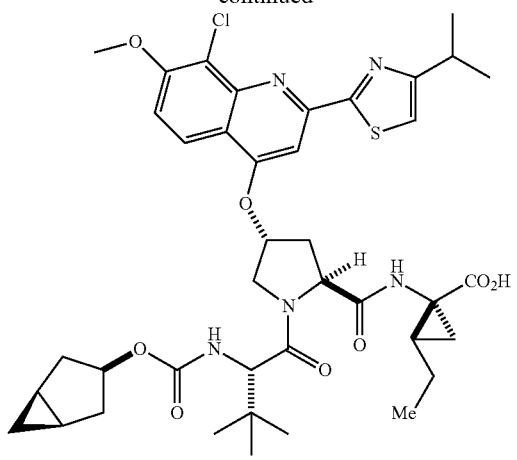
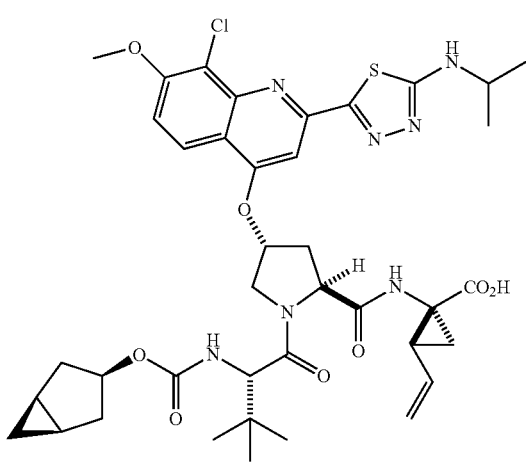
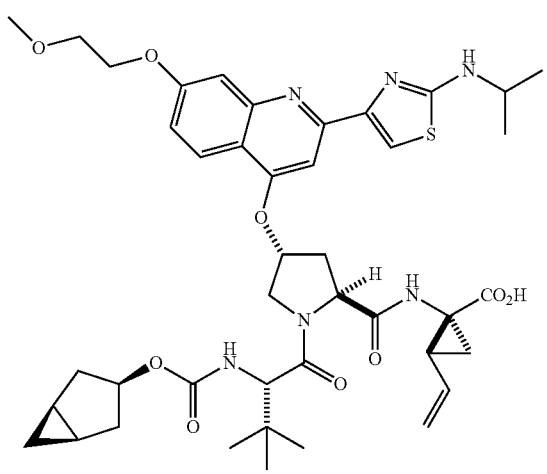
148
-continued
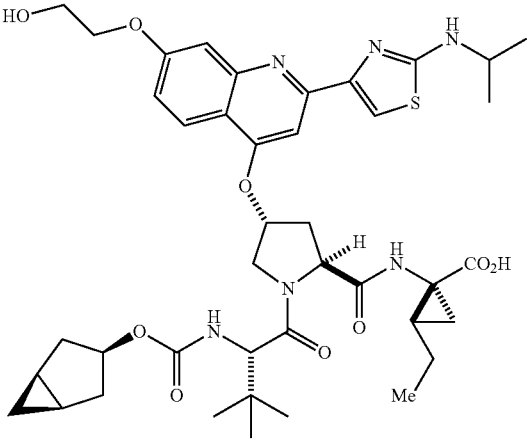
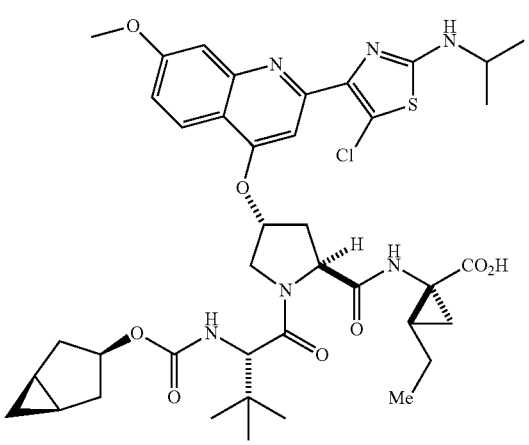
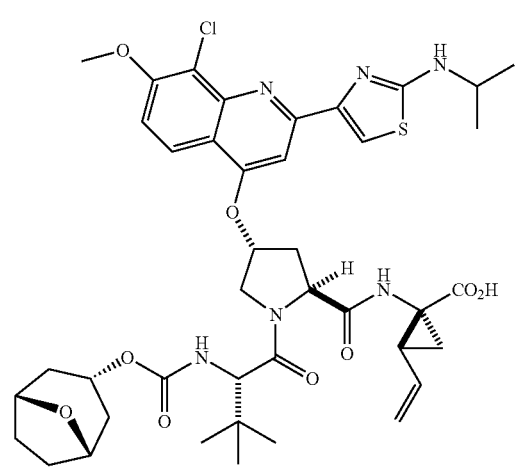

149
-continued
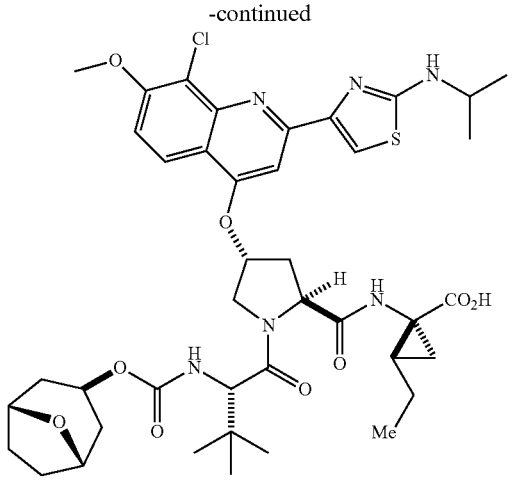
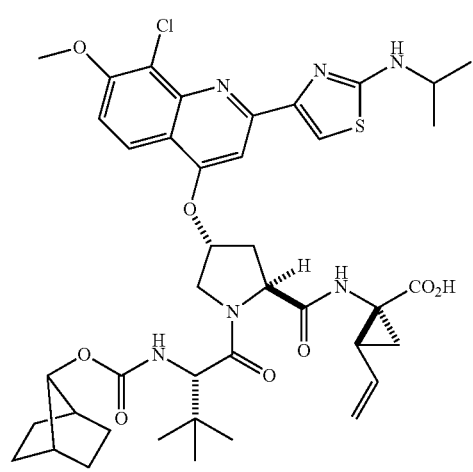
150
-continued
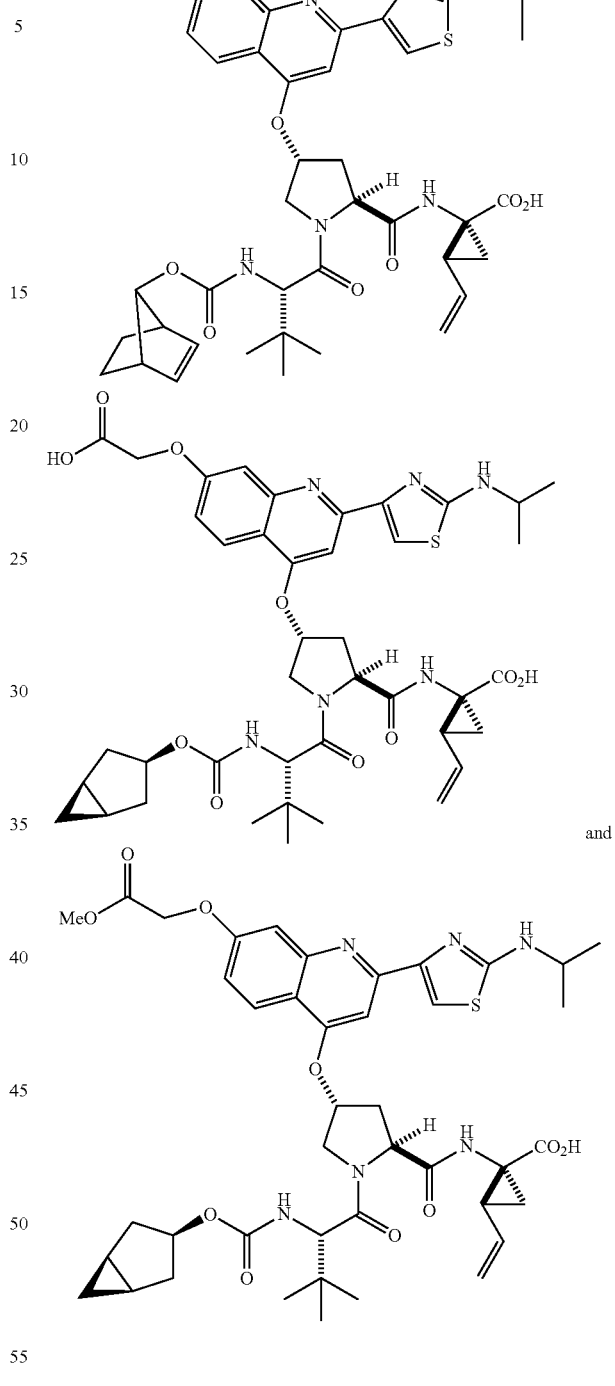
and pharmaceutically acceptable salts and prodrugs thereof.
Specific Embodiment 34
In one specific embodiment the invention provides the compound of Specific Embodiment 1 which is selected from:

151
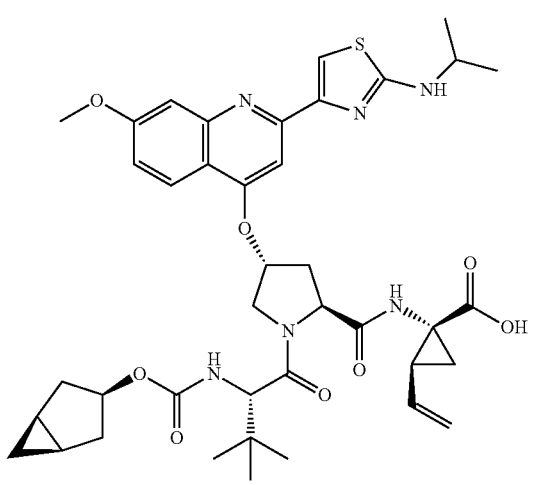
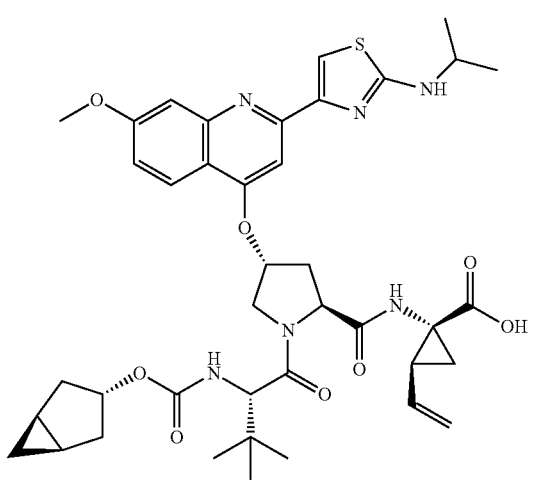
3
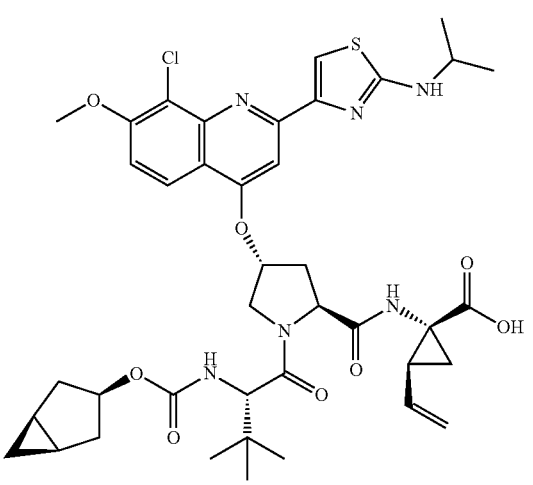
152
-continued
4
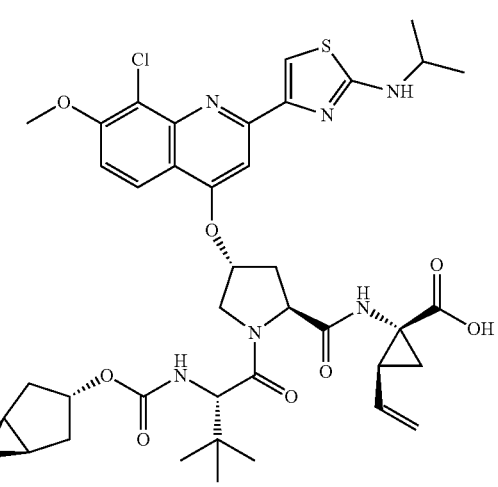
5
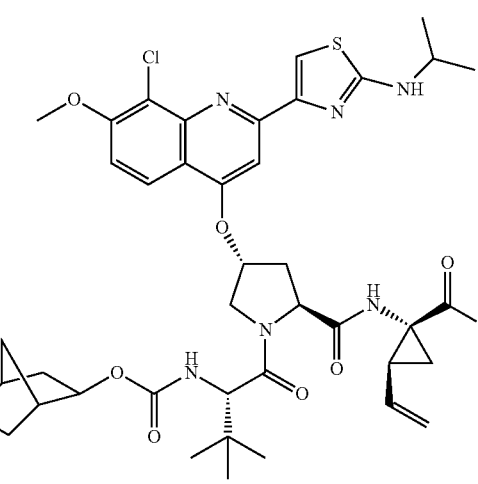
6
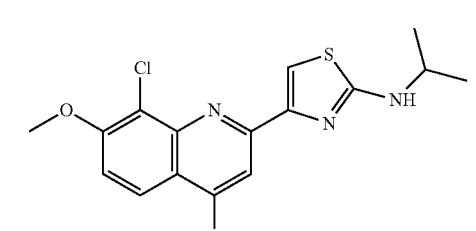

7
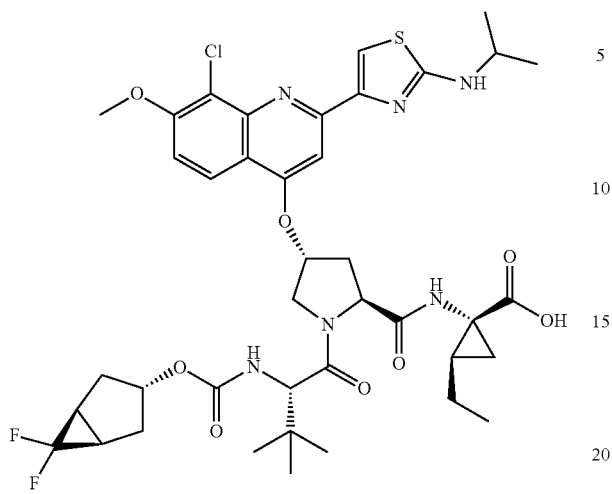
8
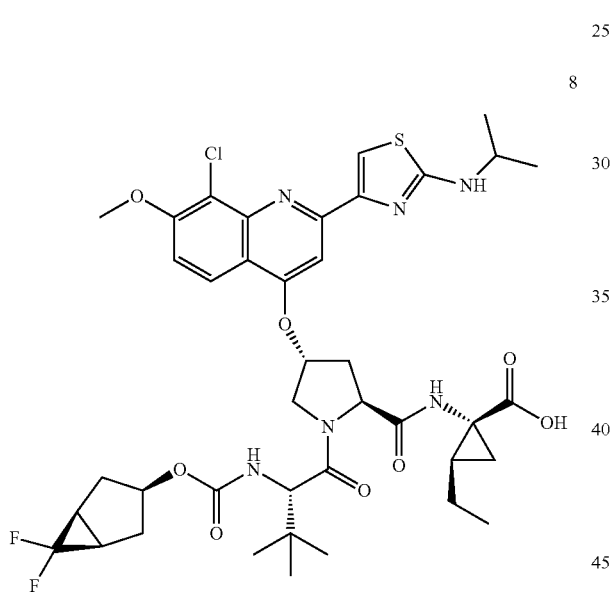
9
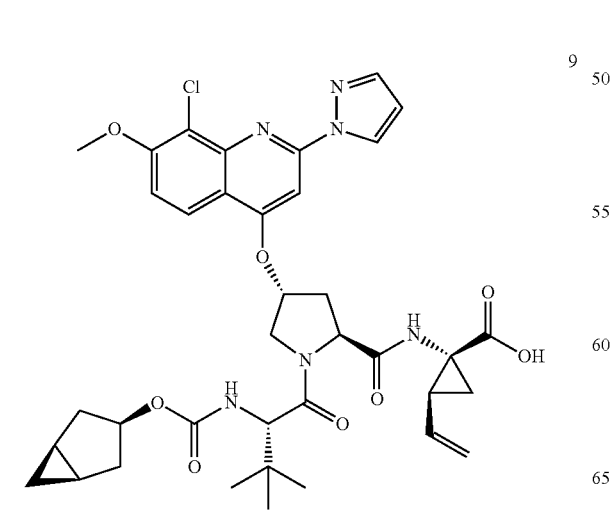
10
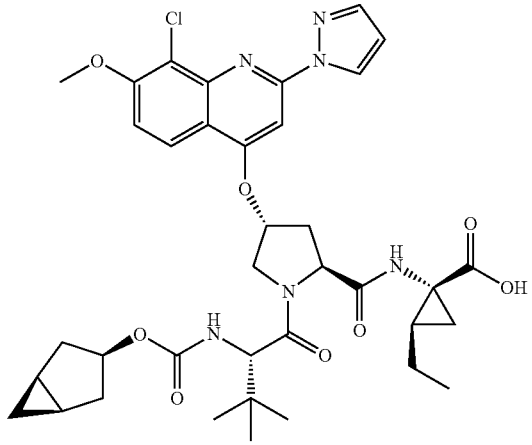
11
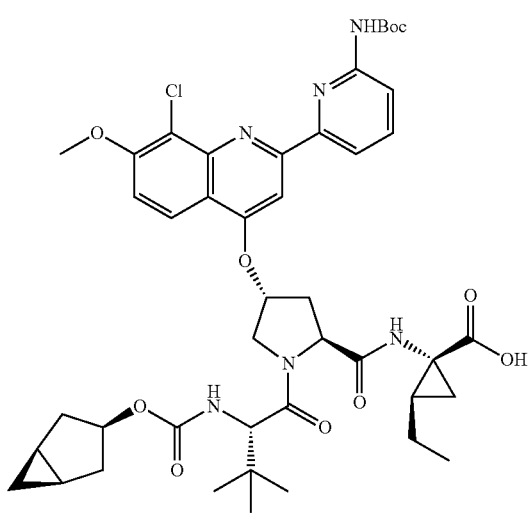
12
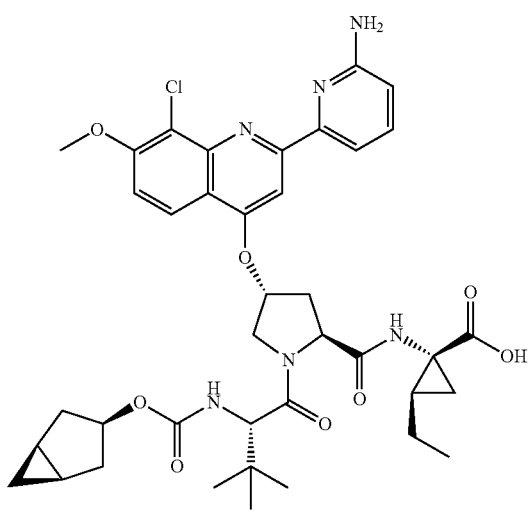

13
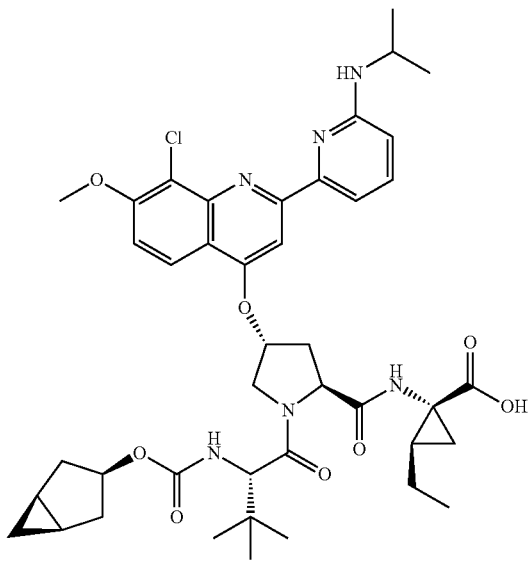
14
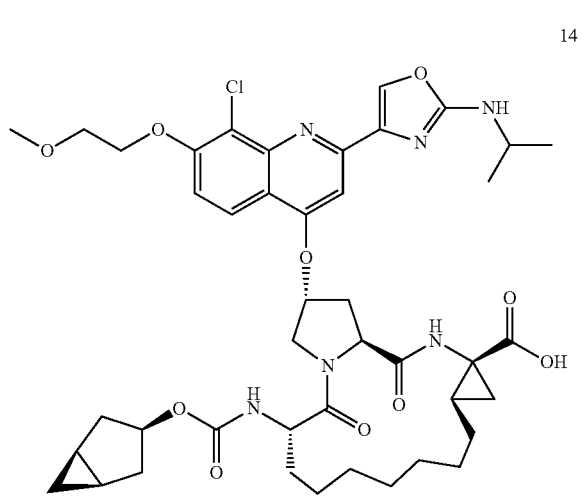
15
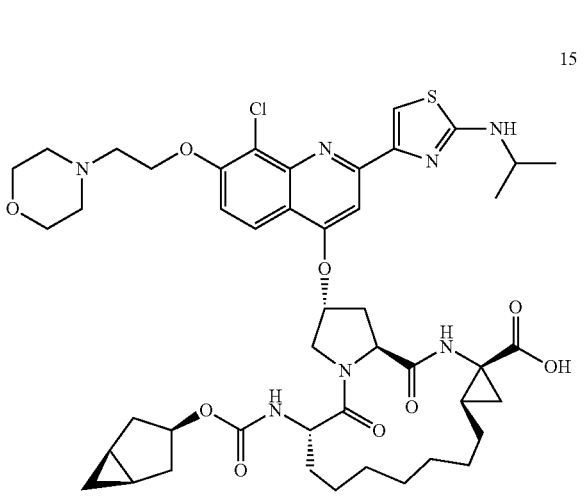
16
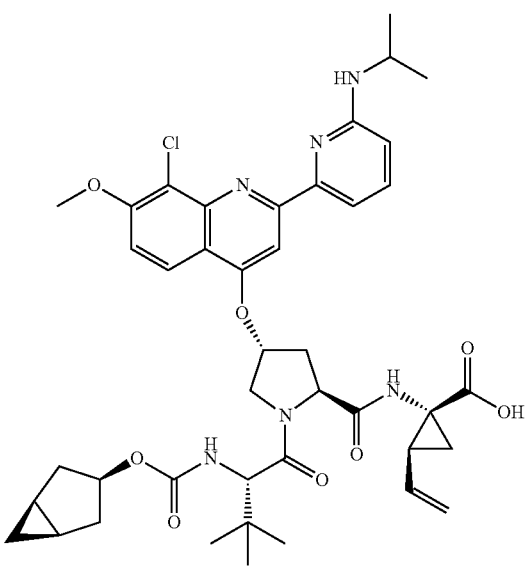
17
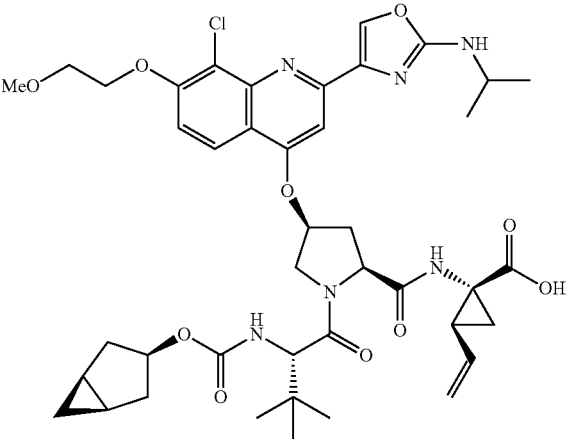
18
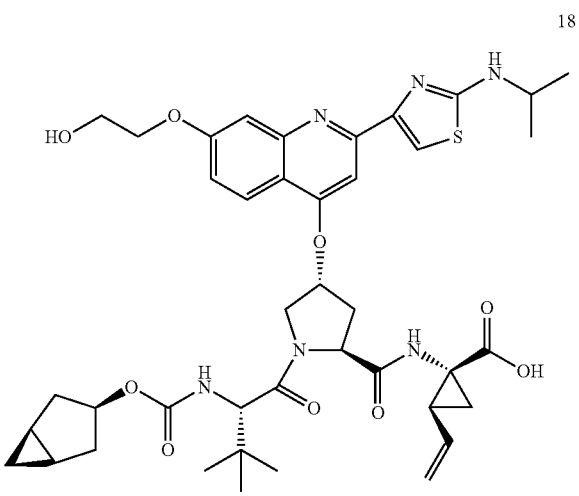

19
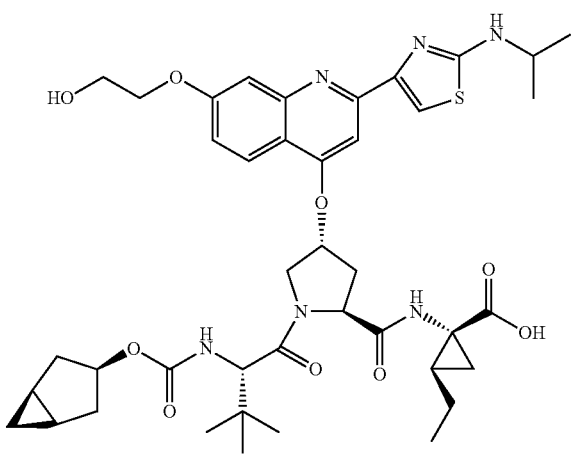
20
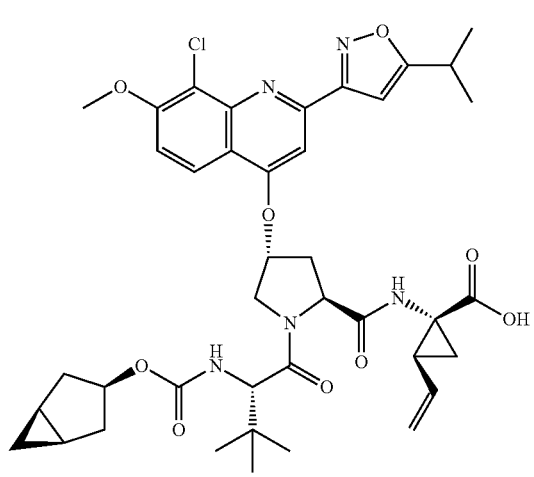
21
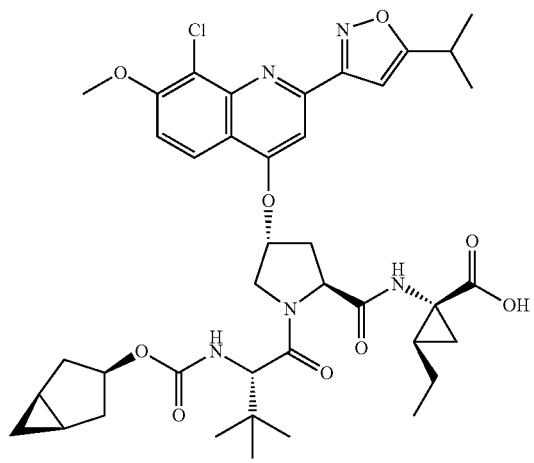
22
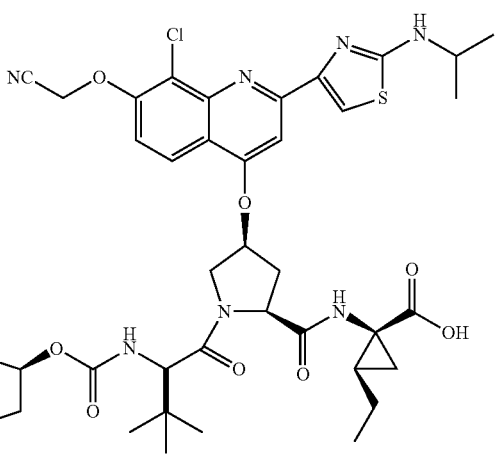
23
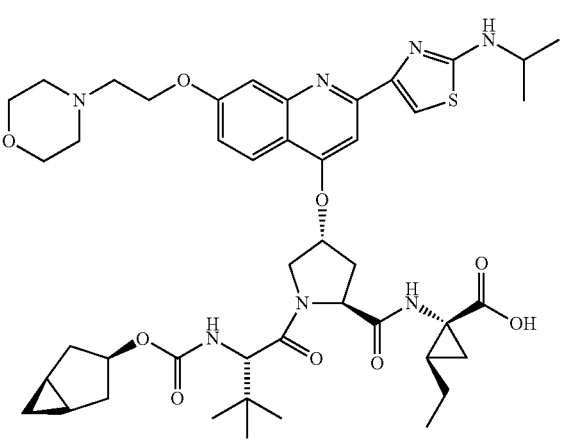
24
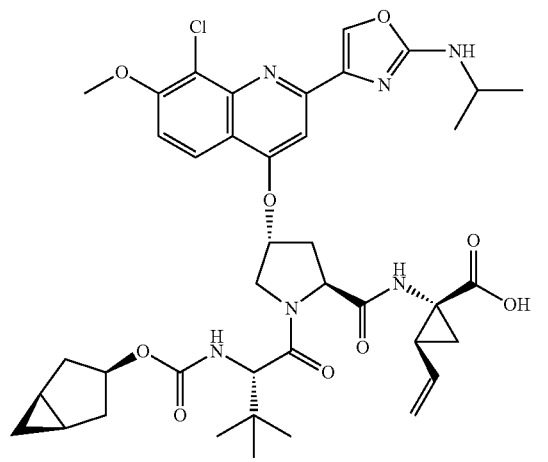

25
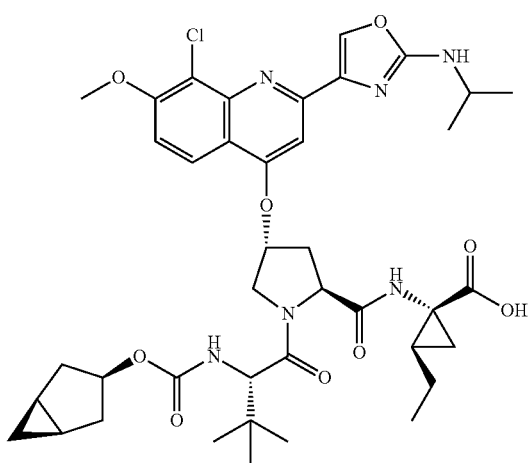
26
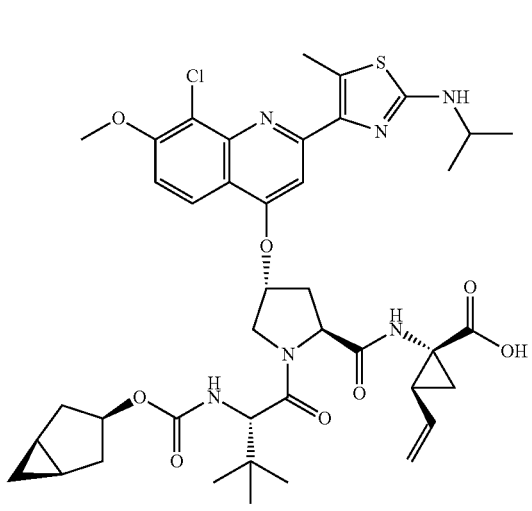
27
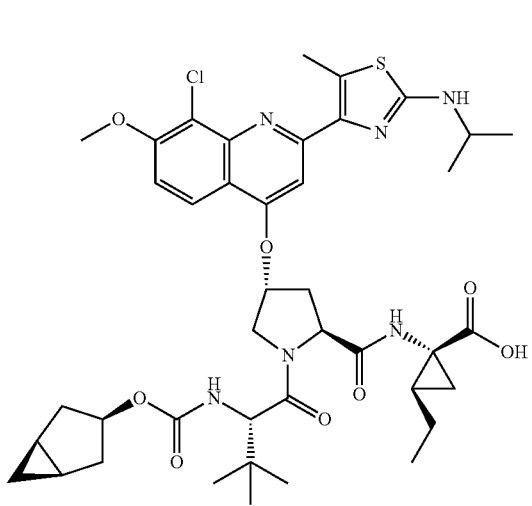
28
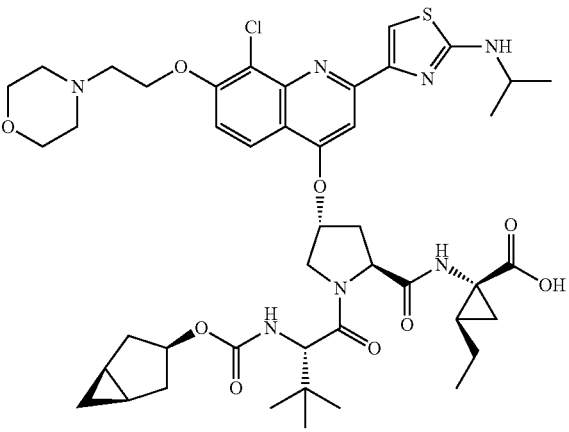
29
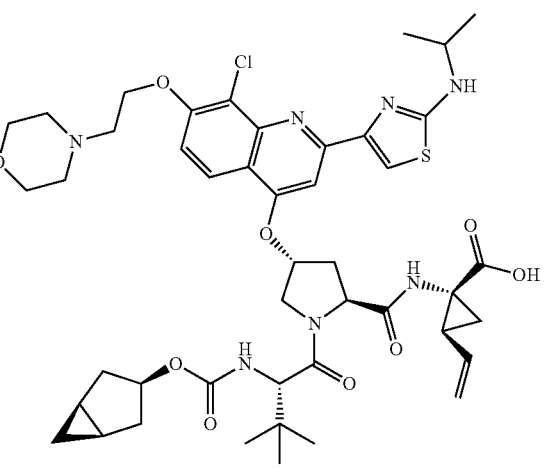
30
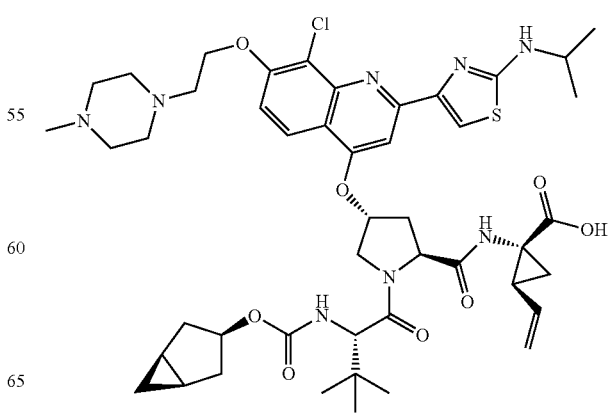

31
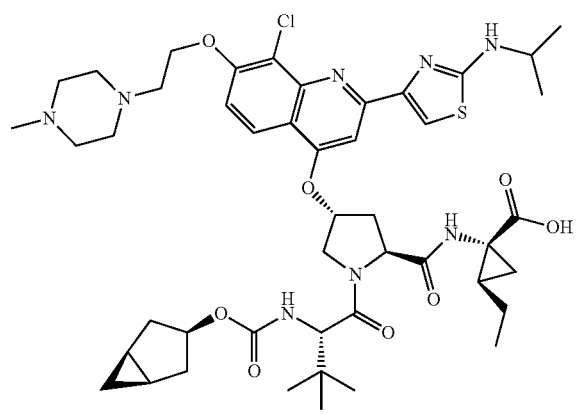
32
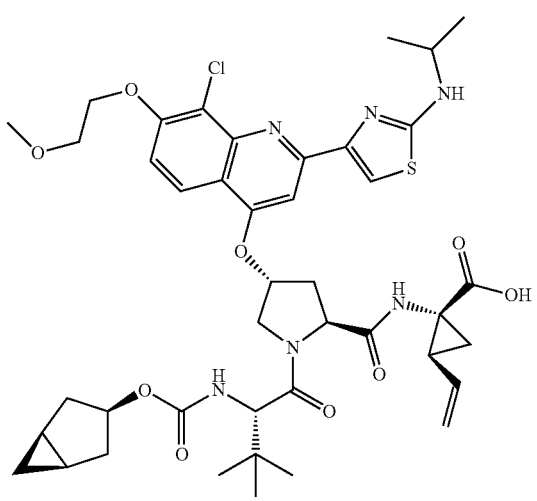
33
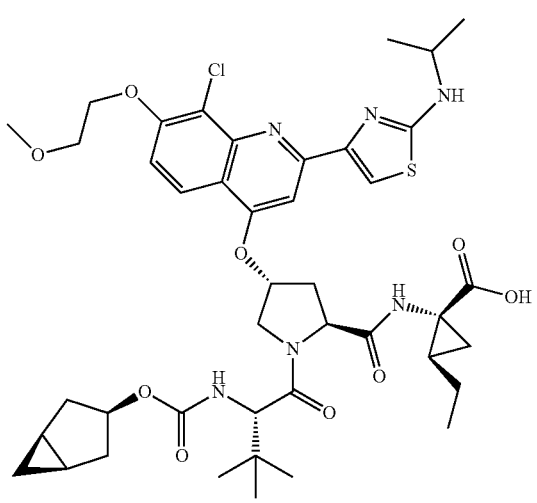
34
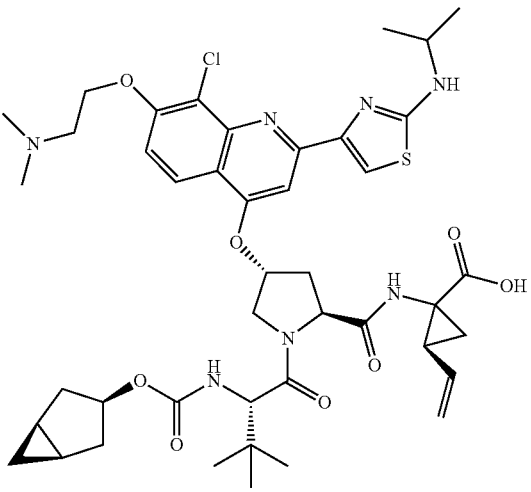
35
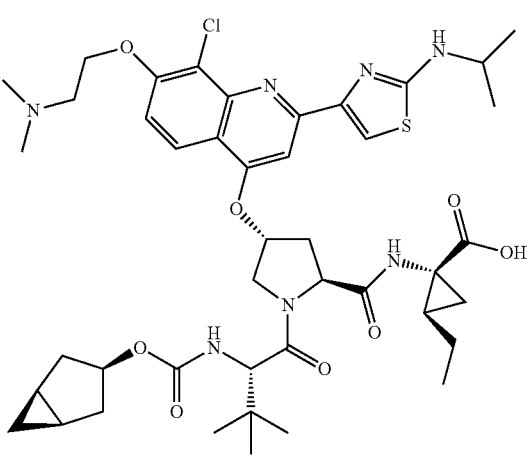
36
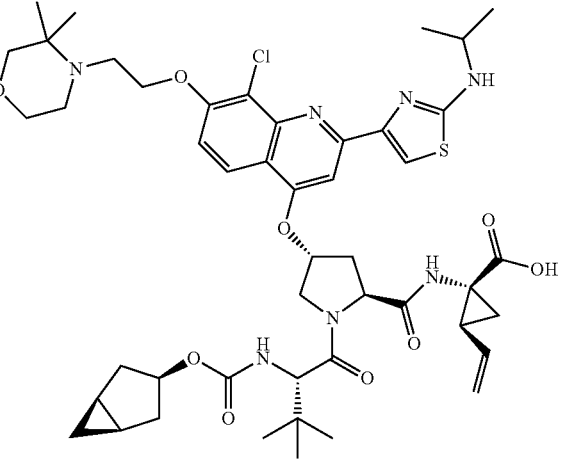

163
-continued
37
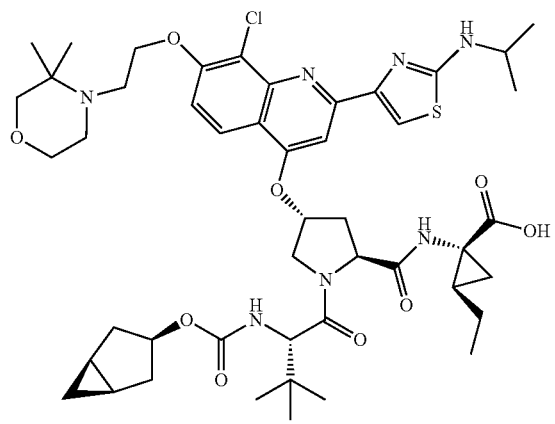
38
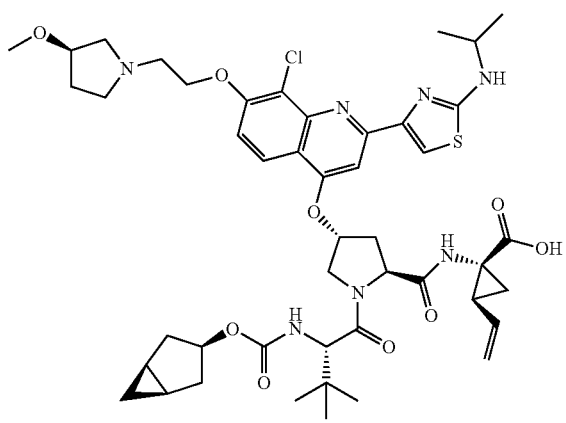
39
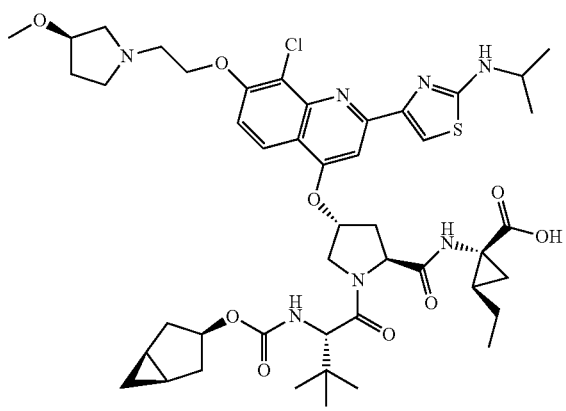
164
-continued
40
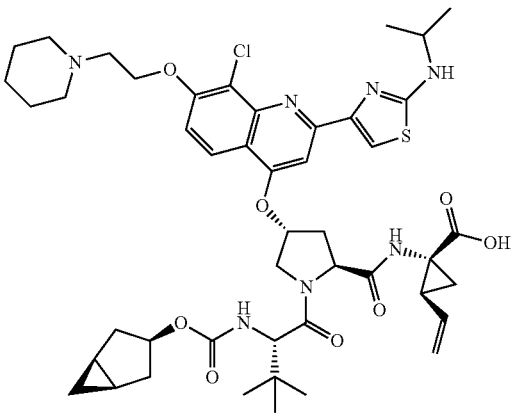
41
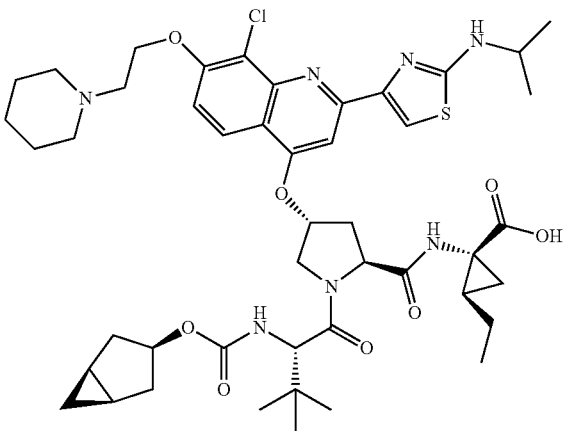
42
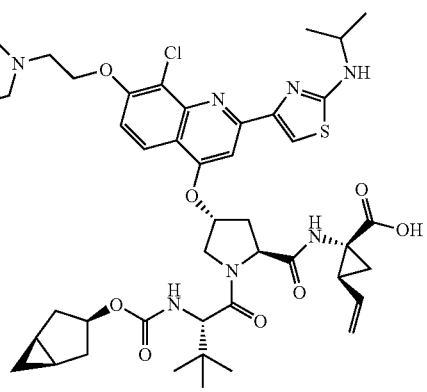

43
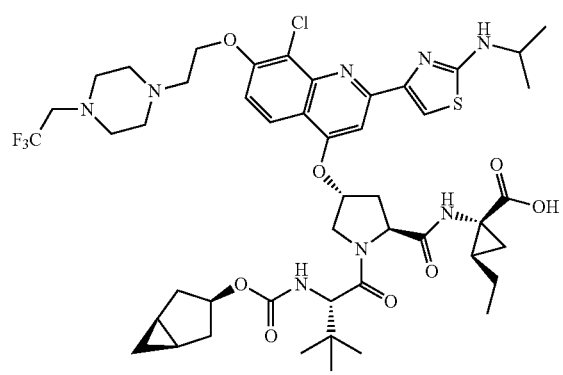
44
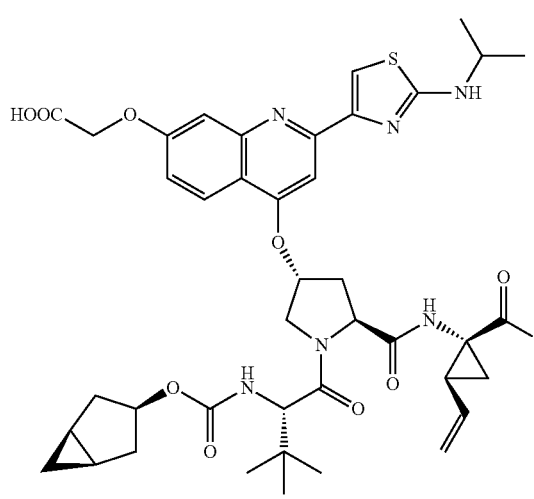
45
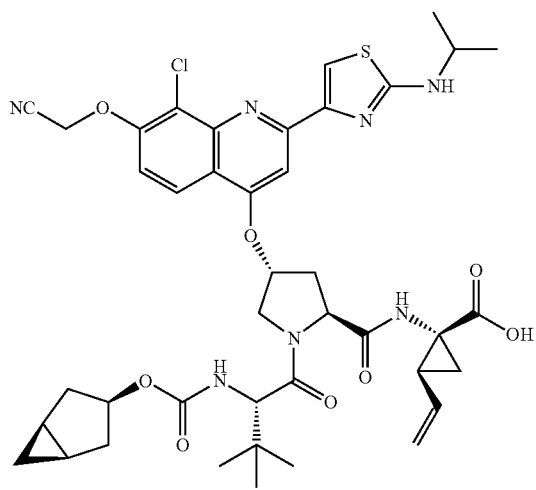
46
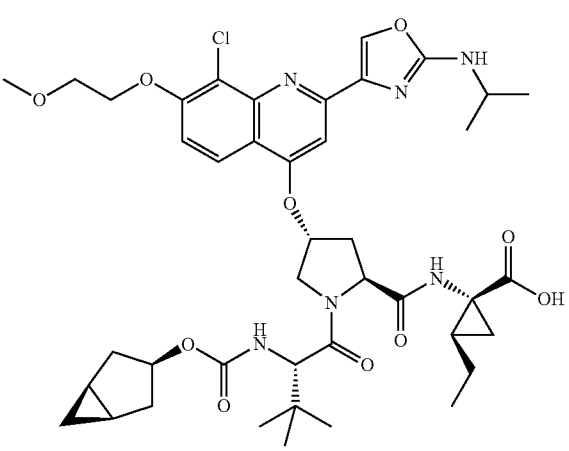
47
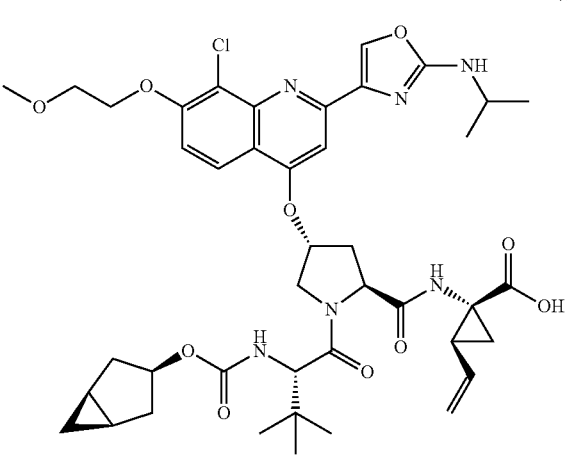
48
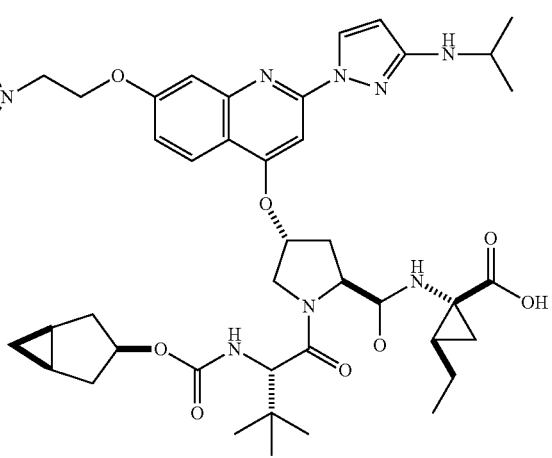

49
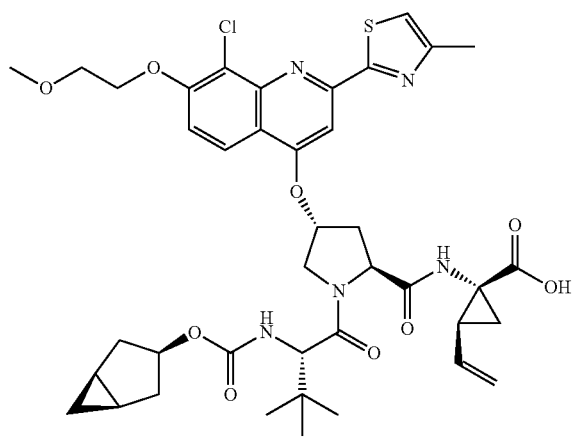
50
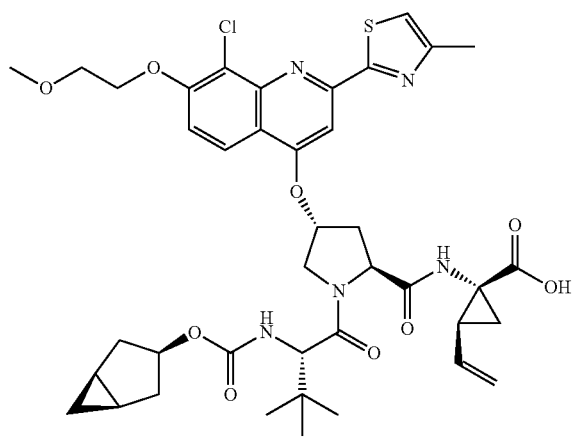
51
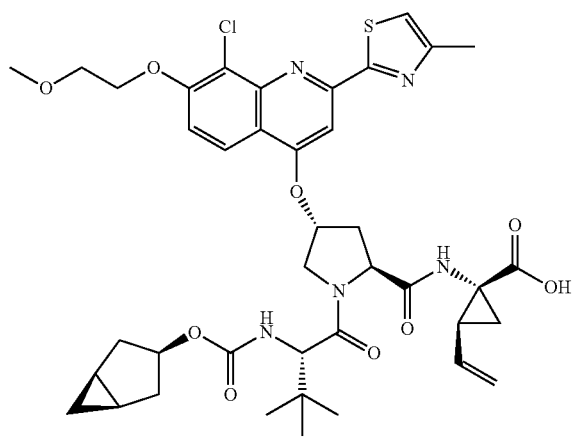
52
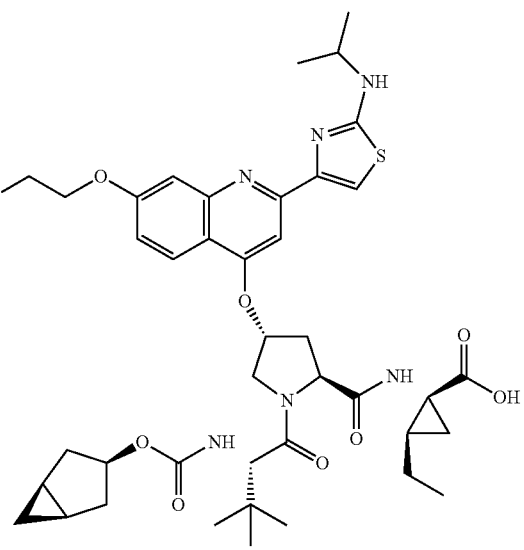
53
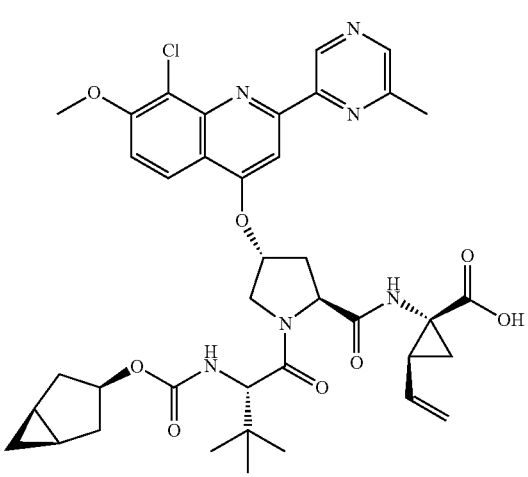
54
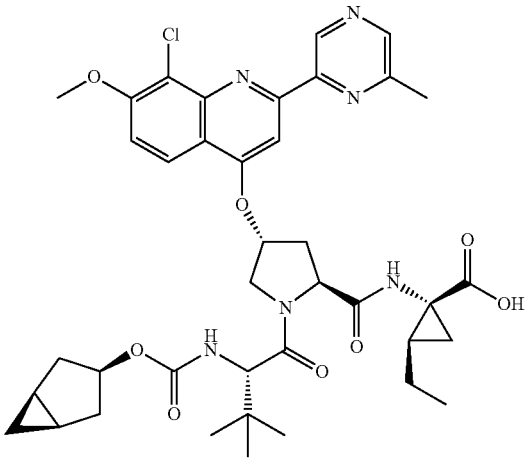

55
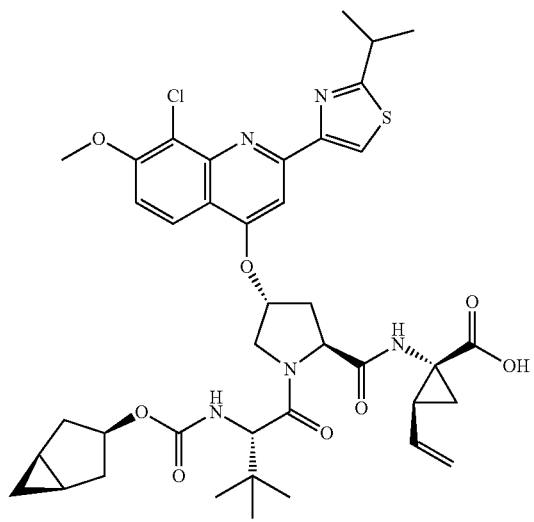
56
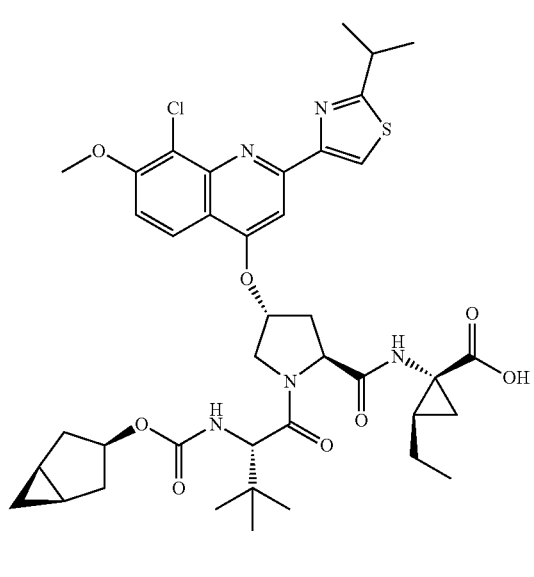
57
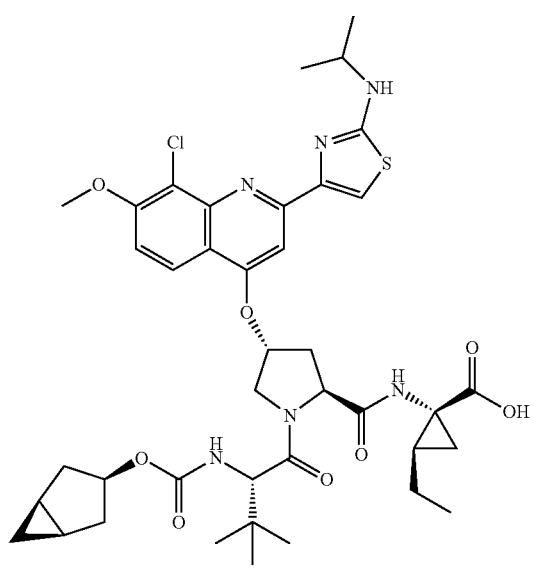
58
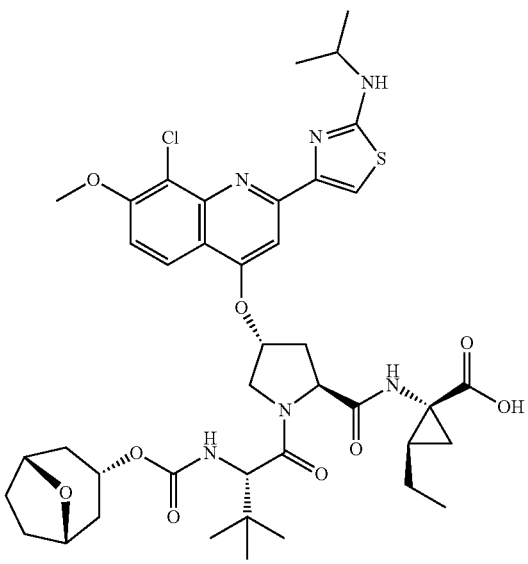
59
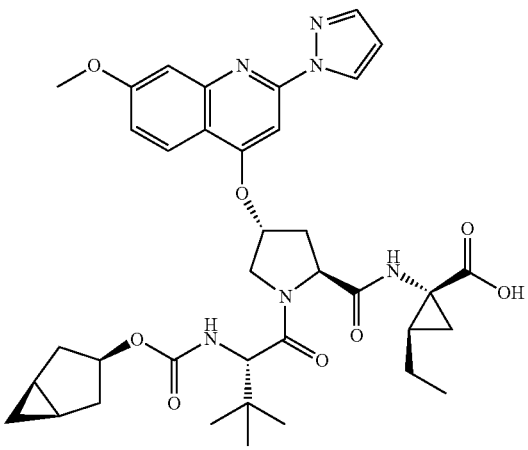
60
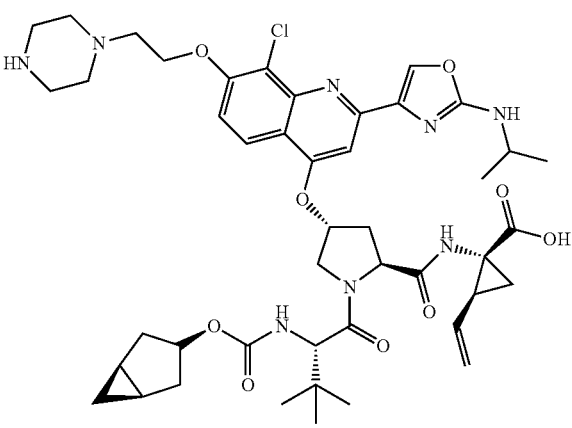

67
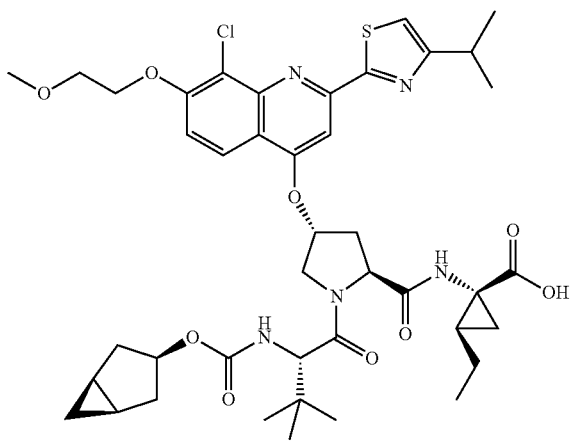
68
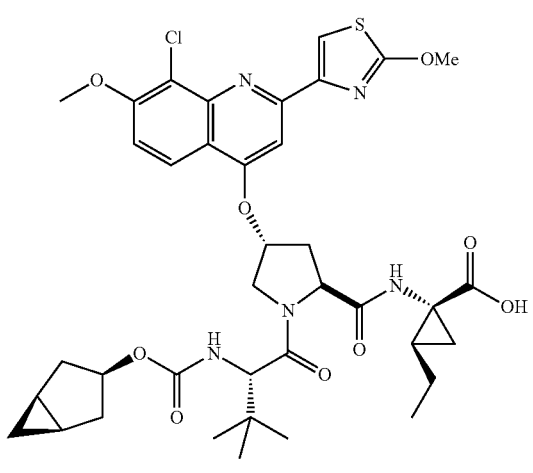
70
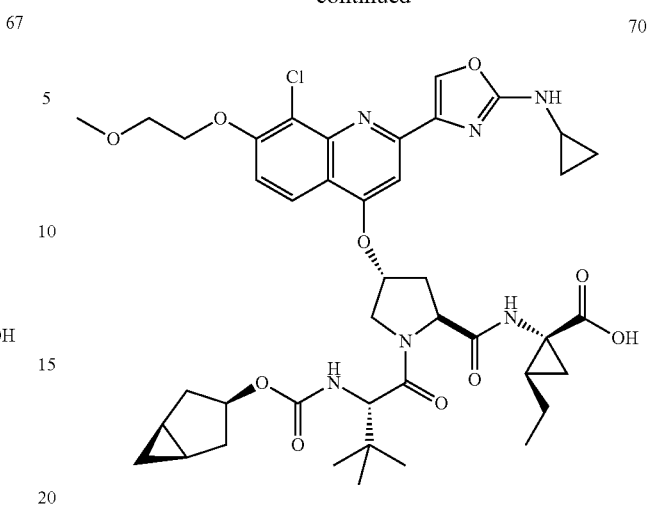
71
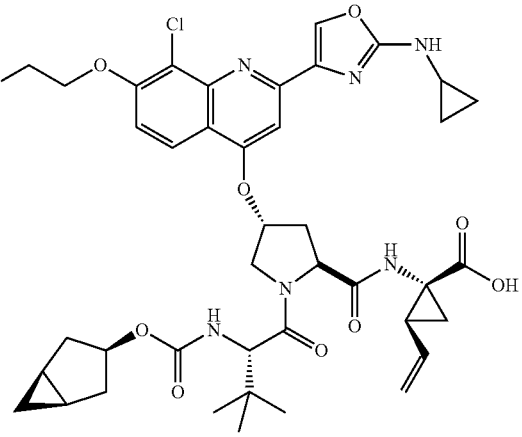
72
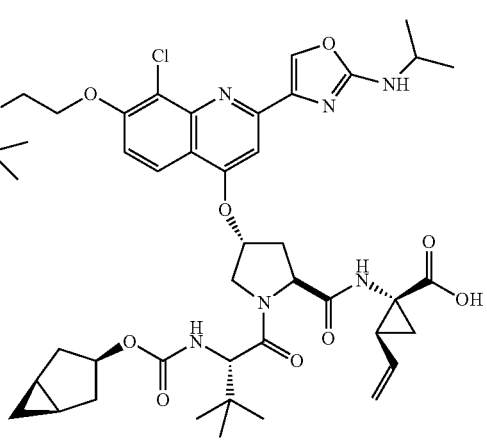

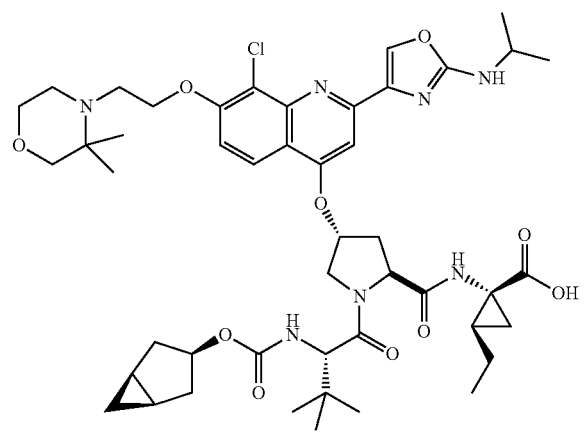
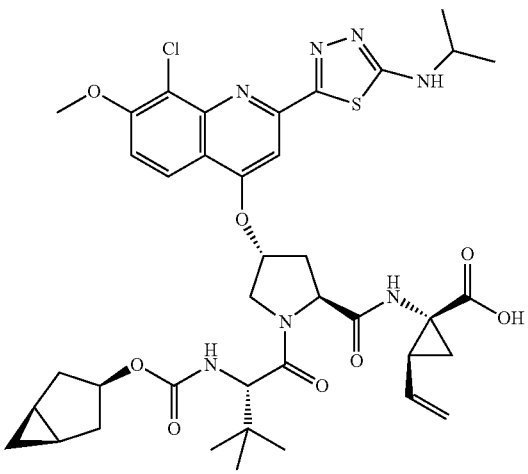
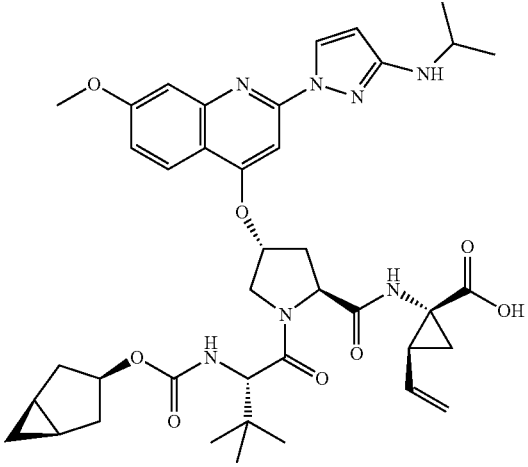
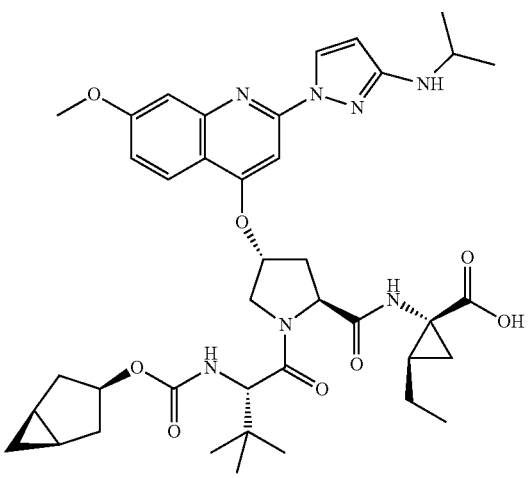

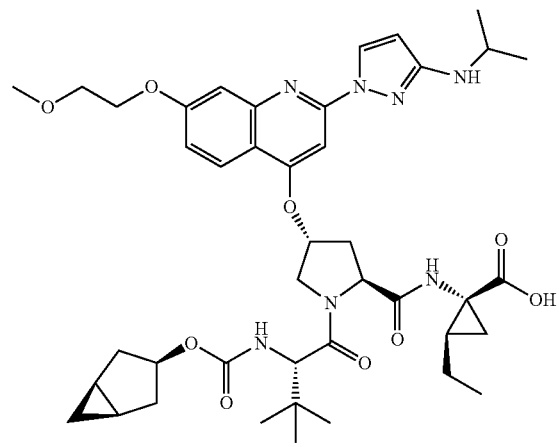
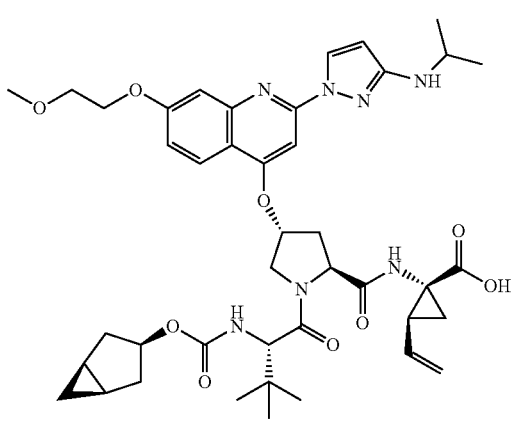
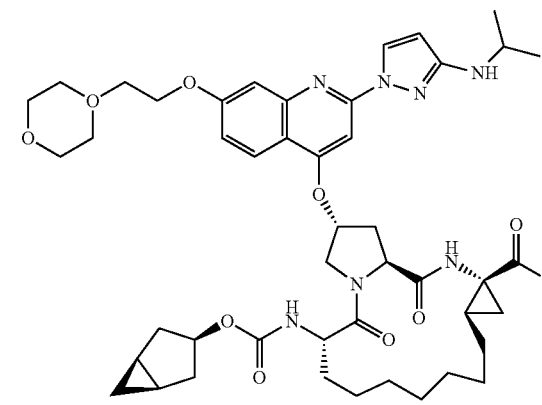
and pharmaceutically acceptable salts and prodrugs thereof.
Specific Embodiment 35
In one specific embodiment the invention provides the compound of Specific Embodiment 1 which is selected from:
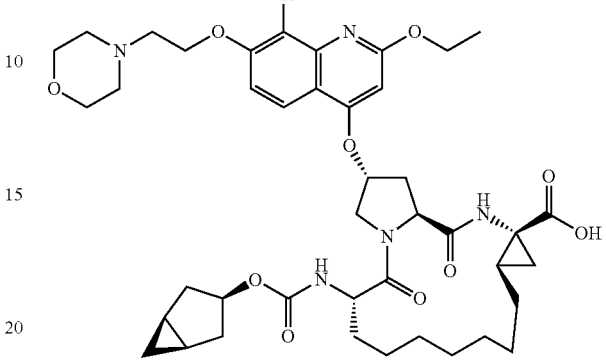
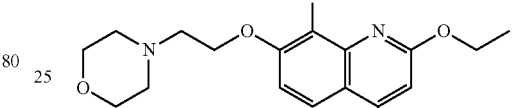
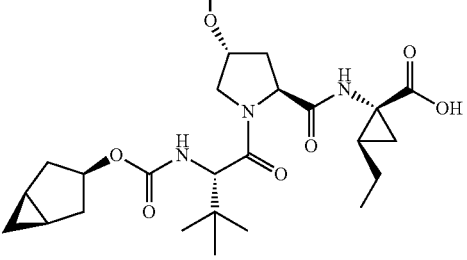

179
-continued
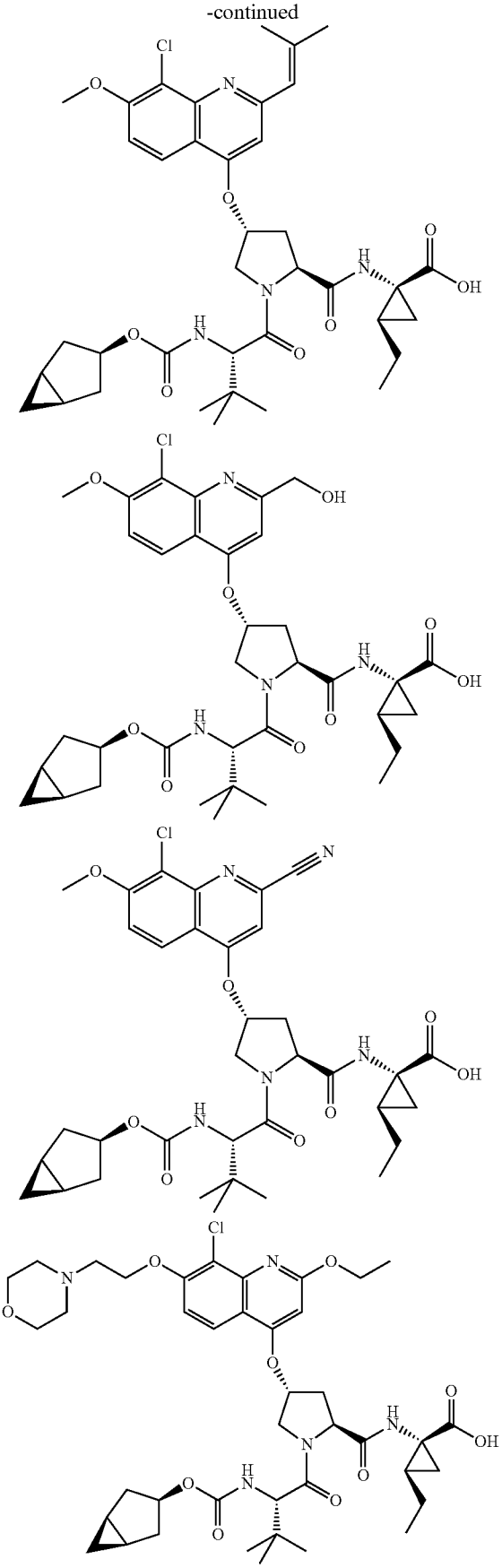
180
-continued
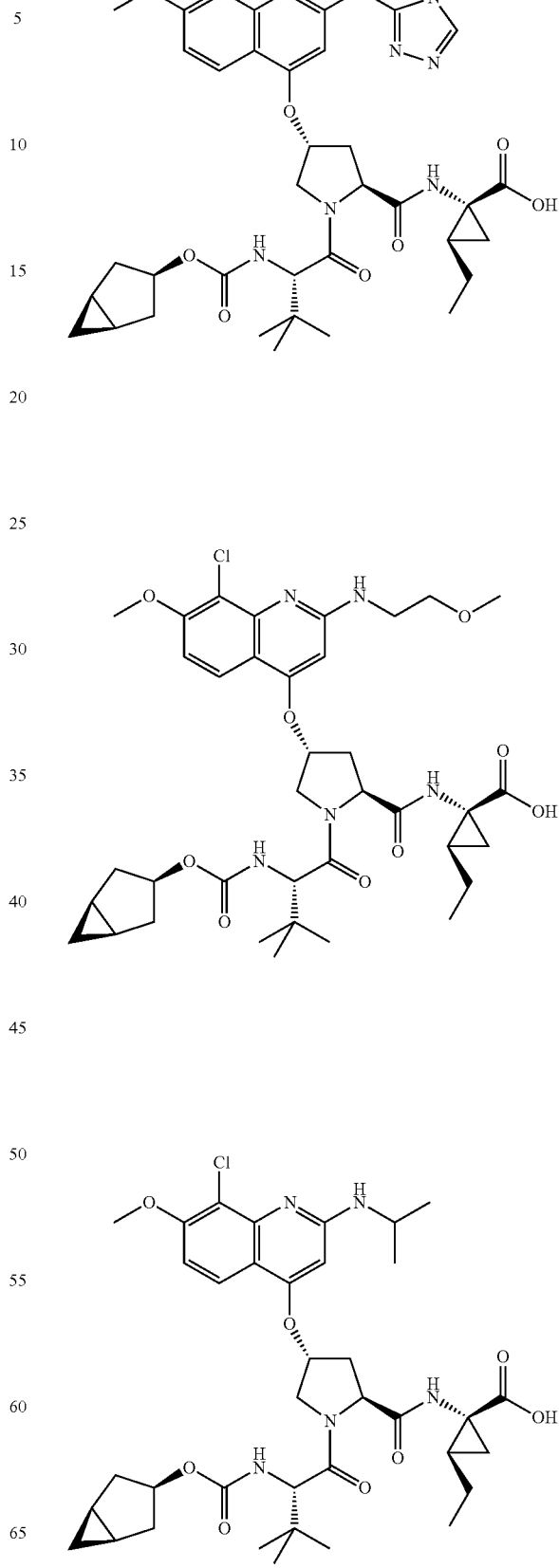

181
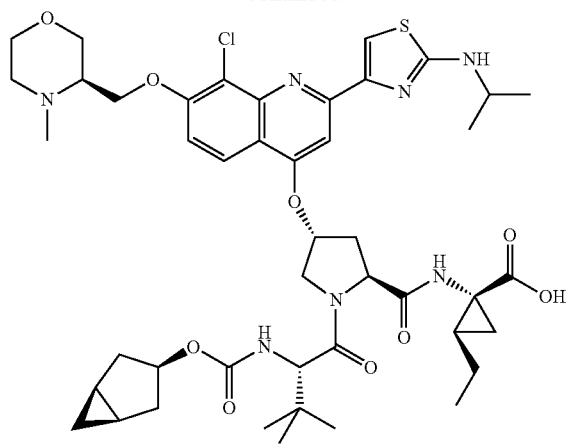
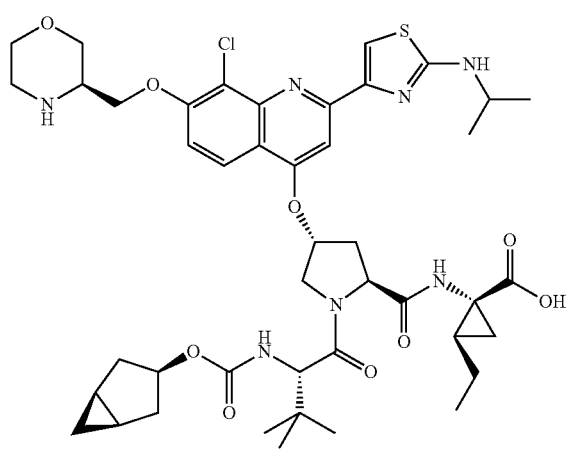
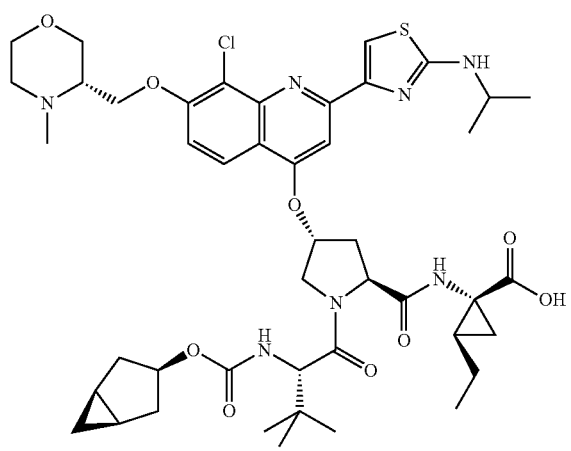
182
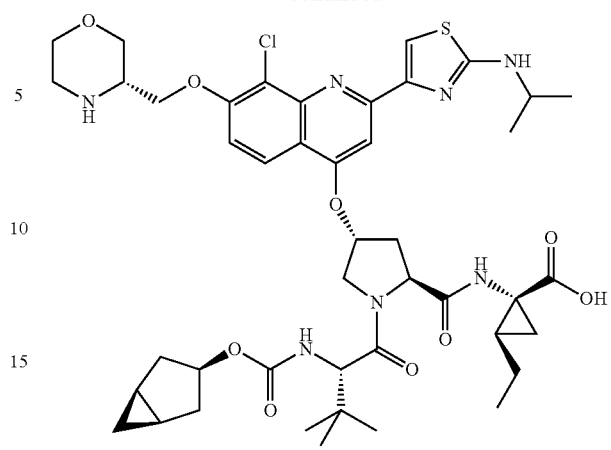
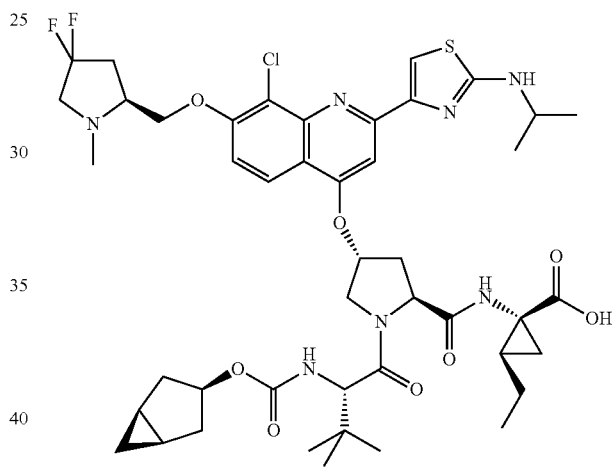
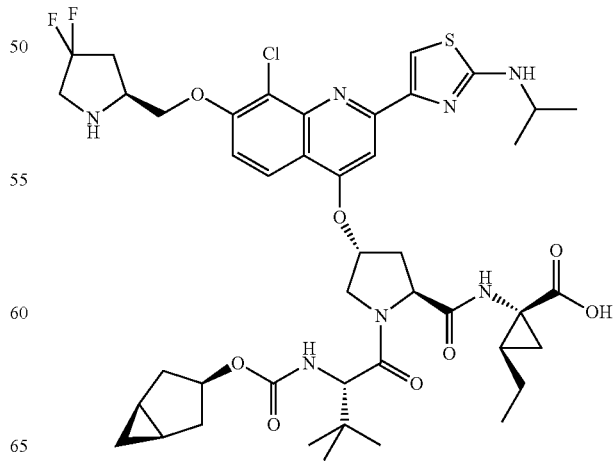

183
-continued
184
-continued
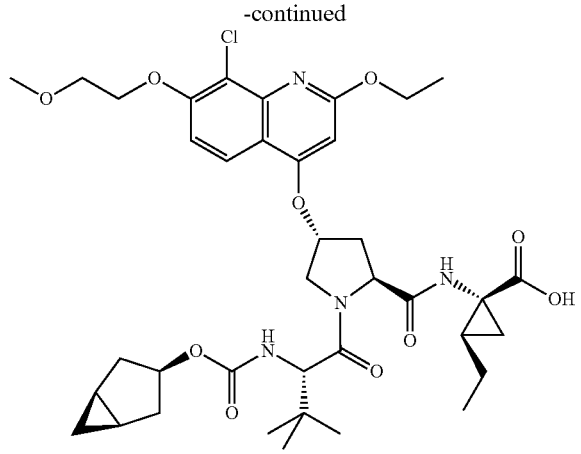
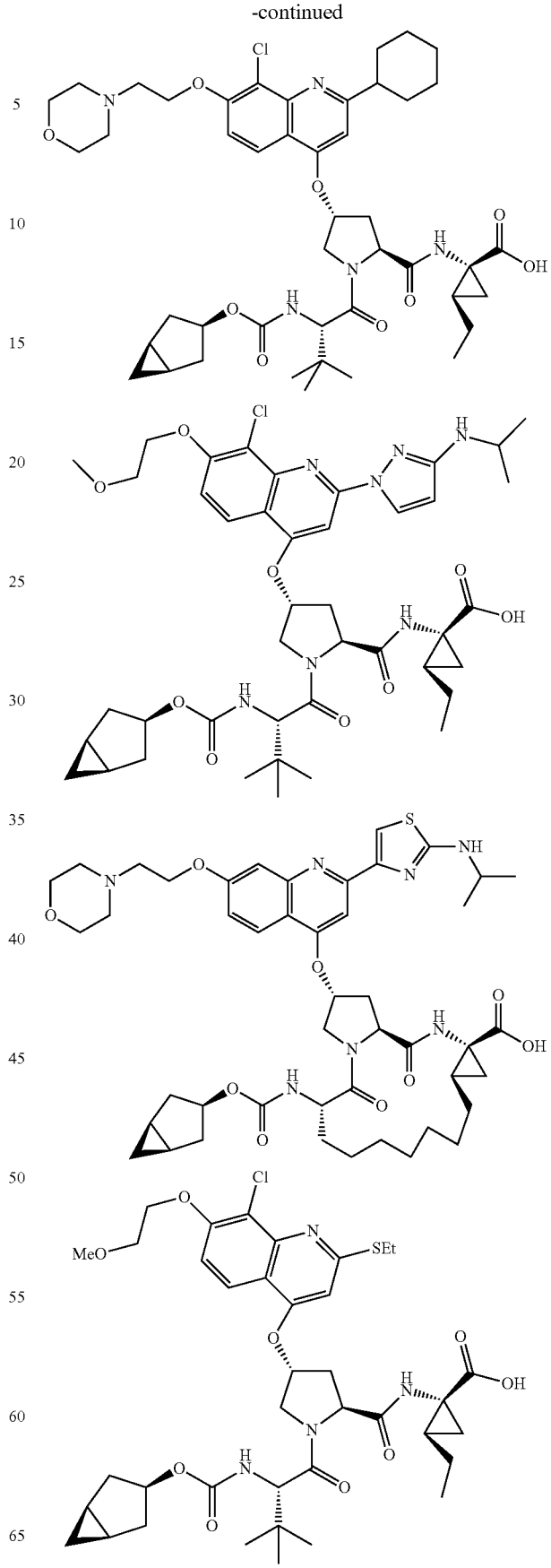

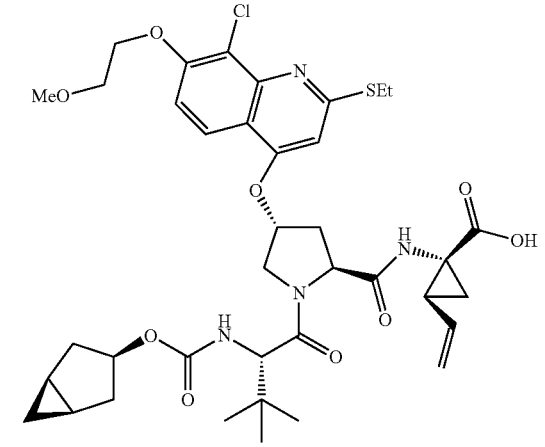
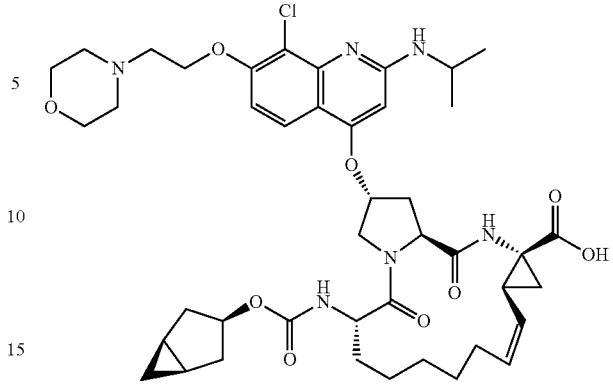
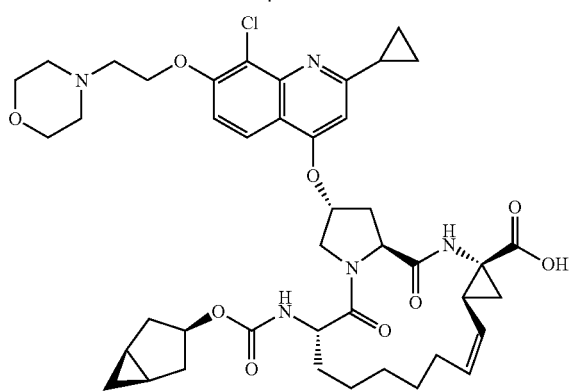
and pharmaceutically acceptable salts and prodrugs thereof.
Specific Embodiment 36
In one specific embodiment the invention provides the compound of Specific Embodiment 1 which is selected from:
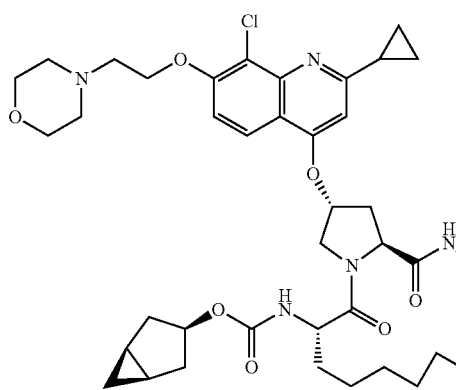
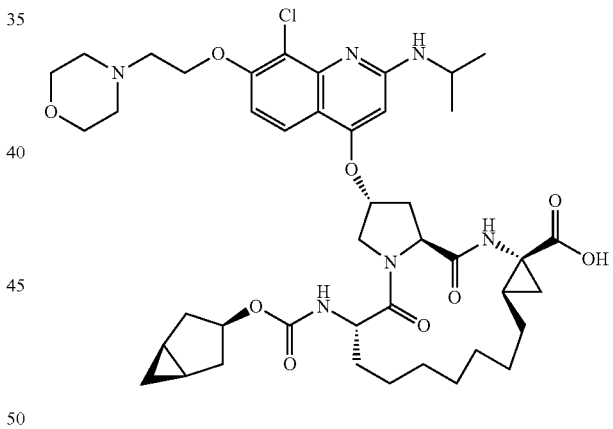
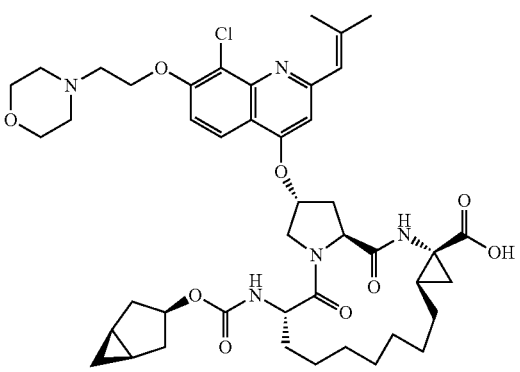
and
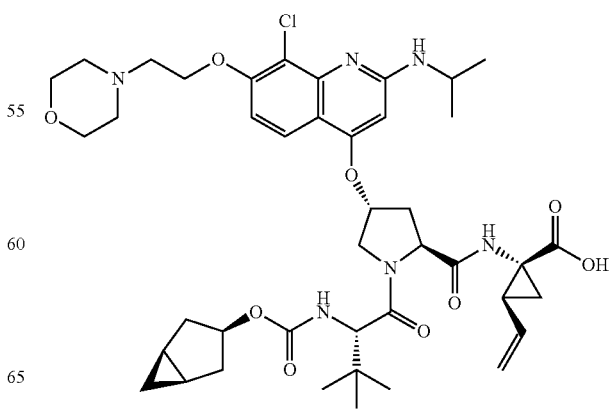

-continued
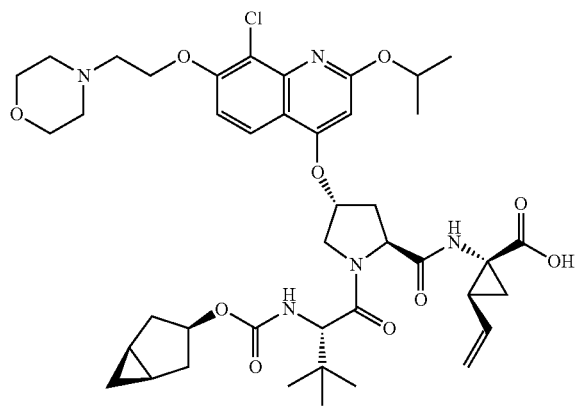
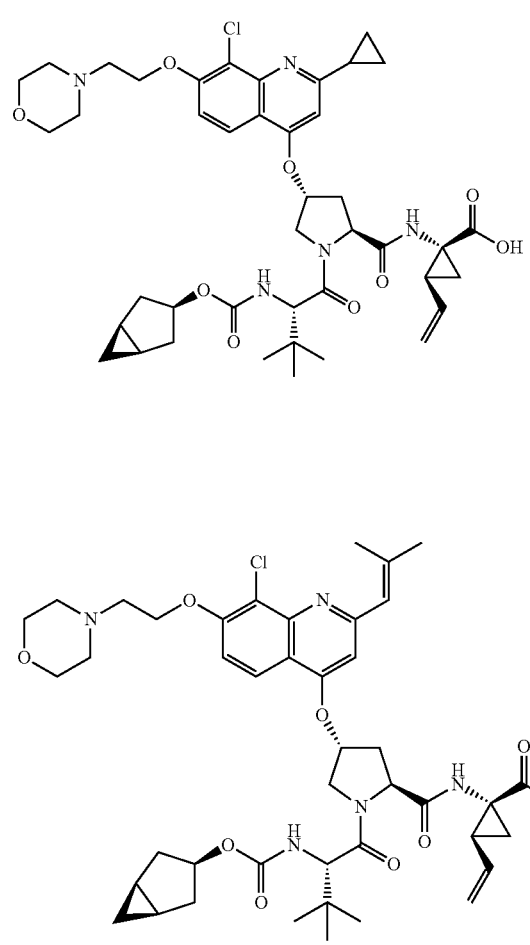
and pharmaceutically acceptable salts and prodrugs thereof.
Specific Embodiment 37
In one specific embodiment the invention provides the compound of Specific Embodiment 1 which is selected from:
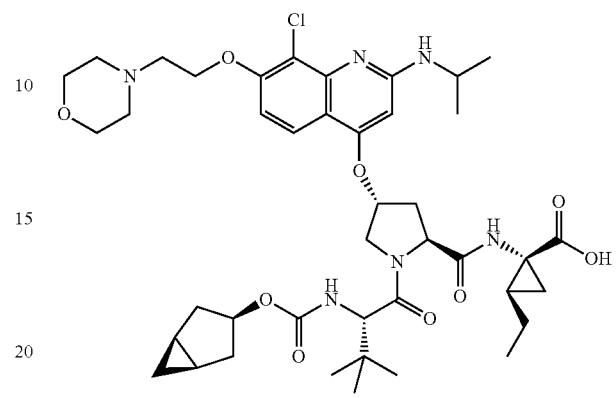
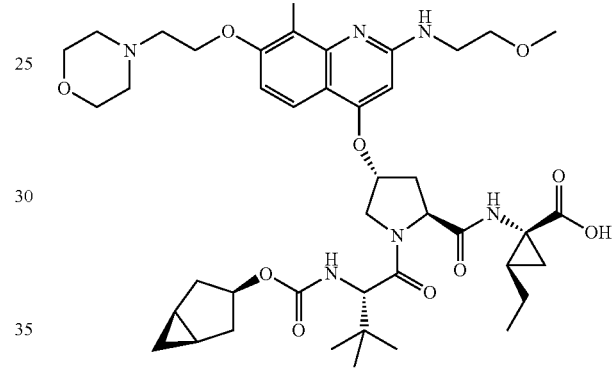
and
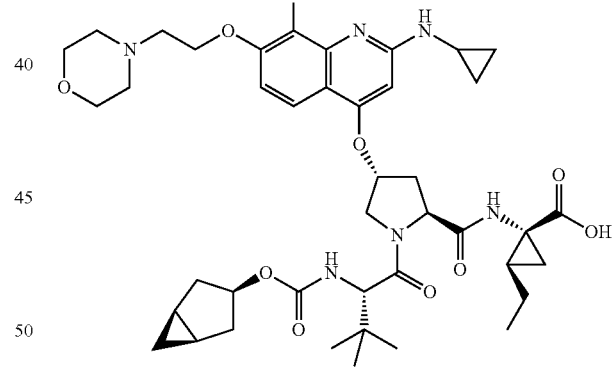
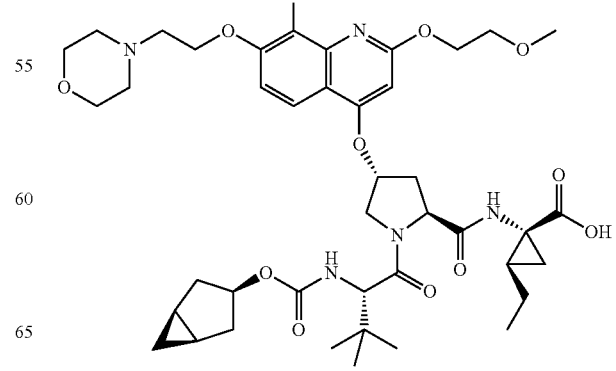

-continued

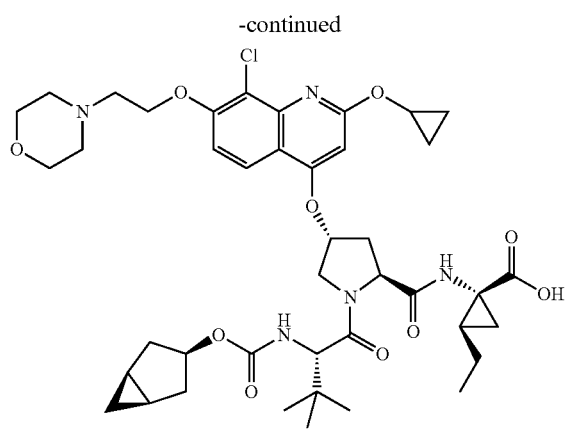

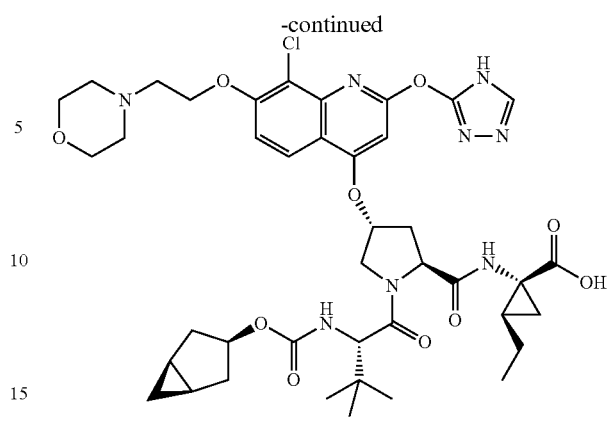

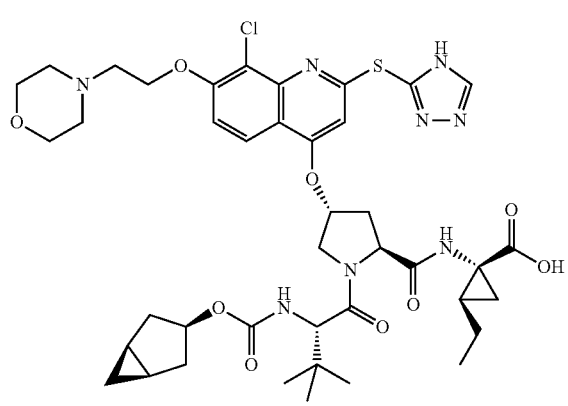

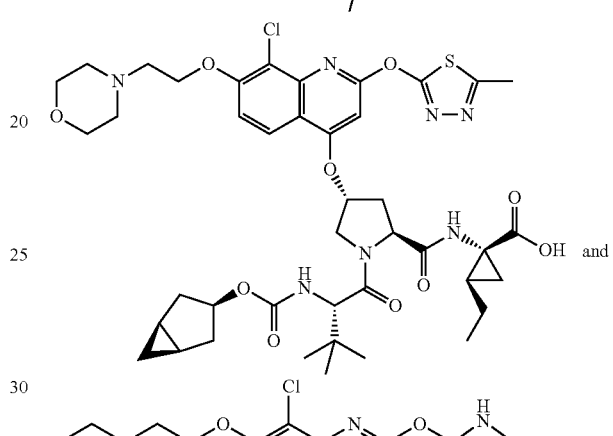

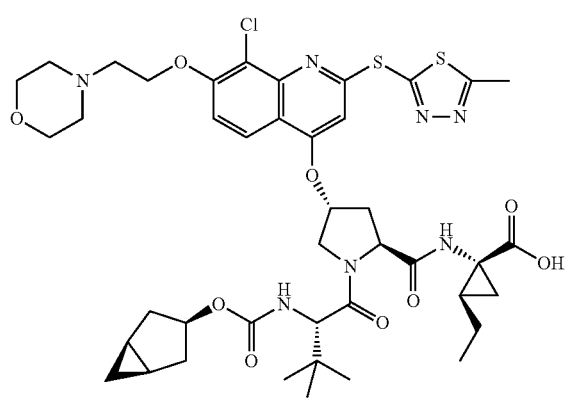

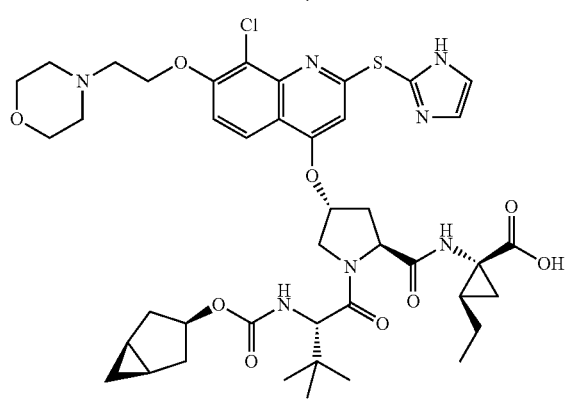

and pharmaceutically acceptable salts and prodrugs thereof.

Specific Embodiment 38

In one specific embodiment the invention provides the compound of any one of Specific Embodiments 1-37 which is a prodrug or a pharmaceutically acceptable salt thereof.

Specific Embodiment 39

In one specific embodiment the invention provides a pharmaceutical composition comprising the compound of any of Specific Embodiments 1-38 and at least one pharmaceutically acceptable carrier.

Specific Embodiment 40

In one specific embodiment the invention provides the pharmaceutical composition according to Specific Embodiment 39 for use in treating disorders associated with HCV.

Specific Embodiment 41

In one specific embodiment the invention provides the pharmaceutical composition of Specific Embodiment 39, further comprising at least one additional therapeutic agent.

Specific Embodiment 42

In one specific embodiment the invention provides the pharmaceutical composition of Specific Embodiment 41, wherein said additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

Specific Embodiment 43

In one specific embodiment the invention provides the pharmaceutical composition according to Specific Embodiment 39, further comprising a nucleoside analogue.

Specific Embodiment 44

In one specific embodiment the invention provides the pharmaceutical composition according to Specific Embodiment 43, further comprising an interferon or pegylated interferon.

Specific Embodiment 45

In one specific embodiment the invention provides the pharmaceutical composition according to Specific Embodiment 43, wherein said nucleoside analogue is selected from ribavirin, viramidine, levovirin, a L-nucleoside, and isatoribine and said interferon is α-interferon or pegylated interferon.

Specific Embodiment 46

In one specific embodiment the invention provides a method of treating disorders associated with hepatitis C, said method comprising administering to an individual a pharmaceutical composition which comprises a therapeutically effective amount of the compound of any of Specific Embodiments 1-37.

Specific Embodiment 47

In one specific embodiment the invention provides a compound or synthetic method described herein.

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples herein below. These methods are intended to illustrate the nature of such preparations and are not intended to limit the scope of applicable methods. Certain compounds of the invention can be used as intermediates for the preparation of other compounds of the invention.

EXAMPLES

Section A: Preparation of Intermediates

1. Preparation of Intermediate I:

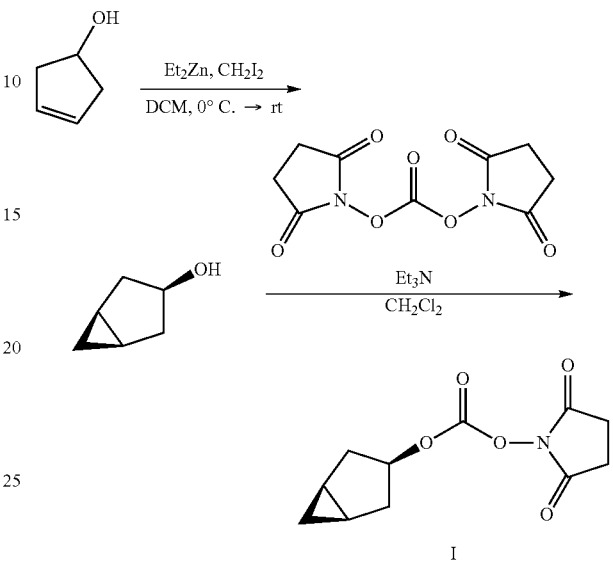

Step 1:
To a dry, argon purged three-neck round bottom flask (1000 mL) were added anhydrous dichloromethane (100 mL) and $Et_2Zn$ (28 mL, 273 mmol) at 0° C. (CAUTION: Source of argon can not be from needle. Use appropriate glass adapter only. A second bubbler can also be attached to the flask to prevent excessive pressure build up.) Cyclopenten-3-ol (10.0 mL, 119 mmol) was then added dropwise (large quantity of ethane gas was produced) to the flask and the reaction mixture was allowed to stir until the evolution of gas had ceased. Diiodomethane (22 mL, 242 mmol) was then added dropwise over a period of 30 min. The reaction was allowed to warm to room temperature and continued to stir overnight under a positive flow of argon, at which point TLC analysis had indicated complete disappearance of the starting alcohol. The reaction was then diluted with $CH_2Cl_2$ and quenched with 2M HCl (white precipitate should be completely dissolved). The biphasic mixture was poured into a reparatory funnel and the organic layer was collected. The solvent was removed under reduced pressure until 100 mL of material remained.

Step 2:
Anhydrous dichloromethane (525 mL) was added to the flask followed by the dropwise addition of triethylamine (34 mL, 245 mmol). The reaction continued to stir at room temperature under a positive flow of nitrogen at which point, disuccinimidylcarbonate (40.7 g, 159 mmol) was added to the flask portion wise. The reaction was allowed to stir until TLC analysis indicated complete disappearance of the starting material (2-3 days). Upon completion, the reaction mixture was quenched with 1M HCl (200 mL×2) and washed with $H_2O$ (200 mL×2). The desired material was extracted using $CH_2Cl_2$ and the combined organic layers were dried using anhydrous $MgSO_4$ and passed through a silica plug. The solvent was removed under reduced pressure and the crude material was purified using flash chromatography ($R_f$=0.33, 1:1 Hex/EtOAc) to provide intermediate I (22 g, 75%): $^1H$ NMR (300 MHz, $CDCl_3$): δ 5.24 (t, 1H), 3.82 (s, 4H), 2.24 (m, 2H), 2.03 (d, 2H), 1.38 (m, 2H), 0.48 (m, 1H), 0.40 (m, 1H).

2. Preparation of Intermediate II:

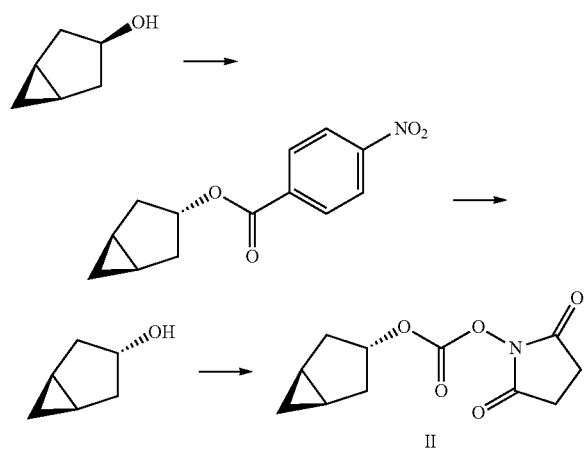

To a solution of cis-3-hydroxybicyclo[3.1.0]hexane (980 mg, 10 mmol), 4-nitrobenzoic acid (2.0 g, 12 mmol) and triphenylphosphine (3.0 g, 12 mmol) in THF (20 mL) was added diisopropyl azodicarboxylate (2.58 mL, 12 mmol) at 0° C. The mixture was stirred for 16 h at room temperature, and then concentrated in vacuo. The residue was purified by silica gel column chromatography (ethyl acetate/hexanes), affording 2.2 g (0.96 g, 77%) of the ester. LC/MS=775.4 (M$^+$+1).

This ester was dissolved in THF (40 mL) and aqueous lithium hydroxide solution (2 g/20 mL) was added. The mixture was stirred for 16 h at room temperature, and then diethyl ether (30 mL) was added. The organic layer was washed with brine, dried over sodium sulfate, and concentrated to a volume of ~10 mL. Dichloromethane (40 mL) was added and dried over sodium sulfate again. The resulting solution of the product alcohol was concentrated to a volume of ~20 mL, which was used for the next reaction directly. Following procedures similar to those for preparation of I, intermediate II was obtained. $^1$H NMR (300 MHz, CDCl$_3$): δ 4.80 (t, 1H), 3.82 (s, 4H), 2.38 (m, 2H), 2.01 (d, 2H), 1.40 (m, 2H), 0.45 (m, 1H), 0.02 (m, 1H).

3. Preparation of Tripeptide Intermediates:

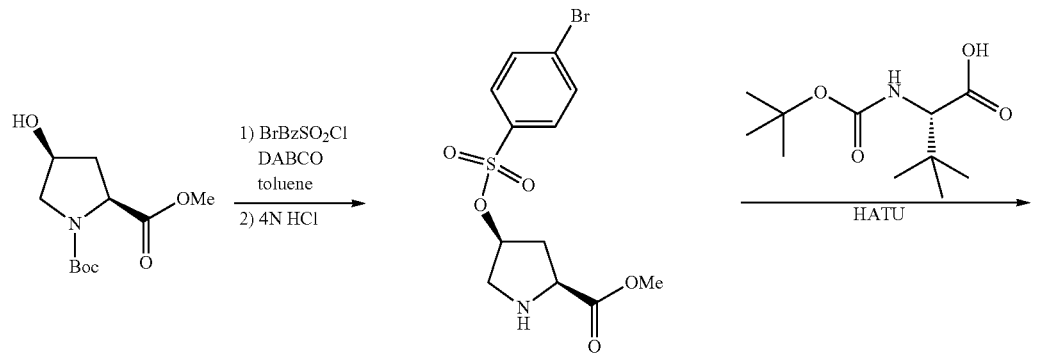

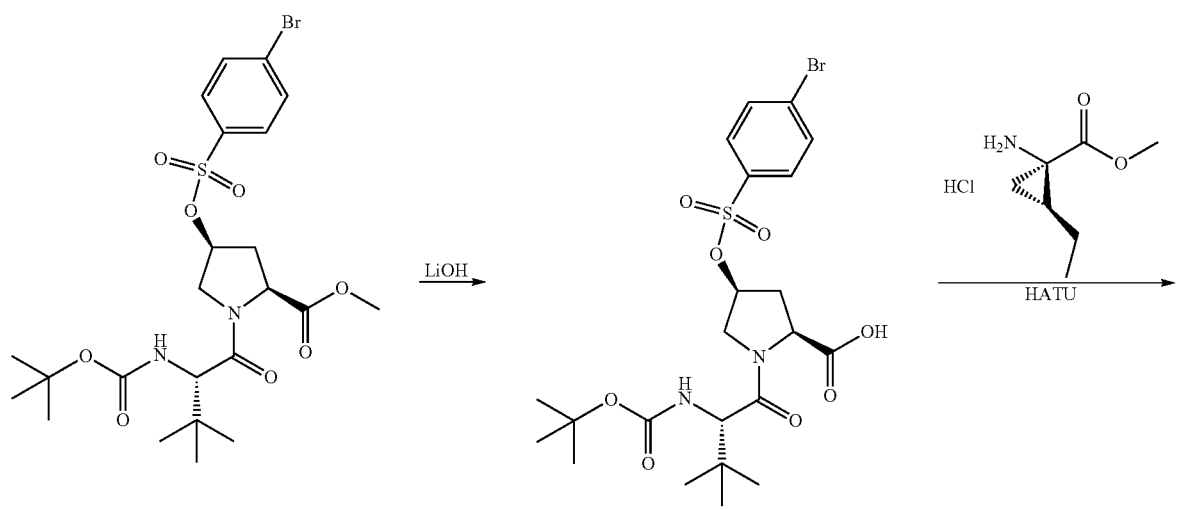

-continued

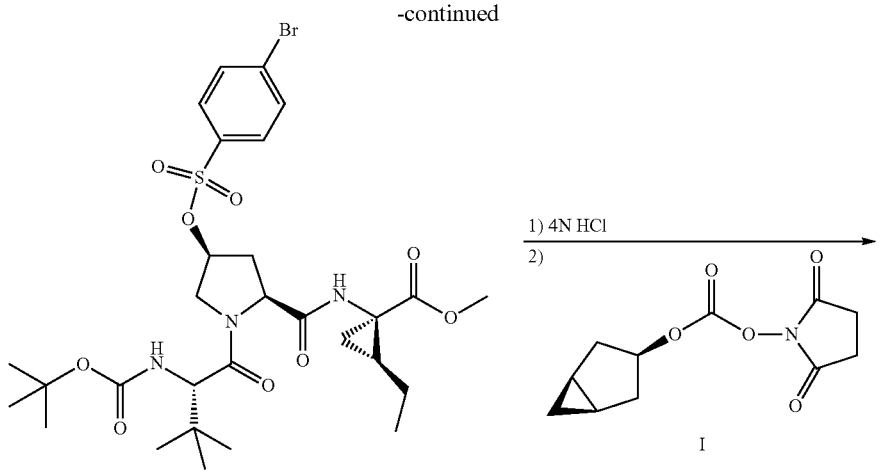

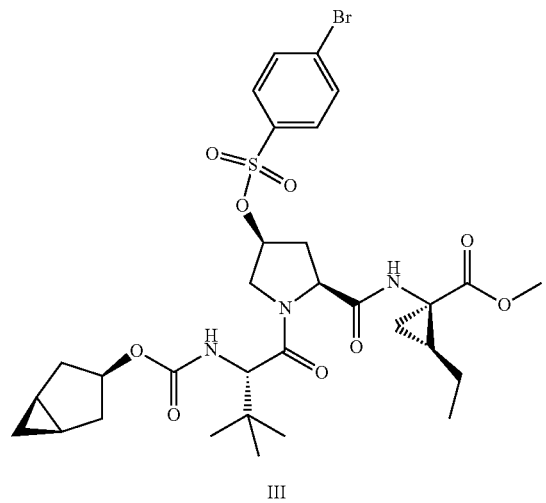

Step 1:

N-t-Boc-cis-4-Hydroxy-L-Proline methyl ester (100.0 g, 407.7 mmol) and DABCO (1.5 eq, 68.6 g, 611.6 mmol) were dissolved in anhydrous toluene (200 mL) in a 2 L three necked round bottom flask with a mechanical stirrer and an addition funnel. After cooling the solution to 0° C. under $N_2$, A solution of 4-Bromo-benzenesulfonyl chloride (1.3 eq, 135.6 g, 530.0 mmol) in 300 mL of toluene was added through addition funnel over 60 minutes. The reaction mixture was stirred and warmed to room temperature overnight (16 hours). The mixture was slowly poured into 2 L 1M $Na_2CO_3$ $_{(aq.)}$, and the product was extracted with EtOAc (2 L). After the organic phase was washed by 0.5 N HCl (2 L), $H_2O$ (1 L), and brine (1 L), it was dried ($MgSO_4$), concentrated to give 195.45 g of a yellow oily brosylate product.

To a solution of the above brosylate (407.7 mmol) in dichloromethane (300 mL) was slowly added 4.0 M HCl in dioxane (500 mL, 5 eq) and the resulting solution was allowed to stir at room temperature for 2 hours. After ether (500 mL) was added to the reaction mixture, the mixture was stirred for 15 min and the white precipitate was collected by filtration. The solid was washed with ether and hexane and then dried under vacuum overnight to obtain 153.0 g of the HCl amine salt, 381.8 mmol, in 94% yield for two steps.

Step 2:

To a solution of Boc-tert-butyl-glycine (97.0 g, 420.0 mmol) in DMF (200 mL) and DCM (200 mL) were added HATU (217.76 g, 572.7 mmol) and Hunig's base (126 mL, 1145.4 mmol) at room temperature. After the mixture was stirred for 20 min at room temperature, a solution of the previous HCl salt (153.0 g, 381.8 mmol) and Hunig's base (126 mL, 1145.4 mmol) in DMF (200 mL) and dichloromethane (200 mL) was added to the above acid mixture in one portion. The reaction mixture was stirred at room temperature for 3 h, with monitoring by LCMS. The reaction mixture was concentrated to remove dichloromethane under reduced pressure and the white solid that formed was filtered off. The remaining DMF solution was diluted with ethyl acetate (1 L), washed successively with 3% LiCl (aq) (3×650 mL), sat'd $NH_4Cl$ (2×500 mL), 0.5N HCl (aq) (2×600 mL), brine (500 mL), sat'd $NaHCO_3$ (3×500 mL), and brine (500 mL). The resulting organic fraction was dried ($MgSO_4$) and concentrated to afford crude tripeptide (111 g).

Step 3:

To a solution of the methyl ester (120 g, 207.8 mmol) in THF (300 mL), MeOH (75 mL) was added a solution of LiOH (26.18 g, 623.4 mmol) in $H_2O$ (150 mL). The solution was allowed to stir at room temperature for 4 hours. The mixture was cooled in an ice-bath while acidifying with 3N HCl to pH about 5.5, stirred for 10 min, and the resulting white solids were collected by filtration. The solids were washed with more water, ether and hexane. The solids were dried under vacuum at 40° C. overnight to give 95.78 g (82%) of the acid.

Step 4:

To a solution of the carboxylic acid (81.4 g, 144.27 mmol) in DMF (200 mL) and dichloromethane (200 mL) was added HATU (82.3 g, 216.4 mmol) and Hunig's base (47.5 mL, 432.8 mmol) at room temperature. After the mixture was stirred for 20 min at room temperature, a solution of amine (158.7 mmol) and Hunig's base (47.5 mL, 1145.4 mmol) in DMF (200 mL) and dichloromethane (200 mL) was added to the above acid mixture in one portion. The reaction mixture was stirred at room temperature for 3 h and monitored by LCMS. After the mixture was concentrated under reduced pressure to remove dichloromethane, the white solids that formed were filtered off. The remaining DMF solution was diluted with ethyl acetate (600 mL) and successively washed with 3% LiCl (aq) (2×550 mL), sat'd NH$_4$Cl (500 mL), 1N HCl (aq) (500 mL), sat'd NaHCO$_3$ (500 mL), and brine (300 mL). The resulting organic fraction was dried (Na$_2$SO$_4$) and concentrated to afford crude tripeptide (111 g).

Step 5:

The crude tripeptide was dissolved in 4N HCl in dioxane (300 mL) at room temperature and stirred for 2 h. It was then concentrated under vacuum, and co-evaporated with dichloromethane (2×200 mL) to dryness. The residue was dissolved in EtOAc (600 mL) and sat'd aq. NaHCO$_3$ (1 L). It was stirred vigorously. After 10 min, carbonic acid bicyclo[3.1.0]hex-3-yl ester 2,5-dioxo-pyrrolidin-1-yl ester (intermediate I, 41.4 g, 173.1 mmol) was added in one portion. After the resulting mixture was stirred for another 30 min, the organic layer was collected and washed with brine (500 mL), dried (Na$_2$SO$_4$), and concentrated. The crude product was purified by flash chromatography on silica gel with ethyl acetate/hexane to afford 94.44 g (92%) of the tripeptide intermediate III.

4. Preparation of Quinoline Intermediate IV:

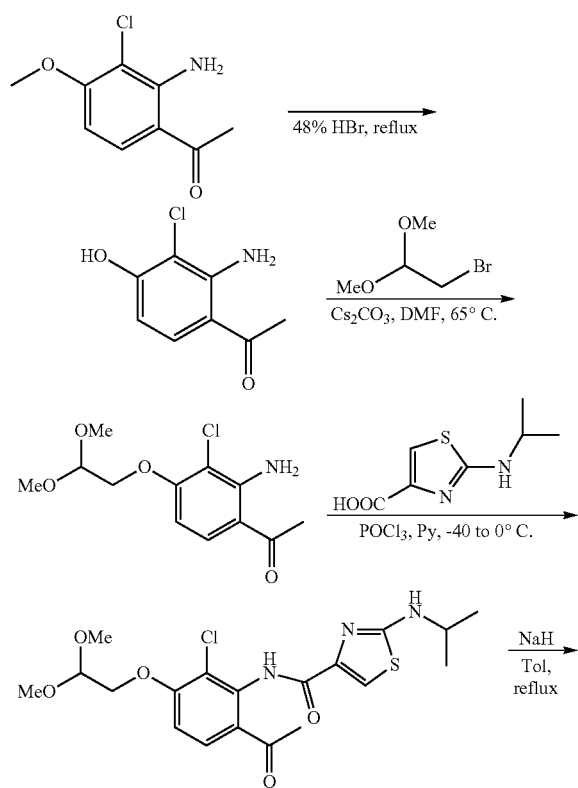

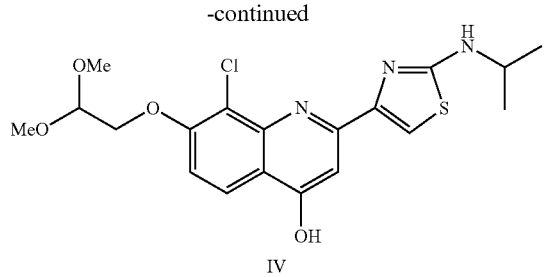

Step 1:

1-(2-Amino-3-chloro-4-hydroxy-phenyl)-ethanone (70.7 g, 354 mmol) was stirred in 48% aq. HBr (500 mL) at 110° C. for 72 h. After the mixture was cooled to 0° C. with stirring, the solids were filtered and washed with water. The resulting solids were triturated with a saturated NaHCO$_3$ solution (~350 mL), filtered, washed with water, and dried under vacuum to give ~40 g (61%) of crude product as a dark brown solids. LC/MS=186 (M$^+$+1).

Step 2:

1-(2-Amino-3-chloro-4-hydroxy-phenyl)-ethanone (40 g, 215 mmol) was dissolved in DMF (360 ml). Cesium carbonate (140 g, 430 mmol) was added, followed by bromoacetaldehyde dimethyl acetal (54.5 g, 323 mmol). The mixture was then vigorously stirred at 65° C. for 24 h. Upon cooling to room temperature, EtOAc (1 L) and H$_2$O (1 L) were added to the mixture. The organic layer was extracted with EtOAc (1×400 ml). The combined organic layer was washed with aqueous 3% LiCl solution (2×1 L), brine, dried (Na$_2$SO$_4$) and concentrated in vacuo. The residue was purified by silica gel chromatography to give the desired product as a white solid (39 g, 67%).

Step 3:

To a mixture of 1-[2-Amino-3-chloro-4-(2,2-dimethoxy-ethoxy)-phenyl]-ethanone (13 g, 47.5 mmol) and isopropylaminothiazole-4-carboxylic acid hydrobromide (12.64 g, 47.5 mmol) in pyridine (150 ml) was slowly added phosphorus oxychloride (9.47 g, 61.8 mmol) at −40° C. The mixture was then stirred at 0° C. for 4 h. Upon completion of the reaction, H$_2$O (30 ml) was added dropwise to the mixture. The mixture was then stirred at 0° C. for another 15 min. The mixture was concentrated in vacuo. The residue was diluted with EtOAc, washed with a sat. NaHCO$_3$ aqueous solution. The organic layer was dried (Na$_2$SO$_4$) and concentrated in vacuo. The residue was dissolved in CH$_2$Cl$_2$, hexanes was added slowly to the solution, and a yellow solid started to crash out. More hexanes were added until not much product was left in the mother liquid (18 g, 85%).

Step 4:

2-Isopropylamino-thiazole-4-carboxylic acid [6-acetyl-2-chloro-3-(2,2-dimethoxy-ethoxy)-phenyl]-amide (18 g, 40.7 mmol) was suspended in toluene (400 ml). NaH (2.4 g, 61 mmol) was added to the vigorously stirred mixture while monitoring H$_2$ evolution. The mixture became a clear solution during heating to reflux. The reaction was complete after refluxing for 3 h. The mixture was cooled to room temperature. A solution of AcOH (69.2 mmol) in H$_2$O (3 vol) was added to the mixture. After vigorous agitation for 1 h at 0° C., the solids were collected by filtration, rinsed forward with H$_2$O. The wet cake was dried under high vacuum to a constant weight to provide intermediate IV (15 g, 86%).

5. Preparation of Quinoline Intermediate V:

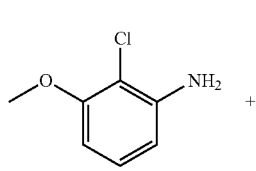

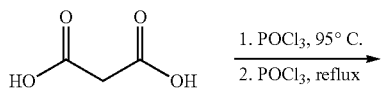

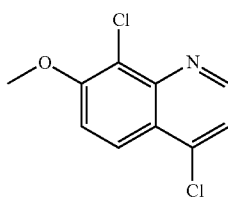

To a mixture of solids 2-chloro-3-methoxy-phenylamine (3.98 g, 25 mmol) and malonic acid (2.63 g, 25 mmol) in a 250-ml round bottom flask was added phosphorus oxychloride (2.5 ml, 27.5 mmol). The mixture was heated to 95° C. foaming slowly occurred during vigorous stirring and stopped in 1.5 h. The mixture was then cooled to room temperature. Phosphorus oxychloride (30 ml) was added to the dark brown tar-like material, heated to 115° C. Upon heating, all material dissolved. After 3 h of refluxing, the mixture was concentrated in vacuo. The residue was diluted with chloroform and poured into ice-water. 3 N aqueous NaOH was added to adjust pH to 10. The aqueous layer was extracted with chloroform. The combined organic layer was washed with brine, dried over sodium sulfate, and concentrated in vacuo. The residue was purified by silica gel column chromatography (ethyl acetate/hexanes), affording the product as a white solid (2.75 g, 46% over 2 steps). LC/MS=261.9 (M$^+$+1).

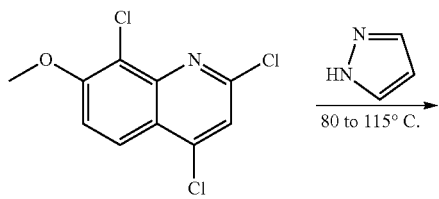

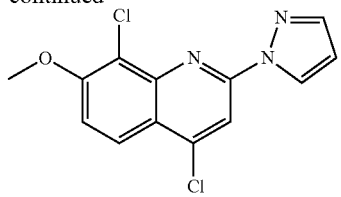

The mixture of pyrazole (3.1 g, 45.7 mmol) and trichloro compound (1.2 g, 4.57 mmol) was heated in a sealed microwave tube. After all solids melted at 80° C., house vacuum was applied to the tube to remove residual moisture and the mixture was left stirring at 115° C. for 18 h. Ethyl acetate and H$_2$O were added to dissolve all the solids. The organic phase was washed with 0.5 N aqueous HCl, and brine. The organics were then dried over sodium sulfate, and concentrated in vacuo. The solids were triturated with ethyl acetate/hexanes and collected by filtration, and further dried under high vacuum to give pyrazole as a pale yellow solid (1.28 g, contaminated with a small amount of bis-addition adduct). LC/MS=294.0 (M$^+$+1).

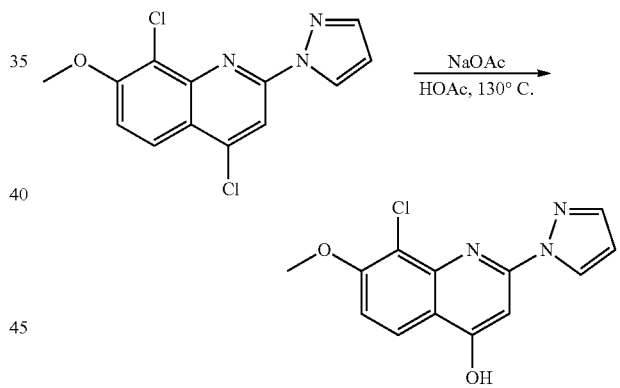

Product (650 mg, 2.2 mmol) from the previous step was suspended in acetic acid (7 ml) with sodium acetate (2.2 g, 27 mmol). The mixture was heated at 130° C. for 3 days in a sealed microwave tube. The mixture solidified during cooling to room temperature. Ethyl acetate and H$_2$O were added to dissolve the mixture. Sat. aqueous sodium bicarbonate was added to the organic layer and stirred for 5 min. The organic layer was then washed with brine, and concentrated in vacuo. The residue was then triturated with ethyl acetate/hexanes. The intermediate V (pure by HPLC) was collected by filtration (300 mg, 50% over 2 steps). LC/MS=276.0 (M$^+$+1).

Section B

Example 1

Preparation of Compound 1

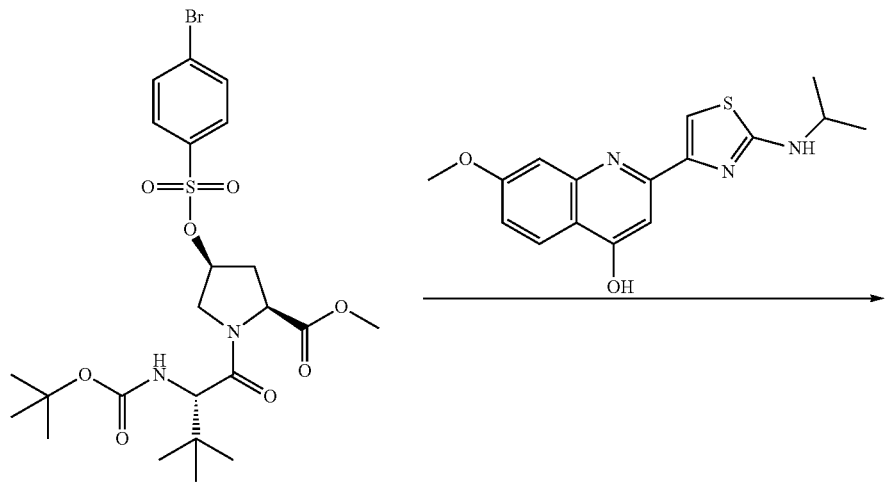

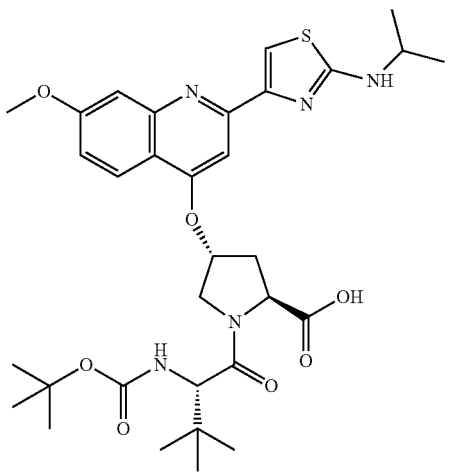

A mixture of the methyl ester (0.62 g, 1.1 mmol), the hydroxyquinoline (0.34 g, 1.1 mmol) and cesium carbonate (0.39 g, 1.2 mmol) in NMP (6 mL) was stirred at 65° C. for 16 h. The mixture was partitioned between ethyl acetate (50 mL) and 3% aqueous LiCl (50 mL). The organic layer was washed with 3% aqueous LiCl (50 mL), and then with brine, dried over sodium sulfate, and concentrated in vacuo. The residue was purified by silica gel column chromatography (ethyl acetate/hexanes), affording the coupled product (0.45 g, 64%) as a red-brown solid. A solution of the above product in THF (2 mL) and MeOH (2 mL) was treated with lithium hydroxide in water (0.29 mg/2 mL) for 3 h at room temperature, and neutralized with 4 N HCl. After removal of volatile solvents, the mixture was extracted with dichloromethane and the extract was concentrated to dryness, affording acid product. LC/MS=642.3 ($M^+ +1$).

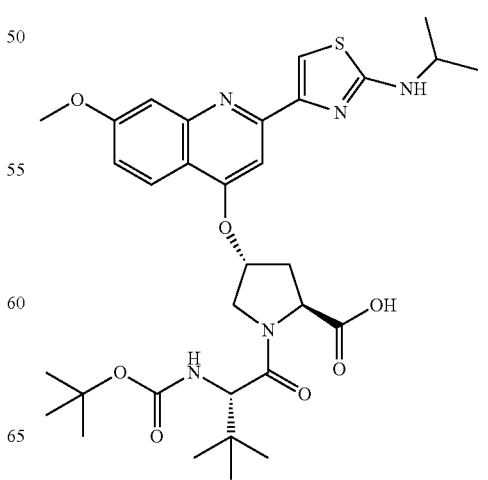

+

-continued

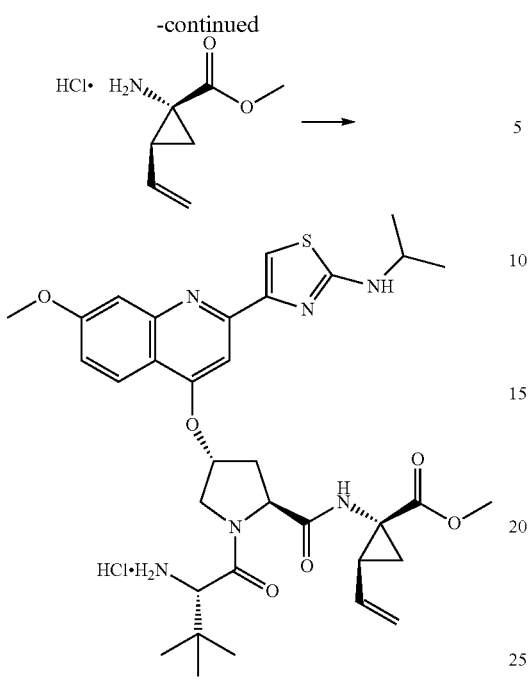

To a solution of the acid (440 mg, 0.69 mmol), (1R,2S)-1-amino-2-vinyl-cyclopropanecarboxylic acid methyl ester hydrochloride (147 mg, 0.82 mmol) and diisopropyl ethyl amine (0.48 mL, 2.8 mmol) was added HATU (390 mg, 1.0 mmol) at 0° C., and stirred for 30 min Ethyl acetate (50 mL) and 3% aqueous LiCl (50 mL) were added to the mixture while stirring. The organic layer was taken and washed with 3% aqueous LiCl (50 mL), and then with brine, dried over sodium sulfate, and concentrated in vacuo. The residue was purified by silica gel column chromatography (ethyl acetate/hexanes), affording the coupled product (0.35 g, 66%) as a red brown solid. LC/MS=765.5 ($M^1$+1). A solution of the above product in dichloromethane (3 mL) was treated with 4N HCl in dioxane (8 mL) for 2 h at room temperature and concentrated to dryness, affording amine.

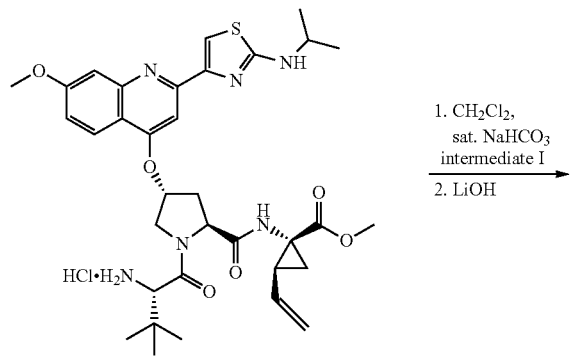

-continued

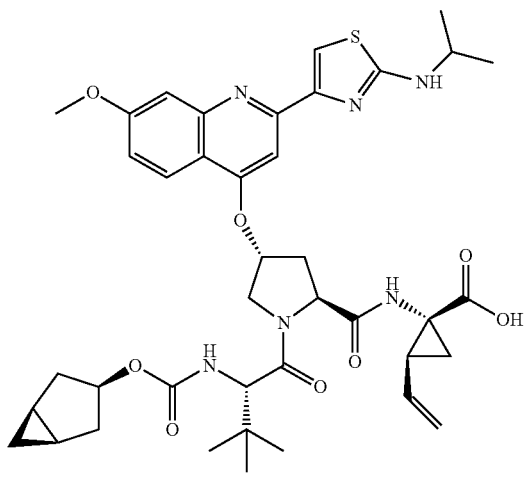

To a biphasic solution of the amine (38 mg, 0.054 mmol) in dichloromethane (20 mL) and 5% aqueous sodium bicarbonate (20 mL) was added a solution of intermediate I in dichloromethane in four portions, until the starting material was completely consumed (30 min. apart, a total of ~25 mg/1 mL). The dichloromethane layer was taken and concentrated. The residue was purified by preparative HPLC using water/acetonitrile (0.05% TFA) as eluents. The methyl ester product was then dissolved in MeOH/water (20 mL/2 mL). Excess lithium hydroxide (100 mg) was added and stirred at room temperature for 24 h. Dichloromethane (40 mL) and 1 N HCl (20 mL) were added sequentially. While stirring, saturated aqueous sodium bicarbonate was dropwise until the aqueous pH became ~7. The dichloromethane layer was concentrated, and the residue was purified by preparative HPLC using water/acetonitrile (0.05% TFA) as eluents, which afforded 14 mg (33%) of the Compound 1. $^1$H NMR (300 MHz, CD$_3$OD): δ 8.75 (s, 1H), 8.24 (d, J=9.6 Hz, 1H), 8.18 (s, 1H), 7.75 (m, 2H), 7.34 (d, J=9.6 Hz, 1H), 5.87 (dd, 1H), 5.77 (brs, 1H), 5.28 (d, J=17.1 Hz, 1H), 5.11 (d, J=10.5 Hz, 1H), 4.74 (t, 1H), 4.64 (d, 1H), 4.51 (t, 1H), 4.20 (m, 2H), 4.09 (m, 1H), 4.05 (s, 3H), 2.78 (m, 1H), 2.59 (m, 1H), 2.20 (q, 1H), 1.95 (dd, 1H), 1.85 (dd, 1H), 1.72 (m, 2H), 1.43 (m, 2H), 1.34 (d, 6H), 1.19 (m, 2H), 1.04 (s, 9H), 0.38 (m, 2H). LC/MS=775.4 ($M^+$+1); LC/MS $R_t$=2.45 min.

Example 2

Preparation of Compound 2

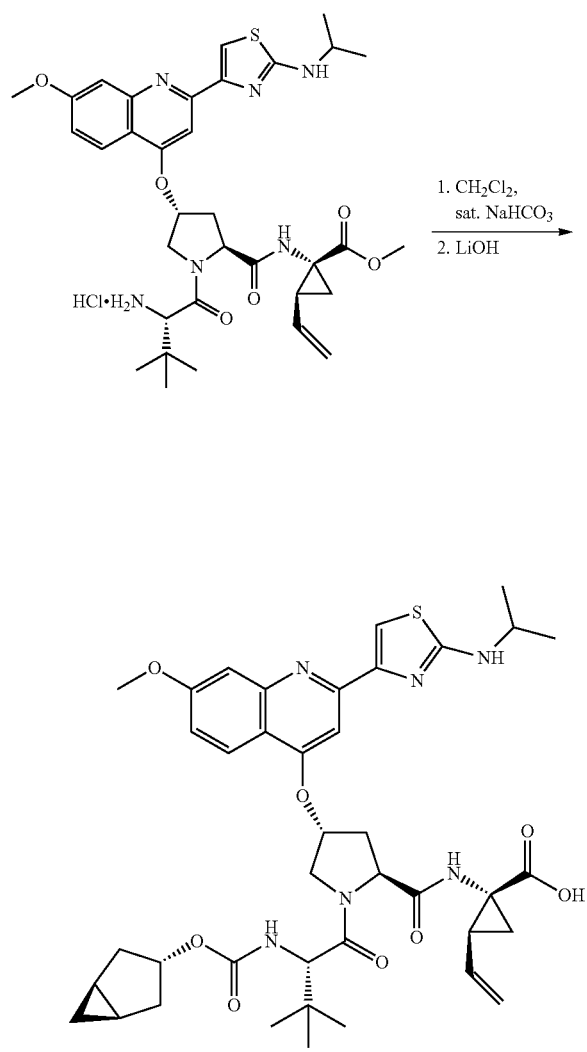

Compound 2 was obtained by following procedures similar to those for preparation of Compound 1 except using the carbonate II. $^1$H NMR (300 MHz, CD$_3$OD): δ 8.75 (s, 1H), 8.28 (d, J=9.6 Hz, 1H), 8.18 (s, 1H), 7.77 (s, 1H), 7.73 (s, 1H), 7.34 (d, J=9.6 Hz, 1H), 5.86 (dd, 1H), 5.77 (brs, 1H), 5.28 (d, J=17.1 Hz, 1H), 5.11 (d, J=10.5 Hz, 1H), 4.72 (t, 1H), 4.64 (d, 1H), 4.18 (m, 1H), 4.12 (m, 2H), 4.06 (s, 3H), 2.78 (m, 1H), 2.58 (m, 1H), 2.20 (q, 1H), 1.93 (dd, 1H), 1.4-1.4 (m, 4H), 1.34 (d, 6H), 1.30 (m, 2H), 1.22 (m, 2H), 1.04 (s, 9H), 0.38 (q, 1H), −0.14 (m, 1H). LC/MS=775.4 (M$^+$+1); LC/MS R$_t$=2.33 min.

Example 3

Preparation of Compound 3

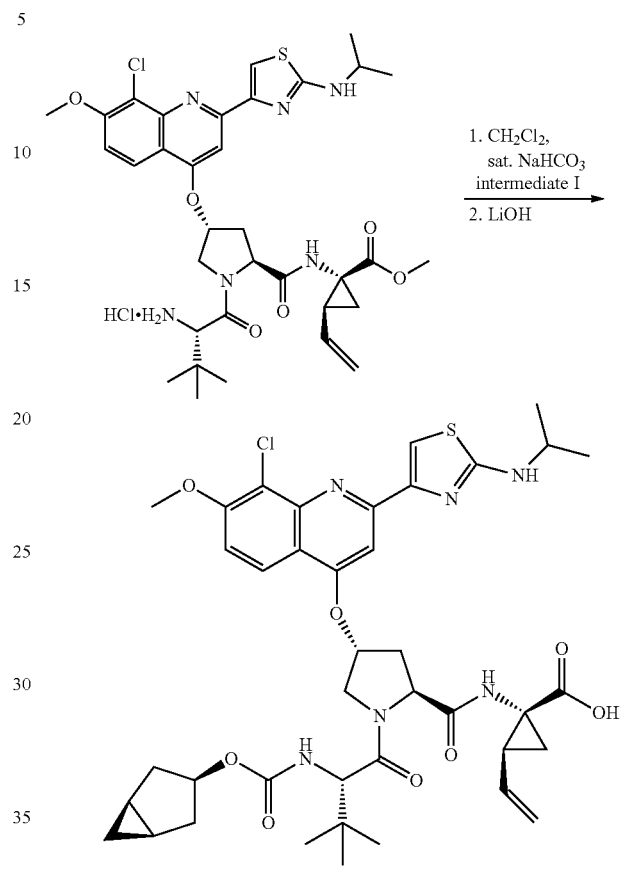

Compound 3 was obtained by following procedures similar to those for preparation of Compound 1, except using tripeptide intermediate that was obtained by following procedures similar to those for preparation of Compound 1 except using 8-chloro-2-(2-isopropylamino-thiazol-4-yl)-7-methoxy-quinolin-4-ol. LC/MS=809.5 (M$^+$+1); LC/MS R$_t$=4.42 min (6 min. run).

Example 4

Preparation of Compound 4

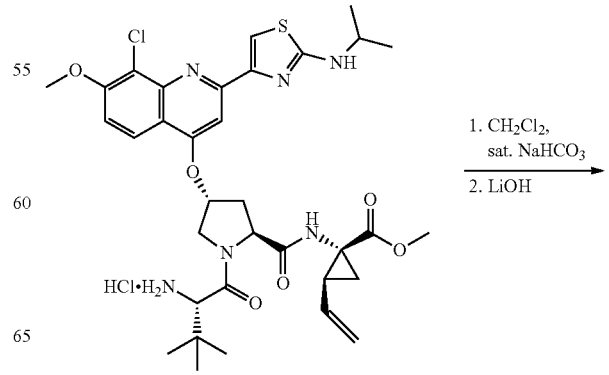

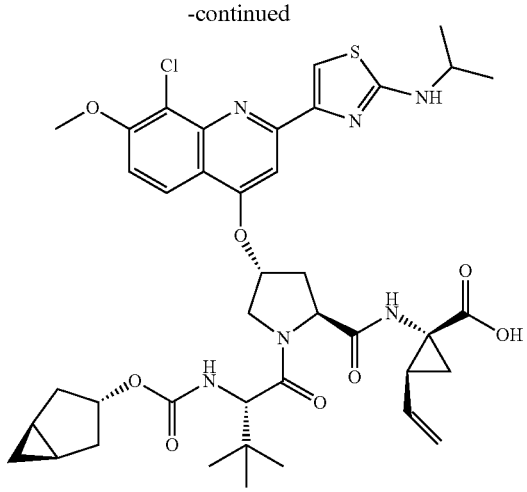
Compound 4 was obtained by following procedures similar to those for preparation of Compound 2 except using tripeptide that was obtained by following procedures similar to those for preparation of Compound 1 except using 8-chloro-2-(2-isopropylamino-thiazol-4-yl)-7-methoxy-quinolin-4-ol. LC/MS=809.5 (M$^+$+1); LC/MS R$_t$=4.38 min (6 min. run).
Example 5
Preparation of Compound 5
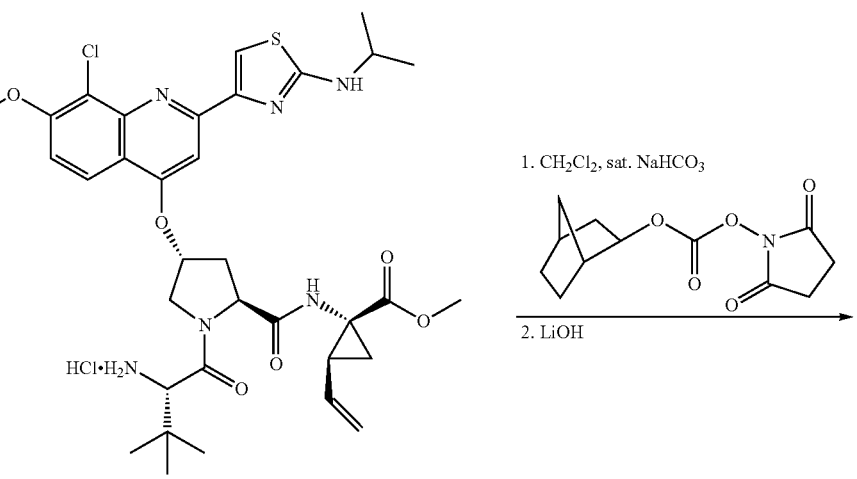
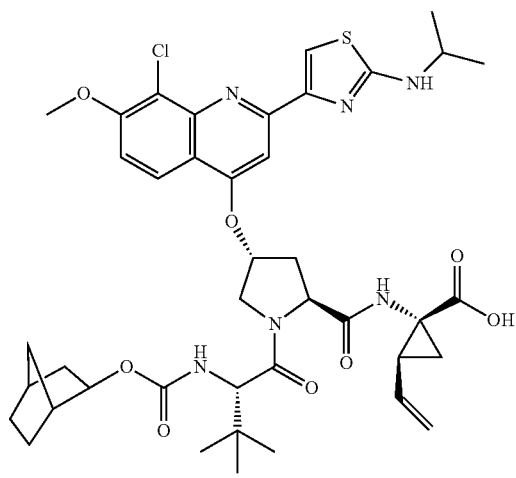

Compound 5 was obtained by following procedures similar to those for preparation of Compound 3 except using carbonate which was obtained by following procedures similar to those for preparation of Compound 1 except using exo-bicyclo[2.2.1]heptan-2-ol. LC/MS=823.3 (M$^+$+1); analytical HPLC R$_t$=5.40 min (7 min run).

Example 6

Preparation of Compound 6

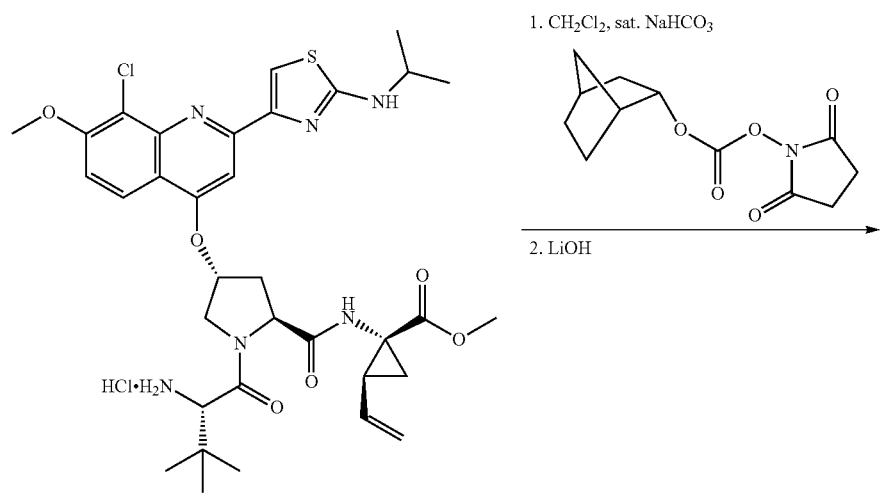

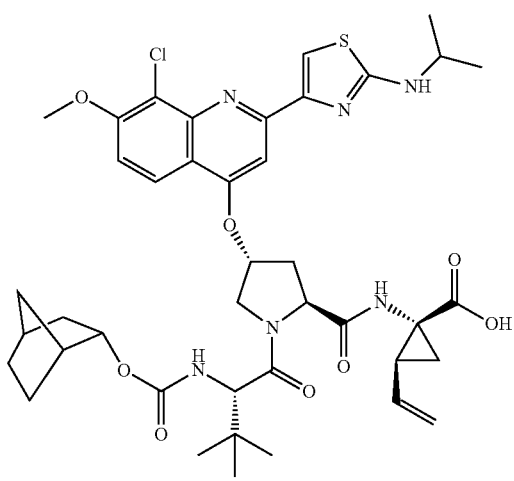

Compound 6 was obtained by following procedures similar to those for preparation of Compound 3 except using carbonate which was obtained by following procedures similar to those for preparation of Compound 1 except using (+)-endo-bicyclo[2.2.1]heptan-2-ol. LC/MS=823.3 (M$^+$+1); analytical HPLC R$_t$=5.41 min (7 min run).

Example 7

Preparation of Compound 7

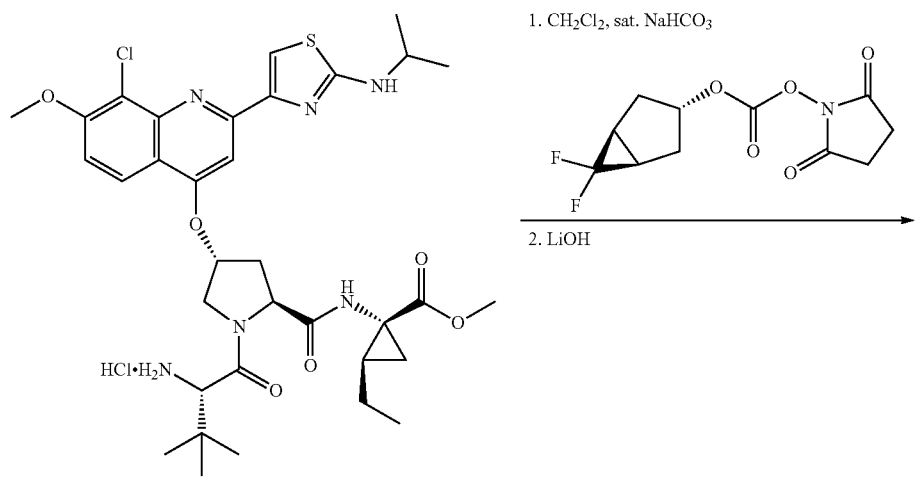

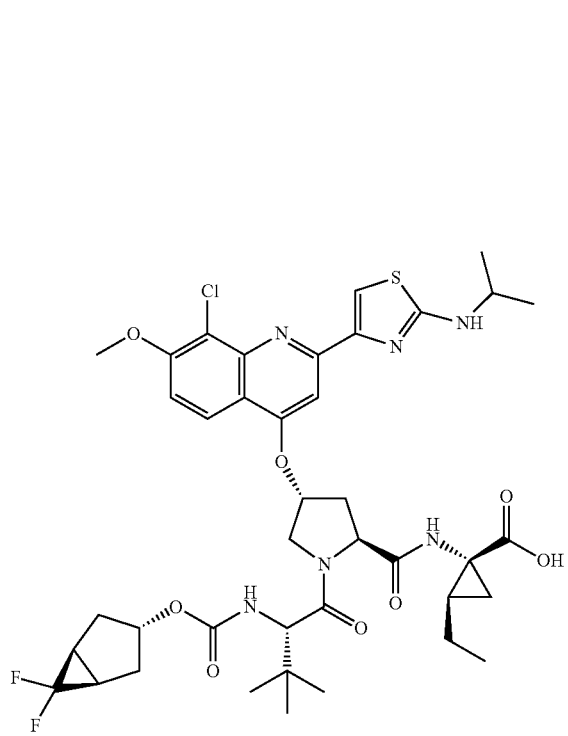

Compound 7 was obtained by following procedures similar to those for preparation of Compound 3 except starting with tripeptide that was obtained by following procedures similar to those for preparation of Compound 1 except using (1R,2S)-1-amino-2-ethyl-cyclopropanecarboxylic acid methyl ester hydrochloride.

The carbonate was obtained by following procedures similar to those for preparation of Compound 1 except using trans-6,6-difluoro-bicyclo[3.1.0]hexan-3-ol (obtained according to WO266640558, followed by silica gel chromatographic separation of the cis and trans isomers). LC/MS=847.5 (M$^+$+1); LC/MS R$_t$=2.76 min.

Example 8
Preparation of Compound 8
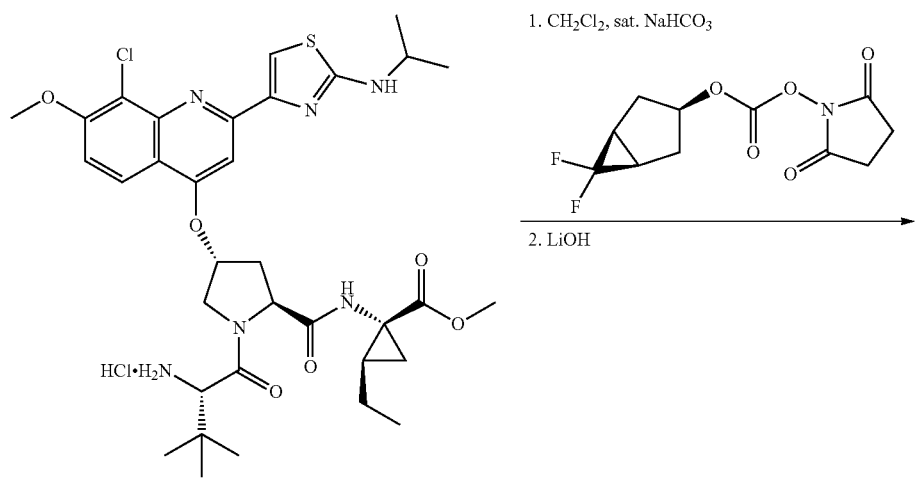
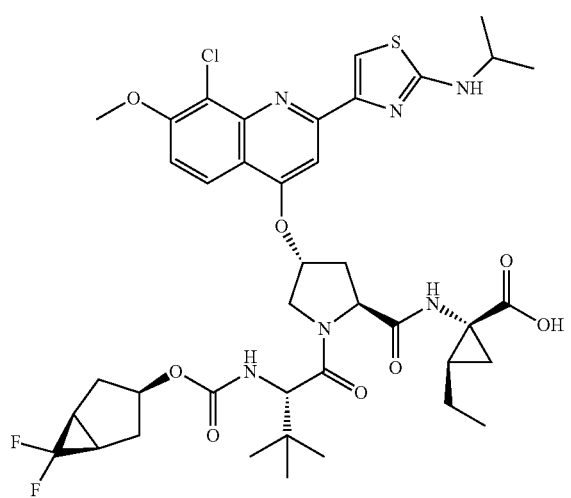
Compound 8 was obtained by following procedures similar to those for preparation of Compound 7 except using the carbonate which was obtained by following procedures similar to those for preparation of Compound 1 except using cis-6,6-difluoro-bicyclo[3.1.0]hexan-3-ol. LC/MS=847.5 (M$^+$+1); LC/MS R$_t$=2.73 min.

Example 9

Preparation of Compound 9

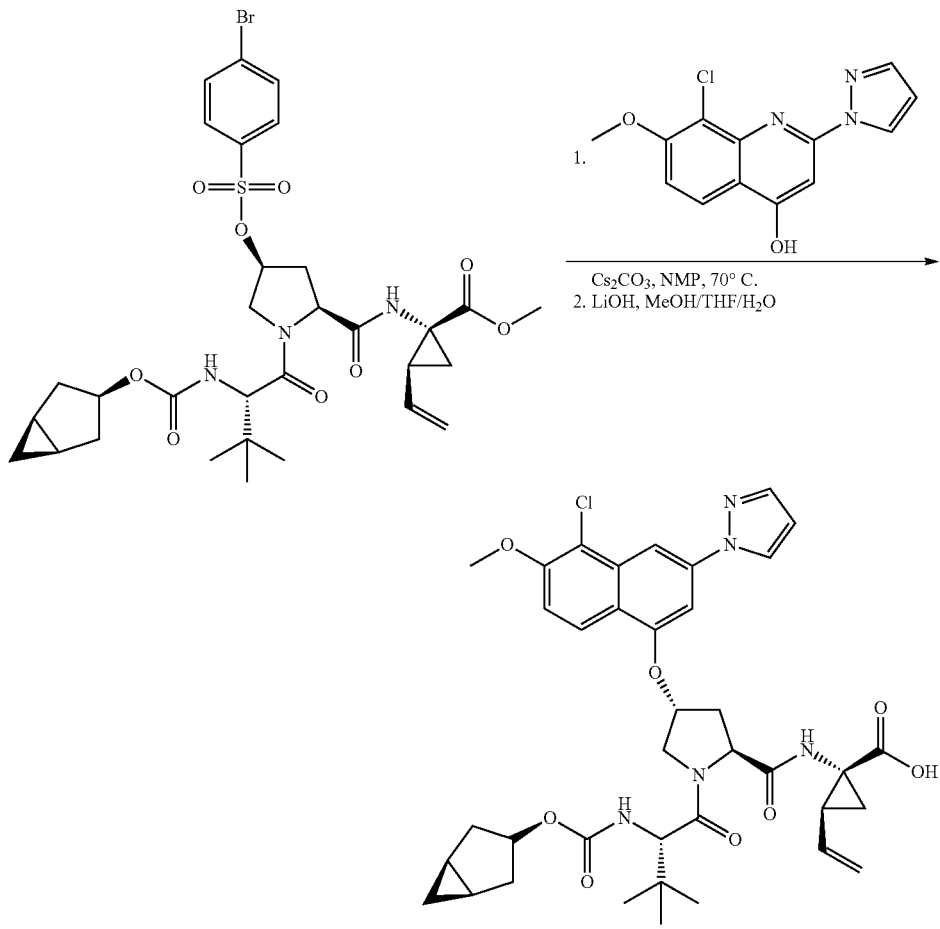

Tripeptide (391 mg, 0.55 mmol) and intermediate V (150 mg, 0.55 mmol) were dissolved in NMP (3 ml). Cesium carbonate (352 mg, 1.08 mmol) was added to the mixture and the mixture was heated at 70° C. for 4 h. Ethyl acetate and 3% aqueous LiCl were added to the residue. The organic layer was washed with 3% aqueous LiCl (×1), and brine. The organic phase was dried over sodium sulfate, and concentrated in vacuo. The residue was dissolved in THF (1.5 ml). Aqueous LiOH (5.5 mmol, 1.5 ml) was added to the mixture, followed by addition of MeOH (2 ml). The reaction was complete after vigorously stirring for 1.5 h at room temperature. 4 N aqueous HCl was added to adjust pH to 5. Ethyl acetate and brine were added to the residue, and the organic layer was concentrated in vacuo. The residue was purified by preparative HPLC using water/acetonitrile (0.05% TFA) as eluents, which afforded Compound 9 (120 mg, some product was lost during the purification due to poor solubility). $^1$H NMR (300 MHz, DMSO-d6): δ 8.78 (s, 1H), 8.56 (s, 1H), 8.04 (d, J=9.3 Hz, 1H), 7.91 (s, 1H), 7.51 (s, 1H), 7.40 (d, J=9.3 Hz, 1H), 7.01 (d, J=8.4 Hz, 1H), 6.67 (s, 1H), 5.64-5.77 (m, 1H), 5.58 (brs, 1H), 5.20 (d, J=17.7 Hz, 1H), 5.05 (d, J=11.4 Hz, 1H), 4.59 (t, 1H), 4.44 (t, J=8.4 Hz, 1H), 4.33 (d, 1H), 3.94-4.07 (m, 2H), 4.02 (s, 3H), 2.48-2.60 (m, 1H), 2.20-2.35 (m, 1H), 1.85-2.11 (m, 2H), 1.72-1.85 (m, 1H), 1.50-1.51 (m, 2H), 1.05-1.35 (m, 4H), 0.93 (s, 9H), 0.39 (q, 1H), 0.25-0.38 (m, 1H). LC/MS=735.4 (M$^+$+1).

Example 10
Preparation of Compound 10
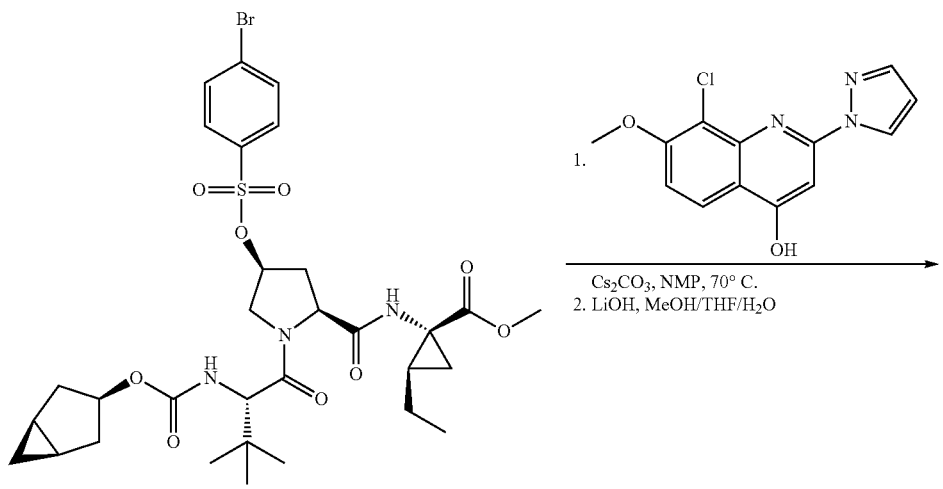
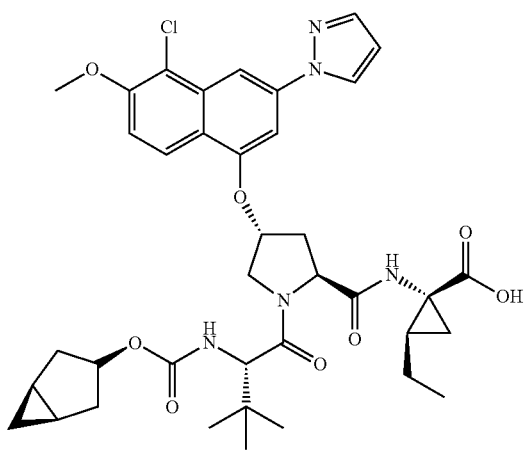
Compound 10 was obtained by following procedures similar to those for preparation of Compound 9. $^1$H NMR (300 MHz, DMSO-d6): δ 8.78 (s, 1H), 8.31 (brs, 1H), 8.04 (d, J=9.6 Hz, 1H), 7.91 (s, 1H), 7.50 (s, 1H), 7.38 (d, J=9.3 Hz, 1H), 6.98 (d, J=9.9 Hz, 1H), 6.66 (s, 1H), 5.56 (s, 1H), 4.59 (t, 1H), 4.44 (t, J=8.4 Hz, 1H), 4.33 (d, 1H), 3.94-4.07 (m, 2H), 4.02 (s, 3H), 2.48-2.60 (m, 1H), 2.20-2.35 (m, 1H), 1.85-2.11 (m, 2H), 1.40-1.60 (m, 2H), 1.06-1.30 (m, 4H), 0.93 (s, 9H), 0.90-1.05 (m, 4H), 0.39 (q, 1H), 0.25-0.38 (m, 1H). LC/MS=737.4 (M$^+$+1).

Example 11
Preparation of Compound 11
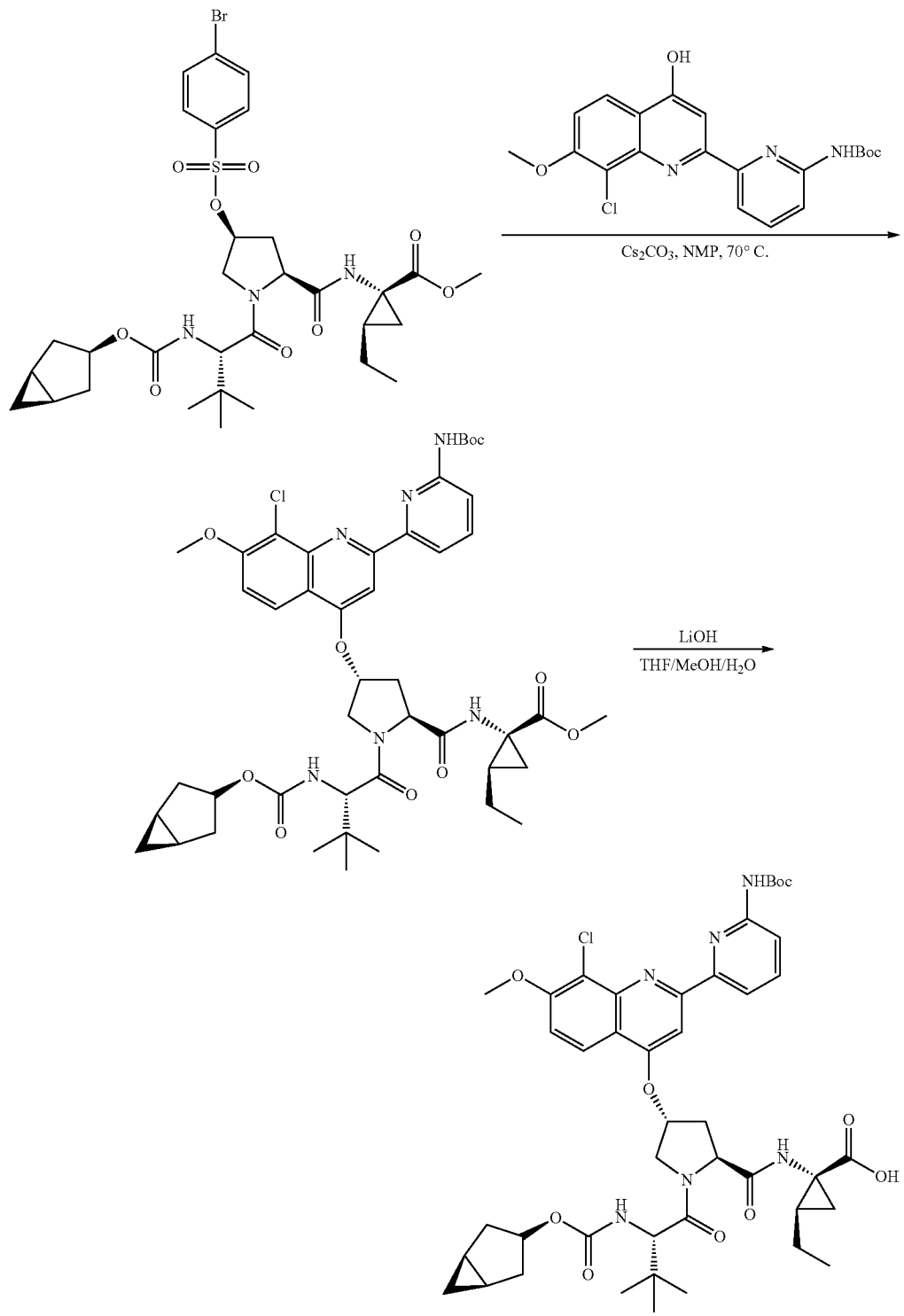
Compound 11 was obtained by following procedures similar to those for preparation of Compound 9. LC/MS=863.5 (M$^+$+1).

Example 12
Preparation of Compound 12
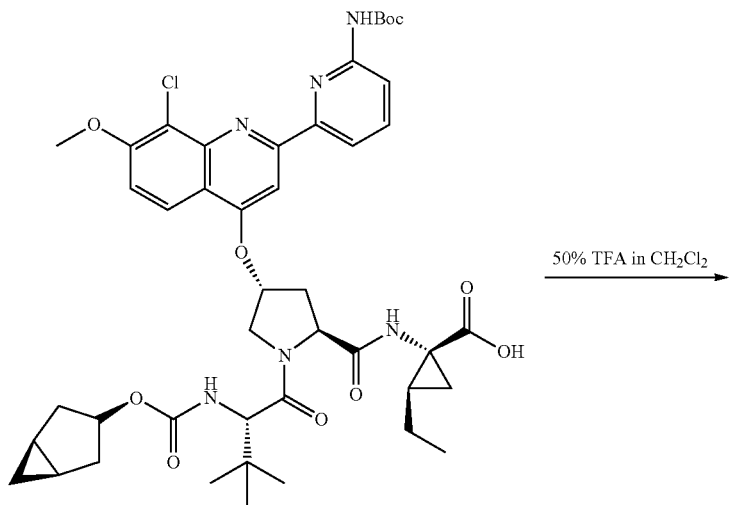
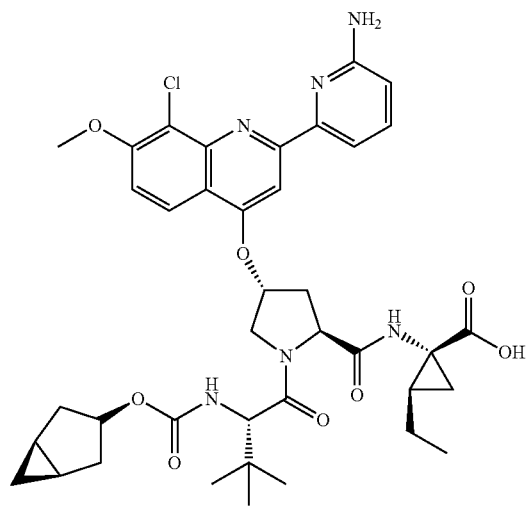
Compound 11 (25 mg) was dissolved in 50% TFA in CH$_2$Cl$_2$. The reaction was complete after stirring for 2 h at room temperature. The mixture was concentrated in vacuo. The residue was dissolved in CH$_3$CN and H$_2$O, frozen and put on the lyophilizer to give Compound 12 as a pale yellow solid (20 mg). LC/MS=763.5 (M$^+$+1).

Example 13

Preparation of Compound 13

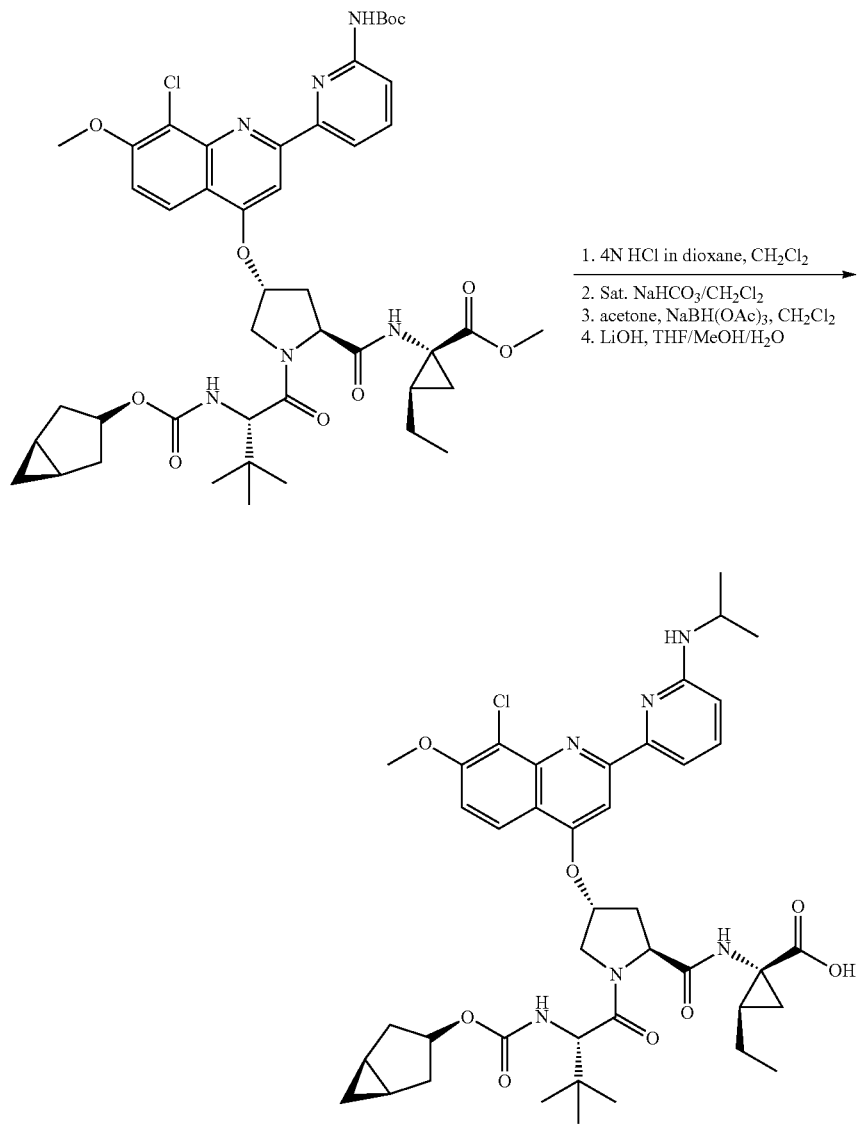

Methyl ester (0.95 g, 1.08 mmol) was dissolved in CH$_2$Cl$_2$ (10 ml), and 4 N HCl in 1,4-dioxane (30 ml) was added. The reaction was complete after stirring at room temperature for 4 h. The mixture was concentrated in vacuo. Saturated sodium bicarbonate aqueous solution (80 ml) and CH$_2$Cl$_2$ (80 ml) were added to the residue. Vigorous stirring was continued until the entire residue dissolved. The organic layer was washed with brine, dried over sodium sulfate, and concentrated in vacuo 250 mg (0.322 mmol) of the material was dissolved in CH$_2$Cl$_2$ (2 ml), and then acetic acid (56 μl, 0.967 mmol) and acetone (72 μl, 0.967) were added. After stirring at room temperature for 20 min, the mixture was cooled to 0° C., and sodium triacetoxyborohydride (102 mg, 0.483 mmol) was added in one portion. After stirring at room temperature for 10 h, saturated sodium bicarbonate aqueous solution and CH$_2$Cl$_2$ were added to the mixture. The organic layer was washed with brine, and concentrated in vacuo. The residue was purified by silica gel column chromatography (ethyl acetate/hexanes) to give the product as a pale yellow solid (180 mg). The solid was dissolved in THF (4 ml), and LiOH (184 mg, 44 mmol) in H$_2$O (4 ml) was added followed by MeOH (4 ml). The reaction was complete in 2 h. The mixture was concentrated in vacuo. TFA was added to adjust the pH to 2. The mixture was concentrated in vacuo. The residue was purified by preparative HPLC using water/acetonitrile (0.05% TFA) as eluents, which afforded Compound 13 as a bright yellow solid (128 mg). $^1$H NMR (300 MHz, CD$_3$OD): δ 8.66 (s, 1H), 8.22 (d, J=9.3 Hz, 1H), 8.00 (m, 1H), 7.94 (d, J=7.5 Hz, 1H), 7.79 (s, 1H), 7.58 (d, J=9.3 Hz, 1H), 7.14 (d, J=8.4 Hz, 1H), 5.70 (s, 1H), 4.72 (t, J=8.4 Hz, 1H), 4.54 (d, J=12.3 Hz, 1H), 4.39 (t, J=6.6 Hz, 1H), 4.01-4.25 (m, 2H), 4.13 (s, 3H), 2.73-2.83 (m, 1H), 2.50-2.62 (m, 1H), 1.85-1.92 (m, 1H), 1.60-1.80 (m, 5H), 1.45-1.60 (3H), 1.47 (d, 6H), 1.10-1.30 (m, 3H), 1.00 (s, 9H), 0.32-0.40 (m, 1H), 0.25-0.35 (m, 1H); LC/MS=805.5 (M$^+$+1).

Example 14

Preparation of Compound 14

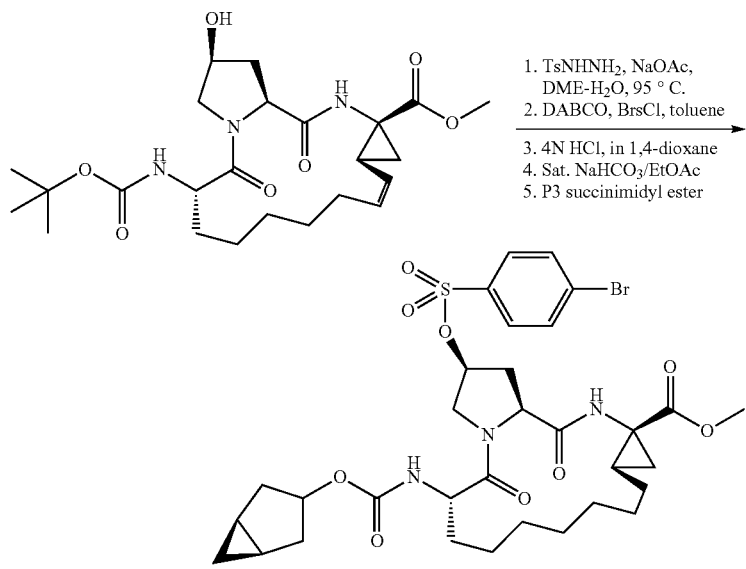

Cyclic tripeptide (5 g, 10.4 mmol) and p-toluenesulfonyl hydrazide (14.6 g, 78.2 mmol) were dissolved in ethylene glycol dimethyl ether (90 ml). Sodium acetate (12.8 g, 156 mmol) was added, followed by $H_2O$ (10 ml). The suspension was then heated to 95° C. The mixture was cooled to room temperature after 8 h stirring. Ethyl acetate and saturated aqueous sodium bicarbonate were added to the mixture. The organic layer was washed with 0.5 N aqueous HCl, brine and concentrated in vacuo. The residue was purified by silica gel column chromatography (ethyl acetate/hexanes) to give the desired product as a white solid (4.2 g, 84%). This solid (4.2 g, 8.7 mmol) and DABCO (3.2 g, 27.9 mmol) were dissolved in toluene (12 ml). 4-bromobenzenesulfonyl chloride (7.1 g 27.9 mmol) in toluene (12 ml) was added dropwise to the mixture. The reaction was left stirring at room temperature overnight. 5% aqueous sodium carbonate and ethyl acetate were added to the mixture and left vigorously stirring for 20 min. The aqueous layer was extracted with ethyl acetate (×1). The combined organic layer was washed with 5% aqueous sodium carbonate (×2), 1 N aqueous HCl (×1), brine, dried over sodium sulfate and concentrated in vacuo to give the crude as an off-white solid. The crude was dissolved in $CH_2Cl_2$, and 4 N HCl in 1,4-dioxane was added. The reaction was complete after 2 h of stirring at room temperature. The mixture was concentrated in vacuo and further dried under high vacuum overnight. To the 2.5 g of the crude residue (~3.9 mmol) was added ethyl acetate and aqueous saturated sodium bicarbonate. The mixture was vigorously stirred until all solids dissolved (keeping pH of the aqueous layer >8). P3 succinimidyl ester (1.13 g, 4.7 mmol) in ethyl acetate was added to the mixture. The reaction was complete in 30 min. The aqueous layer was extracted with ethyl acetate (×1). The combined organic layers were concentrated in vacuo. The residue was purified by silica gel column chromatography (ethyl acetate/hexanes) to give brosylate as a white solid (2.5 g, 88% over 4 steps). LC/MS=724.3 ($M^++1$).

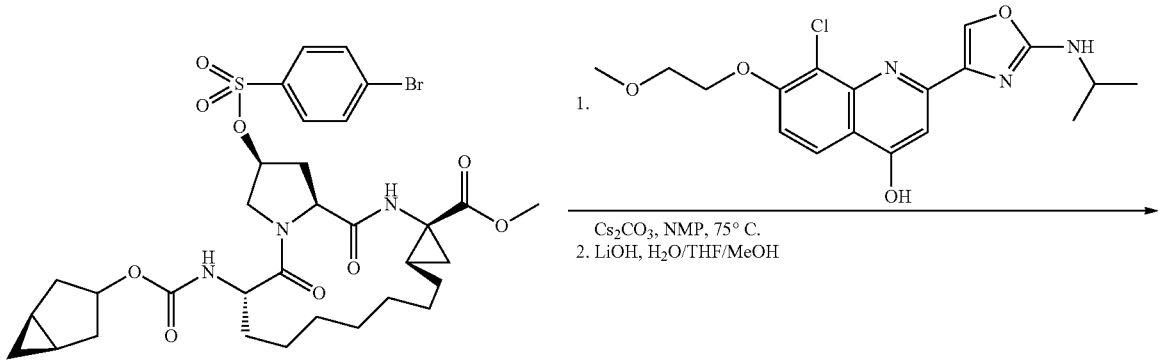

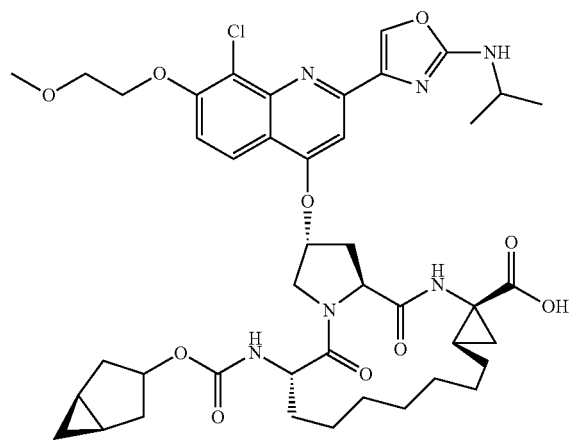
Compound 14 was obtained by following procedures similar to those for preparation of Compound 9 except using macrocyclic tripeptide and quinoline as shown. $^1$H NMR (300 MHz, CD$_3$OD): δ 8.65 (s, 1H), 8.29 (d, J=9.3 Hz, 1H), 7.69 (s, 1H), 7.64 (d, J=9.6 Hz, 1H), 5.71 (s, 1H), 4.78 (d, J=8.1, 1H), 4.72 (d, 1H), 4.40-4.52 (m, 3H), 4.25 (d, 1H), 4.00-4.18 (m, 2H), 3.85-3.89 (m, 1H), 3.47 (s, 3H), 2.63-2.80 (m, 2H), 1.10-2.00 (m, 23H), 1.35 (d, J=6.3 Hz, 6H), 0.30-0.39 (m, 2H). LC/MS=851.5 (M$^+$+1).
Example 15
Preparation of Compound 15
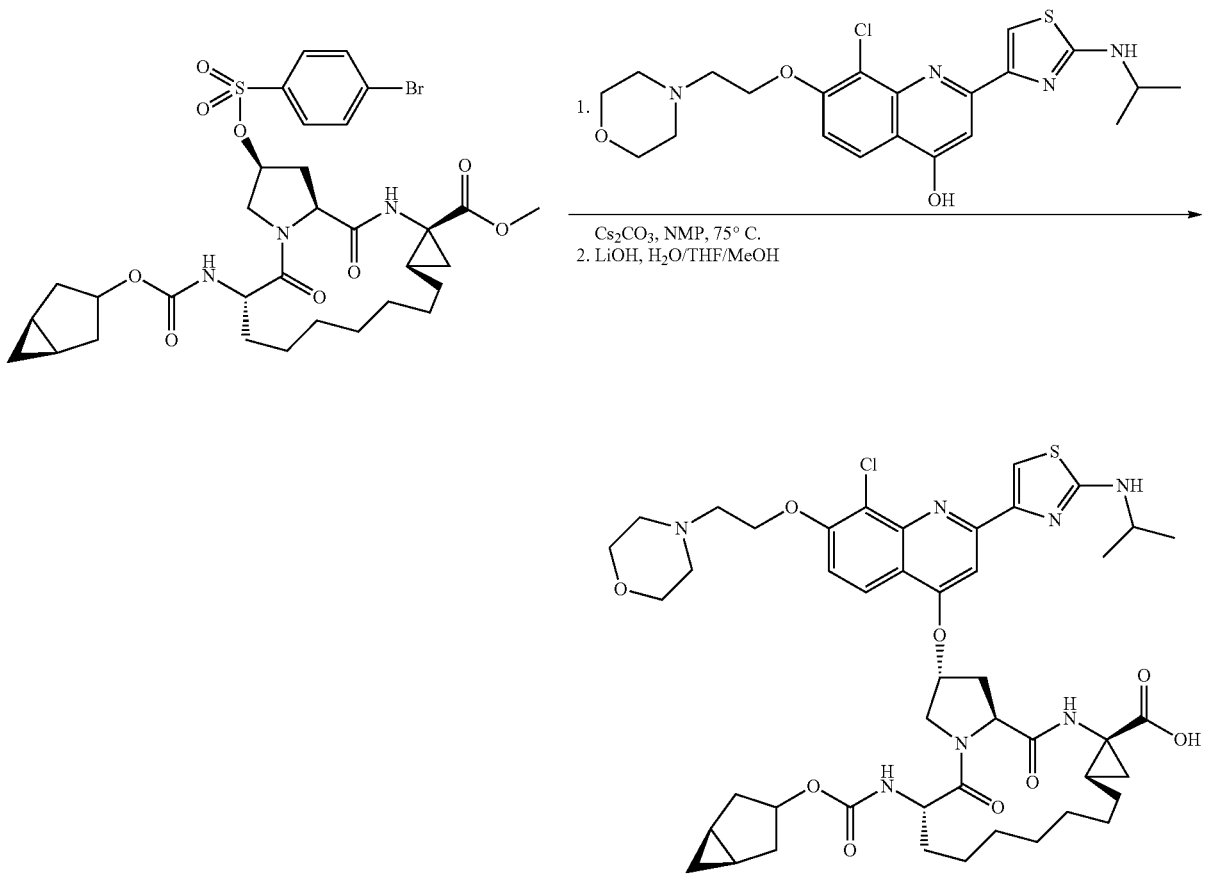 [SMILES: COC(=O)[C@@]12C[C@H]1CCCCCCC[C@H](NC(=O)OC1C[C@@H]3C[C@@H]3C1)C(=O)N1C[C@@H](OS(=O)(=O)c3ccc(Br)cc3)C[C@H]1C(=O)N2 ; CC(C)Nc1nc(-c2cc(O)c3ccc(OCCN4CCOCC4)c(Cl)c3n2)cs1 ; CC(C)Nc1nc(-c2cc(O[C@@H]3C[C@H]4C(=O)N[C@]5(C(=O)O)C[C@H]5CCCCCCC[C@H](NC(=O)OC5C[C@@H]6C[C@@H]6C5)C(=O)N4C3)c3ccc(OCCN4CCOCC4)c(Cl)c3n2)cs1]

Compound 15 was obtained by following procedures similar to those for preparation of Compound 9 except using macrocyclic tripeptide and quinoline as shown. $^1$H NMR (300 MHz, CD$_3$OD): δ 8.65 (s, 1H), 8.33 (d, J=9.6 Hz, 1H), 8.20 (s, 1H), 7.76 (s, 1H), 7.60 (d, J=9.3 Hz, 1H), 5.72 (s, 1H), 4.75-4.82 (m, 3H), 4.58-4.70 (m, 2H), 4.30 (d, 1H), 4.09 (d, 1H), 3.92-4.06 (brs, 4H), 3.81 (t, 2H), 3.59 (brs, 4H), 2.60-2.80 (m, 2H), 1.10-2.00 (m, 23H), 1.38 (d, J=5.4 Hz, 6H), 0.32-0.42 (m, 2H). LC/MS=921.5 (M$^+$+1).
Example 16
Preparation of Compound 16
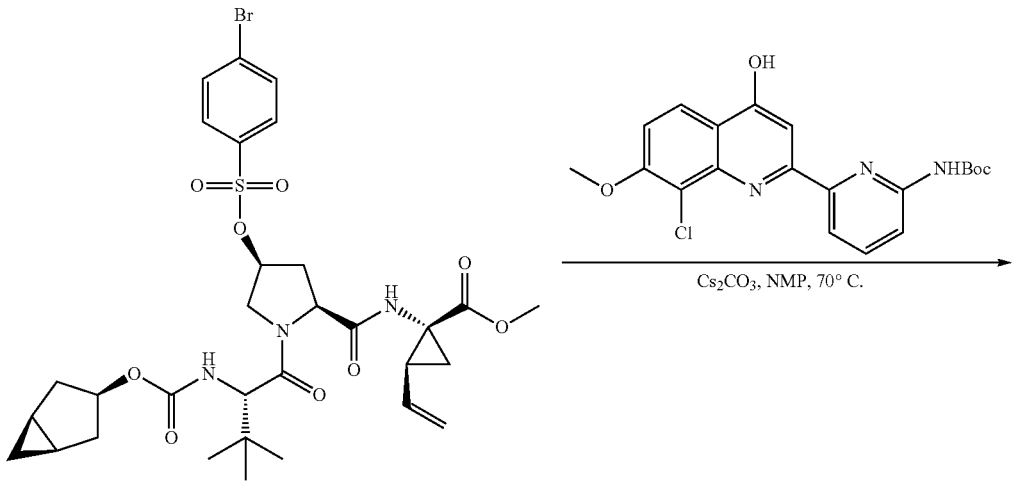
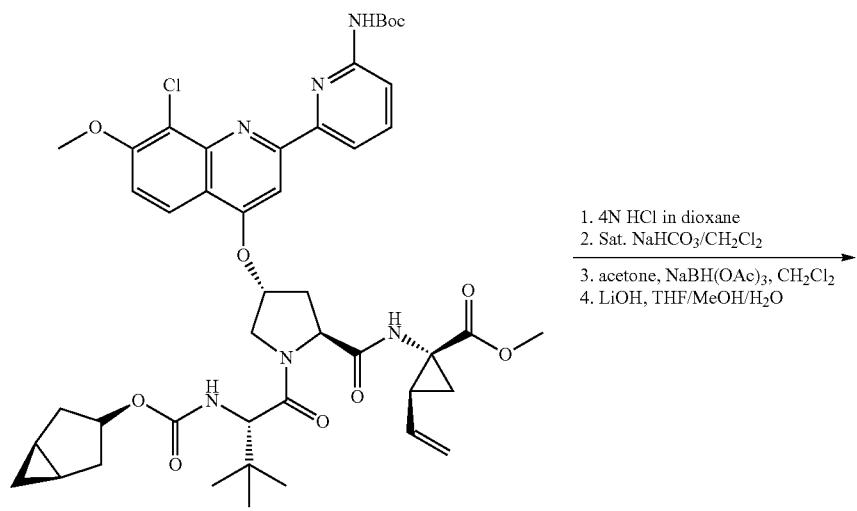

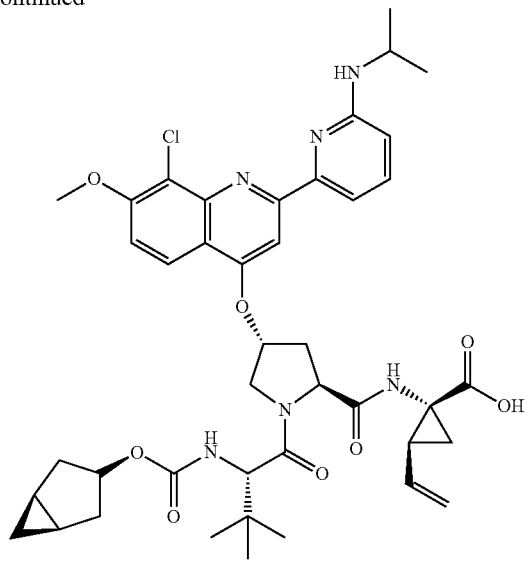

Compound 16 was obtained by following procedures similar to those for preparation of Compound 9. $^1$H NMR (300 MHz, DMSO-d6): δ 8.59 (s, 1H), 8.11 (d, J=9.3 Hz, 1H), 7.80-7.96 (m, 4H), 7.51 (d, J=9.3 Hz, 1H), 7.04 (d, 1H), 5.65-5.78 (m, 1H), 5.58 (s, 1H), 5.18 (d, 1H), 5.06 (d, J=10.5 Hz), 4.62 (t, 1H), 4.45 (t, 1H), 4.32 (t, 1H), 3.90-4.20 (m, 2H), 4.04 (s, 3H), 2.50-2.65 (m, 1H), 2.22-2.38 (m, 1H), 1.78-2.10 (m, 3H), 1.42-1.60 (m, 3H), 1.10-1.38 (3H), 1.47 (d, 6H), 1.10-1.30 (m, 3H), 0.94 (s, 9H), 0.23-0.48 (m, 1H); LC/MS=803.5 (M$^+$+1).

Example 17

Preparation of Compound 17

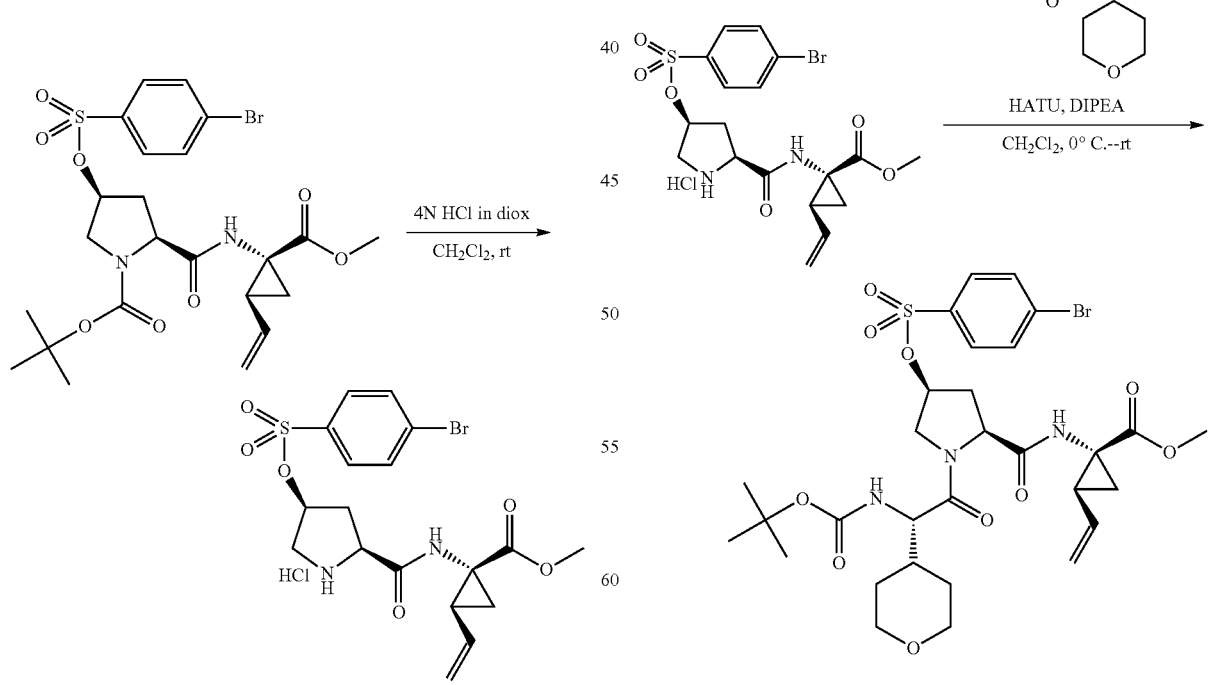

To a dry, nitrogen purged round bottom flask (250 mL) was added the Boc-protected dipeptide. Anhydrous CH$_2$Cl$_2$ (15 mL) was then added to the flask and the resulting clear yellow mixture was stirred until completely homogeneous. Lastly, HCl (5 mL, 4N in dioxane) was added dropwise to the flask and the reaction mixture was stirred at room temperature until complete disappearance of the starting material (1.5 h, as indicated by LC/MS). The solvent was removed under reduced pressure and the amine salt was used in the next step. LC/MS=473.0 (M$^+$+1).

To a round bottom flask (500 mL) containing the amine salt were added the amino acid (951.63 mg, 3.67 mmol) and CH$_2$Cl$_2$ (150 mL). DIPEA (2.56 mL, 14.68 mmol) was then added and the homogeneous mixture was cooled to 0° C. HATU (3.49 g, 9.18 mmol) was then added to the flask and the reaction mixture was allowed to warm to room temperature. The reaction continued to stir at room temp until complete disappearance of the starting material. After stirring overnight, TLC and LC-MS analysis indicated the reaction was complete. The solvent was removed under reduced pressure and the tripeptide was used in the next step as obtained. LC/MS=714.2 (M⁺+1).

complete disappearance of the starting material. The solvent was removed under reduced pressure and the amine salt was used in the next step as obtained. LC/MS=614.1 (M⁺+1).

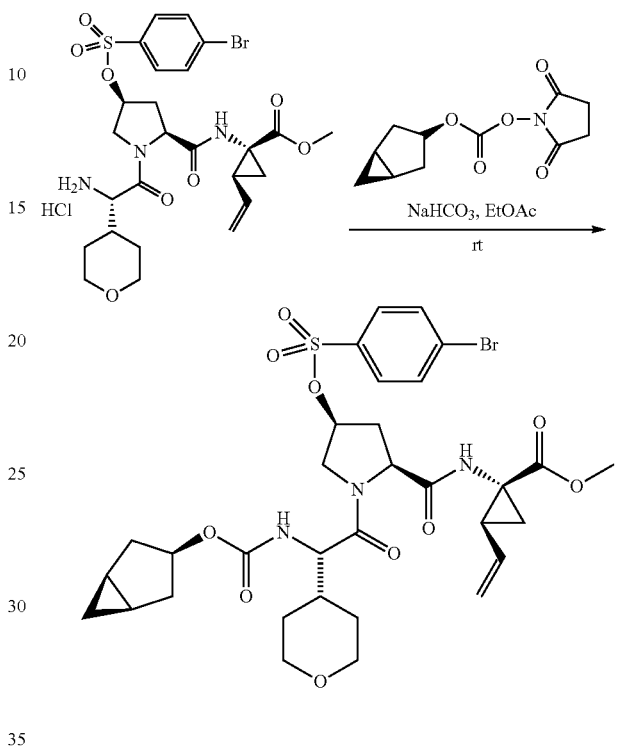

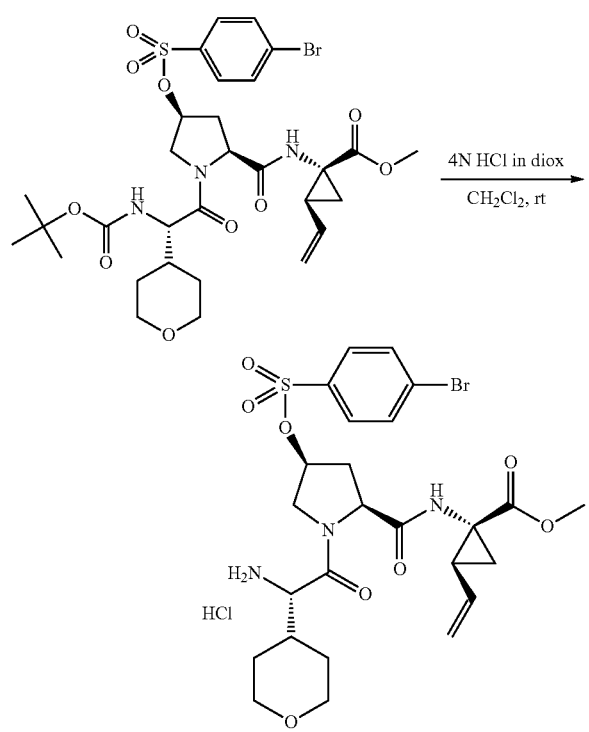

To a round bottom flask (100 mL) containing the tripeptide was added anhydrous CH₂Cl₂ (15 mL). The mixture was allowed to stir for a few minutes. HCl (9.18 mL, 4N in dioxane) was added dropwise. The reaction continued to stir at room temperature for 1.5 h at which point LC-MS indicated To the round bottom flask (250 mL) containing the amine salt was added EtOAc (65 mL). Sat. NaHCO₃ (60 mL) was then added and the biphasic solution was stirred vigorously for 1 h, at which point both phases were homogeneous. A solution of the carbonic ester (1.05 g, 4.40 mmol) and EtOAc (15 mL) was made in a separate round bottom flask (50 mL) and this solution was added to the reaction flask via cannula. The reaction stirred at room temperature for 1 h at which point LC-MS indicated complete disappearance of the starting material. The organic layer was separated and the solvent was removed under reduced pressure. The crude material was purified using flash chromatography (EtOAC/1:1 EtOAc/MeOH). 1.0 g (37% over 4 steps) of the tripeptide was obtained. LC/MS=710.2 (M⁺+1).

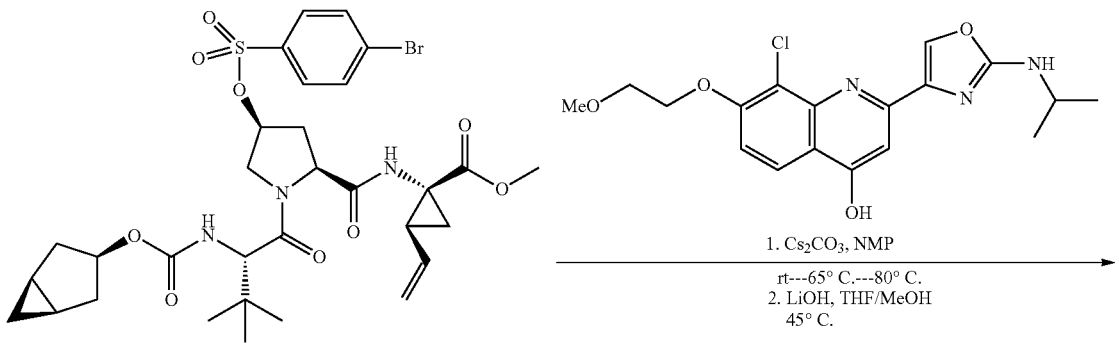

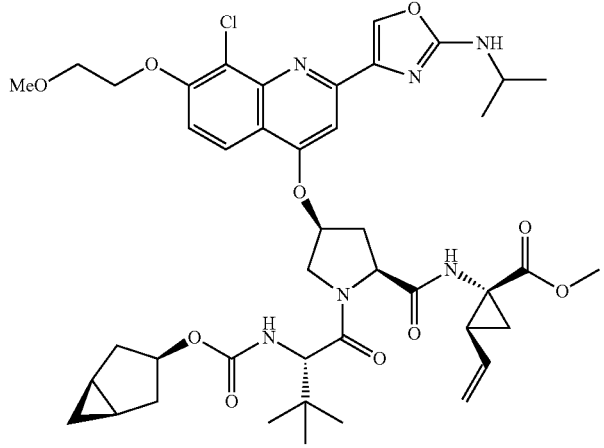

To a dry, argon purged pear shaped flask (50 mL) were added quinoline (500 mg, 1.32 mmol), tripeptide (1.00 g, 1.35 mmol), and anhydrous NMP (4 mL). The flask was mildly warmed to increase dissolution. $Cs_2CO_3$ (531.24 mg, 1.63 mmol) was then added and the flask was placed in a preheated 65° C. oil bath. After 2.5 h of stirring, LC-MS indicated 50% conversion of the starting material to desired product. The temperature of the oil bath was increased to 80° C. and the reaction continued to stir for an additional 2 h. The flask was then cooled to room temperature and a solution of LiOH in $H_2O$ (10 mL, 25 mmol) was added, followed by a 1:1 solution of MeOH/THF (40 mL). The flask was then placed into a pre-heated oil bath set at 45° C. and was allowed to stir until complete disappearance of the starting material. After 3.5 h, the solvent was removed under reduced pressure. The crude material was diluted with EtOAc and neutralized with 1M HCl. The aqueous layer was extracted with EtOAc (3×15 mL) and the combined organic layers were washed with 2% LiCl (3×10 mL) and brine (3×10 mL), and then dried with $MgSO_4$. The solvent was removed under reduced pressure and the crude material was purified using preparative HPLC (water/acetonitrile (0.05% TFA). 400 mg (35% over 2 steps) of the Compound 17 was obtained. $^1H$ NMR ($CDCl_3$, 300 MHz) δ 8.62 (s, 1H), 8.28 (m, 1H), 7.67 (m, 2H), 5.82 (m, 1H), 5.30 (m, 1H), 5.13 (m, 2H), 4.72 (m, 1H), 4.50 (s, 1H), 4.37 (s, 1H), 4.03 (m, 7H), 3.92 (m, 6H), 3.47 (s, 2H), 3.32 (s, 2H), 2.83 (m, 2H), 2.61 (m, 2H), 1.92 (m, 2H), 1.72 (m, 4H), 1.56 (m, 4H), 1.18 (m, 6H), 0.27 (m, 2H).

Example 18

Preparation of Compound 18

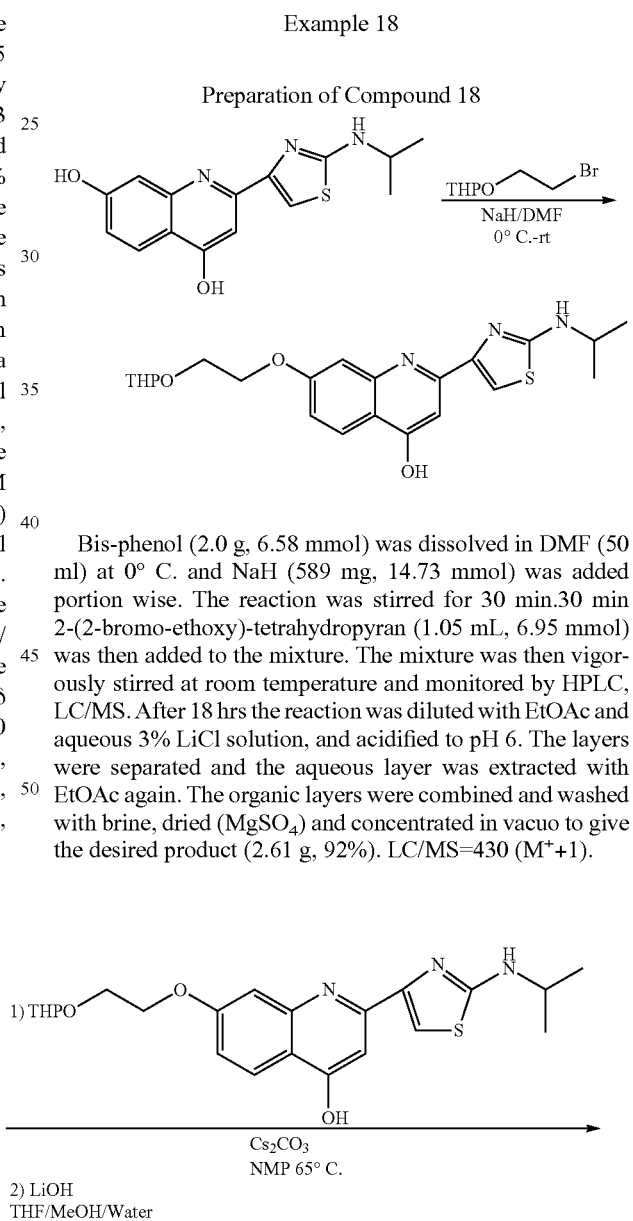

Bis-phenol (2.0 g, 6.58 mmol) was dissolved in DMF (50 ml) at 0° C. and NaH (589 mg, 14.73 mmol) was added portion wise. The reaction was stirred for 30 min.30 min 2-(2-bromo-ethoxy)-tetrahydropyran (1.05 mL, 6.95 mmol) was then added to the mixture. The mixture was then vigorously stirred at room temperature and monitored by HPLC, LC/MS. After 18 hrs the reaction was diluted with EtOAc and aqueous 3% LiCl solution, and acidified to pH 6. The layers were separated and the aqueous layer was extracted with EtOAc again. The organic layers were combined and washed with brine, dried ($MgSO_4$) and concentrated in vacuo to give the desired product (2.61 g, 92%). LC/MS=430 ($M^+$+1).

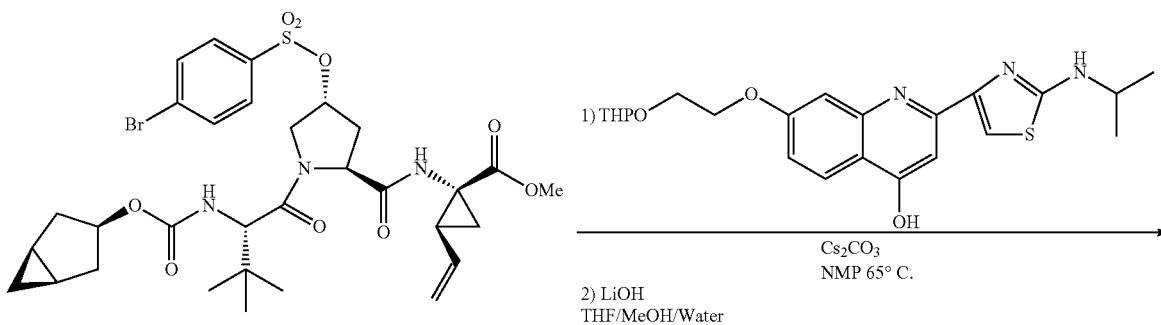

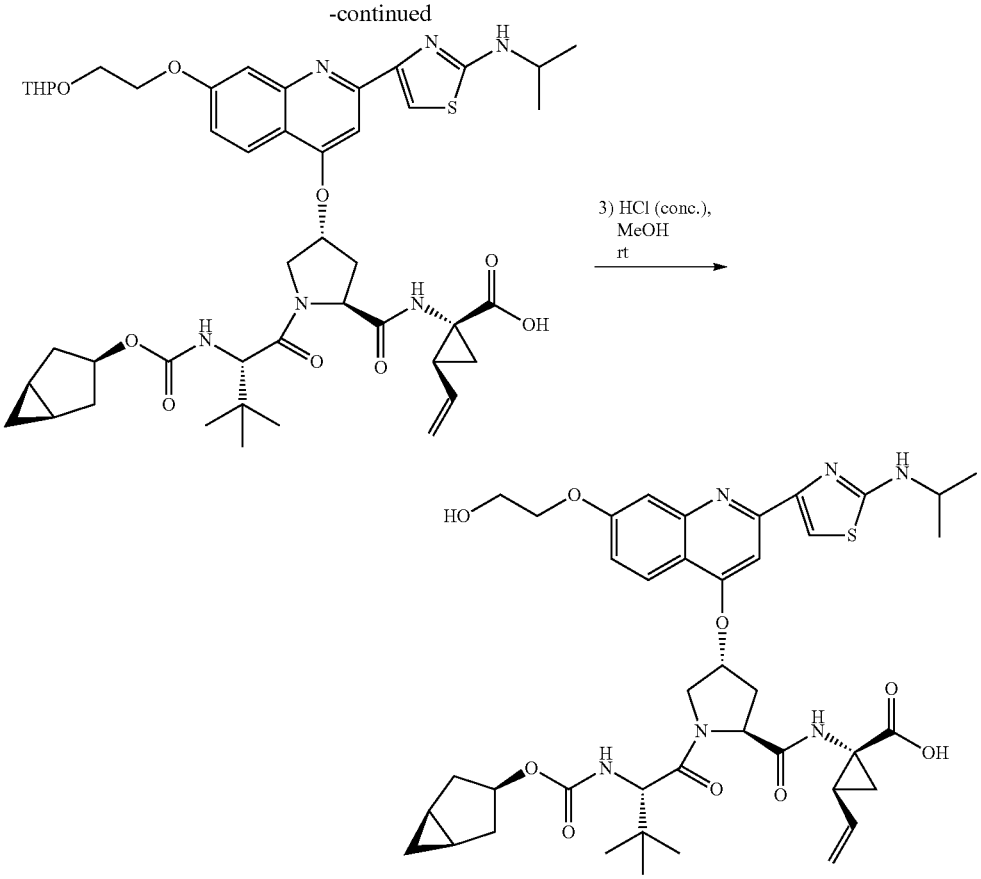

Step 1 & 2:
Used the same procedure as described before. LC/MS=890 (M⁺+1).

Step 3:
The acid (503.5 mg, 0.566 mmol) was dissolved in MeOH (1.80 mL) and cooled to 0° C. Concentrated HCl (1.8 mL) was added to the solution. The mixture was stirred at for 2 h. Upon completion of the reaction, the mixture was concentrated to remove the solvents. The crude product was purified by prep-HPLC to give Compound 18 as a yellow solid (159.2 mg), LC/MS=805 (M⁺+1).

Example 19

Preparation of Compound 19

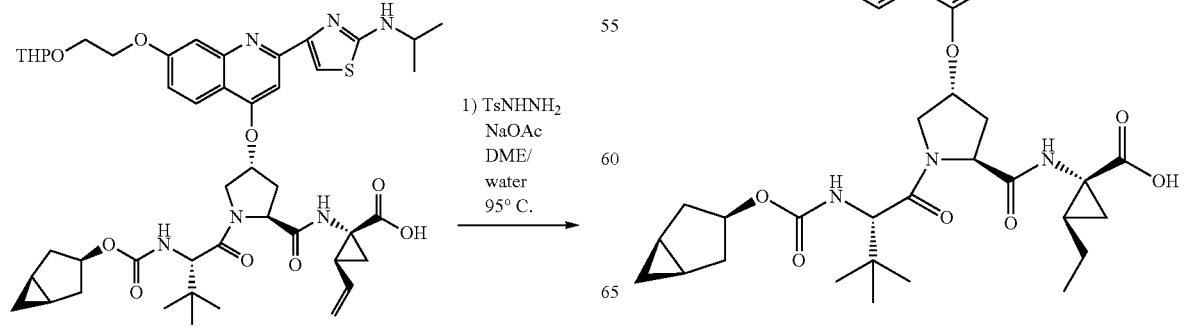

Step 1:

The mixture of acid, p-TsNHNH$_2$, and NaOAc in DME (10 mL)/H$_2$O (1 mL) was heated to 95° C. for 2 h. Upon the completion of the reaction, it was cooled to room temperature, diluted with EtOAc (100 mL) and 1N HCl (to pH about 3). After separated layers, the aq. Layer was back extracted with EtOAc. The organic layers were combined and concentrated. The crude product was purified by prep-HPLC to give a yellow solid. LC/MS=892 (M$^+$+1).

Step 2:

The acid was dissolved in MeOH (3 mL) and cooled to 0° C. Concentrated HCl (3 mL) was added to the solution. The mixture was stirred at for 2 h. Upon completion of the reaction, the mixture was concentrated to remove the solvents. The crude product was purified by prep-HPLC to give desired Compound 19 as a yellow solid (187.7 mg). LC/MS=807 (M$^+$+1). $^1$H NMR (300 MHz, CDCl$_3$): δ 8.80 (b, 1H), 8.20 (d, 1H), 7.9 (m, 1H), 7.50 (m, 1H), 7.30 (d, 1H), 5.90-5.80 (m, 2H), 5.10 (m, 1H), 4.80-4.40 (m, 4H), 4.3 (m, 3H), 4.05 (m, 3H), 3.20 (m, 1H), 3.00-2.70 (m, 1H), 2.20 (m, 2H), 1.80-1.60 (m, 6H), 1.50 (m, 2H), 1.3 (m, 9H), 1.10-0.90 (m, 14H), 0.50 (m, 2H).

Example 20

Preparation of Compound 20

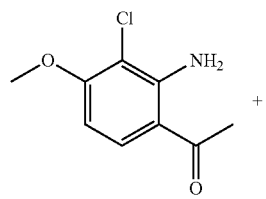

+

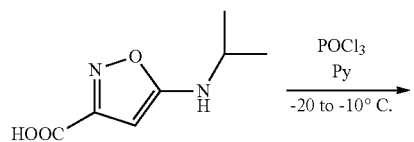

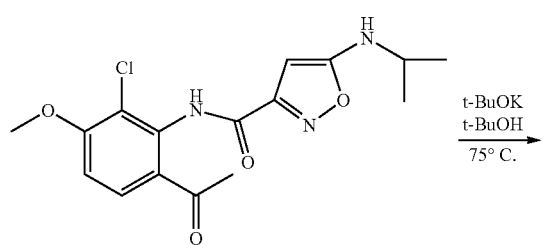

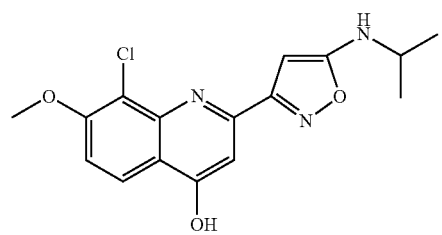

Step 1:

The same procedure was used as mentioned before; starting from aniline (1.877 g) gave 2.56 g of product. LC/MS=337 (M$^+$+1).

Step 2:

The amide compound (1.50 g, 4.45 mmol) was dissolved in t-BuOH (12.5 ml). t-BuOK (9.3 mL, 4.45 mmol) was added to the vigorously stirred mixture. The reaction was complete after 6 h at 75° C. The mixture was cooled to room temperature. It was acidified with 4N HCl (5 mL). The slurry was treated with NaH$_2$PO$_4$ (0.5N) and filtered. The cake was washed with water and ether and then dried to give the desired product, (1.256 g, 89%). LC/MS=319 (M$^+$+1).

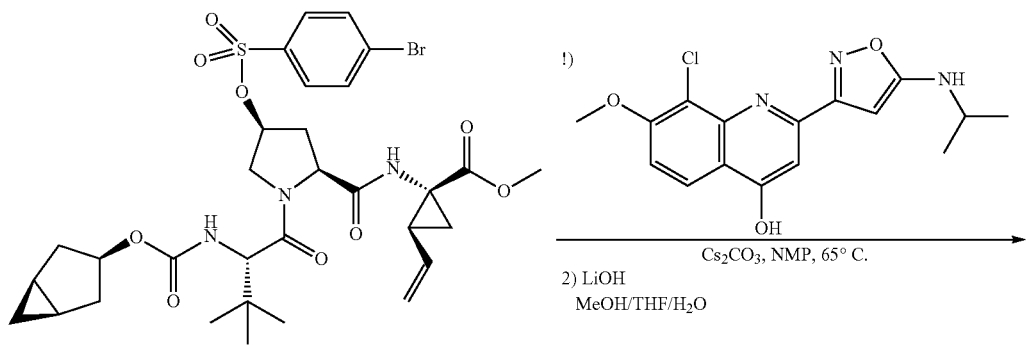

-continued

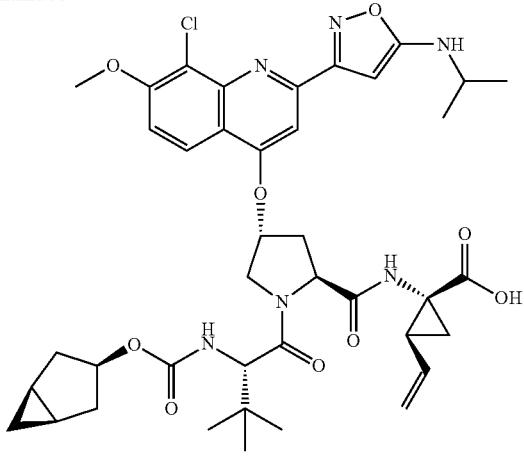

20

Compound 20 was synthesized using procedure described before. LC/MS=779 (M⁺+1). ¹H NMR (300 MHz, CD₃OD): δ 8.13 (d, 1H), 7.51 (s, 1H), 7.47 (d, 1H), 6.91 (s, 1H), 5.90-5.78 (m, 1H), 5.53 (b, 1H), 5.31-5.09 (dd, 2H), 4.68-4.49 m, 3H), 4.21 (s, 1H), 4.07 (b, 5H), 3.22 (m, 1H), 2.72 (m, 1H), 2.51 (m, 1H), 2.20 (m, 1H), 1.97 (m, 1H), 1.85 (m, 1H), 173-1.63 (m, 2H), 1.44 (s, 3H), 1.41 (s, 3H), 1.36-1.14 (m, 4H), 1.01 (s, 9H), 0.97 (s, 2H), 0.33 (m, 2H).

Compound 21 was synthesized using procedure described before. LC/MS=781 (M⁺+1). ¹H NMR (300 MHz, CD₃OD): δ 8.13 (d, 1H), 7.51 (s, 1H), 7.47 (d, 1H), 6.91 (s, 1H), 5.53 (b, 1H) 4.70-4.40 (m, 3H), 4.21 (s, 1H), 4.07 (b, 5H), 3.67 (b, 2H), 2.72 (m, 1H), 2.52 (m, 1H), 2.20 (m, 1H), 1.97 (m, 1H), 1.85 (m, 1H), 173-1.63 (m, 2H), 1.44 (s, 3H), 1.41 (s, 3H), 1.36-1.14 (m, 4H), 1.01 (s, 9H), 0.97 (s, 2H), 0.33 (m, 2H).

Example 21
Preparation of Compound 21

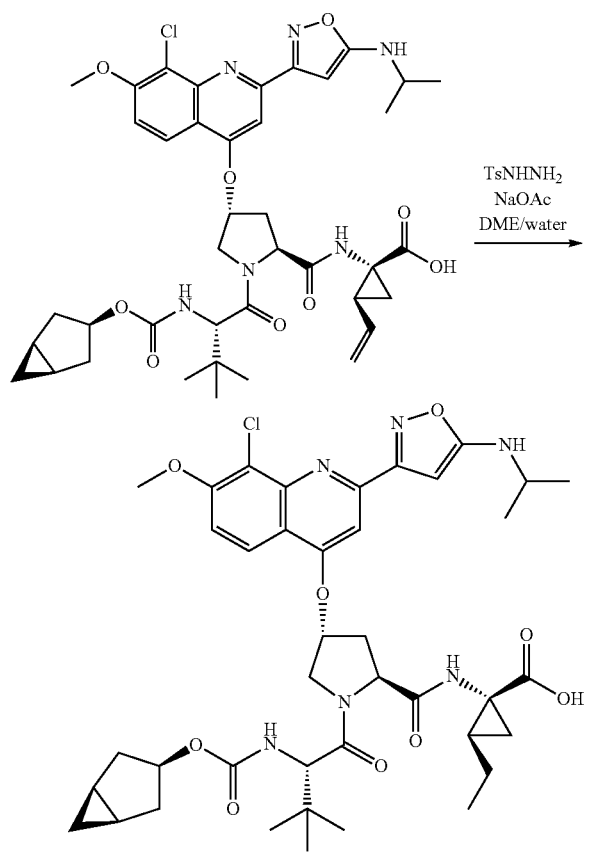

Example 22
Preparation of Compound 22

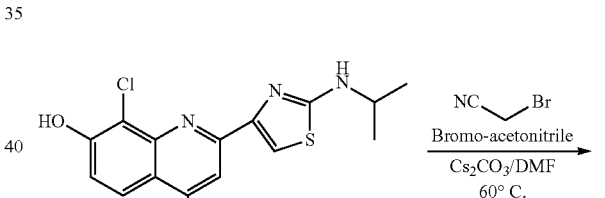

Bis-phenol (600 mg, 1.79 mmol) was dissolved in DMF (18 ml) at 0° C. and Cs₂CO₃ (584 mg, 1.79 mmol) was added to the mixture, followed by bromo-acetonitrile (0.15 mL). The mixture was heated to 65° C. and monitored by HPLC and LC/MS. After 4 hrs the reaction was diluted with EtOAc and aqueous 3% LiCl solution. The layers were separated and the aqueous layer was extracted with EtOAc again. The organic layers were combined and washed with brine, dried (MgSO₄) and concentrated in vacuo to give the crude product (536 mg, 80%). LC/MS=375 (M⁺+1).

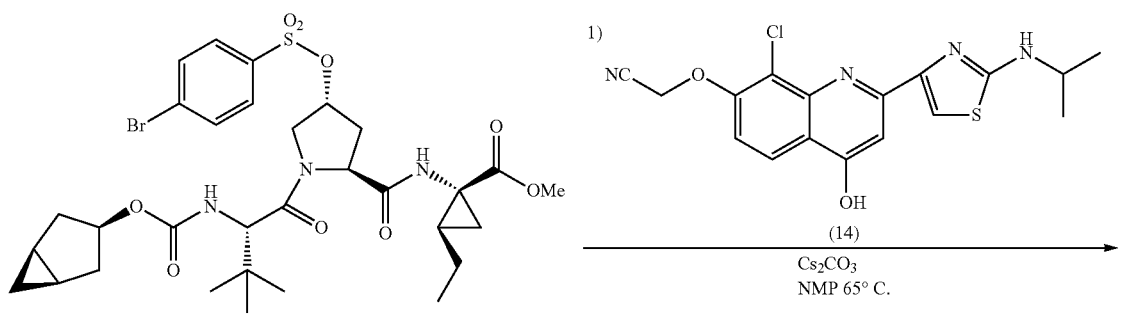

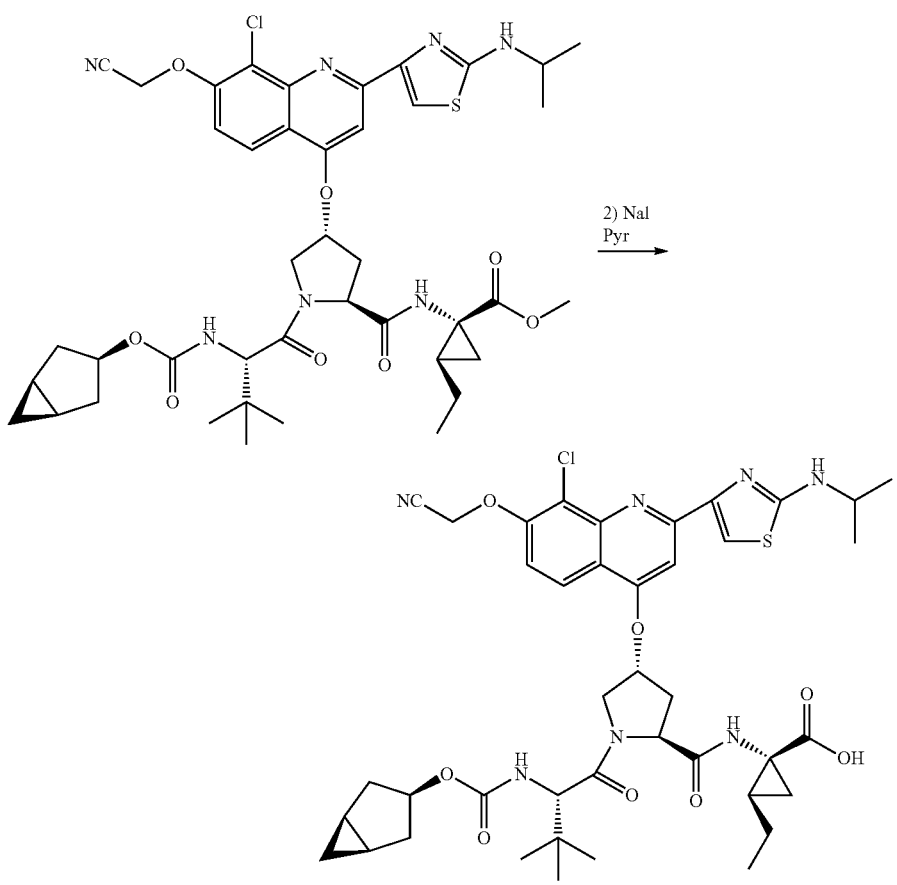

Example 23

Preparation of Compound 23

Step 1:

Use the same procedure as described before. 508 mg of intermediate II gave 491 mg of product. LC/MS=851 (M⁺+1).

Step 2:

The methyl ester (491 mg, 0.578 mmol) and NaI (1.738 g) were mixed in pyridine and heated to 115° C. for 19 h. Upon completion of the reaction, the mixture was cooled to room temperature, diluted with EtOAc and acidified to pH 4 with 0.5 N HCl. Extracted with EtOAc (3×), and the organics were combined and dried over MgSO$_4$. The concentrated crude product was purified by prep-HPLC to give the desired Compound 22 as a yellow solid (71 mg, 14.7%), LC/MS=837 (M⁺+1). $^1$H NMR (300 MHz, CD$_3$OD): δ 8.63 (s, 1H), 8.34 (d, 1H), 8.17 (s, 1H), 7.76 (s, 1H), 7.64 (d, 1H), 5.69 (b, 1H), 5.38 (b, 2H), 4.73-4.50 (m, 3H), 4.16 (s, 1H), 4.20-3.98 (m, 3H), 2.80-2.58 (m, 2H), 2.0-1.8 (m, 2H), 1.66 (m, 4H), 0.98 (s, 2H), 0.34 (m, 2H).

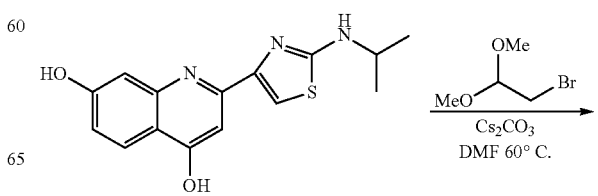

245

-continued

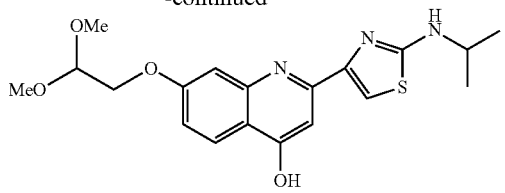

Step 1:

Bis-phenol (7 g, 23.4 mmol) was dissolved in DMF (50 ml), cesium carbonate (15.25 g, 46.8 mmol) was added to the mixture, followed by bromoacetaldehyde dimethyl acetal (4.13 mL, 35.1 mmol). The mixture was then vigorously stirred at 65° C. and monitored by HPLC and LC/MS. Another 0.5 eq of bromoacetaldehyde dimethyl acetal and 1 eq of cesium carbonate were added. After 18 hrs LC/MS indicated no starting material remained, but lots of bis-alkylated by-product formed. The reaction was cooled to room temperature, and diluted with EtOAc. The mixture was washed with aqueous 3% LiCl solution, brine, dried (Na$_2$SO$_4$) and concentrated in vacuo. The residue was purified by silica gel chromatography with MeOH/EtOAc to give the desired product (1.72 g, 19%). LC/MS=390 (M$^+$+1).

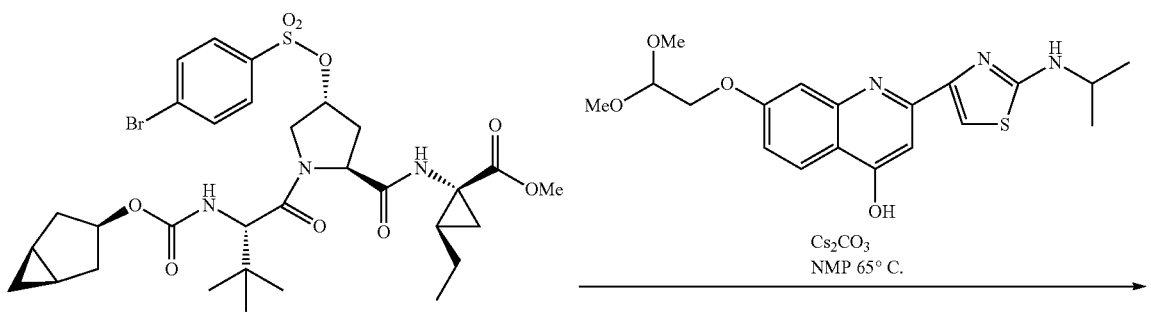

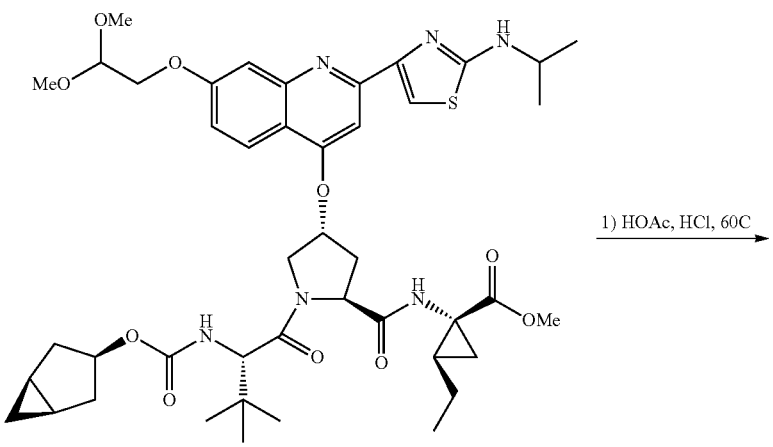

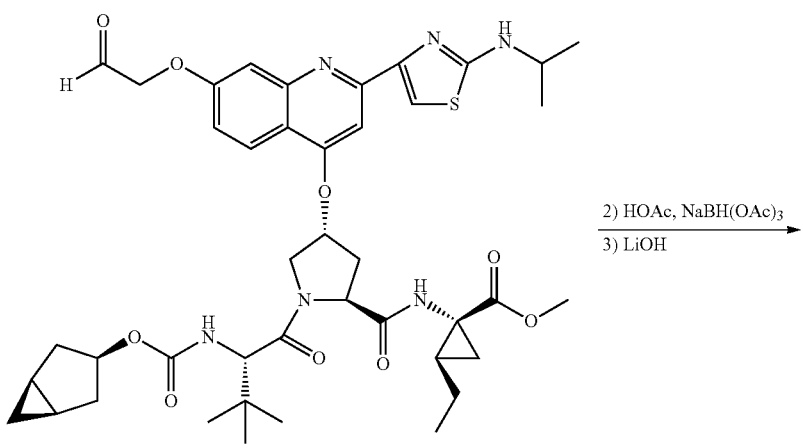

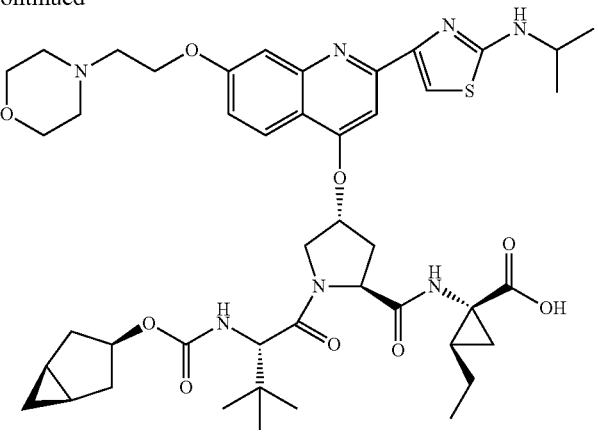

Step 2:

To a mixture of tripeptide (1.46 g, 3.75 mmol) and cesium carbonate (1.58 g, 4.88 mmol) in NMP (18.5 ml) at room temperature was added quinoline (2.94 g, 4.12 mmol) in one portion. The mixture was stirred at 65° C. for 3 h. The reaction was cooled to room temperature, and EtOAc (100 ml) was added to the mixture. The mixture was washed with aqueous 3% LiCl (1×100 ml), brine, dried ($Na_2SO_4$) and concentrated in vacuo. The residue was purified by silica gel chromatography with EtOAc/Hexane to give the desired product as light brown solid (2.07 g, 64%). LC/MS=837 ($M^+$+18).

Step 3:

To a solution of the acetal (1.24 g, 1.43 mmol) in glacial acetic acid (16 mL) was added 1.4 N HCl in $H_2O$ (6 mL). The mixture was stirred at 60° C. for 1.5 h. Upon completion of the reaction, the mixture was concentrated to remove the solvents, coevaporated with toluene (×2) to remove residual acetic acid. After the residue was then dissolved in EtOAc (100 mL) and sat. $NaHCO_3$ (100 mL), the organic layer was separated, washed with brine, dried ($Na_2SO_4$) and concentrated in vacuo. The residue was further dried under high vacuum for 1 h to obtain the aldehyde (1.16 g), and used as is for the next step.

Step 4:

The crude aldehyde was dissolved in $CH_2Cl_2$ (16 ml), and then morpholine (164 μl, 1.89 mmol) and sodium triacetoxyborohydride (462 mg, 2.18 mmol) were added to the mixture at 0° C. Glacial acetic acid (25 μl, 7.8 mmol) was then added dropwise to the mixture. The reaction was complete in 10 min at 0° C. Sat. aqueous $NaHCO_3$ solution was added to quench the reaction. After stirring for another 20 min, the organic layer was washed with brine, dried ($Na_2SO_4$) and concentrated in vacuo. The crude product was clean enough (by LC/MS) to use as is. LC/MS=890 ($M^+$+1).

This crude product was dissolved in THF (60 ml), and then LiOH (1200 mg, 28.6 mmol) in $H_2O$ (20 ml) was added, followed by MeOH (4 ml). The mixture was kept stirring at room temperature for 20 h. Upon completion of the reaction, TFA was added at 0° C., to adjust the pH to 4. The mixture was extracted with EtOAc (2×200 ml). The combined organic layer was washed with brine, dried ($Na_2SO_4$) and concentrated in vacuo to give the crude product. The crude product was purified by prep-HPLC to give Compound 23 as a yellow solid (1.086 g, 73%). LC/MS=876 ($M^+$+1). $^1$H NMR (300 MHz, $CD_3OD$): δ 7.94 (d, 1H), 7.40 (s, 1H), 7.44 (d, 1H), 7.39 (s, 1H), 7.04-7.01 (m, 1H), 5.39 (m, 1H), 4.32-4.20 (m, 5H), 3.80-3.68 (m, 4H), 3.59 (bs, 3H), 3.40 (m, 2H), 3.35-3.24 (m, 4H), 3.93-3.92 (m, 2H), 2.40-2.19 (m, 2H), 1.65-1.47 (m, 2H), 1.33-1.25 (m, 3H), 1.16-1.11 (m, 1H), 1.05-1.01 (m, 1H), 0.96 (s, 3H), 0.95 (s, 3H), 0.86-0.79 (m, 3H), 0.65 (s, 9H), 0.57 (m, 2H).

Example 24

Preparation of Compound 24

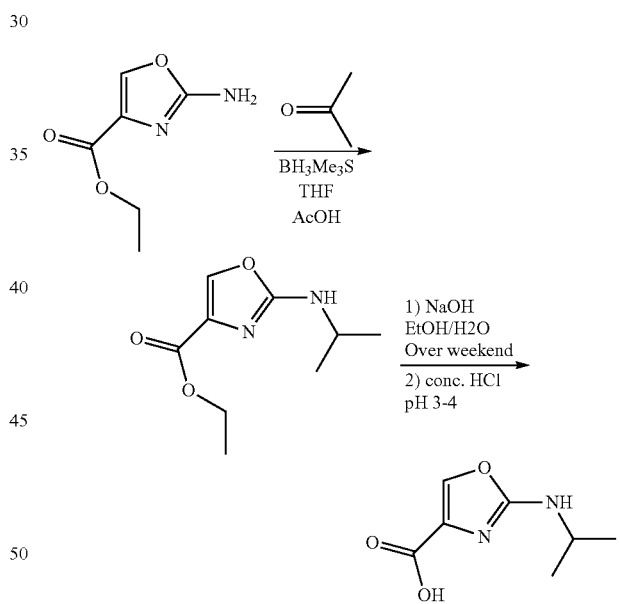

Step 1:

The mixture of 2-amino-oxazole-4-carboxylic acid ethyl ester (500 mg, 3.2 mmol) and acetone (2.35 mL, 32 mmol) in THF (6 mL) was stirred at room temperature. Borane ($BH_3.Sme_2$) (10M in THF, 0.64 mL, 6.4 mmol) was added slowly via syringe to control the exotherm and bubbling. Next, AcOH (0.362 mL, 6.4 mmol) was added in the same manner. (Another 2 eq of borane and AcOH were added 18 h later) The mixture was stirred under a nitrogen atmosphere and monitored by LC/MS. After 3 days at room temperature, the reaction still had some SM left. It was concentrated in vacuo. The resulting residue was dissolved in EtOAc (100 mL), washed with saturated $NH_4Cl$ solution, 0.1 M $NH_4OH$ and brine. The organic phase was dried ($Na_2SO_4$) and con-

249 centrated in vacuo. The crude product was purified by flash chromatography on silica gel, eluting with EtOAc/Hexanes to give the desired product (0.40 g, 64%). LC/MS=199 (M$^+$+1).

Step 2:

To the mixture of ester obtained above (2.5, 10.86 mmol) in EtOH (42 mL) and water (28 mL) was added NaOH (3.1 g, 77.4 mmol). The mixture was stirred at room temperature for 16 h. It was monitored by TLC. After the mixture was done, it was cooled in an ice-bath and acidified by adding conc. HCl to adjust the pH to 3. The mixture was then concentrated in vacuo to remove ethanol. The remaining was extracted with CH$_2$Cl$_2$ (3×200 mL). The organic phases were combined, dried (MgSO$_4$) and concentrated to give the desired product (1.86 g, 87%). LC/MS=171 (M$^+$+1).

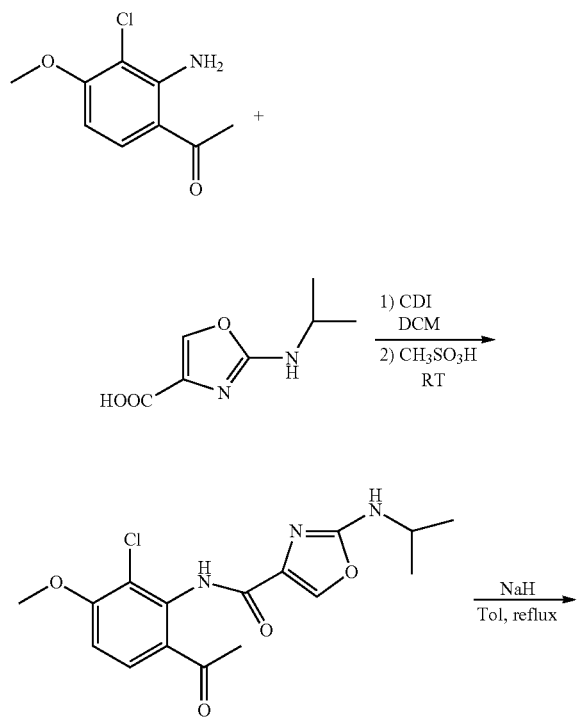

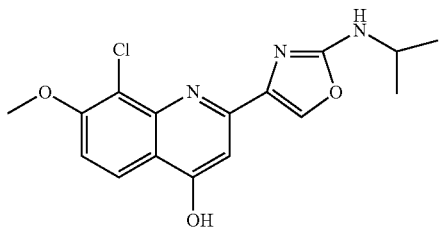

Step 3:

To acid (1.86 g, 10.94 mmol) in DCM (10 ml) was added CDI (1.774 g, 10.94 mmol). The mixture was then stirred at room temperature for 2 h. Aniline (1.446 g, 8.75 mmol) was added followed by CH$_3$SO$_3$H (2.13 mL, 32.82 mmol). The reaction was stirred for 18 h at room temperature. Upon completion of the reaction, it was diluted with DCM (100 mL) and washed with 1N HCl (2×100 mL). To this organic phase, was added K$_2$CO$_3$ (3.02 g, 21.88 mmol) and stirred for 2 h at room temperature. Solids were removed by filtration, and the filtrate was concentrated in vacuo. The residue was purified by flash chromatography on silica gel, eluted with EtOAc/Hexane to give the desired product (863.4 mg, 22%). LC/MS=382 (M$^+$+1).

Step 4:

The methyl ketone obtained above (863.4 mg, 2.45 mmol) was suspended in toluene (20 ml). NaH (147.3 mg, 3.68 mmol) was added to the vigorously stirred mixture while monitoring H$_2$ evolution. The reaction was refluxed (110° C.) for 3 h. The mixture was not a clear solution. LC/MS showed still about ⅓ of starting material left. After cooling, about 80 mg of NaH was carefully added, followed by 20 mL of THF to help the solubility. The mixture was heated for another 2 h and the reaction almost reached completion. After cooling to room temperature, it was quenched by the addition of conc. HCl to adjust the pH to about 2-3. The slurry was stirred for 1 h at room temperature. 10 mL of CH$_3$CN was added, followed by 5 mL H$_2$O, and then 20 mL of ether. The mixture was stirred for another ½ h, and then the solids were collected by filtration and washed with ether and hexane. The wet cake was dried under high vacuum to a constant weight (390 mg of HCl salt, 840 mg, 100%). LC/MS=334 (M$^+$+1).

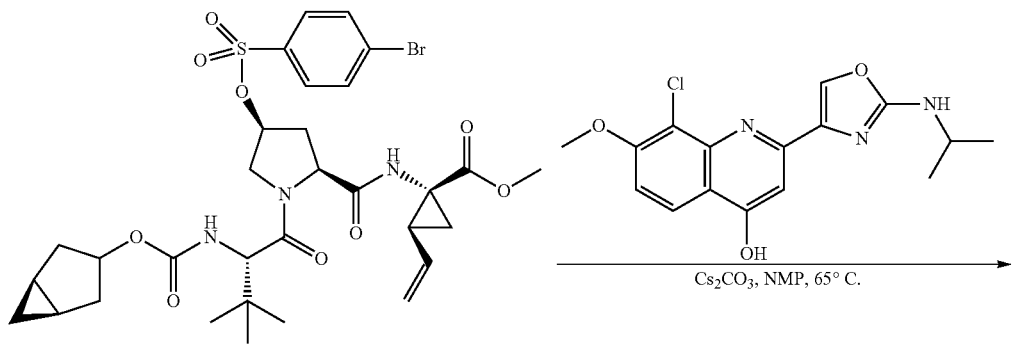

-continued
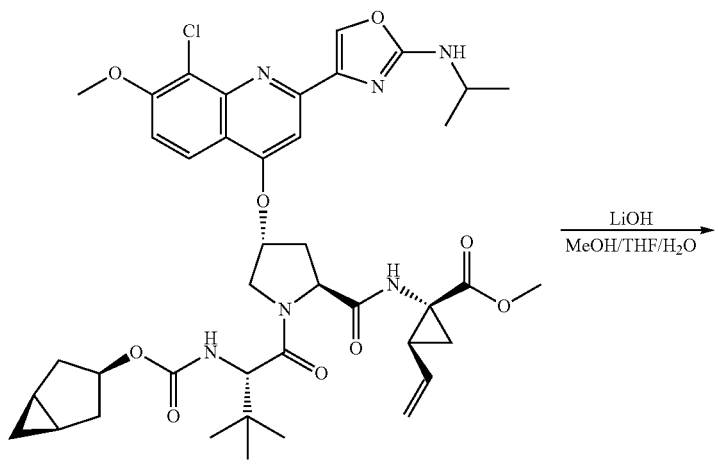
Step 5:
Using the same procedure described before, Compound 24 was obtained after prep HPLC purification as a yellow solid (30 mg). LC/MS=794 (M⁺+1). ¹H NMR (300 MHz, CD$_3$OD): δ 8.74 (s, 1H), 8.54 (s, 1H), 8.25 (d, 1H), 7.59 (m, 2H), 5.90-5.80 (m, 1H), 5.65 (bs, 1H), 5.31-5.09 (dd, 2H), 4.73 (t, 1H), 4.54 (m, 1H), 4.14 (s, 3H), 4.11-3.99 (m, 5H), 2.81-2.60 (m, 2H), 2.2 (m, 1H), 2.00-1.60 (m, 4H), 1.50-1.40 (m, 2H), 1.35 (s, 3H), 1.33 (s, 3H), 1.20 (m, 2H), 1.02 (s, 9H), 0.34 (m, 2H).
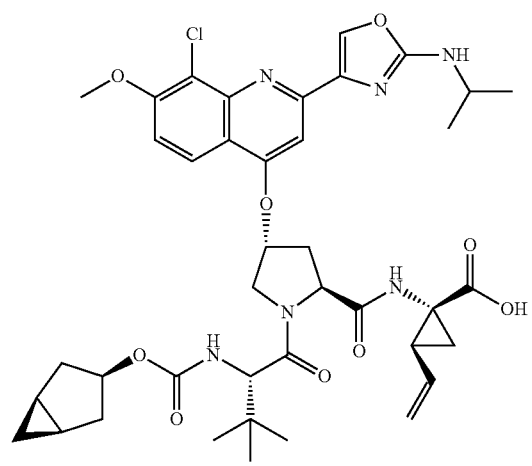
Example 25
Preparation of Compound 25
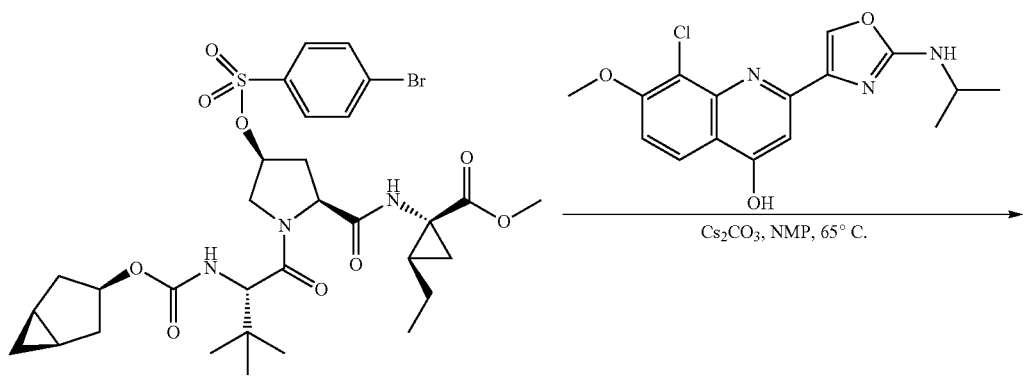

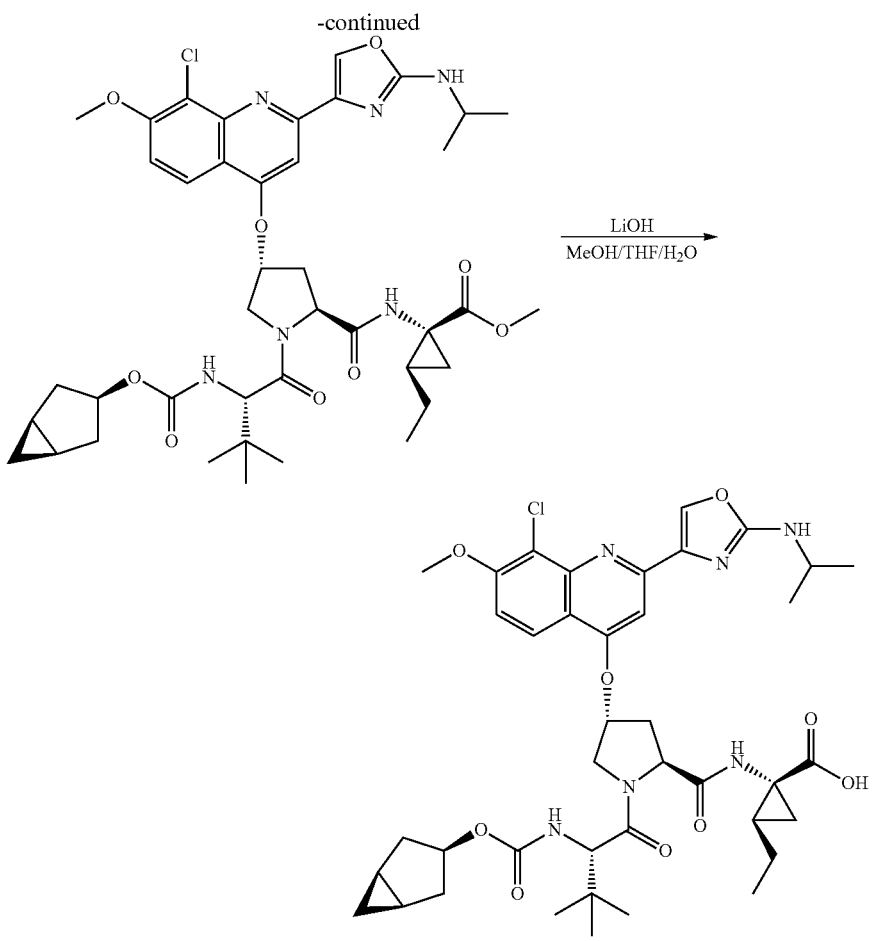

Using the same procedure described before, Compound 25 was obtained after prep HPLC purification as a yellow solid. LC/MS=796 (M++1). $^1$H NMR (300 MHz, CD$_3$OD): δ 8.64 (s, 1H), 8.60 (s, 1H), 8.26 (d, 1H), 7.61 (m, 2H), 5.67 (bs, 1H), 4.73 (t, 1H), 4.53 (m, 1H), 4.15 (s, 3H), 4.12 (m, 5H), 2.81-2.60 (m, 2H), 2.2 (m, 1H), 2.00-1.40 (m, 6H), 1.36 (s, 3H), 1.34 (s, 3H), 1.23 (m, 2H), 1.02 (s, 9H), 0.34 (m, 2H).

Example 26

Preparation of Compound 26

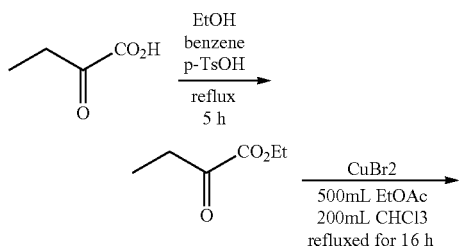

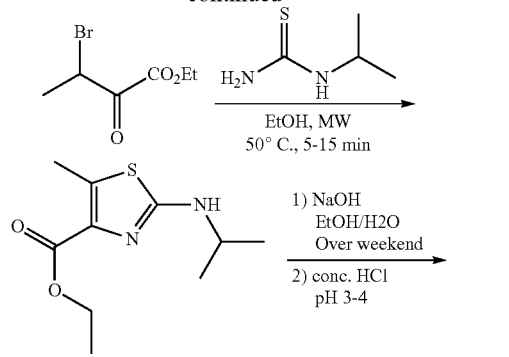

Step 1:

The mixture of 2-oxo-butyric acid (15 g, 147 mmol), p-TsOH (300 mg) in benzene (60 mL) and EtOH (125 mL) was stirred at 90° C. (reflux) for 5 h. After the mixture was cooled to room temperature, it was concentrated in vacuo (water bath t<20° C.). The resulting residue was dissolved in EtOAc (200 mL), washed with a saturated NaHCO$_3$ solution and brine. The organic phase was dried (Na$_2$SO$_4$) and concentrated in vacuo (water bath below 20° C.) to give the desired product (12.2 g, 64%). ¹H NMR (300 MHz, CDCl₃): δ 4.30 (q, 2H), 2.85 (q, 2H), 1.35 (t, 3H), 1.11 (t, 3H).

Step 2:

To a suspension of CuBr₂ (32 g, 147.1 mmol) in EtOAc (500 mL) was added the ester (6.2 g, 47.7 mmol) in CHCl₃ (200 mL). The mixture was stirred at 90° C. (reflux) for 16 h. It was monitored by TLC (EtOAc:Hexane=1:4, R$_f$=0.5, R$_f$=0.4). After the mixture was cooled to room temperature, it was filtered through a bed of silica gel eluting with 200 mL of a 1:1 EtOAc:Hexane solution. The filtrate was concentrated in vacuo (water bath t<20° C.) to give the desired product (10.75 g, 108%). No mass can be detected by LC/MS. ¹H NMR (300 MHz, CDCl₃): δ 5.17 (q, 1H), 4.38 (q, 2H), 1.81 (t, 3H), 1.38 (t, 3H).

Step 3:

The mixture of the bromide (1.672 g, 8 mmol) and isopropyl-thiourea (0.944 g, 8 mmol) in 12 mL of EtOH was microwaved at 50° C. for 15 min. After the mixture was cooled to room temperature, it was concentrated in vacuo. The residue was purified by silica gel flash chromatography, eluting with EtOAc/Hexane to give the desired product. LC/MS=229.9 (M⁺+1).

Step 4:

To the mixture of the ester (1.7 g, 7.45 mmol) in EtOH (12 mL) and water (8 mL) was added NaOH (1.8 g, 44.7 mmol). The mixture was stirred at room temperature for 16 h. The reaction was monitored by TLC. After the reaction was done, it was cooled in an ice-bath and acidified with conc. HCl to adjust the pH to 3. The mixture was then concentrated in vacuo to remove ethanol The remaining slurry was extracted with CH₂Cl₂ (3×200 mL). The organic phases were combined, dried (MgSO₄) and concentrated to give the desired acid product (1.2 g, 80%).

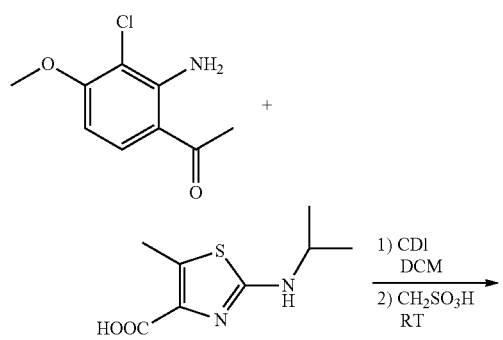

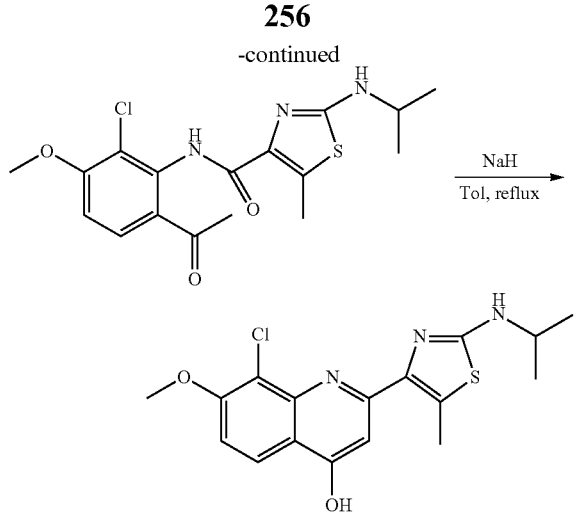

Step 5:

To the acid (1.2 g, 5.99 mmol) in DCM (10 ml) was added CDI (972 mg, 5.99 mmol. The mixture was then stirred at room temperature for 2 h. Aniline (792 mg, 4.89 mmol) was added followed by CH₃SO₃H (1.17 mL, 18 mmol). The reaction was stirred for 18 h at room temperature. Upon completion of the reaction, it was diluted with DCM (100 mL) and washed with 1N HCl (2×100 mL). To the organic phase, was added K₂CO₃ (1.66 g, 12 mmol) and this mixture was stirred for 2 h at room temperature. Solids were removed by filtration and the filtrate was concentrated in vacuo. The residue was purified by silica gel flash chromatography, eluting with EtOAc/Hexane to give the desired amide product (1.46 g, 70%). LC/MS=382 (M⁺+1).

Step 6:

The amide compound (1.46 g, 3.82 mmol) was suspended in toluene (30 ml). NaH (0.23 g, 5.73 mmol) was added to the vigorously stirred mixture while monitoring H₂ evolution. The mixture became a clear solution during heating to reflux. The reaction was complete after refluxing for 3 h. The reaction was cooled to room temperature, quenched with IPA (5 mL), and then heptane (30 mL) was added. The slurry was stirred for 1 h at room temperature. The solids that formed were collected by filtration and washed with ether. The collected solids were dissolved in AcCN/H₂O (2:1) and then acidified with 3N HCl. The resulting slurry was stirred for 1 h, and the solids were again collected by filtration. The wet cake was dried under high vacuum to a constant weight (390 mg of HCl salt, 1.07 mmol, 28%). LC/MS=363 (M⁺+1).

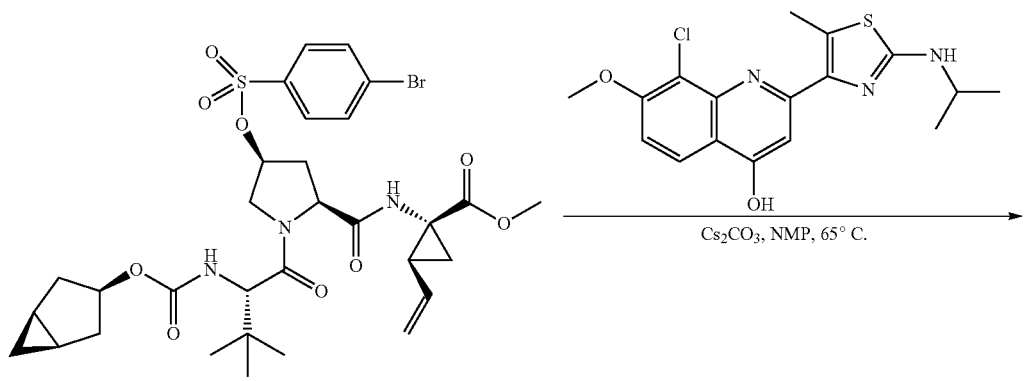

-continued

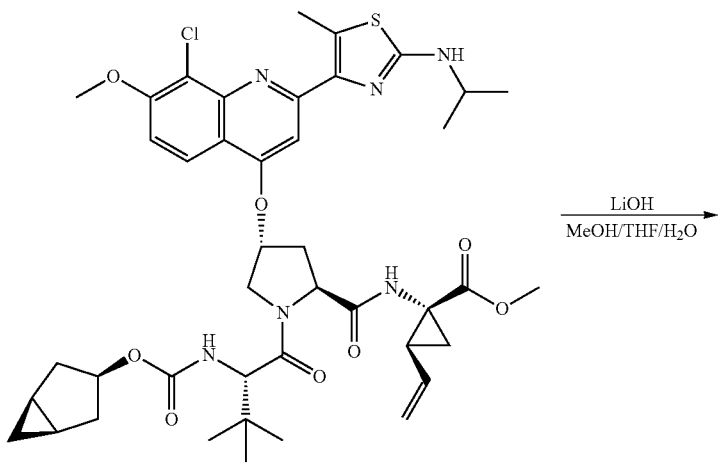

Step 7:

To a mixture of quinoline (0.39 g, 1.07 mmol) and brosylate (692 mg, 0.974 mmol) in NMP (10 ml) was added cesium carbonate (696 mg, 2.14 mmol). The mixture was stirred at 65° C. for 2 h. The reaction was cooled to room temperature, and EtOAc (60 ml) and aqueous solution of 3% LiCl (60 ml) were added to the mixture. The organic layer was washed with brine, dried ($Na_2SO_4$) and concentrated in vacuo. The residue was purified by silica gel chromatography to give the desired methyl ester product as a yellow solid (0.59 g). LC/MS=835).

Step 8:

The methyl ester was dissolved in THF (20 ml), LiOH (0.6 g) in $H_2O$ (10 ml) was added followed by addition of MeOH (1 ml). The mixture was kept stirring at room temperature for 20 h. Upon completion of the reaction, 40% TFA in $H_2O$ was added to adjust pH to 7 at 0° C. The mixture was extracted with EtOAc. The combined organic layer was concentrated in vacuo then purified by prep HPLC to give the compound 26 as a yellow solid (714 mg, 79%). LC/MS=823 ($M^+$+1). $^1H$ NMR (300 MHz, $CD_3OD$): δ 8.74 (s, 1H), 8.26 (d, 1H), 7.59 (d, 1H), 7.35 (s, 1H), 6.00-5.74 (m, 2H), 5.31-5.09 (dd, 2H), 4.69 (t, 1H), 4.52 (dd, 1H), 4.21-3.96 (m, 10H), 2.81 (m, 5H), 2.58 (m, 1H), 2.20 (m, 1H), 1.94 (m, 1H), 1.85-1.60 (m, 4H), 1.45 (m, 1H), 1.38 (s, 3H), 1.35 (s, 3H), 1.20 (m, 2H), 1.01 (s, 9H), 0.33 (m, 2H).

Example 27

Preparation of Compound 27

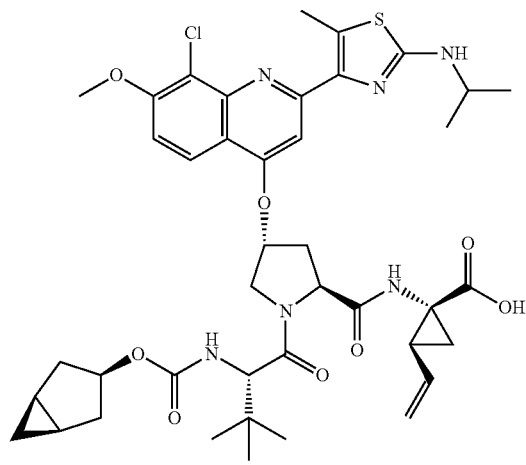

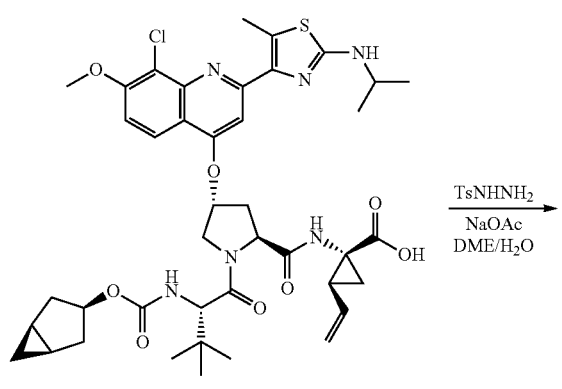

-continued

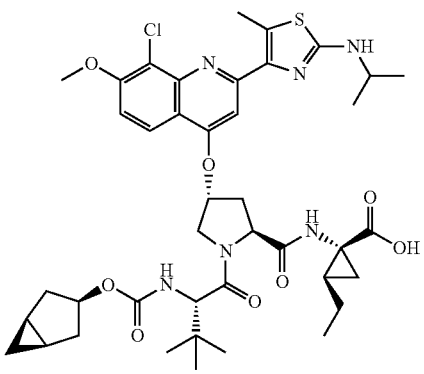

A mixture of compound 26 (320 mg, 0.388 mmol), p-TsNHNH$_2$ (542 mg, 2.91 mmol) and NaOAc (477 mg, 5.82 mmol) in a mixture of DME (10 mL) and H$_2$O (1 mL) was heated at 95° C. for 2 h. Upon completion of the reaction, it was cooled to room temperature, diluted with EtOAc (100 mL) and the pH was adjusted to 3 with 1N HCl. After separation of the organic and aqueous layers, the aqueous layer was back extracted with EtOAc. The organic layers were combined and concentrated. The crude product was purified by prep-HPLC to give compound 27 as a yellow solid (252 mg, 79%). LC/MS=825 (M$^+$+1). $^1$H NMR (300 MHz, CD$_3$OD): δ 8.24 (d, 1H), 7.58 (d, 1H), 7.31 (s, 1H), 5.72 (m, 1H), 4.71 (t, 1H), 4.58 (dd, 1H), 4.43 (t, 1H), 4.14 (s, 3H), 4.05 (m, 1H), 3.93 (m, 1H), 2.81 (s, 3H), 2.59 (m, 1H), 2.40 (dd, 2H), 1.94 (m, 1H), 1.80 (m, 1H), 1.64 (m, 3H), 1.52 (m, 1H), 1.38 (s, 3H), 1.36 (s, 3H), 1.27 (m, 2H), 1.01 (s, 9H), 0.33 (m, 2H).

Example 28

Preparation of Compound 28

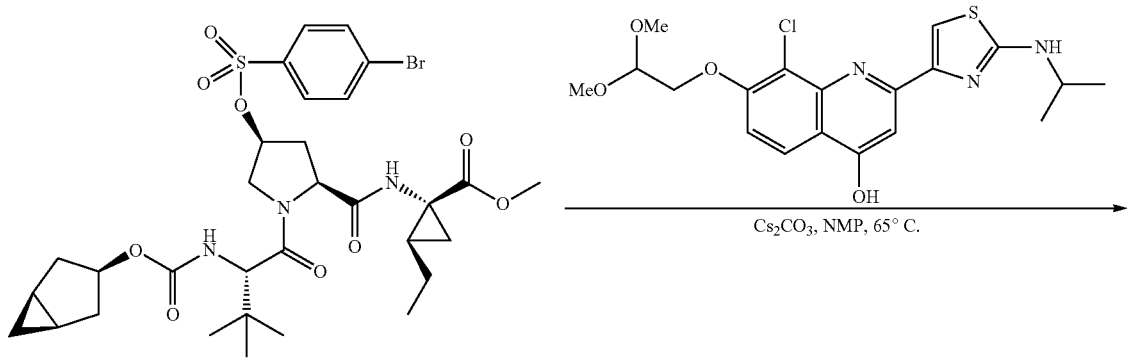

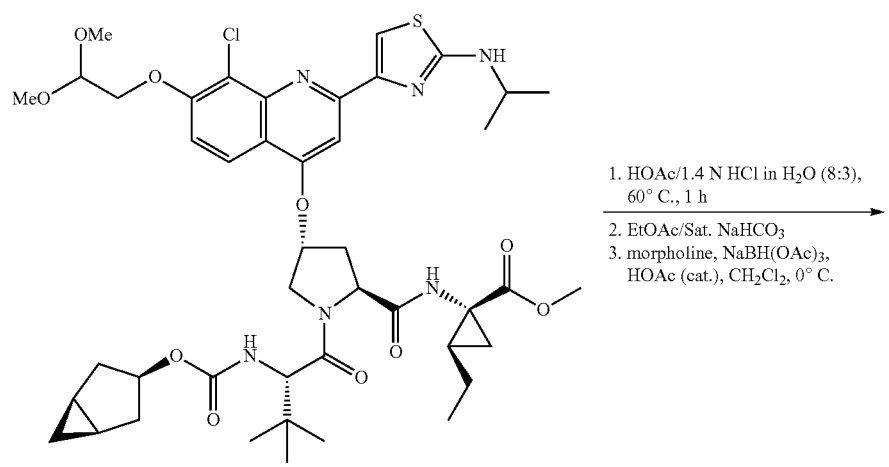

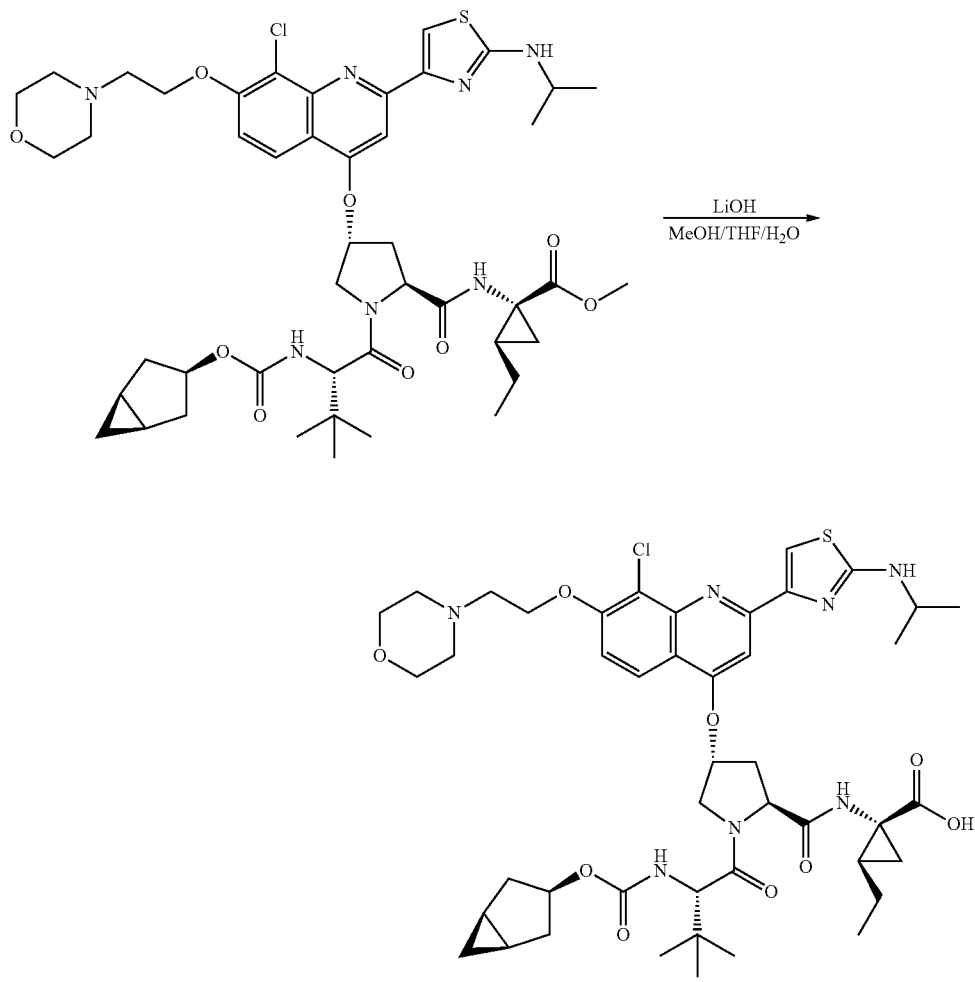

Step 1:

To a mixture of brosylate intermediate III (15 g, 35 mmol) and IV (27.5 g, 38.5 mmol) in NMP (200 ml) was added cesium carbonate (25.1 g, 77 mmol). The mixture was stirred at 65° C. for 5 h. The reaction was cooled to room temperature and EtOAc (600 ml) and an aqueous solution of 3% LiCl (600 ml) were added to the mixture. The organic layer was washed with aqueous 3% LiCl (1×600 ml), brine, dried ($Na_2SO_4$) and concentrated in vacuo. The residue was purified by silica gel chromatography to give the desired methyl ester as a yellow solid (23.6 g, 75%). LC/MS=900.13 ($M^+$+1).

Step 2:

Methyl ester (23.6 g, 26 mmol) was dissolved in glacial acetic acid (200 ml), 1.4 N HCl in $H_2O$ (75 ml) was added to the solution. The mixture was stirred at 60° C. for 1 h. Upon completion of the reaction, the mixture was concentrated to remove the solvents, coevaporated with toluene (×2) to remove residual acetic acid. The residue was then dissolved in EtOAc (500 ml) and sat. NaHCO3 aqueous solution (enough to neutralize the mixture) while monitoring $CO_2$ evolution. The organic layer was washed with brine, dried ($Na_2SO_4$) and concentrated in vacuo. The residue was further dried under high vacuum for 1 h and used as is for the next step. The crude was dissolved in $CH_2Cl_2$ (360 ml), morpholine (3.4 g, 39 mmol) and sodium triacetoxyborohydride (7.2 g, 34 mmol) were added to the mixture at 0° C. Then glacial acetic acid (0.47 g, 7.8 mmol) was added dropwise to the mixture. The reaction was complete in 10 min at 0° C. Sat. $NaHCO_3$ aqueous solution was added to quench the reaction. After stirring for another 20 min, the organic layer was washed with brine, dried ($Na_2SO_4$) and concentrated in vacuo. The residue was purified by silica gel chromatography to give the desired amine product as a yellow solid (12 g, 50%). LC/MS=924.63 ($M^+$+1).

Step 3:

Amine (12 g, 13 mmol) was dissolved in THF (200 ml), LiOH (11 g, 260 mmol) in $H_2O$ (200 ml) was added, followed by MeOH (200 ml). The mixture was kept stirring at room temperature for 20 h. Upon completion of the reaction, 4 N HCl in $H_2O$ was added to adjust pH to 7 at 0° C. The mixture was extracted with EtOAc (2×400 ml). The combined organic layer was washed with brine, dried ($Na_2SO_4$) and concentrated in vacuo to give the Compound 28 as a yellow solid (11 g, 93%). LC/MS=911.52 ($M^+$+1). $^1$H NMR (300 MHz, $CD_3OD$) δ 7.95 (d, 1H), 7.90 (s, 1H), 7.48 (s, 1H), 7.31 (d, 1H), 5.42 (s, 1H), 4.37 (dd, 1H), 4.20 (m, 2H), 3.83-3.56 (m, 7H), 3.50 (m, 2H), 3.39 (m, 2H), 2.45 (m, 1H), 2.27 (m, 1H), 1.62 (m, 2H), 1.50 (m, 1H), 1.33 (m, 2H), 1.18 (m, 1H), 1.05 (m, 8H), 0.90 (m, 3H), 0.76 (m, 11H), 0.14-0.04 (m, 2H)

Example 29

Preparation of Compound 29

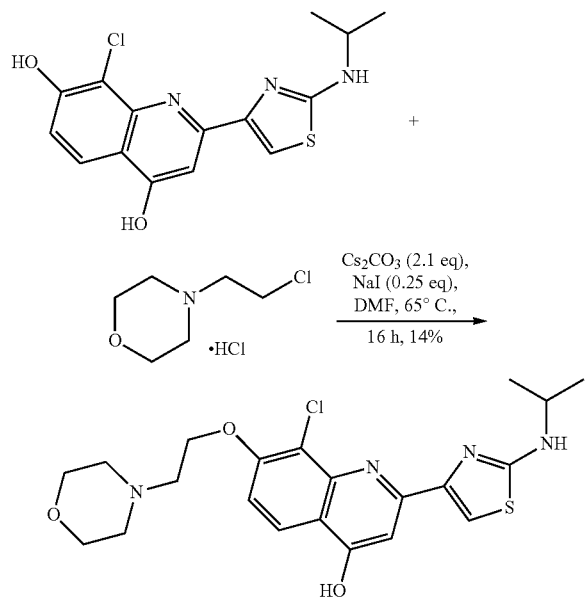 [SMILES: CC(C)Nc1nc(-c2cc(O)c3ccc(O)c(Cl)c3n2)cs1 ; ClCCN1CCOCC1 ; Cl ; CC(C)Nc1nc(-c2cc(O)c3ccc(OCCN4CCOCC4)c(Cl)c3n2)cs1]

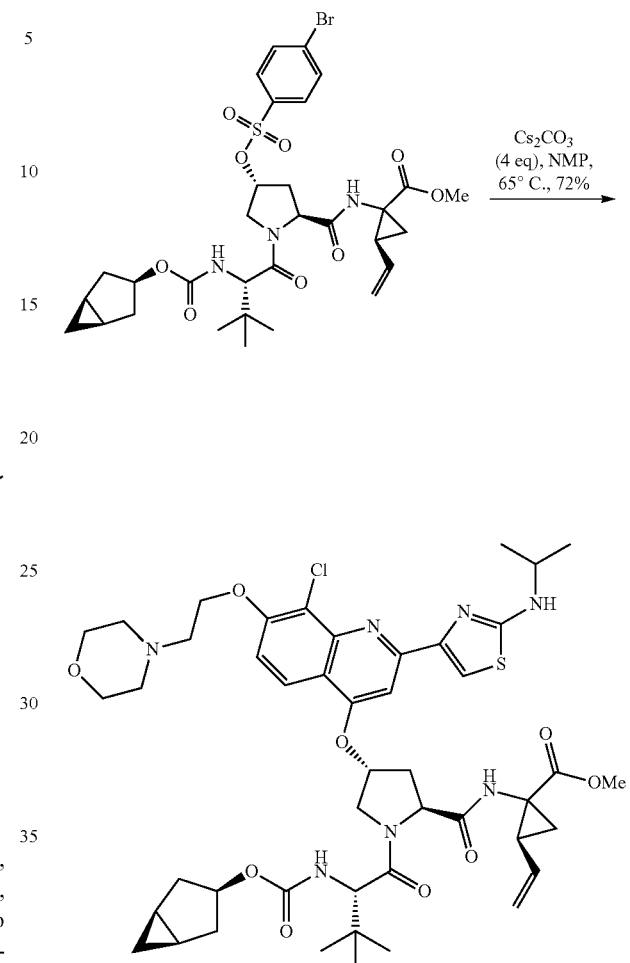

Step 1:

An N₂ purged flask was charged with bisphenol (939 mg, 2.79 mmol), morpholine ethyl chloride (545 mg, 2.93 mmol), Cs₂CO₃ (1.9 g, 5.87 mmol), and NaI (84 mg, 0.56 mmol). To this mixture was then added DMF (20 mL) and the heterogeneous mixture was heated in a preheated 65° C. oil bath for 16 h. The reaction was cooled to room temperature and aliquots were removed and filtered. The desired product was isolated from these aliquots by preparative reverse phase HPLC. This yielded the quinoline product as the TFA salt. Conversion to the HCl salt was effected by dissolving the TFA salt in a MeOH:4N HCl/dioxanes mixture and evaporating. This process was done three times to yield 200 mg of product in a 14% yield. LC/MS=449.32 (M⁺+1)

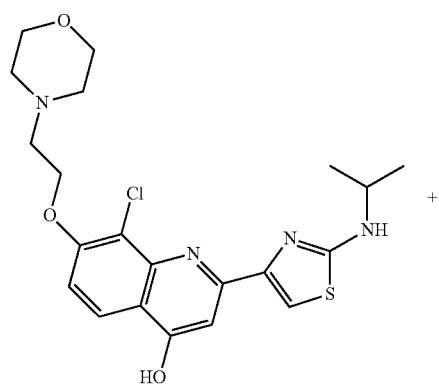

Step 2:

An N₂ purged flask was charged with quinoline (200 mg, 0.38 mmol), brosylate (323 mg, 0.456 mmol), and Cs₂CO₃ (372 mg, 0.76 mmol). To this mixture was then added NMP (5 mL) and the resulting heterogeneous mixture was heated in a preheated 65° C. oil bath for 4.5 h. No reaction as determined by LC/MS. Additional Cs₂CO₃ (124 mg, 0.25 mmol) was added. After 2 h the brosylate was completely consumed, as determined by LC/MS, while quinoline remained. Additional brosylate (68 mg, 0.095 mmol) was added to the reaction and heating was continued overnight. The reaction was complete as determined by LC/MS and HPLC. The reaction was cooled to room temperature and diluted with CH₂Cl₂. A small volume of 5% LiCl$_{(aq.)}$ was added to this and the layers were separated. The aqueous layer was back extracted with CH₂Cl₂ (1×) and the combined organic layers were clarified with MeOH and concentrated. The residue was re-dissolved in MeOH and 317 mg of methyl ester (72% yield) was isolated as a yellow solid by reverse phase HPLC. LC/MS=922.59 (M⁺+1).

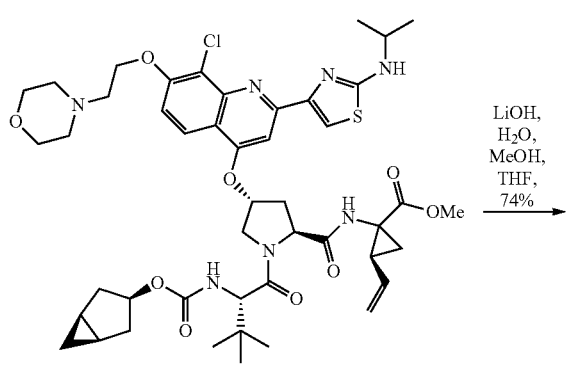

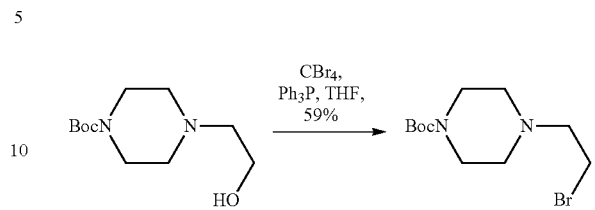

Example 30

Preparation of Compound 30

Step 1:

Alcohol (3.42 g, 0.015 mmol) was dissolved in THF (55 mL). To this solution was added CBr$_4$ (5.47 g, 0.017 mmol). Ph$_3$P (4.46 g, 0.017 mmol) was dissolved in THF (20 mL) and slowly added to the reaction via an addition funnel. The reaction was stirred at room temperature for 16 h. The reaction was complete as determined by TLC. The reaction was diluted with hexanes and the white precipitate that formed was removed by filtration. More solids crashed in the filtrate. The mixture was transferred to a separatory funnel and the organic layer was extracted with sat. NaHCO$_{3(aq.)}$ (2×), dH$_2$O (2×) and brine (1×). The organic layer was dried over Na$_2$SO$_4$ and a small amount of MgSO$_4$. The drying agents were removed by vacuum filtration and bromide (2.59 g, 59% yield) was isolated from the filtrate by silica gel column chromatography, eluting with a mixture of EtOAc/hexanes. The bromide was isolated as a colorless oil that turns to a crystalline solid upon sitting. LC/MS=293.02 (M$^+$+1).

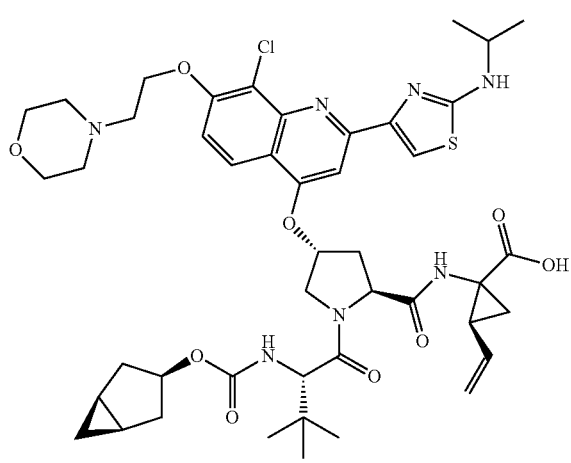

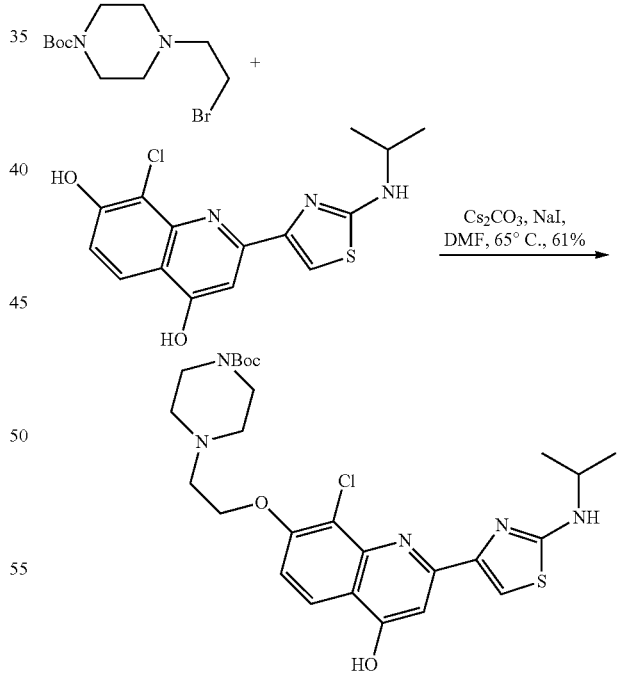

Step 3:

Methyl ester (306 mg, 0.266 mmol) was dissolved in a mixture of THF (1.5 mL) and MeOH (1 mL), and the solution was cooled to 0° C. LiOH.H$_2$O (45 mg, 1.06 mmol) was dissolved in dH$_2$O (0.5 mL) and this was slowly added to the solution of ester in THF/MeOH. Upon complete addition the ice bath was removed. After 2 h the reaction was not complete. Additional LiOH.H$_2$O (23 mg, 0.54 mmol) was added. After another hour the reaction was still not complete, so additional LiOH.H$_2$O (23 mg, 0.54 mmol) was added. After another 3.5 h the reaction appeared complete by HPLC. The reaction was cooled to 0° C. and neutralized with 2N HCl. Compound 29 was directly isolated from the reaction mixture by reverse phase HPLC. 223 mg (74% yield) of 29 was isolated as a yellow solid. LC/MS=910.53 (M$^+$+1). $^1$H NMR (300 MHz, CD$_3$OD) δ 8.33 (d, J=9.3 Hz, 1H), 8.23 (s, 1H), 7.78 (s, 1H), 7.62 (d, J=9.3 Hz, 1H), 5.86 (dd, J=9.9, 16.5 Hz, 1H), 5.73 (s, 1H), 5.29 (d, J=17.1 Hz, 1H), 5.11 (d, J=10.2 Hz, 1H), 4.79 (s, 2H), 4.70 (t, J=8.7 Hz, 1H), 4.56 (m, 2H), 4.20-3.92 (m, 8H), 3.83 (s, 3H), 3.59 (brds, 4H), 2.78 (dd, J=7.2, 14.1 Hz, 1H), 2.61 (m, 1H), 2.21 (q, J=8.9 Hz, 1H), 1.98 (m, 1H), 1.86 (m, 1H), 1.76-1.64 (m, 2H), 1.46 (m, 1H), 1.39 (d, J=6.3 Hz, 6H), 1.19 (m, 2H), 1.04 (s, 12H), 0.38 (m, 2H).

Step 2:

An N$_2$ purged flask was charged with the bromide (738 mg, 2.5 mmol), bisphenol (1 g, 2.4 mmol), Cs$_2$CO$_3$ (1.21 g, 3.7 mmol) and NaI (72 mg, 0.48 mmol). To this mixture was added DMF (24 mL) and the heterogeneous mixture was heated in a preheated 65° C. oil bath. After 2 h very little of the bromide remained. Additional bromide (141 mg, 0.48 mmol)

was added to the reaction and heating continued for 16 h. The reaction was complete, as determined by LC/MS, the next day. The reaction was cooled to room temperature and diluted with EtOAc. This mixture was extracted with 5% LiCl$_{(aq.)}$ basified with a small amount of sat. NaHCO$_{3(aq.)}$ (2×) and brine (1×). The organic phase was then dried over Na$_2$SO$_4$ with a small amount of MgSO$_4$. After removal of the drying agents by vacuum filtration, the quinoline was isolated from the filtrate (800 mg, 61%) as a yellow-brown solid. LC/MS=548.26 (M$^+$+1).

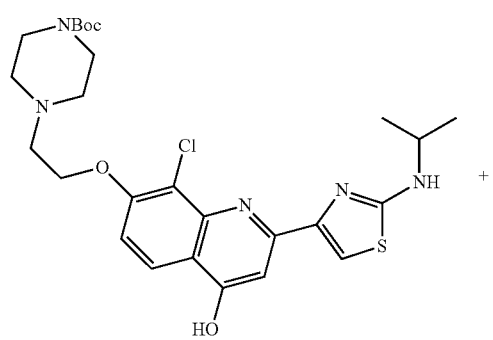

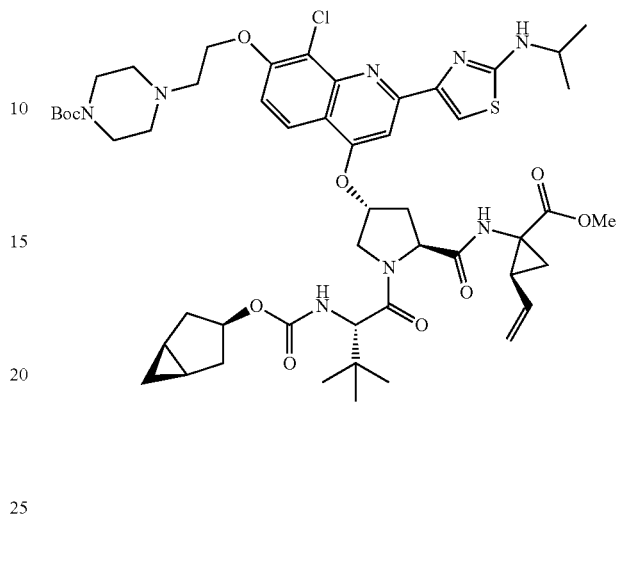

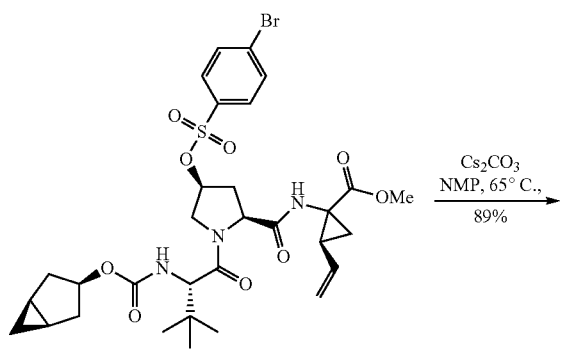

Step 3:

An N$_2$ purged flask was charged with quinoline (800 mg, 1.46 mmol), brosylate (1.24 g, 1.75 mmol) and Cs$_2$CO$_3$ (570 mg, 1.75 mmol). To this mixture was then added NMP (14.6 mL) and the resulting heterogeneous mixture was heated in a preheated 65° C. oil bath. After 2 h the reaction shows a lot of progress. Heating continued for another 9 h and then the reaction was stirred at room temperature for 7 h. The reaction was diluted with EtOAc and the resulting mixture was extracted with 5% LiCl$_{(aq.)}$ (2×), and brine (1×). The organic phase was then dried over Na$_2$SO$_4$ and a small amount of MgSO$_4$. The drying agents were removed by vacuum filtration. The methyl ester was isolated from the filtrate by silica gel column chromatography as a slightly yellow-brown solid (1.33 g, 89%). LC/MS=1021.75 (M$^+$+1).

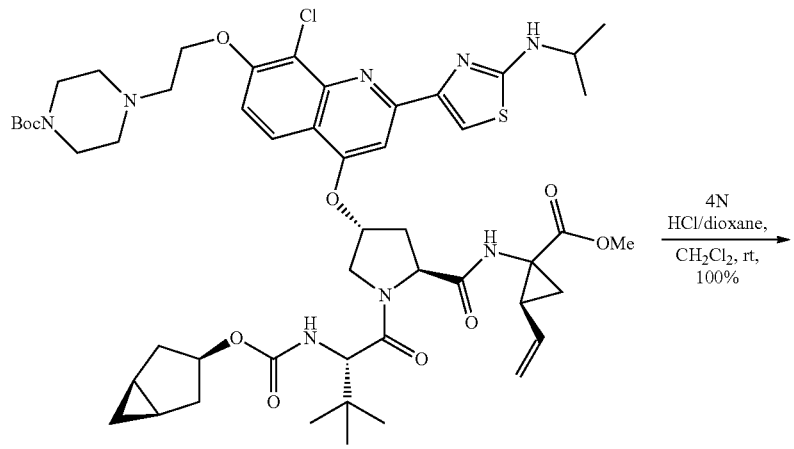

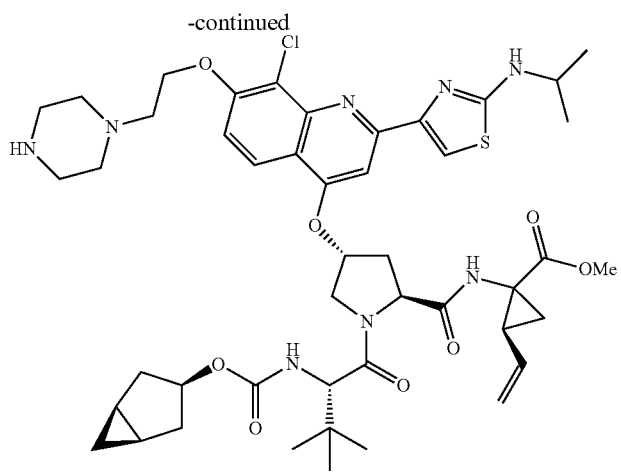

Step 4:

The methyl ester (1.33 g, 1.3 mmol) was dissolved in $CH_2Cl_2$ (10 mL). This solution was cooled to 0° C. and 4N HCl in dioxanes (3.25 mL, 13 mmol) was added dropwise. The cold bath was then removed. The reaction was complete after 2 h, as determined by LC/MS. The reaction was concentrated, re-dissolved in $CH_2Cl_2$, and concentrated again. The residue was re-dissolved in $CH_2Cl_2$ again and then extracted with sat. $NaHCO_{3(aq.)}$ (1×). The organic phase was dried over $Na_2SO_4$ and a small amount of $MgSO_4$. The drying agents were removed by vacuum filtration and the filtrate was concentrated to yield the amine as slightly yellow foam (1.23 g, 100%). LC/MS=921.53 ($M^+$+1).

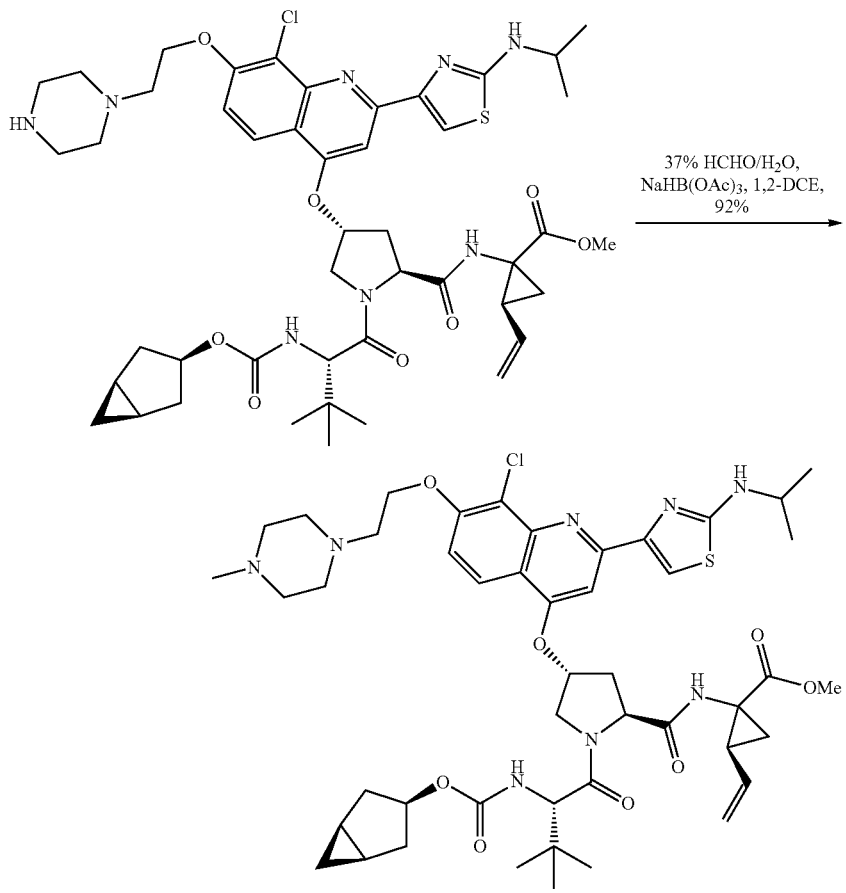

Step 5:

The amine (608 mg, 0.66 mmol) was dissolved in 1,2-DCE (7 mL). To this solution was added 37% $HCHO/H_2O$ (49 µL, 0.66 mmol). To this mixture was then added $NaHB(OAc)_3$ (560 mg, 2.64 mmol). The reaction was determined to be complete by LC/MS after 30 min. The reaction was quenched by the addition of sat. NaHCO$_{3(aq.)}$. The reaction was then diluted with EtOAc and extracted with sat. NaHCO$_{3(aq.)}$ (3×) and brine (1×). The organic phase was then dried over Na$_2$SO$_4$ and a small amount of MgSO$_4$. The drying agents were removed by vacuum filtration and the filtrate was concentrated. The residue was re-dissolved in MeOH and this solution was concentrated. This MeOH dissolution and concentration was repeated 2 more times to yield the methyl amine (569 mg, 92% yield) as a pink-orange foam. LC/MS=935.59 (M$^+$+1).

Step 6:
The methyl ester (615 mg, 0.658 mmol) was dissolved in MeOH (2.2 mL) and THF (3.3 mL). This solution was cooled to 0° C. and a solution of LiOH.H$_2$O (138 mg, 3.29 mmol) in dH$_2$O (0.5 mL) was slowly added. The cold bath was then removed. After 3.5 h reaction was complete, as determined by LC/MS and HPLC. The reaction was cooled to 0° C. and quenched by the addition of 1N HCl. Compound 30 (590 mg, 78% yield) was isolated from the quenched reaction, by reverse phase HPLC, as a yellow solid. LC/MS=921.48 (M$^+$+1). $^1$H NMR (300 MHz, CD$_3$OD) δ 8.30 (d, J=10.2 Hz, 1H),

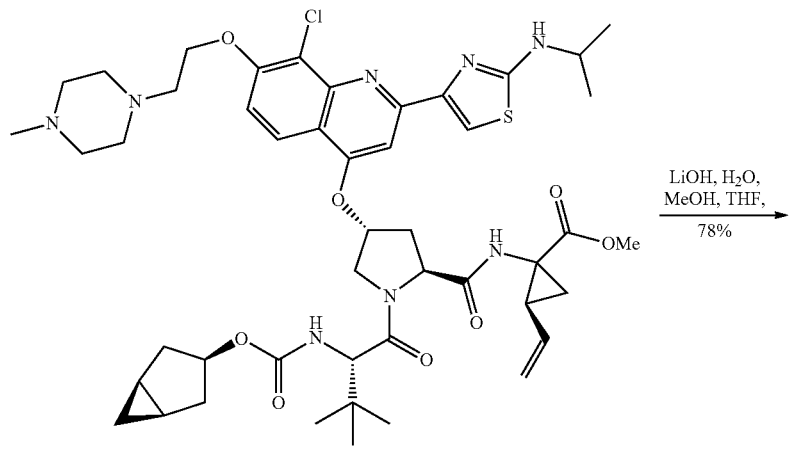

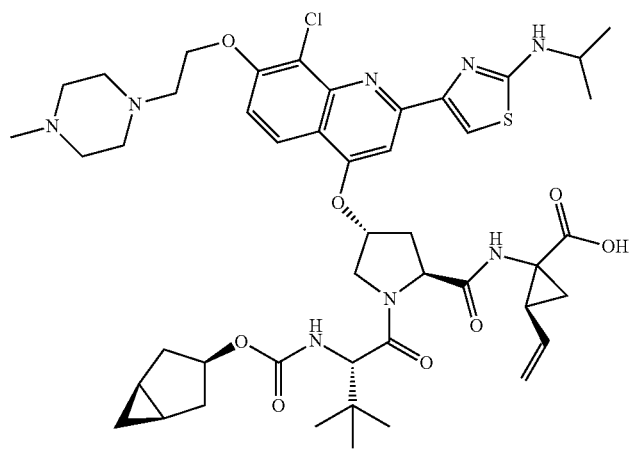

8.29 (s, 1H), 7.81 (s, 1H), 7.62 (d, J=10.2 Hz, 1H), 5.86 (dt, J=9.9, 16.8 Hz, 1H), 5.76 (s, 1H), 5.28 (d, J=17.1 Hz, 1H), 5.11 (d, J=10.2 Hz, 1H), 4.72 (t, J=8.4 Hz, 1H), 5.59 (d, J=5.4 Hz, 3H), 4.47 (t, J=6.3 Hz, 1H), 4.15 (s, 1H), 4.12-3.99 (m, 2H), 3.43 (s, 4H), 3.32-3.18 (m, 8H), 2.93 (s, 3H), 2.80 (dd, J=6.6, 14.1 Hz, 1H), 2.61 (m, 1H), 2.22 (dd, J=8.4, 9 Hz, 1H), 1.95 (m, 1H), 1.86-1.60 (m, 3H), 1.46 (dd, J=5.4, 9.3 Hz, 1H), 1.38 (d, J=6.6 Hz, 6H), 1.20 (m, 2H), 1.03 (s, 12H), 0.34 (m, 2H).

Compound 30 (97 mg, 0.084 mmol) was dissolved in DME (2 mL). To this solution was added dH$_2$O (200 uL), pTolSO$_2$NHNH$_2$ (117 mg, 0.63 mmol) and NaOAc (103 mg, 1.26 mmol). The reaction flask was then placed in a preheated 95° C. oil bath for 2 h. The reaction was determined to be complete by LC/MS. The reaction was cooled to room temperature and a small amount of MeOH was added to make the reaction mono-phasic. The reaction was then filtered and compound 31 (69 mg, 71% yield) was isolated from the filtrate, by reverse phase HPLC, as a yellow solid. LC/MS=923.52 (M$^+$+1). $^1$H NMR (300 MHz, CD$_3$OD) δ 8.29 (d, J=9 Hz, 1H), 8.28 (s, 1H), 7.80 (s, 1H), 7.60 (d, J=9 Hz, 1H), 5.74 (s, 1H), 4.74-4.56 (m, 4H), 4.49 (t, J=6.3 Hz, 1H), 4.15 (s, 1H), 4.18-3.99 (m, 2H), 3.53 (s, 6H), 3.47 (s, 6H), 2.96 (s, 3H), 2.78 (dd, J=7.2, 14.1 Hz, 1H), 2.60 (m, 1H),

Example 31

Preparation of Compound 31

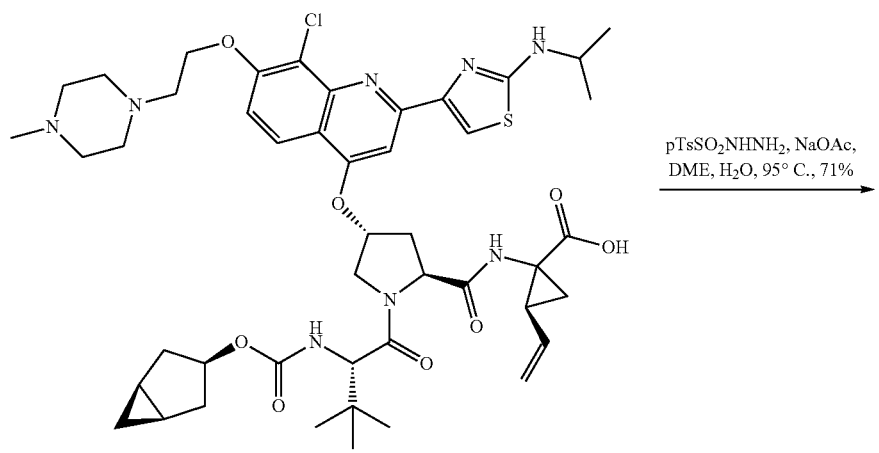

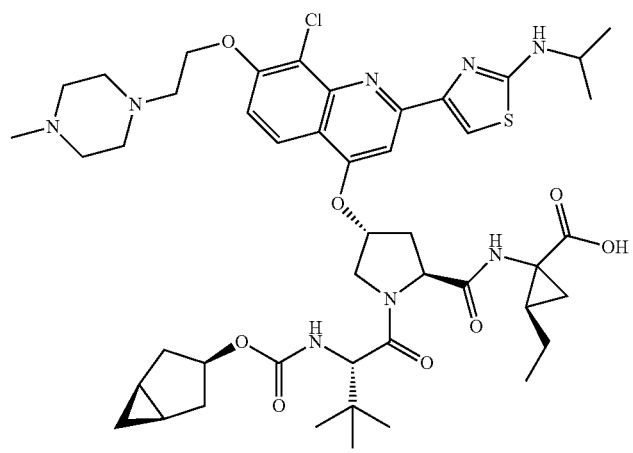

1.96 (m, 1H), 1.82 (m, 1H), 1.65 (m, 3H), 1.52 (t, J=7.5 Hz, 1H), 1.43 (m, 2H), 1.39 (d, J=6.3 Hz, 6H), 1.23 (q, J=3.9 Hz, 2H), 1.20 (m, 1H), 1.02 (s, 14H), 0.37 (m, 2H).

Example 32

Preparation of Compound 32

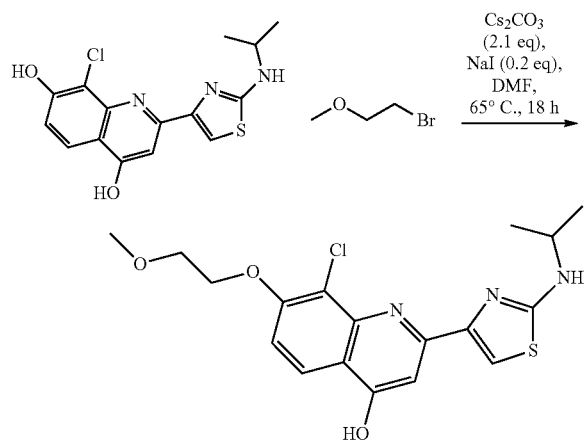

Step 1:

A N$_2$ purged flask was charged with bisphenol (998 mg, 2.97 mmol), bromide (293 µL, 3.11 mmol), Cs$_2$CO$_3$ (2.03 g, 6.24 mmol), and NaI (89 mg, 0.59 mmol). To this mixture was then added DMF (33 mL) and the heterogeneous mixture was heated in a preheated 65° C. oil bath for 7 h and then cooled to room temperature and stirred overnight. The reaction mixture was taken up in 100 mL of EtOAc. The solids were filtered off and washed with 50 mL of EtOAc. The organics were combined and extracted with 3×100 mL of 5% LiCl aqueous, followed by brine. The organics were dried over Na$_2$SO$_4$, the solids were filtered off and the solvent removed under reduced pressure. The crude was taken up in 10 mL of methanol and purified by preparative reverse phase HPLC. This yielded quinoline as the TFA salt. Conversion to the HCl salt was effected by dissolving the TFA salt of quinoline in a MeOH:4N HCl/dioxanes mixture and evaporating. This process was done three times to afford 305 mg of the quinoline in a 24% yield as a yellow solid. LC/MS=394 (M$^+$+1).

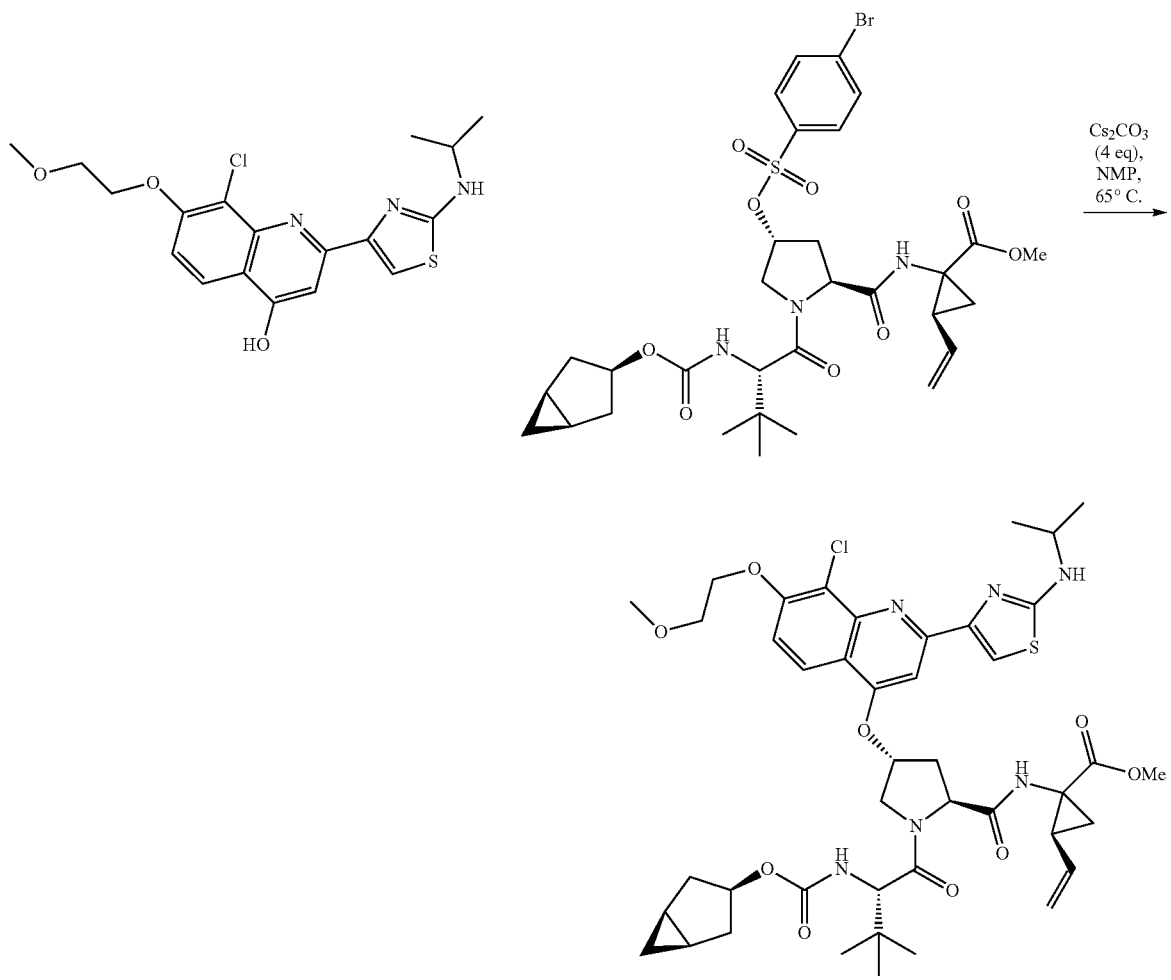 [SMILES: COCCOc1ccc2c(O)cc(-c3csc(NC(C)C)n3)nc2c1Cl ; C=C[C@@H]1CC1(NC(=O)[C@@H]1C[C@@H](OS(=O)(=O)c2ccc(Br)cc2)CN1C(=O)[C@@H](NC(=O)O[C@@H]1C[C@@H]2C[C@@H]2C1)C(C)(C)C)C(=O)OC ; C=C[C@@H]1CC1(NC(=O)[C@@H]1C[C@@H](Oc2cc(-c3csc(NC(C)C)n3)nc3c(Cl)c(OCCOC)ccc23)CN1C(=O)[C@@H](NC(=O)O[C@@H]1C[C@@H]2C[C@@H]2C1)C(C)(C)C)C(=O)OC]

Step 2:

A N₂ purged flask was charged with quinoline (305 mg, 0.78 mmol), brosylate (554 mg, 0.78 mmol), and Cs₂CO₃ (760 mg, 2.34 mmol). To this mixture was then added NMP (10 mL) and the resulting heterogeneous mixture was heated in a preheated 65° C. oil bath for 4.5 h. The reaction was not proceeding, as determined by LC/MS. Additional Cs₂CO₃ (250 mg, 0.78 mmol) was added and the reaction was heated overnight. The reaction was complete as determined by LC/MS and HPLC. The reaction was cooled to room temperature and diluted with EtOAc. A small volume of 5% LiCl$_{(aq.)}$ was added to this and the layers were separated. The aqueous layer was back extracted with EtOAc (1×) and the combined organic layers were dried over Na₂SO₄, filtered and concentrated. The residue was re-dissolved in DCM and 382 mg of methyl ester (57% yield) was isolated as a yellow solid by silica gel chromatography. LC/MS=868 (M⁺+1).

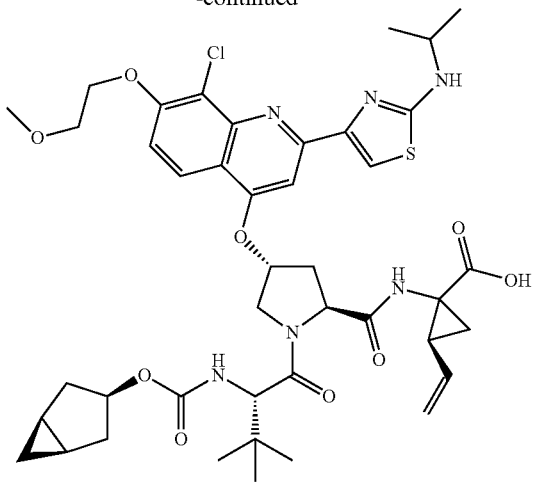

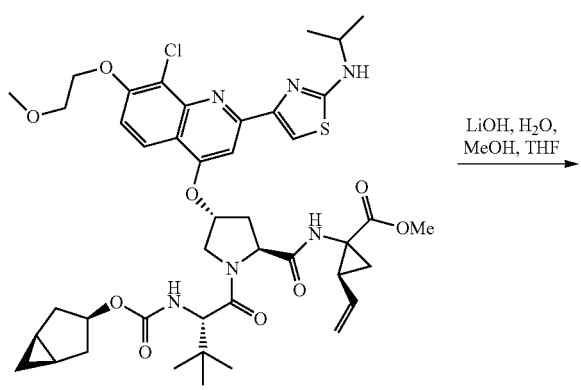

Step 3:

The methyl ester (380 mg, 0.44 mmol) was dissolved in a mixture of THF (5 mL) and MeOH (2.5 mL) and cooled to 0° C. LiOH.H₂O (32 mg, 1.32 mmol) was dissolved in dH₂O (2.5 mL) and this was slowly added to the solution of ester in THF/MeOH. Upon complete addition the ice bath was removed. After 2 h the reaction was not complete. Additional LiOH.H₂O (32 mg, 1.32 mmol) was added. After another hour the reaction was still not complete, so additional LiOH.H₂O (32 mg, 1.32 mmol) was added. After another 3.5 h the reaction appeared complete by HPLC. The reaction was cooled to 0° C. and neutralized with 2N HCl. Compound 32 was directly isolated from the reaction mixture by reverse phase HPLC. 235 mg (63% yield) of 32 was isolated as a yellow solid. LC/MS=853 (M⁺+1). ¹H NMR (300 MHz, CD₃OD) δ 8.75 (s, 1H), 8.29 (s, 1H), 8.27 (d, J=9.4 Hz, 1H), 7.83 (s, 1H), 7.68 (d, J=9.4 Hz, 1H), 5.86 (dd, J=9.1, 16.5 Hz, 1H), 5.77 (s, 1H), 5.31 (d, J=17.4 Hz, 1H), 5.13 (d, J=11 Hz, 1H), 4.75 (t, J=8.9 Hz, 1H), 4.62 (d, J=12.2 Hz, 1H), 4.52 (s, 1H), 4.41 (m, 1H), 4.13-4.05 (m, 4H), 3.87 (s, 3H), 3.31 (s, 3H), 2.76 (m, 1H), 2.61 (m, 1H), 2.22 (q, J=8.7 Hz, 1H), 1.92-1.59 (m, 7H), 1.48 (m, 1H), 1.39 (d, J=6.4 Hz, 6H), 1.20 (m, 2H), 1.02 (s, 9H), 0.49-0.32 (m, 3H).

Example 33

Preparation of Compound 33

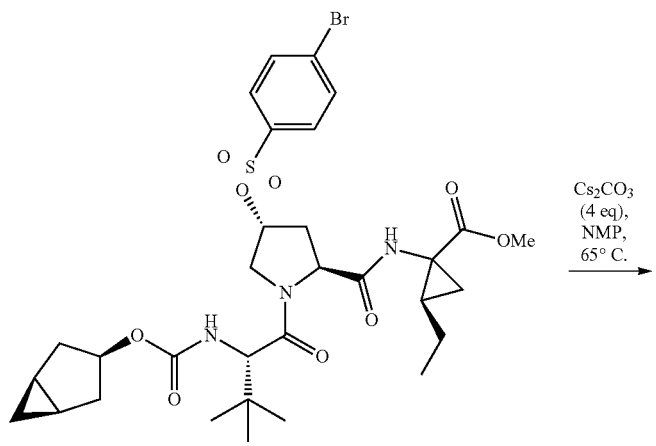

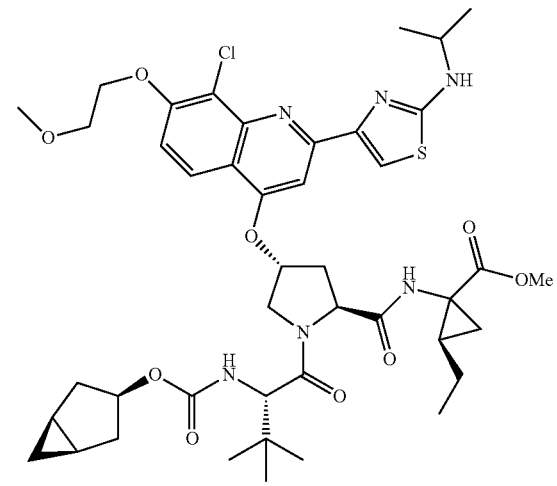

Step 1:

A N₂ purged flask was charged with quinoline (810 mg, 2.05 mmol), intermediate III (1.46 g, 2.05 mmol), and Cs₂CO₃ (1.39 g, 4.3 mmol). To this mixture was then added NMP (10 mL) and the resulting heterogeneous mixture was heated in a preheated 65° C. oil bath for 16 h. The reaction was complete as determined by LC/MS and HPLC. The reaction was cooled to room temperature and diluted with EtOAc. A small volume of 5% LiCl$_{(aq.)}$ was added to this and the layers were separated. The aqueous layer was back extracted with EtOAc (1×) and the combined organic layers were dried over Na₂SO₄, filtered and concentrated. The residue was re-dissolved in DCM and 382 mg of the methyl ester (63% yield) was isolated as a yellow solid by silica gel chromatography. LC/MS=869 (M⁺+1)

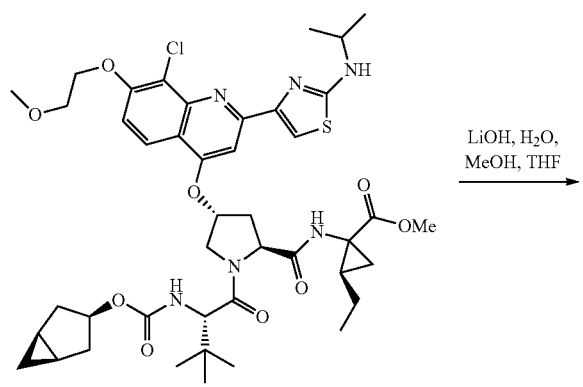

LiOH, H₂O,
MeOH, THF
⟶

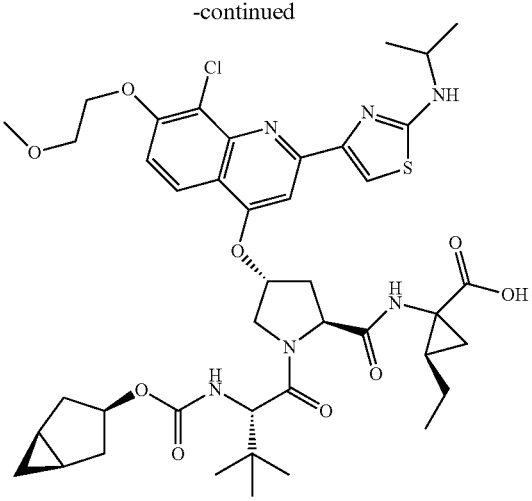

Step 2:

The methyl ester (1.12 g, 1.29 mmol) was dissolved in a mixture of THF (5 mL) and MeOH (2.5 mL). LiOH (309 mg, 12.9 mmol) was dissolved in dH₂O (4 mL) and this was slowly added to the solution of the ester in THF/MeOH, which had been cooled to 0° C. Upon complete addition the ice bath was removed. After 4 h the reaction was 70% complete. The reaction was allowed to stir at room temperature overnight. Additional LiOH.H₂O (32 mg, 1.32 mmol) was added. After another 3.5 h the reaction appeared complete by HPLC. The reaction was cooled to 0° C. and neutralized with 2N HCl. Compound 33 was directly isolated from reaction mixture by reverse phase HPLC. 913 mg (83% yield) of 33 was isolated as a yellow solid. LC/MS=855 (M⁺+1). ¹H NMR (300 MHz, CD₃OD) δ 8.64 (s, 1H), 8.30 (s, 1H), 8.26 (d, J=9.5 Hz, 1H), 7.83 (s, 1H), 7.67 (d, J=9.5 Hz, 1H), 5.76 (s, 1H), 4.75 (t, J=8.3 Hz, 1H), 4.62 (t, J=11.9 Hz, 1H), 4.51 (s, 2H), 4.40 (m, 1H), 4.13-4.05 (m, 4H), 3.87 (s, 3H), 3.31 (s, 3H), 2.78 (m, 1H), 2.60 (m, 1H), 1.94-1.59 (m, 9H), 1.48 (m, 1H), 1.38 (d, J=6.4 Hz, 6H), 1.21 (m, 2H), 1.01 (s, 9H), 0.36-0.32 (m, 3H).

Example 34

Preparation of Compound 34

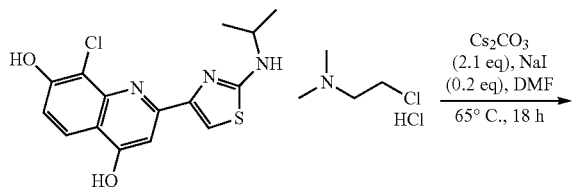

Step 1:

A N$_2$ purged flask was charged with bisphenol (1.02 g, 2.98 mmol), chloride (471 mg, 3.27 mmol), Cs$_2$CO$_3$ (2.01 g, 6.23 mmol), and NaI (89 mg, 0.59 mmol). To this mixture was then added DMF (24 mL) and the heterogeneous mixture was heated in a preheated 65° C. oil bath for 7 h. No reaction progress was detected by LC/MS. Heating was continued overnight. The next day, <20% conversion by LC/MS was observed. An additional 0.8 equivalents of NaI was added and the temperature was increased to 85° C. The reaction mixture was heated again overnight. LC/MS indicated complete conversion. The reaction mixture was filtered through a loose pack of C18. Solvent was then removed under reduced pressure. The crude material was taken up in 10 mL of methanol. The quinoline was purified by preparative reverse phase HPLC. This yielded the quinoline as the TFA salt. Conversion to the HCl salt was effected by dissolving the TFA salt in a MeOH:4N HCl/dioxanes mixture and evaporating. This process was done three times to yield 327 mg of quinoline HCl salt in a 25% yield. LC/MS=408 (M$^+$+1).

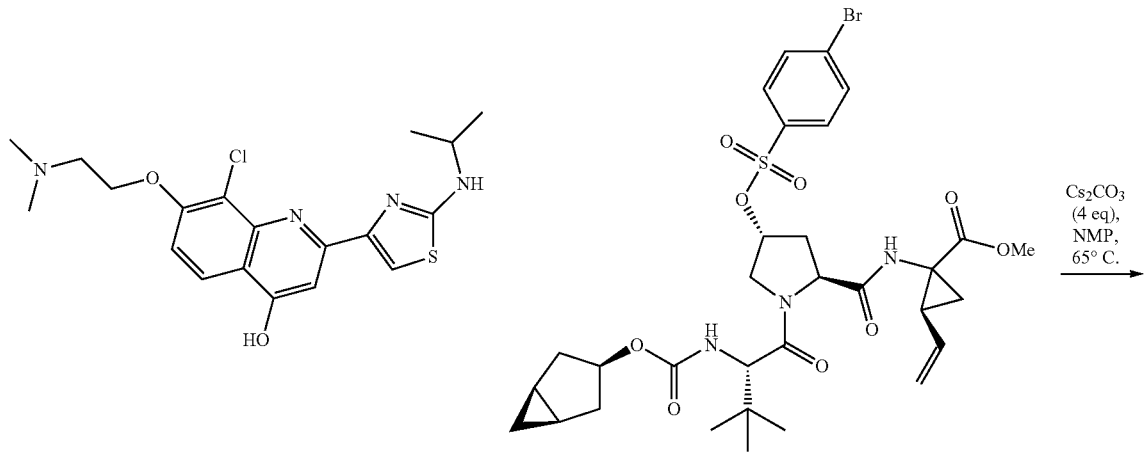

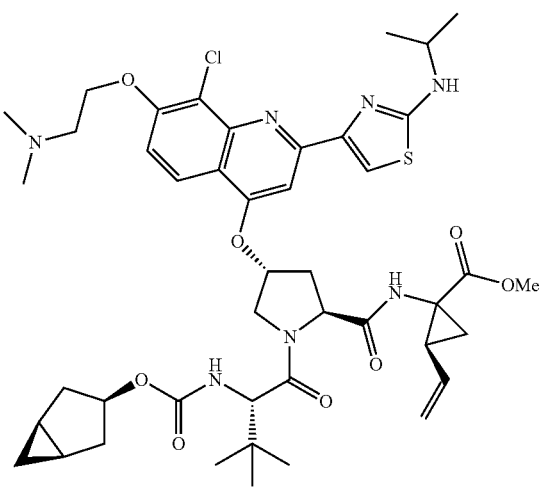

Step 2:

A N₂ purged flask was charged with quinoline (180 mg, 0.375 mmol), brosylate (400 mg, 0.563 mmol), and Cs₂CO₃ (366 mg, 1.13 mmol). To this mixture was then added NMP (5.6 mL) and the resulting heterogeneous mixture was heated in a preheated 65° C. oil bath for 4.5 h. There was no reaction progress, as determined by LC/MS. Additional Cs₂CO₃ (150 mg, 0.45 mmol) was added and the reaction was heated overnight. The reaction was complete as determined by LC/MS and HPLC. The reaction was cooled to room temperature and diluted with EtOAc. A small volume of 5% LiCl$_{(aq.)}$ was added to this and the layers were separated. The aqueous layer was back extracted with EtOAc (1×) and the combined organic layers were dried over Na₂SO₄, filtered and concentrated. The residue was re-dissolved in DCM and 237 mg of the methyl ester (42% yield) was isolated as a yellow solid by silica gel chromatography. LC/MS=881 (M⁺+1).

Step 3:

The methyl ester (237 mg, 0.269 mmol) was dissolved in a mixture of THF (1.5 mL) and MeOH (1 mL). LiOH.H₂O (30 mg, 1.07 mmol) was dissolved in dH₂O (0.5 mL) and this was slowly added to the solution of ester in THF/MeOH, which had been cooled to 0° C. Upon complete addition the ice bath was removed. After 4 h the reaction was 40% complete. The reaction was allowed to stir at room temperature overnight. The reaction was cooled to 0° C. and neutralized with 2N HCl. Compound 34 was directly isolated from the reaction mixture by reverse phase HPLC. 218 mg (94% yield) of 34 was isolated as a yellow solid. LC/MS=867 (M⁺+1).

Example 35

Preparation of Compound 35

Compound 34 (145 mg, 0.167 mmol) was dissolved in DME (1.5 mL). To this solution was added dH₂O (150 uL), pTolSO₂NHNH₂ (187 mg, 1.0 mmol) and NaOAc (150 mg, 1.84 mmol). The reaction flask was then placed in a preheated 95° C. oil bath for 2 h. The reaction was determined to be complete by LC/MS. The reaction was cooled to room temperature and a small amount of MeOH was added to make the reaction mono-phasic. The reaction was then filtered and 35 (97 mg, 63% yield) was isolated from the filtrate, by reverse phase HPLC, as a yellow solid.

LC/MS=868 (M⁺+1).

Example 36

Preparation of Compound 36

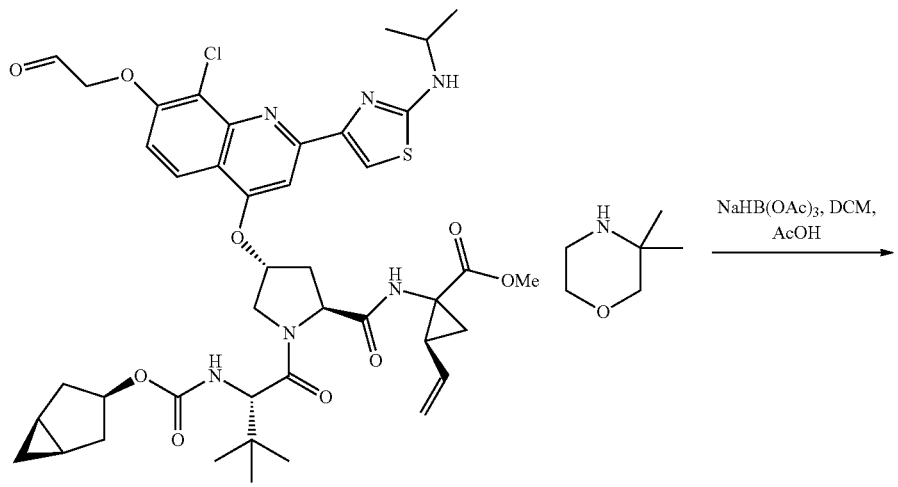

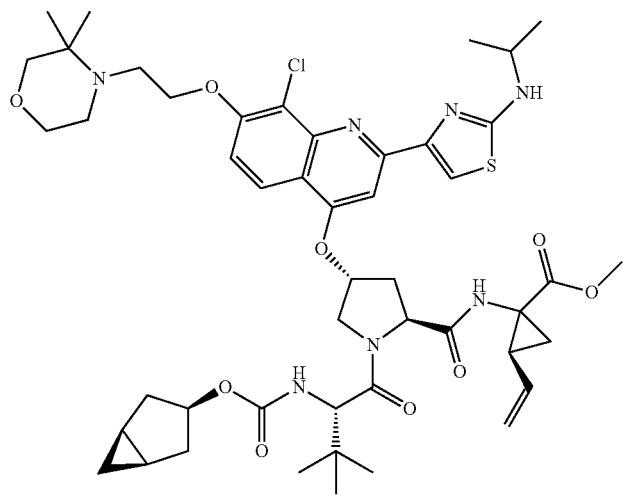

Step 1:

Aldehyde (prepared in similar manner to example 28) (1.17 g, 1.38 mmol) was dissolved in DCM (15 mL). To this solution was added morpholine (239 mgs, 2.07 mmol). To this mixture was then added NaHB(OAc)$_3$ (380 mg, 1.79 mmol), followed immediately by AcOH (24 μL, 0.414 mmol). The reaction was determined to be complete by LC/MS after 10 min. The reaction was quenched by the addition of half sat. NaHCO$_{3(aq.)}$. The reaction was then diluted with DCM and extracted with sat. NaHCO$_{3(aq.)}$ (3×) and brine (1×). The organic phase was then dried over Na$_2$SO$_4$. The drying agents were removed by vacuum filtration and the filtrate was concentrated. The residue was re-dissolved in MeOH and this solution was concentrated. This MeOH dissolution and concentration was repeated 2 more times. The crude material was taken up in minimal DCM and purified by silica gel chromatography to yield the methyl ester (908 mg, 70% yield) as a yellow solid. LC/MS=950 (M$^+$+1).

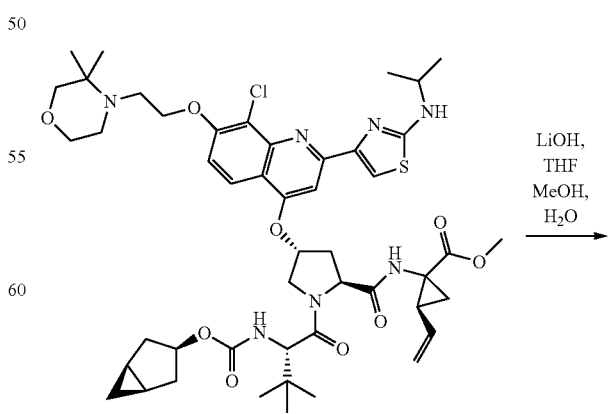

-continued

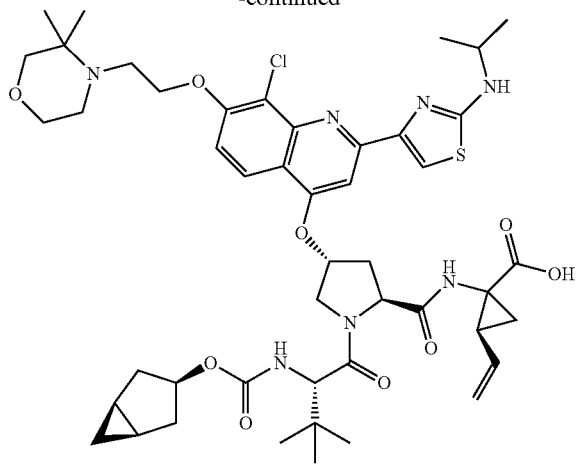

Step 2:
Methyl ester (772 mg, 0.813 mmol) was dissolved in a mixture of THF (7 mL) and MeOH (5 mL). LiOH.H$_2$O (171 mg, 4.07 mmol) was dissolved in dH$_2$O (3 mL) and this was slowly added to the solution of ester in THF/MeOH, which had been cooled to 0° C. Upon complete addition the ice bath was removed. After 3 h the reaction was complete. The reaction was cooled to 0° C. and neutralized with 2N HCl. Compound 36 was extracted into EtOAc. The organics were then extracted with 1N HCl, brine, and then dried over Na$_2$SO$_4$. The solids were removed by filtration and the organics removed under reduced pressure. Compound 36 (701 mgs) was isolated as a yellow solid using prep-HPLC. LC/MS=936 (M$^+$+1).

Example 37

Preparation of Compound 37

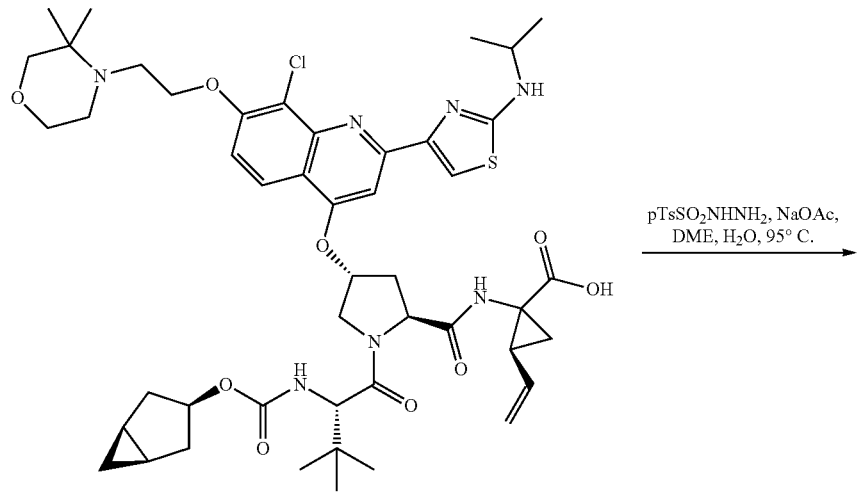

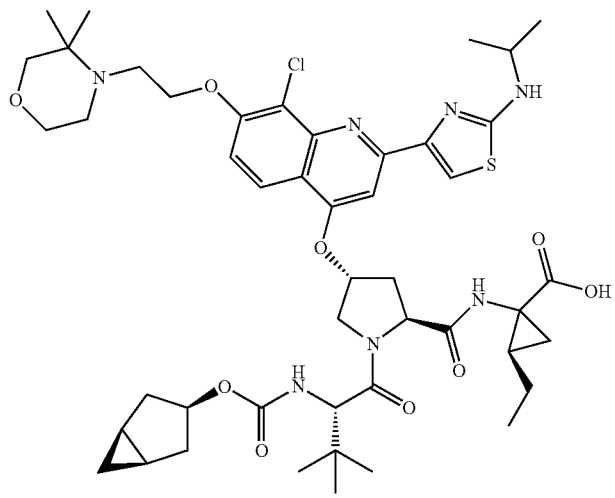

Compound 36 (701 mg, 0.748 mmol) was dissolved in DME (5 mL). To this solution was added dH$_2$O (500 uL), pTolSO$_2$NHNH$_2$ (697 mg, 3.74 mmol) and NaOAc (613 mg, 7.48 mmol). The reaction flask was then placed in a preheated 95° C. oil bath for 2 h. The reaction was determined to be complete by LC/MS. The reaction was cooled to room temperature and a small amount of MeOH was added to make the reaction mono-phasic. The reaction was then filtered and 37 (802 mg, 92% yield) was isolated from the filtrate, by reverse phase HPLC, as a yellow solid. LC/MS=938 (M$^+$+1). $^1$H NMR (400 MHz, CD$_3$OD) δ 8.26 (s, 1H), 7.98 (d, J=9.4 Hz, 1H), 7.86 (s, 1H), 7.42 (s, 1H), 7.24 (d, J=9.5 Hz, 1H), 5.36 (s, 1H), 4.51 (s, 6H), 4.38-4.19 (m, 5H), 3.82-3.45 (m, 5H), 2.53-2.32 (m, 3H), 1.84 (m, 1H), 1.66-1.28 (m, 5H), 1.18 (s, 7H), 1.03 (d, J=6.5 Hz, 6H), 0.89 (m, 1H), 0.67 (s, 14H), 0.14-0.04 (m, 2H).

Example 38

Preparation of Compound 38

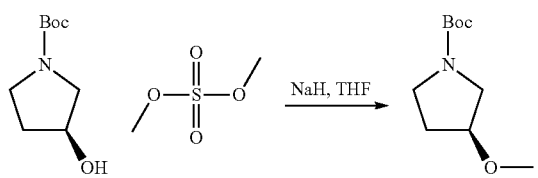

Step 1:

An Ar purged flask was charged with 60% NaH (4.26 g, 106 mmol) and THF (60 mL). The alcohol (5 g, 26.67 mmol) in solution with THF (40 mL), was slowly added. The mixture was stirred at room temperature for 30 min then dimethylsulfate (5.07 mL, 53.3 mmol) was added. The reaction was stirred at room temperature overnight. The reaction was quenched with sat. NH$_4$Cl$_{(aq.)}$ (note: extreme outgassing). The mixture was stirred for 15 min and then the organic layer was separated from the aqueous layer. The aqueous layer was extracted with EtOAc. The organics were combined and concentrated under reduced pressure. The residue was taken up in EtOAc and washed with ½ sat NaHCO$_{3(aq)}$ followed by brine. The organics were dried over Na$_2$SO$_4$, filtered and solvent was removed under reduced pressure to afford the crude methyl ether (8.56 g, 42.03 mmol) as a colorless oil. LC/MS=202 (M$^+$+1).

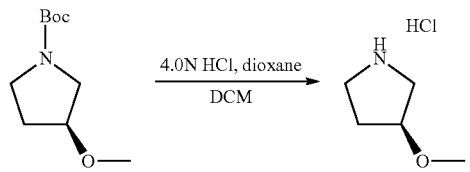

Step 2:

An Ar purged flask was charged with the methyl ether (8.56 g, 42.03 mmol), followed by DCM (30 mL). 4.0 N HCl in dioxane (30 mL, 120 mmol) was slowly added. The reaction was stirred at room temperature for 2 h. The reaction was determined to be complete by LC/MS. The solvent was removed under reduced pressure to afford crude amine (7 g, 50 mmol) and used as is for the next step. LC/MS=102 (M$^+$+1).

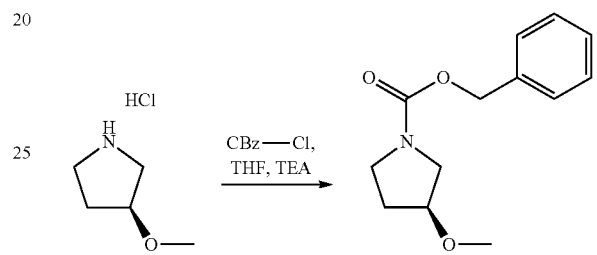

Step 3:

An Ar purged flask was charged with amine (7 g, 50 mmol), THF (150 mL), CBz-Cl (10.7 mL, 76 mmol) and cool to 0° C. with an ice bath. Et$_3$N (21.1 mL, 150 mmol) was slowly added. The reaction was monitored by LCMS. The reaction is complete after 1 h. The solvent was removed under reduced pressure. The residue was taken up in EtOAc and washed with 0.5N HCl$_{(aq)}$, brine, and dryed over Na$_2$SO$_4$. The solvent was removed under reduced pressure. The residue was dissolved in minimal DCM and purified by silica gel chromatography to afford the carbamate (4.52 g, 72% overall yield) as a white solid. LC/MS=236 (M$^+$+1).

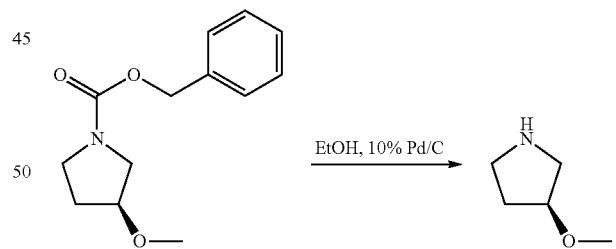

Step 4:

An Ar purged flask was charged with carbamate (4.5 g, 19.1 mmol) and EtOH (50 mL). The flask was evacuated and re-pressurized with Ar. This process was repeated three times. The reaction flask was then charged with 10% Pd/C, and the flask was evacuated. The flask was then refilled with an atmosphere of H$_2$. The reaction was stirred at room temperature under an H$_2$ atmosphere, monitoring the reaction progress by LC/MS. The reaction was complete after 3 h. The solids were removed by vacuum filtration using a PTFE filter. The filtrate was concentrated under reduced pressure. The residue was coevaporated with EtOAc 3×50 mL to afford the crude amine (2.03 g, 20.0 mmol) as a colorless oil. LC/MS=102 (M$^+$+1).

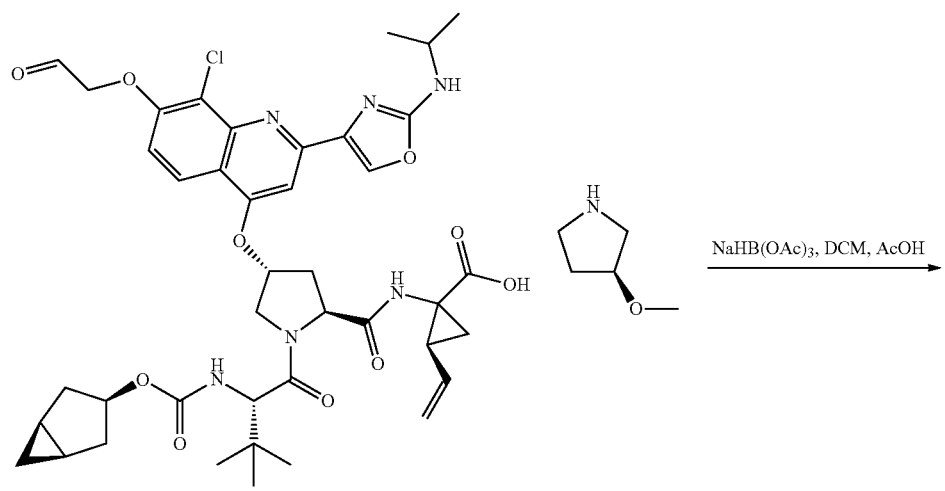

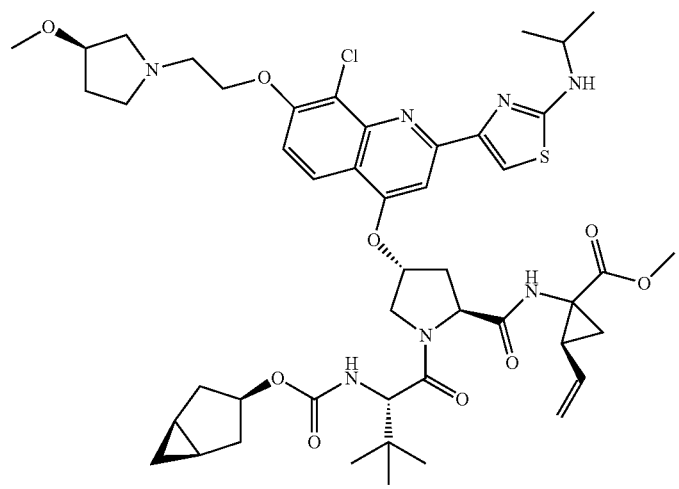

Step 5:

The aldehyde (1.00 g, 1.17 mmol) was dissolved in DCM (15 mL), and the amine (176 mgs, 1.75 mmol) was added. To this mixture was then added NaHB(OAc)$_3$ (322 mg, 1.52 mmol), followed immediately by AcOH (20 μL, 0.3 mmol). The reaction was determined to be complete by LC/MS after 10 min. The reaction was quenched by the addition of ½ sat. NaHCO$_{3(aq.)}$. The reaction was then diluted with DCM and extracted with sat. NaHCO$_{3(aq.)}$ (3×) and brine (1×). The organic phase was then dried over Na$_2$SO$_4$. The drying agents were removed by vacuum filtration and the filtrate was concentrated. The residue was re-dissolved in MeOH and this solution was concentrated. This MeOH dissolution and concentration was repeated 2 more times to afford the crude methyl ester (968 mg, 88% yield) as a yellow solid. LC/MS=936 (M$^+$+1).

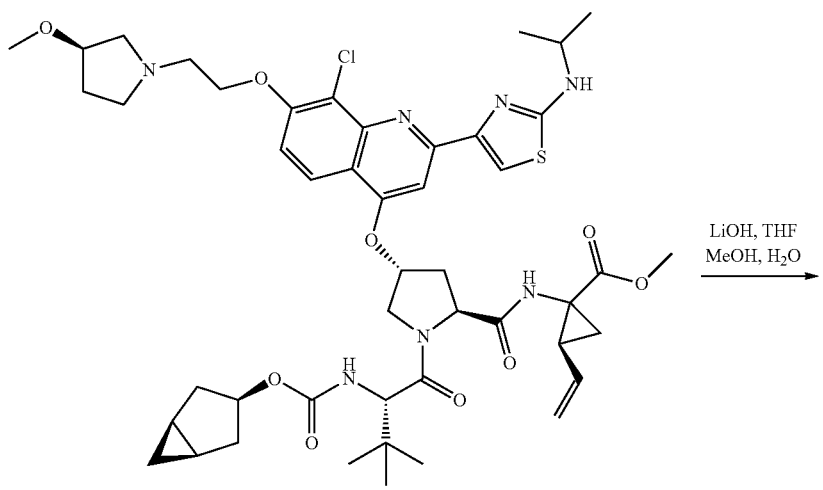

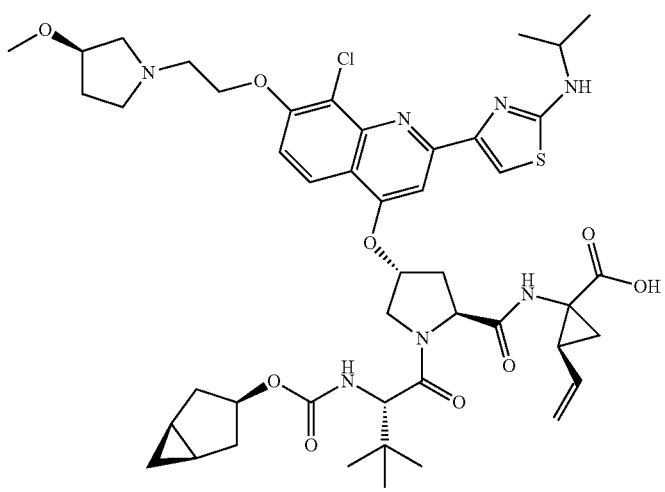

Step 6:

The ester (968 mg, 1.03 mmol) was dissolved in a mixture of THF (10 mL) and MeOH (6 mL). LiOH (200 mg, 4.67 mmol) was dissolved in dH$_2$O (3 mL) and this was slowly added to the solution of ester in THF/MeOH, which had been cooled to 0° C. Upon complete addition the ice bath was removed. After 3 h the reaction was complete. The reaction was cooled to 0° C. and neutralized with 2N HCl. Compound 38 was extracted into EtOAc, which was then extracted with 1N HCl, and brine. The organics were then dried over Na$_2$SO$_4$. The solids were removed by filtration and the volatile organics removed under reduced pressure. Compound 38 (900 mgs) was isolated as a yellow solid. LC/MS=922 (M$^+$+1).

Example 39

Preparation of Compound 39

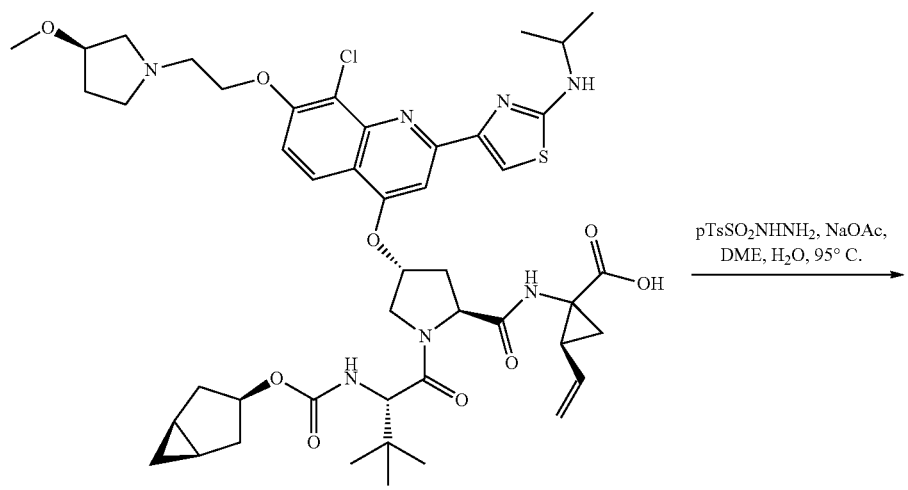

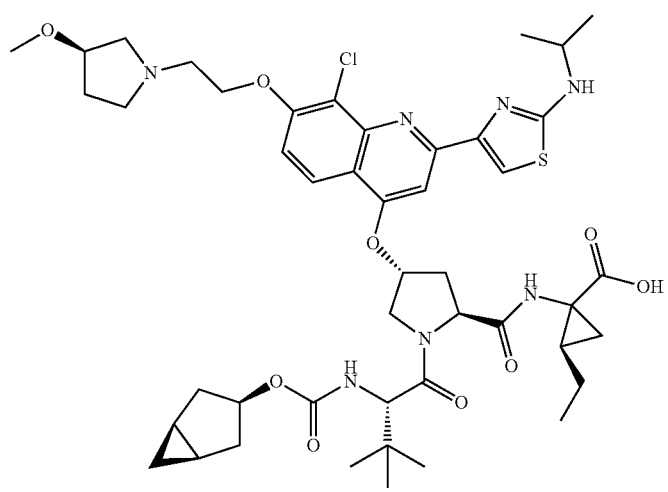

Compound 38 (900 mg, 0.977 mmol) was dissolved in DME (5 mL). To this solution was added dH$_2$O (1 mL), pTolSO$_2$NHNH$_2$ (920 mg, 4.93 mmol) and NaOAc (850 mg, 10.36 mmol). The reaction flask was then placed in a preheated 95° C. oil bath for 2 h. The reaction was determined to be complete by LC/MS. The reaction was cooled to room temperature and a small amount of MeOH was added to make the reaction mono-phasic. The reaction was then filtered and 39 (686 mg, 76% yield) was isolated from the filtrate, by reverse phase HPLC, as a yellow solid. LC/MS=924 (M$^+$+1).

Example 40

Preparation of Compound 40

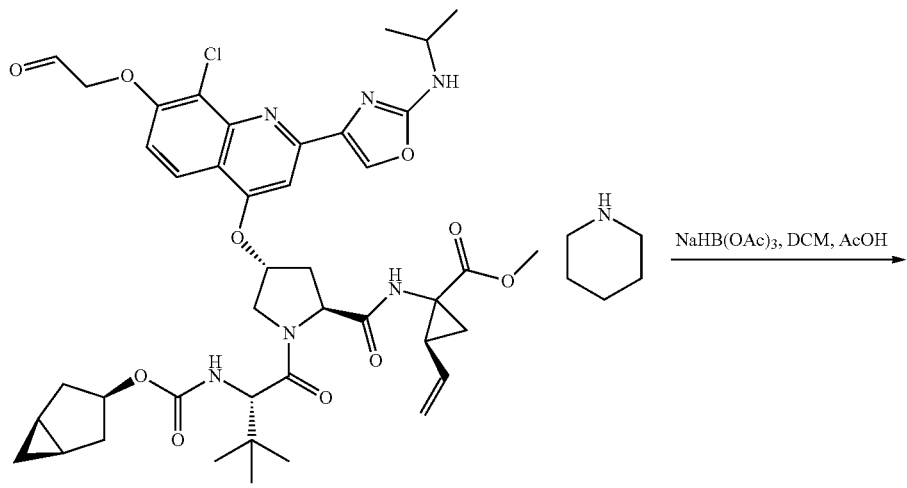

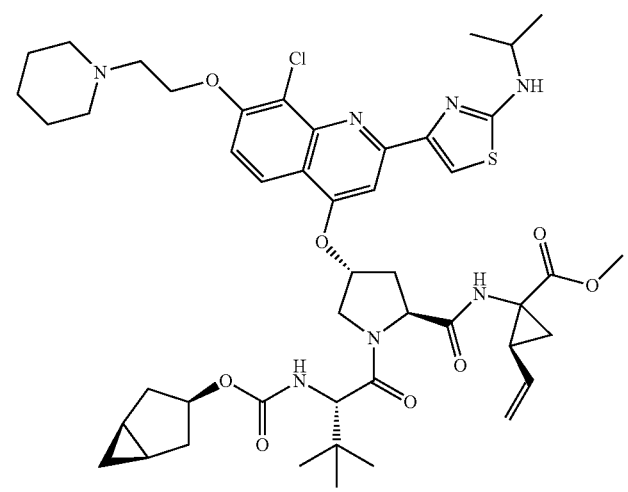

Step 1:

The aldehyde (1.00 g, 1.17 mmol) was dissolved in DCM (15 mL). To this solution was added piperidine (173 μL, 1.75 mmol). To this mixture was then added NaHB(OAc)$_3$ (322 mg, 1.52 mmol), followed immediately by AcOH (20 μL, 0.3 mmol). The reaction was determined to be complete by LC/MS after 10 min. The reaction was quenched by the addition of ½ sat. NaHCO$_{3(aq.)}$. The reaction was then diluted with DCM and extracted with sat. NaHCO$_{3(aq.)}$ (3×) and brine (1×). The organic phase was then dried over Na$_2$SO$_4$. The drying agents were removed by vacuum filtration and the filtrate was concentrated. The residue was re-dissolved in MeOH and this solution was concentrated. This MeOH dissolution and concentration was repeated 2 more times to afford the crude ester (964 mg, 90% yield) as a yellow solid. LC/MS=920 (M$^+$+1).

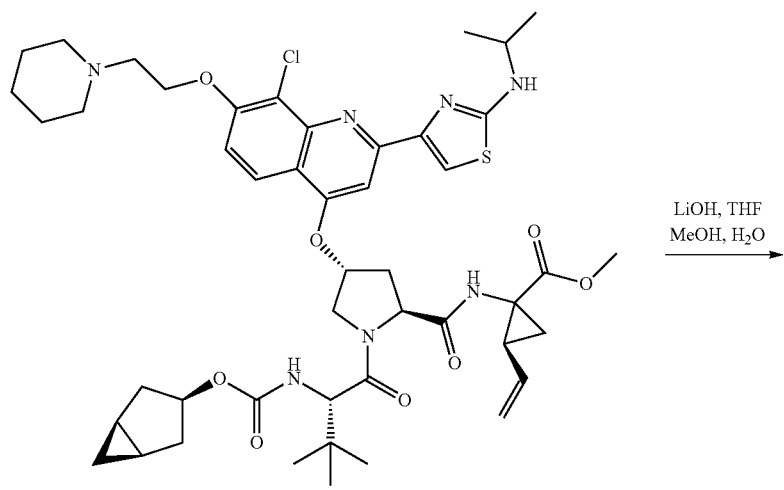

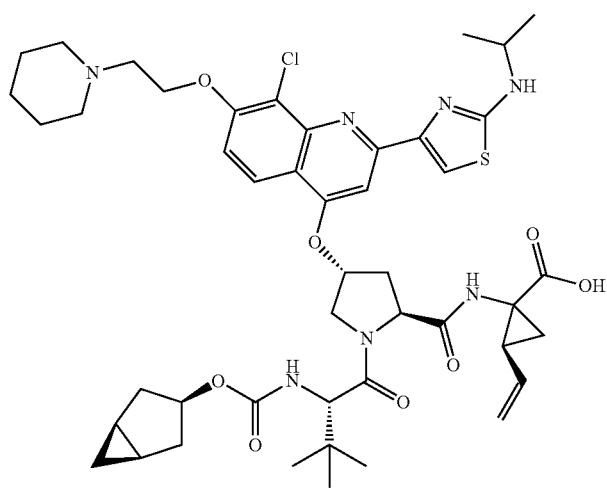

Step 2:

Ester (964 mg, 1.02 mmol) was dissolved in a mixture of THF (10 mL) and MeOH (6 mL). LiOH (200 mg, 4.67 mmol) was dissolved in dH$_2$O (3 mL) and this was slowly added to the solution of ester in THF/MeOH, which had been cooled to 0° C. Upon complete addition the ice bath was removed. After 3 h the reaction was complete. The reaction was cooled to 0° C. and neutralized with 2N HCl. Compound 40 was extracted into EtOAc, which was then extracted with 1N HCl, and then brine. The organics were then dried over Na$_2$SO$_4$. The solids were removed by filtration and the volatile organics removed under reduced pressure. Compound 40 (900 mg) was isolated as a yellow solid. LC/MS=906 (M$^+$+1).

Example 41

Preparation of Compound 41

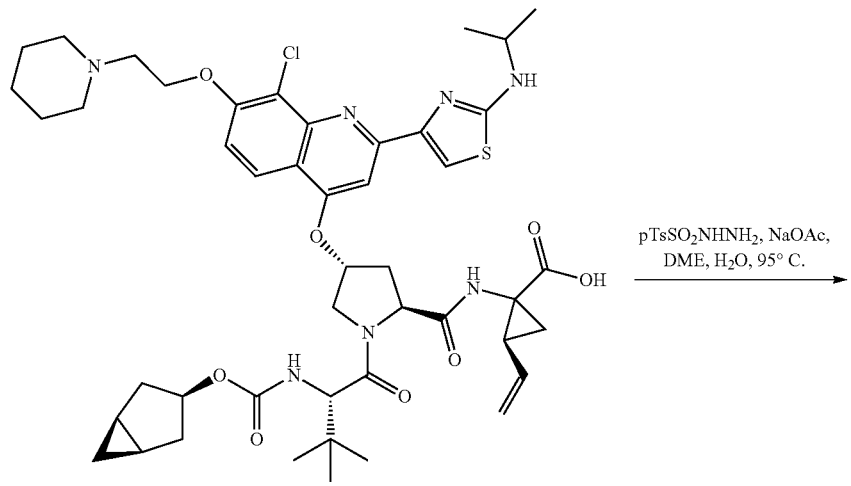

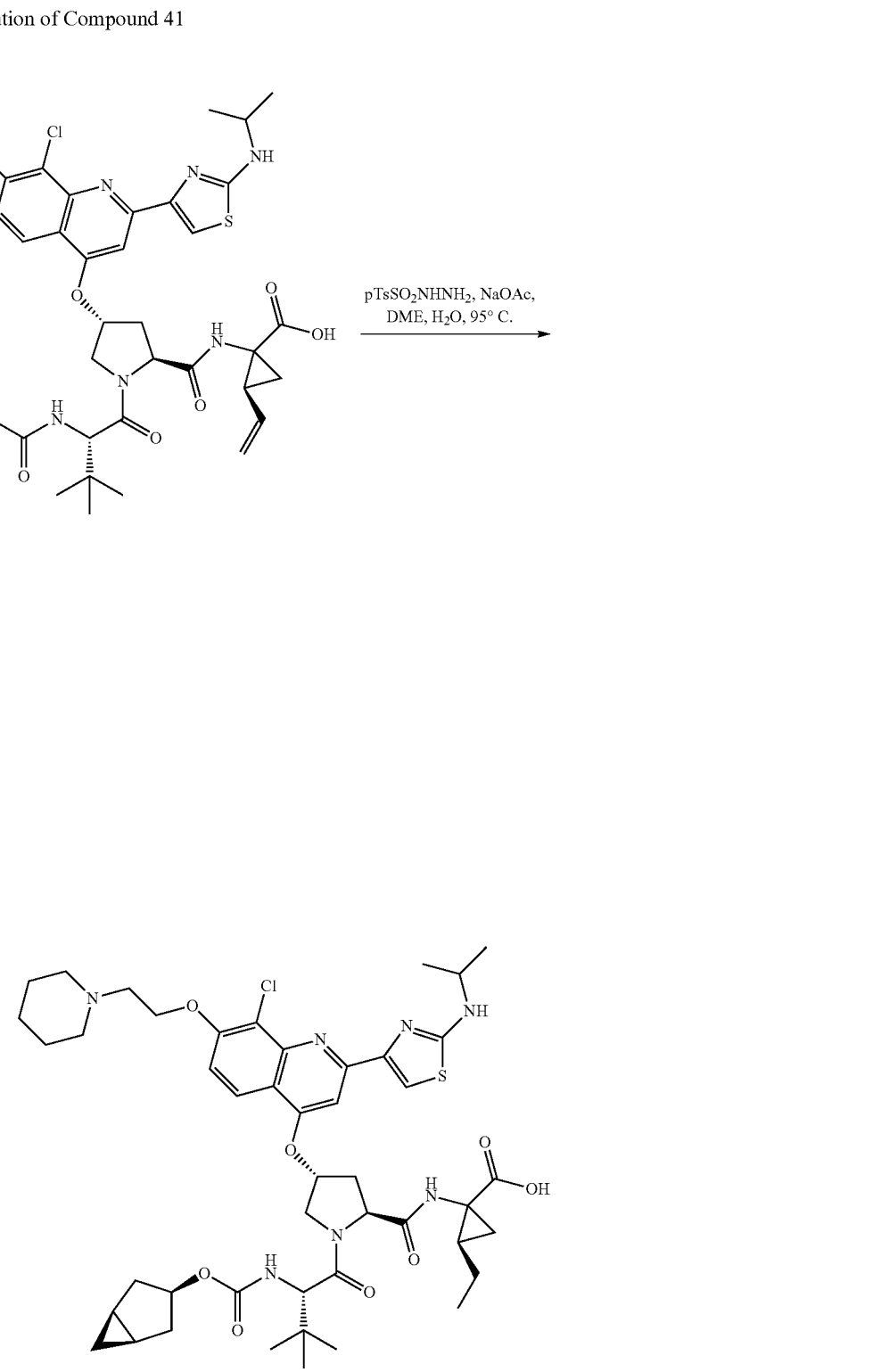

Compound 40 (900 mg, 0.977 mmol) was dissolved in DME (5 mL). To this solution was added dH$_2$O (1 mL), pTolSO$_2$NHNH$_2$ (920 mg, 4.93 mmol) and NaOAc (850 mg, 10.36 mmol). The reaction flask was then placed in a pre-heated 95° C. oil bath for 2 h. The reaction was determined to be complete by LC/MS. The reaction was cooled to room temperature and a small amount of MeOH was added to make the reaction mono-phasic. The reaction was then filtered and 41 (631 mg, 69% yield) was isolated from the filtrate, by reverse phase HPLC, as a yellow solid. LC/MS=908 (M$^+$+1).

Example 42

Preparation of Compound 42

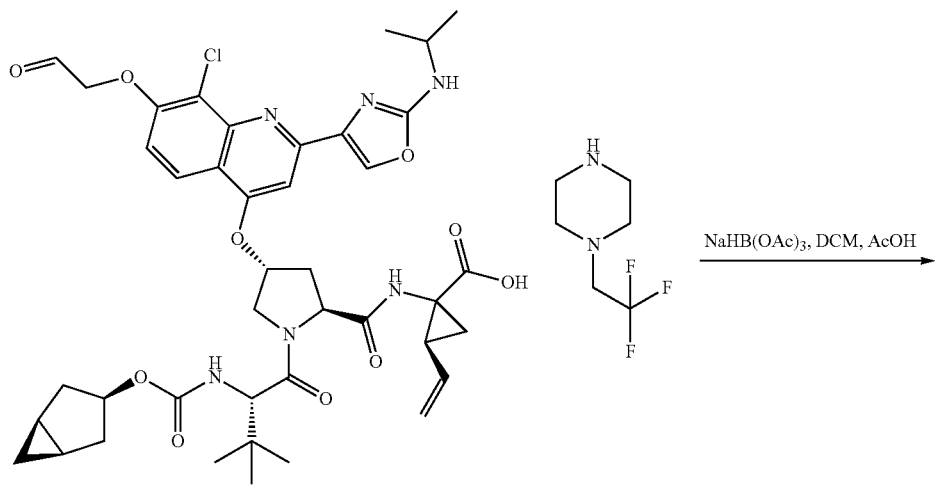

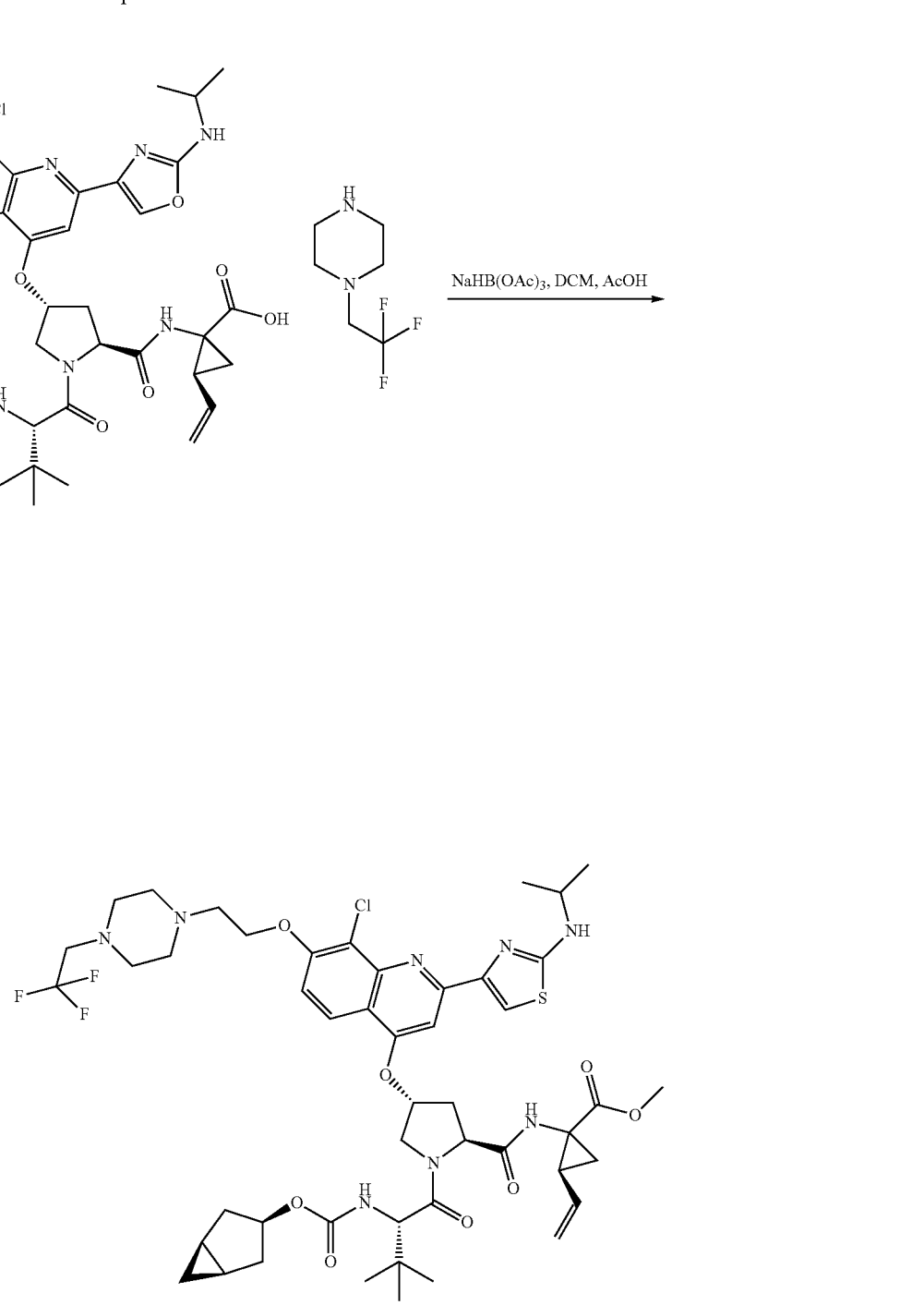

Step 1:

The aldehyde (0.5 g, 0.584 mmol) was dissolved in DCM (8 mL). To this solution was added the amine (181 mg, 0.887 mmol). To this mixture was then added NaHB(OAc)₃ (161 mg, 0.76 mmol), followed immediately by AcOH (10 μL, 0.15 mmol). The reaction was determined to be complete by LC/MS after 10 min. The reaction was quenched by the addition of ½ sat. NaHCO₃(aq.). The reaction was then diluted with DCM and extracted with sat. NaHCO₃(aq.) (3×) and brine (1×). The organic phase was then dried over Na₂SO₄. The drying agent was removed by vacuum filtration and the filtrate was concentrated. The residue was redissolved in MeOH and this solution was concentrated. This MeOH dissolution and concentration was repeated 2 more times to afford the crude ester (503 mg, 95% yield) as a yellow solid. LC/MS=1003 (M⁺+1).

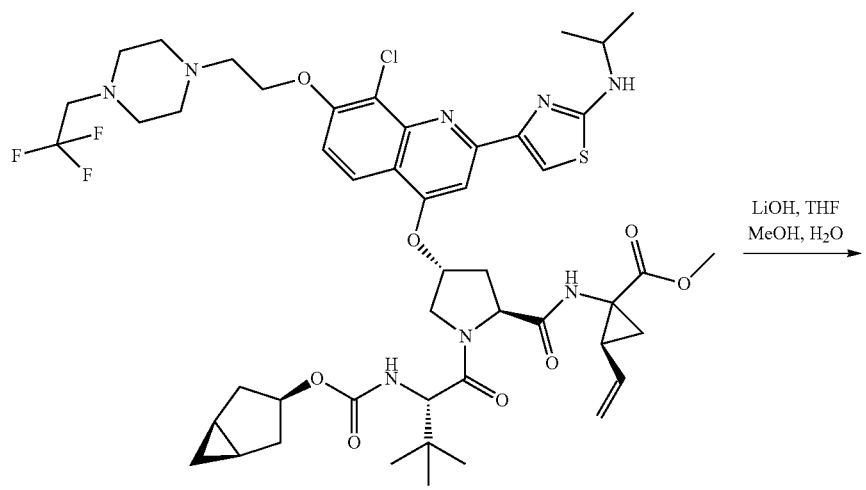

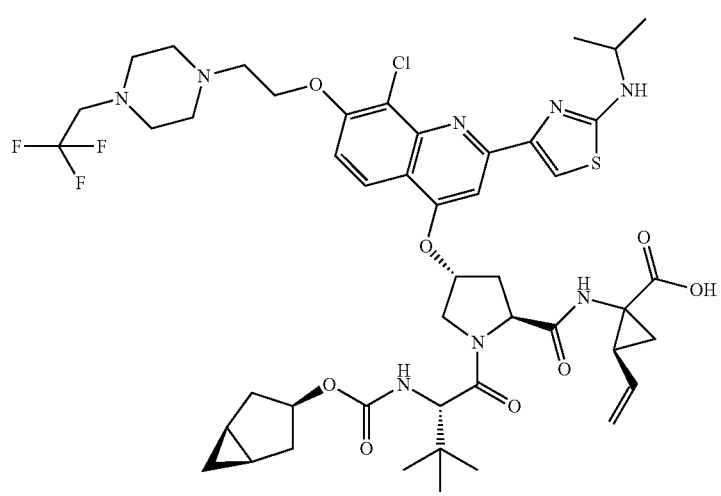

Step 2:

The ester (503 mg, 0.501 mmol) was dissolved in a mixture of THF (5 mL) and MeOH (3 mL). LiOH (100 mg, 2.34 mmol) was dissolved in dH$_2$O (1.5 mL) and this was slowly added to the solution of ester in THF/MeOH, which had been cooled to 0° C. Upon complete addition the ice bath was removed. After 3 h the reaction was complete. The reaction was cooled to 0° C. and neutralized with 2N HCl. Compound 42 was extracted into EtOAc, which was then extracted with 1N HCl, and then brine. The organics were then dried over Na$_2$SO$_4$. The solids were removed by filtration and the volatile organics were removed under reduced pressure. Compound 42 (450 mg) was isolated as a yellow solid. LC/MS=989 (M$^+$+1).

Example 43

Preparation of Compound 43

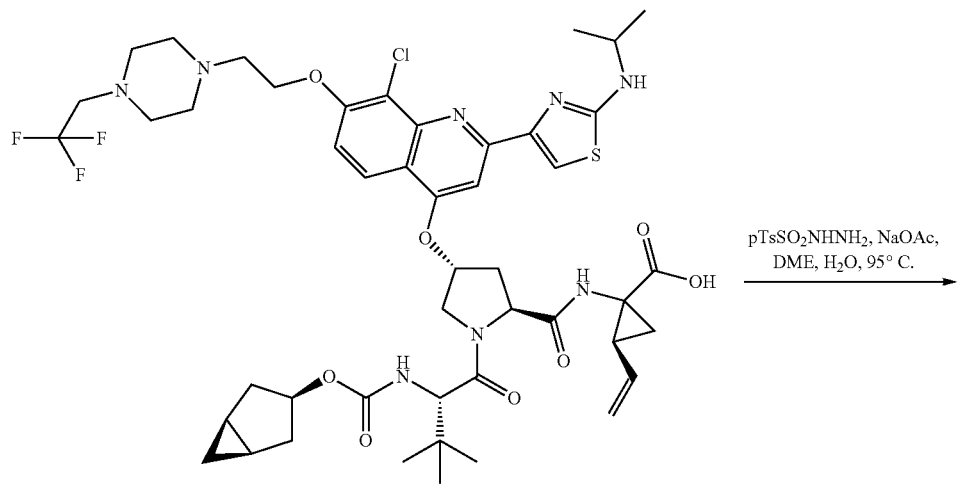

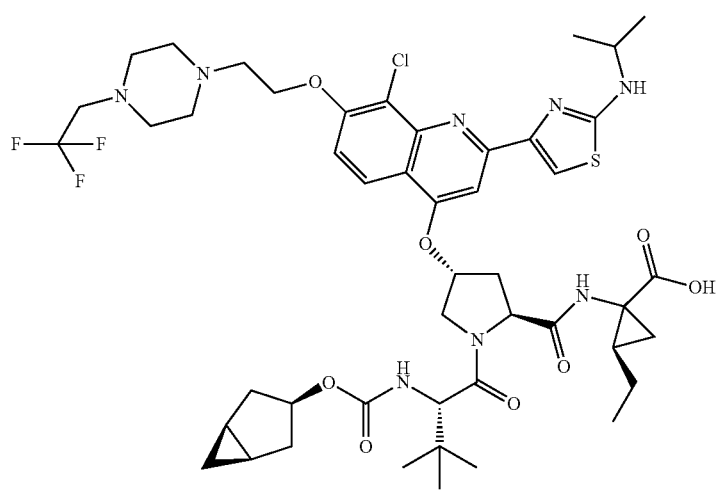

Compound 42 (450 mg, 0.501 mmol) was dissolved in DME (3 mL). To this solution was added dH$_2$O (0.5 mL), pTolSO$_2$NHNH$_2$ (425 mg, 2.46 mmol) and NaOAc (425 mg, 5.17 mmol). The reaction flask was then placed in a preheated 95° C. oil bath for 2 h. The reaction was determined to be complete by LC/MS. The reaction was cooled to room temperature and a small amount of MeOH was added to make the reaction mono-phasic. The reaction was then filtered and 43 (334 mg, 67% yield) was isolated from the filtrate, by reverse phase HPLC, as a yellow solid. LC/MS=991 (M$^+$+1).

Example 44

Preparation of Compound 44

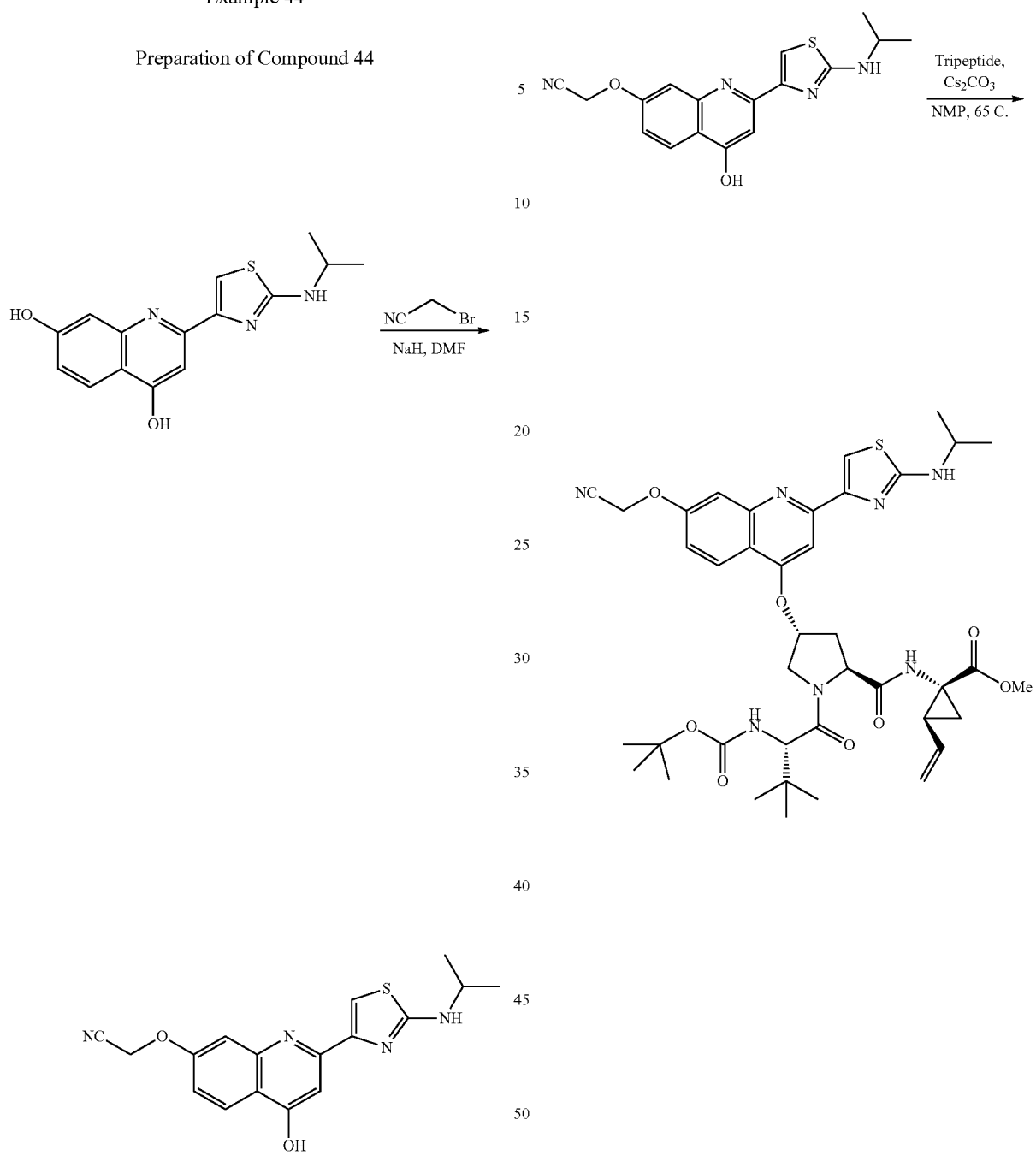

Step 1:

2-(2-isopropylamino-thiazol-4-yl)-quinoline-4,7-diol (2 g, 6.6 mmol) was dissolved in DMF (20 mL) under $N_2$. This was followed with the addition of NaH (60%) (0.56 g, 14.2 mmol) at 0° C. The reaction was stirred at 0° C. for 30 minutes and then bromo-acetonitrile was added. The mixture was warmed up to room temperature, and it was stirred at room temperature overnight. The mixture was diluted with EtOAc, and washed with 1N HCl, while maintaining a pH=4. The desired product crashed out. After filtration, yellow solids were obtained that were fairly pure. This material was used directly in the next step. LC/MS=341.33 ($M^+$+1).

Step 2:

To a mixture of the quinoline obtained above (1.32 g, crude) and brosylate tripeptide (2.9 g, 4.3 mmol) in NMP (10 mL) was added cesium carbonate (2.5 g, 7.7 mmol). The mixture was stirred at 65° C. for 5 h. The reaction was cooled to room temperature, and then EtOAc (600 mL) and aqueous 3% LiCl solution were added to the mixture. The organic layer was separated and washed with aqueous 3% LiCl, brine, dried over $Na_2SO_4$ and concentrated in vacuo. The crude material was purified by silica gel chromatography to give the desired product as a yellow solid (1.18 g, 1.49 mmol). LC/MS=790.38 ($M^+$+1).

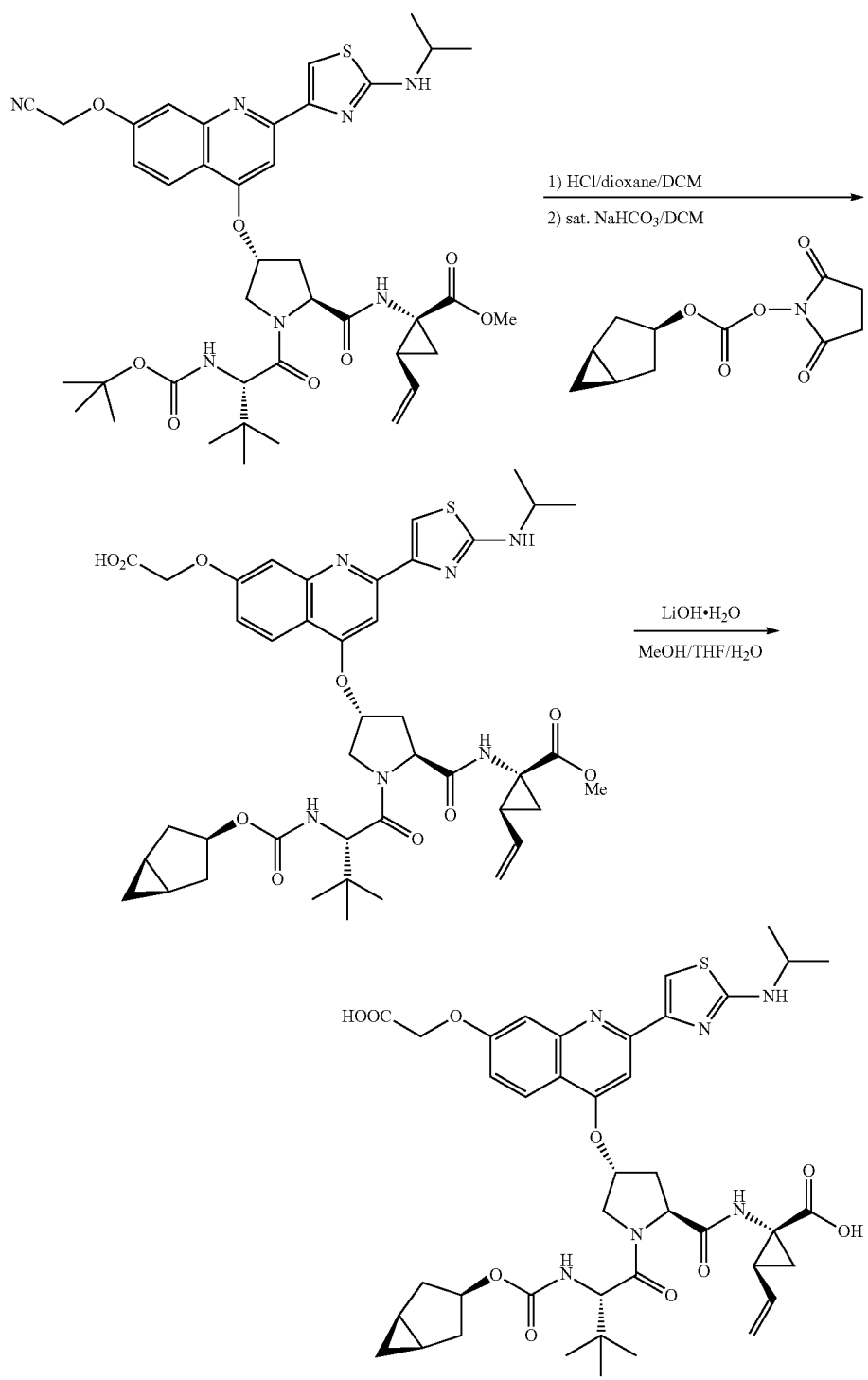

Step 3:

To a solution of Boc tripeptide (1.18 g, 1.5 mmol) in DCM (10 mL) was added 4 N HCl in dioxane (30 mmol, 7.5 mL) at room temperature. The mixture was stirred at room temperature for 2 h. LC/MS showed two products were formed, one of them is the desired de-Boc intermediate, and another one is de-Boc intermediate with C-7 position nitrile hydrolyzed to the acid. The reaction solvent was removed under reduced pressure to give the crude material. To the crude material in DCM was added a sat. NaHCO₃ aqueous solution (15 mL) and the mixture was stirred at room temperature for 1 h. Intermediate I (0.54 g, 2.25 mmol) was added in one portion, and the resulting reaction mixture was stirred at room temperature for another 30 minutes. LC/MS showed two products were formed in a 1:1 ratio; one peak is the desired product and another peak is the corresponding C-7 acid compound. The organic phase was partitioned and washed with brine, dried over Na₂SO₄ and concentrated in vacuo. The crude material was obtained as a yellow solid and was used directly in the next step. LC/MS=814.42 (M⁺+1).

Step 4:

To the above crude material in dioxane was added a LiOH (0.19 g, 4.5 mmol) aqueous solution. The reaction was stirred at room temperature overnight. LC/MS indicated that two major compounds were formed. The reaction solvent was removed in vacuo and the crude material was purified by preparative HPLC. Compound 44 (0.153 g, 0.183 mmol) was obtained as yellow solids. $^1$H NMR (300 MHz, CD$_3$OD) δ 8.30 (d, 1H), 8.18 (s, 1H), 7.73 (m, 2H), 7.41 (d, 1H), 5.92-5.77 (m, 2H), 5.28 (d, 1H), 5.11 (d, 1H), 4.96 (s, 2H), 4.73-4.55 (m, 3H), 4.19-4.06 (m, 3H), 2.78 (m, 1H), 2.58 (m, 1H), 2.21 (m, 1H), 1.96 (m, 2H), 1.74-1.63 (m, 3H), 1.46 (m, 3H), 1.33 (m, 6H), 1.22 (m, 2H), 1.04 (s, 9H), 0.49-0.37 (m, 2H). LC/MS=819.44 (M⁺+1).

Example 45

Preparation of Compound 45

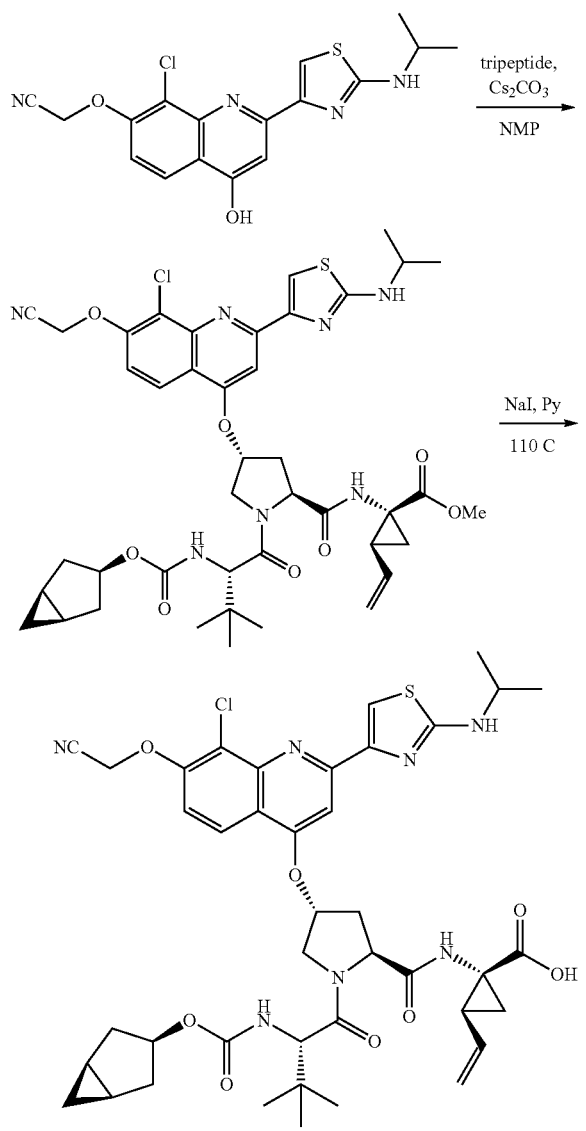

Step 1:

To a mixture of quinoline (0.2 g, 0.53 mmol) and brosylate tripeptide (0.412 g, 0.59 mmol) in NMP (4 mL) was added cesium carbonate (0.345 g, 1.1 mmol). The mixture was stirred at 65° C. for 7 h. The reaction was cooled to room temperature, diluted with EtOAc and washed with an aqueous 3% LiCl solution, brine, and then dried over Na$_2$SO$_4$ and concentrated in vacuo. The crude material was purified by silica gel chromatography to give the desired product as a yellow solid (0.26 g, 0.31 mmol, 59%). LC/MS=848.44 (M⁺+1).

Step 2:

A mixture of ester (0.26 g, 0.31 mmol) and NaI (0.70 g, 0.45 mmol) in pyridine (7 mL) was heated at 110° C. overnight under N$_2$. The reaction was monitored by LC-MS. LC-MS showed 95% conversion. The solvent was removed under reduced pressure. The crude material was purified by preparative HPLC, to yield 45 (0.085 g, 0.1 mmol, 34%) as yellow solid. LC/MS=834.41 (M⁺+1).

Example 46

Preparation of Compound 46

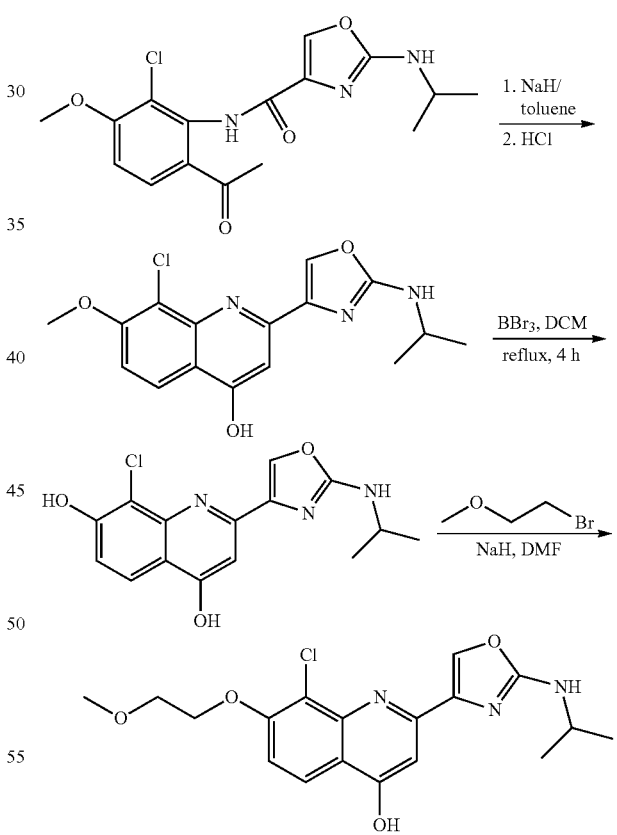

Step 1:

To suspension of amide compound (1.2 g, 3.41 mmol) in toluene (28 mL) was added NaH (60%) (0.20 g, 5.12 mmol) at room temperature. The mixture was heated to reflux and stirred for 2.5 h. LC-MS indicated the reaction was complete. The reaction was cooled to 0° C. and AcOH (0.90 mL, 5.80 mmol) in 3 mL H$_2$O was added, and the mixture was stirred at 0° C. for 45 minutes. During the stirring a lot of yellow solids

315 crashed out. After filtration, the filter cake was washed with H$_2$O, Et$_2$O and dried under high vacuum. The crude yellow solid (1.00 g, 3.00 mol, 88%) was used directly in the next step. LC/MS=334.34 (M$^+$+1).

Step 2:

To a suspension of the crude product obtained above, dissolved in DCM (50 mL), was added BBr$_3$ (1 N in DCM) (13.4 mL, 13.4 mmol). The mixture was heated to reflux and stirred for 4 h. The reaction was cooled to room temperature and poured into ice. 4N NaOH was used to adjust the pH to 14. The aqueous phase was extracted with DCM twice and the pH was adjusted to about 4 with 2 N HCl. Yellow solids crashed out and these were isolated by filtration. The filter cake was washed with H$_2$O, Et$_2$O, and dried under high vacuum. A yellow solid was obtained (0.41 g, 1.28 mmol, 42%) and used directly in the next reaction. LC/MS=320.33 (M$^+$+1).

Step 3:

To a mixture of the bisphenol (0.41 g, 1.28 mmol) and 1-bromo-2-methoxy-ethane (0.18 g, 1.28 mmol) in DMF (3 mL) at room temperature was added NaH (60%) (0.062 g, 2.58 mmol) in one portion. The reaction was stirred overnight under N$_2$. The crude material was purified by prep-HPLC, and the title compound as the desired product (0.202 g, 0.53 mmol, 41%) was obtained as a yellow solid. LC/MS=378.34 (M$^+$+1).

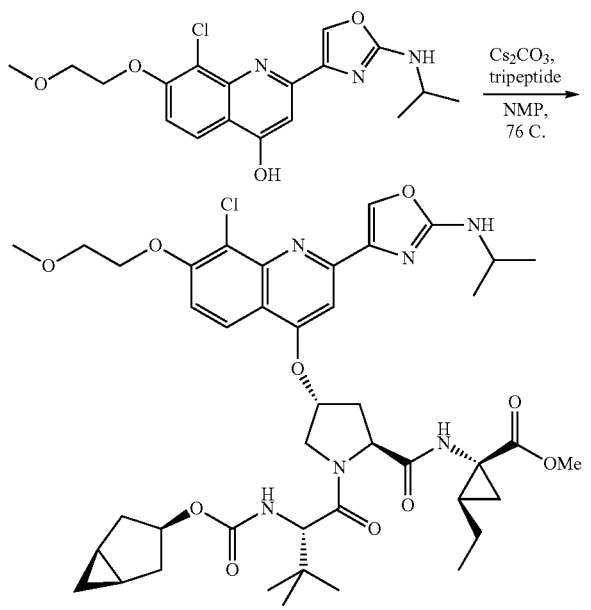

316

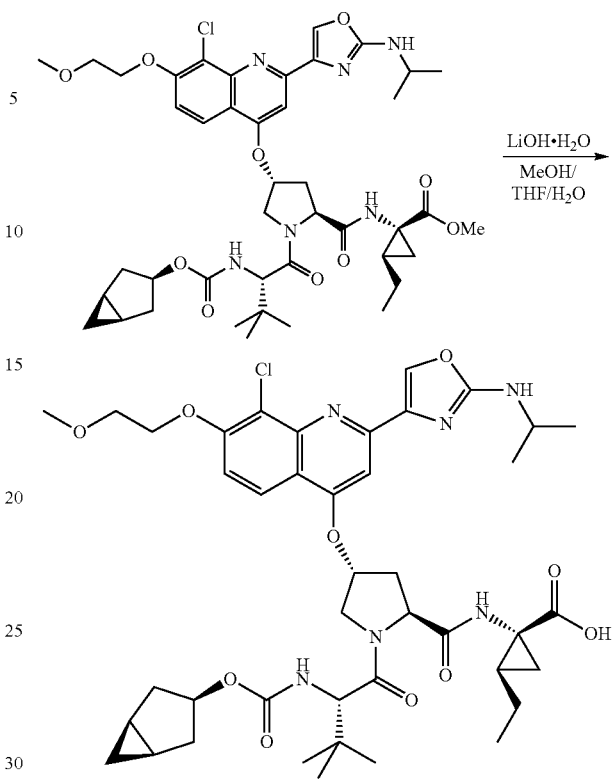

Step 5:

To a solution of the methyl ester (0.19 g, 0.22 mmol) in MeOH (1 mL) and THF (1 mL) was added a LiOH (0.18 g, 4.2 mmol) aqueous solution. The mixture was stirred at room temperature overnight. The crude material was purified by preparative HPLC to afford 46 as a yellow solid compound (0.11 g, 0.13 mmol, 60%). $^1$H NMR (300 MHz, CD$_3$O D): δ 8.64 (s, 1H), 8.26 (d, 1H), 7.69 (s, 1H), 7.64 (d, 1H), 5.69 (s, 1H), 4.72 (dd, 1H), 4.60-4.43 (m, 3H), 4.14-4.01 (m, 3H), 3.87 (s, 2H), 3.47 (s, 2H), 2.74 (m, 1H), 2.63 (m, 1H), 1.97-1.80 (m, 2H), 1.67 (m, 3H), 1.51 (m, 1H), 1.49-1.34 (m, 7H), 1.22 (m, 2H), 1.02 (s, 9H), 0.34 (m, 2H). LC/MS=841.56 (M$^+$+1).

Example 47

Preparation of Compound 47

Step 4:

A mixture of the quinoline (0.2 g, 0.53 mmol), Cs$_2$CO$_3$ (0.35 g, 1.05 mmol) and intermediate III (0.415 g, 0.58 mmol) in NMP (4 mL) was heated to 65° C. (Is it 65 or 76? See your graphic) and stirred for 6 h. 10 mL of EtOAc was added to dilute the reaction, and the mixture was washed with H$_2$O, 5% LiCl, and brine. After drying over Na$_2$SO$_4$ and concentration, the crude material was purified by silica gel chromatography to afford the methyl ester as a form (0.19 g, 0.22 mmol, 42%). LC/MS=854.08 (M$^+$+1).

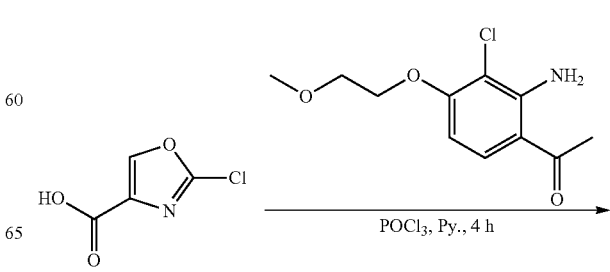

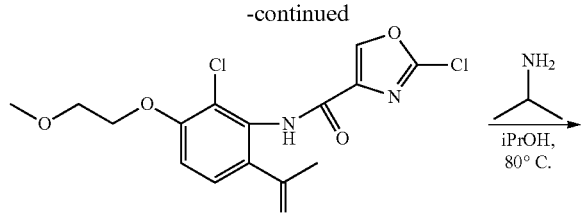

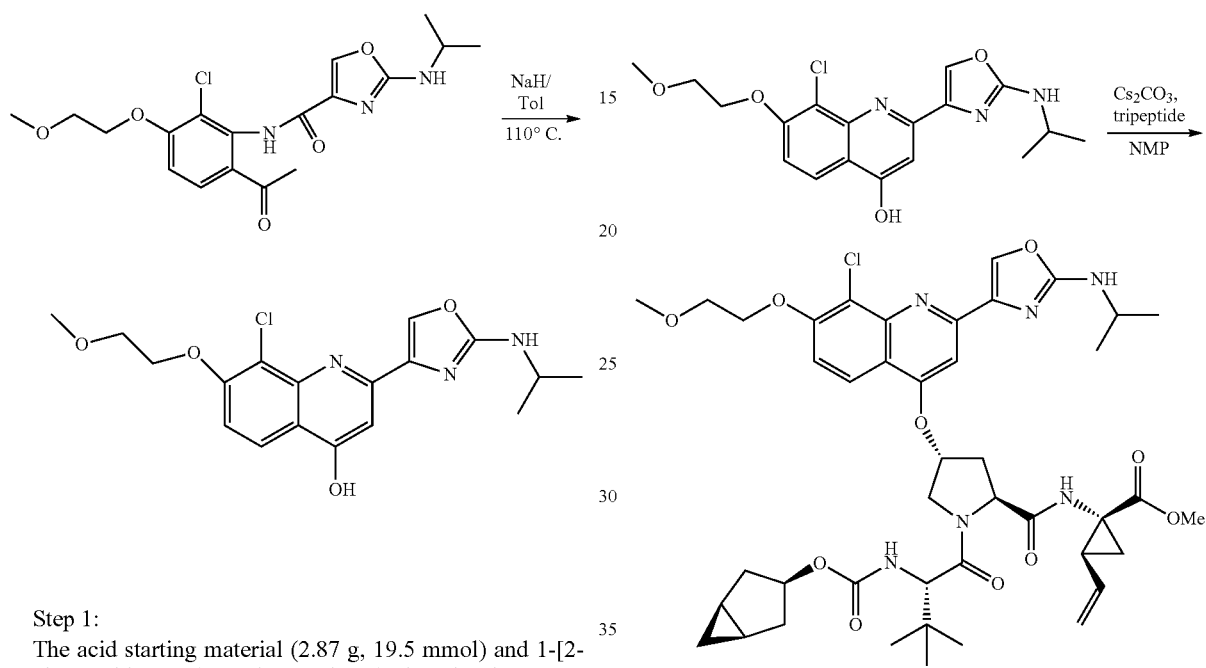

Step 1:

The acid starting material (2.87 g, 19.5 mmol) and 1-[2-Amino-3-chloro-4-(2-methoxy-ethoxy)-phenyl]-ethanone (4.72 g, 19.5 mmol) were dissolved in pyridine (180 mL). The resulting solution was cooled to −30° C., and then POCl₃ was added to the solution, dropwise. After the addition, the reaction was warmed up to −10° C. in 30 minutes and stirred at −10° C. for 4 h. 20 mL of H₂O was added to quench the reaction at 0° C. and the resulting mixture was stirred at 0° C. for 5 minutes. Solvent was removed under reduced pressure. To the residue was added EtOAc, and resulting solution was washed with sat. NaHCO₃, H₂O and brine. After drying over Na₂SO₄ and being concentrated, the crude material was purified by silica gel chromatography to afford the desired product (4.2 g, 11.3 mmol, 58%). LC/MS=373.01 (M⁺+1).

Step 2:

The mixture of amide (2.0 g, 5.4 mmol) and isopropylamine (3.2 g, 54 mmol) in propan-2-ol (20 mL) in a sealed tube was heated to 70° C. After heating 3.5 h, the reaction was cooled to room temperature. And the solvent was removed under reduced pressure. The residue was dissolved in THF (15 mL) and 0.3 N HCl (40 mL) was added to this solution. This mixture was stirred at room temperature. For 24 h. The mixture was partitioned and organic phase was concentrated under reduced pressure. The residue was purified by silica gel chromatography, to afford the amine (0.84 g, 2.13 mmol, 40%). LC/MS=396.21 (M⁺+1).

Step 3:

To a suspension of the amine (1.38 g, 3.49 mmol) in toluene (20 mL) was added NaH (60%) (0.20 g, 5.12 mmol) at room temperature. The mixture was heated to reflux 2.5 h. LC-MS indicated the reaction was complete. The reaction was cooled to 0° C. and AcOH (0.90 mL, 5.80 mmol) in 3 mL of H₂O was added to the reaction, and the mixture was stirred at 0° C. for 45 minutes. During this stirring, the quinoline product crashed out. After filtration, the filter cake was washed with H₂O, Et₂O and dried under high vacuum. A crude yellow solids (1.18 g, 3.13 mol, 90%) with fair purity were obtained and used directly in the next reaction. LC/MS=378.34 (M⁺+1).

Step 4:

A mixture of the quinoline (0.77 g, 2.03 mmol), Cs₂CO₃ (1.3 g, 4 mmol) and tripeptide methyl ester (1.6 g, 2.2 mmol) in NMP (10 mL) was heated to 65° C. and stirred for 6 h. 25 mL of EtOAc was added to dilute the reaction, and the mixture was washed with H₂O, 5% LiCl, and brine. After drying the organics over Na₂SO₄ and concentration, the crude material was purified by silica gel chromatography to afford title compound as a solid (1.2 g, 1.4 mmol, 69%). LC/MS=851.84 (M⁺+1).

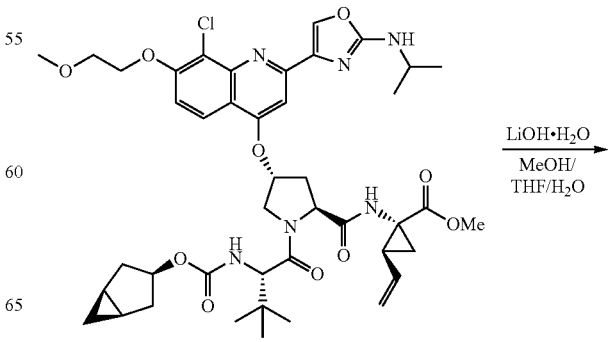

319

-continued

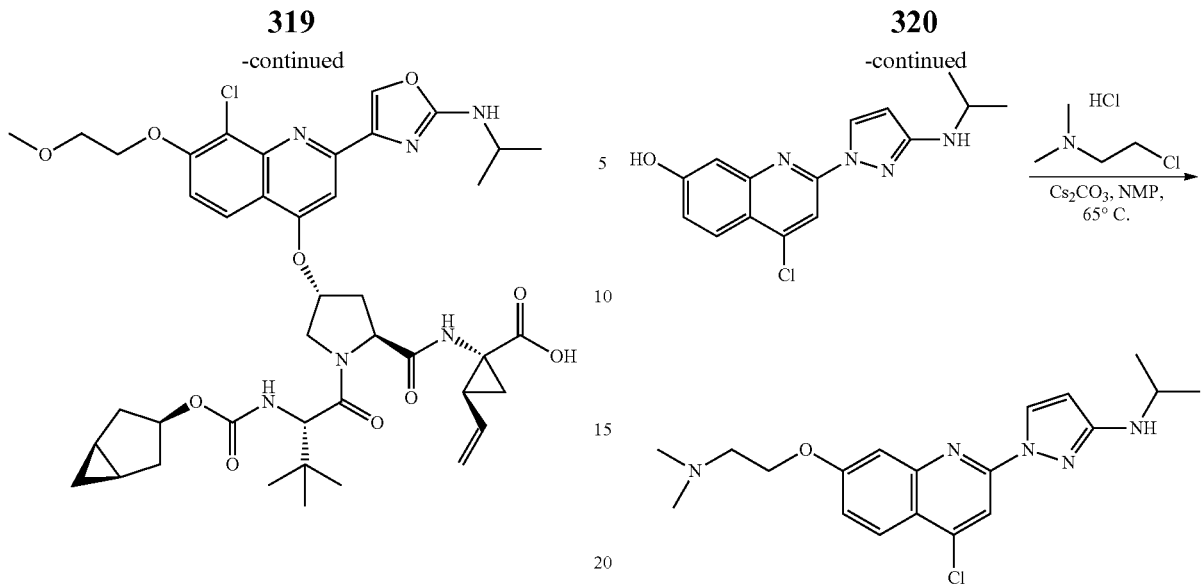

320

-continued

Step 5:

To a solution of the methyl ester (0.5 g, 0.58 mmol) in MeOH (5 mL) and THF (5 mL) was added a LiOH (0.24 g, 5.8 mmol) aqueous solution (How much water?). The mixture was stirred at room temperature overnight. Crude material was purified by preparative HPLC to afford Compound 47 as a yellow solid (0.33 g, 0.4 mmol, 69%). $^1$H NMR (300 MHz, CD$_3$OD): δ 8.58 (s, 1H), 8.26 (d, 1H), 7.66 (s, 1H), 7.62 (d, 1H), 5.89 (m, 1H), 5.67 (bs, 1H), 5.29 (dd, 1H), 5.11 (m, 1H), 4.72 (m, 1H), 4.54-4.49 (m, 4H), 4.15 (s, 1H), 4.10-4.00 (m, 2H), 3.87 (m, 2H), 3.47 (s, 3H), 2.75 (m, 1H), 2.61 (m, 1H), 2.21 (m, 2H), 1.94 (m, 1H), 1.85 (m, 1H), 1.72-1.61 (m, 3H), 1.40-1.10 (m, 9H), 1.02 (s, 9H), 0.49-0.34 (m, 2H). LC/MS=837.94 (M$^+$+1).

Example 48

Preparation of Compound 48

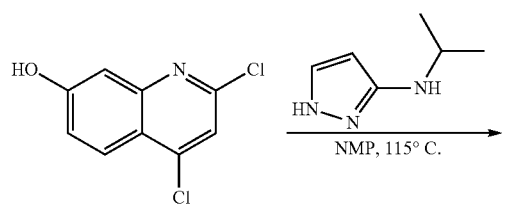

Step 1:

2,4-dichloro-quinolin-7-ol (2.23 g, 10.4 mmol) and isopropyl-(1H-pyrazol-3-yl)-amine (1.44 g, 11.5 mmol) were dissolved in NMP (30 mL) at room temperature. The resulting mixture was heated to 115° C. and stirred for 12 h. The reaction was diluted with EtOAc and washed with 5% LiCl, and brine. After drying the organic fraction over Na$_2$SO$_4$ and concentration, the crude material was purified by silica gel chromatography to afford title compound (1.6 g, 5.28 mmol, 51%). LC/MS=303.30 (M$^+$+1).

Step 2:

Quinoline (0.81 g, 2.67 mmol) and (2-chloro-ethyl)-dimethyl-amine HCl salt (0.42 g, 2.94 mmol) were dissolved in DMF (10 mL). This was followed by the addition of Cs$_2$CO$_3$ (1.74 g, 5.34 mmol). The reaction was heated to 65° C. and stirred for 17 h. The reaction was diluted with EtOAc and washed with 5% LiCl, and brine. After drying the organic fraction over Na$_2$SO$_4$ and concentration, the crude material was purified by silica gel chromatography to afford the title compound (0.5 g, 1.34 mmol, 50%). LC/MS=374.24 (M$^+$+1).

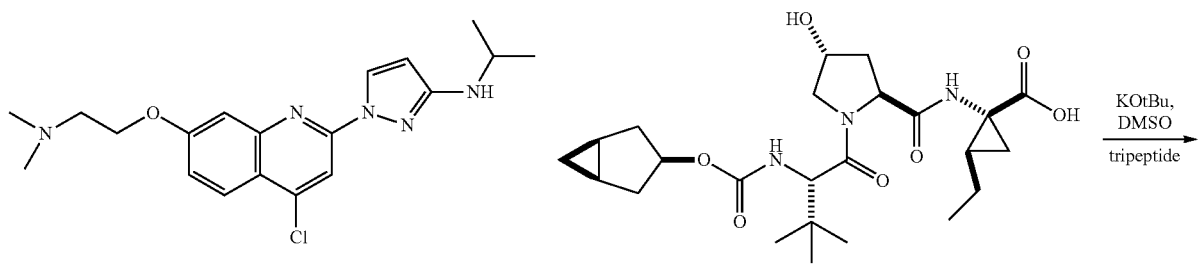

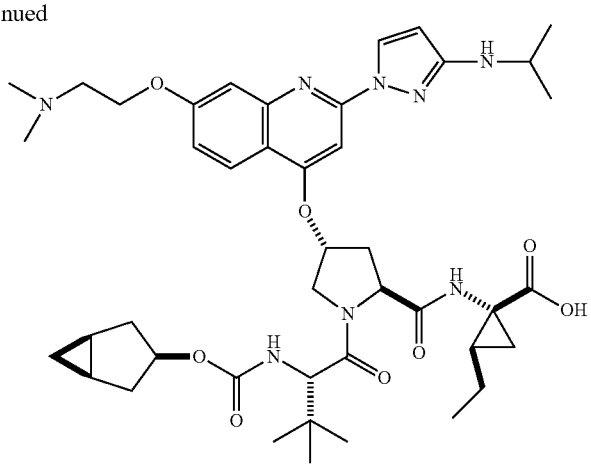

Step 3:

Tripeptide acid (0.51 g, 1.06 mmol) was dissolved in DMSO (10 mL). To this solution was added KO$^t$Bu (0.6 g, 5.3 mmol). The mixture was stirred at room temperature. For 1.5 h. The chloroquinoline (0.44 g, 1.17 mmol) was then added to the reaction in one potion, and the resulting reaction was stirred at room temperature overnight. 0.5 mL AcOH was added into the reaction and the reaction mixture was purified by preparative HPLC to afford compound 48 (0.309 g, 0.37 mmol, 36%). $^1$H NMR (300 MHz, CDCl$_3$) $^1$H NMR (300 MHz, CD$_3$O D): δ 8.64 (s, 1H), 8.16 (d, 1H), 7.68 (s, 1H), 7.34 (d, 1H), 7.28 (d, 1H), 6.28 (m, 1H), 5.62 (bs, 1H), 4.64 (dd, 2H), 4.55 (m, 2H), 4.19 (s, 1H), 4.15-3.97 (m, 2H), 3.69 (m, 2H), 3.30 (s, 2H), 3.02 (s, 6H), 2.90-2.53 (m, 3H), 2.02-1.80 (m, 3H), 1.71-1.98 (m, 3H), 1.51-1.34 (m, 3H), 1.29 (d, 6H), 1.23-1.06 (m, 3H), 1.02 (s, 9H), 0.49-0.34 (m, 2H). LC/MS=817.71 (M$^+$+1).

Example 49

Preparation of Compound 49

Step 1:

A mixture of α-chloro acetone (10.4 g, 112.8 mmol) and amino-thioxo-acetic acid ethyl ester (5.0 g, 37.6 mmol) in ethanol (100 mL) was stirred at 80° C. for 6 h. After concentration, the residue was purified by silica gel column chromatography, affording the ester (3.2 g, 50%) as white solids. The ethyl ester product (1.5 g, 8.8 mmol) was then dissolved in a THF/MeOH/water (10 mL/10 mL/10 mL) mixture. Excess lithium hydroxide (3.0 g) was added and the reaction mixture was stirred at room temperature for 1 h. Ethyl acetate (100 mL) was added to the reaction mixture. The pH was adjusted to 4 by slowly adding 1N HCl to the mixture. After separation, the organic layer was dried over MgSO$_4$. After concentration, the desired product (0.8 g, 64%) was obtained as white solids. LC/MS=143.7 (M$^+$+1).

Step 2:

To a mixture of the acid (0.36 g, 2.47 mmol) and the aniline (0.40 g, 1.65 mmol) in pyridine (15 mL) was slowly added POCl$_3$ (0.38 g, 2.47 mmol) at −40° C. The mixture was then stirred at 0° C. for 4 h. Upon completion of the reaction, H$_2$O (5 mL) was added dropwise to the mixture. The mixture was then stirred at 0° C. for another 15 min. The mixture was concentrated in vacuo. The residue was diluted with EtOAc, and washed with sat. NaHCO$_3$ aqueous solution. The organic layer was dried (Na$_2$SO$_4$) and concentrated in vacuo. The residue was purified by silica gel column chromatography, affording the amide (0.45 g, 74%) as solids. The amide (0.45 g, 1.22 mmol) was suspended in t-BuOH (10 mL). t-BuOK (0.29 g, 2.57 mmol) was added to the vigorously stirred mixture. The mixture was heated to 75° C. for 4 h. The mixture was cooled to room temperature. 4 N HCl/dioxane (1 mL) was slowly added to acidify the mixture. After concentration, the crude was poured into 1N KH$_2$PO$_4$/H$_2$O (50 mL). The solids that formed were isolated by filtration and washed with water. After drying under high vacuum overnight, the quinoline (0.4 g, 93%) was obtained as solids. LC/MS=350.8 (M$^+$+1).

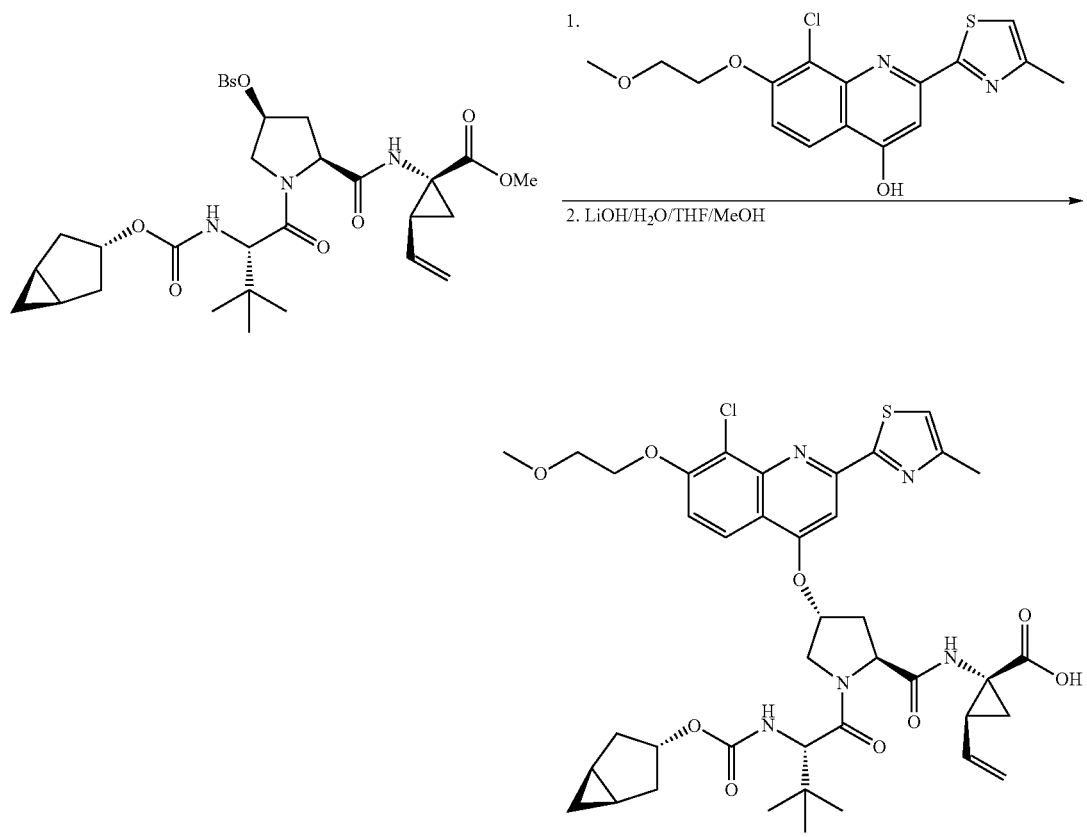

Step 3:

To a mixture of tripeptide (0.20 g, 0.28 mmol) and quinoline (0.10 g, 0.28 mmol) in NMP (5 mL) was added cesium carbonate (0.18 g, 0.56 mmol). The mixture was stirred at 85° C. for 6 h. The reaction was cooled to room temperature, and EtOAc (50 mL) and an aqueous 3% LiCl (50 mL) solution were added to the mixture. The organic layer was washed with aqueous 3% LiCl (1×50 mL), brine, dried ($Na_2SO_4$) and concentrated in vacuo. The residue was purified by silica gel chromatography to give the desired methyl ester product as yellow solids (0.15 g, 65%).

Step 4:

The methyl ester (0.15 g, 0.18 mmol) was dissolved in THF (2 mL), and a solution of LiOH (0.05 g, 1.8 mmol) in $H_2O$ (2 mL) was added, followed by the addition of MeOH (2 mL). The mixture was kept stirring at room temperature for 3 h. Upon completion of the reaction, 4 N HCl in $H_2O$ was added at 0° C. to adjust the pH to 4. The mixture was extracted with EtOAc (2×20 mL). The combined organic layer was washed with brine, dried ($Na_2SO_4$) and concentrated in vacuo to give compound 49 as yellow solids (0.14 g, 95%). $^1$H NMR (300 MHz, $CD_3OD$): δ 8.10 (d, J=9.6 Hz, 1H), 7.70 (s, 1H), 7.44 (d, J=9.6 Hz, 1H), 7.36 (s, 1H), 5.82 (dd, 1H), 5.53 (brs, 1H), 5.30 (d, J=17.1 Hz, 1H), 5.12 (d, J=10.2 Hz, 1H), 4.65 (m, 1H), 4.58 (m, 1H), 4.39 (m, 2H), 4.22 (s, 1H), 4.10 (m, 2H), 3.86 (m, 2H), 3.49 (m, 4H), 2.83 (m, 3H), 2.57 (m, 3H), 2.39 (m, 1H), 2.18 (m, 1H), 2.07 (m, 1H), 1.84 (m, 1H), 1.68 (m, 2H), 1.44 (m, 1H), 1.35 (m, 1H), 1.23 (m, 1H), 1.04 (s, 9H), 0.48 (m, 1H), 0.30 (m, 1H). LC/MS=810.4 ($M^+$+1).

Example 50

Preparation of Compound 50

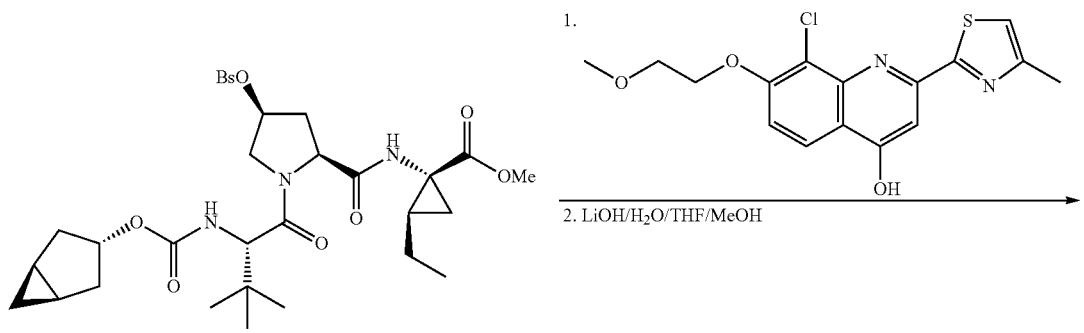

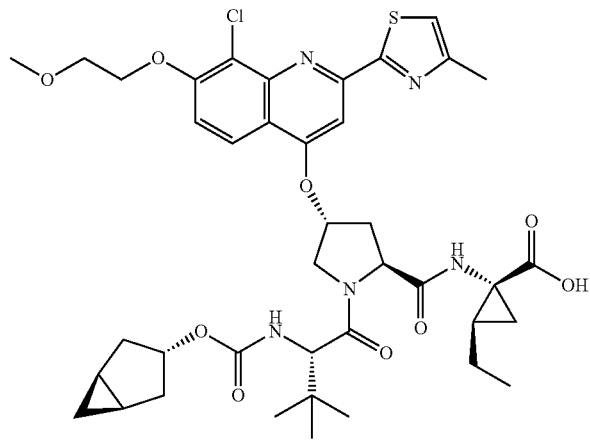
Compound 50 was obtained by following procedures similar to those for preparation of Compound 49. $^1$H NMR (300 MHz, CD$_3$OD): δ 8.62 (s, 1H), 8.08 (d, J=8.7 Hz, 1H), 7.69 (s, 1H), 7.42 (d, J=9.3 Hz, 1H), 7.34 (s, 1H), 5.51 (brs, 1H), 4.65-4.52 (m, 2H), 4.38 (m, 2H), 4.22 (s, 1H), 4.10 (m, 1H), 3.85 (m, 2H), 3.49 (s, 3H), 2.74 (m, 1H), 2.56 (s, 3H), 2.20 (m, 1H), 2.08 (m, 1H), 1.85 (m, 1H), 1.68 (m, 3H), 1.50-1.21 (m, 7H), 1.02 (m, 12H), 0.48 (m, 1H), 0.30 (m, 1H). LC/MS=812.6 (M$^+$+1).
Example 51
Preparation of Compound 51
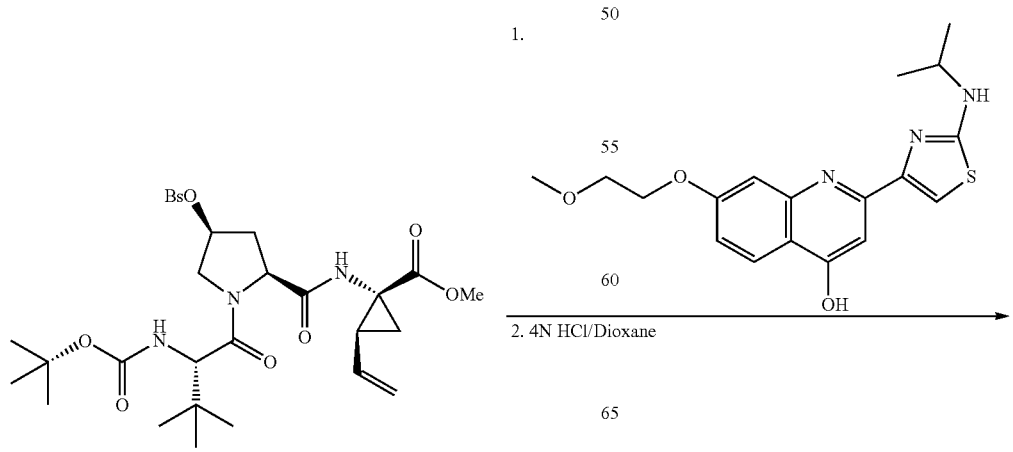

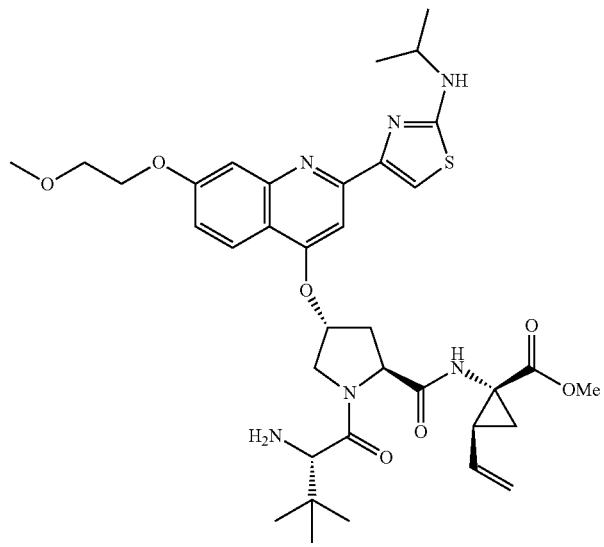

Step 1:

To a mixture of tripeptide (1.30 g, 1.92 mmol) and quinoline (0.55 g, 1.53 mmol) in NMP (15 mL) was added cesium carbonate (0.94 g, 2.88 mmol). The mixture was stirred at 85° C. for 6 h. The reaction was cooled to room temperature, and EtOAc (50 mL) and an aqueous 3% LiCl (50 mL) solution were added to the mixture. The organic layer was washed with aqueous 3% LiCl (1×50 mL), brine, dried (Na$_2$SO$_4$) and concentrated in vacuo. The residue was purified by silica gel chromatography to give the desired methyl ester product as a yellow solid (0.85 g, 65%).

A solution of the above product in dichloromethane (10 mL) was treated with 4N HCl in dioxane (20 mL) for 2 h at room temperature and concentrated to dryness, affording the amine compound as the HCl salt. LC/MS=708.9 (M$^+$+1).

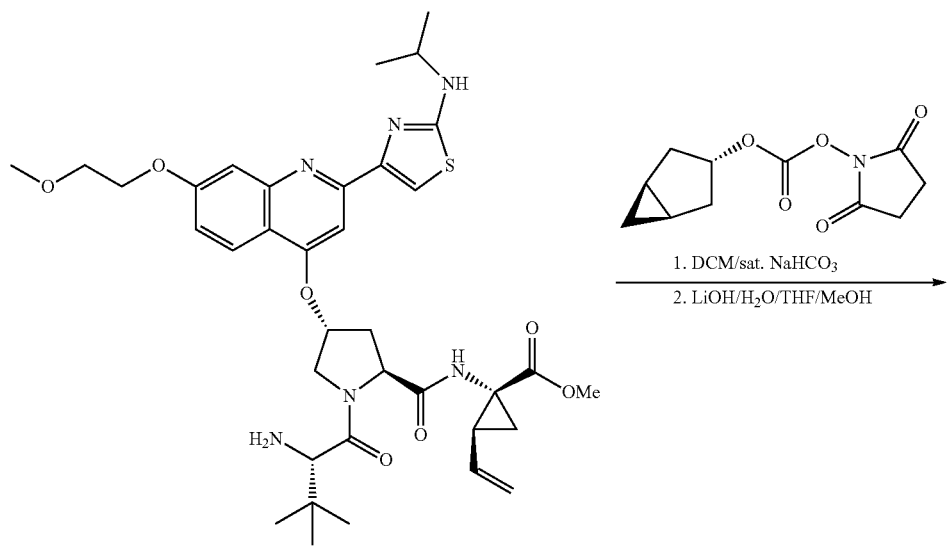

-continued

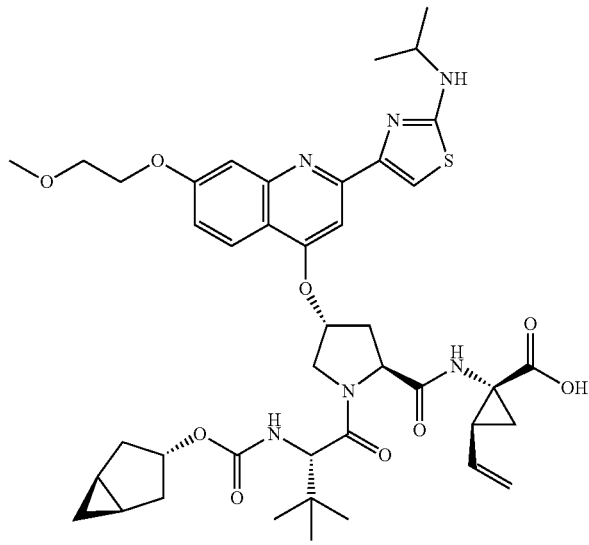

Step 2:

To a biphasic solution of the amine (0.71 g, 1.0 mmol) in dichloromethane (40 mL) and 5% aqueous sodium bicarbonate (40 mL) was added a solution of intermediate I (0.36 g, 1.5 mmol) in dichloromethane in four portions. These additions continued until the starting material was completely consumed. The dichloromethane layer was taken and concentrated. The methyl ester product was then dissolved in a mixture of THF/MeOH/water (5 mL/5 mL/5 mL). Excess lithium hydroxide (240 mg) was added and the reaction was stirred at room temperature for 4 h. Ethyl acetate (40 mL) was added and the pH was adjusted to 4 by slowly adding 1 N HCl to the mixture. After separation, the organic layer was concentrated. The residue was purified by preparative HPLC using water/acetonitrile (0.05% TFA) as eluents, which afforded Compound 51 (750 mg, 91%) as a yellow solid. $^1$H NMR (300 MHz, CD$_3$OD): δ 8.76 (s, 1H), 8.25 (d, J=9.6 Hz, 1H), 8.18 (s, 1H), 7.75 (m, 2H), 7.36 (d, J=9.3 Hz, 1H), 5.91-5.82 (m, 1H), 5.77 (brs, 1H), 5.31 (d, J=15.9 Hz, 1H), 5.12 (d, J=10.2 Hz, 1H), 4.74 (m, 1H), 4.62 (m, 1H), 4.52 (m, 1H), 4.36 (m, 2H), 4.25-4.05 (m, 3H), 3.87 (m, 2H), 3.46 (s, 3H), 2.82 (m, 1H), 2.61 (m, 1H), 2.22 (m, 2H), 1.99-1.62 (m, 5H), 1.35 (d, J=6.3 Hz, 6H), 1.49-1.21 (m, 4H), 1.02 (m, 9H), 0.48 (m, 1H), 0.34 (m, 1H). LC/MS=819.5 (M$^+$+1).

Example 52

Preparation of Compound 52

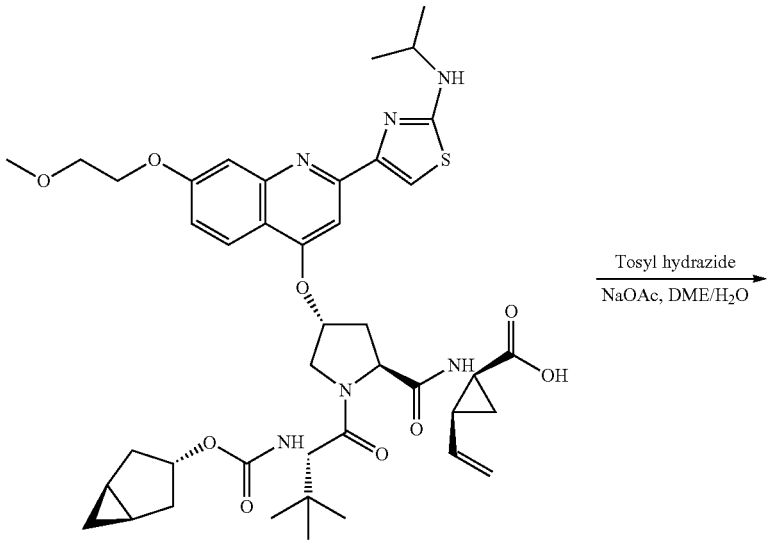

Tosyl hydrazide
NaOAc, DME/H$_2$O

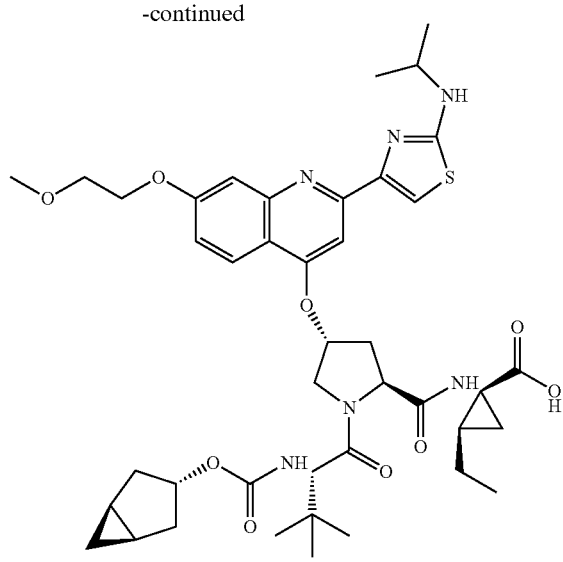

To a mixture of 51 (0.60 g, 0.73 mmol) and sodium acetate (0.83 g, 10.2 mmol) in DME/H$_2$O (9 mL/1 mL) was added p-toluenesulfonhydrazide (0.96 g, 5.1 mmol). The mixture was stirred at 95° C. for 3 h. The reaction was cooled to room temperature, and EtOAc (50 ml) was added to the mixture. The organic layer was washed with aqueous 0.05 N HCl (1×50 ml), dried (Na$_2$SO$_4$) and concentrated in vacuo. The residue was purified by preparative HPLC using water/acetonitrile (0.05% TFA) as eluents, which afforded Compound 52 (450 mg, 75%) as a yellow solid. $^1$H NMR (300 MHz, CD$_3$OD): δ 8.65 (s, 1H), 8.27 (d, J=9.0 Hz, 1H), 8.18 (s, 1H), 7.76 (m, 2H), 7.38 (d, J=9.0 Hz, 1H), 5.77 (brs, 1H), 4.74 (t, 1H), 4.62 (d, 1H), 4.52 (t, 1H), 4.37 (m, 2H), 4.18-4.04 (m, 3H), 3.86 (m, 2H), 3.46 (s, 3H), 2.76 (m, 1H), 2.58 (m, 1H), 2.20 (q, 1H), 1.97-1.85 (m, 2H), 1.70-1.65 (m, 3H), 1.54 (m, 1H), 1.46-1.41 (m, 2H), 1.35 (m, 6H), 1.22 (m, 2H), 1.02 (m, 12H), 0.48 (m, 1H), 0.30 (m, 1H). LC/MS=821.6 (M$^+$+1).

Example 53

Preparation of Compound 53

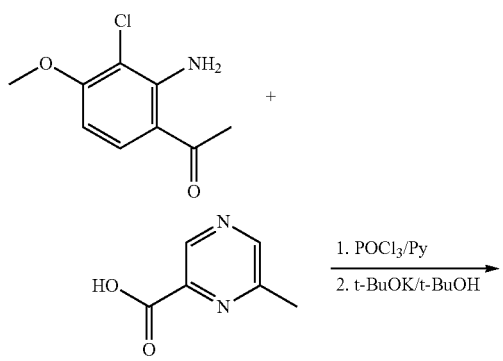

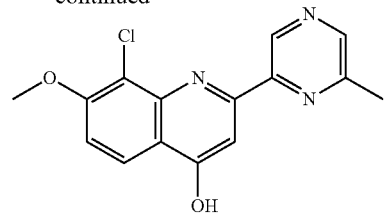

Step 1:

To a mixture of aniline (1.21 g, 6.06 mmol) and acid (0.84 g, 6.09 mmol) in pyridine (55 mL) was slowly added POCl$_3$ (1.02 g, 6.68 mmol) at −40° C. The mixture was then stirred at 0° C. for 4 h. Upon completion of the reaction, H$_2$O (5 mL) was added dropwise to the mixture. The mixture was then stirred at 0° C. for another 15 min. The mixture was concentrated in vacuo. The residue was diluted with EtOAc, and washed with a sat. NaHCO$_3$ aqueous solution. The organic layer was dried (Na$_2$SO$_4$) and concentrated in vacuo. The residue was purified by silica gel column chromatography (ethyl acetate/hexanes), affording the amide (1.77 g, 92%) as a solid. The amide (1.70 g, 5.3 mmol) was suspended in t-BuOH (40 mL). t-BuOK (1.30 g, 11.2 mmol) was added to the vigorously stirred mixture. The mixture was heated to 75° C. for 5 h. The mixture was cooled to room temperature. 4 N HCl/Dioxane (5 mL) was slowly added to acidify the mixture. After concentration, the crude was poured into 1N KH$_2$PO$_4$/H$_2$O (100 mL). The solid formed isolated by filtration and washed with water. After drying under high vacuum overnight, quinoline (1.5 g, 94%) was obtained as a solid. LC/MS=302.4 (M$^+$+1).

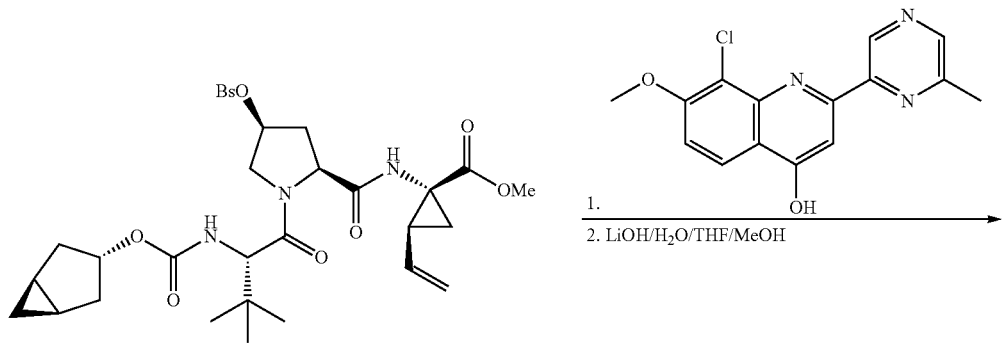
Step 2:
Compound 53 was obtained by the procedures similar to those for preparation of Compound 50 except using quinoline obtained from above. $^1$H NMR (300 MHz, DMSO): δ 12.43 (brs, 1H), 9.59 (s, 1H), 8.69 (s, 1H), 8.57 (m, 1H), 8.13 (d, J=8.7 Hz, 1H), 7.83 (s, 1H), 7.51 (d, J=8.7 Hz, 1H), 7.06 (d, J=8.7 Hz, 1H), 5.68 (m, 1H), 5.60 (brs, 1H), 5.21 (d, J=18.0 Hz, 1H), 5.07 (d, J=9.9 Hz, 1H), 4.67 (m, 1H), 4.45 (m, 1H), 4.32 (m, 1H), 4.04 (m, 4H), 2.66 (s, 3H), 2.28 (m, 2H), 2.03-1.80 (m, 4H), 1.35-1.19 (m, 4H), 0.95 (s, 9H), 0.44 (m, 1H), 0.33 (m, 1H). LC/MS=761.5 (M$^+$+1).
Example 54
Preparation of Compound 54
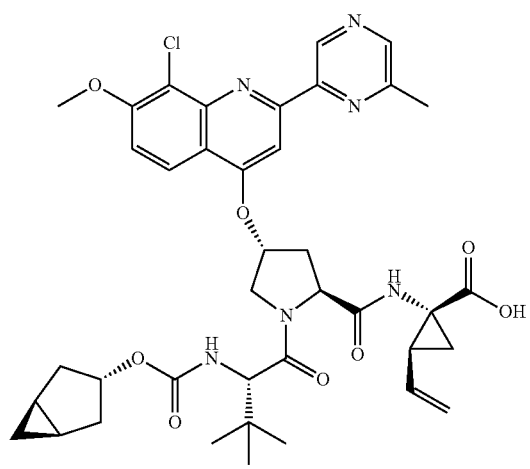
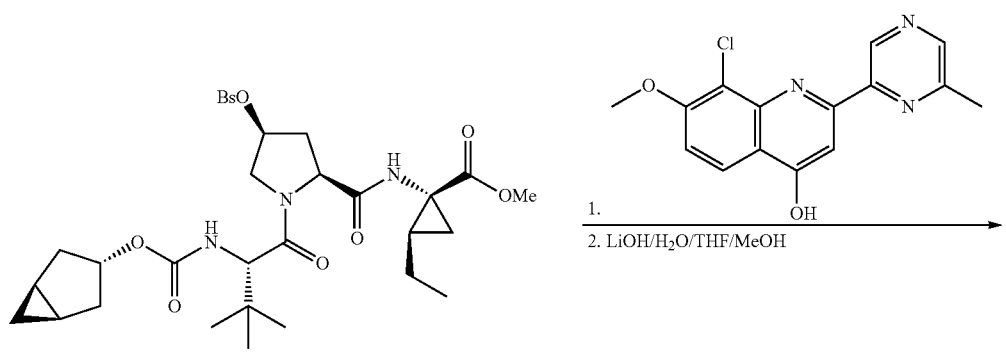

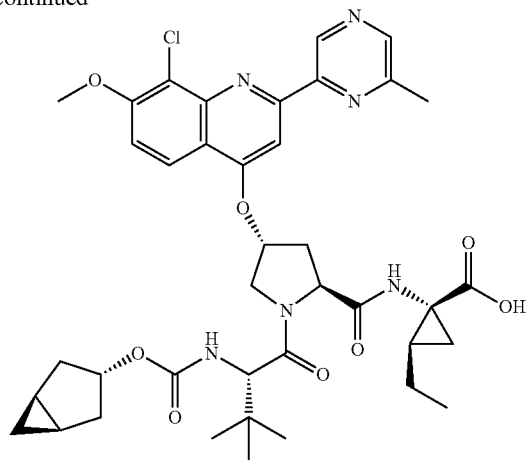
Compound 54 was obtained by the procedures similar to those for preparation of compound 50. Compound 52. ¹H NMR (300 MHz, DMSO): δ 9.59 (s, 1H), 8.69 (s, 1H), 8.41 (m, 1H), 8.14 (d, J=9.3 Hz, 1H), 7.84 (s, 1H), 7.51 (d, J=8.7 Hz, 1H), 7.04 (d, J=8.7 Hz, 1H), 5.60 (brs, 1H), 4.68 (m, 1H), 4.45 (m, 1H), 4.29 (m, 1H), 4.04 (m, 5H), 2.67 (m, 4H), 2.28 (m, 2H), 2.03-1.80 (m, 4H), 1.58-1.42 (m, 4H), 0.94 (m, 12H), 0.44 (m, 1H), 0.35 (m, 1H). LC/MS=763.3 (M⁺+1).
Example 55
Preparation of Compound 55
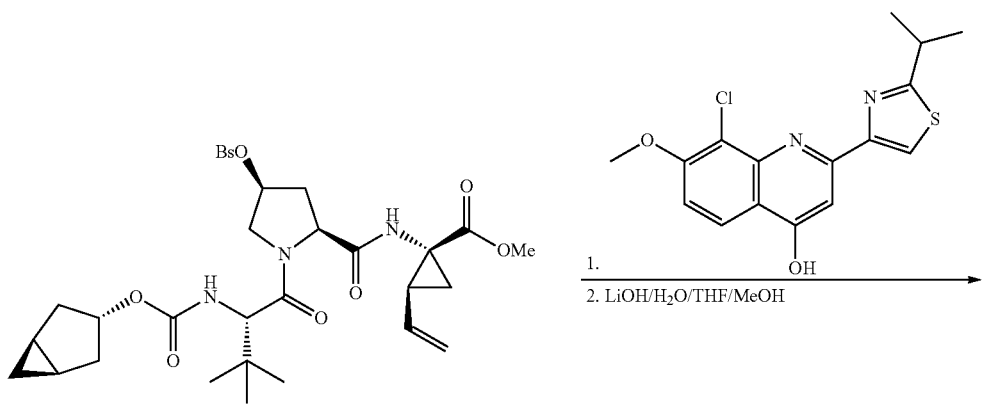
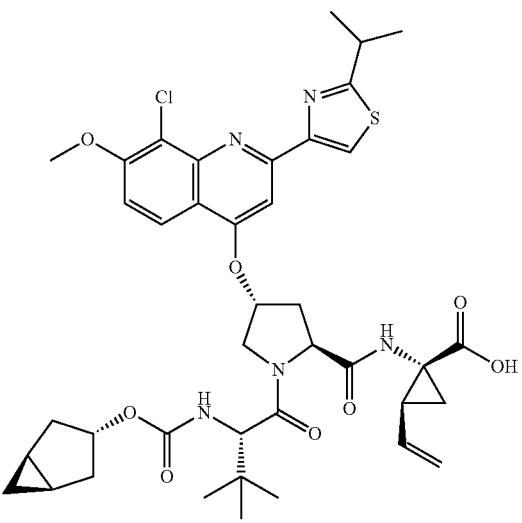

Compound 55 was obtained by the procedures similar to those for preparation of Compound 50 except using the P2 quinoline as shown. $^1$H NMR (300 MHz, CD$_3$OD): δ 9.01 (s, 1H), 8.76 (s, 1H), 8.37 (d, J=9.0 Hz, 1H), 7.99 (s, 1H), 7.70 (d, J=9.9 Hz, 1H), 5.89 (m, 1H), 5.83 (brs, 1H), 5.31 (d, J=15.3 Hz, 1H), 5.13 (d, J=9.6 Hz, 1H), 4.75 (m, 1H), 4.65 (m, 1H), 4.41 (m, 1H), 4.19-4.07 (m, 5H), 3.56 (m, 1H), 2.82 (m, 1H), 2.63 (m, 1H), 2.22 (m, 1H), 1.91 (m, 1H), 1.75-1.63 (m, 2H), 1.56 (d, J=7.2 Hz, 6H), 1.49-1.20 (m, 5H), 0.98 (s, 9H), 0.48 (q, 1H), 0.34 (m, 1H). LC/MS=794.5 (M$^+$+1).

Example 56

Preparation of Compound 56

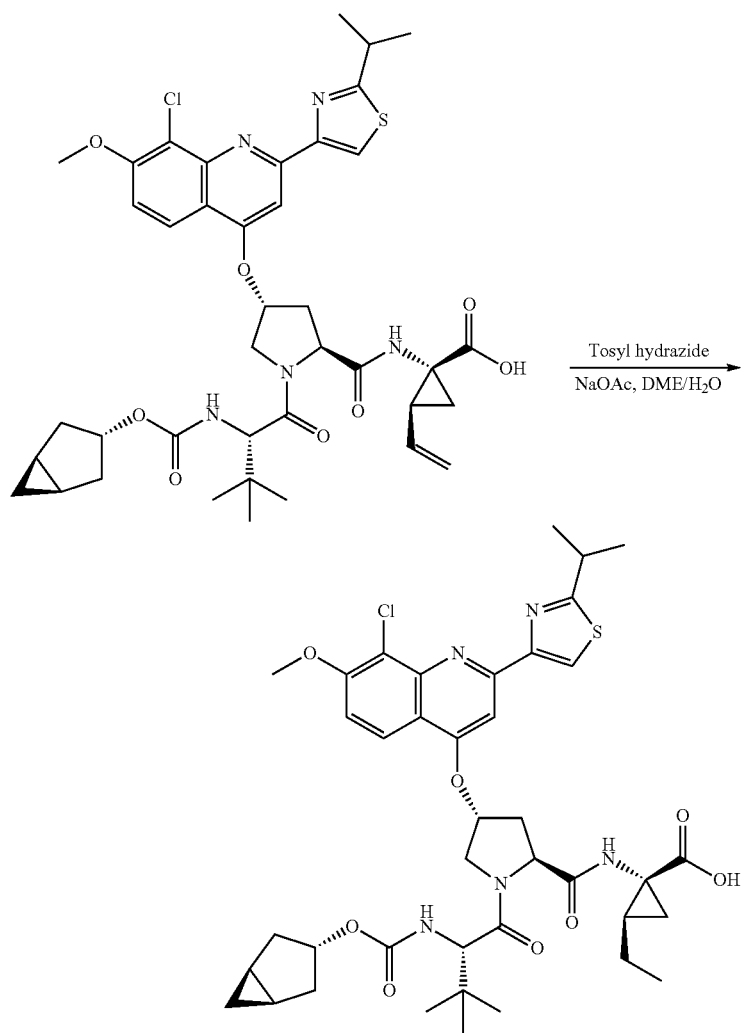

Compound 56 was obtained by the procedures similar to those for preparation of Compound 52 except using 55 as reactant. $^1$H NMR (300 MHz, CD$_3$OD): δ 8.92 (s, 1H), 8.65 (s, 1H), 8.30 (d, J=9.6 Hz, 1H), 7.92 (s, 1H), 7.63 (d, J=9.3 Hz, 1H), 5.77 (brs, 1H), 4.75 (m, 1H), 4.62 (m, 1H), 4.45 (m, 1H), 4.16 (m, 5H), 3.55 (m, 1H), 2.79 (m, 1H), 2.61 (m, 1H), 2.20 (m, 1H), 1.97 (m, 1H), 1.89 (m, 1H), 1.80 (m, 3H), 1.56 (d, J=6.9 Hz, 6H), 1.59-1.22 (m, 6H), 1.05 (m, 12H), 0.48 (q, 1H), 0.30 (m, 1H). LC/MS=796.4 (M$^+$+1).

Example 57
Preparation of Compound 57
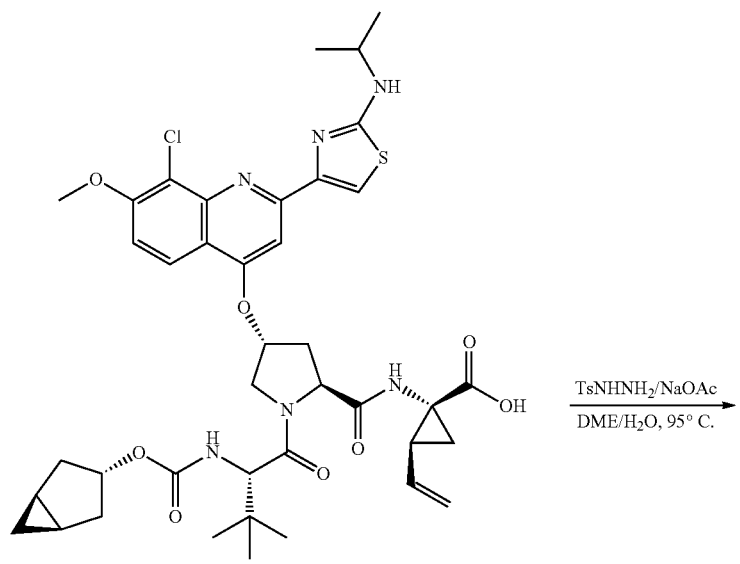
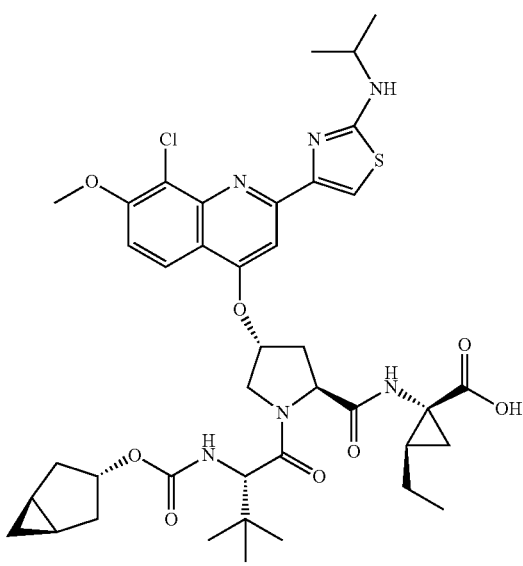
Compound 57 was obtained by the procedures similar to those for preparation of Compound 52. $^1$H NMR (300 MHz, CD$_3$OD): δ 8.33 (m, 1H), 7.83 (s, 1H), 7.65 (d, J=9.6 Hz, 1H), 5.77 (brs, 1H), 4.77 (m, 1H), 4.62 (m, 1H), 4.42 (m, 1H), 4.17 (s, 3H), 4.17-4.05 (m, 3H), 2.79 (m, 1H), 2.61 (m, 1H), 2.20 (m, 1H), 1.98 (m, 1H), 1.79 (m, 1H), 1.70-1.49 (m, 4H), 1.45-1.21 (m, 5H), 1.38 (d, J=6.6 Hz, 6H), 1.05 (m, 12H), 0.48 (m, 1H), 0.30 (m, 1H). LC/MS=811.4 (M$^+$+1).

Example 58

Preparation of Compound 58

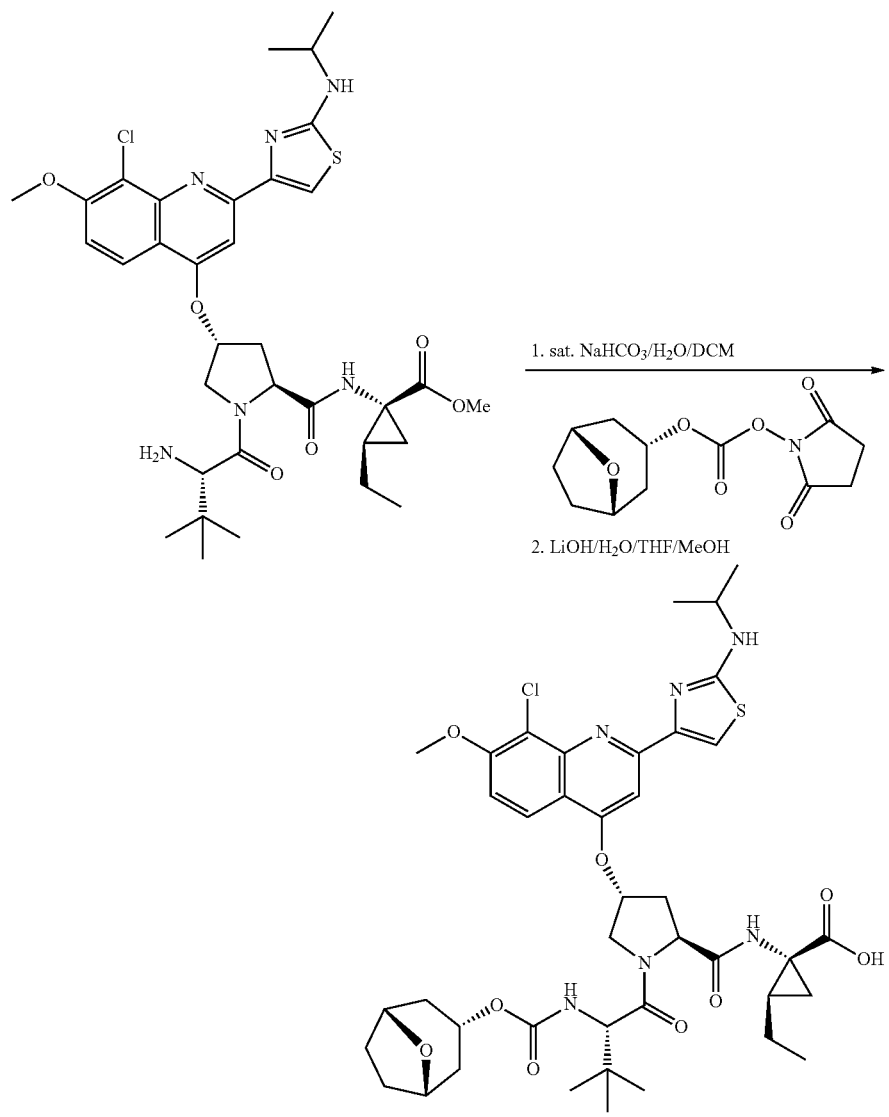

To a biphasic solution of the amine (0.15 g, 0.19 mmol) in dichloromethane (10 mL) and 5% aqueous sodium bicarbonate (10 mL) was added a solution of carbonate (0.08 g, 0.29 mmol) in dichloromethane in four portions, until the starting material amine was completely consumed. The dichloromethane layer was taken and concentrated. The methyl ester product was then dissolved in a mixture of THF/MeOH/water (2 mL/2 mL/2 mL). Excess lithium hydroxide (46 mg) was added and the reaction was stirred at room temperature for 4 h. Ethyl acetate (40 mL) was added and the pH was adjusted to 4 by slowly adding 1 N HCl/H$_2$O to the mixture. After separation, the organic layer was concentrated. The residue was purified by preparative HPLC using water/acetonitrile (0.05% TFA) as eluents, which afforded Compound 58 (140 mg, 88%) as a yellow solid. $^1$H NMR (300 MHz, CD$_3$OD): δ 8.66 (m, 1H), 8.32 (m, 2H), 7.82 (s, 1H), 7.63 (d, J=9.3 Hz, 1H), 5.76 (brs, 1H), 4.77 (m, 1H), 4.66 (m, 1H), 4.28-4.03 (m, 8H), 2.84 (m, 1H), 2.65 (m, 1H), 2.08 (m, 2H), 1.86-1.63 (m, 6H), 1.79 (m, 1H), 1.70-1.49 (m, 3H), 1.55-1.36 (m, 2H), 1.39 (d, J=6.9 Hz, 6H), 1.28 (m, 2H) 1.04 (m, 12H), LC/MS=841.4 (M$^+$+1).

Example 59

Preparation of Compound 59

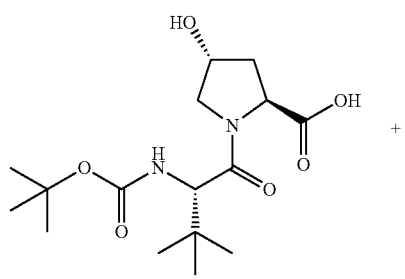

343
-continued

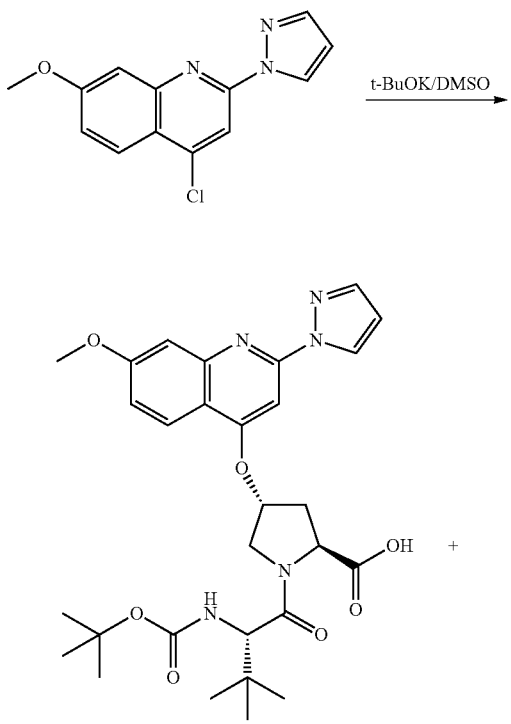

344
-continued

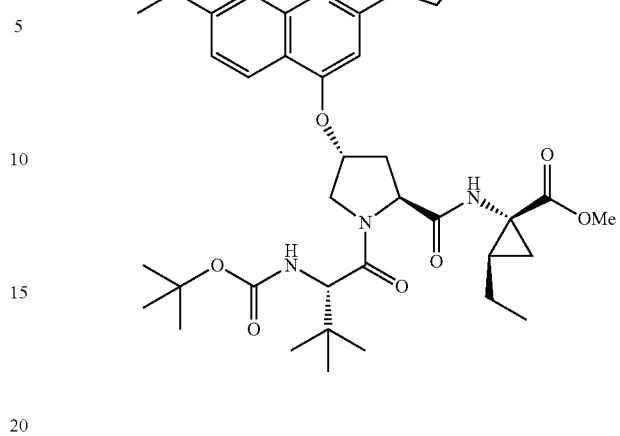

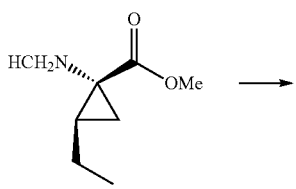

To a solution of alcohol (0.40 g, 1.1 mmol) in DMSO (5 mL) was slowly added potassium tert-butoxide (0.38 g, 3.3 mmol). This was followed by the addition of the chloroquinoline (0.32 g, 1.2 mmol). The reaction mixture was stirred at room temperature overnight. Ethyl acetate (50 mL) was added to the mixture and the pH was adjusted to 2 by adding 1N HCl. After separation, the organic layer was dried over $Na_2SO_4$. After concentration, the crude product was dried under high vacuum overnight and used for the next step directly.

To a solution of the acid (0.60 g, crude, 1.1 mmol), (1R, 2S)-1-amino-2-ethyl-cyclopropanecarboxylic acid methyl ester hydrochloride (0.22 g, 1.2 mmol) and NMM (0.56 g, 5.5 mmol) was added HATU (0.63 g, 1.65 mmol) at 0° C. The reaction was stirred for 30 min. Ethyl acetate (50 mL) and 3% aqueous LiCl (50 mL) were added to the mixture while stirring. The organic layer was taken and washed with 3% aqueous LiCl (50 mL), and then with brine, dried over $Na_2SO_4$, and concentrated in vacuo. The residue was purified by silica gel column chromatography (ethyl acetate/hexanes), affording the coupled tripeptide product (0.28 g, 37%) as white solids. LC/MS=692.8 ($M^+$+1).

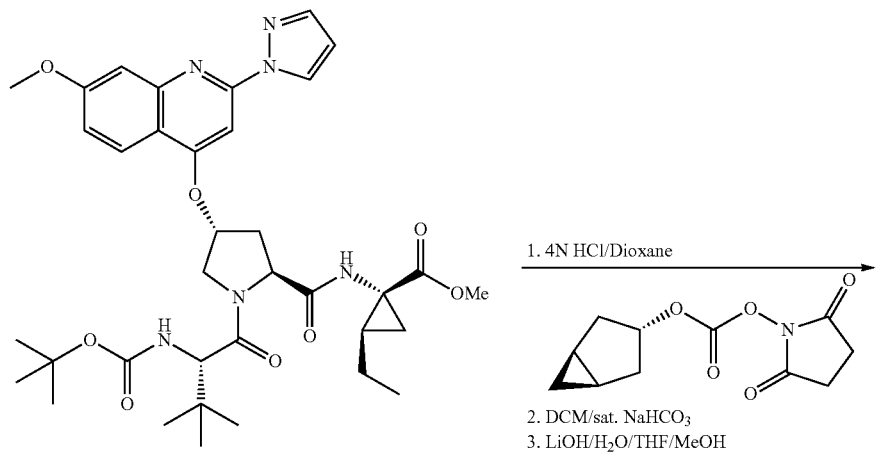

1. 4N HCl/Dioxane
2. DCM/sat. $NaHCO_3$
3. LiOH/$H_2O$/THF/MeOH

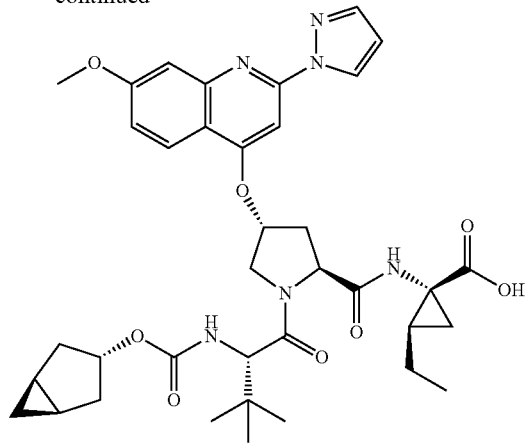

Compound 59 was obtained by following procedures similar to those described above. $^1$H NMR (300 MHz, CD$_3$OD): δ 8.81 (s, 1H), 8.05 (d, J=9.3 Hz, 1H), 7.91 (s, 1H), 7.49 (s, 1H), 7.35 (m, 1H), 7.12 (d, J=9.0 Hz, 1H), 6.67 (s, 1H), 5.53 (brs, 1H), 4.65 (m, 2H), 4.55 (d, J=12.3 Hz, 1H), 4.22-4.16 (m, 3H), 3.95 (s, 3H), 2.75 (m, 1H), 2.56 (m, 1H), 2.20 (m, 1H), 2.10-1.85 (m, 3H), 1.71-1.64 (m, 3H), 1.52-1.38 (m, 3H), 1.29-1.20 (m, 2H), 1.02 (m, 12H), 0.48 (m, 1H), 0.36 (m, 1H). LC/MS=703.4 (M$^+$+1).

Example 60

Preparation of Compound 60

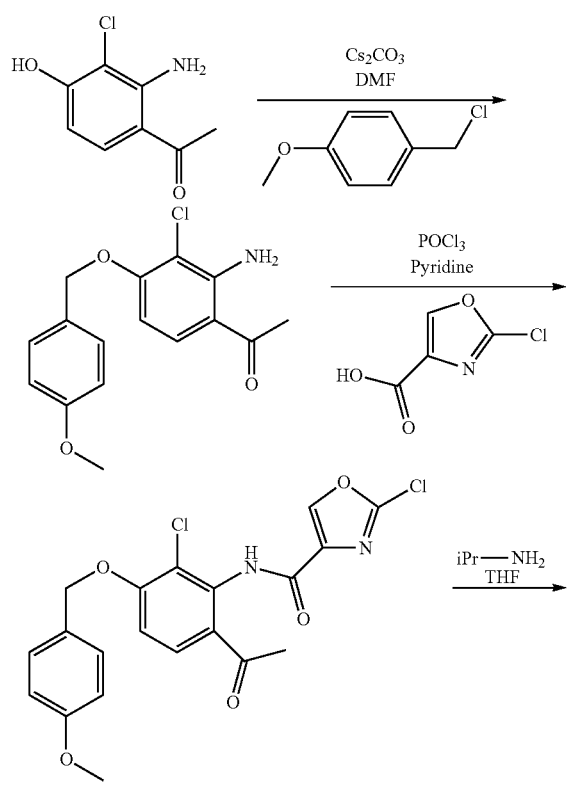

Step 1:

The aniline (38.3 g, 206 mmol) and 1-chloromethyl-4-methoxy-benzene (29.4 mL, 216 mmol) were dissolved in anhydrous DMF (412 mL) and treated with Cs$_2$CO$_3$ (77.2 g, 326 mmol), then stirred for 90 min. at 50° C. The reaction mixture was concentrated, and then partitioned between H$_2$O and EtOAc to get a homogeneous solution. EtOAc was then evaporated. The solid crashed was filtered, and then washed with H$_2$O, MeOH, 30% DCM/Hexane, and 50% EtOAc/Hexane. The solid was dried under high vacuum to provide the PMB protected product (52.2 g, 83%) LC/MS=306 (M$^+$+1).

Step 2:

The aniline (52.2 g, 171 mmol) and the acid (29.0 g, 196 mmol) were dissolved in anhydrous Pyridine (853 mL) and treated with POCl$_3$ (18.8 mL, 205 mmol) at −8° C. After 60 min. stirring, the reaction mixture was concentrated and partitioned with EtOAc and 1N HCl, then extracted with EtOAc and DCM. After removal of solvent, the crude product was purified by column chromatography (30-80% EtOAc/Hexane) on silica to provide the amide (44.6 g, 60%), m/z 436. (M+H).

347

Step 3:

Amide (9.04 g, 20.8 mmol) and isopropyl amine (17.7 mL, 208 mmol) in THF (177 mL) were stirred for 4 hours at 65° C. The mixture was concentrated and partitioned between EtOAc and 1N HCl, and then extracted with EtOAc and DCM. After removal of solvent, the crude product was purified by silica gel column chromatography (50-80% EtOAc/Hexane) to provide the amine (6.06 g, 64%). LC/MS=457.8 ($M^++1$).

Step 4:

Amine (18.4 g, 40.3 mmol) was suspended in toluene (300 mL), and then NaH (2.42 g, 60.4 mmol) was added. The mixture was stirred for 80 min at 125° C. After cooling to room temperature, AcOH (3.76 mL, 66.4 mmol) in $H_2O$ (300 mL) was added. The solid formed was filtered and washed with $H_2O$ and toluene, and then dried under high vacuum overnight to give the quinoline (15.0 g, 84%). LC/MS=440 ($M^++1$).

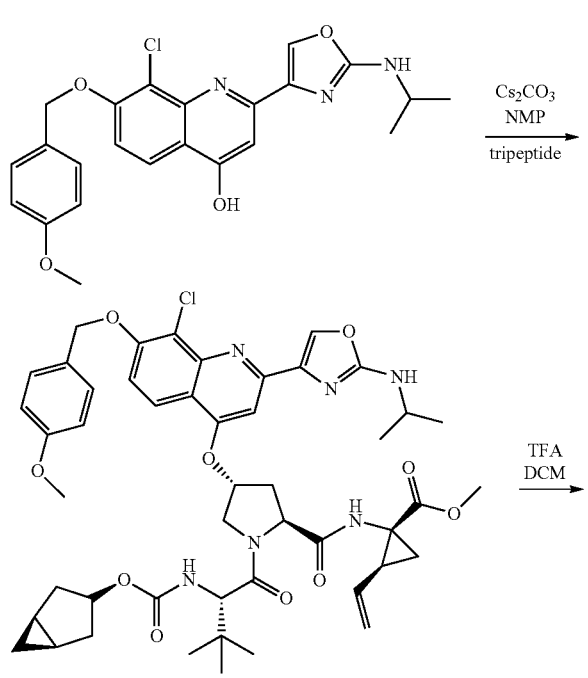

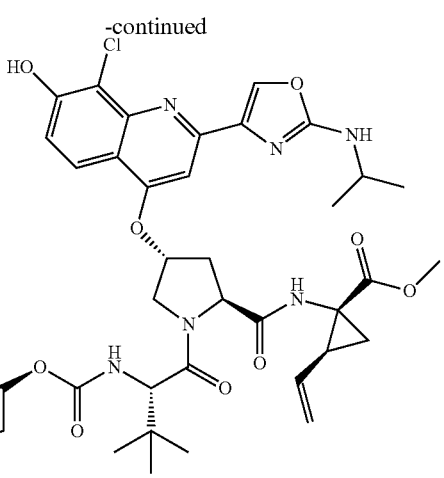

Step 5:

The quinoline (1.00 g, 2.27 mmol), tripeptide brosylate (1.78 g, 2.50 mmol) and $Cs_2CO_3$ (1.85 g, 5.68 mmol) in NMP were stirred for three and half hours at 65° C. The reaction mixture was partitioned between EtOAc and brine, and then extracted with EtOAc. After evaporation of the volatile organics, the crude product was purified by silica gel column chromatography (50-100% EtOAc/Hexane) to provide the ester (1.64 g, 79%). LC/MS=914 ($M^++1$).

Step 6:

To the ester (6.29 g, 6.89 mmol) in DCM (100 mL) was added TFA (10 mL). After stirring for 100 min. at room temperature, 100 mL of toluene was added, and then the mixture was concentrated. The crude was partitioned between sat. $NaHCO_3$ and DCM, and then extracted with DCM. After removal of the volatile organics, the crude product was purified by silica gel column chromatography (65-100% EtOAc/Hexane) to provide the phenol (4.50 g, 82%). LC/MS=793.7 ($M^++1$).

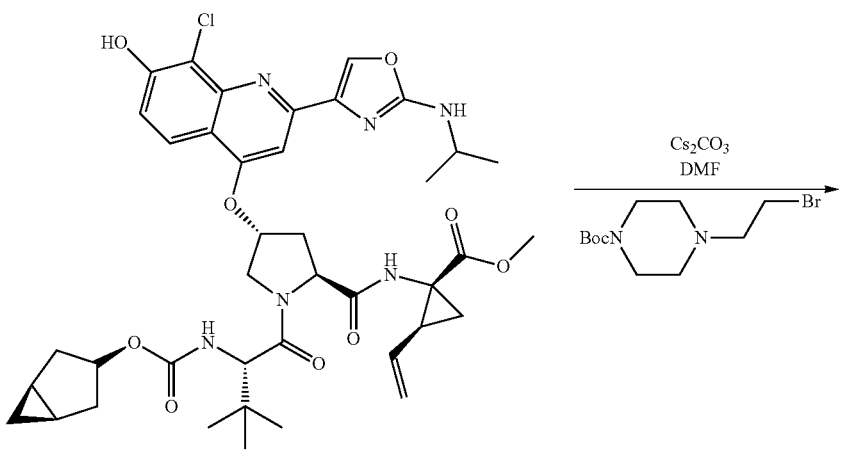

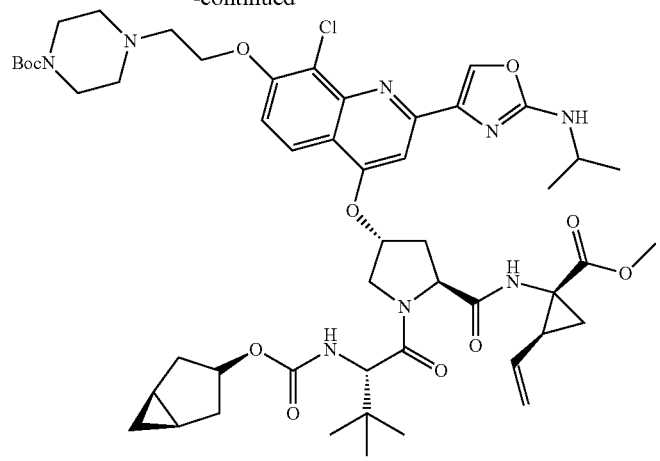

Step 7:

The phenol (520 mg, 0.655 mmol) and bromide (231 mg, 0.787 mmol) were dissolved in anhydrous DMF (5 mL) and treated with Cs$_2$CO$_3$ (534 mg, 1.64 mmol). The reaction was then stirred for 45 min at 50° C. The reaction mixture was partitioned between H$_2$O and EtOAc, and extracted with EtOAc. The extract was washed with brine and dried over Na$_2$SO$_4$. After removal of the volatile organics, the crude product was purified by silica gel column chromatography (80-100% EtOAc/Hexane) to provide the ester (600 mg, 91%). LC/MS=1005.7 (M$^+$+1).

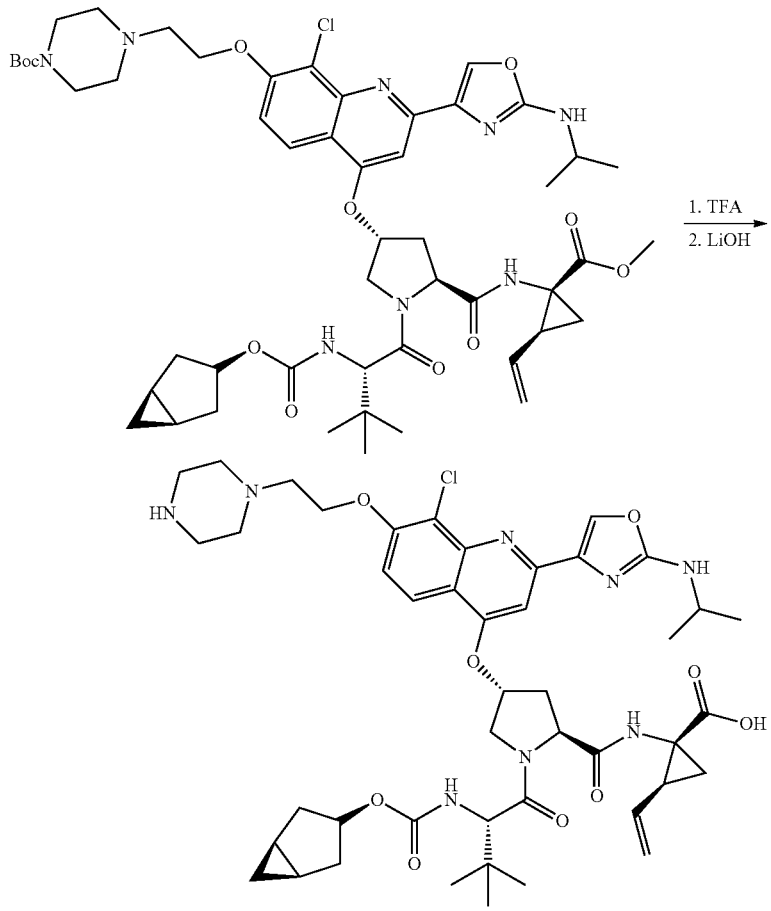

Step 8:

The ester (600 mg, 0.597 mmol) was dissolved in anhydrous DCM (6 mL), and then treated with 4 N HCl/dioxane (3 mL, 12.0 mmol). After stirring for 2 hours at room temperature, toluene (6 mL) was added, and the reaction was concentrated. The resulting solid was dissolved in THF (5.37 mL) after drying under high vacuum for 30 min. To the mixture were added MeOH (1.79 mL) and 2N LiOH (3.58 mL). After stirring for 65 min at 40° C., the reaction mixture was cooled to room temperature. The reaction mixture was neutralized with 2 N HCl (3.8 mL) and concentrated. The crude material was purified by preparative HPLC to provide Compound 60 (301 mg, 50%): $^1$H NMR (CD$_3$OD, 300 MHz): δ 8.63 (s, 1H), 8.47 (s, 1H), 8.16 (d, 1H), 7.53 (s, 1H), 7.48 (d, 1H), 5.80-5.71 (m, 1H), 5.56 (bs, 1H), 5.18 (d, 1H), 5.10 (d, 1H), 4.61 (t, 1H), 4.49-4.41 (m, 3H), 4.06-3.89 (m, 3H), 3.29-3.18 (m, 8H), 3.14 (t, 2H), 3.07 (t, 2H), 2.67-2.62 (m, 1H), 2.54-2.51 (m, 1H), 2.14-2.08 (m, 1H), 1.89-1.84 (m, 1H), 1.76-1.71 (m, 1H), 1.63-1.53 (m, 2H), 1.38-1.31 (m, 2H), 1.27-1.24 (d, 6H), 1.13-1.08 (m, 2H), 0.93 (s, 9H), 0.29-0.23 (m, 2H); LC/MS=891 (M$^+$+1).

Example 61

Preparation of Compound 61

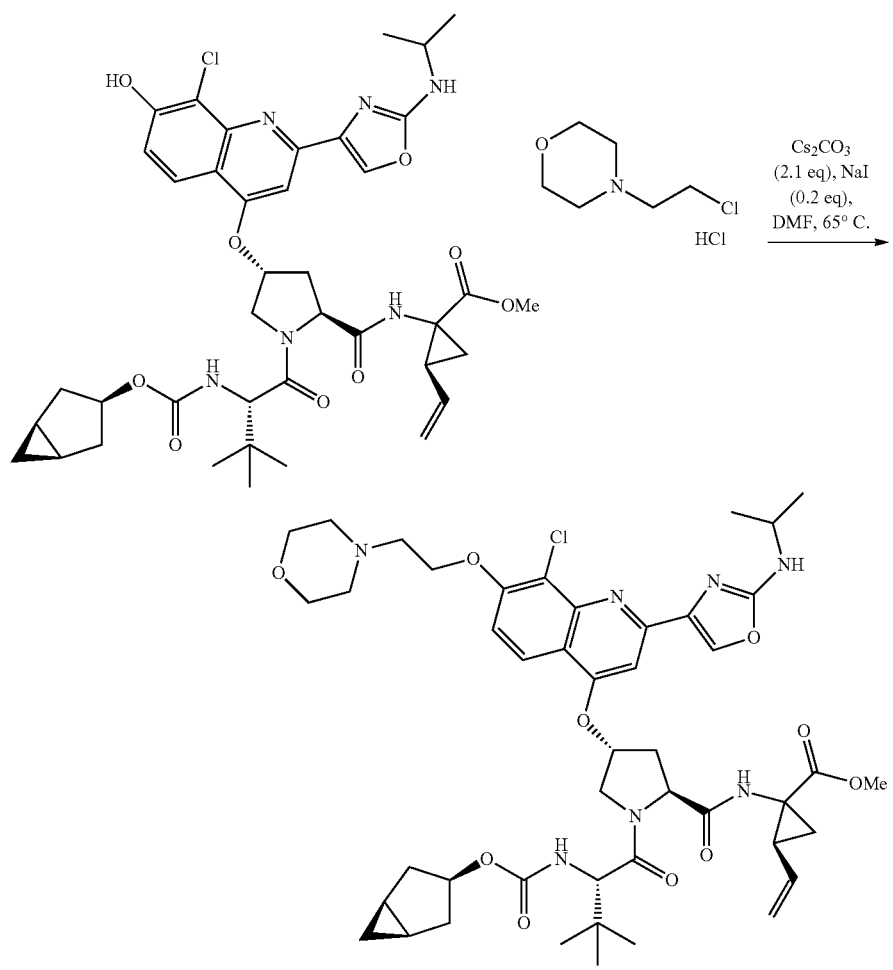

Step 1:

An N$_2$ purged flask was charged with phenol (604 mg, 0.761 mmol), the chloride (170 mg, 0.913 mmol), Cs$_2$CO$_3$ (620 mg, 1.90 mmol), and NaI (60 mg, 0.45 mmol). To this mixture was then added DMF (7 mL) and the heterogeneous mixture was heated in a preheated 65° C. oil bath. After 30 min, the reaction was <40% complete by LC/MS. After 6 h, the reaction was complete. The reaction mixture was diluted with EtOAc and washed with 3×100 mL 5% LiCl, 100 mL ½ sat NaHCO$_{3(aq)}$, and brine. The organics were dried over Na$_2$SO$_4$, solids were removed by filtration and the filtrate was concentrated. The crude methyl ester was used as is for the next step. LC/MS=907 (M$^+$+1).

2H), 5.53 (dd, J=9.0, 15.8 Hz, 1H), 5.20 (s, 1H), 4.93 (d, J=17.4 Hz, 1H), 4.74 (d, J=10.2 Hz, 1H), 4.33 (m, 4H), 4.11 (d, J=12.7 Hz, 1H), 3.84-3.22 (m, 12H), 2.93 (brs, 8H), 2.29 (q, J=4.5 Hz, 1H), 1.87 (m, 1H), 1.66 (m, 1H), 1.55 (m, 1H), 1.35 (m, 1H), 1.14 (m, 1H), 0.97 (d, J=6.45 Hz, 6H), 0.87 (m, 1H), 0.67 (s, 9H), 0.13-0.01 (m, 2H).

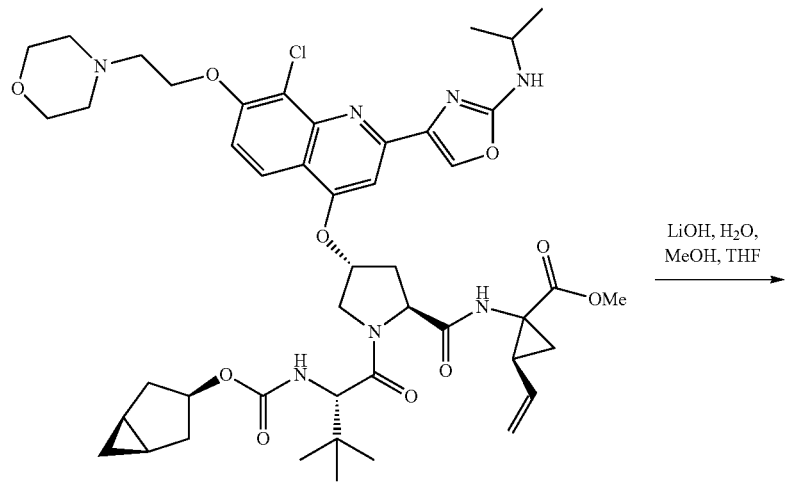

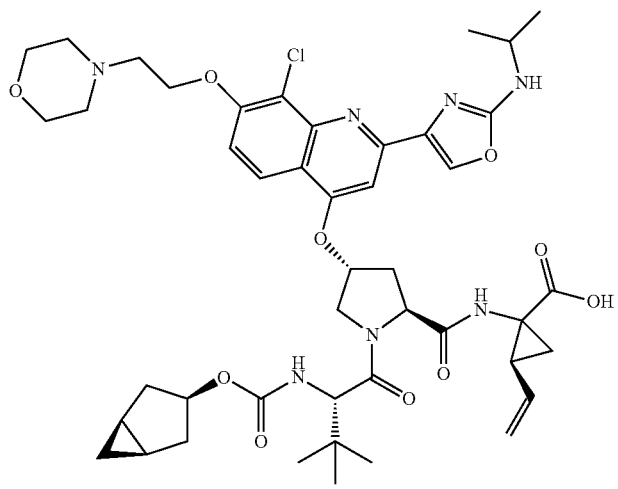

Step 2:

The ester (620 mg, 0.69 mmol) was dissolved in a mixture of THF (6 mL) and MeOH (2 mL). LiOH.H$_2$O (143 mg, 3.41 mmol) was dissolved in dH$_2$O (2 mL) and this was slowly added to the solution of ester in THF/MeOH, which had been cooled to 0° C. Upon complete addition the ice bath was removed. After 3 h the reaction was complete. The reaction was cooled to 0° C. and neutralized with 2 N HCl. Compound 61 was directly isolated from the reaction mixture by reverse phase HPLC to afford 472 mg (78% yield) as off-white solids.

LC/MS=892 (M$^+$+1). $^1$H NMR (400 MHz, CDCl$_3$): δ 8.31 (s, 1H), 8.02 (s, 1H), 7.89 (d, J=9.2 Hz, 1H), 7.18-7.14 (m,

Example 62

Preparation of Compound 62

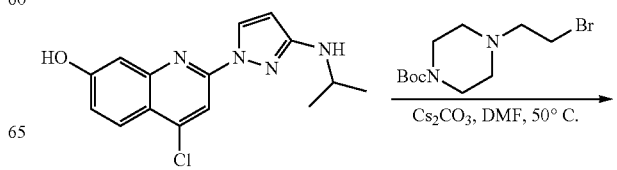

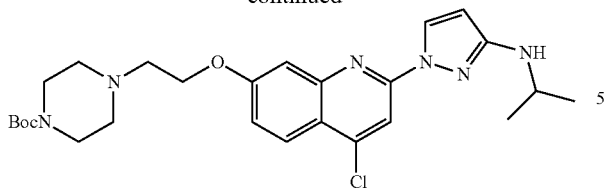

Step 1:

To a solution of phenol (1.10 g, 4.64 mmol) in DMF (21 mL) was added bromide (1.40 g, 4.77 mmol, 1.2 equiv.) and cesium carbonate (3.80 g, 11.6 mmol, 2.5 equiv.). The resulting mixture was placed in a preheated bath (50° C., external temperature, oil bath), and stirred vigorously for 55 min. Upon cooling to room temperature, the reaction mixture was diluted with EtOAc and washed with water (1×). The water layer was back extracted with EtOAc (1×). The combined organic layers were washed with brine, dried over $Na_2SO_4$, and concentrated. The crude product was purified by column chromatography (50% to 75% EtOAc/hexanes) to provide the quinoline (1.71 g, 50%); LC/MS found 515.28 ($M^++H$, $C_{26}H_{36}ClN_6O_3$ requires 515.25).

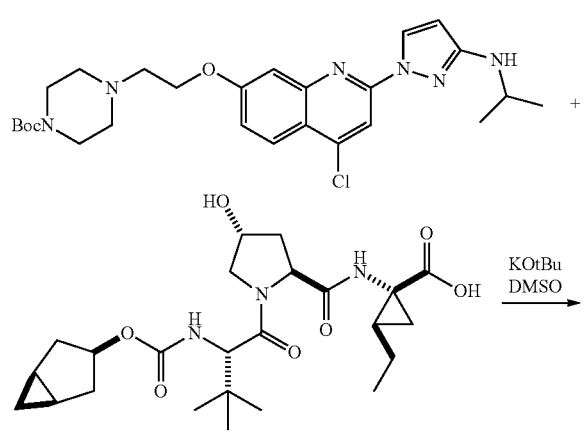

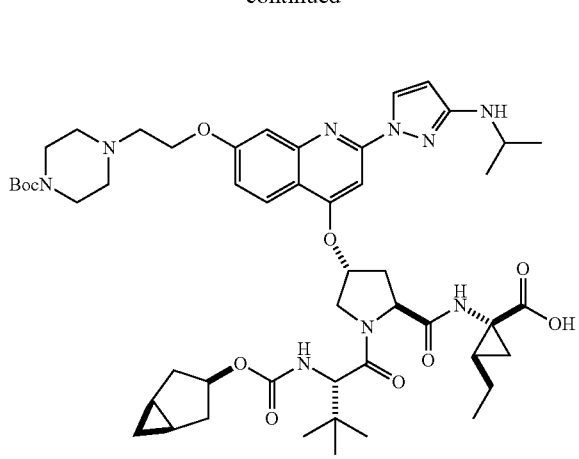

Step 2:

To a solution of tripeptide acid (303 mg, 0.634 mmol) in DMSO (3.3 mL) was added potassium tert-butoxide (365 mg, 3.17 mmol, 5 equiv.). The resulting slurry was stirred at room temperature for 2 h. A solution of quinoline (359 mg, 0.697 mmol, 1.1 equiv.) in DMSO (3 mL) was added dropwise to the reaction mixture. The resulting slurry was stirred at room temperature for 16.5 h. The reaction was quenched with acetic acid (0.3 mL) and purified by reverse phase HPLC (30 to 90% MeCN/$H_2O$-1% TFA) to provide acid (100 mg, 16%); LC/MS found 958.27 ($M^++H$, $C_{50}H_{72}N_9O_{10}$ requires 958.54).

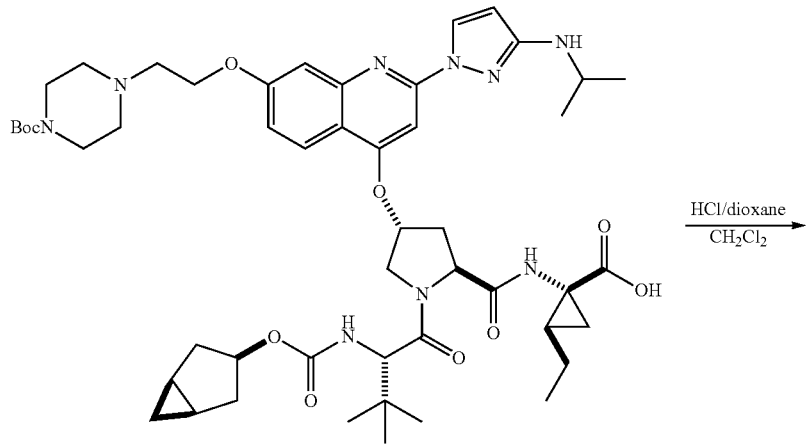

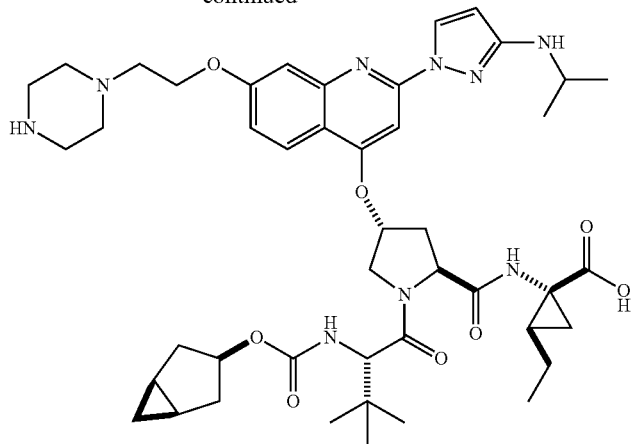

Step 3:

To a solution of acid (100 mg, 0.104 mmol) in $CH_2Cl_2$ (0.2 mL) was added a solution of 4 N HCl in dioxane (1.0 mL). The resulting mixture was stirred at room temperature for 1.25 hour, concentrated and purified by reverse phase HPLC (30 to 90% $MeCN/H_2O$-1% TFA) to provide Compound 62 (10 mg, 11%): $^1$H NMR ($d_3$-MeOD, 400 MHz): δ 8.48 (s, 1H), 7.98 (d, 1H), 7.43 (s, 1H), 7.21 (s, 1H), 7.05 (dd, 1H), 7.03 (d, 1H), 6.10 (d, 1H), 5.49 (s, 1H), 4.52-4.56 (m, 2H), 4.41 (d, 1H), 4.23 (t, 2H), 4.10 (s, 1H), 3.97 (m, 2H), 3.85 (t, 1H), 3.18 (q, 4H), 2.93 (t, 2H), 2.85 (m, 4H), 2.61 (m, 1H), 2.46 (m, 1H), 2.03 (m, 1H), 1.89 (m, 1H), 1.80 (m, 2H), 1.55 (t, 4H), 1.41 (m, 2H), 1.35 (d, 2H), 1.19 (d, 8H), 0.92 (s, 9H); LCMS found 858.30 ($M^+$+H, $C_{45}H_{64}N_9O_8$ requires 858.49).

Example 63

Preparation of Compound 63

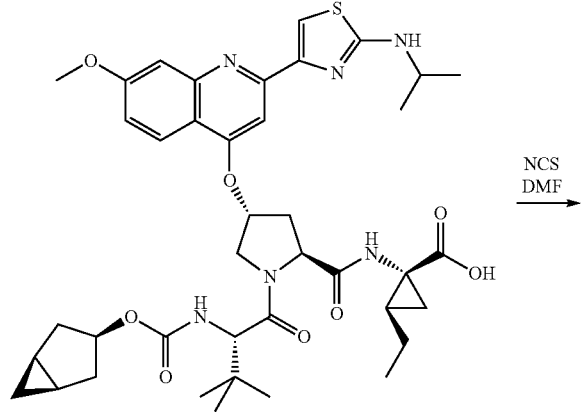

NCS
DMF
→

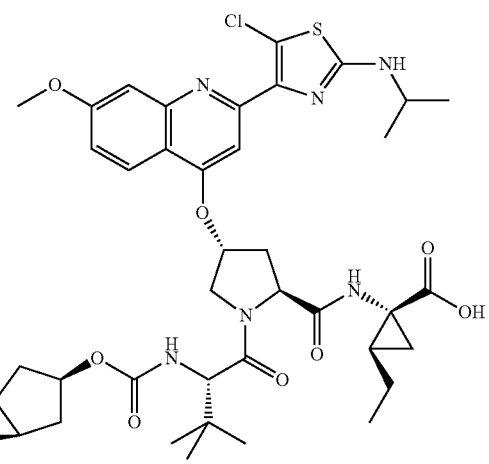

A solution of 89.5 mg (0.115 mmol) of acid and 15.5 mg (0.116 mmol) of N-chlorosuccinmide in 2 mL of DMF was stirred at 0° C. for 20 h and an additional 5 mg of N-chlorosuccinmide was added to the reaction. The resulting solution was stirred at 0° C. for 42 h. After the solution was filtered, the product was purified by repeated preparative HPLC and the purified product was freeze-dried to obtain 78.4 mg of the Compound 63. $^1$H NMR (300 MHz, $CD_3OD$): δ 8.63 (s, 1H), 8.30 (d, 1H, J=9.0 Hz), 7.87 (s, 1H), 7.74 (s, 1H), 7.38 (d, 1H, J=9.0 Hz), 5.76 (s, 1H), 4.62-4.74 (m, 2H), 4.55 (appt t, 1H, J=6.8 Hz), 4.13-4.24 (m, 2H), 4.05-4.13 (m, 1H), 4.06 (s, 3H), 2.75-2.85 (m, 1H), 2.55-2.67 (m, 1H), 1.82-2.05 (m, 2H), 1.60-1.72 (m, 3H), 1.37-1.58 (m, 3H), 1.32 (d, 6H, J=6.6 Hz), 1.14-1.27 (m, 3H), 0.95-1.06 (m, 12H), 0.35-0.44 (m, 2H); LC/MS=811 ($M^+$+1).

Example 64

Preparation of Compound 64

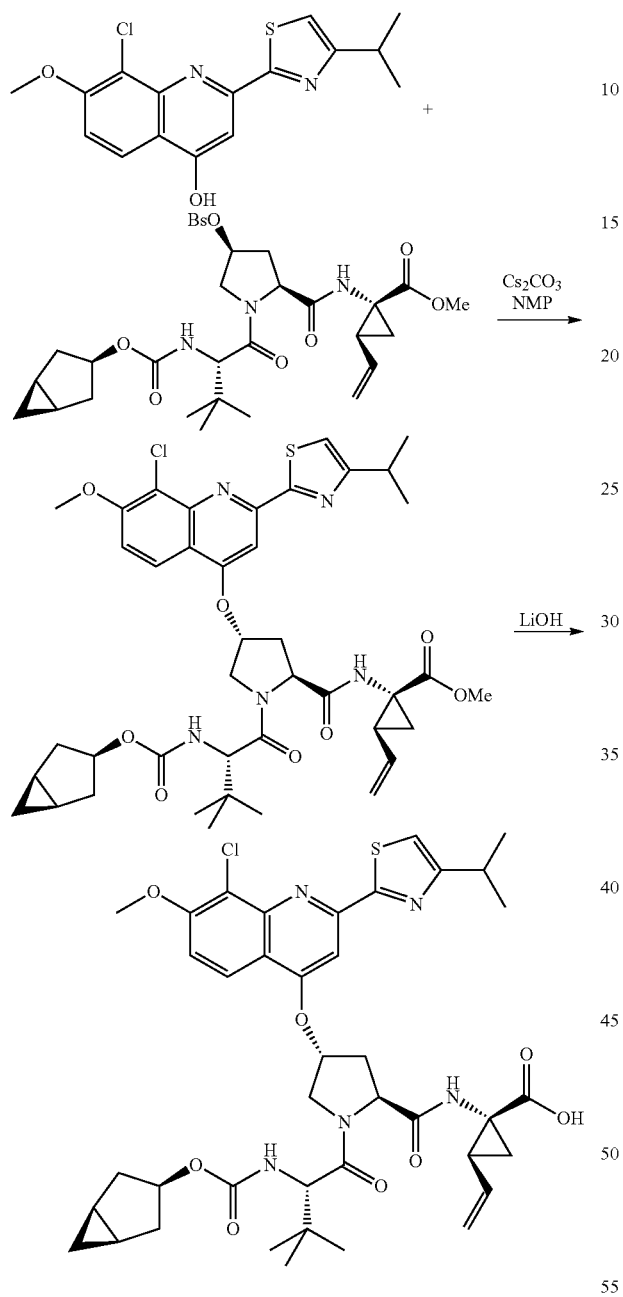

Step 1:

A mixture of 1.0 g (1.41 mmol) of the tripeptide, 448.9 mg (1.34 mmol) of quinoline, and 920 mg (2.82 mmol) of cesium carbonate in N-methylpyrrolidine was stirred in a 65° C. bath for 6 h. After the mixture was diluted with ethyl acetate (20 mL) and 5% aqueous LiCl solution (20 mL), the resulting mixture was stirred at room temperature for 30 min and the two phases were separated. The aqueous fraction was extracted with ethyl acetate (20 mL). The organic fractions were washed with water, combined, dried (MgSO₄), and concentrated. The residue was purified by silica gel chromatography using a hexane and ethyl acetate mixture as eluent, to give 864 mg (76%) of tripeptide with some impurities. LC/MS=808 (M⁺+1).

Step 2:

A mixture of 864 mg (1.07 mmol) of methyl ester and 128.5 mg (5.37 mmol) of LiOH in THF (5 mL), methanol (5 mL), and water (5 mL) was stirred at room temperature for 14.5 h. The reaction was concentrated to a half volume using a rotary evaporator. After the concentrated solution was acidified by adding 0.83 mL (10.77 mmol) of trifluoroacetic acid, the mixture was diluted with water (5 mL) and methanol (5 mL) and stirred in a 0° C. bath for 1 h. The solids were filtered, washed with water, and dried under vacuum. The solids were dissolved in a dioxane-acetonitrile-water mixture by heating and then freeze-dried to obtain 818 mg of compound 64. ¹H NMR (300 MHz, CD₃OD): δ 8.09 (d, 1H, J=9.3 Hz), 7.72 (s, 1H), 7.40 (d, 1H, J=9.3 Hz), 7.34 (s, 1H), 5.77-5.92 (m, 1H), 5.56 (s, 1H), 5.28 (d, 1H, J=18.0 Hz), 5.10 (d, 1H, J=10.2 Hz), 4.56-4.70 (m, 2H), 4.52 (m, 1H), 4.24 (br s, 1H), 4.00-4.16 (m, 2H), 4.06 (s, 3H), 3.23 (hept, 1H, J=6.6 Hz), 2.72-2.82 (m, 1H), 2.45-2.58 (m, 1H), 2.07-2.26 (m, 1H), 1.92-2.06 (m, 1H), 1.76-1.92 (m, 1H), 1.62-1.76 (m, 2H), 1.26-1.50 (m, 1H), 1.41 (d, 6H, J=6.6 Hz), 1.12-1.26 (m, 2H), 1.02 (m, 9H), 0.27-0.42 (m, 2H); LC/MS=794 (M⁺+1).

Example 65

Preparation of Compound 65

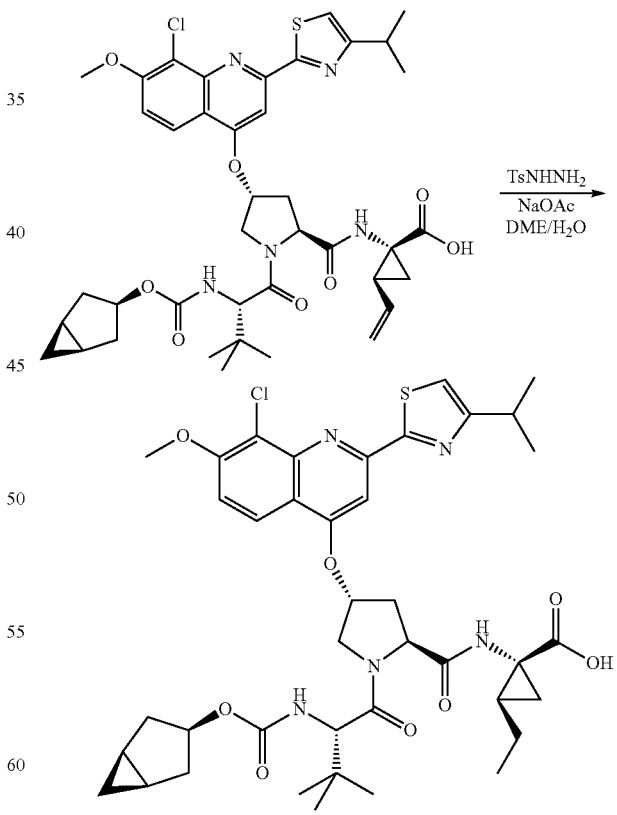

A mixture of 520.9 mg (0.573 mmol) of compound 64, 810 mg (4.35 mmol) of tosylhydrazide, and 707 mg (8.62 mmol) of sodium acetate in dimethoxyethane (10 mL) and water (1 mL) was stirred in a 95° C. bath for 1 h. The reaction mixture was diluted with water and a small amount of an aq. NaHCO$_3$ solution. This mixture was then extracted with ethyl acetate (×2). The combined extracts were dried (MgSO$_4$) and concentrated. The residue was triturated with 50% aq. Methanol at 0° C. for 1 h and the solids that formed were isolated by filtration. The solids were dissolved in a mixture of dioxane, acetonitrile, and water, acidified by adding 2-3 drops of trifluoroacetic acid, and freeze-dried to obtain 447 mg of compound 65. $^1$H NMR (300 MHz, CD$_3$OD): δ 8.07 (d, 1H, J=9.0 Hz), 7.70 (s, 1H), 7.39 (d, 1H, J=9.0 Hz), 7.34 (s, 1H), 5.54 (s, 1H), 4.56-4.69 (m, 2H), 4.51 (m, 1H), 4.23 (br s, 1H), 4.00-4.14 (m, 2H), 4.05 (s, 3H), 3.22 (hept, 1H, J=6.9 Hz), 2.68-2.80 (m, 1H), 2.40-2.58 (m, 1H), 1.93-2.06 (m, 1H), 1.78-1.93 (m, 1H), 1.58-1.72 (m, 3H), 1.37-1.58 (m, 1H), 1.41 (d, 6H, J=6.9 Hz), 1.27-1.37 (m, 1H), 1.10-1.27 (m, 3H), 0.94-1.10 (m, 12H), 0.27-0.42 (m, 2H); LC/MS=796 (M$^+$+1).

Example 66

Preparation of Compound 66

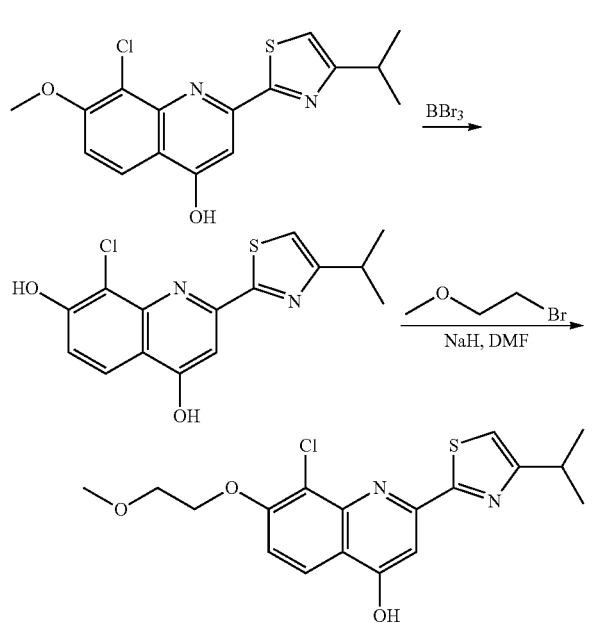

Step 1:

A solution of 2.721 g (8.13 mmol) of methyl ether in 100 mL of CH$_2$Cl$_2$ was stirred at room temperature. 42 mL (42 mmol) of BBr$_3$ in CH$_2$Cl$_2$ was then added. The resulting mixture was refluxed in a 50° C. bath for 5 h and then an additional 8.4 mL (8.4 mmol) of BBr$_3$ in CH$_2$Cl$_2$ was added. After 2 h of reflux, an additional 8.4 mL (8.4 mmol) of BBr$_3$ in CH$_2$Cl$_2$ was added and the resulting mixture was refluxed for 18 h. The resulting mixture was poured into 300 g of ice and the mixture was basified by adding ~18 g (~450 mmol) of NaOH. After the two phases were separated, the aqueous fraction was extracted with water (100 mL). The two aqueous fractions were washed with CH$_2$Cl$_2$, combined, and brought to pH ~6 using conc. HCl. The resulting mixture was stirred in an ice bath for 1 h and filtered. The solids were washed with water and dried. The solids were triturated in 100 mL water at room temperature for 1 h and the solids that formed were filtered and washed with water before drying under vacuum to obtain 2.566 g (98%) of bisphenol.

Step 2:

A mixture of 2.454 g (7.65 mmol) of bisphenol and 671 mg (16.78 mmol) of 60% NaH was placed in a 250 mL round bottom flask and 40 mL of DMF was added at 0° C. After the mixture was stirred at 0° C. for 30 min, 0.80 mL (8.51 mmol) of 2-bromoethyl methyl ether was added. The resulting mixture was stirred at 4° C. for 48 h and diluted with ethyl acetate (120 mL) and 5% aqueous LiCl solution (120 mL). After the mixture was adjusted to pH 4-6 with 1 N HCl and diluted with additional ethyl acetate (~1 L), the mixture was stirred at room temperature for 1 h. The upper organic fraction was separated from the lower aqueous fraction, which contained solids. The solids in the aqueous fraction were dissolved with ethyl acetate (1 L) and the organic fraction was separated. The two organic fractions were washed with water (1 L), combined, dried (MgSO$_4$) and concentrated. The residue was triturated with 200 mL of CH$_2$Cl$_2$ and the insoluble material was filtered. The filtrate was concentrated and purified by silica gel chromatography using with a mixture of hexane, ethyl acetate, and methanol as eluent, to obtain 732 mg of the quinoline. LC/MS=379 (M$^+$+1).

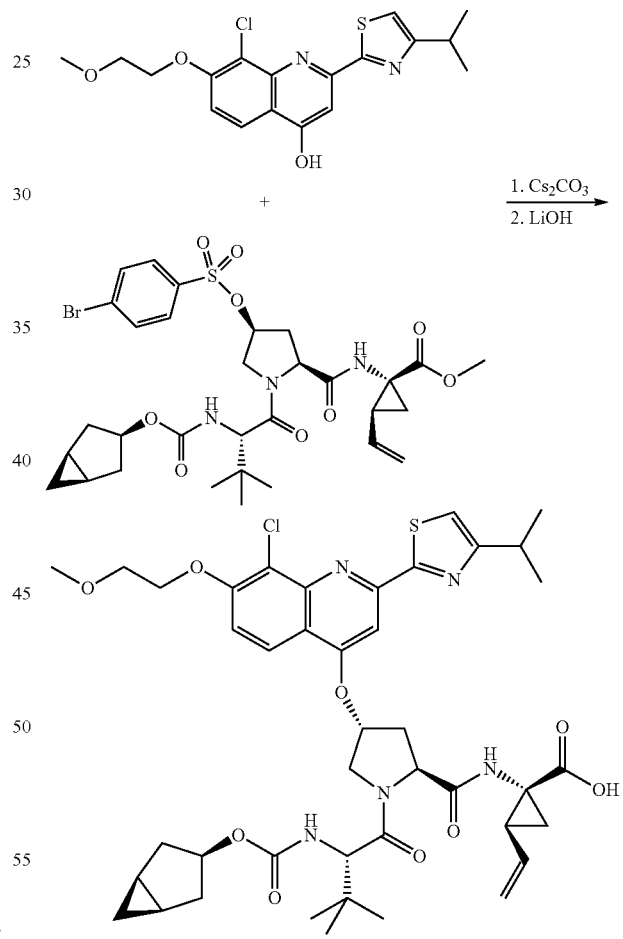

Step 3:

A mixture of 595 mg (0.837 mmol) of tripeptide, 300 mg (0.791 mmol) of quinoline, and 546 mg (1.68 mmol) of cesium carbonate in 4.2 mL of N-methylpyrrolidine was stirred in a 65° C. bath for 16.5 h. After the mixture was diluted with ethyl acetate (20 mL) and a 5% aqueous LiCl solution (20 mL), the resulting mixture was stirred at room temperature for 30 min and the two phases were separated.

363

The aqueous fraction was extracted with ethyl acetate (20 mL). The organic fractions were washed with water (×2), combined, dried (MgSO$_4$), and concentrated. The residue was purified by silica gel chromatography using with a mixture of hexane and ethyl acetate as eluent, to give 410 mg (61%) of the methyl ester with some impurities. LC/MS=852 (M$^+$+1).

Step 4:

A mixture of 410 mg (0.48 mmol) of ester and 115 mg (4.81 mmol) of LiOH in THF (2 mL), methanol (2 mL), and water (2 mL) was stirred at room temperature for 4 h and then concentrated. The residue was dissolved in DMF and acidified by adding 0.45 mL (5.84 mmol) of trifluoroacetic acid. The mixture was diluted with ethyl acetate (200 mL), washed with water (×2), dried (MgSO$_4$), and concentrated. The residue was dissolved in dioxane and freeze-dried to get 372 mg of compound 66. $^1$H NMR (300 MHz, CD$_3$OD): δ 8.73 (s, 1H), 8.08 (d, 1H, J=8.6 Hz), 7.73 (s, 1H), 7.41 (d, 1H, J=9.0 Hz), 7.34 (s, 1H), 5.76-5.94 (m, 1H), 5.56 (s, 1H), 5.28 (d, 1H, J=16.8 Hz), 5.10 (d, 1H, J=10.8 Hz), 4.57-4.70 (m, 2H), 4.52 (m, 1H), 4.38 (br m, 2H), 4.23 (br, 1H), 4.05-4.16 (m, 1H), 3.86 (br m, 2H), 3.49 (s, 3H), 3.23 (hept, 1H, J=6.6 Hz), 2.70-2.82 (m, 1H), 2.46-2.58 (m, 1H), 2.12-2.26 (m, 1H), 1.83-2.07 (m, 2H), 1.62-1.75 (m, 2H), 1.37-1.48 (m, 2H), 1.41 (d, 6H, J=6.6 Hz), 1.26-1.37 (m, 1H), 1.19 (br, 1H), 1.02 (s, 9H), 0.27-0.42 (m, 2H); LC/MS=838 (M$^+$+1).

Example 67

Preparation of Compound 67

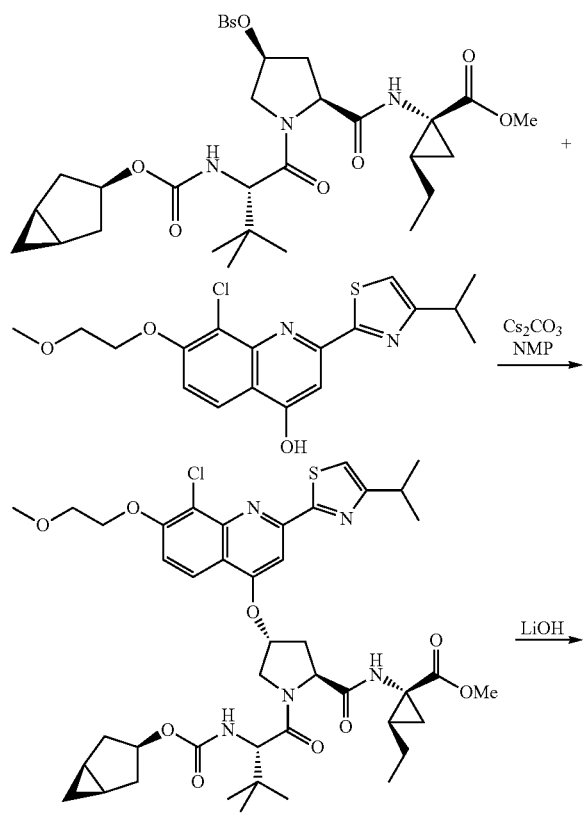

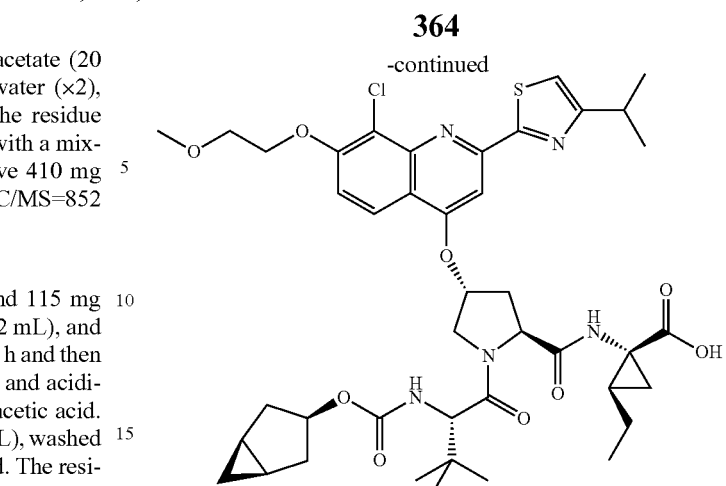

Step 1:

A mixture of 628 mg (0.881 mmol) of intermediate III, 317 mg (0.837 mmol) of quinoline, and 632 mg (1.94 mmol) of cesium carbonate in 4.4 mL of N-methylpyrrolidine was stirred in a 65° C. bath for 16 h. After the mixture was diluted with ethyl acetate (20 mL) and a 5% aqueous LiCl solution (20 mL), the resulting mixture was stirred at room temperature for 30 min and the two phases were separated. The aqueous fraction was extracted with ethyl acetate (20 mL). The organic fractions were washed with water (×2), combined, dried (MgSO$_4$), and concentrated. The residue was purified by silica gel chromatography using with a mixture of hexane and ethyl acetate as eluent, to give 504 mg (71%) of ester. LC/MS=854 (M$^+$+1).

Step 2:

A mixture of 504 mg (0.59 mmol) of ester and 71 mg (2.96 mmol) of LiOH in THF (2 mL), methanol (2 mL), and water (2 mL) was stirred at room temperature for 15 h. An additional 71 mg (2.96 mmol) of LiOH was added and the mixture was stirred at room temperature for 6 h. After the solution was concentrated, the residue was dissolved in ethyl acetate and acidified by adding trifluoroacetic acid. The solution was washed with water (×2), dried (MgSO$_4$), and concentrated. The residue was triturated in 50% aq. Methanol (5 mL) at 0° C. for 2 h and filtered. After the solids were washed with water, they were dried under vacuum to obtain 535 mg (95%) of compound 67. $^1$H NMR (300 MHz, CD$_3$OD): δ 8.09 (d, 1H, J=8.7 Hz), 7.74 (s, 1H), 7.42 (d, 1H, J=8.7 Hz), 7.37 (s, 1H), 5.57 (s, 1H), 4.48-4.70 (m, 3H), 4.39 (m, 2H), 4.22 (m, 1H), 4.04-4.16 (m, 1H), 3.86 (m, 2H), 3.49 (s, 3H), 3.23 (hept, 1H, J=6.9 Hz), 2.69-2.82 (m, 1H), 2.46-2.60 (m, 1H), 1.76-2.08 (m, 2H), 1.27-1.76 (m, 6H), 1.41 (d, 6H, J=6.9 Hz), 1.22 (m, 3H), 1.01 (s, 9H), 0.90-1.10 (m, 3H), 0.28-0.42 (m, 2H); LC/MS=840 (M$^+$+1).

Example 68

Preparation of Compound 68

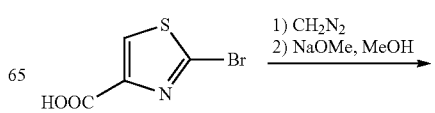

-continued

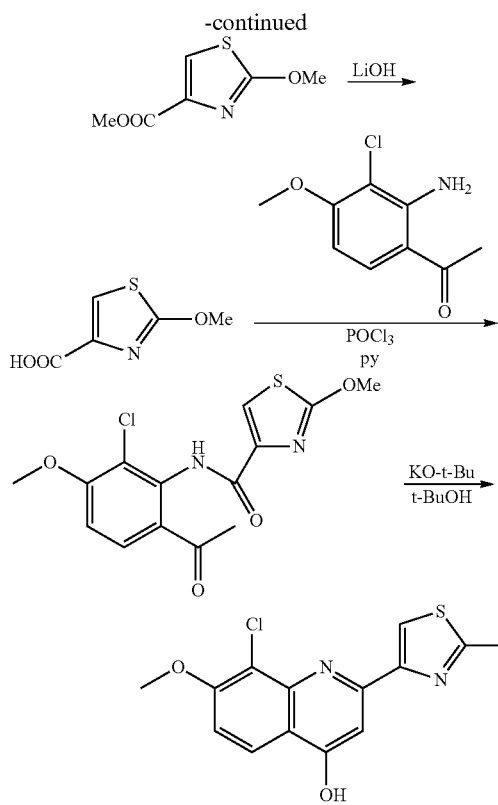

Step 1:

A slurry of 2.000 g (9.62 mmol) of acid in methanol (20 mL) and toluene (20 mL) was stirred at 0° C. as 8 mL (16 mmol) of 2.0 M TMSCHN$_2$ in ether was added dropwise. After 30 min at 0° C. and 10 min at room temperature, the solution was concentrated at using a rotary evaporator with the bath temp <30° C., and the residue was further dried under vacuum. To the residue in methanol (15 mL) was added 3.75 mL (16.4 mmol) of 25% sodium methoxide in methanol and the resulting solution was refluxed in a 70° C. bath for 1 h. After the solution was concentrated, the residue was adsorbed on silica gel and purified by chromatography to obtain 997 mg of ester. LC/MS=174 (M$^+$+1).

Step 2:

A solution of 992 mg of ester and 274 mg (11.44 mmol) of LiOH in THF (9 mL), methanol (3 mL) and water (3 mL) was stirred at room temperature for 30 min. The mixture was concentrated to ~⅓ volume, diluted with water (25 mL) and then extracted with ethyl acetate (25 mL). The organic washing was extracted with water (1×25 mL). The aqueous fractions were combined and acidified with 1 N HCl (15 mL) and the product was extracted with ethyl acetate (3×30 mL). The combined extracts were dried (MgSO$_4$) and concentrated to afford 835 mg (92%) of acid. LC/MS=160 (M$^+$+1).

Step 3:

A solution of 824 mg of acid and 274 mg (5.18 mmol) of LiOH in pyridine (50 mL) was stirred at −30 min. The resulting mixture was stirred in a freezer for 2.5 h and then quenched with 2.5 mL of water and concentrated. The residue was dissolved in ethyl acetate and a saturated aq. NaHCO$_3$ solution. The aqueous fraction was extracted with water (1×1). The aqueous fractions were dried (MgSO$_4$) and concentrated. The residue was purified by silica gel chromatography to obtain 495 mg (28%) of acid. LC/MS=341 (M$^+$+1).

Step 4:

A mixture of 495 mg (1.45 mmol) of amide and 350 mg (3.12 mmol) of potassium tert-butoxide in tert-BuOH (7.3 mL) was stirred at 75° C. for 7.5 h. The mixture was concentrated after 1.5 mL (6 mmol) of 4 N HCl in dioxane was added. The residue was triturated with 1 N NaH$_2$PO$_4$ (25 mL) at room temperature for 1 h and filtered. The solids were washed with water and then ether, and dried in vacuum to obtain 423 mg of quinoline. LC/MS=323 (M$^+$+1).

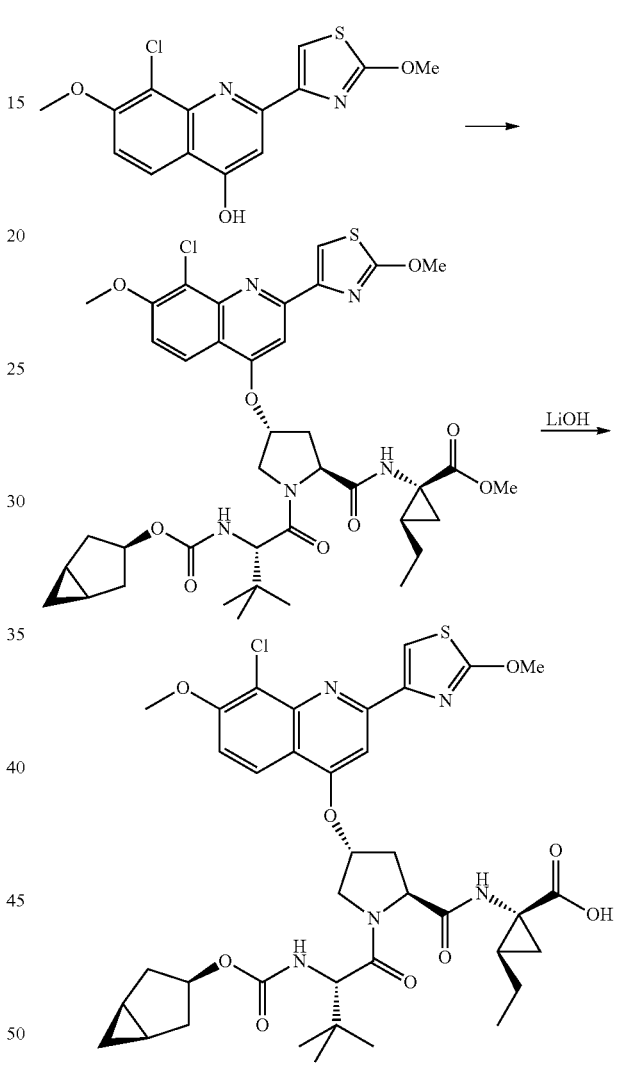

Step 5:

A mixture of 302 mg (0.424 mmol) of tripeptide, 130 mg (0.402 mmol) of quinoline, and 304 mg (0.932 mmol) of cesium carbonate in 3 mL of N-methylpyrrolidine was stirred in a 65° C. bath for 16 h. After the mixture was diluted with ethyl acetate (15 mL) and a 5% aqueous LiCl solution (15 mL), the resulting mixture was stirred at room temperature for 30 min and the two phases were separated after further dilution with water and ethyl acetate. The organic fraction was washed with water (×1), dried (MgSO$_4$), and concentrated. The residue was purified by silica gel chromatography using with a mixture of hexane and ethyl acetate as eluent, to give 199 mg (62%) of ester with some impurities. LC/MS=798 (M$^+$+1).

Step 5:

A mixture of 302 mg (0.424 mmol) of intermediate III, 130 mg (0.402 mmol) of quinoline, and 304 mg (0.932 mmol) of cesium carbonate in 3 mL of N-methylpyrrolidine was stirred at 65° C. bath for 16 h. After the mixture was diluted with ethyl acetate (15 mL) and 5% aqueous LiCl solution (15 mL), the resulting mixture was stirred at room temperature for 30 min and the two phases were separated after further dilution with water and ethyl acetate. The organic fraction was washed with water (×1), dried (MgSO$_4$), and concentrated. The residue was purified by chromatography using combi-flash with hexane-ethyl acetate to give 199 mg (62%) of ester with some impurities. LC/MS=798 (M$^+$+1).

A mixture of 199 mg (0.25 mmol) of ester and 59 mg (2.48 mmol) of LiOH in THF (4 mL), methanol (2 mL), and water (2 mL) was stirred at room temperature for 20 h and concentrated. The residue was dissolved in ethyl acetate and water, and acidified by adding 0.3 mL (4.04 mmol) of trifluoroacetic acid. After the two phases were separated, the aqueous fraction was extracted with ethyl acetate. After the combined organic fractions were dried (MgSO$_4$) and concentrated, the residue was purified by preparative HPLC to obtain 132 mg of compound 68. $^1$H NMR (300 MHz, CD$_3$OD): δ 8.48 (s, 1H), 8.08 (d, 1H, J=9.6 Hz), 7.86 (s, 1H), 7.63 (d, 1H, J=9.6 Hz), 5.76 (br, 1H), 4.76 (m, 1H), 4.60 (m, 1H), 4.45 (t, 1H), 4.31 (s, 3H), 4.17 (s, 3H), 4.15 (m, 1H), 4.03-4.12 (m, 1H), 2.74-2.85 (m, 1H), 2.55-2.67 (m, 1H), 1.86-2.02 (m, 1H), 1.74-1.86 (m, 1H), 1.28-1.74 (m, 6H), 1.12-1.28 (m, 3H), 1.02 (m, 9H), 0.96-1.12 (m, 3H), 0.30-0.44 (m, 2H); LC/MS=784 (M$^+$+1).

Example 69

Preparation of Compound 69

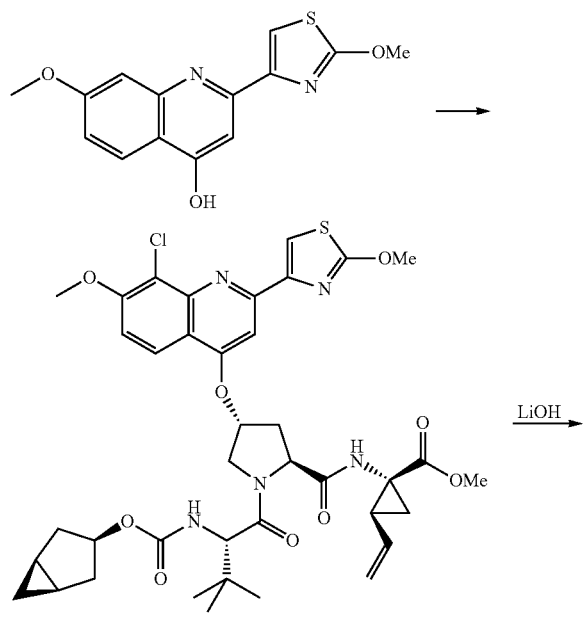

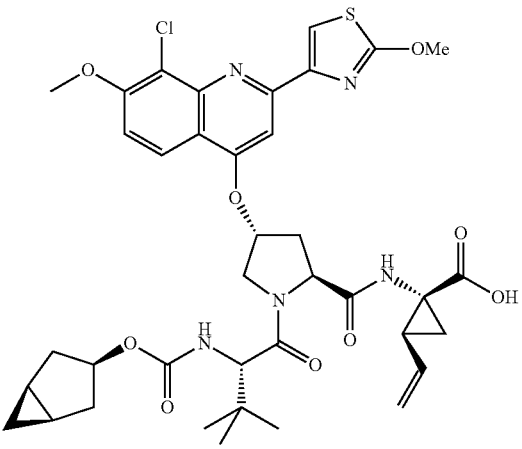

A mixture of 101 mg (0.142 mmol) of the tripeptide, 44 mg (0.136 mmol) of quinoline, and 104 mg (0.320 mmol) of cesium carbonate in 1 mL of N-methylpyrrolidine was stirred in a 65° C. bath for 16 h. After the mixture was diluted with ethyl acetate (5 mL) and a 5% aqueous LiCl solution (5 mL), the resulting mixture was stirred at room temperature for 30 min. The two phases were separated after further dilution with water and ethyl acetate. The organic fraction was washed with water (×1), dried (MgSO$_4$), and concentrated. The residue was purified by silica gel chromatography using with a mixture of hexane and ethyl acetate as eluent, to give 71 mg of the ester with some impurities. LC/MS=796 (M$^+$+1).

A mixture of 71 mg (0.090 mmol) of ester and 21 mg (0.881 mmol) of LiOH in THF (2 mL), methanol (1 mL), and water (1 mL) was stirred at room temperature for 5 h and then concentrated. The residue was dissolved in ethyl acetate and water, and acidified by adding 0.1 mL of trifluoroacetic acid. After the two phases were separated, the aqueous fraction was extracted with ethyl acetate. After the combined organic fractions were dried (MgSO$_4$) and concentrated, the residue was purified by preparative HPLC to obtain 54 mg of compound 69. $^1$H NMR (300 MHz, CD$_3$OD): δ 8.75 (s, 1H), 8.48 (s, 1H), 8.31 (d, 1H, J=9.6 Hz), 7.86 (s, 1H), 7.63 (d, 1H, J=9.0 Hz), 5.86 (m, 1H), 5.77 (br, 1H), 5.29 (d, 1H, J=17.1 Hz), 5.12 (d, 1H, J=10.8 Hz), 4.73 (m, 1H), 4.60 (m, 1H),), 4.45 (m, 1H), 4.31 (s, 3H), 4.17 (s, 3H), 4.15 (m, 1H), 4.05-4.13 (m, 1H), 2.74-2.92 (m, 1H), 2.54-2.66 (m, 1H), 2.14-2.27 (m, 1H), 1.87-2.02 (m, 2H), 1.76-1.87 (m, 1H), 1.69-1.76 (m, 1H), 1.63 (m, 1H), 1.42-1.50 (m, 1H), 1.28-1.42 (m, 1H), 1.19 (br, 1H), 1.03 (m, 9H), 0.30-0.44 (m, 2H); LC/MS=782 (M$^+$+1).

Example 70

Preparation of Compound 70

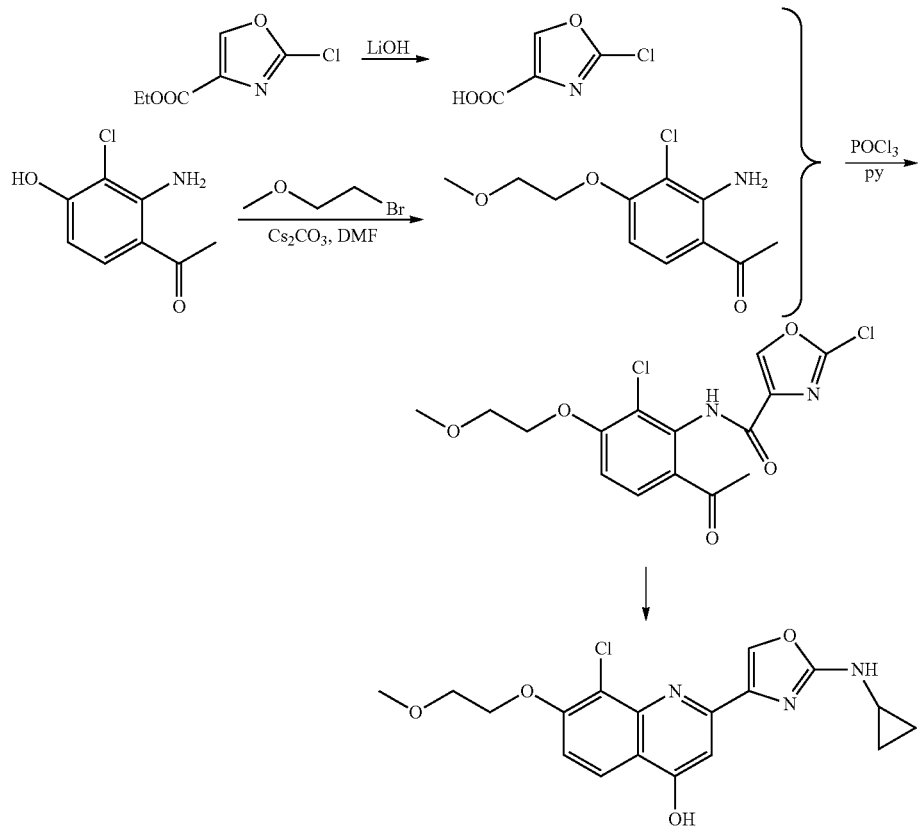

Step 1:

A solution of 7.413 g (42.22 mmol) of ester in THF (45 mL) was stirred in a 0° C. bath as 1 N LiOH (45 mL) was added over 30 min. After addition, the solution was stirred at 0° C. for 2 h and acidified by adding 13 mL (52 mmol) of 4 N HCl. The resulting mixture was concentrated to a half volume under reduced pressure. After the concentrated mixture was diluted with water, the product was extracted with ethyl acetate (100 mL×2). The extracts were combined, washed with brine (50 mL×1), dried (MgSO$_4$), and concentrated to afford 5.972 (96%) of acid.

Step 2:

A mixture of 3.345 g (18.02 mmol) of crude phenol and 7.055 g (21.65 mmol) of cesium carbonate in DMF (30 mL) was stirred at room temperature as 1.9 mL (20.22 mmol) of 2-bromoethyl methyl ether was added. The mixture was stirred at 65° C. for 5 h and diluted with ethyl acetate (500 mL) and 5% aq. LiCl (250 mL). After the two layers were separated, the aqueous fraction was extracted with ethyl acetate (300 mL) and the organic fractions were washed with water (300 mL), the organics were combined, dried (MgSO$_4$), and concentrated. The residue was purified by silica gel chromatography using a mixture of hexane and ethyl acetate as eluent, to give 3.611 g (82%) of aniline. LC/MS=244 (M$^+$+1).

Step 3:

A mixture of 778 mg (5.28 mmol) of acid and 1.157 g (4.75 mmol) of aniline in DMF (30 mL) was stirred in a −25° C. bath as 1.9 mL (5.90 mmol) of POCl$_3$ was added. The mixture was stirred in a −5~−15° C. for 3 h and then 2.5 mL) and 5% aq. LiCl (250 mL). After 5 min, the mixture was concentrated. The residue was purified by silica gel chromatography using with a mixture of hexane, and ethyl acetate as eluent, to give 1.131 g (64%) of amide LC/MS=373 (M$^+$+1).

Step 4:

A mixture of 1.031 g (2.76 mmol) of amide in THF (9.5 mL) and cyclopropylamine (1.9 mL, 27.42 mmol) was placed in a pressure tube, stirred in a 65° C. bath for 5 h, and concentrated. After the residue was combined with water and the mixture was stirred at room temperature for 24 h and then diluted with a saturated aq. NaHCO3 solution (50 mL). The product was then extracted with ethyl acetate (100 mL×2). The organic extracts were combined, washed with water (100 mL), dried (MgSO$_4$) and concentrated, the product was purified by silica gel chromatography using with a mixture of hexane and ethyl acetate as eluent, to give 769 mg (71%) of amine. LC/MS=394 (M$^+$+1).

Step 5:

A suspension of 767 mg (1.95 mmol) of amine and 119 mg (2.98 mmol) of NaH (60% dispersion in mineral oil) in toluene (11.5 mL) was refluxed at 110° C. bath for 3 h before an additional 41 mg (1.03 mmol) of 60% NaH was added. After 2 h of reflux, an additional 80 mg (2.0 mmol) of 60% NaH was added and the mixture was refluxed for 1 h and then cooled to room temperature. To the suspension was added a solution of 0.38 mL (6.64 mmol) of acetic acid in 2.3 mL water and the resulting mixture was stirred in a 0° C. bath for 30 min and filtered. The collected solids were washed with water and dried under vacuum to get 612 mg (84%) of quinoline. LC/MS=376 (M$^+$+1).

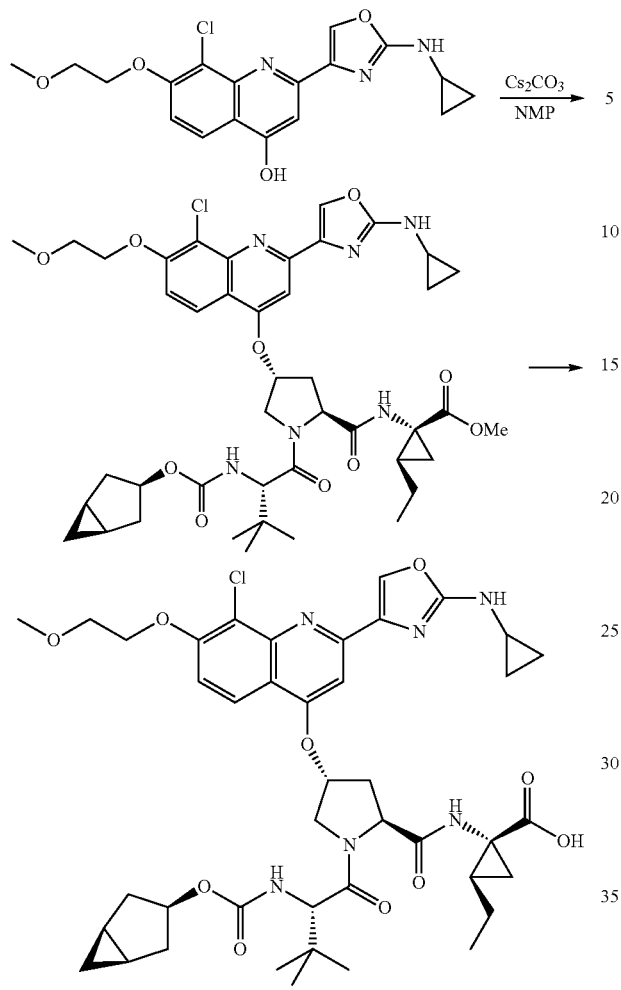

Step 6:

A mixture of 663 mg (0.930 mmol) of tripeptide III, 332 mg (0.883 mmol) of quinoline, and 674 mg (2.07 mmol) of cesium carbonate in 6.6 mL of N-methylpyrrolidine was stirred in a 65° C. bath for 16 h. After the mixture was diluted with ethyl acetate (15 mL) and a 5% aqueous LiCl solution (26 mL), the resulting mixture was stirred at room temperature for 30 min, additional 5% aqueous LiCl solution and ethyl acetate were added and the two phases were separated. The aqueous fraction was extracted with ethyl acetate (×1) and two organic fractions were washed with water (×1), combined, dried (MgSO$_4$), and concentrated. The residue was purified by silica gel chromatography using a mixture of hexane and ethyl acetate as eluent, to give 359 mg of ester compound. LC/MS=851 (M$^+$+1).

Step 7:

A mixture of 359 mg (0.423 mmol) of ester and 200 mg (8.35 mmol) of LiOH in THF (5 mL), methanol (5 mL), and water (5 mL) was stirred at room temperature for 16 h. After the solution was acidified by adding trifluoroacetic acid, the mixture was concentrated. The residue was dissolved in ethyl acetate, washed with water, dried (MgSO$_4$), and concentrated. The residue was purified by silica gel chromatography, using a mixture of hexane and ethyl acetate as eluent, and the collected product was freeze-dried with trifluoroacetic acid to give 261 mg of compound 70. $^1$H NMR (300 MHz, CD$_3$OD): δ 8.66 (s, 1H), 8.27 (d, 1H, J=9.7 Hz), 7.70 (s, 1H), 7.64 (d, 1H, J=9.7 Hz), 5.68 (s, 1H), 4.35-4.78 (m, 4H), 4.02-4.20 (m, 2H), 3.87 (br, 2H), 3.47 (s, 3H), 2.4-2.9 (m, 2H), 1.89-2.04 (m, 1H), 1.77-1.89 (m, 1H), 1.28-1.77 (m, 4H), 1.23 (m, 3H), 0.94-1.11 (m, 12H), 0.85-0.94 (m, 2H), 0.70 (br, 2H), 0.28-0.44 (m, 2H); LC/MS=837 (M$^+$+1).

Example 71

Preparation of Compound 71

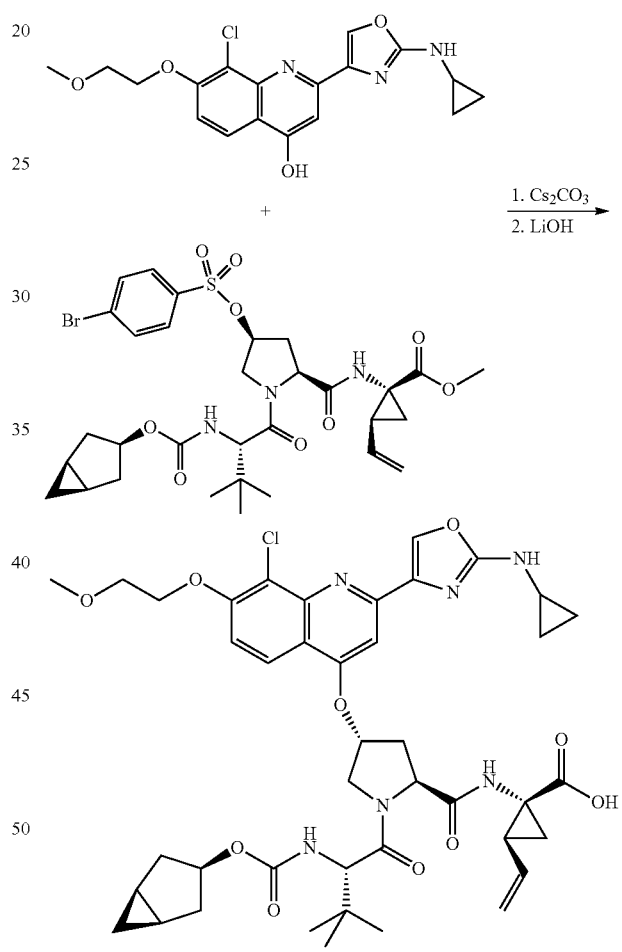

A mixture of 557 mg (0.784 mmol) of tripeptide, 279 mg (0.741 mmol) of the quinoline, and 563 mg (1.73 mmol) of cesium carbonate in 5.6 mL of N-methylpyrrolidine was stirred in a 65° C. bath for 16 h. The reaction mixture was cooled to room temperature, and diluted with ethyl acetate (5 mL) and a 5% aqueous LiCl solution (20 mL). The resulting mixture was stirred at room temperature for 30 min and the two phases were separated after further dilution with a 5% aqueous LiCl solution (30 mL) and ethyl acetate (50 mL). The aqueous fraction was extracted with ethyl acetate (×1) and two organic fractions were washed with water (×1), combined, dried (MgSO$_4$), and concentrated. The residue was purified by silica gel chromatography, using a mixture of hexane and ethyl acetate as eluent, to give 288 mg (46%) of ester. LC/MS=849 (M$^+$+1).

A mixture of 288 mg (0.339 mmol) of the ester and 41 mg (1.71 mmol) of LiOH in THF (4 mL), methanol (4 mL), and water (4 mL) was stirred at room temperature for 16 h. After the solution was acidified by adding trifluoroacetic acid, the mixture was concentrated. The residue was dissolved in ethyl acetate, washed with water, dried (MgSO$_4$), and concentrated. The residue was purified by silica gel chromatography, using a mixture of hexane and ethyl acetate as eluent, and the collected product was freeze-dried with trifluoroacetic acid to give 238 mg of compound 71. $^1$H NMR (300 MHz, CD$_3$OD): δ 8.58 (s, 1H), 8.24 (d, 1H, J=8.7 Hz), 7.64 (s, 1H), 7.60 (d, 1H, J=8.7 Hz), 5.77-5.96 (m, 1H), 5.66 (s, 1H), 5.29 (d, 1H, J=17.4 Hz), 5.11 (d, 1H, J=9.9 Hz), 4.71 (m, 1H), 4.42-4.62 (m, 3H), 4.04-4.20 (m, 2H), 3.87 (br, 2H), 3.47 (s, 3H), 2.54-2.88 (m, 2H), 2.10-2.30 (m, 1H), 1.55-2.06 (m, 5H), 1.27-1.50 (m, 3H), 1.21 (m, 3H), 1.03 (m, 9H), 0.80-0.93 (m, 2H), 0.69 (br, 2H), 0.30-0.44 (m, 2H); LC/MS=835 (M$^+$+1).

Example 72

Preparation of Compound 72

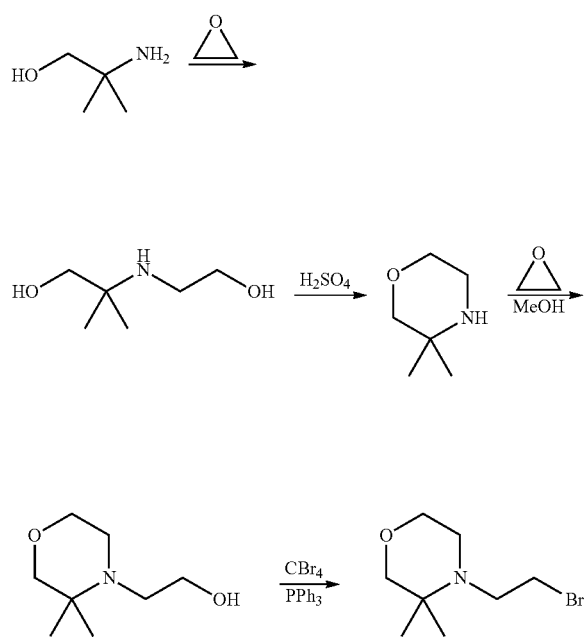

Step 1:

2-(2-Hydroxy-ethylamino)-2-methyl-propan-1-ol was prepared from 2-amino-2-methyl-propan-1-ol following a modified procedure from Cottle et al. *J. Chem. Soc.* 1946, 289. To a solution of 2-amino-2-methyl-propan-1-ol (250 mL, 2.61 mol, 1.76 equiv.) in H$_2$O (400 mL) at −5° C. (external temperature, NaCl/ice bath) was added ethylene oxide (65.25 g, 1.48 mol, condensed at −78° C.). The solution was stirred over 16 hours, during which time the temperature warmed to room temperature. The H$_2$O was removed in vacuo and the remaining 2-amino-2-methyl-propan-1-ol was distilled. The crude residue was dissolved in boiling EtOAc and precipitated with the addition of hexanes to provide 2-(2-Hydroxy-ethylamino)-2-methyl-propan-1-ol (145.5 g, 74%) as colorless crystals. LC/MS found 134.03 (M$^+$+H, C$_6$H$_{16}$NO$_2$ requires 134.12).

Step 2:

3,3-Dimethylmorpholine was prepared from 2-(2-Hydroxy-ethylamino)-2-methyl-propan-1-ol following a modified procedure from Cottle et al. *J. Chem. Soc.* 1946, 289. To H$_2$SO$_4$ (110 mL, 2.06 mol, 1.85 equiv.) at 3° C. (internal temperature, ice bath) was slowly added 2-(2-Hydroxy-ethylamino)-2-methyl-propan-1-ol (145.5 g, 1.09 mol) in portions. The internal temperature of the reaction rose to 70° C. The resulting solution was heated to 185° C. (internal temperature, oil bath) for 2 hours, during which time the solution turns brown. Upon cooling to room temperature, H$_2$O (250 mL) was added followed by the slow addition of solid NaOH until the pH of the solution was basic. The solution was diluted with EtOAc (500 mL) and the biphasic mixture was stirred vigorously for 15 hours. The solution was then filtered through celite and washed with H$_2$O and EtOAc. The organic layer was separated and washed with brine. The aqueous layers were twice back-extracted with EtOAc. The resulting organic layers were combined, dried over Na$_2$SO$_4$ and concentrated in vacuo (pressure >80 torr). The crude product was distilled (76° C., 98 torr) to provide 3,3-dimethylmorpholine (46.0 g, 36%) as a colorless oil. LC/MS found 116.04 (M$^+$+H, C$_6$H$_{14}$NO requires 116.11).

Step 3:

In a pressure vessel containing 3,3-dimethylmorpholine (12.15 g, 106 mmol) in MeOH (17 mL) at −78° C. (external temperature, acetone/CO$_2$(s)) was added ethylene oxide (6.2 mL, 125 mmol, 1.2 equiv., condensed at −78° C.). The solution was sealed and stirred over 20 hours, during which time the temperature warmed to room temperature. The reaction mixture was concentrated in vacuo and the crude product was distilled (75° C., 0.5 torr) to provide 2-(3,3-dimethyl-morpholin-4-yl)-ethanol (14 g, 82%) as a colorless oil contaminated with ~15% of 3,3-dimethyl-morpholine. LC/MS found 160.10 (M$^+$+H, C$_8$H$_{18}$NO$_2$ requires 160.13).

Step 4:

To a solution of 2-(3,3-dimethyl-morpholin-4-yl)-ethanol (7.2 g, 45 mmol) and CBr$_4$ (16.4 g, 49 mmol, 1.1 equiv.) in THF (150 mL) was added dropwise a solution of PPh$_3$ (12.9 g, 49 mmol, 1.1 equiv.) in THF (75 mL). The resulting slurry was stirred at room temperature for 19 hours, at which time the slurry was diluted with hexanes and filtered. The filtrate was concentrated in vacuo and the resulting oil was diluted with CH$_2$Cl$_2$. The solution was then washed twice with NaHCO$_3$ (aqueous, saturated) and brine. The aqueous layers were back-extracted with CH$_2$Cl$_2$ and the combined organic layers were dried over Na$_2$SO$_4$ and concentrated. The crude product was distilled (65° C., 0.5 torr) to provide 4-(2-Bromo-ethyl)-3,3-dimethyl-morpholine (5.4 g, 54%) as a yellow oil. $^1$H NMR (CDCl$_3$, 400 MHz) δ 3.69 (t, 2H), 3.28 (s, 2H), 3.28 (t, 2H), 2.70 (t, 2H), 2.58 (t, 2H), 0.99 (s, 6H); LC/MS found 222.02 (M$^+$+H, C$_8$H$_{17}$BrNO requires 222.05).

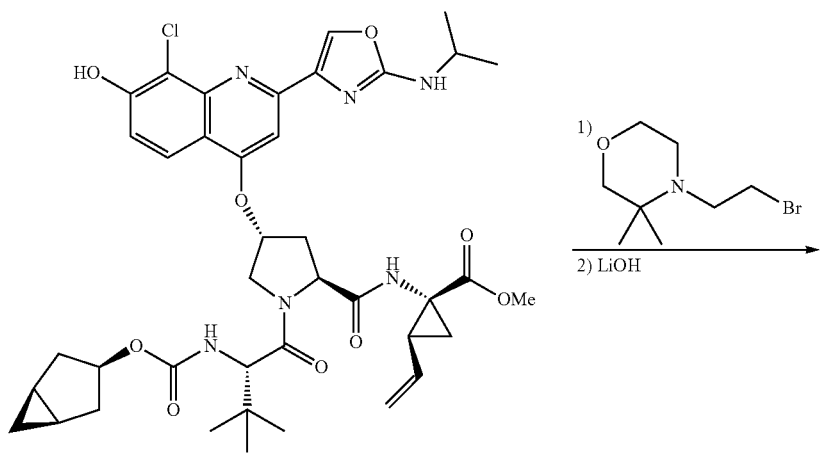

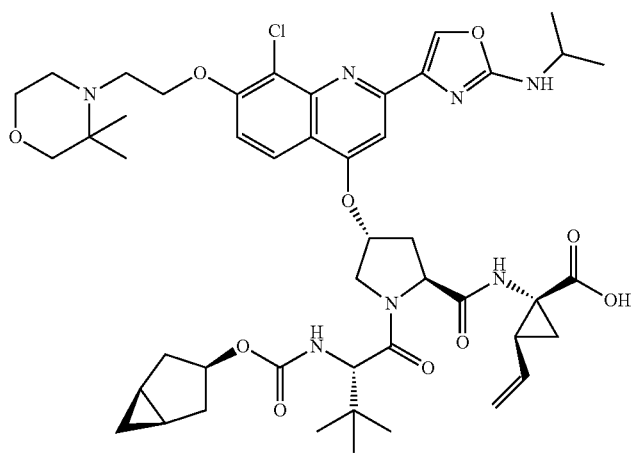

Step 5:

To a solution of tripeptide intermediate (504 mg, 0.63 mmol) in DMF (6 mL) was added 4-(2-Bromo-ethyl)-3,3-dimethyl-morpholine (165 mg, 0.74 mmol, 1.2 equiv) and Cs$_2$CO$_3$ (520 mg, 1.59 mmol, 2.5 equiv.). The slurry was heated to 50° C. (external temperature, oil bath) for 45 min. Additional 4-(2-Bromo-ethyl)-3,3-dimethyl-morpholine (410 mg, 1.84 mmol, 3 equiv.) was added in portions until the reaction was judged complete by HPLC. The reaction mixture was cooled to room temperature, diluted with EtOAc, and washed with brine. The aqueous layer was back-extracted with EtOAc and the combined organic layers were dried over Na$_2$SO$_4$ and concentrated in vacuo. The crude product was dissolved in a mixture of THF (4 mL) and MeOH (1.2 mL), to which was added LiOH (1N (aqueous), 3.2 mL, 5 equiv.). The slurry was stirred at room temperature for 12 hours, at which time HCl (1N, 3.2 mL) was added and the solution was concentrated in vacuo. The crude product was purified by reverse phase HPLC (30 to 95% MeCN/H$_2$O/0.1% TFA) to provide compound 72 (498 mg, 85%) as a yellow powder. $^1$H NMR (d$_3$-MeOD, 400 MHz, 4:1 mixture of rotomers) Major rotomer): δ 8.70 (s, 1H), 8.43 (s, 1H), 8.26 (d, 1H), 7.50 (s, 1H), 7.52 (d, 1H), 5.86 (dt, 1H), 5.59 (s, 1H), 5.28 (dd, 1H), 5.10 (dd, 1H), 4.69 (m, 3H), 4.48 (d, 1H), 3.95-4.21 (m, 4H), 3.75 (m, 3H), 2.67 (m, 3H), 2.17 (m, 1H), 2.04 (m, 1H), 1.94 (m, 1H), 1.84 (m, 1H), 1.65-1.73 (m, 2H), 1.53 (s, 6H), 1.43-1.53 (m, 2H), 1.40 (m, 1H) 1.35 (s, 3H), 1.33 (s, 3H), 1.21-1.27 (m, 2H), 1.06 (m, 2H), 1.04 (s, 9H), 0.39 (m, 2H); LC/MS found 920.15 (M$^+$+H, C$_{47}$H$_{63}$ClN$_7$O$_{10}$ requires 920.43).

Example 73

Preparation of Compound 73

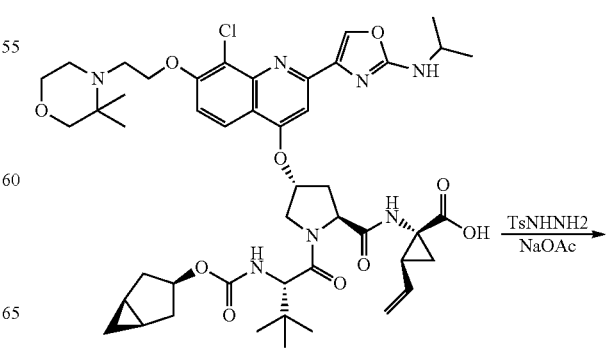

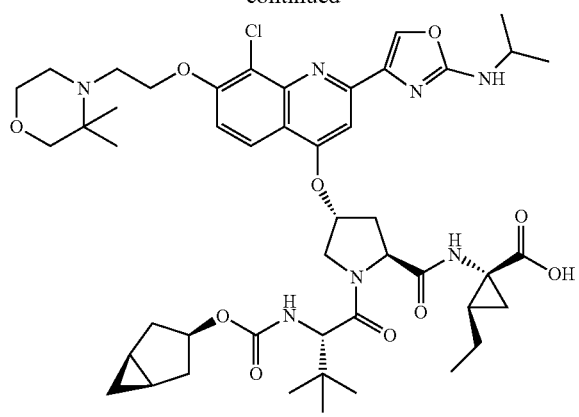

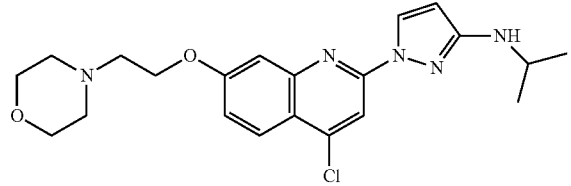

To a solution of compound 72 (164 mg, 0.18 mmol) in DME (3.6 mL) and H$_2$O (0.4 mL) was added p-toluenesulfonyl hydrazide (251 mg, 1.35 mmol, 7.5 equiv.) and NaOAc (221 mg, 2.69 mmol, 15 equiv.). The reaction mixture was heated to 95° C. (external temperature, oil bath) for 1.25 hours. The solution was cooled to room temperature and diluted with MeOH and filtered. The filtrate was purified by reverse phase HPLC (20 to 65% MeCN/H$_2$O/0.1% TFA) to provide compound 73 (35 mg, 21%) as a yellow powder. $^1$H NMR (d$_3$-MeOD, 400 MHz, 4:1 mixture of rotomers) Major rotomer□: δ 8.59 rotomer (s, 1H), 8.43 (s, 1H), 8.25 (d, 1H), 7.53 (s, 1H), 7.50 (d, 1H), 5.59 (s, 1H), 4.66 (m, 3H), 4.47 (d, 1H), 3.95-4.21 (m, 4H), 3.75 (m, 4H), 2.67 (m, 4H), 2.22 (m, 2H), 2.01 (m, 1H), 1.91 (m, 1H), 1.65-1.73 (m, 4H), 1.53 (s, 6H), 1.43-1.53 (m, 4H), 1.35 (s, 3H), 1.33 (s, 3H), 1.21-1.27 (m, 3H), 1.04 (s, 9H), 0.39 (m, 2H); LC/MS found 922.15 (M$^+$+H, C$_{47}$H$_{65}$ClN$_7$O$_{10}$ requires 922.45).

Example 74

Preparation of Compound 74

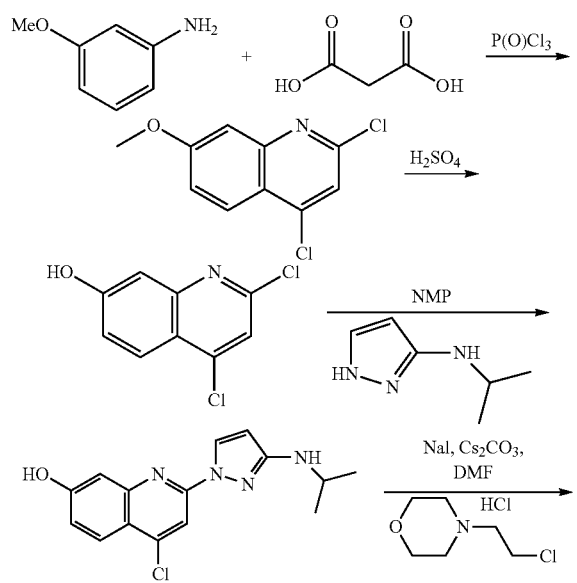

Step 1:

To a three neck flask fitted with an overhead stirrer and reflux condenser was added malonic acid (25.4 g, 244 mmol) and m-anisidine (27 mL, 244 mmol). Phosphorous oxychloride (33.5 mL, 366 mmol) was then added in portions. After gas evolution ceased, the slurry was slowly heated to 95° C. and stirred for 30 min. The resultant foam was then cooled to room temperature and phosphorous oxychloride (100 mL, 732 mmol) was added. The mixture was heated to 120° C. and stirred for 3 h. After being cooled in an ice-bath, ice-water was slowly added to quench the remaining phosphorous oxychloride, followed by 5N NaOH, until the solution reached pH=8. The mixture was then diluted with ethyl acetate and the organic layer was collected. The organic phase then washed with water and brine. After drying over sodium sulfate and being concentrated, the crude residue was purified by column chromatography on silica (CH$_2$Cl$_2$) to provide the dichloride.

Step 2:

The dichloride was dissolved in sulfuric acid (150 mL) and heated in a 160° C. oil bath for 2 h. After cooling to room temperature the mixture was poured into ice-cold water. The suspension was diluted with ethyl acetate then the organic phase was washed with water and saturated aqueous NaHCO$_3$. The organic phase was then dried over sodium sulfate and concentrated to afford phenol (18.4 g, 35% over two steps).

Step 3:

To phenol (2.13 g, 9.95 mmol) in 1-methyl2-pyrollidinone (5 mL) was added pyrazole (1.37 g, 10.9 mmol) and the mixture was heated to 115° C. overnight. After cooling to room temperature the reaction mixture was diluted with ethyl acetate and washed with saturated aqueous NaHCO$_3$ and brine. The organic phase was then dried over sodium sulfate and concentrated to afford desired product (2.92 g, 97%).

Step 4:

A solution of phenol obtained above (2.92 g, 9.68 mmol), 4-(2-chloroethyl) morpholine hydrochloride (2.16 g, 11.6 mmol), Cs$_2$CO$_3$ (6.94 g, 21.3 mmol) and NaI (200 mg, 1.33 mmol) was heated to 65° C. overnight. After cooling to room temperature, the reaction mixture was diluted with ethyl acetate and then washed with saturated aqueous NaHCO$_3$ and brine. The organic phase was then dried over sodium sulfate, concentrated, and purified by HPLC to afford quinoline intermediate (1.54 g, 38%).

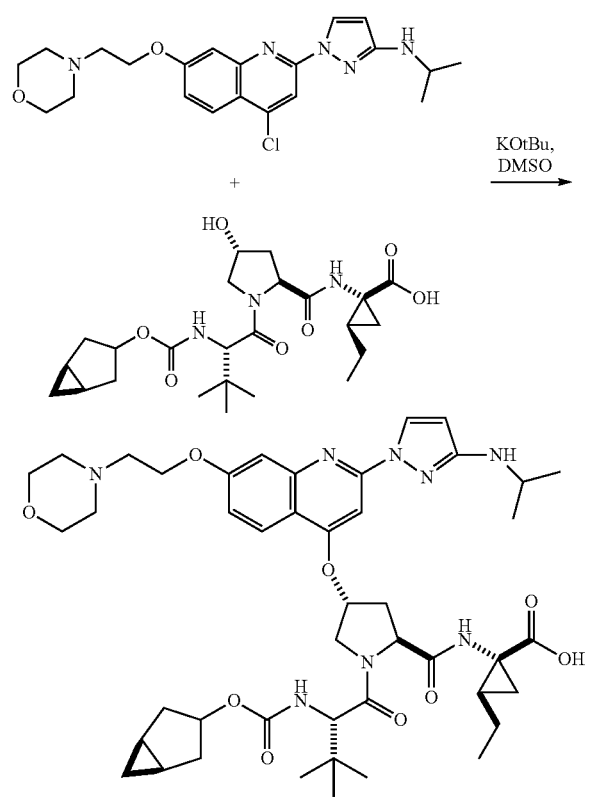

Step 5:
Tripeptide (500 mg, 1.04 mmol) was dissolved in anhydrous DMSO (10 mL) and then treated with solid KOtBu (350 mg, 3.12 mmol). After stirring for 1 h at room temperature, the quinoline intermediate (380 mg, 1.97 mmol) was added and the reaction was stirred overnight. The reaction was then quenched with acetic acid (700 µl) and purified by HPLC to afford compound 74 (161 mg, 18%). $^1$H NMR (CD$_3$OD, 300 MHz) δ 8.57 (s, 1H), 8.11 (d, 1H), 7.53 (s, 1H), 7.31 (s, 1H), 7.18 (dd, 1H), 6.17 (d, 1H), 5.56 (m, 1H), 4.71 (t, 1H), 4.64 (t, 1H), 4.59-4.55 (m, 2H), 4.50 (d, 1H), 4.17 (s, 1H), 4.10-3.78 (m, 6H), 3.75-3.71 (m, 2H), 3.64-3.28 (m, 4H), 2.72-2.53 (m, 2H), 2.05-1.88 (m, 2H), 1.73-1.61 (m, 3H), 1.50 (dd, 1H), 2.53 (dd, 1H), 1.38-1.02 (m, 5H), 1.29 (s, 3H), 1.37 (s, 3H), 1.02 (s, 9H), 0.40-0.37 (m, 2H); LRMS calcd for C$_{45}$H$_{63}$N$_8$O$_9$ [M+H]$^+$: 859.5, found 859.2.

Example 75

Preparation of Compound 75

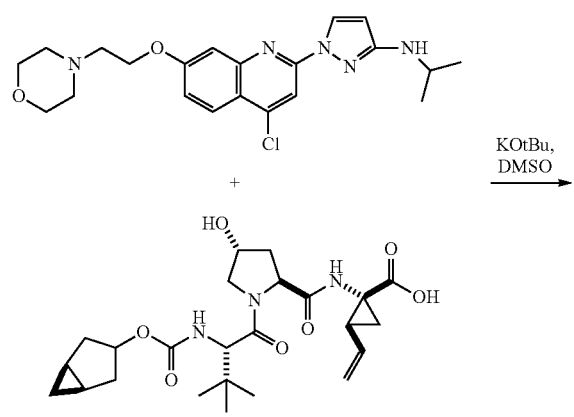

Tripeptide (450 mg, 0.94 mmol) was dissolved in anhydrous DMSO (10 mL) and treated with solid KOtBu (582 mg, 5.18 mmol). After 1 h at room temperature, quinoline (437 mg, 1.04 mmol) was added and the reaction was stirred overnight. The reaction was quenched with acetic acid (400 µL) then purified by HPLC to afford Compound 75 (632 mg, 80%). $^1$H NMR (CD$_3$OD, 400 MHz) δ 8.68 (s, 1H), 8.58 (d, 1H), 8.12 (d, 1H), 7.56 (d, 1H), 7.31 (s, 1H), 7.19 (dd, 1H), 6.19 (d, 1H), 5.86-5.79 (m, 1H), 5.57 (m, 1H), 5.26 (dd, 1H), 5.09 (dd, 1H), 4.70 (t, 1H), 4.64 (t, 1H), 4.59-4.56 (m, 2H), 4.51 (d, 1H), 4.21 (s, 1H), 4.13-3.84 (m, 6H), 3.75-3.73 (m, 2H), 3.30-3.65 (m, 4H), 2.74-2.68 (m, 1H), 2.58-2.51 (m, 1H), 2.22-2.16 (m, 1H), 2.05-1.98 (m, 1H), 1.94-1.89 (m, 1H), 1.73-1.64 (m, 2H), 1.52 (d, 1H), 1.44 (dd, 1H), 1.29 (s, 3H), 1.27 (s, 3H), 1.26-1.18 (m, 2H), 1.03 (s, 9H), 0.40-0.37 (m, 2H); LRMS calcd for C$_{45}$H$_{61}$N$_8$O$_9$ [M+H]$^+$: 857.5, found 857.2.

Example 76

Preparation of Compound 76

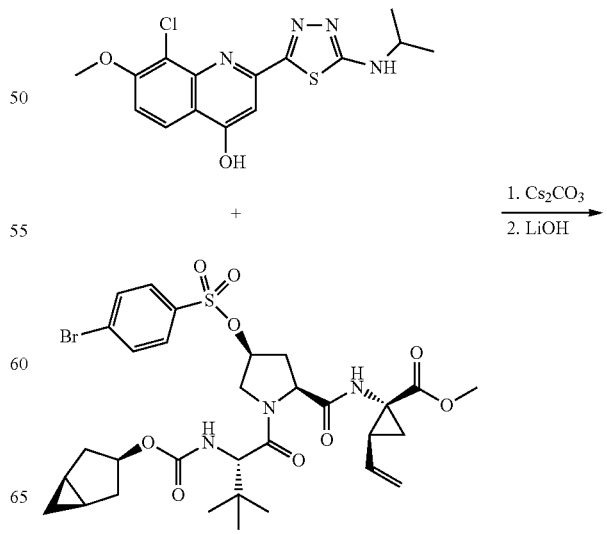

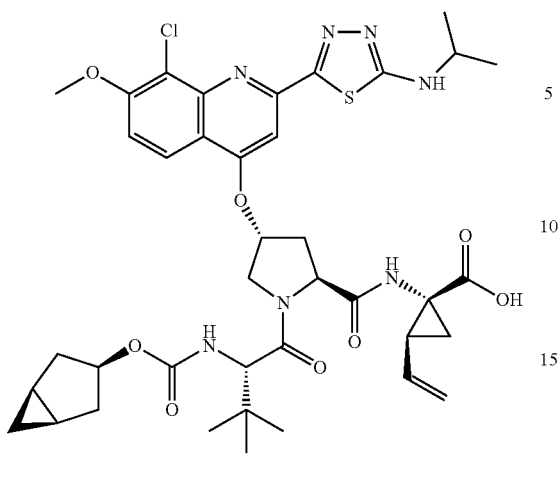

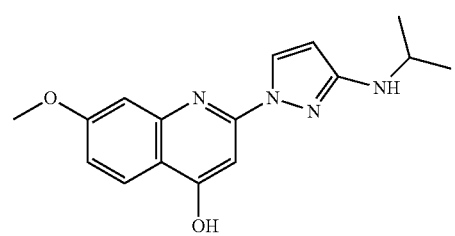

A mixture of 1-{[1-[2-(bicyclo[3.1.0]hex-3-yloxycarbonylamino)-3,3-dimethyl-butyryl]-4-(4-bromo-benzenesulfonyloxy)-pyrrolidine-2-carbonyl]-amino}-2-vinyl-cyclopropanecarboxylic acid methyl ester (100 mg, 0.14 mmol), 2-(5-isopropylamino-[1,3,4]thiadiazol-2-yl)-7-methoxy-quinolin-4-ol (62 mg, 0.18 mmol) and cesium carbonate (60 mg, 0.18 mmol) in NMP (1 mL) was stirred at 65° C. for 3 h. The mixture was neutralized with TFA (0.16 mL), and purified by HPLC to obtain the ester. This was dissolved in methanol (10 mL), THF (15 mL) and aqueous lithium hydroxide (120 mg/3 mL). The mixture was stirred at 45° C. for 1 h, concentrated to remove the volatile solvents, neutralized with 1 N HCl, and extracted with ethyl acetate. The organic extract was concentrated and purified by HPLC, affording compound 76 (5.5 mg, 5%). LC/MS=810.5 (M$^+$+1).

Example 77

Preparation of Compound 77

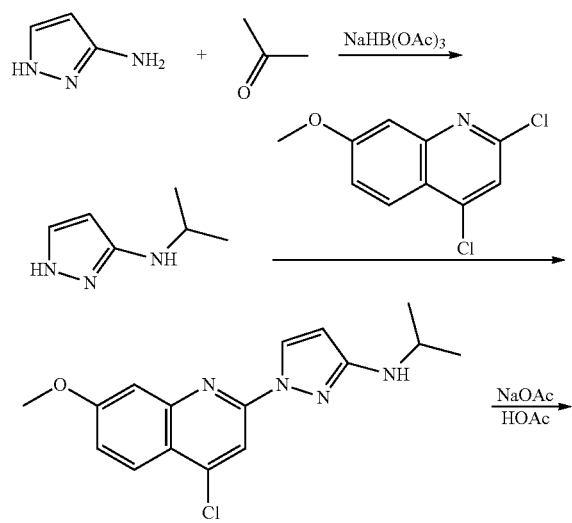

Step 1:

To a mixture of 1H-pyrazol-3-ylamine (8.3 g, 100 mmol), acetone (7.4 mL, 100 mmol) and acetic acid (12 mL, 200 mmol) in THF (280 mL) was added, in portions, sodium triacetoxyborohydride (27 g, 120 mmol) while cooling with an ice-water bath. The mixture was stirred at room temperature for 1 h and then at 50° C. for 3 h. After cooling to room temperature, 10 N NaOH (40 mL) was added dropwise, and stirred gently for 1 h. The clear solution was isolated with decantation. The gummy residue was washed with THF (2×50 mL). All the THF solutions were combined and concentrated. The residue was purified by silica gel column chromatography (EtOAc), affording isopropyl-(1H-pyrazol-3-yl)-amine (8.5 g, 68%) as a colorless oil. $^1$H NMR (300 MHz, CDCl$_3$): δ 7.34 (d, 1H), 5.62 (d, 1H), 3.58 (m, 1H), 1.22 (d, 6H).

Step 2:

A mixture of 2,4-dichloro-7-methoxy-quinoline (1.34 g, 5.88 mmol) and isopropyl-(1H-pyrazol-3-yl)-amine (1.10 g, 8.80 mmol) was heated at 115° C. for 3 h while stirring in a sealed tube. After ~20 min. of heating, the pressure built up in the tube was released by using a needle. The mixture was then dissolved in dichloromethane and loaded onto a silica gel column. Elution with dichloromethane and methanol afforded [1-(4-chloro-7-methoxy-quinolin-2-yl)-1H-pyrazol-3-yl]-isopropyl-amine (1.53 g, 82%). LC/MS=317.2 (M$^+$+1).

Step 3:

A mixture of [1-(4-chloro-7-methoxy-quinolin-2-yl)-1H-pyrazol-3-yl]-isopropyl-amine (0.52 g, 1.6 mmol) and sodium acetate monohydrate (1.0 g) in acetic acid (5 mL) was stirred at 130° C. for 2 d. The mixture was concentrated and then partitioned between ethyl acetate (50 mL) and water (50 mL). The organic layer was concentrated in vacuo. The residue was purified by silica gel column chromatography (ethyl acetate/hexanes), affording [1-(4-hydroxy-7-methoxy-quinolin-2-yl)-1H-pyrazol-3-yl]-isopropyl-amine (0.09 g, 19%). LC/MS=299.1 (M$^+$+1).

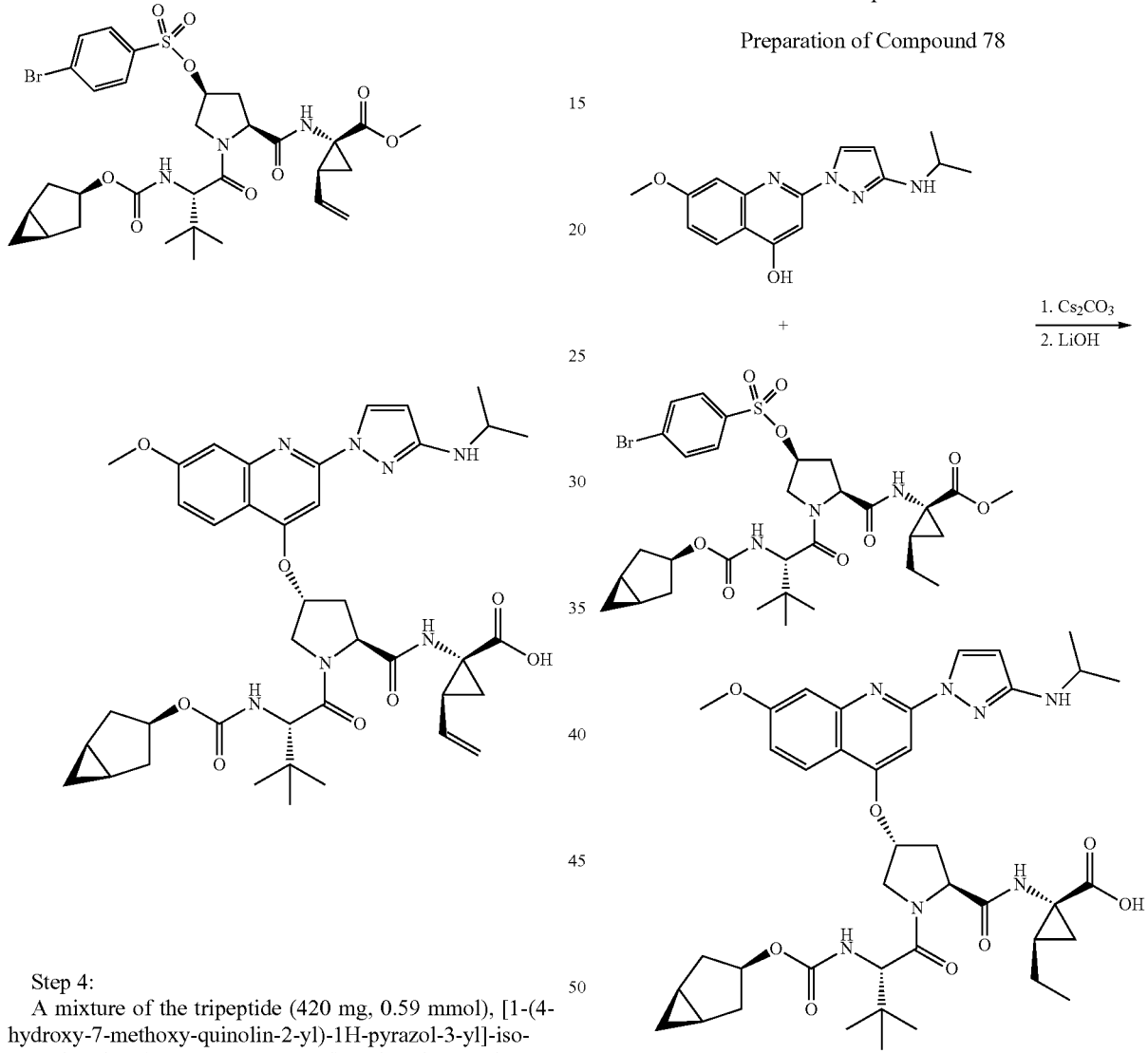

Step 4:

A mixture of the tripeptide (420 mg, 0.59 mmol), [1-(4-hydroxy-7-methoxy-quinolin-2-yl)-1H-pyrazol-3-yl]-isopropyl-amine (174 mg, 0.58 mmol) and cesium carbonate (0.22 mg, 0.68 mmol) in NMP (2 mL) was stirred at 65° C. for 16 h. To this mixture, a solution of LiOH hydrate (400 mg) in water (3 mL) was added. While stirring at 40° C., methanol was added until the mixture became nearly homogeneous, which was then stirred for 2 h. After removal of the volatile solvents, the mixture was partitioned between ethyl acetate and a 3% LiCl aqueous solution. The aqueous solution was neutralized with 1N HCl before the organic layer was taken out. The aqueous layer was extracted with ethyl acetate. The ethyl acetate layers were combined and concentrated. The residue was purified by HPLC, affording compound 77 (260 mg, 51%) as a TFA salt. $^1$H NMR (300 MHz, CD$_3$OD): δ 8.60 (d, J=3.0 Hz, 1H), 8.07 (d, J=9.0 Hz, 1H), 7.62 (s, 1H), 7.29 (s, 1H), 7.17 (d, J=9.3 Hz, 1H), 6.26 (d, J=2.7 Hz, 1H), 5.85 (m, 1H), 5.63 (brs, 1H), 5.28 (d, J=16.2 Hz, 1H), 5.11 (d, J=10.5 Hz, 1H), 4.69 (t, 1H), 4.56 (m, 1H), 4.16 (m, 1H), 3.99 (s, 3H), 2.74 (m, 1H), 2.55 (m, 1H), 2.21 (q, 1H), 1.98 (m, 1H), 1.84 (m, 1H), 1.70 (m, 2H), 1.44 (m, 2H), 1.31 (d, 6H), 1.21 (m, 2H), 1.04 (s, 9H), 0.98 (m, 2H), 0.34 (m, 2H). LC/MS=758.5 (M$^+$+1).

Example 78

Preparation of Compound 78

Following procedures similar to those for preparation of 77 except using intermediate III, Compound, compound 78 was obtained. $^1$H NMR (300 MHz, CD$_3$OD): δ 8.65 (s, 1H, exchangeable), 8.61 (d, J=2.7 Hz, 1H), 8.09 (d, J=9.0 Hz, 1H), 7.62 (s, 1H), 7.30 (s, 1H), 7.17 (d, J=9.6 Hz, 1H), 6.25 (d, J=2.7 Hz, 1H), 5.63 (brs, 1H), 4.69 (t, 1H), 4.55 (m, 2H), 4.18 (m, 1H), 4.05 (m, 2H), 4.00 (s, 3H), 2.74 (m, 1H), 2.55 (m, 1H), 1.95 (m, 1H), 1.82 (m, 1H), 1.65 (m, 2H), 1.41 (m, 4H), 1.30 (d, 6H), 1.22 (m, 4H), 1.02 (s, 9H), 0.98 (m, 2H), 0.35 (m, 2H). LC/MS=760.5 (M$^+$+1).

Example 79
Preparation of Compound 79
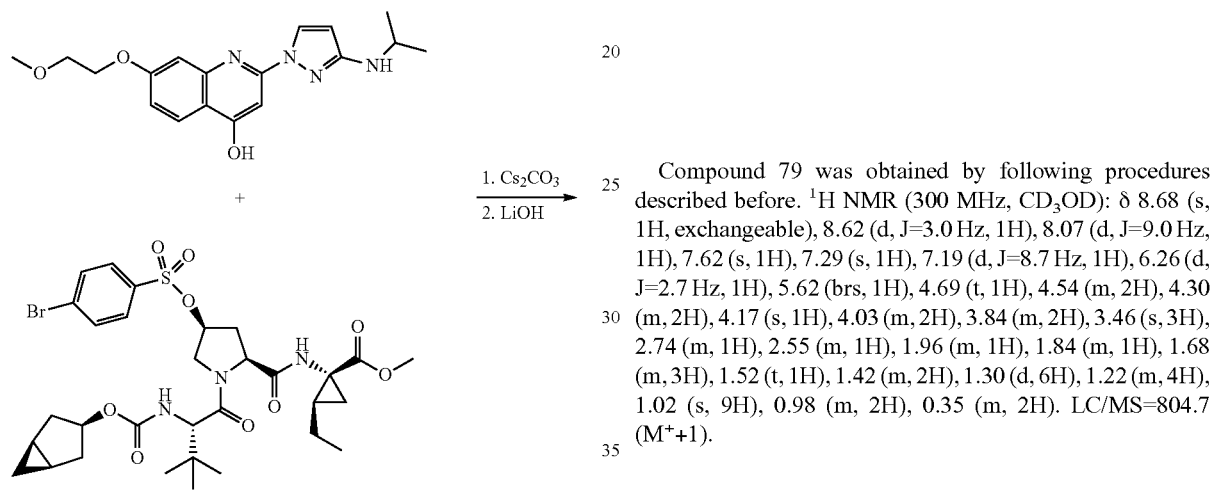
Compound 79 was obtained by following procedures described before. $^1$H NMR (300 MHz, CD$_3$OD): δ 8.68 (s, 1H, exchangeable), 8.62 (d, J=3.0 Hz, 1H), 8.07 (d, J=9.0 Hz, 1H), 7.62 (s, 1H), 7.29 (s, 1H), 7.19 (d, J=8.7 Hz, 1H), 6.26 (d, J=2.7 Hz, 1H), 5.62 (brs, 1H), 4.69 (t, 1H), 4.54 (m, 2H), 4.30 (m, 2H), 4.17 (s, 1H), 4.03 (m, 2H), 3.84 (m, 2H), 3.46 (s, 3H), 2.74 (m, 1H), 2.55 (m, 1H), 1.96 (m, 1H), 1.84 (m, 1H), 1.68 (m, 3H), 1.52 (t, 1H), 1.42 (m, 2H), 1.30 (d, 6H), 1.22 (m, 4H), 1.02 (s, 9H), 0.98 (m, 2H), 0.35 (m, 2H). LC/MS=804.7 (M$^+$+1).
Example 80
Preparation of Compound 80
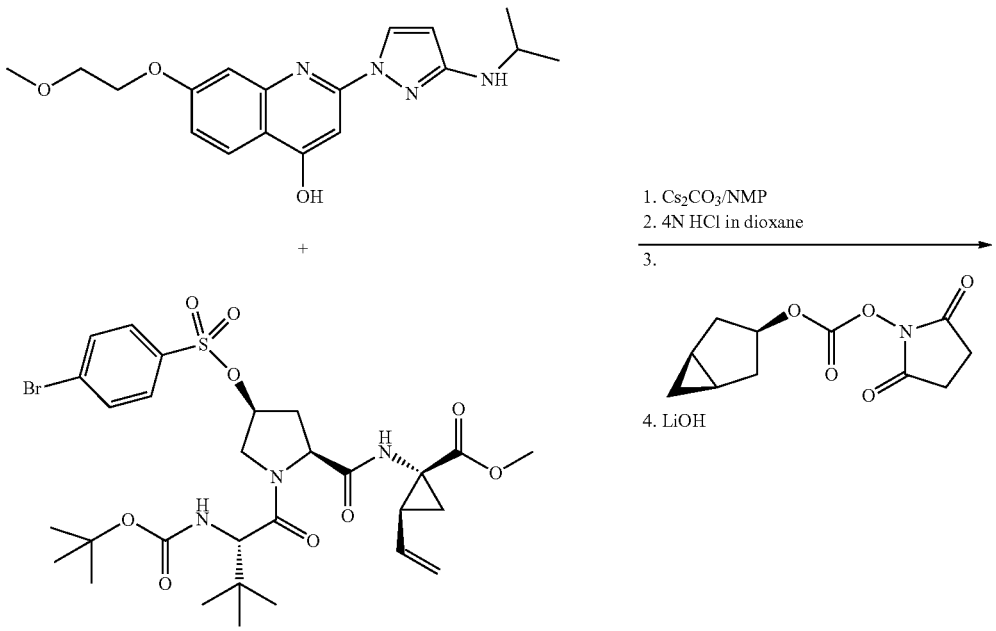

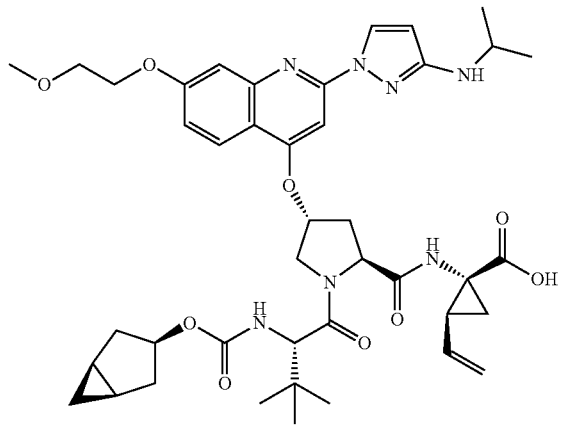

Step 1:

A mixture of the tripeptide (830 mg, 1.2 mmol), 2-(3-isopropylamino-pyrazol-1-yl)-7-(2-methoxy-ethoxy)-quinolin-4-ol (410 mg, 1.2 mmol) and cesium carbonate (440 mg, 1.35 mmol) in NMP (4 mL) was stirred at 65° C. for 16 h. The mixture was partitioned between ethyl acetate (30 mL) and 3% LiCl (30 mL). The aqueous layer was extracted with ethyl acetate (2×30 mL). The ethyl acetate extracts were combined and concentrated.

Step 2:

The crude coupled product thus formed was dissolved in dichloromethane (20 mL) and 4N HCl in dioxane (20 mL) was added. The mixture was stirred for 1 h at room temperature and concentrated to dryness. The residue was partitioned between ethyl acetate and saturated sodium bicarbonate. To this biphasic solution, a solution of intermediate I (344 mg, 1.4 mmol) in ethyl acetate (3 mL) was added dropwise, while gently stirring. The ethyl acetate layer was taken and concentrated.

Step 3:

The resulting residue was then re-dissolved in THF (20 mL), MeOH (20 mL), and water (10 mL) containing LiOH monohydrate (1.0 g), and stirred at 45° C. for 1 h. After removal of volatile solvents, the solution was neutralized with 1 N HCl to pH ~5 and extracted with ethyl acetate (50 mL). The organic extract was concentrated and purified by HPLC affording compound 80 (632 mg as a TFA salt, 57%) as a pale yellow solid, after lyophilization of the desired fractions. $^1$H NMR (300 MHz, CD$_3$OD): δ 8.75 (s, 1H, exchangeable), 8.57 (d, J=2.7 Hz, 1H), 8.05 (d, J=9.3 Hz, 1H), 7.55 (s, 1H), 7.25 (s, 1H), 7.16 (d, J=9.0 Hz, 1H), 6.24 (d, J=2.7 Hz, 1H), 5.86 (m, 1H), 5.58 (brs, 1H), 5.28 (d, J=15.9 Hz, 1H), 5.11 (d, J=10.5 Hz, 1H), 4.71 (t, 1H), 4.54 (m, 2H), 4.28 (m, 2H), 4.18 (s, 1H), 4.03 (m, 2H), 3.83 (m, 2H), 3.46 (s, 3H), 2.74 (m, 1H), 2.55 (m, 1H), 2.20 (m, 1H), 1.96 (m, 1H), 1.84 (m, 1H), 1.68 (m, 2H), 1.42 (m, 2H), 1.30 (d, 6H), 1.22 (m, 1H), 1.02 (s, 9H), 0.98 (m, 2H), 0.36 (m, 2H). LC/MS=802.7 (M$^+$+1).

Example 81

Preparation of Compound 81

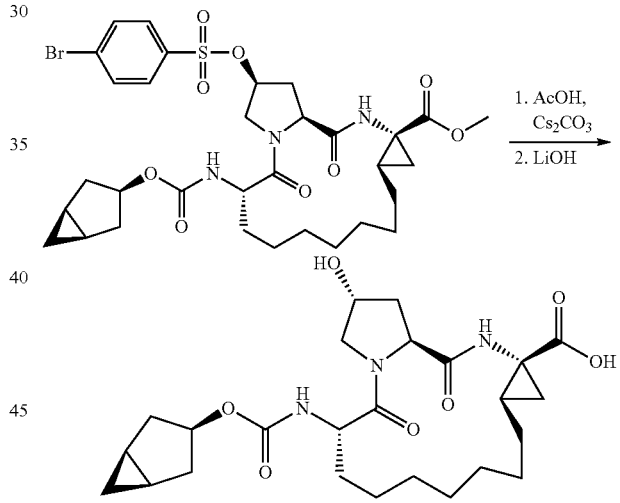

Step 1:

To a mixture of brosylate methyl ester (1.41 g, 1.95 mmol) and cesium carbonate (1.90 g, 5.82 mmol) in NMP (6.5 mL) was added acetic acid (0.35 mL, 5.82 mmol). The resulting mixture was stirred at room temperature for 30 min. and then 65° C. for 16 h. The mixture was partitioned between ethyl acetate (40 mL) and 3% aqueous LiCl (40 mL). The ethyl acetate layer was concentrated to dryness, and re-dissolved in methanol (20 mL) and THF (20 mL). Aqueous lithium hydroxide (1.0 g/10 mL) was added and stirred at room temperature for 16 h. An additional lithium hydroxide solution (0.5 g/5 mL) was added and stirred at 45° C. for 2 h. After removal of the volatile solvents, ethyl acetate (40 mL) was added. The aqueous layer was neutralized with 6 N HCl to pH ~2. The ethyl acetate layer was then washed with brine, and concentrated to dryness, affording alcohol (920 mg, 96%) as a colorless solid. LC/MS=490.3 (M$^-$−1).

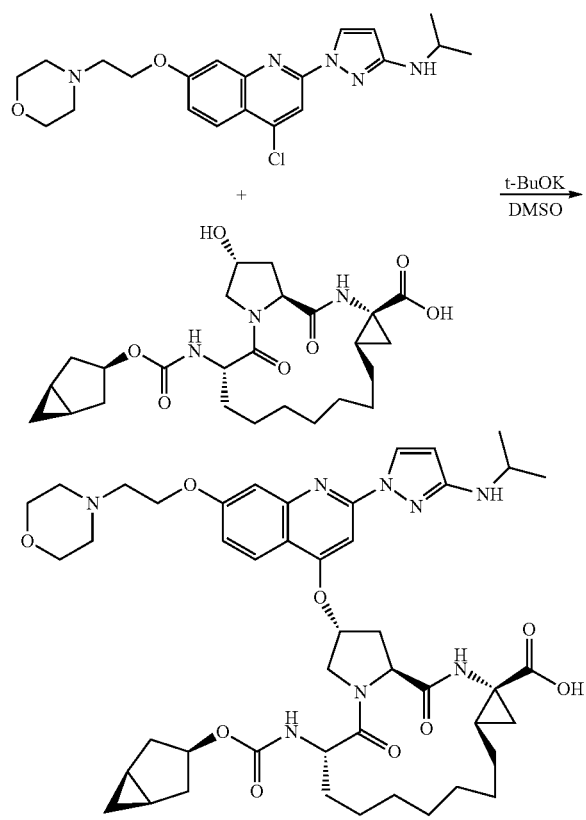

Step 2:

To a solution of alcohol (420 mg, 0.85 mmol) in DMSO (10 mL) was added 1.0 M potassium t-butoxide in THF and stirred at room temperature for 30 min. A solution of {1-[4-chloro-7-(2-morpholin-4-yl-ethoxy)-quinolin-2-yl]-1H-pyrazol-3-yl}-isopropyl-amine (440 mg, 1.06 mmol) in THF (2 mL) was added. The mixture was then stirred for 16 h at room temperature, neutralized with acetic acid, and concentrated to remove the volatile solvent. The residue was subjected to HPLC, affording compound 81 (340 mg as the TFA salt, 35%) as a yellowish solid upon lyophilization. $^1$H NMR (300 MHz, CD$_3$OD): δ 8.62 (d, J=2.7 Hz, 1H), 8.17 (d, J=9.3 Hz, 1H), 7.62 (s, 1H), 7.33 (s, 1H), 7.23 (d, J=9.3 Hz, 1H), 6.25 (d, J=2.4 Hz, 1H), 5.62 (brs, 1H), 4.75 (m, 2H), 4.67 (s, 1H), 4.59 (m, 2H), 4.33 (d, J=6.6 Hz, 1H), 3.8-4.1 (m, 6H), 3.75 (m, 2H), 3.49 (brs, 4H) 2.68 (m, 2H), 1.1-2.1 (m, 28H, including doublet of J=6.3 Hz at 1.30 ppm for isopropyl Me), 0.39 (m, 2H). LC/MS=871.6 (M$^+$+1).

Example 82

Preparation of Compound 82

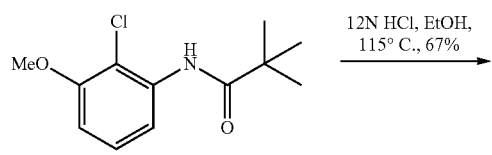

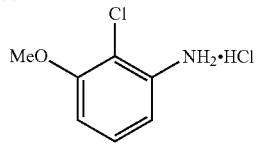

Step 1:

The amide (18.8 g, 0.078 mmol) was dissolved in EtOH (75 mL). To this solution was added 12 N HCl$_{(aq.)}$. The reaction mixture was then placed in a preheated 115° C. bath and stirred for 5 h. The reaction was cooled to room temperature and then further cooled with an ice bath. The small white needles that formed were isolated by vacuum filtration, washed with Et$_2$O, and placed under high vacuum for 16 h. The yield of the hydrochloride salt was 10.1 g (67%). LC/MS=158.3 (M$^+$+1).

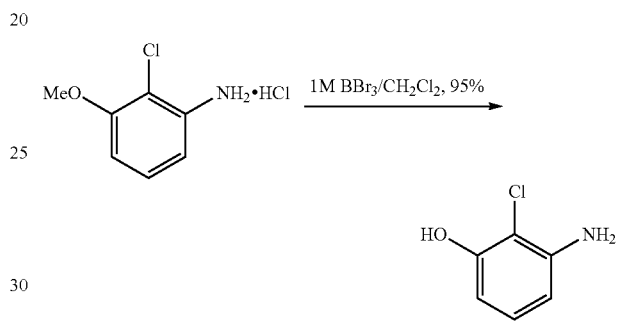

Step 2:

The amine (10.1 g, 0.052 mol) was dissolved in a 1 M solution of BBr$_3$ in CH$_2$Cl$_2$ (163 mL, 0.163 mol). This resulted in copious smoking and out-gassing. The reaction was placed in a preheated 40° C. bath. The reactions N$_2$ line was replaced with a drying tube filled with CaSO$_4$. The reaction was heated for 8 h and then stirred at room temperature overnight. The next day the reaction was complete as determined by LC/MS. The reaction was placed in an ice bath and MeOH was added very slowly, resulting in copious HBr gas formation. The reaction eventually turned very thick, as a white suspension forms. Additional MeOH was added to this suspension until everything went into solution. This was then concentrated to a white syrup. This was dissolved in dH$_2$O and this solution was extracted with EtOAc (2×). These washes were set aside as they contained pure phenol. The aqueous layer was then brought to pH=7 with solid NaHCO$_3$ and extracted with additional EtOAc (2×). These organic washes were combined, extracted with brine and dried over Na$_2$SO$_4$. The drying agent was removed by vacuum filtration and the filtrate was concentrated. The phenol was isolated from this residue by silica gel column chromatography, eluting with a mixture of EtOAc and hexanes. This material was combined with the original EtOAc extracts containing pure phenol, to yield 7.07 g (95%) of a slightly off-white solid. LC/MS=144.3 (M$^+$+1).

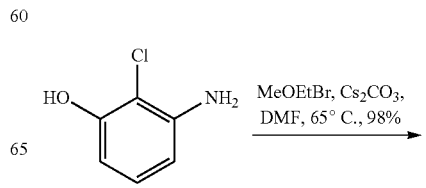

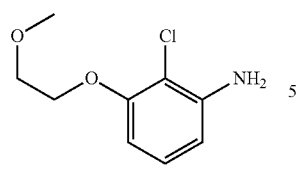

Step 3:

To a flask charged with the phenol (3.5 g, 0.024 mol) and Cs₂CO₃ (9.4 g, 0.029 mol) was added DMF (120 mL) and then MeOEtBr (2.52 mL, 0.027 mol). This mixture was then placed in a preheated 65° C. bath. The reaction was stirred for 4.25 h additional MeOEtBr (200 µL, 0.0021 mol) was added. After an additional hour of stirring the reaction was cooled to room temperature The reaction was partitioned between EtOAc and 5% LiCl$_{(aq.)}$. The solids that formed were dissolved by adding dH₂O to the mixture. The layers were separated and the organic layer was washed with additional 5% LiCl$_{(aq.)}$ (2×) and brine (1×). The organic layer was then dried over Na₂SO₄. The drying agent was removed by vacuum filtration and the filtrate was concentrated. The phenolic ether was isolated from the residue by silica gel column chromatography, eluting with a mixture of EtOAc and hexanes, as a colorless liquid (4.7 g, 98%). LC/MS=202.2 (M⁺+1).

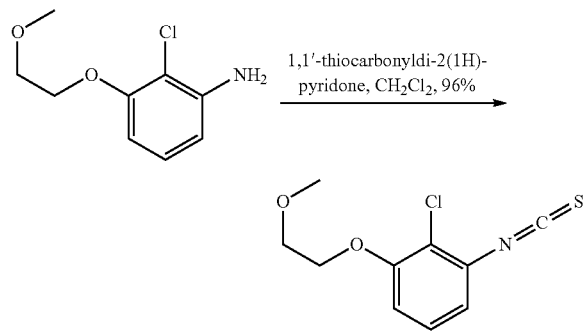

Step 4:

The aniline (4.7 g, 0.023 mol) was dissolved in CH₂Cl₂ (125 mL). To this solution was added 1,1'-thiocarbonyldi-2 (1H)-pyridone (5.58 g, 0.023 mol) in one portion. The reaction was allowed to stir at room temperature for 2 h. The reaction was then concentrated, resulting in white solids crashing out of solution. Everything was re-dissolved in CH₂Cl₂ and the isothiocyanate was isolated by silica gel column chromatography, eluting with a mixture of EtOAc and hexanes, as a white solid (5.36 g, 96%). ¹H NMR (400 MHz, (CD₃)₂SO): δ 7.35 (t, J=8 Hz, 1H), 7.19 (dd, J=8.8, 4.6 Hz, 1H), 7.14 (dd, J=8, 1.6 Hz, 1H), 4.22 (m, 2H), 3.69 (m, 2H), 3.32 (s, 3H).

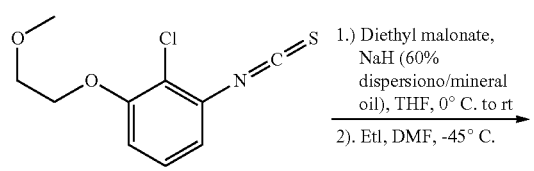

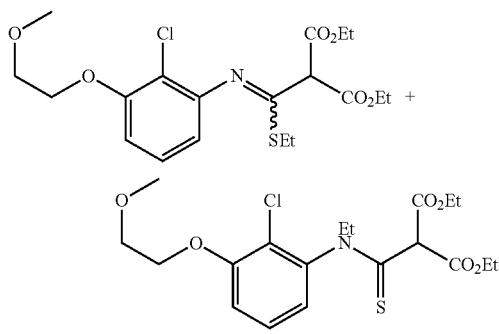

Step 5:

To a slurry of NaH, 60% dispersion in mineral oil, (1.06 g, 0.026 mol) in THF (120 mL), that was cooled in an ice bath, diethyl malonate (3.34 mL, 0.022 mol) was added in a dropwise fashion. The ice bath was then removed and the reaction was stirred at room temperature for 1.5 h. The reaction was then cooled in an ice bath and a solution of the isothiocyanate (5.36 g, 0.022 mol) in THF (80 mL) was added in a slow, continuous stream. The flask in which the solution of the isothiocyanate and THF was made in was rinsed with more THF (20 mL) and this was also added to the reaction. The cold bath was then removed and the reaction was stirred for 3 h. The reaction was then concentrated and the resulting yellow foam was placed under high vacuum overnight.

A solution of the above synthesized product in DMF (100 mL) was cooled to −45° C. Ethyl iodide (2.13 mL, 0.026 mol) was slowly added to the reaction in a drop-wise fashion. The reaction was stirred for 2 h in a −45° C. bath and then left to warm and stir overnight. The reaction was diluted with dH₂O, resulting in it turning opaque with a white precipitate. The quenched reaction was then extracted with a 1:1 mixture of Et₂O and hexanes, followed by Et₂O, and then EtOAc. The EtOAc extracts were combined and back-extracted with a 5% aqueous solution of LiCl (2×). The organics were combined and extracted with brine and then dried over Na₂SO₄. The drying agent was then removed by vacuum filtration and the filtrate was concentrated. A mixture of S-alkylated and N-alkylated compounds were isolated from this residue by silica gel column chromatography, eluting with a mixture of EtOAc and hexanes, as a waxy crystalline solid (9.11 g, 96%). LC/MS (R$_T$=3.95)=432.2 (M⁺+1); LC/MS (R$_T$=4.02)=432.0 (M⁺+1).

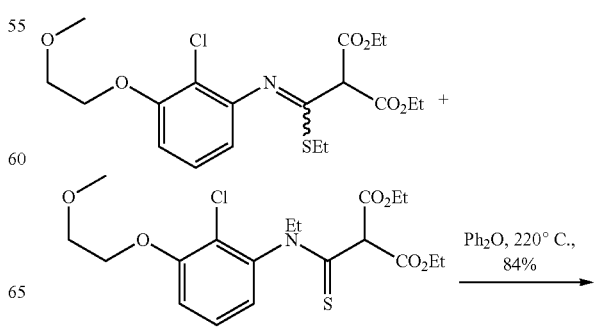

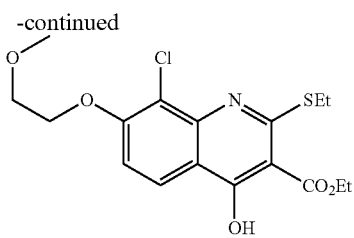

Step 6:

A mixture of S-alkylated and N-alkylated compounds (9.1 g, 0.021 mol) was dissolved in Ph₂O (80 mL). This solution was placed in a preheated 320° C. sand bath. After 17 minutes with an internal temperature of 220° C. the reaction was determined to be complete by TLC analysis. The reaction was cooled to room temperature and the quinoline was isolated by loading the reaction directly onto a silica gel column. The Ph₂O was eluted off using an eluent of 100% hexanes. The quinoline was then eluted off the column by ramping the percentage of EtOAc in the eluent to 35%. The quinoline was isolated as a white, crystalline solid (6.8 g, 84%). LC/MS=386.2 (M⁺+1).

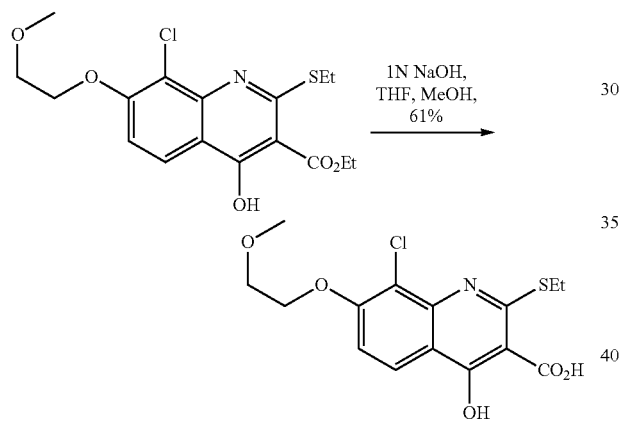

Step 7:

The quinoline (6.8 g, 0.0176 mol) was mixed with THF (40 mL). MeOH was then added (40 mL) and then 1N NaOH$_{(aq.)}$ (88 mL, 0.088 mol) was added in one portion. Everything goes into solution and the reaction heats up. The reaction was then placed in a preheated 85° C. bath and stirred for 19.5 h and checked by LC/MS. The reaction was not complete so additional NaOH (1.2 g in 20 mL of dH₂O) was added and the reaction was kept stirring. After an additional 4 h, the reflux condenser was removed and the reaction was concentrated by evaporating some of the organic solvents in the reaction. The reflux condenser was then put back on the reaction flask and heating continued for another 10 h. The reaction was allowed to cool to room temperature and stir overnight. At this point the reaction was complete, as determined by LC/MS. The reaction was placed in an ice bath and brought to pH=4 with 4 N HCl. This caused the quenched reaction to turn thick with precipitate. This was extracted with CH₂Cl₂. The organic phases were concentrated and the residue was suspended in MeOH. The white solids were isolated by vacuum filtration, to yield the carboxylic acid as a shiny white solid (3.84 g, 61%). LC/MS=358.1 (M⁺+1).

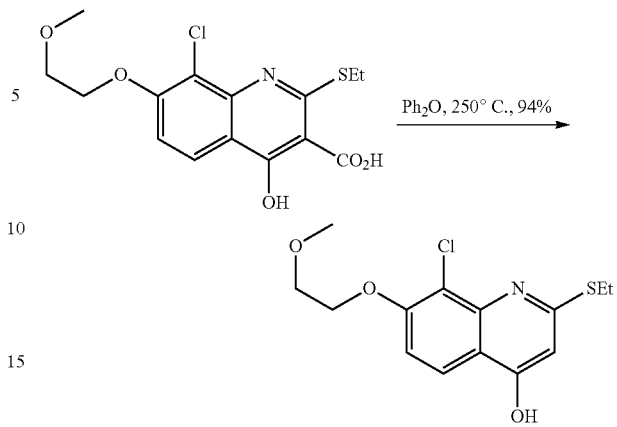

Step 8:

The carboxylic acid (3.84 g, 0.0107 mol) was suspended in Ph₂O (32 mL). This mixture was placed in a pre-heated 310° C. sand bath. When the internal temperature reached 150° C. the carboxylic acid went into solution. The reaction was kept at an internal temperature of 250° C. for 15 minutes and then cooled to room temperature Solids crashed out of solution upon cooling. These solids were isolated by vacuum filtration, washing the filter cake with hexanes, to yield the de-carboxylated quinoline as a pale yellow solid (3.19 g, 94%). LC/MS=314.2 (M⁺+1).

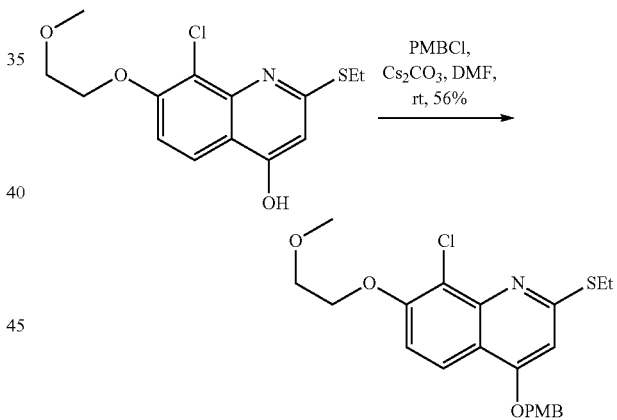

Step 9:

The de-carboxylated quinoline (2.59 g, 0.0083 mol) was dissolved in DMF (28 mL). To this solution was added Cs₂CO₃ (8.1 g, 0.0249 mol), followed 3 minutes later with PMBCl (1.69 mL, 0.01245 mol). The reaction was stirred for 16 h at room temperature The reaction was determined to be complete by LC/MS. The reaction was quenched by the addition of 5% LiCl$_{(aq.)}$ and EtOAc. The aqueous layer was diluted with dH₂O and the layers were separated. The organic layer was extracted with dH₂O (1×), 5% LiCl$_{(aq.)}$ (3×) and brine (1×). The organic phase was then dried over a mixture of Na₂SO₄ and MgSO₄. The drying agents were removed by vacuum filtration and the filtrate was concentrated. The PMB protected quinoline was isolated from the residue by silica gel column chromatography, eluting with a mixture of EtOAc and hexanes (2.04 g, 56%). LC/MS=434.1 (M⁺+1).

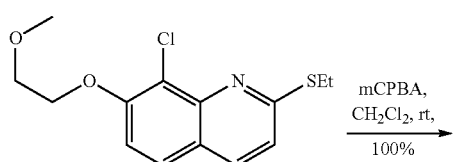

Step 10:

The PMB protected quinoline (2.0 g, 0.00461 mol) was dissolved in CH$_2$Cl$_2$ (46 mL). To this solution was added mCPBA (4.59 g, 0.00922 mol) in one portion. Reaction monitored by LC/MS. Additional mCPBA (700 mg) was added to the reaction after 30 minutes and after 3 h (180 mg). The reaction progress was monitored by LC/MS. After 3.5 h the reaction was diluted with CH$_2$Cl$_2$ and sat. NaHSO$_{3(aq.)}$ was added to the reaction. All solids dissolved into these two layers. The layers were separated and the organic layer was washed with sat. NaHSO$_{3(aq.)}$ (1×) and 2 N NaOH (2×). The organic phase was dried over Na$_2$SO$_4$. The drying agent was removed by vacuum filtration and the filtrate was concentrated to yield the sulfone (2.19 g, 100%) as a crystalline white solid. LC/MS=466.1 (M$^+$+1), 488.2 ((M$^+$+23).

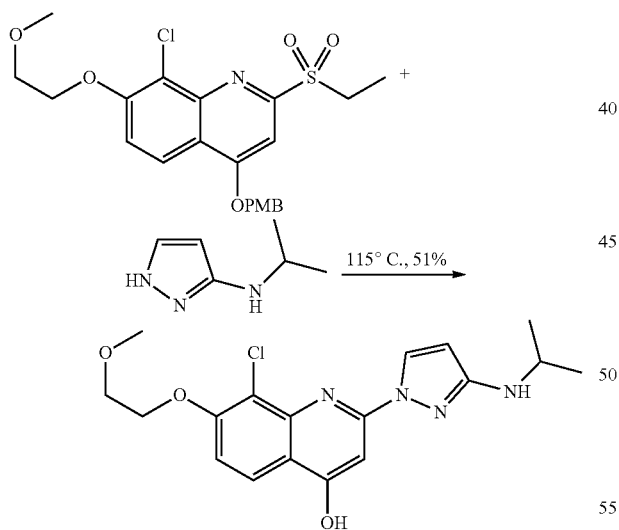

Step 11:

To a flask containing the sulfone (600 mg, 0.00129 mol) was added the iPr-aminopyrazole (1.6 g, 0.01288 mol). The reaction flask was placed in a pre-heated oil bath at 115° C. The reaction was stirred for 24 h and then cooled to room temperature The reaction was partitioned between dH$_2$O and EtOAc. The organic phase was extracted with dH$_2$O (1×), brine (1×) and then dried over Na$_2$SO$_4$. The drying agent was removed by vacuum filtration and the quinoline product was semi-purified by first removing gross impurities by silica gel chromatography, eluting with EtOAc and hexanes, and then flushing the column with a mixture of MeOH and CH$_2$Cl$_2$ to recover the still impure product. The purification was finished by reverse phase HPLC to yield the product quinoline (250 mg, 51%) as a yellow solid. LC/MS=377.1 (M$^+$+1).

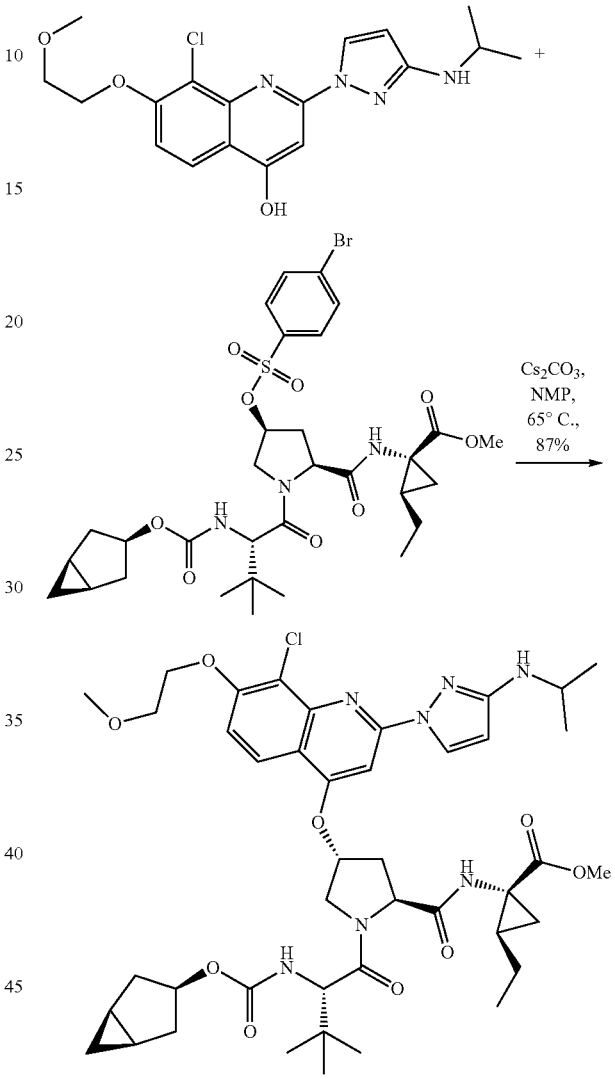

Step 12:

A round bottom flask was charged with the quinoline (236 mg, 0.626 mmol), intermediate III (446 mg, 0.626 mmol), and Cs$_2$CO$_3$ (358 mg, 1.10 mmol). NMP (3.2 mL) was added and the reaction flask was placed in a 65° C. oil bath. The progress of the reaction was monitored by LC/MS. After 5.5 h there was no more reaction progress. The reaction was cooled to room temperature and partitioned between EtOAc and dH$_2$O. The layers were separated and the organic phase was then extracted with dH$_2$O (1×), 5% LiCl$_{(aq.)}$ (3×) and brine (1×). The organic phase was then dried over a mixture of Na$_2$SO$_4$ and MgSO$_4$. The drying agents were removed by vacuum filtration and the filtrate was concentrated. The coupled product was isolated by silica gel column chromatography, eluting with a mixture of EtOAc and hexanes, as a white solid (465 mg, 87%). LC/MS=852.1 (M$^+$+1).

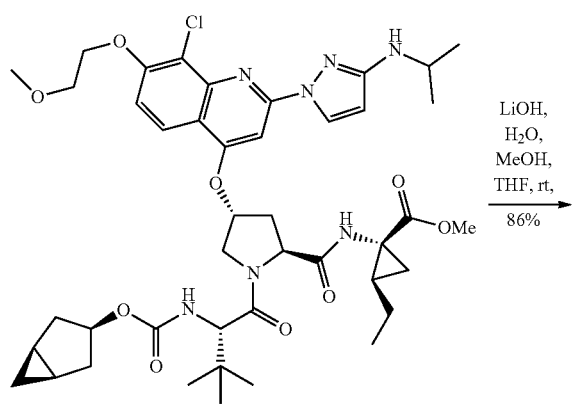

LiOH,
H₂O,
MeOH,
THF, rt,
86%

Step 13:
The methyl ester (465 mg, 0.542 mmol) was dissolved in THF (2.7 mL) and MeOH (1.8 mL). In a separate flask a solution of LiOH (114 mg, 2.71 mmol) in dH₂O (900 □M) was prepared and added to the first flask at room temperature The reaction flask was then placed in a 32° C. oil bath. The reaction progress was monitored by LC/MS. After 6 h the reaction was cooled to room temperature The reaction was neutralized with 2 N HCl and clarified with MeOH. The mixture was stored in a freezer overnight. Compound 82 was isolated from the mixture by reverse phase HPLC and then freeze drying to yield a yellow powder (434 mg, 86%). LC/MS=839.0 (M⁺+1). ¹H NMR (400 MHz, CD₃CN): δ 8.65 (d, J=2.8 Hz, 1H), 8.61 (s, 1H), 8.01 (d, J=9.2 Hz, 1H), 7.31 (d, J=9.2 Hz, 1H), 7.31 (s, 1H), 6.21 (d, J=2.8 Hz, 1H), 5.50 (s, 1H), 4.67 (t, J=8 Hz, 1H), 4.58 (t, J=6.8 Hz, 1H), 4.49 (d, J=11.6 Hz, 1H), 4.37 (t, J=4.4 Hz, 2H), 4.20 (s, 1H), 4.05 (d, J=9.2 Hz, 1H), 3.86 (m, 1H), 3.85 (t, J=4.4 Hz, 1H), 3.48 (s, 3H), 2.70 (dd, J=13.6, 8 Hz, 1H), 2.56 (m, 1H), 2.00 (m, 1H), 1.88 (m, 1H), 1.67 (m, 3H), 1.51 (quint, J=8 Hz, 1H), 1.39 (m, 2H), 1.32 (d, J=6.8 Hz, 6H), 1.22 (dd, J=9.2, 4.4 Hz, 2H), 1.18 (m, 1H), 1.01 (m, 12H), 0.38 (m, 1H), 0.33 (m, 1H).

Example 83

Preparation of Compound 83

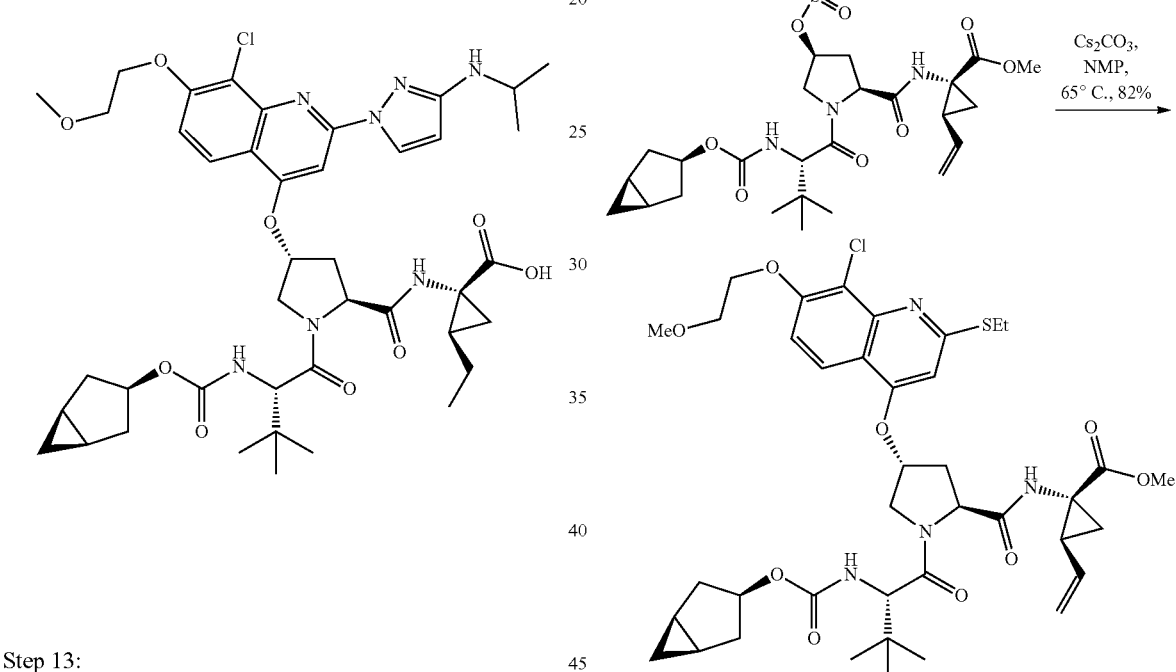

Step 1:
A round bottom flask was charged with the quinoline (288 mg, 0.918 mmol), intermediate III (654 mg, 0.917 mmol), and Cs₂CO₃ (523 mg, 1.61 mmol). This mixture was then suspended in NMP. The reaction was then placed in a 65° C. bath and stirred for 7.5 h. The reaction was cooled to room temperature and partitioned between dH₂O and EtOAc. The organic layer was then extracted with dH₂O (1×), 5% LiCl₍ₐq.₎ (3×) and brine (1×). The organic phase was then dried over a mixture of Na₂SO₄ and MgSO₄. The drying agents were removed by vacuum filtration and the filtrate was concentrated. The coupled product was isolated from the residue by silica gel column chromatography, eluting with a mixture of EtOAc and hexanes, as a white solid (590 mg, 82%). LC/MS=787.7 (M⁺+1).

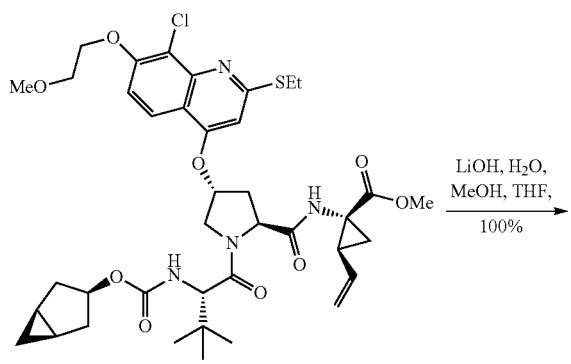

1.32 (dd, J=7.6, 5.6 Hz, 1H), 1.24 (d, J=14.4 Hz, 1H), 1.06 (t, J=7.6 Hz, 3H), 0.97 (m, 2H), 0.80 (m, 2H), 0.58 (s, 9H), −0.02 (m, 2H).

Example 84

Preparation of Compound 84

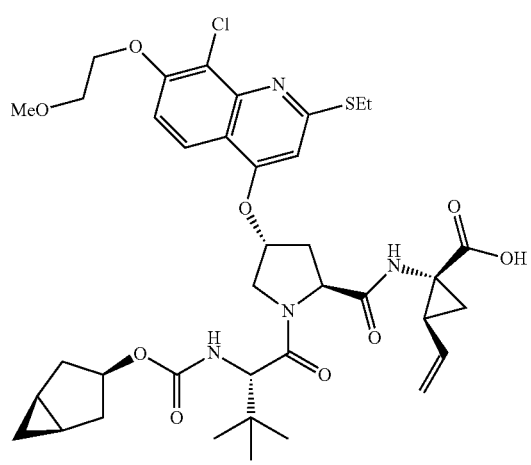

Step 2:

The methyl ester (590 mg, 0.749 mmol) was dissolved in THF (3.75 mL) and MeOH (2.5 mL). This solution was cooled in an ice bath and then a solution of LiOH (157 mg, 3.74 mmol) in dH$_2$O (3.75 mL) was added drop-wise. The ice bath was then removed and the reaction was stirred at room temperature for 4 h. The reaction was cooled again in an ice bath and the pH of the reaction was brought to 1-2 using 1N HCl. The solution turned opaque with fine white solids. The reaction was extracted with EtOAc (2×) and the combined organic layers were extracted with brine and dried over Na$_2$SO$_4$. The drying agent was removed by vacuum filtration and the filtrate was concentrated to yield compound 83 as a white foam (598 mg). 106 mg of crude compound 83 was purified by reverse phase HPLC and then freeze dried to yield a white powder (88 mg). LC/MS=773.5 (M$^+$+1). $^1$H NMR (400 MHz, CD$_3$CN): δ 7.51 (d, J=9.2 Hz, 1H), 7.16 (s, 1H), 6.82 (d, J=9.2 Hz, 1H), 6.26 (s, 1H), 5.95 (d, J=8.4 Hz, 1H), 5.33 (dt, J=19.6, 9.6 Hz, 1H), 4.91 (s, 1H), 4.89 (d, J=11.2 Hz, 1H), 4.71 (d, J=11.2 Hz, 1H), 4.31 (t, J=6.4 Hz, 1H), 4.08 (t, J=8.8 Hz, 1H), 3.99 (d, J=12 Hz, 1H), 3.93 (d, J=3.2 Hz, 2H), 3.86 (m, 1H), 3.55 (d, J=10.4 Hz, 1H), 3.39 (t, J=10.4 Hz, 2H), 3.02 (s, 3H), 2.98 (quart., J=7.2 Hz, 2H), 2.16 (dd, J=14.4, 7.2 Hz, 1H), 1.94 (m, 1H), 1.77, (quart., J=8.8 Hz, 1H), 1.61 (m, 1H), 1.56 (quint., J=2.4 Hz, 1H), 1.48 (m, 1H), Compound 83 (490 mg, 0.634 mmol) was dissolved in DME (6.34 mL). To this solution was added dH$_2$O (634 μL), pTolSO$_2$NHNH$_2$ (884 mg, 4.75 mmol), and then NaOAc (780 mg, 9.51 mmol). The reaction was then placed in a 95° C. bath and stirred for 1.75 h. The reaction was cooled to room temperature and compound 84 was purified by reverse phase HPLC and then freeze dried to yield an off-white powder (270 mg, 55%). LC/MS=775.7 (M$^+$+1). $^1$H NMR (400 MHz, CD$_3$COD): δ 7.99 (d, J=9.2 Hz, 1H), 7.33 (d, J=9.2 Hz, 1H), 6.82 (s, 1H), 5.51 (s, 1H), 4.64 (t, J=8.4 Hz, 1H), 4.52 (t, J=7.2 Hz, 1H), 4.48 (d, J=13.6 Hz, 1H), 4.38 (d, J=3.2 Hz, 2H), 4.16 (s, 1H), 4.00 (dd, J=14, 4.4 Hz, 1H), 3.84 (t, J=4.4 Hz, 2H), 3.47 (s, 3H), 3.44 (dd, J=6.8, 2 Hz, 2H), 2.69 (dd, J=14.4, 8 Hz, 1H), 2.49 (ddd, J=14.4, 9.6, 4.4 Hz, 1H), 1.98 (m, 1H), 1.85 (m, 1H), 1.65 (dt, J=14.8, 7.6 Hz, 3H), 1.50 (t, J=7.6 Hz, 4H), 1.40 (dd, J=8, 4.8 Hz, 1H), 1.34 (d, J=14.4 Hz, 1H), 1.20 (m, 3H), 1.00 (s, 12H), 0.36 (m, 1H), 0.32 (quint., J=4 Hz, 1H).

Example 85

Preparation of Compound 85

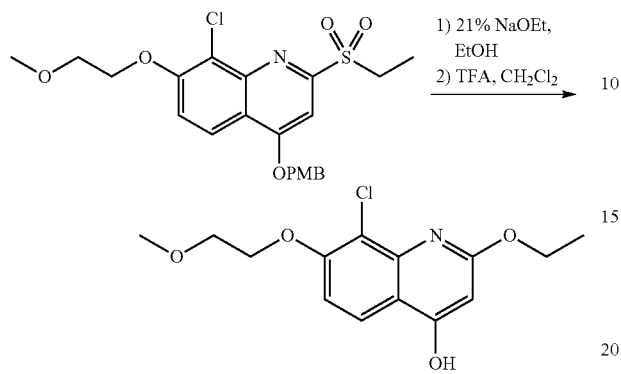

Step 1:

To a solution of the quinoline (450 mg, 0.965 mmol) in THF (5.0 mL) was added slowly 21% NaOEt in ethanol (1.10 mL, 2.89 mmol). After the solution was stirred at room temperature for 10 min, 2N HCl (10 mL) was added. The resulting mixture was stirred for 5 min, diluted with EtOAc (10 mL) and stirred for 5 min. After two layers were separated, the aqueous layer was extracted with EtOAc (10 mL). Combined organic fractions were dried ($Na_2SO_4$) and concentrated. The residue was purified by silica gel chromatography using a mixture of hexanes and ethyl acetate as the eluent to afford 385 mg (96%) of the PMB protected ethoxy quinoline. LC/MS=418 ($M^+$+1).

Step 2:

A solution of the PMB protected quinoline 385 mg (0.923 mmol) in dichloromethane (5.0 mL) and TFA (5.0 mL) was stirred at room temperature for 10 min. The color goes from colorless to purple as the reaction proceeds. The solution was concentrated under reduced pressure, adjusted the pH to 8 using 5% sodium bicarbonate, then extracted with EtOAc (20 mL×2). The combined organic extracts were dried ($Na_2SO_4$) and concentrated. The residue was purified by silica gel chromatography using a mixture of hexanes and ethyl acetate as the eluent to afford 254 mg (92%) of the hydroxyl quinoline. LC/MS=298 ($M^+$+1).

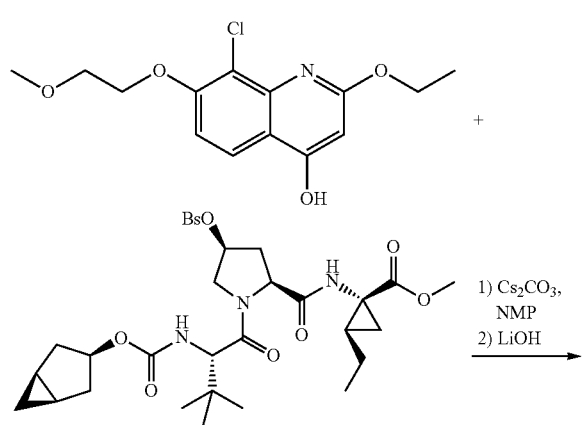

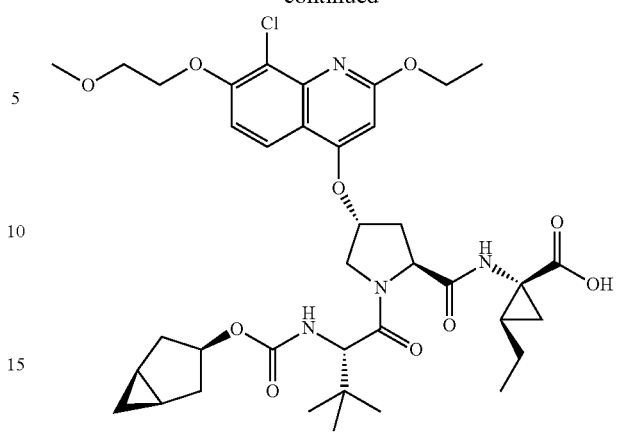

Step 3:

A mixture of intermediate III (800 mg, 1.12 mmol), quinoline (332 mg, 1.12 mmol) and cesium carbonate (802 mg, 2.46 mmol) in NMP (5 mL) was stirred as 65° C. for 16 h. The mixture was then diluted with EtOAc (20 mL) and 5% LiCl (20 mL) and stirred at room temperature for 30 min. The two layers were separated and the aqueous was extracted with EtOAc (20 mL). The combined organic fractions were washed with 5% LiCl (3×20 mL), water, and then brine. The organic fraction was dried ($Na_2SO_4$) and concentrated. The crude material was purified by silica gel chromatography using a mixture of hexanes and ethyl acetate as the eluent to afford 685 mg (79%) of the ester. LC/MS=773 ($M^+$+1).

Step 4:

To a mixture of ester (685 mg, 0.88 mmol) in THF (3 mL) and methanol (5 mL), was added a solution of LiOH monohydrate (210 mg, 5.0 mmol) in water (3 mL). The mixture was stirred at 35° C. for 3 h. The solution was concentrated under reduced pressure and the pH was adjusted to 2 with 10% HCl. Methanol (5 mL) was added to the mixture and was purified by reverse phase preparative HPLC using a mixture of acetonitrile 0.1% TFA and water 0.1% TFA as the eluent to afford 323 mg (48%) of compound 85. $^1$H NMR (400 MHz, $CD_3OD$): 5 (ppm) 7.85 (d, J=9.2 Hz, 1H), 7.15 (d, J=9.2 Hz, 1H), 6.37 (s, 1H), 5.34 (br, 1H), 4.53-4.35 (br, 5H), 4.24 (br, 2H), 4.08 (s, 1H), 3.99-3.87 (br, 1H), 3.74-3.72 (m, 2H), 3.36 (s, 3H), 2.60 (m, 1H), 2.40 (m, 1H), 1.93 (m, 1H), 1.82 (m, 2H), 1.58-1.52 (br, 4H), 1.43-1.36 (br, 4H), 1.31-1.21 (br, 2H), 1.13-1.03 (br, 3H), 0.91 (s, 9H), 0.84 (s, 1H), 0.21-0.02 (br, 2H). LC/MS=760 ($M^+$+1).

Example 86

Preparation of Compound 86

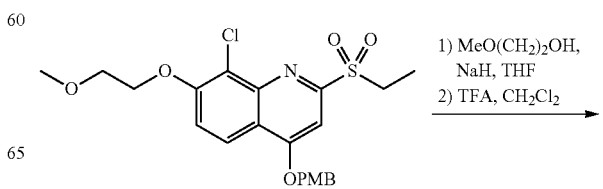

403
-continued

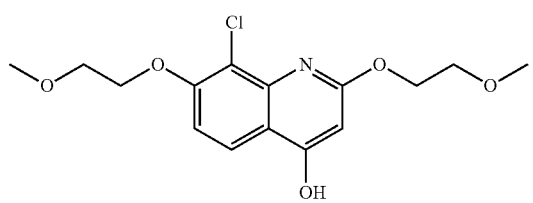

404
-continued

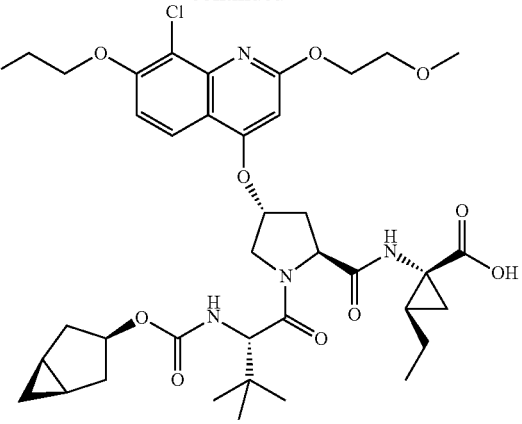

Step 1:

To a mixture of NaH (214 mg, 5.35 mmol) in THF (3.5 mL) was added 2-methoxyethyl alcohol (253 µL, 3.21 mmol) dropwise. After the mixture was stirred at room temperature for 15 min, a solution of the quinoline (534 mg, 1.07 mmol) in THF (1.5 mL) was added, and the resulting solution was stirred for 10 min. The reaction was quenched by addition of 2N HCl (10 mL) and the resulting mixture was stirred for 5 min. After the mixture was diluted with EtOAc (20 mL) and stirred for 5 min, two layers were separated and the aqueous fraction was extracted with EtOAc (20 mL). The combined organic fractions were dried (Na$_2$SO$_4$) and concentrate. The residue was purified by silica gel chromatography using a mixture of hexanes and ethyl acetate as the eluent to afford 504 mg (98%) of the PMB protected bis-methoxyethoxy quinoline. LC/MS=448 (M$^+$+1).

Step 2:

A solution of the PMB protected quinoline 504 mg (1.12 mmol) in dichloromethane (5.0 mL), and TFA (5.0 mL) was stirred at room temperature for 10 min. The color goes from colorless to purple as the reaction proceeds. The solution was concentrated under reduced pressure, adjusted the pH to 8 using 5% sodium bicarbonate, then extracted with EtOAc (2×10 mL). The combined organic fractions were dried (Na$_2$SO$_4$) and concentrated. The residue was purified by silica gel chromatography using a mixture of hexanes and ethyl acetate as the eluent to afford 367 mg (100%) of the hydroxyl quinoline. LC/MS=328 (M$^+$+1).

Step 3:

A mixture of intermediate III (800 mg, 1.12 mmol), quinoline (367 mg, 1.12 mmol) and cesium carbonate (802 mg, 2.46 mmol) in NMP (5 mL) was stirred as 65° C. for 16 h. The mixture was then diluted with EtOAc (20 mL) and 5% LiCl (20 mL) and stirred at room temperature for 30 min. The two layers were separated and the aqueous fraction was extracted with EtOAc (20 mL). After the combined organic fractions were washed with LiCl (3×20 mL), water, and then brine, it was dried (Na$_2$SO$_4$) and concentrated. The residue was purified by silica gel chromatography using a mixture of hexanes and ethyl acetate as the eluent to afford 829 mg (92%) of the ester. LC/MS=803 (M$^+$+1).

Step 4:

To a mixture of ester (829 mg, 1.02 mmol) in THF (3 mL) and methanol (5 mL), was added a solution of LiOH monohydrate (210 mg, 5.0 mmol) in water (3 mL). The mixture was stirred at 35° C. for 3 h. The solution was concentrated under reduced pressure and the pH was adjusted to 2 with 10% HCl. Methanol (5 mL) was added to the mixture and was purified by reverse phase preparative HPLC using a mixture of acetonitrile 0.1% TFA and water 0.1% TFA as the eluent to afford 528 mg (66%) of compound 86. $^1$H NMR (400 MHz, CD$_3$OD): δ (ppm) 7.81 (d, J=8.99 Hz, 1H), 7.10 (d, J=9.2 Hz, 1H), 6.35 (s, 1H), 5.28 (br, 1H), 4.59-4.36 (br, 5H), 4.22 (br, 2H), 4.08 (s, 1H), 3.89-3.85 (br, 1H), 3.75-3.70 (m, 2H), 3.36 (s, 3H), 3.34 (s, 3H), 2.58 (m, 1H), 2.38 (m, 1H), 1.93 (m, 1H), 1.82 (m, H), 1.58-1.50 (br, 4H), 1.42-1.23 (br, 4H), 1.1-1.05 (br, 3H), 0.88 (s, 9H), 0.82 (s, 1H), 0.19-0.2 (br, 2H). LC/MS=790 (M$^+$+1).

Example 87

Preparation of Compound 87

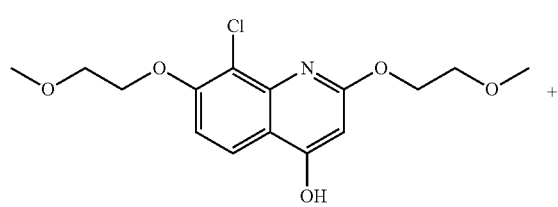

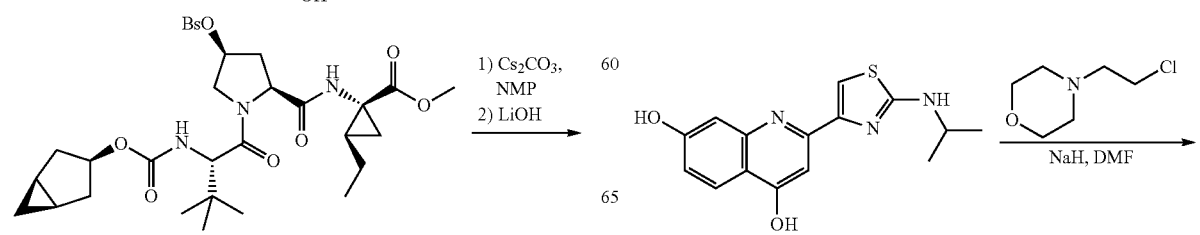

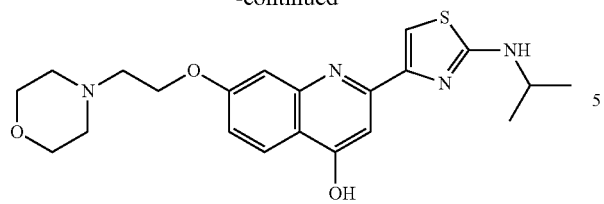

Step 1:

The dihydroxyquinoline (2 g, 6.6 mmol) was dissolved in DMF (50 ml) at 0° C. and NaH (792 mg, 19.8 mmol) was added in portions. It was stirred at 0° C. for 30 min, followed by addition of 4-(2-chloroethyl)-morpholine hydrochloric acid (1.36 g, 7.3 mmol). The mixture was stirred at 60° C. for 5 h then room temperature overnight. The mixture was diluted with EtOAc and aqueous 3% LiCl solution. The two layers were separated and the aqueous fraction was extracted with EtOAc again. The combined organic fractions were washed with brine, dried (MgSO$_4$), and concentrated in vacuo. The residue was purified by flash chromatography on silica gel with MeOH/EtOAc to yield 1.46 g (43%) of the desired product. LC/MS=415 (M$^+$+1).

Step 2:

Compound 87 (570 mg as TFA salt, 74%) was obtained by the procedures similar to those for preparation of compound 82 using macrocyclic tripeptide (1.2 g mg, 1.7 mmol, with >30% impurities) and quinoline (500 mg, 0.965, with 20% impurities). $^1$H NMR (300 MHz, CD$_3$OD): δ 8.64 (s, 1H), 8.33 (d, 1H), 8.22 (s, 1H), 7.83 (s, 1H), 7.78 (d, 1H), 7.41 (dd, 1H), 5.7 (b, 1H), 4.78-4.62 (m, 5H), 4.30 (d, 1H), 4.29-4.07 (m, 7H), 3.79 (t, 2H), 3.54 (brs, 4H), 2.80-2.60 (m, 2H), 1.10-2.04 (m, 34H), 0.97-0.92 (m, 1H), 0.32-0.42 (m, 2H). LC/MS=888.7 (M$^+$+1).

Example 88

Preparation of Compound 88

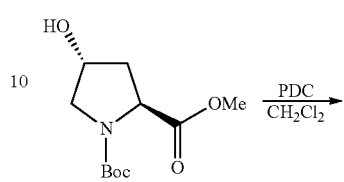

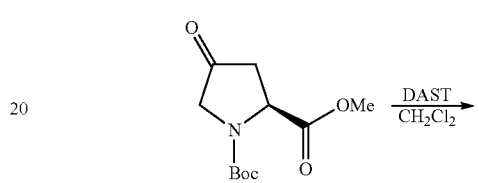

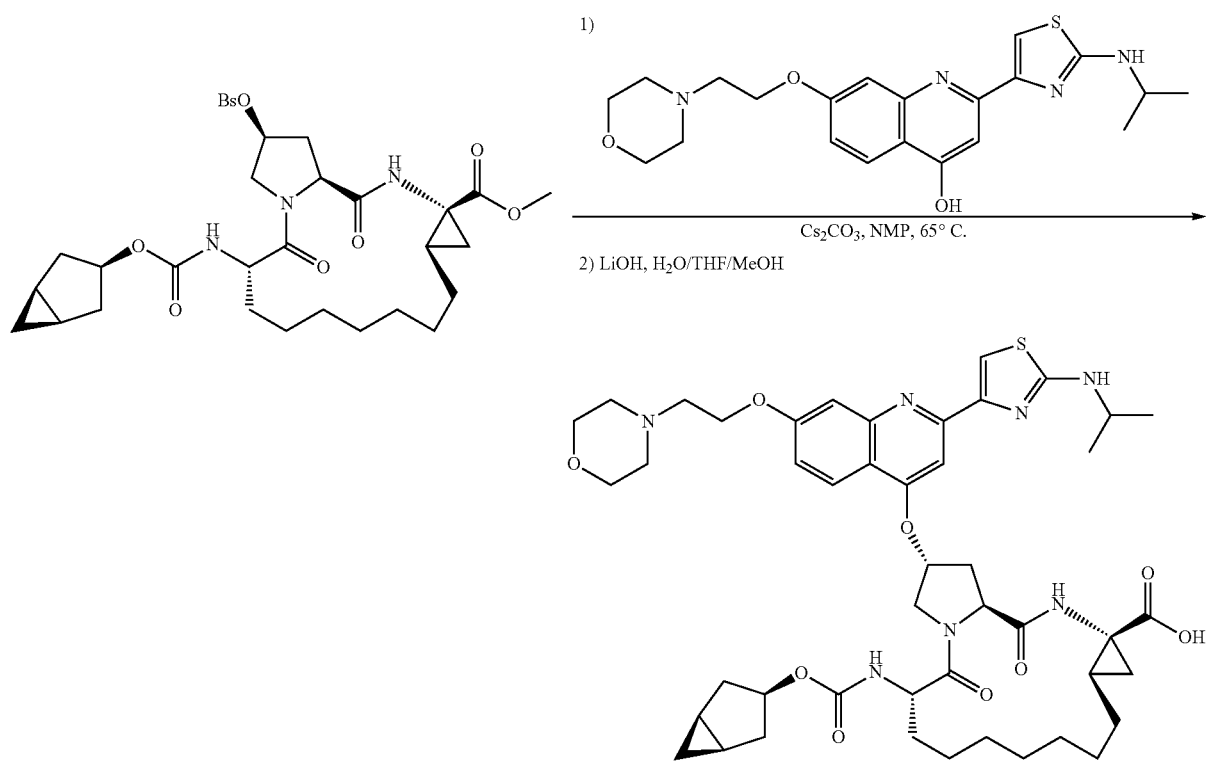

-continued

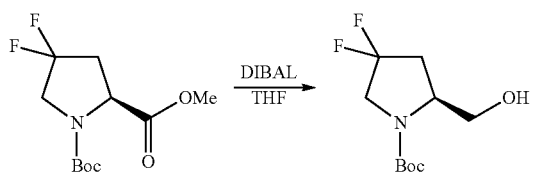

Step 1:

A mixture of the protected hydroxyproline (10 g, 40.8 mmol), PDC (23.0 g, 61.2 mmol) and 10 g of 4A molecular sieves in dichloromethane (150 mL) was stirred at room temperature for 4 days. It was filtered through a pile of Celite, washed pad with more dichloromethane. The filtrate was concentrated and the residue was purified by flash chromatography on silica gel with EtOAc/Hexane to afford 7.86 g (79%) desired ketone. LC/MS=144 (M$^+$+1-Boc).

Step 2:

A mixture of the ketone (4.3 g, 17.7 mmol) in dichloromethane (80 mL) was stirred at −78° C. under N$_2$ as DAST (5.8 mL, 44.25 mmol) was added slowly. The mixture was allowed to warm to room temperature and stirred for 24 h. The reaction mixture was quenched with ice-water. After the two layers were separated, the aqueous fraction was extracted with dichloromethane (300 mL) and the combined organic fractions were dried (MgSO$_4$) and concentrated in vacuo. The crude product was purified by flash chromatography on silica gel with EtOAc/hexane to obtain 4.37 g (93%) of the difluoro compound. LC/MS=166 (M$^+$+1-Boc).

Step 3:

A mixture of difluoro-ester (4.37 g, 16.5 mmol) in THF (50 mL) was stirred at −78° C. under N$_2$ as 1 M DIBAL in THF (36.3 mL, 36.3 mmol) was added dropwise over 30 min period. The mixture was allowed to warm to room temperature and stirred for 48 h. The mixture was diluted with EtOAc (100 mL) and sat. sodium potassium tartrate (100 mL), and the resulting mixture was vigorously stirred for 30 min until two phases were apparent. After the two layers were separated, the aqueous fraction was extracted with EtOAc (2×100 mL) and the combined organic fractions were washed with brine, dried (MgSO$_4$), and concentrated in vacuo. The crude product was purified by flash chromatography on silica gel with EtOAc/hexane, gave 1.56 g (40%) of the alcohol. LC/MS=138 (M$^+$+1-Boc).

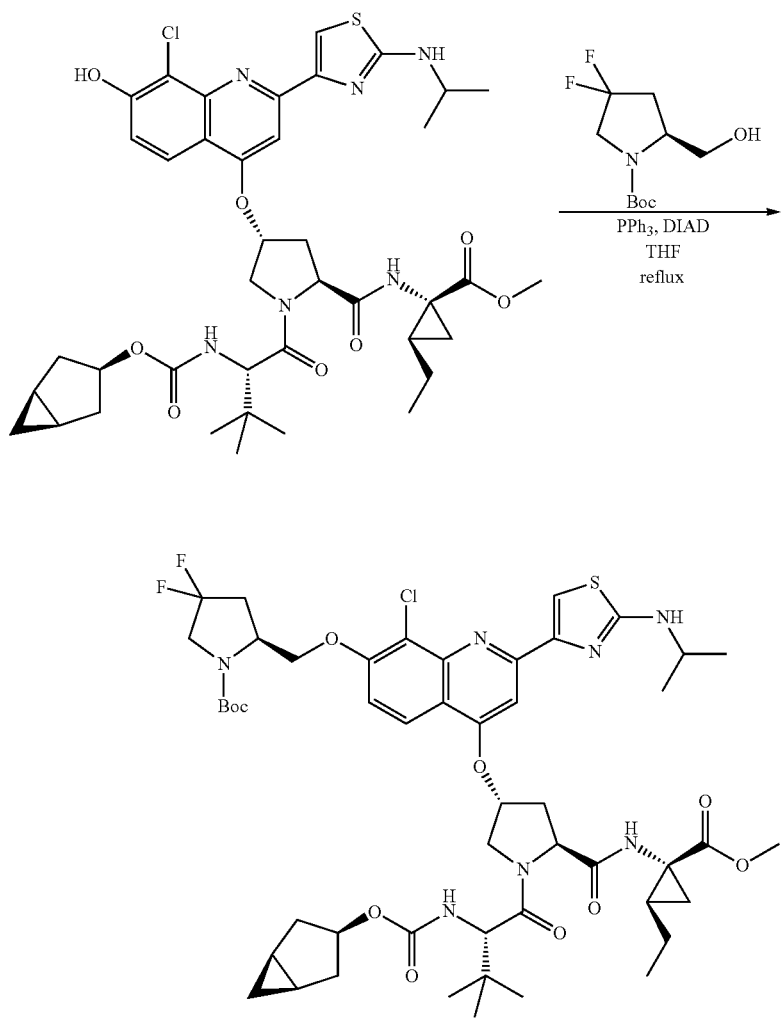

Step 4:

A mixture of the tripeptide (500 mg, 0.616 mmol) and the alcohol (175 mg, 0.739 mmol) in the previous step, PPh$_3$ (261 mg, 0.986 mmol), and DIAD (0.191 mL, 0.986 mmol) in THF (10 mL) was refluxed for 3 h. After the mixture was cooled to room temperature and concentrated, the residue was purified by flash chromatography on silica gel with EtOAc/Hexane to afford 628 mg (99%) of the desired product. LC/MS=1031.3 (M$^+$+1).

409    410

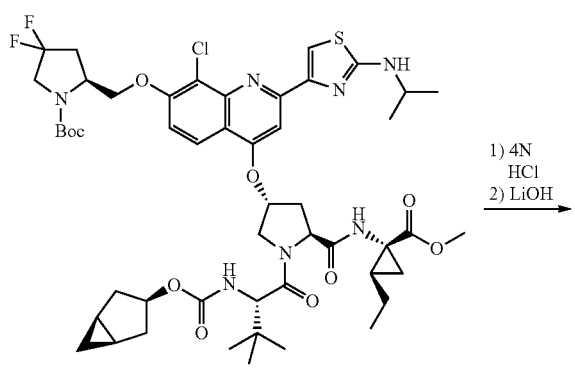

Step 5:

The above Boc-protected compound was dissolved in 4N HCl in dioxane (10 mL) and stirred at room temperature for 2 h. The mixture was concentrated in vacuo to give the crude product. LC/MS=930.2 (M$^+$+1).

Step 6:

The above compound was dissolved in THF (3 mL), MeOH (3 mL), and water (10 mL) with LiOH (462 mg, 11.56 mmol) and stirred at room temperature for 24 h. The solution was acidified with TFA and then concentrated in vacuo. The residue was purified by prep-HPLC to afford 500.8 mg (76% for two steps) of compound 88 as bis-TFA salt. $^1$H NMR (300 MHz, CD$_3$OD): δ 8.64 (s, 1H), 8.33 (d, 1H), 8.22 (s, 1H), 7.78 (s, 1H), 7.60 (d, 1H), 5.72 (b, 1H), 4.90-4.55 (m, 5H), 4.22-4.13 (m, 2H), 4.00-3.88 (m, 2H), 3.00-2.60 (m, 3H), 2.00-1.80 (m, 2H), 1.70-1.65 (m, 2H), 1.57-1.40 (m, 2H), 1.40 (s, 3H), 1.38 (s, 3H), 1.22 (m, 2H), 1.03-0.92 (m, 10H), 0.35 (m, 2H). LC/MS=916.2 (M$^+$+1).

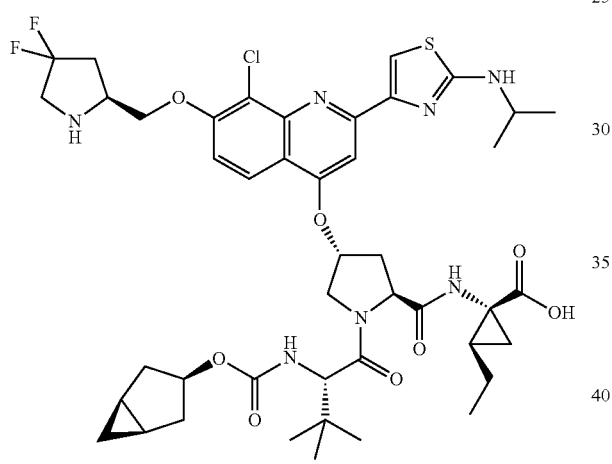

Example 89

Preparation of Compound 89

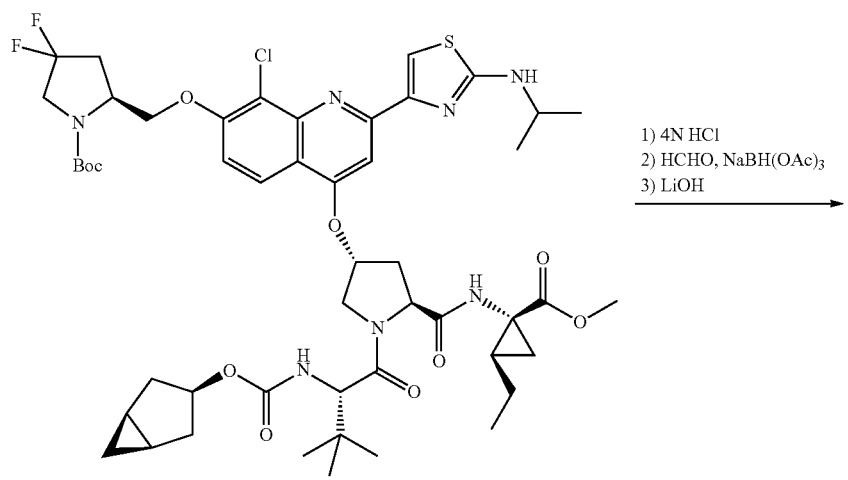

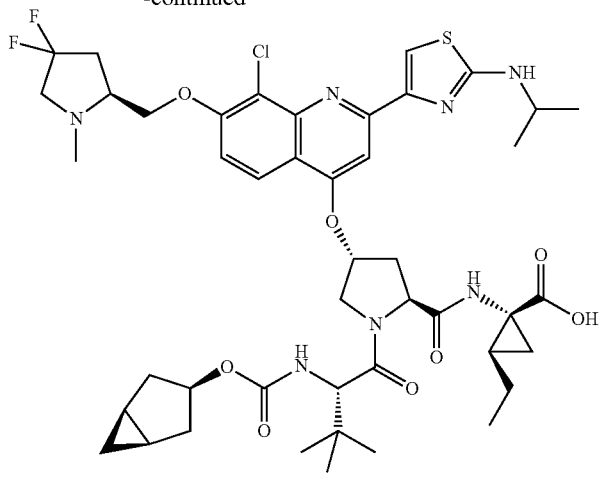

Step 1:
The Boc deprotection was performed by the procedure in example 88, Step 5.

Step 2:
To a solution of the above de-Boc compound in 1,2-dichloroethane (6 mL) were added NaBH(OAc)$_3$ (520 mg, 2.45 mmol) and formaldehyde (37% in water, 0.1 mL, 1.23 mmol) at room temperature. After 1 hr, the mixture was concentrated, diluted with EtOAc (100 mL), washed with sat. NaHCO$_3$ and brine, dried (Na$_2$SO$_4$), and concentrated in vacuo to give the crude methylated compound. LC/MS=944.2 (M$^+$+1).

Step 3:
The above methylated compound was dissolved in THF (3 mL), MeOH (3 mL), and water (10 mL) with LiOH (500 mg) and stirred at room temperature for 24 h. The solution was acidified with TFA and then concentrated in vacuo. The crude product was purified by prep-HPLC to afford 510 mg (69% for 3 steps) of compound 89 as bis-TFA salt. $^1$H NMR (300 MHz, CD$_3$OD): δ 8.64 (s, 1H), 8.31 (d, 1H), 8.23 (s, 1H), 7.73 (s, 1H), 7.62 (d, 1H), 5.72 (b, 1H), 4.90-4.50 (m, 5H), 4.30-3.68 (m, 7H), 3.20 (s, 3H), 3.05-2.60 (m, 3H), 2.00-1.80 (m, 2H), 1.70-1.63 (m, 2H), 1.54-1.40 (m, 2H), 1.40 (s, 3H), 1.38 (s, 3H), 1.22 (m, 2H), 1.03-0.92 (m, 10H), 0.34 (m, 2H). LC/MS=930.2 (M$^+$+1).

Example 90

Preparation of Compound 90

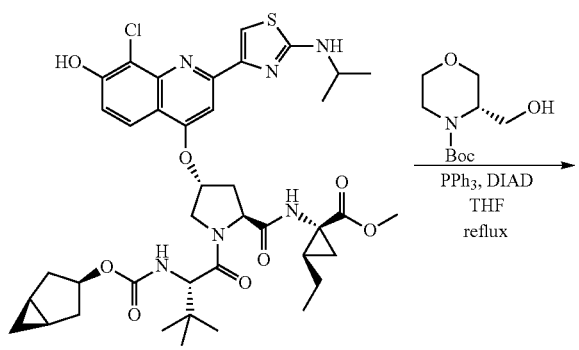

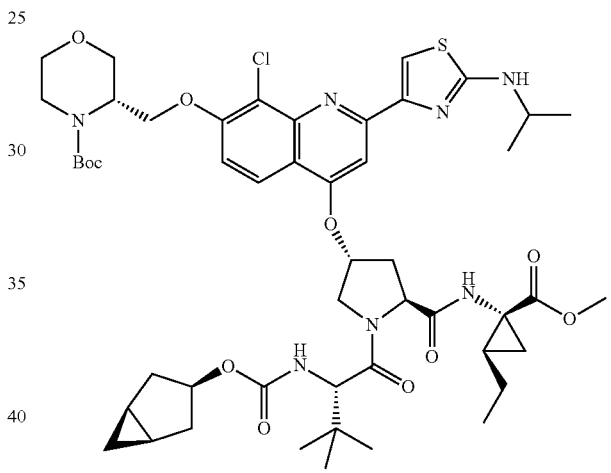

Step 1:
A mixture of the reactant (1.17 g, 1.44 mmol) and 3-hydroxymethyl-morpholine-4-carboxylic acid tert-butyl ester (376 mg, 1.73 mmol), PPh$_3$ (604 mg, 2.30 mmol) and DIAD (0.445 mL, 2.30 mmol) in THF (15 mL) was refluxed for 3 h. LC/MS showed some product faulted along with other by products and lots of starting material. Another half portions of reagents were added and refluxed overnight. The mixture was cooled to room temperature, diluted with EtOAc (100 mL), washed with sat. NaHCO$_3$ and brine, dried (Na$_2$SO$_4$), and concentrated in vacuo. The residue was purified by flash chromatography on silica gel with EtOAc/Hexane followed by prep-HPLC to afford 142 mg (10%) of the desired product. LC/MS=1010.3 (M$^+$+1).

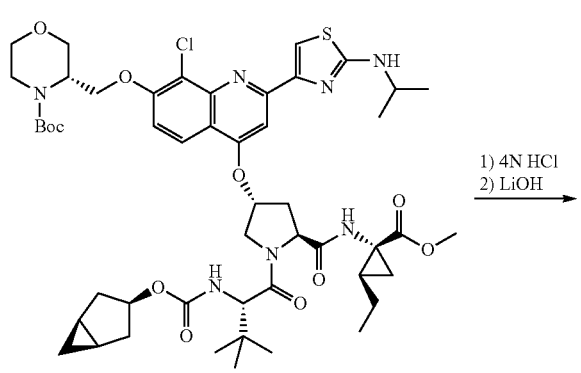

Step 2:

Above Boc-protected compound (55 mg, 0.054 mmol) was dissolved in 4N HCl in dioxane (3 mL) and stirred at room temperature for 1 h. The mixture was diluted with EtOAc (20 mL), washed with sat. NaHCO$_3$ and brine, dried (Na$_2$SO$_4$), and concentrated in vacuo to give the crude deprotected product. LC/MS=910.3 (M$^+$+1).

Step 3:

Above compound and LiOH (50 mg) were dissolved in THF (5 mL), MeOH (0.5 mL), and water (2 mL) and stirred at room temperature for 24 h. The solution was acidified with TFA and then concentrated in vacuo to give the crude product, which was purified by prep-HPLC to afford 17 mg (28% for two steps) of compound 90. $^1$H NMR (300 MHz, CD$_3$OD): δ 8.64 (s, 1H), 8.31 (d, 1H), 8.25 (s, 1H), 7.80 (s, 1H), 7.68-7.55 (m, 4H), 5.72 (b, 1H), 4.79-4.47 (m, 5H), 4.25-3.84 (m, 10H), 3.50-3.39 (m, 2H), 2.86-2.60 (m, 2H), 2.00-1.80 (m, 2H), 1.70-1.62 (m, 2H), 1.54-1.40 (m, 2H), 1.40 (s, 3H), 1.38 (s, 3H), 1.34-1.20 (m, 4H), 1.03-0.92 (m, 10H), 0.35 (m, 2H). LC/MS=896.2 (M$^+$+1).

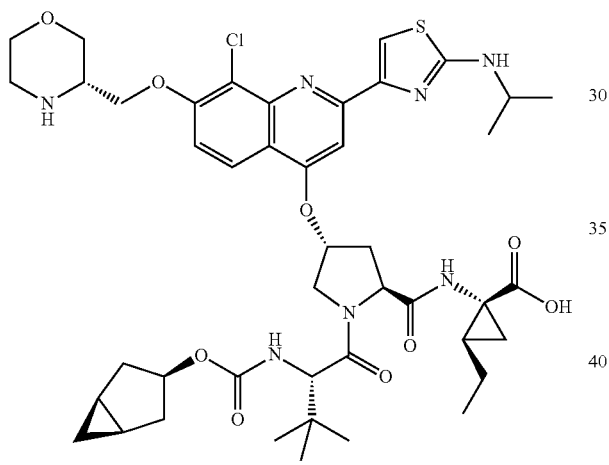

Example 91

Preparation of Compound 91

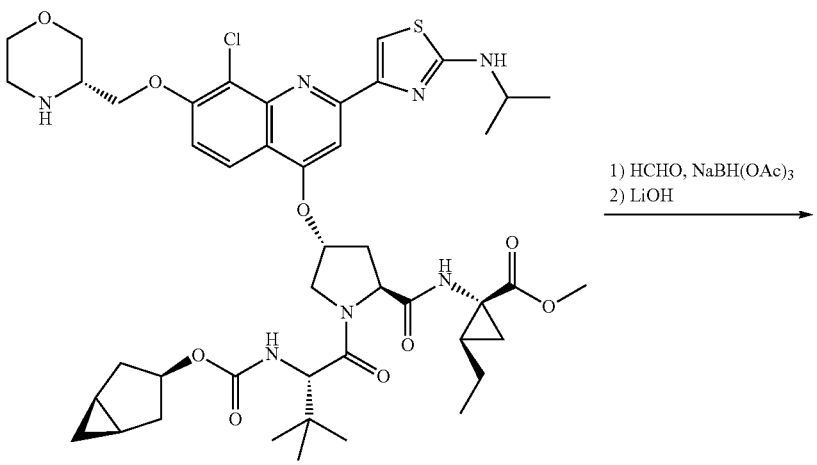

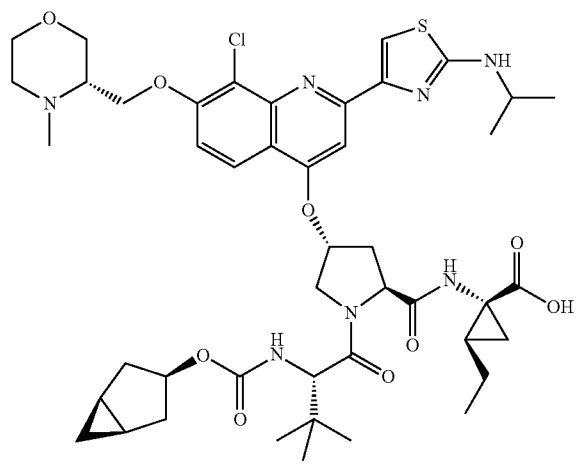

Compound 91 was obtained by the procedures described in Example 89. After purified by prep-HPLC, 25.5 mg (27%) of Compound 91 was obtained as bis-TFA salt. $^1$H NMR (300 MHz, CD$_3$OD): δ 8.64 (s, 1H), 8.29 (d, 1H), 8.23 (s, 1H), 7.78 (s, 1H), 7.73 (m, 1H), 5.72 (b, 1H), 4.79-4.47 (m, 5H), 4.30-3.95 (m, 10H), 3.61-3.43 (m, 2H), 3.17 (s, 3H), 2.86-2.50 (m, 2H), 2.00-1.80 (m, 2H), 1.70-1.61 (m, 2H), 1.57-1.40 (m, 2H), 1.40 (s, 3H), 1.38 (s, 3H), 1.34-1.20 (m, 4H), 1.05-0.90 (m, 10H), 0.35 (m, 2H). LC/MS=910.3 (M$^+$+1).

Example 92

Preparation of Compound 92

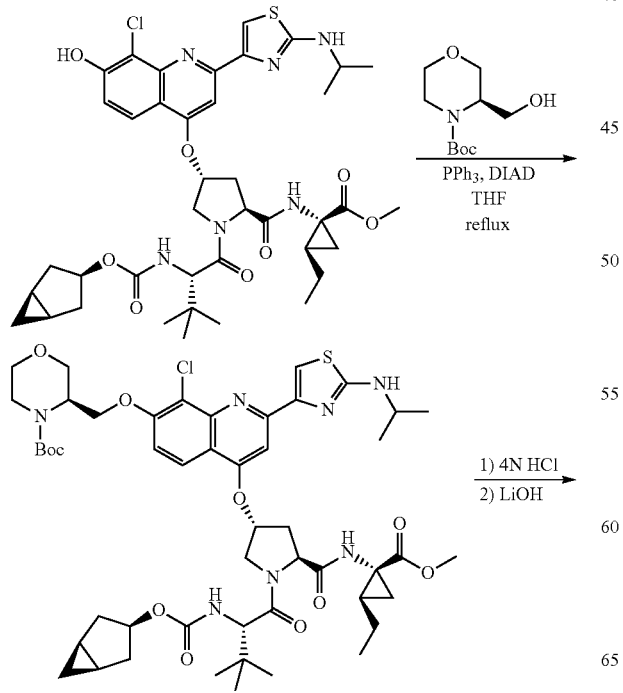

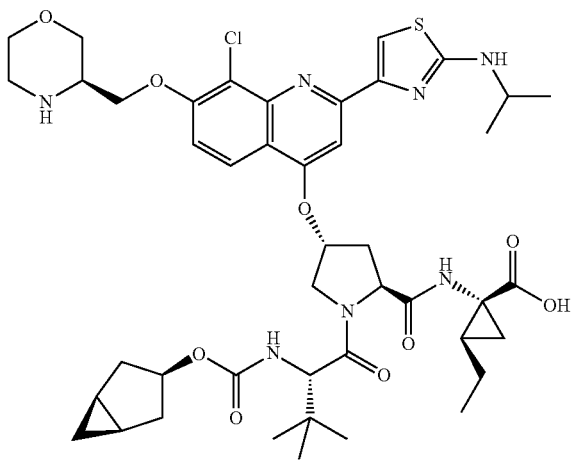

Compound 92 was obtained by the procedures described in example 90. After purified by prep-HPLC, 17.4 mg of compound 92 was obtained as bis-TFA salt. $^1$H NMR (300 MHz, CD$_3$OD): δ 8.64 (s, 1H), 8.29 (d, 1H), 8.22 (s, 1H), 7.78 (s, 1H), 7.61 (d, 1H), 5.71 (b, 1H), 4.73-4.49 (m, 5H), 4.25-3.84 (m, 10H), 3.50-3.39 (m, 2H), 2.86-2.60 (m, 2H), 2.00-1.80 (m, 2H), 1.70-1.62 (m, 2H), 1.54-1.40 (m, 2H), 1.40 (s, 3H), 1.38 (s, 3H), 1.30-1.20 (m, 4H), 1.05-0.91 (m, 10H), 0.33 (m, 2H). LC/MS=896.2 (M$^+$+1).

Example 93
Preparation of Compound 93
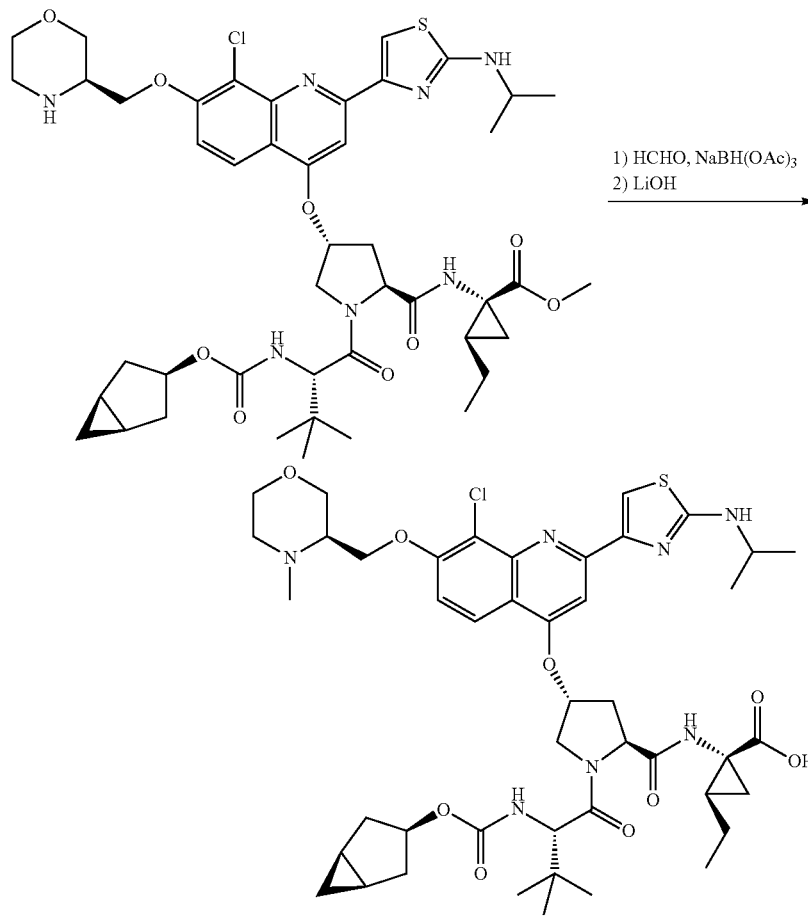
Compound 93 was obtained by the procedures described in example 89. After purified by prep-HPLC, 16.0 mg of compound 93 was obtained as bis-TFA salt. $^1$H NMR (300 MHz, CD$_3$OD): δ 8.63 (s, 1H), 8.31 (d, 1H), 8.24 (s, 1H), 7.80 (s, 1H), 7.64 (s, 1H), 5.72 (b, 1H), 4.75-4.47 (m, 5H), 4.20-3.92 (m, 10H), 3.61-3.40 (m, 2H), 3.18 (s, 3H), 2.80-2.55 (m, 2H), 2.00-1.80 (m, 2H), 1.70-1.62 (m, 2H), 1.50-1.40 (m, 2H), 1.40 (s, 3H), 1.38 (s, 3H), 1.20-1.10 (m, 4H), 1.05-0.97 (m, 10H), 0.35 (m, 2H). LC/MS=910.3 (M$^+$+1).
Example 94
Preparation of Compound 94
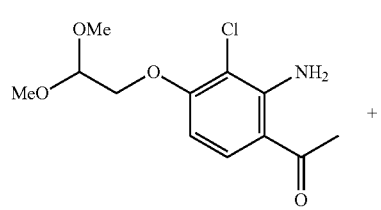
+
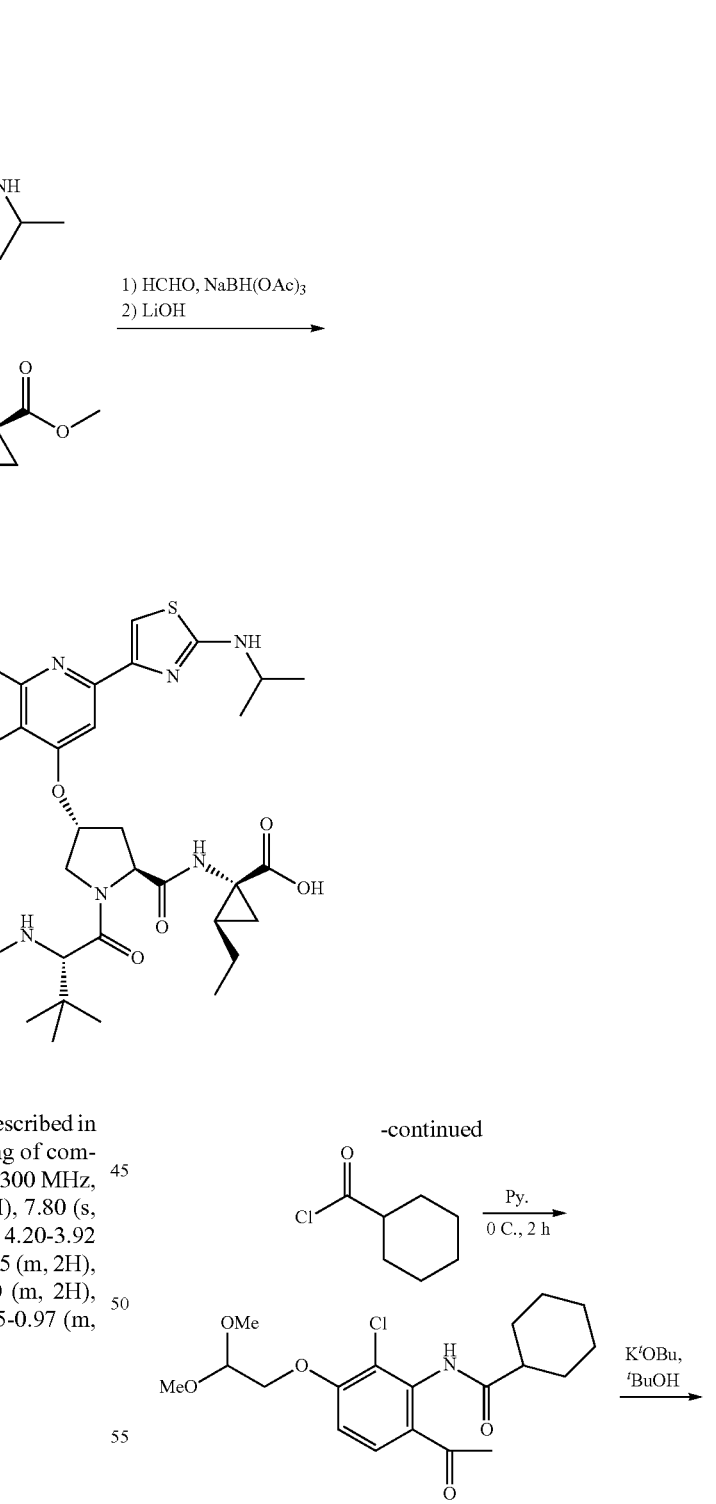
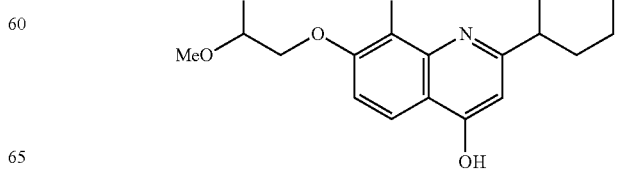

Step 1:
To a solution of 1-[2-Amino-3-chloro-4-(2,2-dimethoxy-ethoxy)-phenyl]-ethanone (2 g, 7.3 mmol) in pyridine (20 mL) was slowly added cyclohexanecarbonyl chloride (1.12 g, 7.7 mmol) at 0° C. After the mixture was stirred at room temperature for 2 h, H$_2$O (10 mL) was added to the mixture. The product was extracted with EtOAc, washed with brine, dried (Na$_2$SO$_4$), and concentrated in vacuo. The residue was purified by silica gel chromatography to obtain 1.9 g, (65%) of the amide as white solids. LC/MS=383.8 (M$^+$+1).

Step 2:
The amide (1.9 g, 5.0 mmol) and t-BuOK (0.62 g, 0.55 mmol) were dissolved in t-BuOH (20 mL) at room temperature and stirred under reflux for 2 h. Upon completion of the reaction, 3N HCl was added to the reaction to adjust pH around 3, which resulted the precipitation of the product. The solids were filtered, washed with ether, and dried under high vacuum to afford the quinoline as white solids (1.6 g, 100%). LC/MS=366.1 (M$^+$+1).

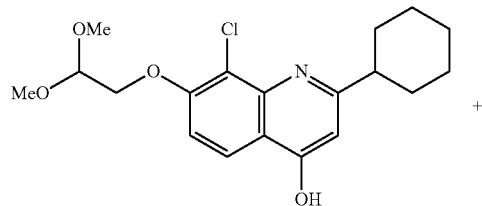

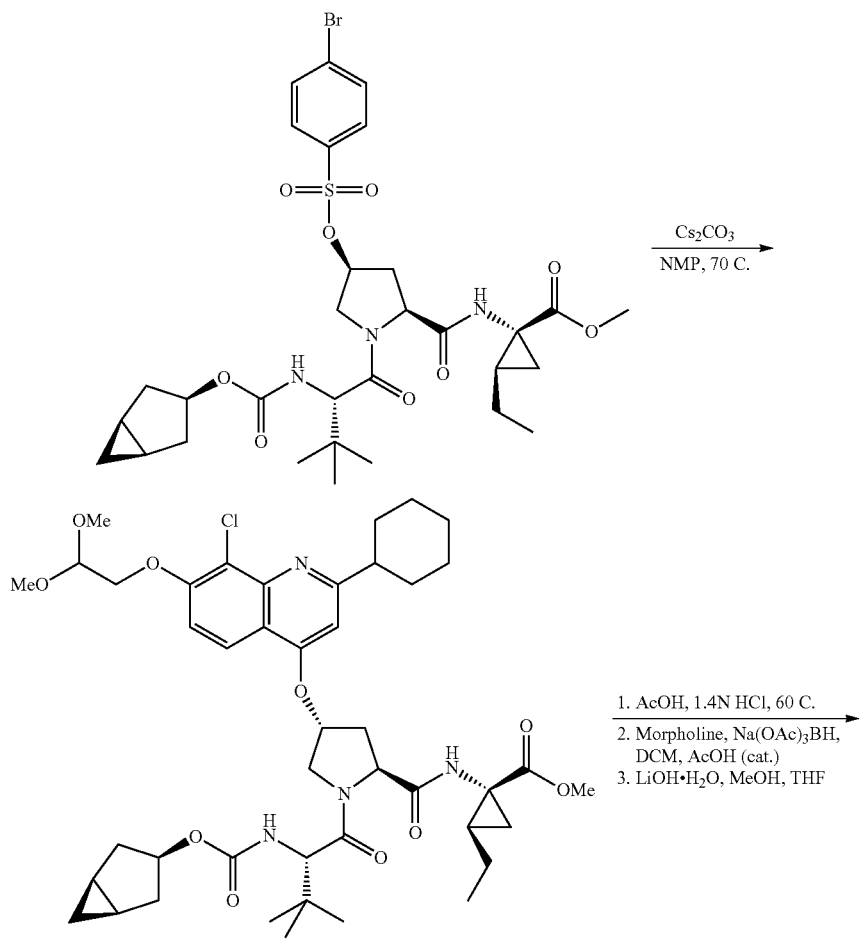

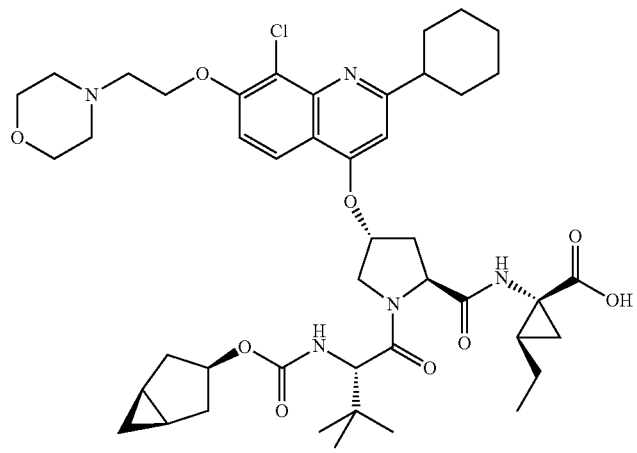
Step 3:
Compound 94 (170 mg) was synthesized using the same procedure described before to prepare compound 82. LC/MS=852.9 (M$^+$+1). $^1$H NMR (300 MHz, CD$_3$OD): δ 8.06 (d, 1H), 7.32 (d, 1H), 7.04 (s, 1H), 5.45 (b, 2H), 4.34 (dd, 1H), 4.25 (d, 1H), 4.15 (dd, 1H), 3.79-2.98 (m, 11H), 2.42 (m, 1H), 2.25 (m, 1H), 1.75-1.61 (m, 3H), 1.54-1.45 (m, 3H), 1.35-1.00 (m, 10H), 0.91-0.84 (m, 2H), 0.73-0.61 (m, 12H), 0.14-0.03 (m, 2H).
Example 95
Preparation of Compound 95
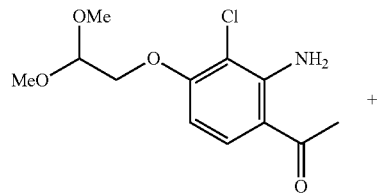
+
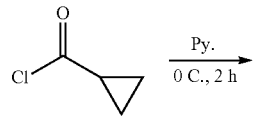
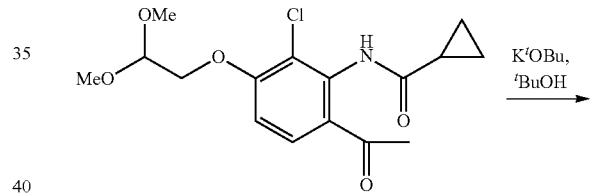
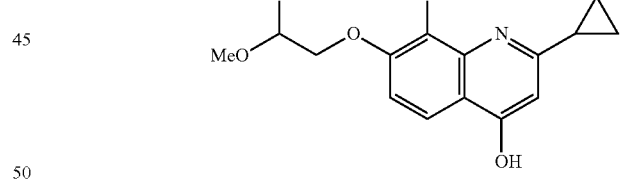
Step 1 and Step 2:
The quinoline was synthesized using the procedure described before in example 94. LC/MS=324.2 (M$^+$+1).
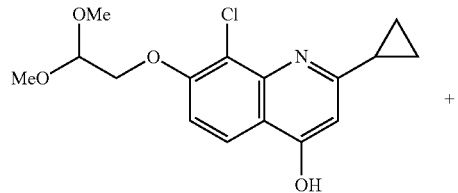
+

-continued
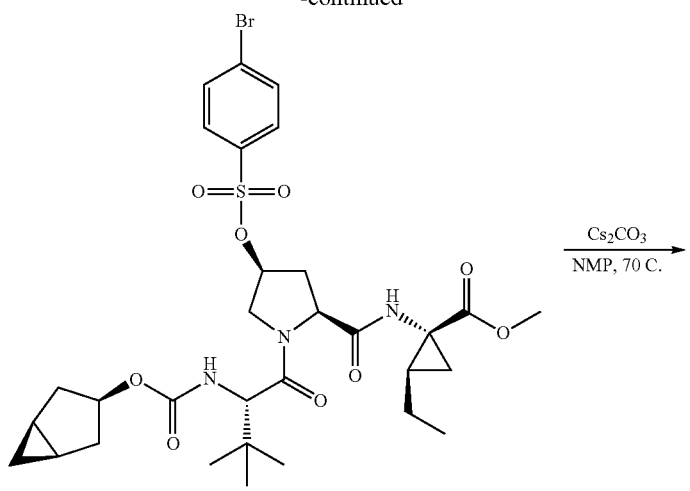
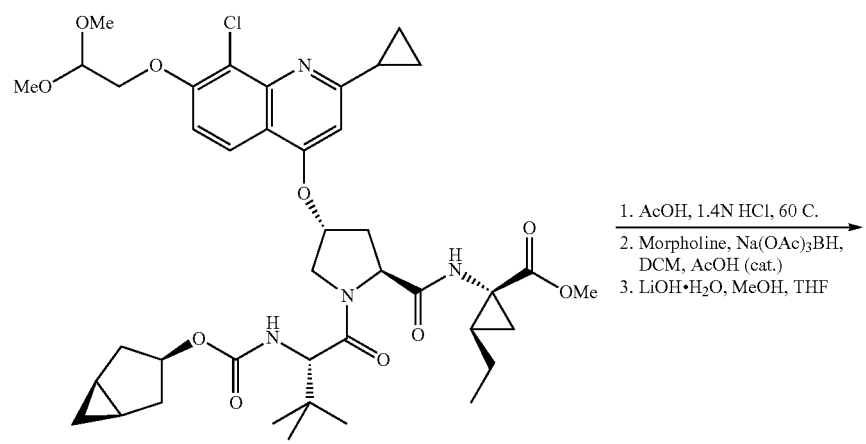
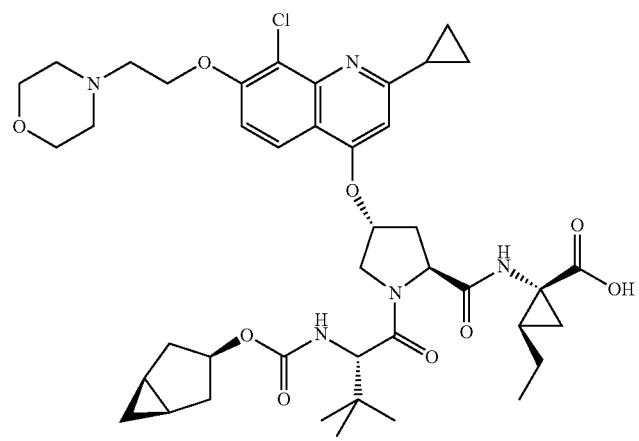

Step 3:
Compound 95 (550 mg) was synthesized using the same procedure described before to prepare compound 82. LC/MS=810.5 (M$^+$+1). $^1$H NMR (300 MHz, CD$_3$OD): δ 8.33 (d, 1H), 7.60 (d, 1H), 6.77 (s, 1H), 5.69 (bs, 1H), 4.78 (b, 2H), 4.66 (dd, 1H), 4.51 (m, 1H), 4.13-3.31 (m, 11H), 2.96-2.68 (m, 2H), 2.57-2.49 (m, 1H), 2.01-1.81 (m, 2H), 1.69-1.35 (m, 10H), 1.24-1.10 (m, 2H), 1.05-0.94 (m, 12H), 0.36-0.33 (m, 2H).
-continued
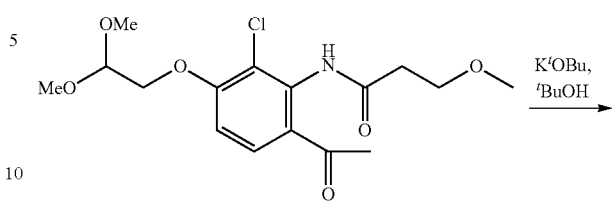
Example 96
Preparation of Compound 96
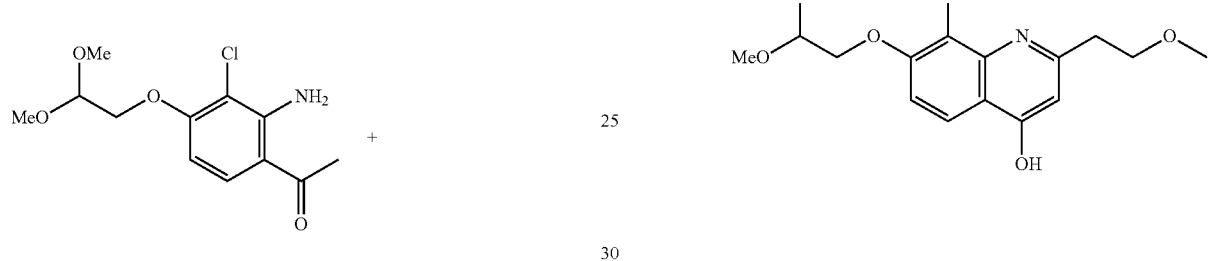
Step 1 and Step 2:
The quinoline was synthesized using the procedure described before in example 94. LC/MS=342.7 (M$^+$+1).
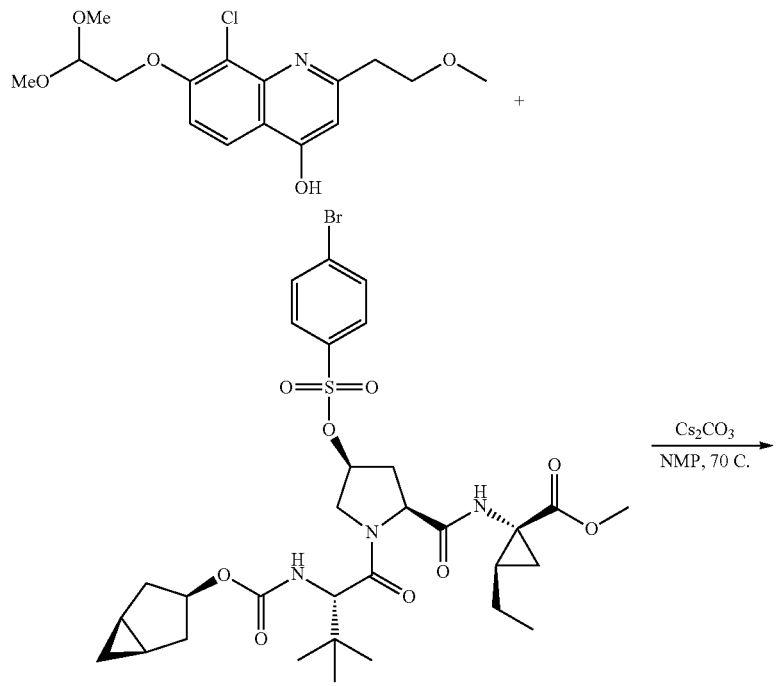

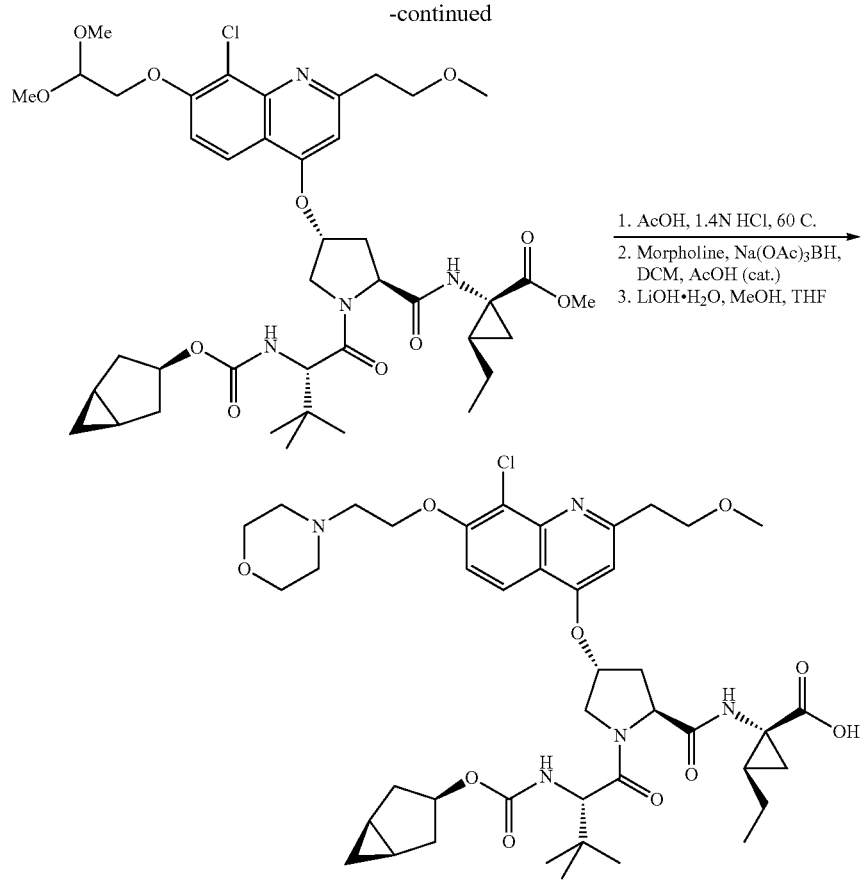

Step 3:

Compound 96 (260 mg) was synthesized using the same procedure described before to prepare compound 82. LC/MS=829.4 (M⁺+1).

Example 97

Preparation of Compound 97

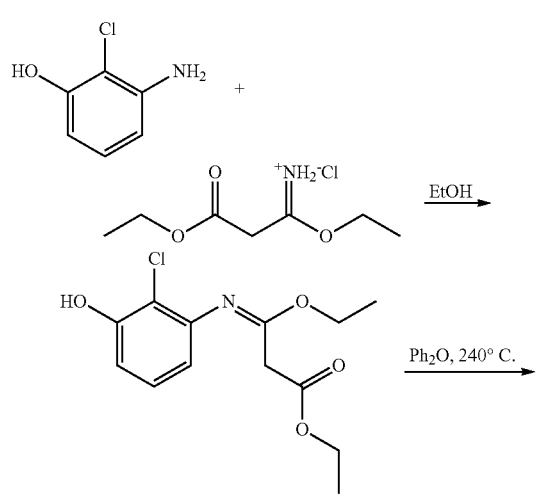

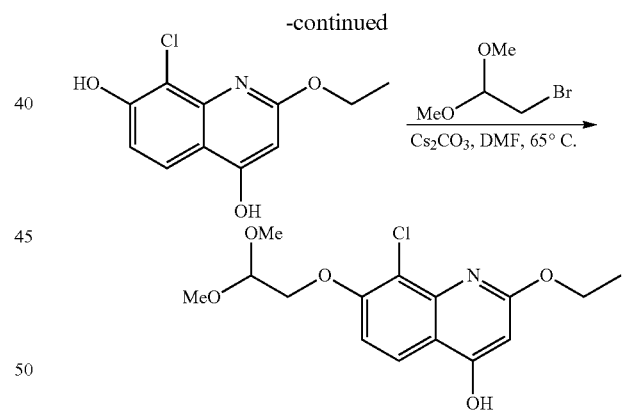

Step 1:

The imidate salt (2.99 g, 16 mmol) and the aniline (2 g, 14.5 mmol) were dissolved in ethanol (7 mL) under N₂ atmosphere. The reaction mixture was stirred at 30° C. overnight. After the mixture was filtered, the filtrate was concentrated. The residue was purified by silica gel chromatography to obtain the condensation product in form of colorless oil (3.6 g, 87%). LC/MS=285.9 (M⁺+1).

Step 2:

A solution of the condensation product (3.6 g, 87%) in diphenyl ether (36 mL) was placed in a hot sand bath (300° C.) and the mixture was allowed to stir for 12 minutes while the solution temperature was kept around 240-250° C. The mixture was cooled to room temperature and desired product was precipitated in brown solids. The solids were filtered, washed with hexane, and dried under high vacuum to afford the quinoline (2.33 g, 9.7 mmol, 77%). LC/MS=240.0 (M⁺+1).

Step 3:
To a solution of the quinoline (2.33 g, 9.7 mmol) in DMF (30 mL) were added cesium carbonate (12.64 g, 39 mmol) and 2-Bromo-1,1-dimethoxy-ethane (2.6 g, 15 mmol). The resulting mixture was stirred at 65° C. for 10 h. After the mixture was filtered, the filtrate was diluted with EtOAc and H₂O, and 3N HCl was added to adjust pH to 3. Organic fraction separated was washed with 5% LiCl and brine, dried (Na₂SO₄), and concentrated in vacuo. The residue was purified by silica gel chromatography to afford 8-Chloro-7-(2,2-dimethoxy-ethoxy)-2-ethoxy-quinolin-4-ol as white solids (1.27 g, 3.87 mmol, 40%). LC/MS=328.1 (M⁺+1).

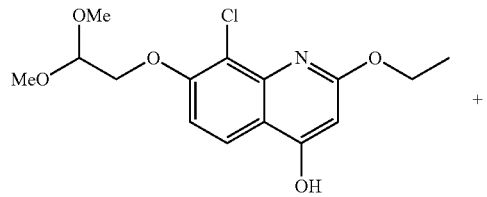

+

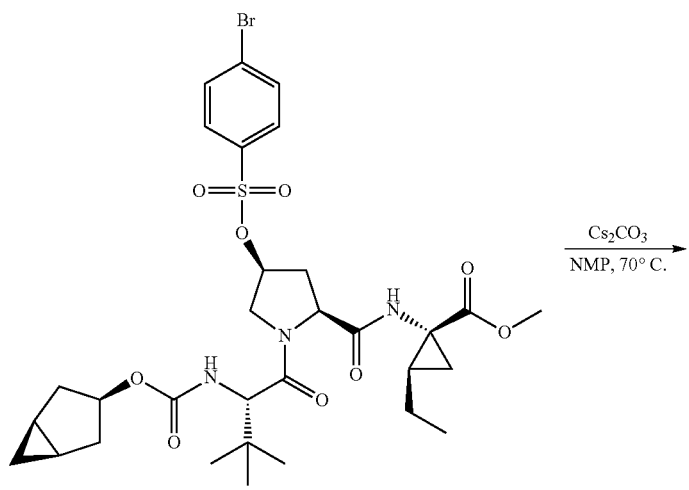

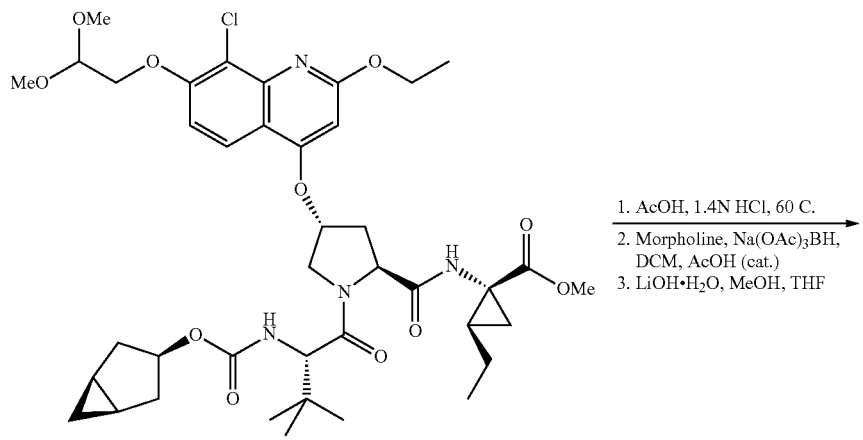

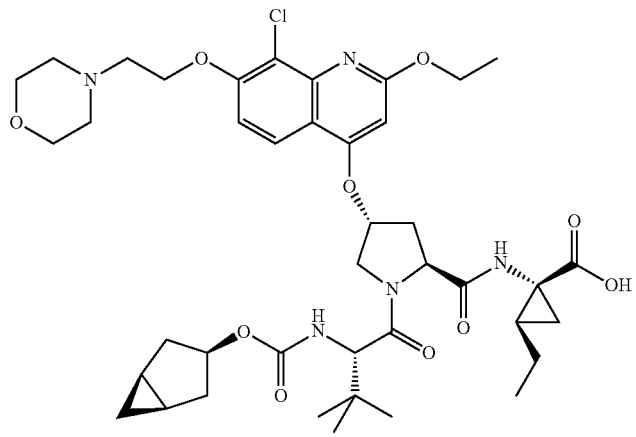
Step 4:
Compound 97 (754 mg) was synthesized using the same procedure described before to prepare compound 82. LC/MS=814.6 (M$^+$+1). $^1$H NMR (300 MHz, CD$_3$OD): δ 7.61 (d, 1H), 6.82 (d, 1H), 6.01 (s, 1H), 5.01 (s, 1H), 4.41-4.30 (m, 1H), 4.29-4.19 (m, 3H), 4.15-4.01 (m, 2H), 3.95-2.95 (m, 12H), 2.30 (m, 1H), 2.10 (m, 1H), 2.84-0.59 (m, 19H), 0.2-0.04 (m, 2H).
Example 98
Preparation of Compound 98
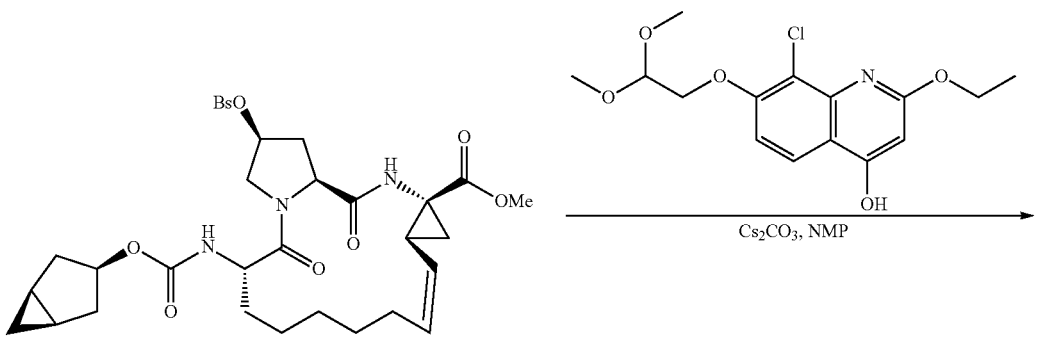
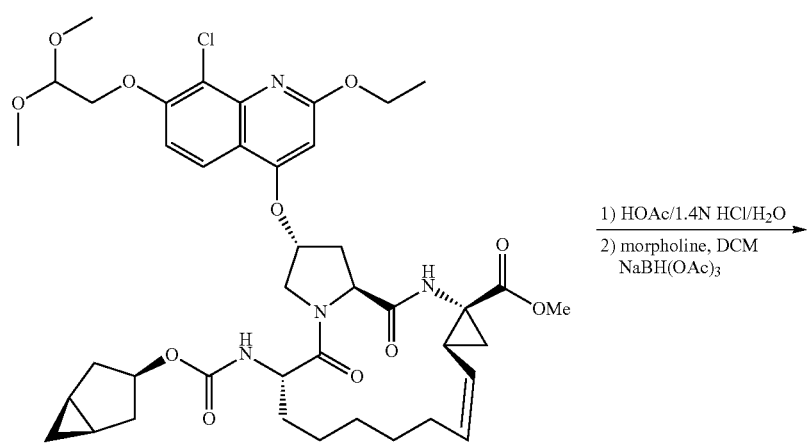

-continued

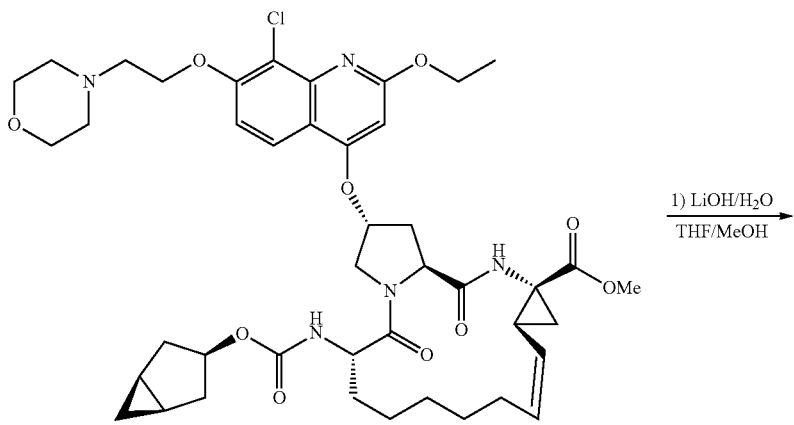

1) LiOH/H$_2$O
THF/MeOH

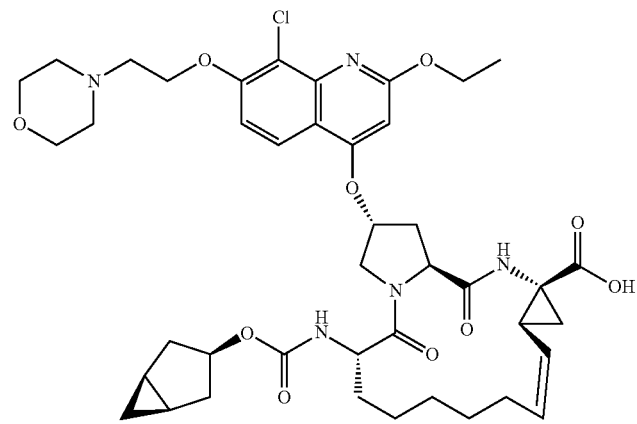

Step 1:

To a mixture of the brosylate (1.1 g, 1.52 mmol) and cesium carbonate (0.99 g, 3.04 mmol) in NMP (10 mL) was added the quinoline (0.40 g, 1.22 mmol) at room temperature in one portion. The mixture was stirred at 85° C. for 3 h, cooled to room temperature, and diluted with EtOAc (100 mL). The mixture was washed with aqueous 3% LiCl (1×100 mL), brine, dried (Na$_2$SO$_4$) and concentrated in vacuo. The residue was purified by silica gel chromatography with EtOAc/Hexane to give the desired product as light brown solid (0.70 g, 71%). LC/MS=813 (M$^+$+1).

Step 2:

To a solution of the ester (0.70 g, 0.86 mmol) in HOAc (10 mL) was added 1.4 N aq. HCl (5 mL) and the resulting solution was stirred at 60° C. for 1.5 h. Upon completion of the reaction, the mixture was concentrated to remove the solvents. After the residue was dissolved in EtOAc (100 mL) and washed with sat. NaHCO$_3$, the organic layer was dried (Na$_2$SO$_4$) and concentrated to afford the crude aldehyde. To a solution of the crude aldehyde in CH$_2$Cl$_2$ (20 mL) were added morpholine (112 µL, 1.29 mmol) and sodium triacetoxyborohydride (237 mg, 1.12 mmol) at 0° C. Glacial acetic acid (25 µL, 7.8 mmol) was then added dropwise to the mixture. The reaction was completed in 10 min at 0° C. Sat. NaHCO$_3$ solution was added to quench the reaction. After stirring the mixture for 20 min, the separated organic layer was washed with brine, dried (Na$_2$SO$_4$) and concentrated in vacuo. The crude product was clean enough (by LC/MS) to use as is. LC/MS=838 (M$^+$+1).

Step 3:

To a solution of this crude product in THF (6 mL), a solution of LiOH (384 mg, 16 mmol) in H$_2$O (6 mL) was added, followed by MeOH (6 mL). The mixture was stirred at room temperature for 20 h. Upon completion of the reaction, TFA was added at 0° C. to adjust the pH to 4 and the product was extracted with EtOAc (2×100 mL). The combined organic layer was washed with brine, dried (Na$_2$SO$_4$), and concentrated in vacuo. The product was purified by prep-HPLC to give Compound 98 as white solids (0.51 g, 53%). LC/MS=824 (M$^+$+1). $^1$H NMR (400 MHz, CD$_3$OD): δ 8.05 (d, J=8.8 Hz 1H), 7.21 (d, J=9.2 Hz, 1H), 6.38 (s, 1H), 5.61 (m, 1H), 5.39 (m, 2H), 4.87 (m, 1H), 4.63-4.54 (m, 5H), 4.26 (m, 1H), 4.07 (m, 2H), 4.01 (m, 1H), 3.87 (m, 1H), 3.76 (m, 3H), 3.48 (m, 2H), 2.63-2.54 (m, 1H), 2.54-2.47 (m, 2H), 2.33-2.67 (m, 1H), 2.04-1.89 (m, 3H), 1.87 (m, 1H), 1.75 (m, 2H), 1.67-1.59 (m, 3H), 1.55 (m, 2H), 1.46-1.37 (m, 8H), 1.29-1.14 (m, 4H), 0.39 (m, 2H).

Example 99

Preparation of Compound 99

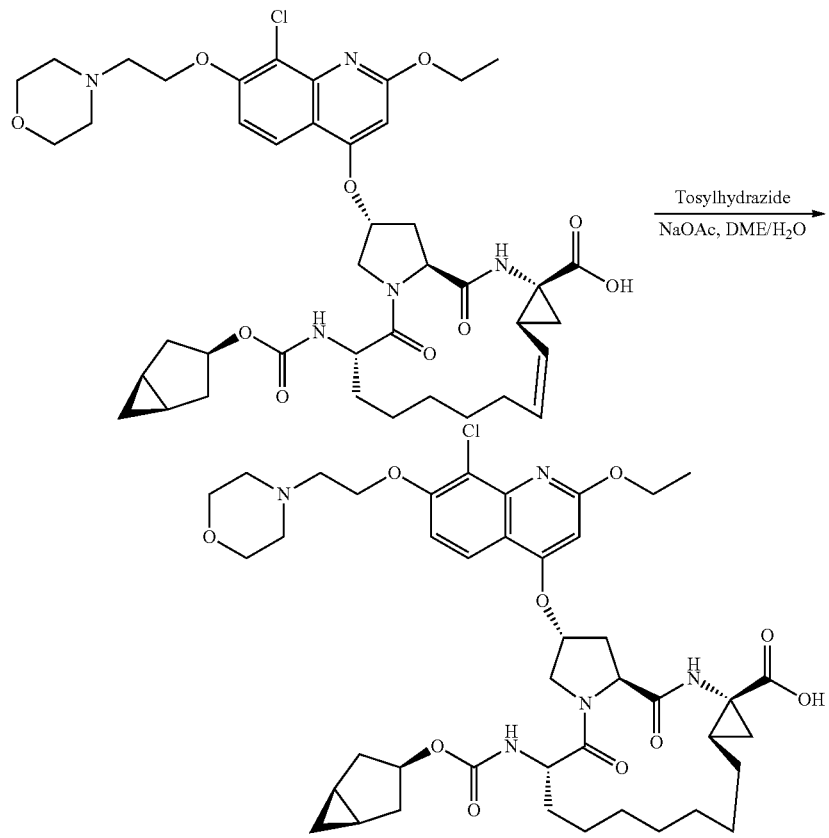

Compound 98 (0.20 g, 0.24 mmol) and p-toluenesulfonyl hydrazide (0.31 g, 1.68 mmol) were dissolved in ethylene glycol dimethyl ether (2 mL) and sodium acetate (0.28 g, 3.36 mmol) and H$_2$O (0.2 mL) were added. The suspension was then heated at 95° C. with stirring for 3 h. The mixture was cooled to room temperature, diluted with DMF (4 mL), and purified by prep-HPLC to give compound 99 as white solids (0.12 g, 60%). LC/MS=826 (M$^+$+1). $^1$H NMR (400 MHz, CD$_3$OD): δ 8.03 (d, J=9.2 Hz, 1H), 7.23 (d, J=9.2), 3.42 (m, 2H), 2.59 (m, 2H), 2.04-1.89 (m, 3H), 1.87 (m, 1H), Hz, 1H), 6.41 (s, 1H), 5.38 (bs, 1H), 4.75-4.69 (m, 2H), 4.61-4.54 (m, 6H), 4.49 (m, 1H), 4.32 (m, 1H), 4.08-3.98 (m, 5H), 3.75 (m, 5H 1.75 (m, 2H), 1.67-1.59 (m, 3H), 1.55 (m, 2H), 1.46-1.37 (m, 8H), 1.29-1.14 (4H), 0.37 (m, 2H).

Example 100

Preparation of Compound 100

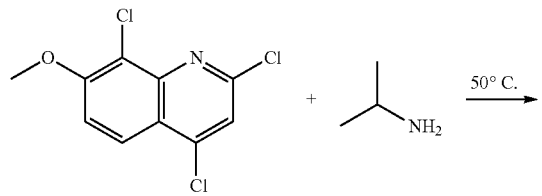

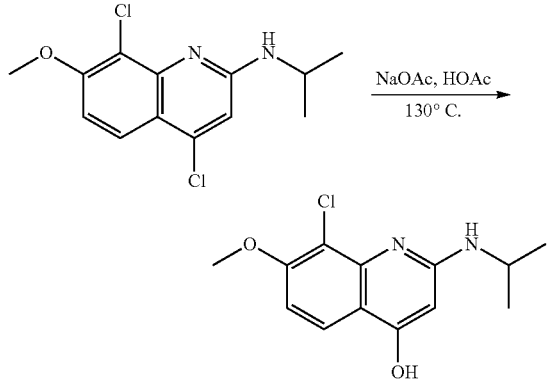

Step 1:
2,4,8-Trichloro-7-methoxyquinoline (0.32 g, 1.19 mmol) was dissolved in isopropylamine (4 mL) in a sealed tube and stirred at 50° C. for 10 h. The reaction mixture was diluted with EtOAc, washed with H$_2$O, dried (Na$_2$SO$_4$), and concentrated in vacuo. The residue was purified by silica gel chromatography to afford the dichloroquinoline (0.231 g, 0.81 mmol, 68%). LC/MS=285.1 (M$^+$+1).

Step 2:
A mixture of the dichloroquinoline (0.145 g, 0.51 mmol) and sodium acetate (0.625 g, 7.6 mmol) in HOAc (2 mL) was placed in a sealed tube and stirred at 130° C. for 17 h. After the mixture was cooled to room temperature, the solidified mixture was dissolved by additional EtOAc, and washed with H₂O and sat. NaHCO₃ (3×). Along the wash with sat. NaHCO₃, the desired product was crashed out and filtered. The filter cake was treated with toluene and concentrated (3×) to afford 8-Chloro-2-isopropylamino-7-methoxy-quinolin-4-ol (0.09 g, 67%). LC/MS=267.1 (M⁺+1).

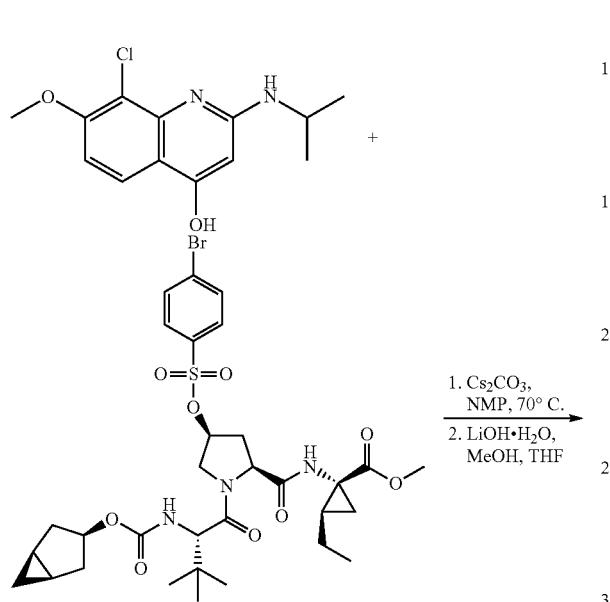

Step 3:
Compound 100 (110 mg) was synthesized using the same procedure described before to prepare compound 82. LC/MS=728.4 (M⁺+1). ¹H NMR (300 MHz, CD₃OD): δ 8.02 (d, 1H), 7.26 (d, 1H), 6.45 (bs, 1H), 5.61 (bs, 1H), 5.06 (bs, 1H), 4.68 (dd, 1H), 4.56-4.45 (m, 2H), 4.25-3.97 (m, 6H), 3.32 (s, 1H), 2.76-2.68 (m, 2H), 2.56-2.49 (m, 1H), 2.14 (m, 1H), 1.99-1.78 (m, 2H), 1.68-1.64 (m, 3H), 1.53-1.16 (m, 6H), 1.05-0.94 (m, 14H), 0.37-0.30 (m, 2H).

Example 101

Preparation of Compound 101

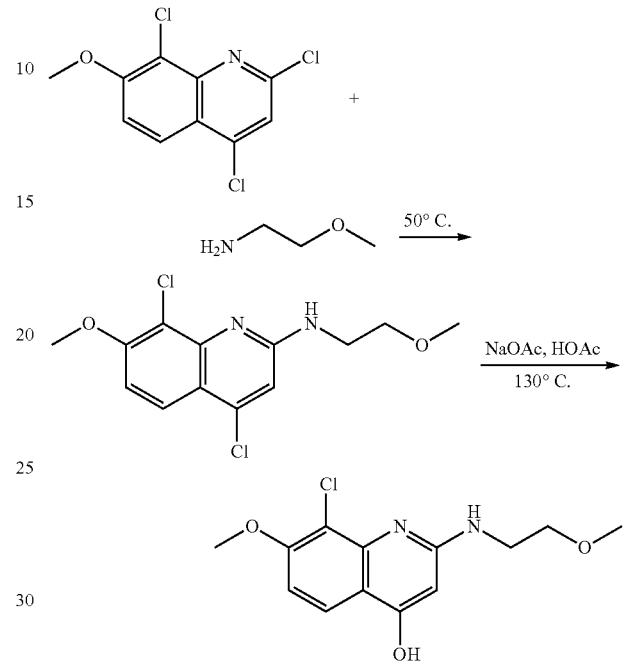

Step 1 and Step 2:
The quinoline was synthesized using the similar procedure described before in example 100. LC/MS=283.1 (M⁺+1).

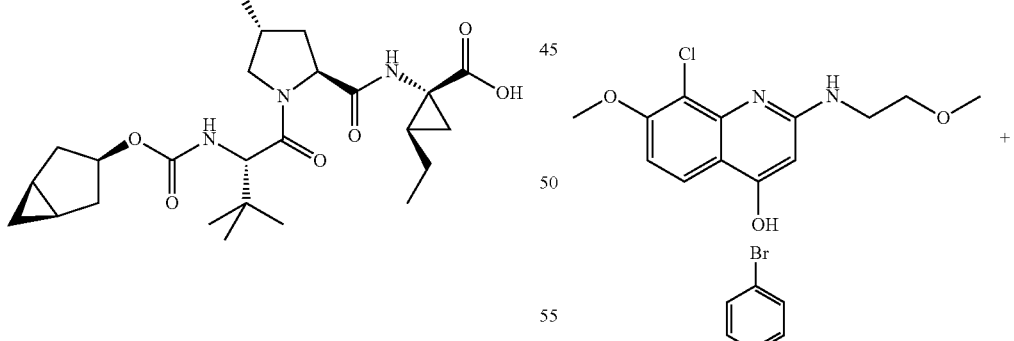

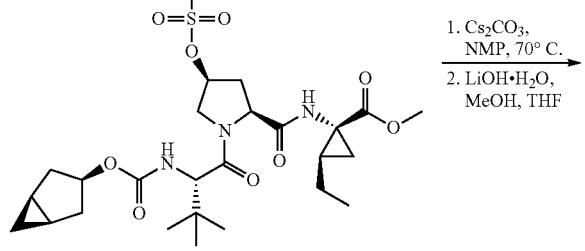

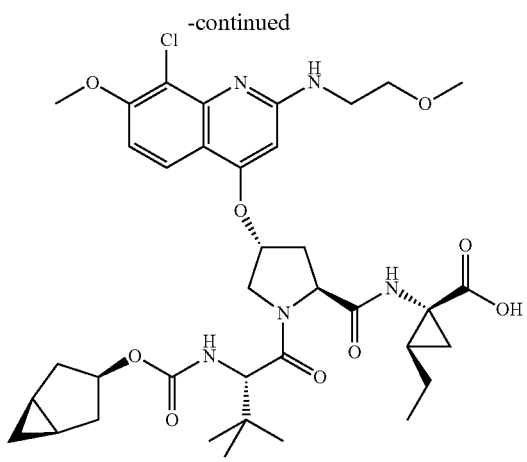

Step 3:

Compound 101 (82 mg) was synthesized using the same procedure described before to prepare compound 82. LC/MS=744.4 (M$^+$+1). $^1$H NMR (300 MHz, CD$_3$OD): δ 8.02 (d, 1H), 7.306 (d, 1H), 6.51-6.37 (m, 1H), 5.58-5.45 (m, 1H), 4.68 (dd, 1H), 4.56-4.44 (m, 2H), 4.15-3.96 (m, 5H), 3.79 (m, 4H), 3.55-3.47 (m, 2H), 3.31 (m, 1H), 2.72-2.49 (m, 2H), 2.14 (m, 1H), 1.99-1.78 (m, 2H), 1.68-1.64 (m, 3H), 1.53-1.22 (m, 6H), 1.20-0.94 (m, 14H), 0.37-0.30 (m, 2H).

Example 102

Preparation of Compound 102

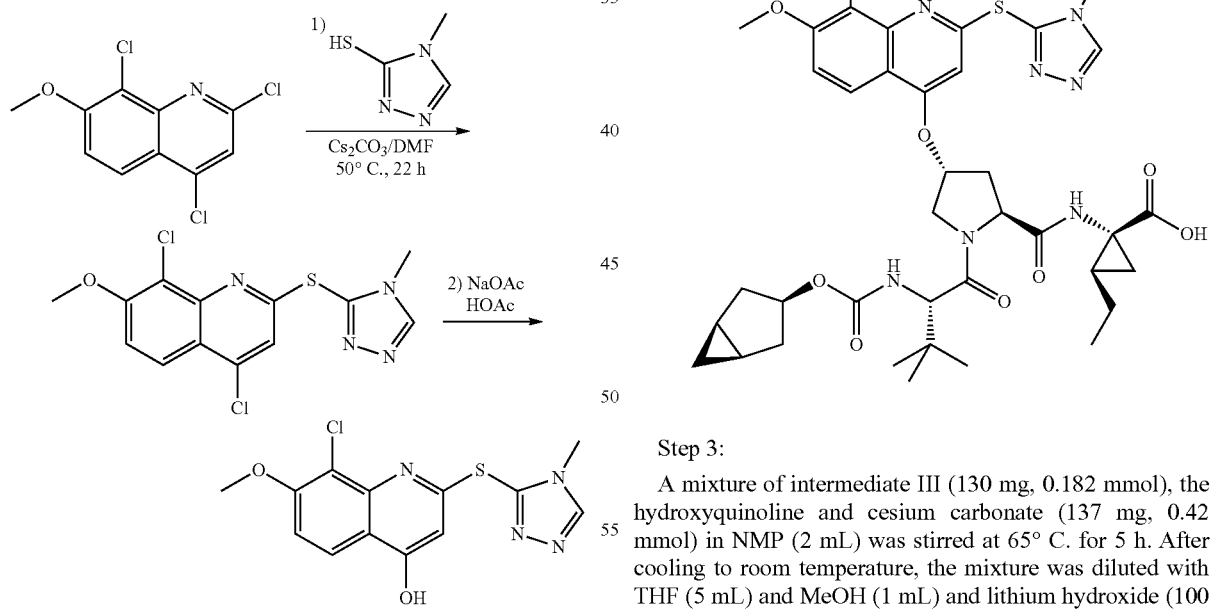

Step 1:

A mixture of 2,4,8-Trichloro-7-methoxy-quinoline (100 mg, 0.38 mmol), 4-methyl-4H-1,2,4-triazole-3-thiol (44 mg, 0.38 mmol), and cesium carbonate (185 mg, 0.57 mmol) in DMF (2 mL) was stirred at 50° C. for 22 h. LC/MS showed some product formed along with other by-products. The mixture was cooled to room temperature, diluted with EtOAc (100 mL), and washed with 3% LiCl and brine. The organic layer and insoluble material were combined and concentrated in vacuo. The residue was purified by prep-HPLC to afford 89 mg (67%) of the monosubstituted product. LC/MS=341.2 (M$^+$+1).

Step 2:

A mixture of the above dichloroquinoline (48 mg, 0.14 mmol) and NaOAc (173 mg, 2.11 mmol) in HOAc (2 mL) was stirred at 130° C. for 36 h in a sealed tube. After cooling to room temperature, the mixture was diluted with EtOAc (20 mL), and washed with sat. NaHCO$_3$ and brine. The organic layer and insoluble material were combined and concentrated in vacuo to give the white solid compound which was clean desired hydroxyquinoline product, used as is for the next step. LC/MS=323.11 (M$^+$+1).

Step 3:

A mixture of intermediate III (130 mg, 0.182 mmol), the hydroxyquinoline and cesium carbonate (137 mg, 0.42 mmol) in NMP (2 mL) was stirred at 65° C. for 5 h. After cooling to room temperature, the mixture was diluted with THF (5 mL) and MeOH (1 mL) and lithium hydroxide (100 mg) in water (3 mL) was added to the mixture. The mixture was stirred for 16 hrs at room temperature, and neutralized with TFA. After removal of volatile solvents, the residue was purified by prep-HPLC to afford 53 mg (42% for two steps) of compound 102 as TFA salt. $^1$H NMR (300 MHz, CD$_3$OD): δ 8.85 (s, 1H), 8.11 (d, 1H), 7.44 (d, 1H), 6.22 (s, 1H), 5.81 (b, 1H), 4.50 (m, 1H), 4.3-4.0 (m, 4H), 4.06 (s, 3H), 3.72 (s, 3H), 2.47 (m, 2H), 2.04 (m, 2H), 1.75-1.1.79 (m, 10H), 1.03-0.92 (m, 14H), 0.44 (m, 2H). LC/MS=784.1 (M$^+$+1).

Example 103

Preparation of Compound 103

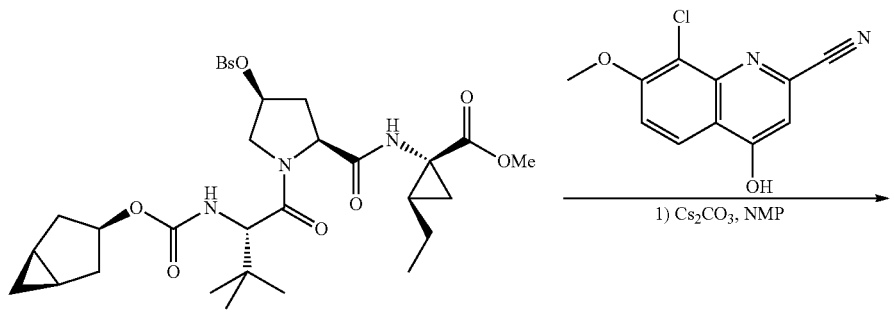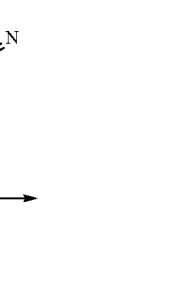

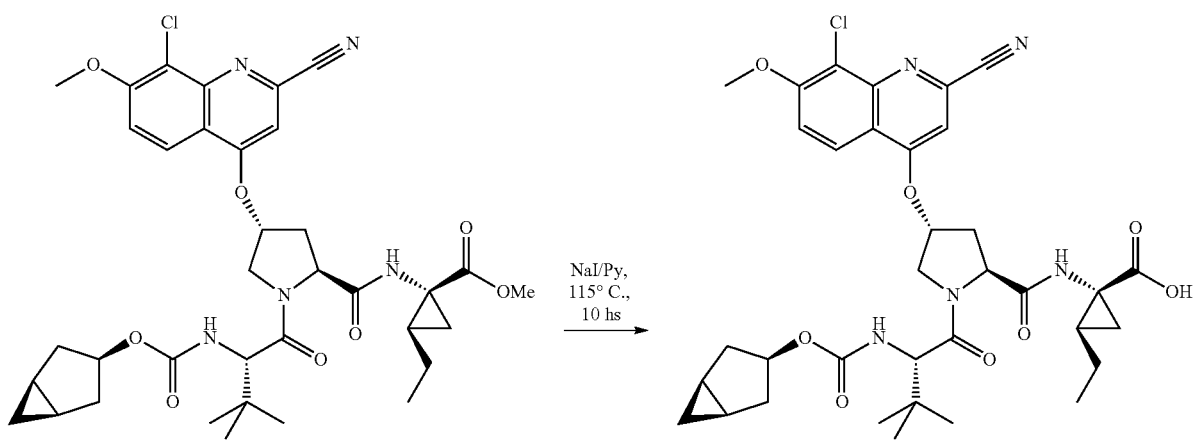

Step 1:

To a mixture of intermediate III (0.15 g, 0.21 mmol) and cesium carbonate (0.14 g, 0.42 mmol) in NMP (5 mL) was added the quinoline (0.05 g, 0.21 mmol) at room temperature in one portion. The mixture was stirred at 85° C. for 3 h, cooled to room temperature, and diluted with EtOAc (30 mL). The mixture was washed with aqueous 3% LiCl (1×20 mL), brine, dried ($Na_2SO_4$), and concentrated in vacuo. The residue was purified by silica gel chromatography with EtOAc/Hexane to give the desired product as light brown solid (0.09 g, 60%). LC/MS=710 ($M^+$+1).

Step 2:

The ester (0.06 g, 0.085 mmol) and sodium iodide (0.25 g, 1.67 mmol) were dissolved in pyridine (3 mL) and heated to 115° C. for 7 h. The reaction mixture was cooled to room temperature and concentrated to remove most of pyridine. The residue was dissolved in DMF (2 mL) and purified by prep-HPLC to give compound 103 as solids (0.02 g, 35%). LC/MS=696 ($M^+$+1). $^1$H NMR (300 MHz, $CD_3OD$): δ 8.15 (d, J=9.0 Hz, 1H), 7.57 (d, J=9.3 Hz, 1H), 7.40 (s, 1H), 5.49 (s, 1H), 4.69 (m, 1H), 4.51-4.41 (m, 2H), 4.16 (m, 1H), 4.08 (s, 3H), 4.01 (m, 1H), 2.69 (m, 1H), 2.49 (m, 1H), 2.00 (m, 1H), 1.91 (m, 1H), 1.69 (m, 2H), 1.50 (m, 1H), 1.43-1.36 (m, 3H), 1.25-1.13 (m, 3H), 1.04-0.95 (m, 12H), 0.35-0.27 (m, 2H).

Example 104

Preparation of Compound 104

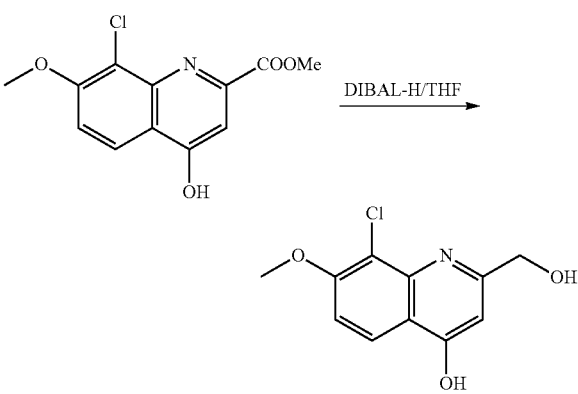

Step 1:

The methyl ester quinoline (0.20 g, 0.75 mmol) was dissolved in THF (5 mL) and cooled to 0° C. as 1 M DIBAL in hexane (2.3 mL, 2.30 mmol) was added. After the mixture was stirred at room temperature for 1 h, H$_2$O (2 mL) was slowly added to the mixture. The pH of the mixture was adjusted to 2 by adding 1 N HCl. Solids formed were filtered and dried in vacuo overnight to afford the alcohol (180 mg, 93%). LC/MS=240 (M$^+$+1).

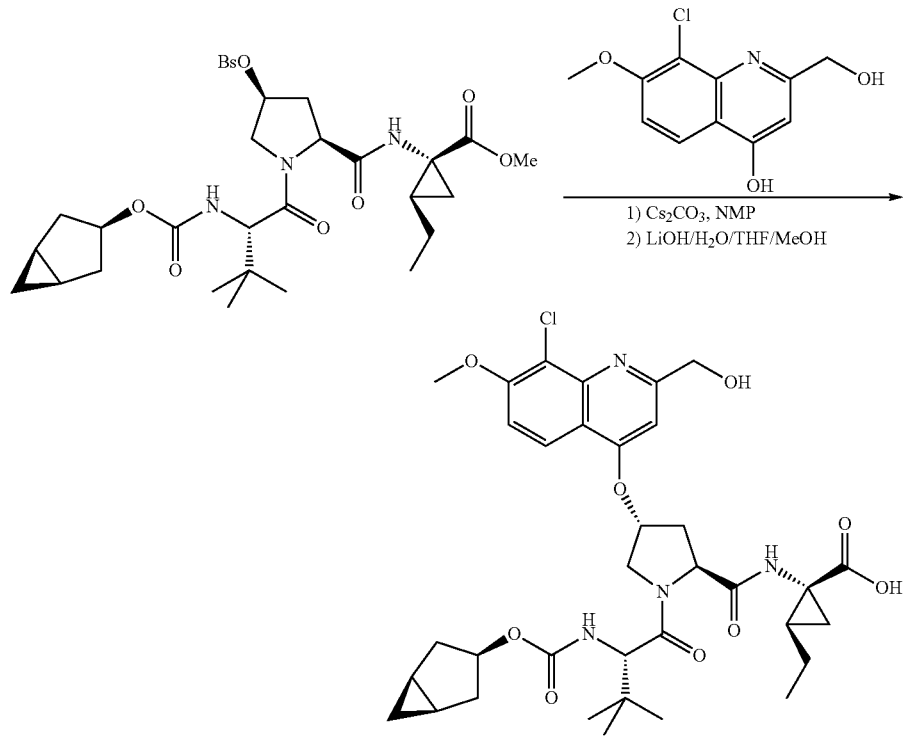

Step 2:

Compound 104 (0.31 g, 56%) was synthesized using the procedure described before to prepare compound 82. LC/MS=701 (M$^+$+1). $^1$H NMR (300 MHz, CD$_3$OD) δ 8.41 (d, J=9.9 Hz, 1H), 7.74 (d, J=9.3 Hz, 1H), 7.54 (s, 1H), 5.75 (s, 1H), 5.16 (s, 2H), 4.73 (m, 1H), 4.61 (m, 1H), 4.49 (m, 1H), 4.33 (m, 1H), 4.19 (s, 3H), 4.09 (m, 1H), 2.85 (m, 1H), 2.60 (m, 1H), 2.20 (m, 1H), 1.94 (m, 1H), 1.91 (m, 1H), 1.69 (m, 2H), 1.50 (m, 1H), 1.43-1.36 (m, 3H), 1.25-1.13 (m, 3H), 1.04-0.95 (m, 12H), 0.38-0.31 (m, 2H).

Example 105

Preparation of Compound 105

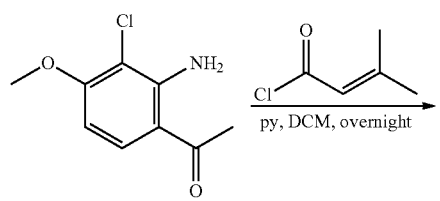

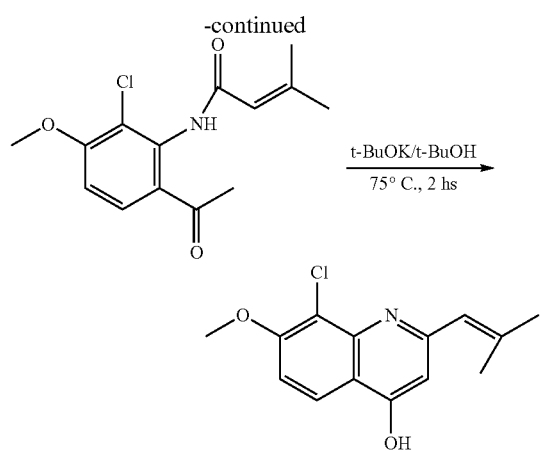

Step 1:

A solution of the aniline (0.30 g, 1.5 mmol) and pyridine (0.24 g, 3.0 mmol) in dichloromethane (10 mL) was stirred at 0° C. while 3,3-dimethylacryloyl chloride (0.24 g, 2.0 mmol) was added over 15 min, and the reaction mixture was stirred at room temperature overnight. After the mixture was concentrated, the residue was dissolved in EtOAc (50 mL) and washed by sat. NaHCO$_3$, 1 N HCl, and brine. The organic fraction was dried (Na$_2$SO$_4$), concentrated, and purified by silica gel chromatography with EtOAc/Hexane to give the desired amide as light brown solids (0.35 g, 80.3%). LC/MS=282 (M$^+$+1).

445

Step 2:

A solution of the amide (0.32 g, 1.1 mmol) in t-BuOH (10 mL) was stirred vigorously as t-BuOK (0.27 g, 2.4 mmol) was added. The reaction was heated at 75° C. for 3 h and cooled to room temperature. After the mixture was acidified with 4 N HCl (1 mL) and concentrated, the residue was dissolved in EtOAc (30), and washed with H$_2$O (10 mL) and brine (10 mL). The organic fraction was dried (Na$_2$SO$_4$), concentrated, and purified by silica gel chromatography with EtOAc/Hexane to give the desired quinoline as light brown solids (0.11 g, 37%). LC/MS=264 (M$^+$+1).

446

-continued

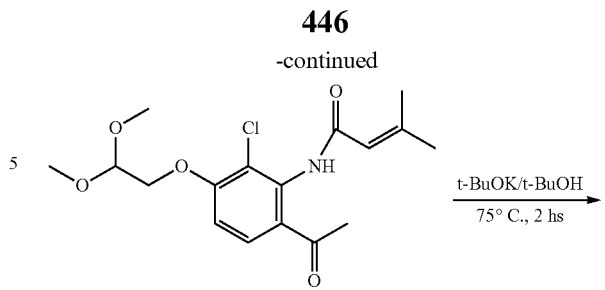

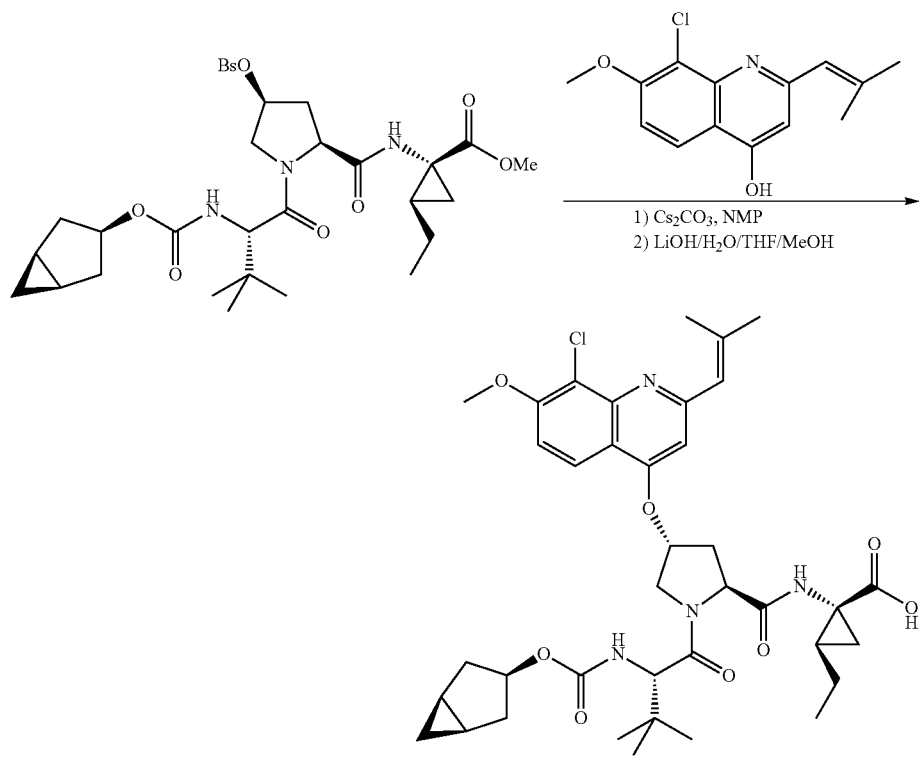

Step 3:

Compound 105 (0.10 g, 66%) was synthesized using the procedure described before to prepare compound 82. LC/MS=725 (M$^+$+1). $^1$H NMR (400 MHz, CD$_3$OD) δ 8.35 (s, J=9.6 Hz, 1H), 8.30 (s, 1H), 7.67 (d, J=9.6 Hz, 1H), 7.33 (s, 1H), 6.79 (s, 1H), 5.73 (s, 1H), 4.76 (t, J=8.8 Hz, 1H), 4.64 (d, J=12.4 Hz, 1H), 4.30 (t, J=10.8 Hz, 1H), 4.16 (s, 1H), 4.08-4.01 (m, 2H), 2.80 (m, 1H), 2.60 (m, 1H), 2.22 (d, J=12.8 Hz, 6H), 1.92 (m, 1H), 1.48 (m, 1H), 1.74-1.40 (m, 6H), 1.27-1.13 (m, 4H), 1.04-0.96 (m, 12H), 0.36-0.32 (m, 2H).

Example 106

Preparation of Compound 106

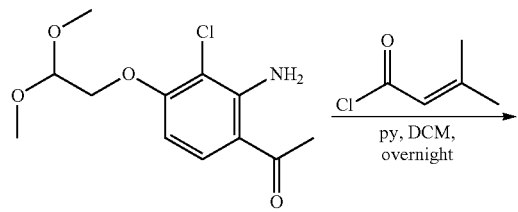

-continued

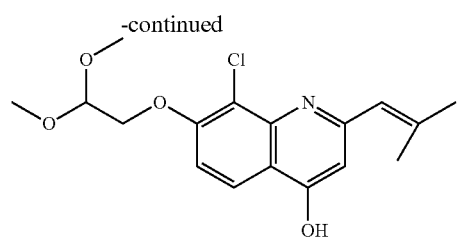

Step 1:

A solution of the aniline (8.0 g, 29.3 mmol) and pyridine (4.6 g, 58.6 mmol)) in dichloromethane (100 mL) was stirred at 0° C. while 3,3-dimethylacryloyl chloride (4.2 g, 35.2 mmol) was added over 15 min. The reaction mixture was stirred at room temperature overnight. After the mixture was concentrated, the residue was dissolved in EtOAc (200 mL) and washed by sat. NaHCO$_3$, 1 N HCl, and brine. The organic fraction was dried (Na$_2$SO$_4$), concentrated, and purified by silica gel chromatography with EtOAc/Hexane to give the desired amide as light brown solids (6.0 g, 57.6%). LC/MS=355 (M⁺+1).

Step 2:

A solution of the amide (6.0 g, 16.9 mmol) in t-BuOH (120 mL) was stirred vigorously as t-BuOK (3.9 g, 35.4 mmol) was added. The mixture was heated at 75° C. for 3 h and cooled to room temperature. After the mixture was acidified with 4 N HCl (10 mL) and concentrated, the residue was dissolved in EtOAc (200 mL), and washed with H₂O (50 mL) and brine (100 mL). The organic fraction was dried (Na₂SO₄), concentrated, and purified by silica gel chromatography with EtOAc/Hexane to give the desired quinoline as light brown solid (1.62 g, 28%). LC/MS=338 (M⁺+1).

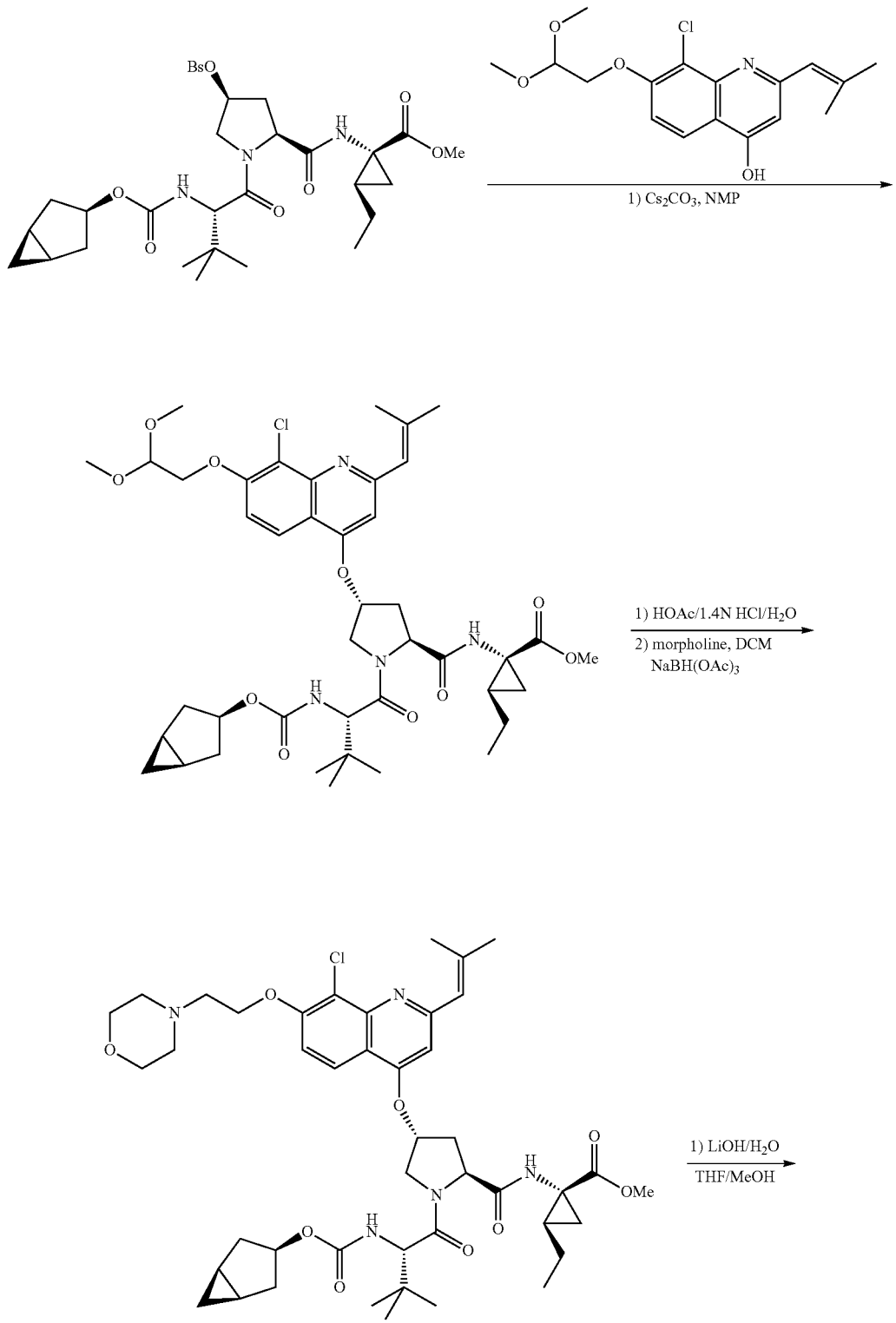

-continued
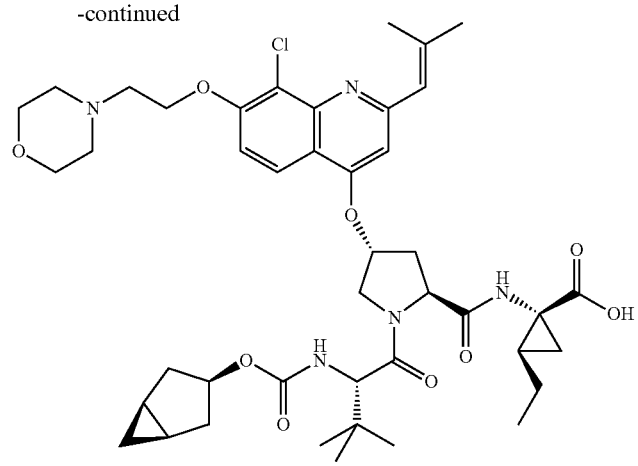
Step 3:
Compound 106 (0.51 g, 75%) was synthesized using the procedure described before to prepare compound 98. LC/MS=824 (M$^+$+1). $^1$H NMR (300 MHz, CD$_3$OD) δ 8.30 (s, J=9.3 Hz, 1H), 8.30 (s, 1H), 7.57 (d, J=9.3 Hz, 1H), 7.18 (s, 1H), 6.69 (s, 1H), 5.62 (s, 1H), 4.74-4.67 (m, 3H), 4.58-4.52 (m, 2H), 4.16 (m, 1H), 4.08-3.99 (m, 6H), 3.79 (m, 2H), 3.57 (m, 4H), 2.80 (m, 1H), 2.60 (m, 1H), 2.29 (s, 3H), 2.14 (s, 3H), 2.02 (m, 1H), 1.91 (m, 1H), 1.69 (m, 3H), 1.50 (m, 1H), 1.43-1.36 (m, 2H), 1.24-1.13 (m, 3H), 1.04-0.96 (m, 12H), 0.36-0.32 (m, 2H).
Example 107
Preparation of Compound 107
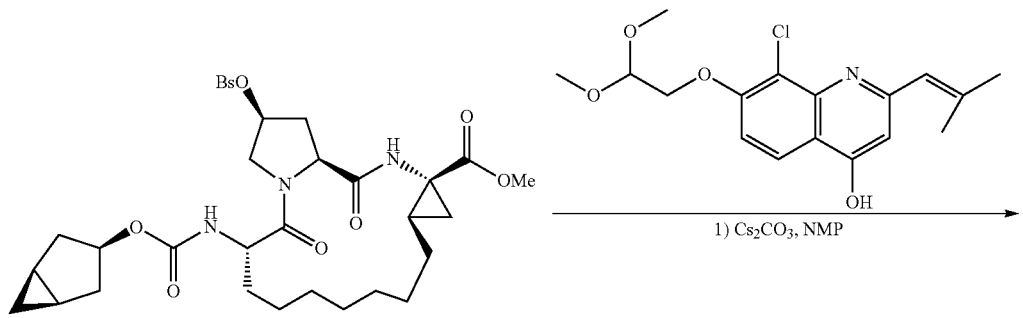
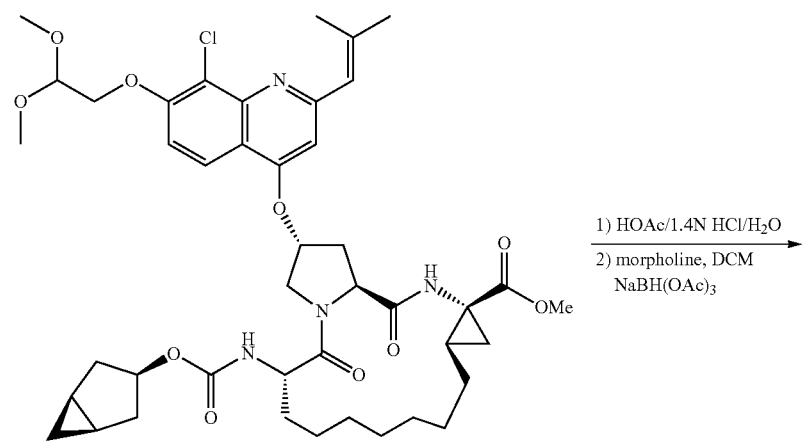

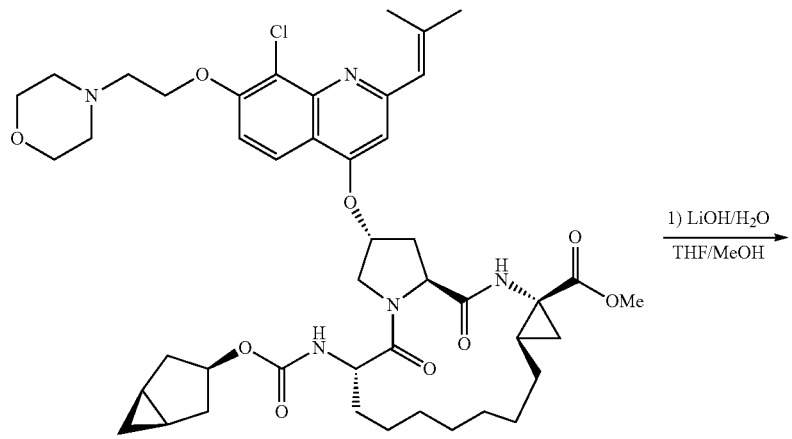
1) LiOH/H₂O
THF/MeOH
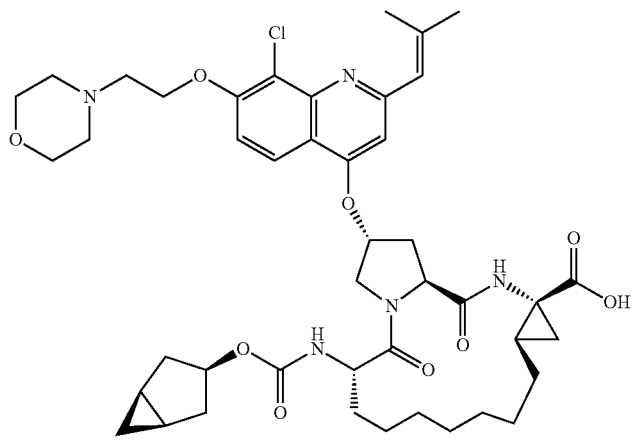
Compound 107 (0.14 g, 70%) was synthesized using the procedure described before to prepare compound 98. LC/MS=836 (M⁺+1). ¹H NMR (400 MHz, CD₃OD): δ 8.41 (d, J=9.2 Hz, 1H), 7.68 (d, J=9.2 Hz, 1H), 7.34 (s, 1H), 6.78 (s, 1H), 5.74 (bs, 1H), 4.81-4.72 (m, 5H), 4.48 (m, 1H), 4.24 (m, 1H), 4.06-3.99 (m, 4H), 4.08-3.98 (m, 5H), 3.82 (m, 2H), 3.57 (m, 4H), 2.74-2.67 (m, 2H), 2.24 (d, J=21.2 Hz, 6H), 2.04-1.89 (m, 2H), 1.87 (m, 1H), 1.75 (m, 2H), 1.67-1.59 (m, 3H), 1.55 (m, 2H), 1.46-1.37 (m, 4H), 1.29-1.14 (m, 4H), 0.37 (m, 2H).
Example 108
Preparation of Compound 108
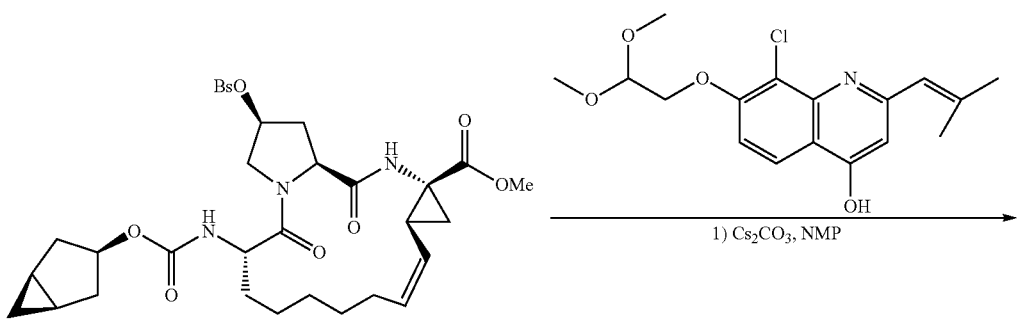
1) Cs₂CO₃, NMP

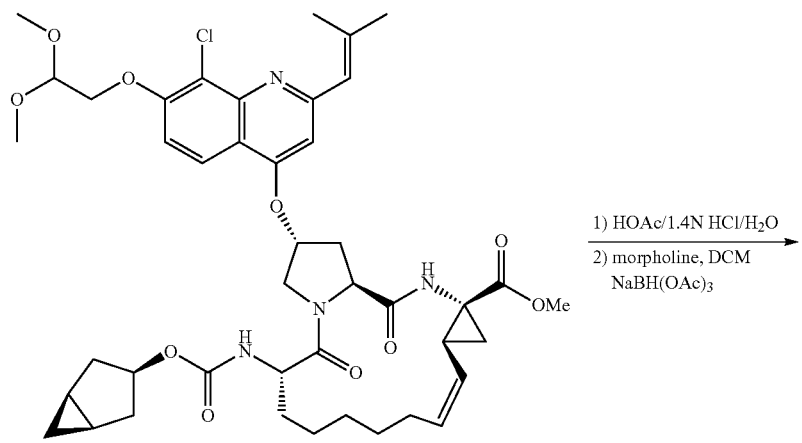
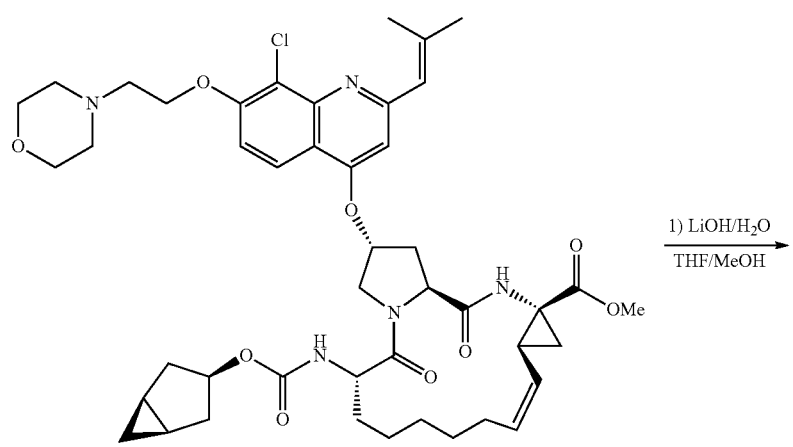
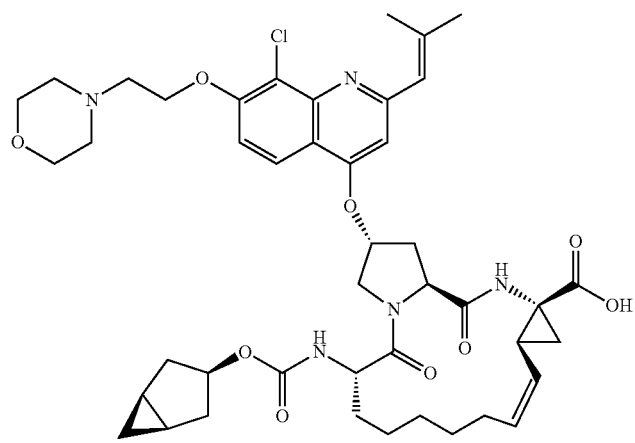
Compound 108 (0.17 g, 60%) was synthesized using the procedure described before to prepare compound 98. LC/MS=834 (M$^+$+1). $^1$H NMR (400 MHz, CD$_3$OD): δ 8.43 (d, J=9.2 Hz, 1H), 7.66 (d, J=9.6 Hz, 1H), 7.35 (s, 1H), 6.78 (s, 1H), 5.77 (bs, 1H), 5.62 (m, 1H), 5.38 (m, 1H), 4.81 (m, 4H), 4.72 (t, J=8.0 Hz, 1H), 4.39 (t, J=6.8 Hz, 1H), 4.13 (m, 1H), 4.05-3.99 (m, 4H), 3.82 (m, 2H), 3.56 (m, 3H), 2.74-2.67 (m, 2H), 2.22 (d, J=16.0 Hz, 6H), 1.93-1.88 (m, 2H), 1.78-1.74 (m, 2H), 1.67-1.59 (m, 3H), 1.55 (m, 2H), 1.46-1.37 (m, 4H), 1.29-1.14 (m, 4H), 0.35 (m, 2H).

Example 109
Preparation of Compound 109
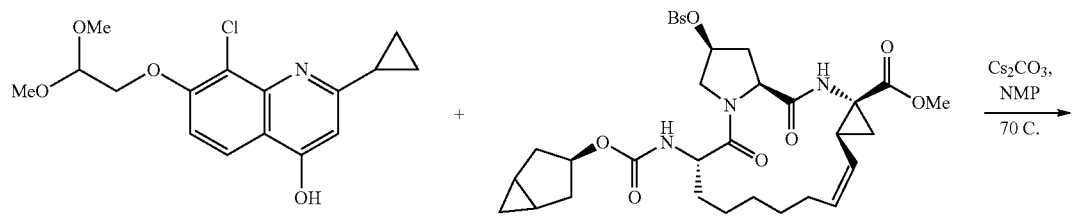
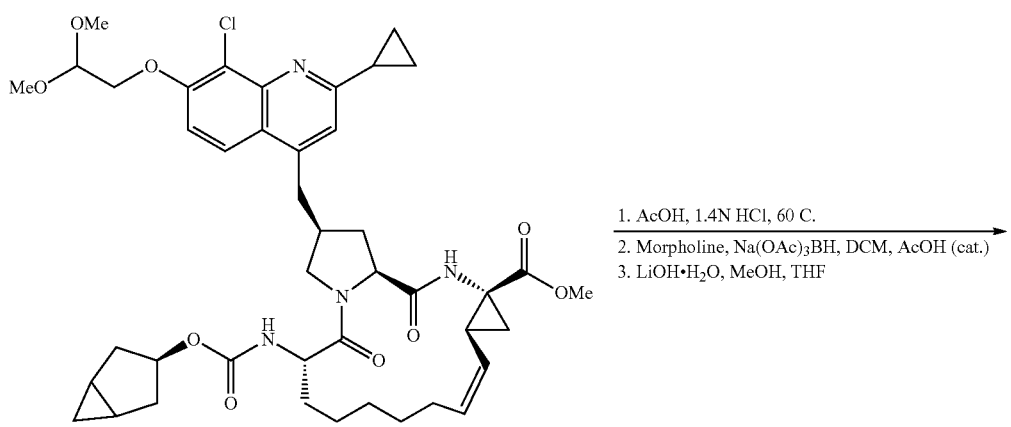
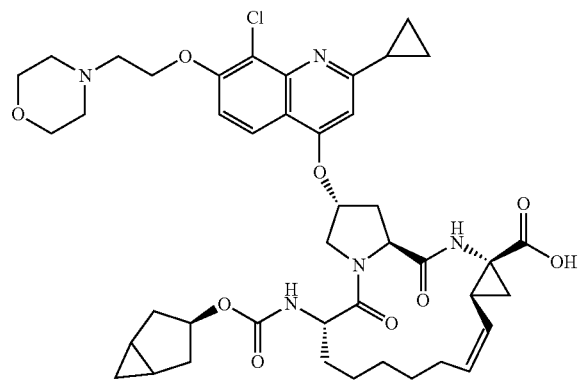
Compound 109 was synthesized using the procedure described before to prepare compound 98. LC/MS=820.55 (M$^+$+1). $^1$H NMR (300 MHz, CD$_3$OD): δ 8.00 (d, 1H), 7.23 (d, 1H), 6.46 (s, 1H), 5.37 (b, 1H), 5.29 (m, 1H), 5.04 (dd, 1H), 4.42-4.31 (m, 5H), 4.19 (dd, 1H), 3.84 (m, 1H), 3.71-3.65 (m, 5H), 3.47 (m, 1H), 3.24 (m, 4H), 2.98 (m, 3H), 2.37 (m, 2H), 2.27-2.15 (m, 2H), 1.96 (m, 1H), 1.67-1.44 (m, 2H), 1.34-1.07 (m, 10H), 0.93-0.82 (m, 2H), 0.05-0.00 (m, 1H).

Example 110

Preparation of Compound 110

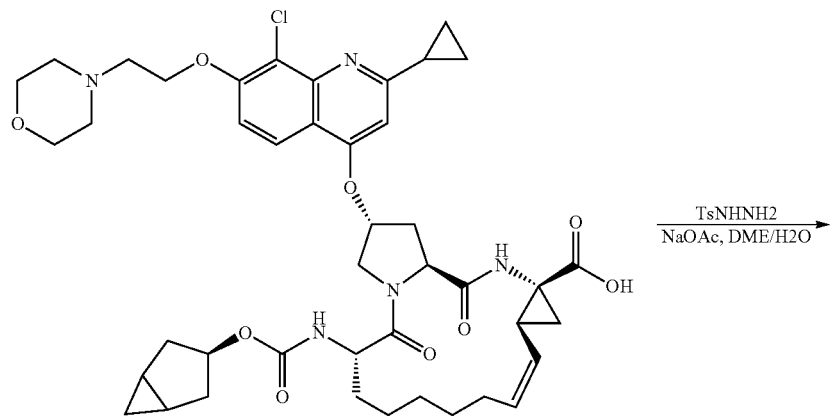

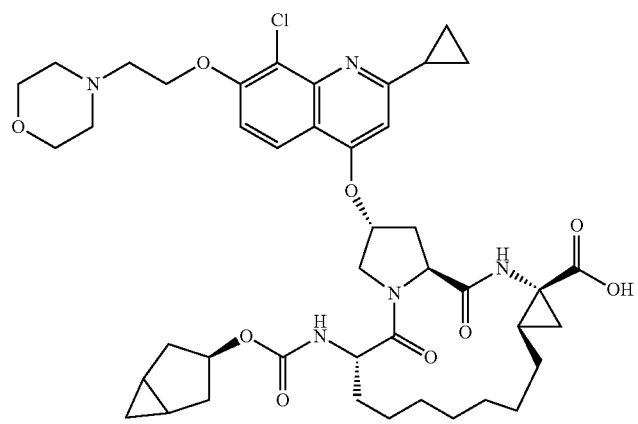

Compound 110 was synthesized using the procedure described before to prepare compound 99. LC/MS=822.38 (M$^+$+1). $^1$H NMR (300 MHz, CD$_3$OD): δ 8.23 (d, 1H), 7.49 (d, 1H), 6.68 (s, 1H), 5.59 (s, 1H), 4.68-4.61 (m, 3H), 4.52 (dd, 1H), 4.45 (dd, 1H), 4.17 (m, 1H), 3.95-3.80 (m, 4H), 3.71 (m, 2H), 3.48 (b, 3H), 3.22 (m, 1H), 2.69-2.52 (m, 3H), 1.91-1.84 (m, 1H), 1.79-1.64 (m, 3H), 1.59-1.08 (m, 20H), 0.31-0.24 (m, 1H).

Example 111

Preparation of Compound 111

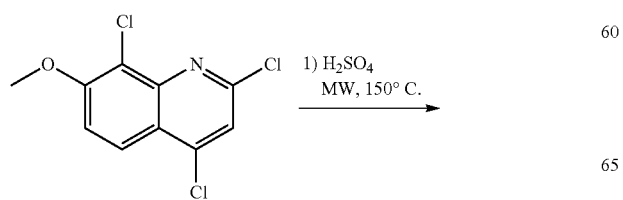

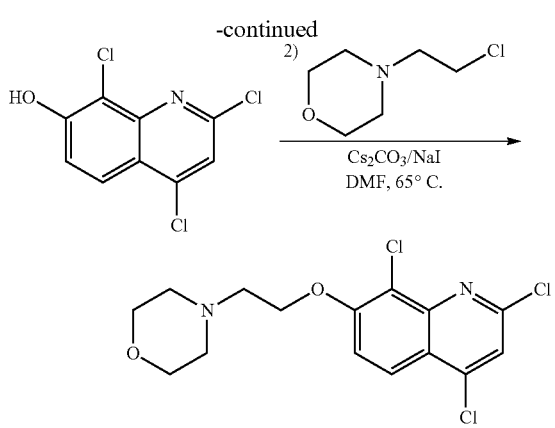

Step 1:
A mixture of 2,4,8-trichloro-7-methoxy-quinoline (2.48 mg, 9.45 mmol) and H$_2$SO$_4$ (20 mL) was sealed in a microwave tube and heated at 150° C. for 1 hr in the microwave reactor. After cooling to room temperature, the mixture was slowly poured into ice-water mixture with vigorous stirring.

The brown solid was filtered, washed with cold water, and dried to afford 1.54 g (66%) of the desired product. LC/MS=350.24 (M$^+$+3).

Step 2:

To a solution of 2,4,8-trichloroquinolin-7-ol (1.74 g, 7.0 mmol) in DMF (70 mL) were added Cs$_2$CO$_3$ (10.26 g, 31.5 mmol) and NaI (210 mg, 1.4 mmol). The mixture was heated to 65° C. for 4 h. After cooling to room temperature, the mixture was diluted with EtOAc and aqueous 3% LiCl solution. After the two layers were separated, the organic fraction was dried (Na$_2$SO$_4$) and concentrated in vacuo. The residue was purified by flash chromatography on silica gel using EtOAc/hexane then MeOH/EtOAc as eluents to obtain 1.9 g (75%) of the desired product. LC/MS=363.0 (M$^+$+3).

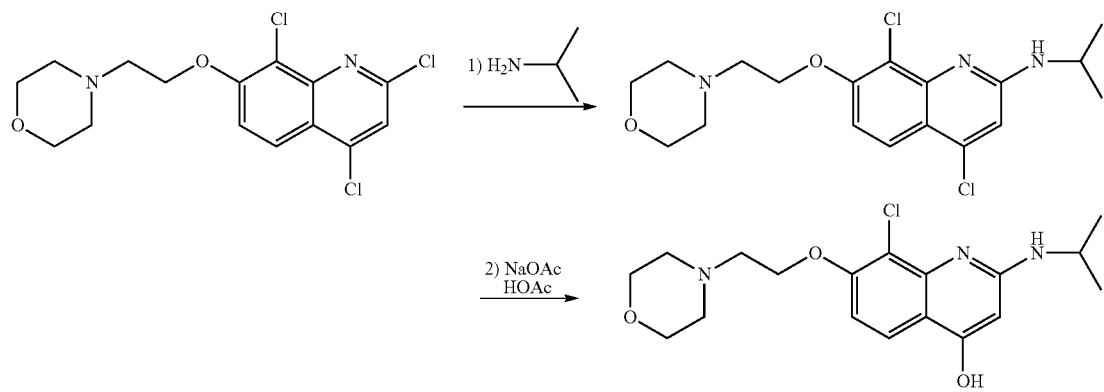

Step 3:

A mixture of 2,4,8-trichloro-7-(2-morpholin-4-yl-ethoxy)-quinoline (900 mg, 2.49 mmol) and isopropylamine (30 mL) was sealed in a sealed tube and heated to 50° C. for 10 h. After the mixture was concentrated, the residue was purified by flash chromatography on silica gel using EtOAc/hexane as eluent to afford 930 mg (97%) of the desired product. LC/MS=384.0 (M$^+$+1).

Step 4:

A solution of the above 4,8-Dichloroquinoline (930 mg, 2.42 mmol) and sodium acetate (3.0 g, 36.3 mmol) in acetic acid (12 mL) was heated to 130° C. for 18 h. After the mixture was concentrated in vacuo, the residue was purified by prep-HPLC to give 882 mg (76%) of the desired hydroxyquinoline product. LC/MS=366.0 (M$^+$+1).

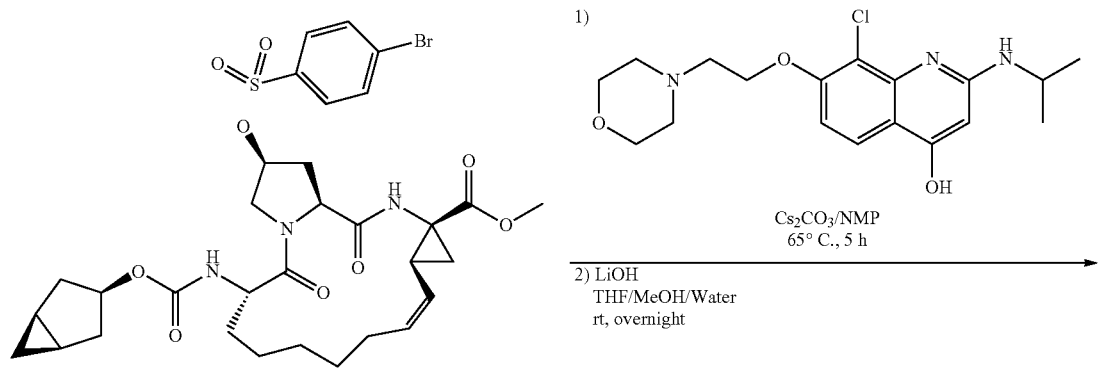

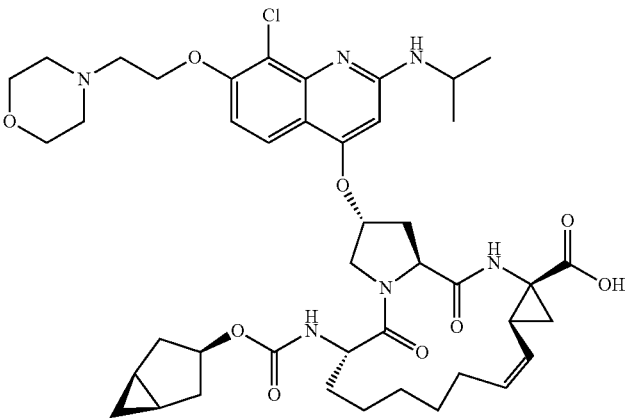
Step 5:
Compound 111 (400 mg) was synthesized using the procedure described before to prepare compound 98. LC/MS=837.4 (M$^+$+1). $^1$H NMR (400 MHz, CD$_3$OD): δ 8.63 (s, 1H), 8.38 (d, 1H), 8.24 (s, 1H), 7.80 (d, 1H), 6.94 (s, 1H), 6.16 (b, 1H), 5.29 (m, 2H), 5.03 (t, 1H), 4.37 (m, 4H), 4.23 (m, 1H), 3.90 (m, 2H), 3.70 (m, 4H), 3.45 (t, 2H), 3.21 (b, 3H), 2.98 (s, 1H), 2.40 (m, 1H), 2.20 (m, 2H), 1.98 (q, 1H), 1.63-1.28 (m, 6H), 1.20-1.07 (m, 10H), 1.04-0.84 (m, 2H), 0.39 (m, 2H).
Example 112
Using procedures similar to those described herein, the following compounds of formula (I) can also be prepared.
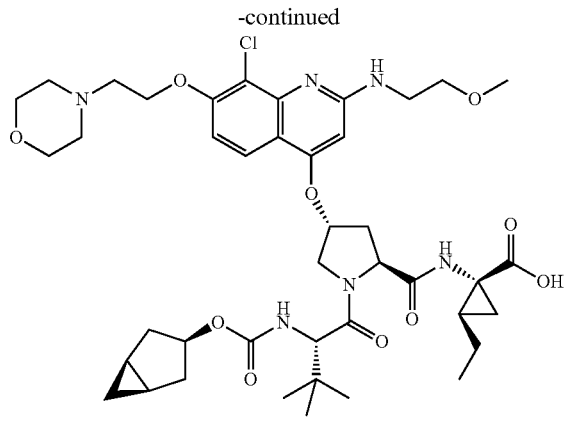
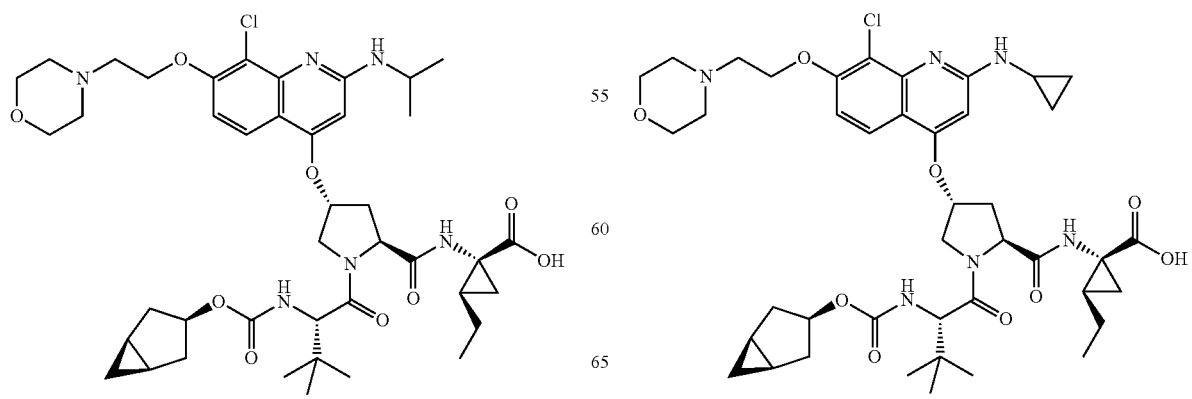

463
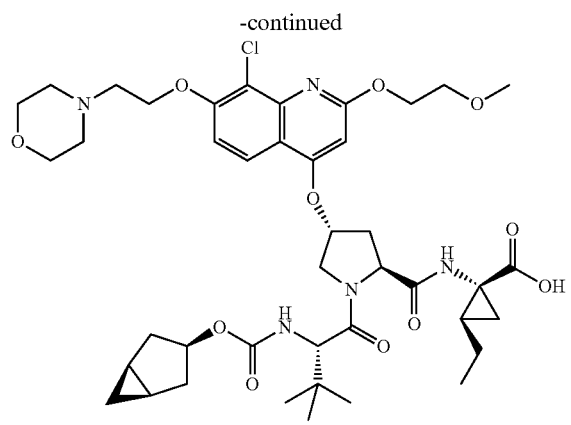
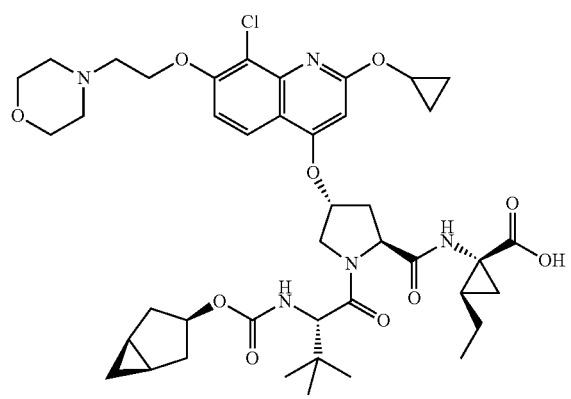
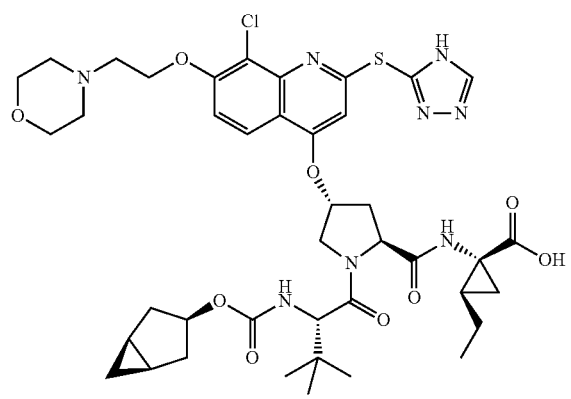
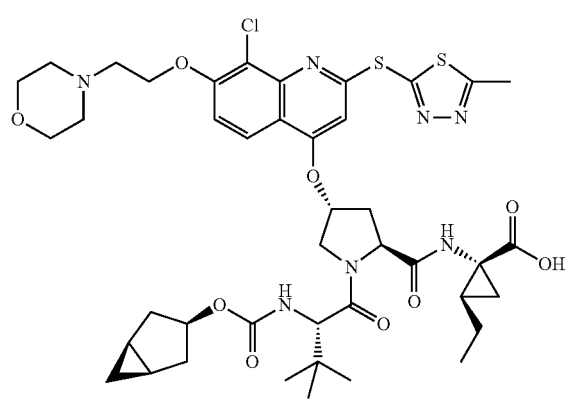
464
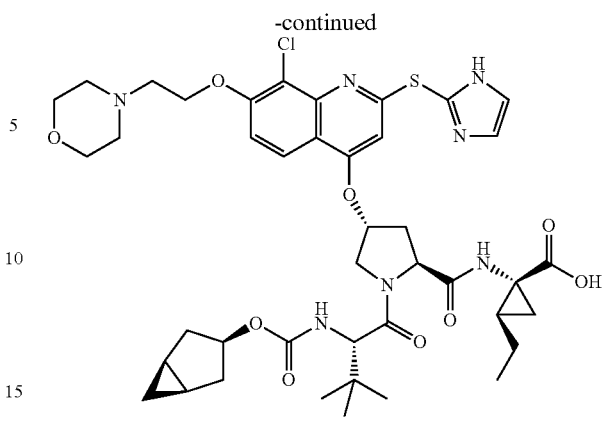
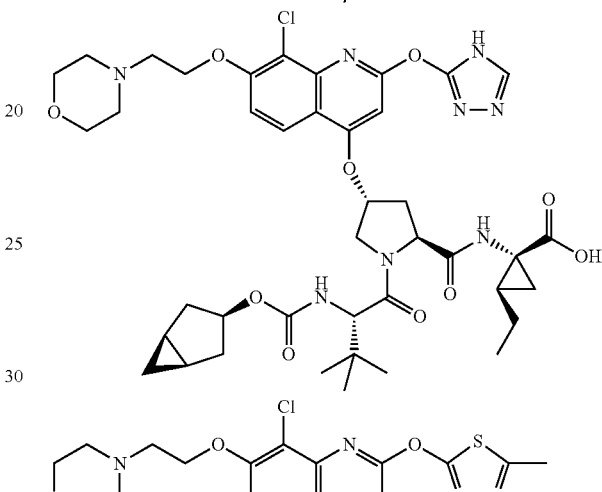
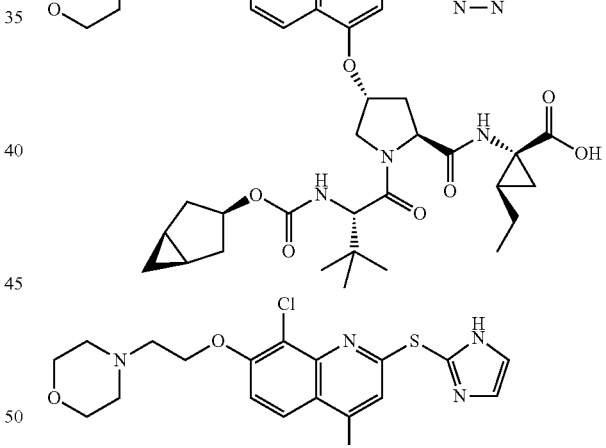
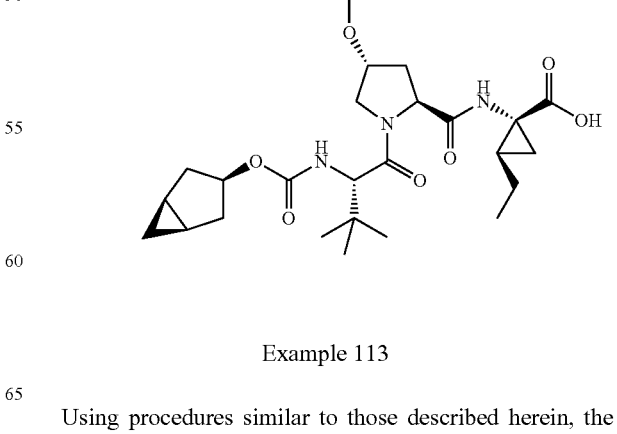
Example 113
Using procedures similar to those described herein, the following compounds of formula (I) can also be prepared.

| 465 | 466 |
|---|---|
| 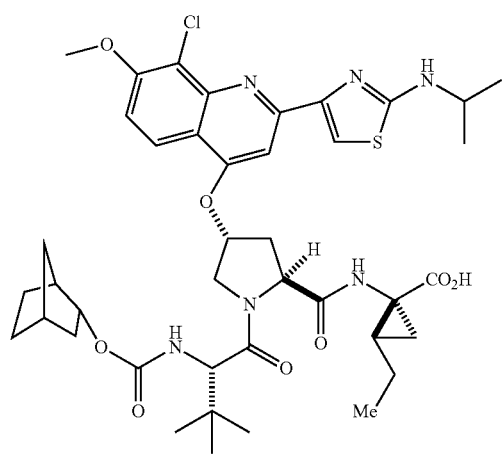 | 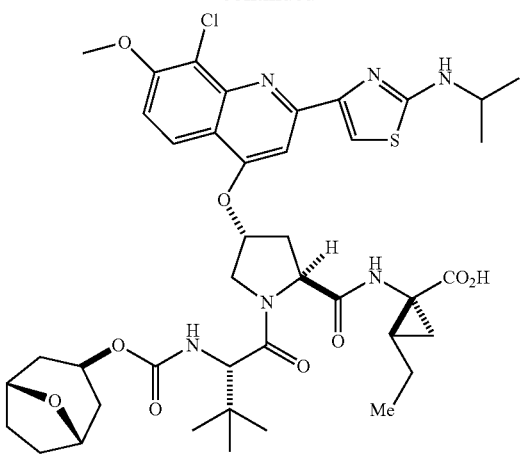 |
| 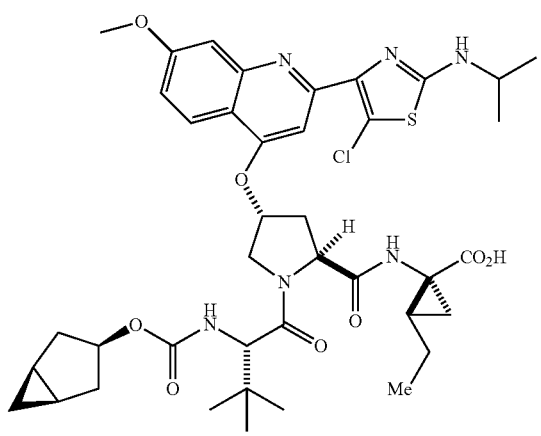 | 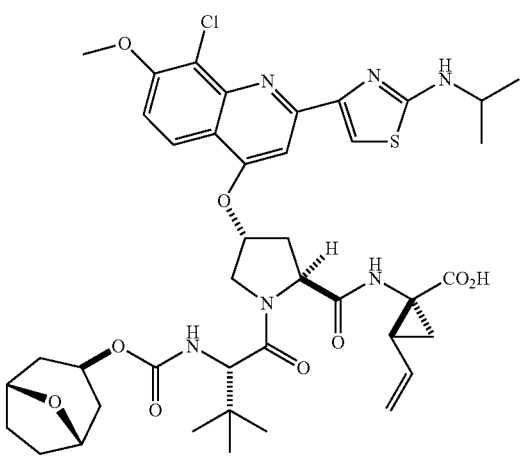 |
| 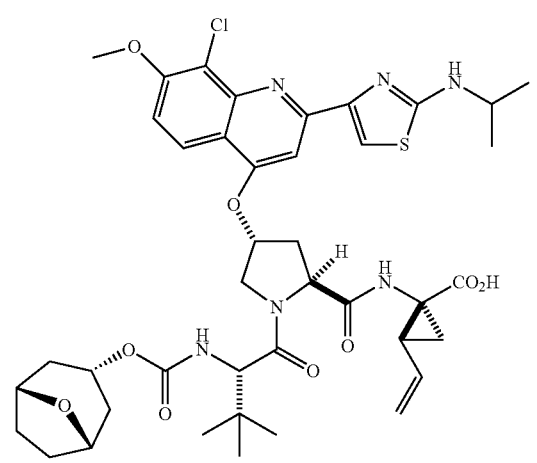 | 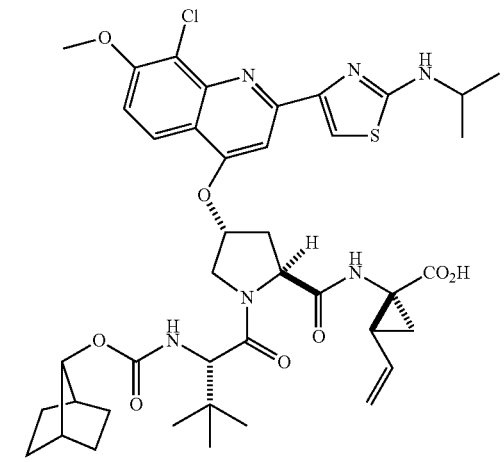 |

467
-continued
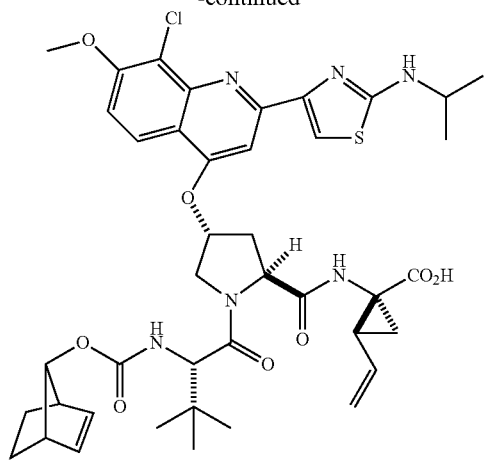
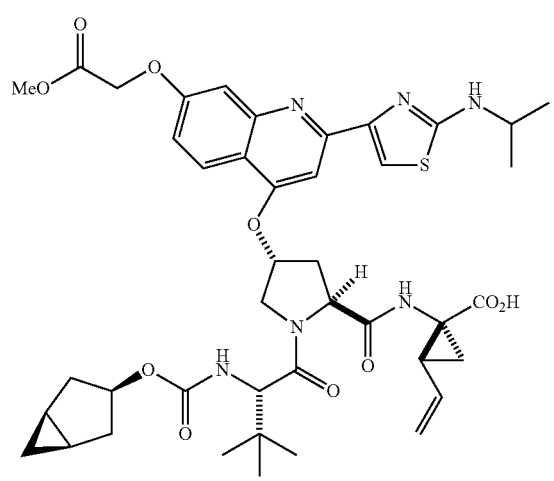
Example 114
Using procedures similar to those described herein, the following compounds of formula (I) can also be prepared.
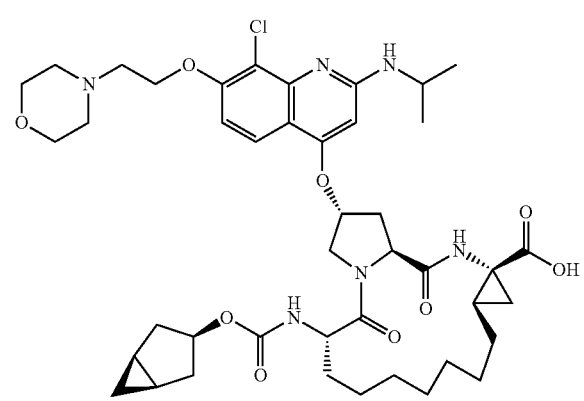
468
-continued
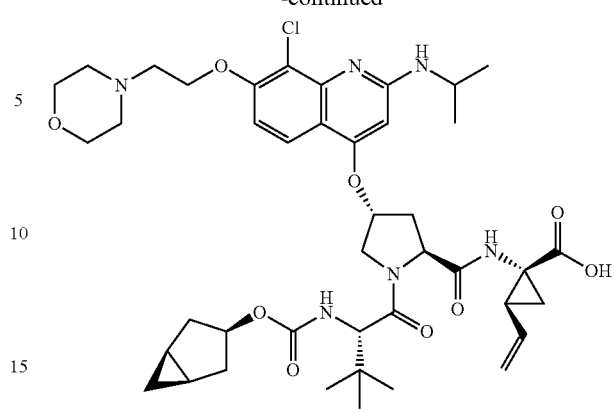
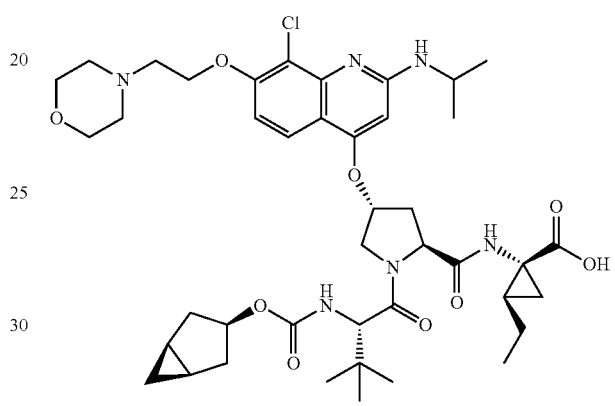
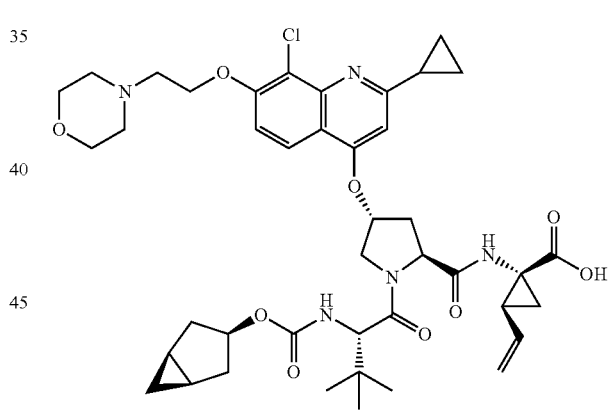
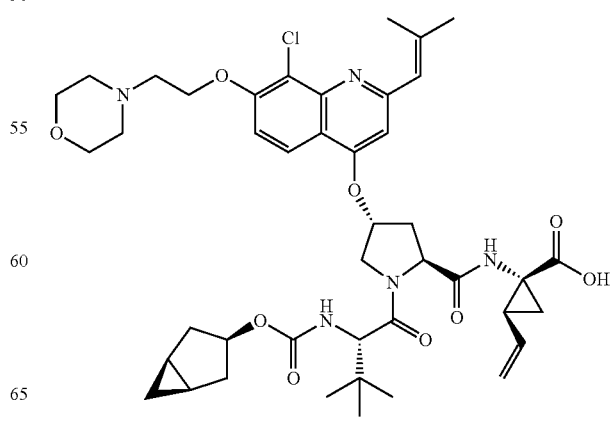

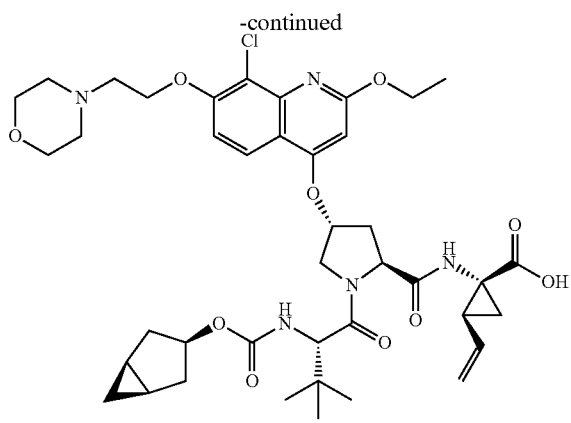

Example 115

The following illustrate representative pharmaceutical dosage forms, containing a compound of formula I ("Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Biological Assays

NS3 Enzymatic Potency:

Purified NS3 protease is complexed with NS4A peptide and then incubated with serial dilutions of the compounds (DMSO used as solvent). Reactions are started by addition of dual-labeled peptide substrate and the resulting kinetic increase in fluorescence is measured. Non-linear regression of velocity data is performed to calculate $IC_{50}$s. Activity is initially tested against genotype 1b protease. Depending on the potency obtained against genotype 1b, additional genotypes (1a, 2a, 3) and or protease inhibitor resistant enzymes (D168Y, D168V, or A156T mutants) may be tested. BILN-2061 is used as a control during all assays. The compounds of Examples 1-81 were evaluated in this assay and were found to have $IC_{50}$ values of less than about 1 μM.

Replicon Potency and Cytotoxicity:

Huh-luc cells (stably replicating Bartenschlager's 1389luc-ubi-neo/NS3-3'/ET genotype 1b replicon) is treated with serial dilutions of compound (DMSO is used as solvent) for 72 hours. Replicon copy number is measured by bioluminescence and non-linear regression is performed to calculate $EC_{50}$s. Parallel plates treated with the same drug dilutions are assayed for cytotoxicity using the Promega CellTiter-Glo cell viability assay. Depending on the potency achieved against the 1b replicon, compounds may be tested against a genotype 1a replicon and/or inhibitor resistant replicons encoding D168Y or A156T mutations. BILN-2061 is used as a control during all assays. The compounds of Examples 1-81 were evaluated in this assay and were found to have $EC_{50}$ values of less than about 5 μM.

Effect of Serum Proteins on Replicon Potency

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

Enyzmatic Selectivity:

The inhibition of mammalian proteases including Porcine Pancreatic Elastase, Human Leukocyte Elastase, Protease 3, and Cathepsin D are measured at $K_m$ for the respective substrates for each enzyme. $IC_{50}$ for each enzyme is compared to the $IC_{50}$ obtained with NS3 1b protease to calculate selectivity.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$:

Huh-luc cultures are incubated with compound at concentrations equal to $EC_{50}$. At multiple time points (0-72 hours), cells are washed 2× with cold medium and extracted with 85% acetonitrile; a sample of the media at each time-point is also extracted. Cell and media extracts are analyzed by LC/MS/MS to determine the molar concentration of compounds in each fraction Solubility and Stability:

Solubility is determined by taking an aliquot of 10 mM DMSO stock solution and preparing the compound at a final concentration of 100 µM in the test media solutions (PBS, pH 7.4 and 0.1 N HCl, pH 1.5) with a total DMSO concentration of 1%. The test media solutions are incubated at room temperature with shaking for 1 hr. The solutions are then centrifuged and the recovered supernatants are assayed on the HPLC/UV. Solubility will be calculated by comparing the amount of compound detected in the defined test solution compared to the amount detected in DMSO at the same concentration. The stability of compounds after a 1 hour incubation in the test media at 37° C. is also determined Stability in Cryopreserved Human, Dog, and Rat Hepatocytes:

Each compound is incubated for up to 1 hour in hepatocyte suspensions (100 µl, 80,000 cells per well) at 37° C. Cryopreserved hepatocytes are reconstituted in the serum-free incubation medium. The suspension is transferred into 96-well plates (50 µL/well). The compounds are diluted to 2 µM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data is also scaled up to represent intrinsic hepatic clearance and/or total hepatic clearance.

Stability in Hepatic S9 Fraction from Human, Dog, and Rat:

Each compound is incubated for up to 1 hour in S9 suspension (500 µl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Both forward (A-to-B) and reverse (B-to-A) permeability is measured. Caco-2 monolayers are grown to confluence on collagen-coated, microporous, polycarbonate membranes in 12-well Costar Transwell® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation, at 1 hr and 2 hr after incubation, a 200-µL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 µM. The spiked plasma and phosphate buffer is placed into opposite sides of the assembled dialysis cells, which is then rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left(\frac{C_f}{C_b + C_f}\right)$$

Where $C_f$ and $C_b$ are free and bound concentrations determined as the post-dialysis buffer and plasma concentrations, respectively CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 min after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds are incubated for up to 2 hour in plasma (rat, dog, monkey, or human) at 37° C. Compounds are added to the plasma at final concentrations of 1 and 10 ug/mL. Aliquots are taken at 0, 5, 15, 30, 60, and 120 min after adding the compound. Concentration of compounds and major metabolites at each timepoint are measured by LC/MS/MS.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A compound selected from the group consisting of:

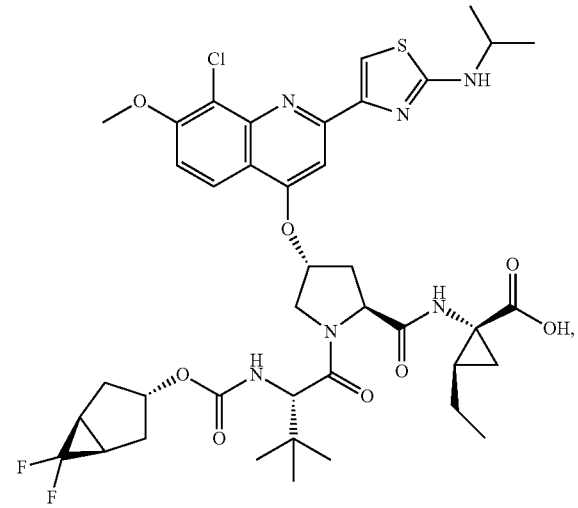

473
-continued
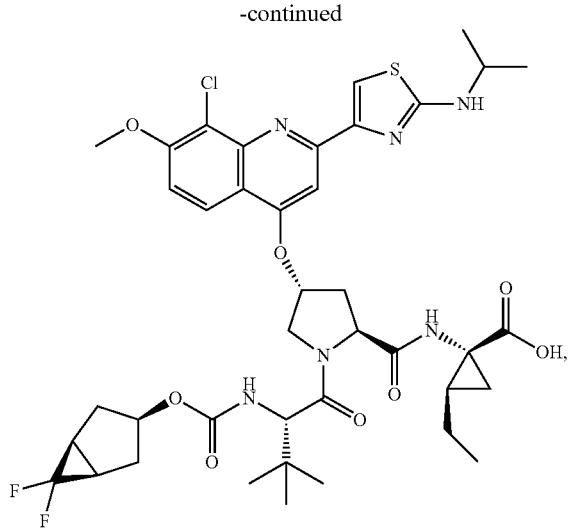
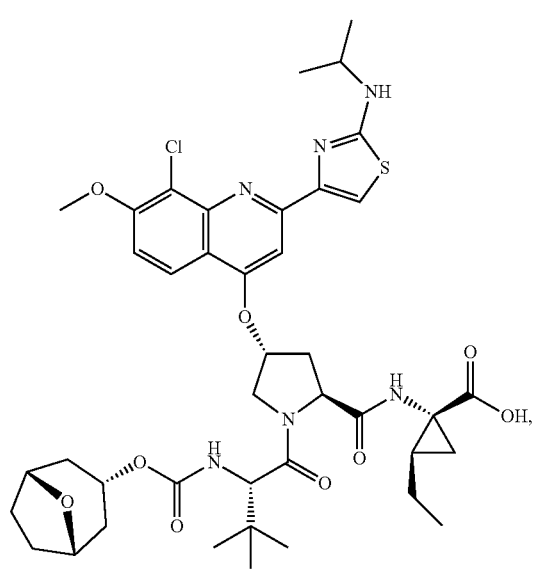
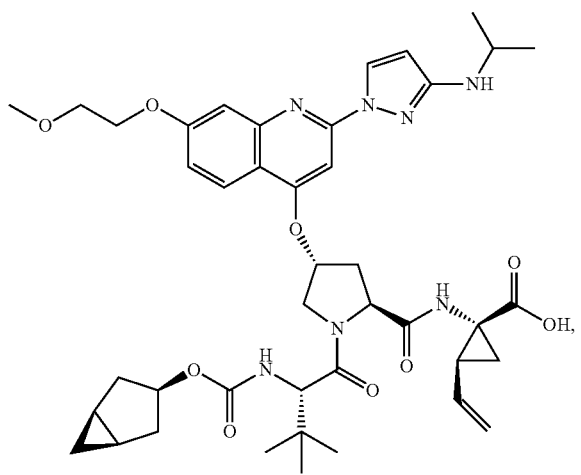
474
-continued
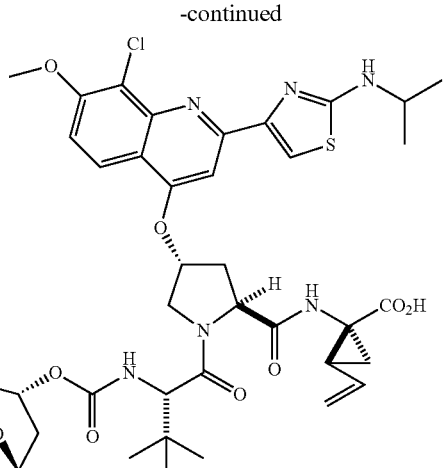
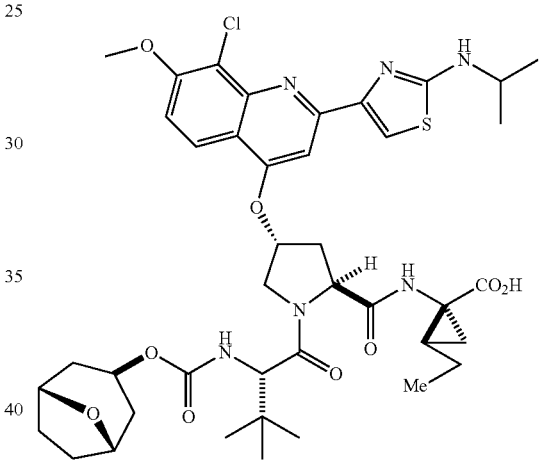
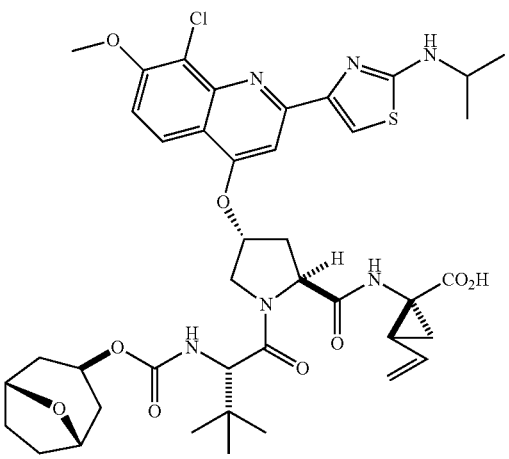

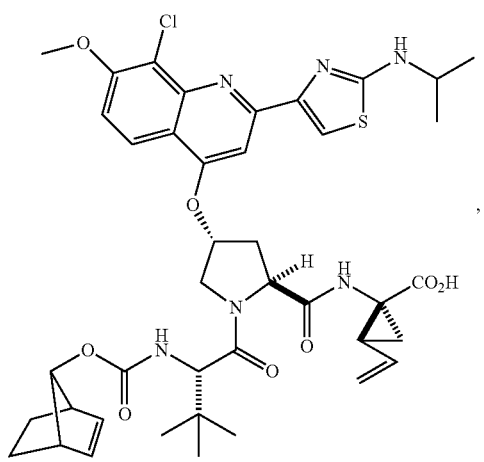
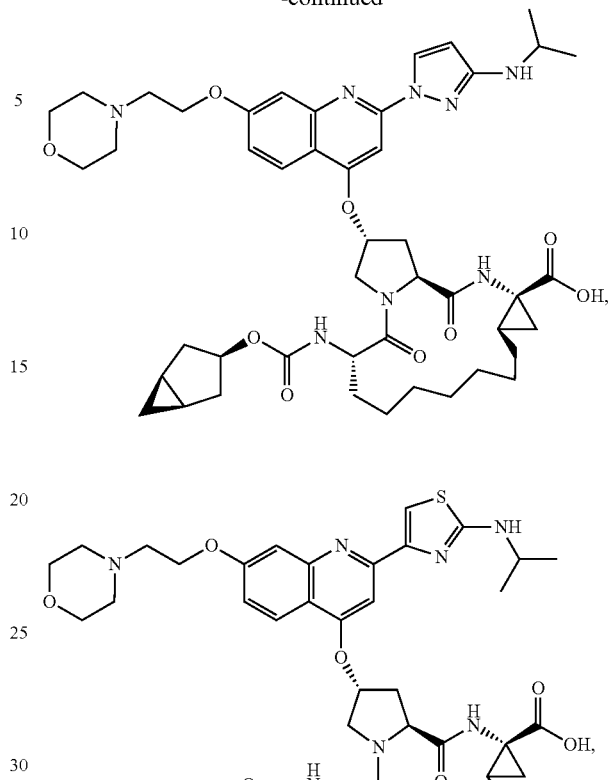
or a pharmaceutically acceptable salt thereof.
2. A compound selected from the group consisting of:
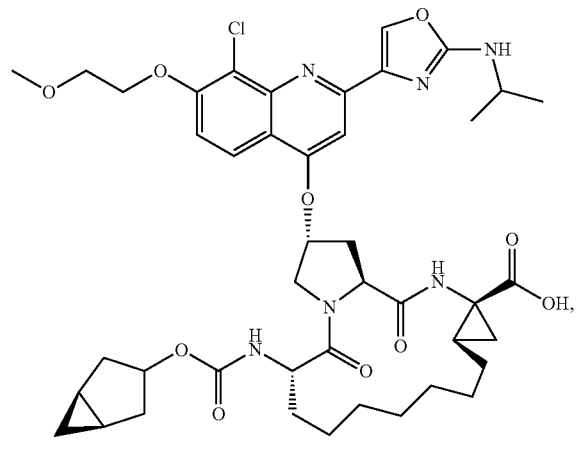
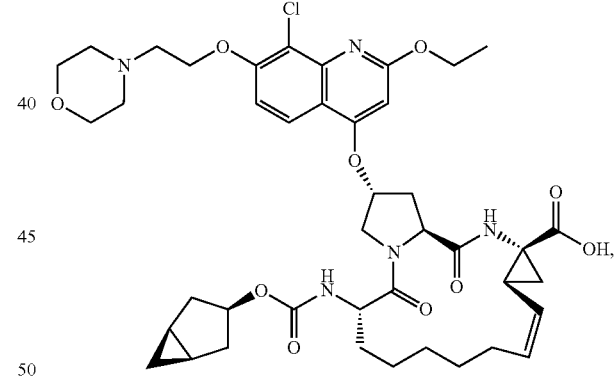
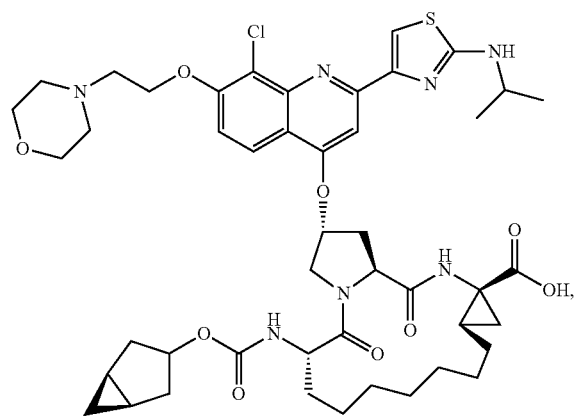
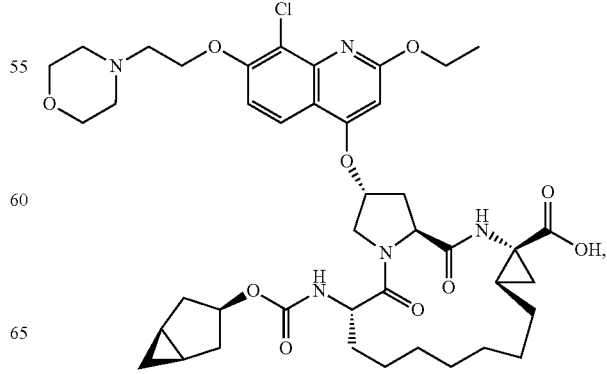

-continued

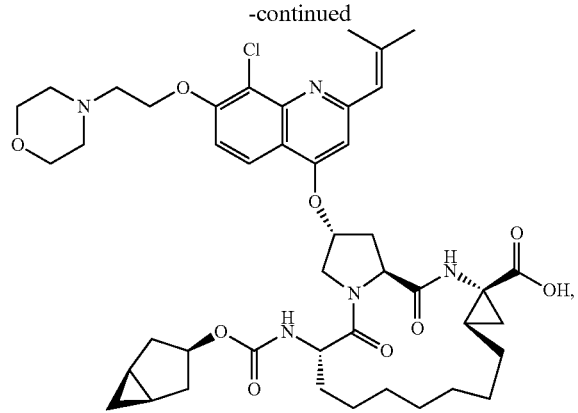

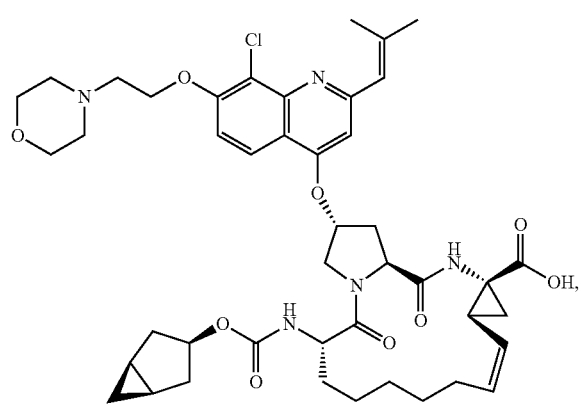

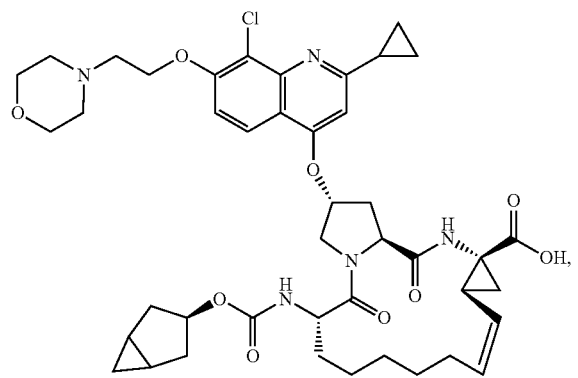

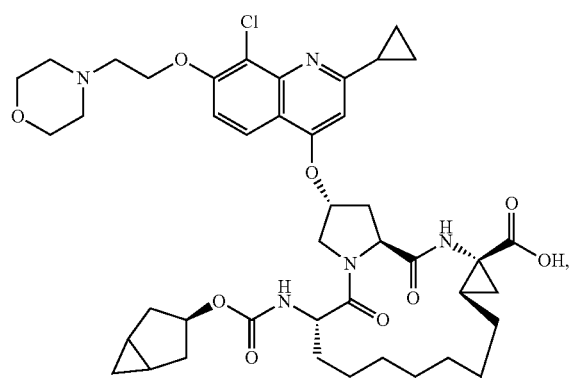

-continued

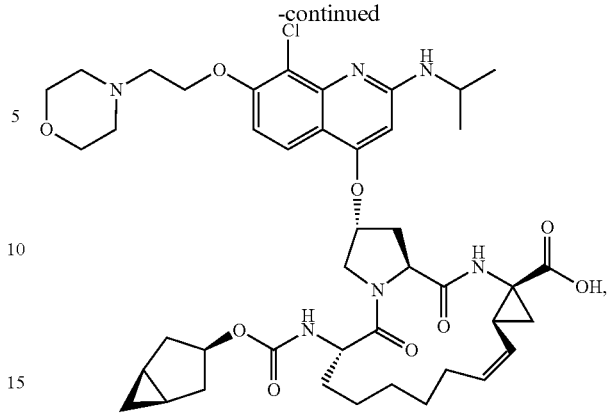

and

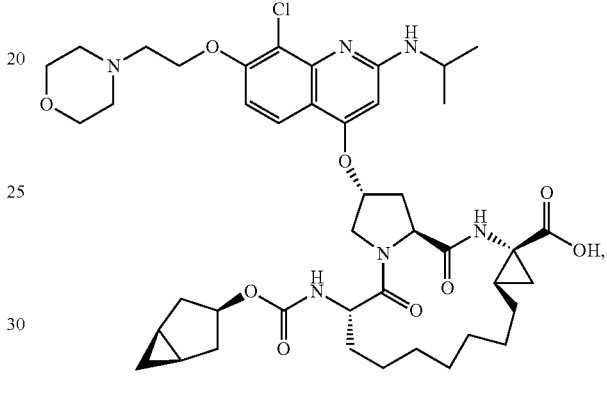

or a pharmaceutically acceptable salt thereof.

3. A method of treating hepatitis C, said method comprising administering to an individual in need thereof a pharmaceutical composition which comprises a therapeutically effective amount of a compound of claim 1 or a pharmaceutically acceptable salt thereof.

4. The method of claim 3, wherein the pharmaceutical composition further comprises at least one additional therapeutic agent.

5. The method of claim 4, wherein the additional therapeutic agent is selected from the group consisting of interferons, ribavirin analogues, NS3 protease inhibitors, NS5b polymerase inhibitors, alpha-glucosidase 1 inhibitors, hepatoprotectants, and non-nucleoside inhibitors of HCV.

6. The method of claim 3, wherein the pharmaceutical composition further comprises a nucleoside analogue.

7. The method of claim 6, wherein the pharmaceutical composition further comprises an interferon or pegylated interferon.

8. The method of claim 6, wherein the nucleoside analogue is selected from the group consisting of ribavirin, viramidine, levovirin, a L-nucleoside, and isatoribine.

9. A method of treating hepatitis C, said method comprising administering to an individual in need thereof a pharmaceutical composition which comprises a therapeutically effective amount of a compound of claim 2 or a pharmaceutically acceptable salt thereof.

10. The method of claim 9, wherein the pharmaceutical composition further comprises at least one additional therapeutic agent.

11. The method of claim 10, wherein the additional therapeutic agent is selected from the group consisting of interferons, ribavirin analogues, NS3 protease inhibitors, NS5b polymerase inhibitors, alpha-glucosidase 1 inhibitors, hepatoprotectants, and non-nucleoside inhibitors of HCV.

12. The method of claim 9, wherein the pharmaceutical composition further comprises a nucleoside analogue.

13. The method of claim 12, wherein the pharmaceutical composition further comprises an interferon or pegylated interferon.

14. The method of claim 12, wherein the nucleoside analogue is selected from the group consisting of ribavirin, viramidine, levovirin, a L-nucleoside, and isatoribine.

* * * * *